(12) United States Patent
Alanine et al.

(10) Patent No.: US 12,012,466 B2
(45) Date of Patent: Jun. 18, 2024

(54) **PEPTIDE MACROCYCLES AGAINST *ACINETOBACTER BAUMANNII***

(71) Applicant: Hoffmann-La Roche Inc., Little Falls, NJ (US)

(72) Inventors: Alexander Alanine, Basel (CH); Julien Beignet, Saint-Herblon (FR); Konrad Bleicher, Basel (CH); Bernhard Fasching, Basel (CH); Hans Hilpert, Basel (CH); Taishan Hu, Shanghai (CH); Dwight MacDonald, Pointe-Claire (CA); Stephen Jackson, Lévis (CA); Sabine Kolczewski, Basel (CH); Carsten Kroll, Basel (CH); Adrian Schaeublin, Basel (CH); Hong Shen, Shanghai (CN); Theodor Stoll, Basel (CH); Helmut Thomas, Sherbrooke (CA); Amal Wahhab, Laval (CA); Claudia Zampaloni, Basel (CH)

(73) Assignee: Hoffmann-La Roche Inc., Little Falls, NJ (US)

( * ) Notice: Subject to any disclaimer, the term of this patent is extended or adjusted under 35 U.S.C. 154(b) by 0 days.

(21) Appl. No.: 17/377,338

(22) Filed: Jul. 15, 2021

(65) Prior Publication Data
US 2022/0411468 A1    Dec. 29, 2022

Related U.S. Application Data

(60) Continuation of application No. 16/006,564, filed on Jun. 12, 2018, now Pat. No. 11,098,080, which is a division of application No. 15/336,128, filed on Oct. 27, 2016, now Pat. No. 10,030,047.

(30) Foreign Application Priority Data

Oct. 27, 2015  (EP) ..................................... 15191743
Sep. 26, 2016  (WO) ................. PCT/CN2016/100125

(51) Int. Cl.
| C07K 5/08 | (2006.01) |
| C07K 5/02 | (2006.01) |
| C07K 5/068 | (2006.01) |
| C07K 5/083 | (2006.01) |
| C07K 5/087 | (2006.01) |
| C07K 5/09 | (2006.01) |
| C07K 5/097 | (2006.01) |
| A61K 38/00 | (2006.01) |

(52) U.S. Cl.
CPC .............. *C07K 5/0827* (2013.01); *C07K 5/02* (2013.01); *C07K 5/06086* (2013.01); *C07K 5/08* (2013.01); *C07K 5/0806* (2013.01); *C07K 5/0808* (2013.01); *C07K 5/081* (2013.01); *C07K 5/0812* (2013.01); *C07K 5/0815* (2013.01); *C07K 5/0821* (2013.01); *A61K 38/00* (2013.01)

(58) Field of Classification Search
None
See application file for complete search history.

(56) References Cited

U.S. PATENT DOCUMENTS

| 7,521,420 B2 | 4/2009 | Fraser et al. |
| 10,030,047 B2 | 7/2018 | Alanine et al. |
| 11,066,443 B2 | 7/2021 | Alanine et al. |
| 11,098,080 B2 | 8/2021 | Alanine et al. |
| 11,505,573 B2 | 11/2022 | Bleicher et al. |
| 11,819,532 B2 | 11/2023 | Bleicher et al. |
| 2005/0256037 A1 | 11/2005 | Lampe et al. |
| 2006/0004185 A1 | 1/2006 | Leese et al. |
| 2006/0025566 A1 | 2/2006 | Hoveyda et al. |

(Continued)

FOREIGN PATENT DOCUMENTS

| CN | 103387601 A | 11/2013 |
| EP | 1 498 422 A1 | 1/2005 |

(Continued)

OTHER PUBLICATIONS

Azuma, H., et al., "A publication of reliable methods for the preparation of organic compounds," Org. Synth. 88:152-161 (2011).

(Continued)

*Primary Examiner* — Ronald T Niebauer
(74) *Attorney, Agent, or Firm* — Andre T. Krammer

(57) ABSTRACT

The present invention provides compounds of formula (I)

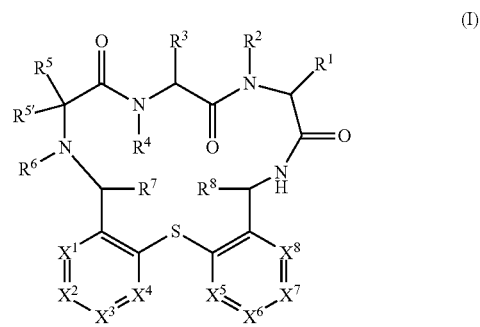

wherein $X^1$ to $X^8$ and $R^1$ to $R^8$ are as described herein, as well as pharmaceutically acceptable salts thereof. Further the present invention is concerned with the manufacture of the compounds of formula (I), pharmaceutical compositions comprising them and their use as medicaments for the treatment of diseases and infections caused by *Acinetobacter baumannii*.

5 Claims, No Drawings

(56) References Cited

U.S. PATENT DOCUMENTS

| | | |
|---|---|---|
| 2006/0258571 A1 | 11/2006 | Lampe et al. |
| 2007/0021331 A1 | 1/2007 | Fraser et al. |
| 2008/0275018 A1 | 11/2008 | Endermann et al. |
| 2019/0300569 A1 | 10/2019 | Bleicher et al. |
| 2019/0321440 A1 | 10/2019 | Bleicher et al. |
| 2020/0040031 A1 | 2/2020 | Alanine et al. |

FOREIGN PATENT DOCUMENTS

| | | |
|---|---|---|
| EP | 3 388 444 A1 | 10/2018 |
| WO | 01/14346 A1 | 3/2001 |
| WO | 03/106480 A1 | 12/2003 |
| WO | 2004/012816 A1 | 2/2004 |
| WO | 2004/018478 A2 | 3/2004 |
| WO | 2004/111077 A1 | 12/2004 |
| WO | 2005/012331 A1 | 2/2005 |
| WO | 2005/012332 A1 | 2/2005 |
| WO | 2005/090388 A1 | 9/2005 |
| WO | 2005/118613 A2 | 12/2005 |
| WO | 2005/118613 A3 | 12/2005 |
| WO | 2006/009645 A1 | 1/2006 |
| WO | 2006/009674 A1 | 1/2006 |
| WO | 2006/009674 A8 | 1/2006 |
| WO | 2006/074964 A1 | 7/2006 |
| WO | 2006/103015 A1 | 10/2006 |
| WO | 2007/131966 A1 | 11/2007 |
| WO | 2008/095999 A1 | 8/2008 |
| WO | 2009/099677 A2 | 8/2009 |
| WO | 2010/022249 A2 | 2/2010 |
| WO | 2010/022249 A3 | 2/2010 |
| WO | 2011/050270 A2 | 4/2011 |
| WO | 2011/050276 A1 | 4/2011 |
| WO | 2011/053821 A1 | 5/2011 |
| WO | 2012/021874 A2 | 2/2012 |
| WO | 2013/033645 A1 | 3/2013 |
| WO | 2013/123266 A1 | 8/2013 |
| WO | 2014/081886 A1 | 5/2014 |
| WO | 2014/110420 A1 | 7/2014 |
| WO | 2016/016291 A1 | 2/2016 |
| WO | 2018/189065 A1 | 10/2018 |
| WO | 2019/185572 A1 | 10/2019 |
| WO | 2019/206853 A1 | 10/2019 |

OTHER PUBLICATIONS

Ballatore, C., et al., "Carboxylic Acid (Bio)Isosteres in Drug Design," Chem. Med. Chem. 8(3):385-395 (2013).

Balraju, V., et al., "Synthesis of Cyclic Peptides Constrained with Biarylamine Linkers Using Buchwald-Hartwig C—N Coupling," J. Org. Chem. 71(23):8954-8956 (2006).

Belikov, V.G. Pharmaceutical Chemistry, Tutorial, 4$^{th}$, revised and expanded edition, Moscow, MEDPress-Inform, 2007, pp. 27-29 (including English Translation).

Luther, A. et al. "Advances in macrocyclic peptide-based antibiotics," Bioorg. Med. Chem. 26 (10) 2850-2858 (2018).

International Search Report and Written Opinion for PCT/EP2018/058957, dated May 28, 2018, 10 pages.

International Search Report and Written Opinion for PCT/EP2019/057489, dated May 17, 2019, 10 pages.

International Search Report for PCT/EP2016/075499, dated Jan. 5, 2017, 6 pages.

International Search Report for PCT/EP2019/060272, dated Jul. 9, 2019, 4 pages.

Marsault, E., et al., "Efficient parallel synthesis of macrocyclic peptidomimetics," Bioorg. Med. Chem. Lett. 18(16):4731-4735 (2008).

Wang, W et at. "Practical, asymmetric synthesis of aromatic-substituted bulky and hydrophobic tryptophan and phenylalanine derivatives," Tetrahedron 58(15):3101-3110 (2002).

Wang, W et at. "Design and synthesis of novel χ2-constrained phenylalanine, naphthylalanine, and tryptophan analogues and their use in biologically active melanotropin peptides," Tetrahedron 58(36):7365-7374 (2002).

Webster, A., et al., "Synthesis of biaryl-linked cyclic peptoids," Tetrahedron Lett. 58(10):1010-1014 (2017).

Written Opinion of the International Searching Authority for PCT/EP2019/060272, dated Jul. 9, 2019, 10 pages.

Written Opinion of the International Searching Authority for PCT/EP2016/075499, dated Jan. 5, 2017, 6 pages.

PEPTIDE MACROCYCLES AGAINST ACINETOBACTER BAUMANNII

CROSS-REFERENCE TO RELATED APPLICATIONS

This application is continuation application of U.S. patent application Ser. No. 16/006,564, filed on Jun. 12, 2018, which is a divisional to U.S. patent application Ser. No. 15/336,128, filed on Oct. 27, 2016, which claims priority to International Patent Application No. PCT/CN2016/100125, filed on Sep. 26, 2016, and European Patent Application No. 15191743.2, filed on Oct. 27, 2015, each of which is incorporated herein by reference in its entirety.

INTRODUCTION

The present invention provides compounds which exhibit activity against *Acinetobacter baumannii*, their manufacture, pharmaceutical compositions comprising them and their use as medicaments for the treatment of diseases and infections caused by *Acinetobacter baumannii*.

In particular, the present invention relates to compounds of formula (I)

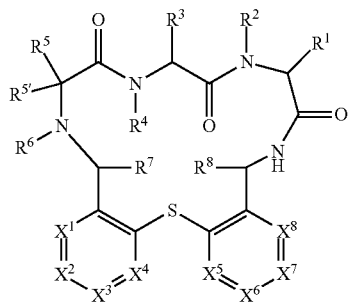

wherein $X^1$ to $X^8$ and $R^1$ to $R^8$ are as described herein, and pharmaceutically acceptable salts thereof.

BACKGROUND

*Acinetobacter baumannii* is a Gram-negative, aerobic, nonfermenting bacterium recognized over the last decades as an emergining pathogen with very limited treatment options.

*A. baumannii* is considered to be a serious threat by the US Centers for Disease Control and Prevention and belongs to the so called 'ESKAPE' pathogens (*Enterococcus faecium, Staphylococcus aureus, Klebsiella pneumoniae, Acinetobacter baumannii, Pseudomonas aeruginosa* and *Enterobacter* species & *E. coli*) that currently cause the majority of nosocomial infections and effectively "escape" the activity of antimicrobial agents.

*A. baumannii* is most often encountered in intensive care units and surgical wards, where extensive antibiotic use has enabled selection for resistance against all known antimicrobials and where it causes infections that include bacteremia, pneumonia, meningitis, urinary tract infection, and wound infection.

*A. baumannii* has an exceptional ability to upregulate and acquire resistance determinats and shows an environmental persistance that allows its survival and spread in the nosocomial setting, making this organism a frequent cause of outbreaks of infection and an endemic, health care-associated pathogen.

Due to increasing antibiotic resistance to most if not all available therapeutic options, Muti-Drug Resistant (MDR) *A. baumannii* infections, especially those caused by Carbapenem resistant *A. baumannii*, are extremely difficult or even impossible to treat with high mortality rate as well as increased morbidity and length of stay in intensive care unit. *Acinetobacter baumannii* has been defined and still remains "a prime example of a mismatch between unmet medical needs and the current antimicrobial research and development pipeline" according to the Antimicrobial Availability Task Force (AATF) of the Infectious Diseases Society of America (IDSA). Thus, there is a high demand and need to identify compounds suitable for the treatment of diseases and infections caused by *Acinetobacter baumannii*.

The present invention provides a novel chemotype (peptide macrocycles) that exhibits activity against drug-susceptible as well as drug-resistant strains of *Acinetobacter baumannii*. The molecules have been routinely tested against drug susceptible *A. baumannii* strains (ATCC19606 and ATCC 17978) and in addition over a panel of ten clinical isolates. Some representative molecules were selected for in vivo profiling. Both, the pharmacokinetic profile as well as the efficacy in a mouse septicemia model are indicative of a great potential for further development of the compound class.

DETAILED DESCRIPTION OF THE INVENTION

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below.

All publications, patent applications, patents, and other references mentioned herein are incorporated by reference in their entirety.

The nomenclature used in this Application is based on IUPAC systematic nomenclature, unless indicated otherwise.

AutoNom 2000 (Automatic Nomenclature) for ISIS/Draw was employed to generate IUPAC chemical names.

Any open valency appearing on a carbon, oxygen, sulfur or nitrogen atom in the structures herein indicates the presence of a hydrogen, unless indicated otherwise.

The term "moiety" refers to an atom or group of chemically bonded atoms that is attached to another atom or molecule by one or more chemical bonds thereby forming part of a molecule. For example, the variables $R^1$, $R^2$ and $R^3$ of formula (I) refer to moieties that are attached to the core structure of formula (I) by a covalent bond.

When indicating the number of substituents, the term "one or more" refers to the range from one substituent to the highest possible number of substitution, i.e. replacement of one hydrogen up to replacement of all hydrogens by substituents.

The term "optional" or "optionally" denotes that a subsequently described event or circumstance can but need not occur, and that the description includes instances where the event or circumstance occurs and instances in which it does not.

The term "substituent" denotes an atom or a group of atoms replacing a hydrogen atom on the parent molecule.

The term "substituted" denotes that a specified group bears one or more substituents. Where any group can carry multiple substituents and a variety of possible substituents is provided, the substituents are independently selected and need not to be the same. The term "unsubstituted" means that the specified group bears no substituents. The term "optionally substituted" means that the specified group is unsubstituted or substituted by one or more substituents, independently chosen from the group of possible substituents. When indicating the number of substituents, the term "one or more" means from one substituent to the highest possible number of substitution, i.e. replacement of one hydrogen up to replacement of all hydrogens by substituents.

The term "compound(s) of this invention" and "compound(s) of the present invention" refers to compounds as disclosed herein and stereoisomers, tautomers, solvates, and salts (e.g., pharmaceutically acceptable salts) thereof.

When the compounds of the invention are solids, it is understood by those skilled in the art that these compounds, and their solvates and salts, may exist in different solid forms, particularly different crystal forms, all of which are intended to be within the scope of the present invention and specified formulas.

The term, "structurally related substances" denotes substances that share a common or core structure of the substance that has biological activity, such as a common pharmacophore or olfactophore. Such structurally related substances can differ from each other, however, in their substituent groups.

The term "pharmaceutically acceptable esters" denotes derivatives of the compounds of present invention, in which a carboxy group has been converted to an ester, wherein carboxy group means —C(O)O—. Methyl-, ethyl-, methoxymethyl-, methylthiomethyl-, and pivaloyloxymethylesters are examples of such suitable esters. The term "pharmaceutically acceptable esters" furthermore embraces derivatives of the compounds of present invention in which hydroxy groups have been converted to the corresponding esters with inorganic or organic acids such as nitric acid, sulfuric acid, phosphoric acid, citric acid, formic acid, maleic acid, acetic acid, succinic acid, tartaric acid, methanesulfonic acid, or p-toluenesulfonic acid, and which are non toxic to living organisms.

The term "pharmaceutically acceptable salts" denotes salts which are not biologically or otherwise undesirable. Pharmaceutically acceptable salts include both acid and base addition salts.

The term "pharmaceutically acceptable acid addition salt" denotes those pharmaceutically acceptable salts formed with inorganic acids such as hydrochloric acid, hydrobromic acid, sulfuric acid, nitric acid, carbonic acid, phosphoric acid, and organic acids selected from aliphatic, cycloaliphatic, aromatic, araliphatic, heterocyclic, carboxylic, and sulfonic classes of organic acids such as formic acid, acetic acid, propionic acid, glycolic acid, gluconic acid, lactic acid, pyruvic acid, oxalic acid, malic acid, maleic acid, maloneic acid, succinic acid, fumaric acid, tartaric acid, citric acid, aspartic acid, ascorbic acid, glutamic acid, anthranilic acid, benzoic acid, cinnamic acid, mandelic acid, embonic acid, phenylacetic acid, methanesulfonic acid, ethanesulfonic acid, p-toluenesulfonic acid, and salicyclic acid.

The term "pharmaceutically acceptable base addition salt" denotes those pharmaceutically acceptable salts formed with an organic or inorganic base. Examples of acceptable inorganic bases include sodium, potassium, ammonium, calcium, magnesium, iron, zinc, copper, manganese, and aluminum salts. Salts derived from pharmaceutically acceptable organic nontoxic bases includes salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, and polyamine resins.

Stereochemical definitions and conventions used herein generally follow S. P. Parker, Ed., McGraw-Hill Dictionary of Chemical Terms (1984) McGraw-Hill Book Company, New York; and Eliel, E. and Wilen, S., "Stereochemistry of Organic Compounds", John Wiley & Sons, Inc., New York, 1994. In describing an optically active compound, the prefixes D and L, or R and S, are used to denote the absolute configuration of the molecule about its chiral center(s). The substituents attached to the chiral center under consideration are ranked in accordance with the Sequence Rule of Cahn, Ingold and Prelog. (Cahn et al. Angew. Chem. Inter. Edit. 1966, 5, 385; errata 511). The prefixes D and L or (+) and (−) are employed to designate the sign of rotation of plane-polarized light by the compound, with (−) or L designating that the compound is levorotatory. A compound prefixed with (+) or D is dextrorotatory.

The term "halo", "halogen", and "halide" are used interchangeably herein and denote fluoro, chloro, bromo, or iodo. Particular examples of halo are fluoro and chloro.

The term "alkyl" denotes a monovalent linear or branched saturated hydrocarbon group of 1 to 12 carbon atoms. In particular embodiments, alkyl has 1 to 7 carbon atoms, and in more particular embodiments 1 to 4 carbon atoms. Examples of alkyl include methyl, ethyl, propyl, isopropyl, n-butyl, iso-butyl, sec-butyl, or tert-butyl. Particular examples of alkyl are methyl, ethyl, isopropyl, n-butyl, sec-butyl and tert-butyl, most particularly methyl and ethyl.

The term "alkoxy" denotes a group of the formula —O—R', wherein R' is an alkyl group. Examples of alkoxy moieties include methoxy, ethoxy, isopropoxy, and tert-butoxy. Particular examples of alkoxy is methoxy.

The term "haloalkyl" denotes an alkyl group wherein at least one of the hydrogen atoms of the alkyl group has been replaced by same or different halogen atoms, particularly fluoro atoms. Examples of haloalkyl include monofluoro-, difluoro- or trifluoro-methyl, -ethyl or -propyl, for example 3,3,3-trifluoropropyl, 2-fluoroethyl, 2,2,2-trifluoroethyl, fluoromethyl, or trifluoromethyl. The term "perhaloalkyl" denotes an alkyl group where all hydrogen atoms of the alkyl group have been replaced by the same or different halogen atoms. Particular examples of haloalkyl is trifluoromethyl.

The term "haloalkoxy" denotes an alkoxy group wherein at least one of the hydrogen atoms of the alkoxy group has been replaced by same or different halogen atoms, particularly fluoro atoms. Examples of haloalkoxyl include monofluoro-, difluoro- or trifluoro-methoxy, -ethoxy or -propoxy, for example 3,3,3-trifluoropropoxy, 2-fluoroethoxy, 2,2,2-trifluoroethoxy, fluoromethoxy, or trifluoromethoxy. The term "perhaloalkoxy" denotes an alkoxy group where all hydrogen atoms of the alkoxy group have been replaced by the same or different halogen atoms.

The term "hydroxyalkyl" denotes an alkyl group wherein at least one of the hydrogen atoms of the alkyl group has been replaced by a hydroxy group. Examples of hydroxyalky include hydroxymethyl, 2-hydroxy ethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 2-hydroxy-1-hydroxymethylethyl, 2,3-dihydroxybutyl, 3,4-dihydroxybutyl or 2-(hydroxymethyl)-3-hydroxypropyl.

The term "bicyclic ring system" denotes two rings which are fused to each other via a common single or double bond (annelated bicyclic ring system), via a sequence of three or more common atoms (bridged bicyclic ring system) or via a common single atom (spiro bicyclic ring system). Bicyclic ring systems can be saturated, partially unsaturated, unsaturated or aromatic. Bicyclic ring systems can comprise heteroatoms selected from N, O and S.

The term "cycloalkyl" denotes a monovalent saturated monocyclic or bicyclic hydrocarbon group of 3 to 10 ring carbon atoms. In particular embodiments cycloalkyl denotes a monovalent saturated monocyclic hydrocarbon group of 3 to 8 ring carbon atoms. Bicyclic means consisting of two saturated carbocycles having one or more carbon atoms in common. Particular cycloalkyl groups are monocyclic. Examples for monocyclic cycloalkyl are cyclopropyl, cyclobutanyl, cyclopentyl, cyclohexyl or cycloheptyl. Examples for bicyclic cycloalkyl are bicyclo[2.2.1]heptanyl, or bicyclo[2.2.2]octanyl. Particular cycloalkyl is cyclopropyl.

The term "heterocycloalkyl" denotes a monovalent saturated or partly unsaturated mono- or bicyclic ring system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, piperazinyl, morpholinyl, thiomorpholinyl, 1,1-dioxo-thiomorpholin-4-yl, azepanyl, diazepanyl, homopiperazinyl, or oxazepanyl. Examples for bicyclic saturated heterocycloalkyl are 8-aza-bicyclo[3.2.1]octyl, quinuclidinyl, 8-oxa-3-aza-bicyclo[3,2,1]octyl, 9-aza-bicyclo[3.3.1]nonyl, 3-oxa-9-aza-bicyclo[3.3.1]nonyl, or 3-thia-9-aza-bicyclo[3.3.1]nonyl. Examples for partly unsaturated heterocycloalkyl are dihydrofuryl, imidazolinyl, dihydro-oxazolyl, tetrahydro-pyridinyl, or dihydropyranyl. Particular examples of heterocycloalkyl are pyrrolidinyl, piperidinyl, piperazinyl, morpholinyl, 2-oxa-5-aza-bicyclo[2.2.1]heptyl and dihydropyranyl. Particular examples of saturated heterocycloalkyl are pyrrolidinyl, piperidinyl, piperazinyl, morpholinyl and 2-oxa-5-aza-bicyclo[2.2.1]heptyl. Particular examples of partly unsaturated heterocycloalkyl are dihydropyranyl and dihydroindolyl.

The term "aromatic" denotes the conventional idea of aromaticity as defined in the literature, in particular in IUPAC—Compendium of Chemical Terminology, 2nd, A. D. McNaught & A. Wilkinson (Eds). Blackwell Scientific Publications, Oxford (1997).

The term "aryl" denotes a monovalent aromatic carbocyclic mono- or bicyclic ring system comprising 6 to 10 carbon ring atoms. Examples of aryl moieties include phenyl and naphthyl, most particularly phenyl. Particular aryl substituted by aryl is biphenyl.

The term "heteroaryl" denotes a monovalent aromatic heterocyclic mono- or bicyclic ring system of 5 to 12 ring atoms, comprising 1, 2, 3 or 4 heteroatoms selected from N, O and S, the remaining ring atoms being carbon. Examples of heteroaryl moieties include pyrrolyl, furanyl, thienyl, imidazolyl, oxazolyl, thiazolyl, triazolyl, oxadiazolyl, thiadiazolyl, tetrazolyl, pyridinyl, pyrazinyl, pyrazolyl, pyridazinyl, pyrimidinyl, triazinyl, azepinyl, diazepinyl, isoxazolyl, benzofuranyl, isothiazolyl, benzothienyl, indolyl, isoindolyl, isobenzofuranyl, benzimidazolyl, benzoxazolyl, benzoisoxazolyl, benzothiazolyl, benzoisothiazolyl, benzooxadiazolyl, benzothiadiazolyl, benzotriazolyl, purinyl, quinolinyl, isoquinolinyl, quinazolinyl, or quinoxalinyl. Particular examples of heteroaryl are imidazolyl, pyrazolyl, pyrrolyl, isoxazolyl, pyridinyl, pyrazinyl, pyridazinyl, pyrimidinyl, indolyl and quinolyl. Most particular examples of heteroaryl are pyridinyl and indolyl.

The term "protecting group" denotes the group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups.

The term "amino-protecting group" denotes groups intended to protect an amino group and includes benzyl, benzyloxycarbonyl (carbobenzyloxy, CBZ), Fmoc (9-Fluorenylmethyloxycarbonyl), p-methoxybenzyloxycarbonyl, p-nitrobenzyloxycarbonyl, tert-butoxycarbonyl (BOC), and trifluoroacetyl. Further examples of these groups are found in T. W. Greene and P. G. M. Wuts, "Protective Groups in Organic Synthesis", 2nd ed., John Wiley & Sons, Inc., New York, NY, 1991, chapter 7; E. Haslam, "Protective Groups in Organic Chemistry", J. G. W. McOmie, Ed., Plenum Press, New York, NY, 1973, Chapter 5, and T. W. Greene, "Protective Groups in Organic Synthesis", John Wiley and Sons, New York, NY, 1981. The term "protected amino group" refers to an amino group substituted by an amino-protecting groups.

The term "carboxy-protecting group" denotes groups intended to protect a carboxy group and includes ester groups and heterocycloalkyl groups. Examples of such ester groups include substituted arylalkyl esters, including esters with substituted benzyls, such as 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, pentamethylbenzyl, 3,4-methylenedioxybenzyl, benzhydryl, 4,4'-dimethoxybenzhydryl, 2,2',4,4'-tetramethoxybenzhydryl, esters with alkyl or substituted alkyl such as methyl, ethyl, t-butyl allyl or t-amyl, triphenylmethyl (trityl), 4-methoxytrityl, 4,4'-dimethoxytrityl, 4,4',4"-trimethoxytrityl, 2-phenylprop-2-yl, thioesters such as t-butyl thioester, silyl esters such as trimethylsilyl, t-butyldimethylsilyl esters, phenacyl, 2,2,2-trichloroethyl, beta-(trimethylsilyl)ethyl, beta-(di(n-butyl)methylsilyl)ethyl, p-toluenesulfonylethyl, 4-nitrobenzylsulfonylethyl, allyl, cinnamyl, and 1-(trimethylsilylmethyl)prop-1-en-3-yl. Another example of carboxy-protecting groups are heterocycloalkyl groups such as 1,3-oxazolinyl. Further examples of these groups are found in T. W. Greene and P. G. M. Wuts, "Protective Groups in Organic Synthesis", 2nd ed., John Wiley & Sons, Inc., New York, N.Y., 1991, chapter 5; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, NY, 1981, Chapter 5. The term "protected carboxy group" denotes a carboxy group substituted by a carboxy-protecting group.

The term "hydroxy-protecting group" denotes groups intended to protect a hydroxy group and include ester- and ether-forming groups, in particular tetrahydropyranyloxy, benzoyl, acetoxy, carbamoyloxy, benzyl, and silylethers (e.g. TBS, TBDPS) groups. Further examples of these groups are found in T. W. Greene and P. G. M. Wuts, "Protective Groups in Organic Synthesis", 2nd ed., John Wiley & Sons, Inc., New York, NY, 1991, chapters 2-3; E. Haslam, "Protective Groups in Organic Chemistry", J. G. W. McOmie, Ed., Plenum Press, New York, N.Y., 1973, Chapter 5, and T. W. Greene, "Protective Groups in Organic Synthesis", John Wiley and Sons, New York, NY, 1981. The term "protected hydroxy group" refers to a hydroxy group substituted by a hydroxy-protecting group.

The term "deprotection" or "deprotecting" denotes the process by which a protective group is removed after the selective reaction is completed. Deprotecting reagents include acids, bases or hydrogen, in particular potassium or sodium carbonates, lithium hydroxide in alcoholic solutions, zinc in methanol, acetic acid, trifluoroacetic acid, palladium catalysts, or boron tribromide.

The term "active pharmaceutical ingredient" (or "API") denotes the compound or molecule in a pharmaceutical composition that has a particular biological activity.

The terms "pharmaceutical composition" and "pharmaceutical formulation" (or "formulation") are used interchangeably and denote a mixture or solution comprising a therapeutically effective amount of an active pharmaceutical ingredient together with pharmaceutically acceptable excipients to be administered to a mammal, e.g., a human in need thereof.

The term "pharmaceutically acceptable" denotes an attribute of a material which is useful in preparing a pharmaceutical composition that is generally safe, non-toxic, and neither biologically nor otherwise undesirable and is acceptable for veterinary as well as human pharmaceutical use.

The terms "pharmaceutically acceptable excipient", "pharmaceutically acceptable carrier" and "therapeutically inert excipient" can be used interchangeably and denote any pharmaceutically acceptable ingredient in a pharmaceutical composition having no therapeutic activity and being non-toxic to the subject administered, such as disintegrators, binders, fillers, solvents, buffers, tonicity agents, stabilizers, antioxidants, surfactants, carriers, diluents or lubricants used in formulating pharmaceutical products.

The term "therapeutically effective amount" denotes an amount of a compound or molecule of the present invention that, when administered to a subject, (i) treats or prevents the particular disease, condition or disorder, (ii) attenuates, ameliorates or eliminates one or more symptoms of the particular disease, condition, or disorder, or (iii) prevents or delays the onset of one or more symptoms of the particular disease, condition or disorder described herein. The therapeutically effective amount will vary depending on the compound, the disease state being treated, the severity of the disease treated, the age and relative health of the subject, the route and form of administration, the judgement of the attending medical or veterinary practitioner, and other factors.

The term "treating" or "treatment" of a disease state includes inhibiting the disease state, i.e., arresting the development of the disease state or its clinical symptoms, or relieving the disease state, i.e., causing temporary or permanent regression of the disease state or its clinical symptoms.

The term "preventing" or "prevention" of a disease state denotes causing the clinical symptoms of the disease state not to develop in a subject that can be exposed to or predisposed to the disease state, but does not yet experience or display symptoms of the disease state.

The term "amino acid" as used herein denotes an organic molecule possessing an amino moiety located at a-position to a carboxylic group. Examples of amino acids include: arginine, glycine, ornithine, lysine, histidine, glutamic acid, asparagic acid, isoleucine, leucine, alanine, phenylalanine, tyrosine, tryptophane, methionine, serine, proline. The amino acid employed is optionally in each case the L-form.

In detail, the present invention relates to a compound of formula (I)

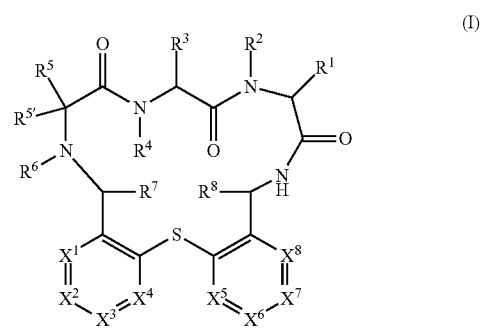

wherein:
$X^1$ is $C-L^1-R^{11}$ or N,
$X^2$ is $C-L^2-R^{12}$ or N,
$X^3$ is $C-L^3-R^{13}$ or N,
$X^4$ is $C-L^4-R^{14}$ or N, with the proviso that not more than three of $X^1$, $X^2$, $X^3$ and $X^4$ are N;
$X^5$ is $C-L^5-R^{15}$ or N,
$X^6$ is $C-L^6-R^{16}$ or N,
$X^7$ is $C-L^7 R^{17}$ or N,
$X^8$ is $C-L^8-R^{18}$ or N, with the proviso that not more than three of $X^5$, $X^6$, $X^7$ and $X^8$ are N;
$R^1$ is $—(CH_2)_m$-heteroaryl or $—(CH_2)_m$-heterocycloalkyl, wherein heteroaryl is optionally substituted with one or more halo, cyano, $C_{1-7}$-alkyl, $C_{1-7}$-haloalkyl, $C_{3-7}$-cycloalkyl or $C_{1-7}$-alkoxy;
$R^2$, $R^4$ and $R^6$ are each individually selected from hydrogen, $C_{1-7}$-alkyl, $C_{1-7}$-haloalkyl, and $C_{3-7}$-cycloalkyl;
$R^3$ is $—C_{1-7}$-alkyl, $—(CH_2)_n—NR^{20}R^{21}$, $—(CH_2)_n—C(O)NR^{20}R^{21}$ or $—(CH_2)_n—O—(CH_2)_q—NR^{20}R^{21}$;
$R^5$ is hydrogen, $C_{1-7}$-alkyl, hydroxy-$C_{1-7}$-alkyl, $—(CH_2)_o—NR^{22}R^{23}$, $—(CH_2)_o—C(O)—NR^{22}R^{23}$, $—(CH_2)_o—O—(CH_2)_q—NR^{20}R^{21}$, $—(CH_2)_o—NH—C(NH)—NR^{22}R^{23}$, $—(CH_2)_o—NH—C(O)—NR^{22}R^{23}$, $—(CH_2)_o—NH—C(O)—OR^{26}$, $—(CH_2)_o—C_{3-7}$-cycloalkyl, $—(CH_2)_o$-heterocycloalkyl, $—(CH_2)_o$-heteroaryl, $—(CH_2)_o$-aryl, wherein cycloalkyl, heterocycloalkyl, heteroaryl and aryl are optionally substituted by halo, cyano, $C_{1-7}$-alkyl, $C_{1-7}$-haloalkyl, $C_{1-7}$-alkoxy or aryl;
$R^{5'}$ is hydrogen or $C_{1-7}$-alkyl;
$R^7$ and $R^8$ are each individually selected from hydrogen, $C_{1-7}$-alkyl, $C_{1-7}$-haloalkyl, $C_{3-7}$-cycloalkyl and $C_{1-7}$-alkoxy;
$R^{11}$, $R^{12}$, $R^{13}$, $R^{14}$, $R^{15}$ and $R^{16}$ are each individually selected from hydrogen, halogen, cyano, $C_{1-7}$-alkyl, $C_{1-7}$-haloalkyl, $—NR^{24}R^{25}$, $C_{1-7}$-alkyl-$NR^{24}R^{25}$, hydroxy, $C_{1-7}$-alkoxy, halo$C_{1-7}$-alkoxy, $—B(OH)_2$, benzyloxy-propynyl ($—C≡C—CH_2—O$-benzyl), $C_{3-7}$-cycloalkyl, heterocycloalkyl, aryl and heteroaryl, wherein heteroaryl is optionally substituted with one $C_{1-7}$-haloalkyl or $C_{1-7}$-alkoxy;

$R^{17}$ is hydrogen, halogen, cyano, $C_{1-7}$-alkyl, $C_{1-7}$-haloalkyl, —$NR^{24}R^{25}$, $C_{1-7}$-alkyl-$NR^{24}R^{25}$, hydroxy, $C_{1-7}$-alkoxy, halo$C_{1-7}$-alkoxy, $B(OH)_2$, benzyloxy-prop-1-ynyl, $C_{3-7}$-cycloalkyl, heterocycloalkyl, aryl and heteroaryl, wherein heterocycloalkyl is optionally substituted with one —$NR^{24}R^{25}$, wherein aryl and heteroaryl are optionally substituted with one, two or three substituents selected from the list of halogen, cyano, $C_{1-7}$-alkyl, $C_{1-7}$-haloalkyl, $C_{1-7}$-hydroxyalkyl, hydroxy, $C_{1-7}$-alkoxy, —$NR^{24}R^{25}$, —$SO_2$—$C_{1-7}$-alkyl, —$SO_2$—$NR^{24}R^{25}$, heterocycloalkyl and heterocycloalkyl substituted with $C_{1-7}$-alkyl;

$R^{18}$ is hydrogen, halogen, cyano, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —$NR^{24}R^{25}$, $C_{1-7}$-alkyl-$NR^{24}R^{25}$, $C_{3-7}$-cycloalkyl, heterocycloalkyl, aryl and heteroaryl, wherein aryl and heteroaryl are optionally substituted with one, two or three substituents selected from the list of halogen, cyano, $C_{1-7}$-alkyl $C_{1-7}$-haloalkyl, hydroxy, $C_{1-7}$-alkoxy, —$NR^{24}R^{25}$, $C_{1-7}$-alkyl-$NR^{24}R^{25}$, —CO—NH—$(CH_2)_r$—$NR^{24}R^{25}$, —CO—NH—$(CH_2)_r$—OH, —CO—NH—$(CH_2)_r$-heterocycloalkyl, —CO—OH, —O—$C_{1-7}$-hydroxyalkyl, —O—$(CH_2)_r$—CO—OH, —$SO_2$—$C_{1-7}$-alkyl, —$SO_2$—$NR^{24}R^{25}$, heterocycloalkyl, —O-heterocycloalkyl and heterocycloalkyl substituted with $C_{1-7}$-alkyl;

$R^{21}$ and $R^{23}$ are each individually selected from hydrogen and $C_{1-7}$-alkyl;

$R^{24}$ and $R^{25}$ are each individually selected from hydrogen, $C_{1-7}$-alkyl, $C_{1-7}$-haloalkyl, $C_{1-7}$-hydroxyalkyl, and $C_{3-7}$-cycloalkyl;

$R^{26}$ is hydrogen, $C_{1-7}$-alkyl or benzyl;

$L^1$, $L^2$, $L^3$, $L^4$, $L^5$, $L^6$, $L^7$ and $L^8$ are each individually selected from a single bond, —C(O)—, —$SO_2$—, —$(CH_2)_p$—, —CH=CH— and —C≡C—;

m is 1, 2, 3, or 4;

n is 1, 2, 3, or 4;

o is 0, 1, 2, 3, or 4;

p is 1, 2, 3, or 4;

q is 1, 2, 3, or 4;

r is 1, 2, 3, or 4;

or a pharmaceutically acceptable salt thereof.

Particular embodiments of the present invention are compounds of formula (I) or a pharmaceutically acceptable salt thereof.

Further, it is to be understood that every embodiment relating to a specific $X^1$ to $X^8$, $R^1$ to $R^{23}$, m, n or o as disclosed herein may be combined with any other embodiment relating to another $X^1$ to $X^8$, $R^1$ to $R^{23}$, m, n or o as disclosed herein.

A particular embodiment of present invention relates to a compound of formula (I')

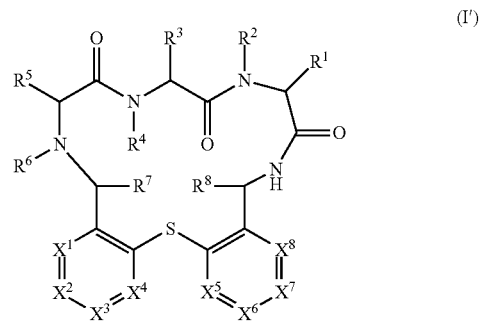

(I')

wherein:

$X^1$ is C-$L^1$-$R^{11}$ or N, $X^2$ is C-$L^2$-$R^{12}$ or N, $X^3$ is C-$L^3$-$R^{13}$ or N, $X^4$ is C-$L^4$-$R^{14}$ or N, with the proviso that not more than three of $X^1$, $X^2$, $X^3$ and $X^4$ are N;

$X^5$ is C-$L^5$-$R^{15}$ or N, $X^6$ is C-$L^6$-$R^{16}$ or N, $X^7$ is C-$L^7$ $R^{17}$ or N, $X^8$ is C-$L^8$-$R^{18}$ or N, with the proviso that not more than three of $X^5$, $X^6$, $X^7$ and $X^8$ are N;

$R^1$ is —$(CH_2)_m$-heteroaryl, wherein heteroaryl is optionally substituted with one or more halo, cyano, $C_{1-7}$-alkyl, $C_{1-7}$-haloalkyl, $C_{3-7}$-cycloalkyl or $C_{1-7}$-alkoxy;

$R^2$, $R^4$ and $R^6$ are each individually selected from hydrogen, $C_{1-7}$-alkyl, $C_{1-7}$-haloalkyl, and $C_{3-7}$-cycloalkyl;

$R^3$ is —$(CH_2)_n$—$NR^{20}R^{21}$;

$R^5$ is $C_{1-7}$-alkyl, hydroxy-$C_{1-7}$-alkyl, —$(CH_2)_o$—$NR^{22}R^{23}$, —$(CH_2)_o$—C(O)—$NR^{22}R^{23}$, —$(CH_2)_o$—NH—C(O)—$NR^{22}R^{23}$, —$(CH_2)_o$—$C_{3-7}$-cycloalkyl, —$(CH_2)_o$-heterocycloalkyl, —$(CH_2)_o$-heteroaryl, —$(CH_2)_o$-aryl, wherein cycloalkyl, heterocycloalkyl, heteroaryl and aryl are optionally substituted by halo, cyano, $C_{1-7}$-alkyl, $C_{1-7}$-haloalkyl or $C_{1-7}$-alkoxy;

$R^7$ and $R^8$ are each individually selected from hydrogen, $C_{1-7}$-alkyl, $C_{1-7}$-haloalkyl, $C_{3-7}$-cycloalkyl and $C_{1-7}$-alkoxy;

$R^{11}$, $R^{12}$, $R^{13}$, $R^{14}$, $R^{15}$, $R^{16}$, $R^{17}$ and $R^{18}$ are each individually selected from hydrogen, halogen, cyano, $C_{1-7}$-alkyl, $C_{1-7}$-haloalkyl, —$NR^{24}R^{25}$, hydroxy, $C_{1-7}$-alkoxy, halo$C_{1-7}$-alkoxy, $C_{3-7}$-cycloalkyl, heterocycloalkyl, aryl and heteroaryl;

$R^{20}$ and $R^{22}$ are each individually selected from hydrogen, $C_{1-7}$-alkyl, $C_{1-7}$-haloalkyl, $C_{3-7}$-cycloalkyl and —C(=NH)—$NH_2$;

$R^{21}$ and $R^{23}$ are each individually selected from hydrogen and $C_{1-7}$-alkyl;

$R^{24}$ and $R^{25}$ are each individually selected from hydrogen, $C_{1-7}$-alkyl, $C_{1-7}$-haloalkyl, and $C_{3-7}$-cycloalkyl;

$L^1$, $L^2$, $L^3$, $L^4$, $L^5$, $L^6$, $L^7$ and $L^8$ are each individually selected from a single bond, —C(O)—, —$SO_2$—, —$(CH_2)_p$—, —CH=CH— and —C≡C—;

m, n, o and p are each individually selected from 1, 2, 3 and 4;

or a pharmaceutically acceptable salt thereof.

A particular embodiment of the present invention relates to a compound of formula (I) or (I') wherein:

$X^1$ is $CR^{11}$ or N, $X^2$ is $CR^{12}$ or N, $X^3$ is $CR^{13}$ or N, $X^4$ is $CR^{14}$ or N, with the proviso that not more than two of $X^1$, $X^2$, $X^3$ and $X^4$ are N;

$X^5$ is $CR^{15}$ or N,
$X^6$ is $CR^{16}$ or N,
$X^7$ is $CR^{17}$ or N,
$X^8$ is $CR^{18}$ or N, with the proviso that not more than two of $X^5$, $X^6$, $X^7$ and $X^8$ are N;
$R^1$ is —$(CH_2)_m$-heteroaryl or —$(CH_2)_m$-heterocycloalkyl; wherein heteroaryl is optionally substituted with one or more halo, cyano, $C_{1-7}$-alkyl, $C_{1-7}$-haloalkyl, $C_{3-7}$-cycloalkyl or $C_{1-7}$-alkoxy; and wherein heterocycloalkyl is partly unsaturated;
$R^2$, $R^4$ and $R^6$ are each individually selected from hydrogen, $C_{1-7}$-alkyl, $C_{1-7}$-haloalkyl, and $C_{3-7}$-cycloalkyl;
$R^3$ is —$C_{1-7}$-alkyl, —$(CH_2)_n$—$NR^{20}R^{21}$, —$(CH_2)_n$—C(O)$NR^{20}R^{21}$ or —$(CH_2)_n$—O—$(CH_2)_q$—$NR^{20}R^{21}$;
$R^5$ is hydrogen, $C_{1-7}$-alkyl, hydroxy-$C_{1-7}$-alkyl, —$(CH_2)_o$—$NR^{22}R^{23}$, —$(CH_2)_o$—C(O)—$NR^{22}R^{23}$, —$(CH_2)_o$—O—$(CH_2)_q$—$NR^{20}R^{21}$, —$(CH_2)_o$—NH—C(NH)—$NR^{22}R^{23}$, —$(CH_2)_o$—NH—C(O)—$NR^{22}R^{23}$, —$(CH_2)_o$—NH—C(O)—$OR^{26}$, —$(CH_2)_o$-heterocycloalkyl, —$(CH_2)_o$-heteroaryl, —$(CH_2)_o$-aryl,
 wherein cycloalkyl, heterocycloalkyl, heteroaryl and aryl are optionally substituted by halo, cyano, $C_{1-7}$-alkyl, $C_{1-7}$-haloalkyl, $C_{1-7}$-alkoxy or aryl;
$R^7$ and $R^8$ are each individually selected from hydrogen, $C_{1-7}$-alkyl, $C_{1-7}$-haloalkyl, $C_{3-7}$-cycloalkyl and $C_{1-7}$-alkoxy;
$R^{11}$, $R^{12}$, $R^{13}$, $R^{14}$, $R^{15}$ and $R^{16}$ are each individually selected from hydrogen, halogen, cyano, $C_{1-7}$-alkyl, $C_{1-7}$-haloalkyl, —$NR^{24}R^{25}$, $C_{1-7}$-alkyl-$NR^{24}R^{25}$, hydroxy, $C_{1-7}$-alkoxy, halo$C_{1-7}$-alkoxy, —$B(OH)_2$, benzyloxy-propynyl, $C_{3-7}$-cycloalkyl, heterocycloalkyl, aryl and heteroaryl,
 wherein heteroaryl is optionally substituted with one $C_{1-7}$-haloalkyl or $C_{1-7}$-alkoxy;
$R^{17}$ is hydrogen, halogen, cyano, $C_{1-7}$-alkyl, $C_{1-7}$-haloalkyl, —$NR^{24}R^{25}$, $C_{1-7}$-alkyl-$NR^{24}R^{25}$, hydroxy, $C_{1-7}$-alkoxy, halo$C_{1-7}$-alkoxy, —$B(OH)_2$, benzyloxy-propynyl, $C_{3-7}$-cycloalkyl, heterocycloalkyl, aryl and heteroaryl,
 wherein heterocycloalkyl is optionally substituted with one —$NR^{24}R^{25}$,
 wherein aryl and heteroaryl are optionally substituted with one, two or three substituents selected from the list of halogen, cyano, $C_{1-7}$-alkyl, $C_{1-7}$-haloalkyl, $C_{1-7}$-hydroxyalkyl, hydroxy, $C_{1-7}$-alkoxy, —$NR^{24}R^{25}$, —$SO_2$—$C_{1-7}$-alkyl, —$SO_2$—$NR^{24}R^{25}$, heterocycloalkyl and heterocycloalkyl substituted with $C_{1-7}$-alkyl;
$R^{18}$ is hydrogen, halogen, cyano, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, —$NR^{24}R^{25}$, $C_{1-7}$-alkyl-$NR^{24}R^{25}$, $C_{3-7}$-cycloalkyl, heterocycloalkyl, aryl and heteroaryl,
 wherein aryl and heteroaryl are optionally substituted with one, two or three substituents selected from the list of halogen, cyano, $C_{1-7}$-alkyl $C_{1-7}$-haloalkyl, hydroxy, $C_{1-7}$-alkoxy, —$NR^{24}R^{25}$, $C_{1-7}$-alkyl-$NR^{24}R^{25}$, —CO—NH—$(CH_2)_r$—$NR^{24}R^{25}$, —CO—NH—$(CH_2)_r$—OH, —CO—NH—$(CH_2)_r$-heterocycloalkyl, —CO—OH, —O—$C_{1-7}$-hydroxyalkyl, —O—$(CH_2)_r$—CO—OH, —$SO_2$—$C_{1-7}$-alkyl, —$SO_2$—$NR^{24}R^{25}$, heterocycloalkyl, —O-heterocycloalkyl and heterocycloalkyl substituted with $C_{1-7}$-alkyl;
$R^{20}$ and $R^{22}$ are each individually selected from hydrogen, $C_{1-7}$-alkyl, $C_{1-7}$-haloalkyl, $C_{3-7}$-cycloalkyl and —C(=NH)—$NH_2$;

$R^{21}$ and $R^{23}$ are each individually selected from hydrogen and $C_{1-7}$-alkyl;
$R^{24}$ and $R^{25}$ are each individually selected from hydrogen, $C_{1-7}$-alkyl, $C_{1-7}$-haloalkyl, $C_{1-7}$-hydroxyalkyl, and $C_{3-7}$-cycloalkyl;
$R^{26}$ is hydrogen, $C_{1-7}$-alkyl or benzyl;
m, n, o, p, q and r are each individually selected from 1, 2, 3 and 4;
or a pharmaceutically acceptable salt thereof.
A particular embodiment of the present invention relates to a compound of formula (Ia)

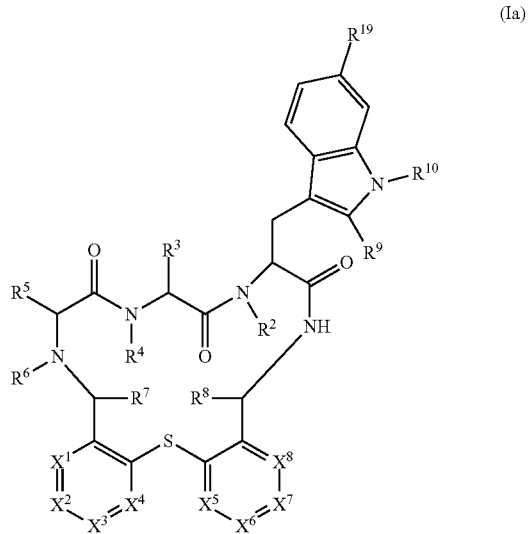

(Ia)

wherein
$X^1$ to $X^8$, and $R^2$ to $R^8$ are as defined herein;
$R^9$ is hydrogen, halo, cyano, $C_{1-7}$-alkyl, $C_{1-7}$-haloalkyl, $C_{1-7}$-alkoxy, $C_{1-7}$-haloalkoxy and $C_{3-7}$-cycloalkyl;
$R^{10}$ is hydrogen, $C_{1-7}$-alkyl, $C_{1-7}$-haloalkyl, or $C_{3-7}$-cycloalkyl;
$R^{19}$ is hydrogen, halo, cyano, $C_{1-7}$-alkyl, $C_{1-7}$-haloalkyl, $C_{1-7}$-alkoxy, $C_{1-7}$-haloalkoxy and $C_{3-7}$-cycloalkyl;
or a pharmaceutically acceptable salt thereof.
A particular embodiment of the present invention relates to a compound of formula (Ib)

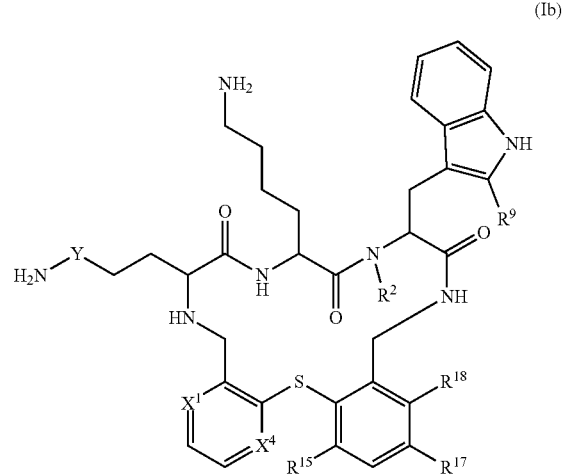

(Ib)

wherein $X^1$, $X^4$, $R^2$, $R^{15}$, $R^{17}$, $R^{18}$ and $R^9$ are as defined herein and Y is —$CH_2$— or —CO—; or a pharmaceutically acceptable salt thereof.

A particular embodiment of the present invention relates to a compound of formula (Ic)

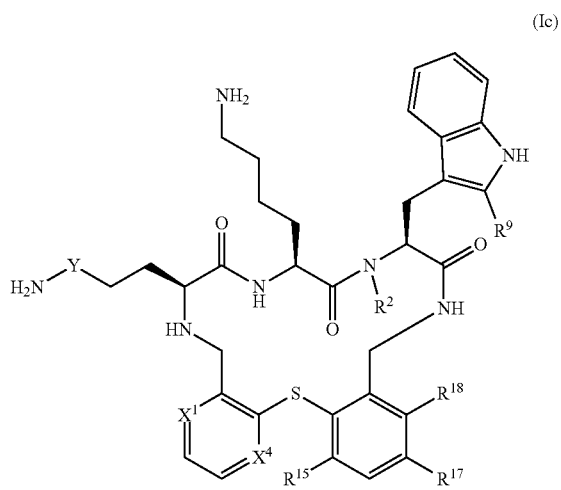

(Ic)

wherein $X^1$, $X^4$, $R^2$, $R^{15}$, $R^{17}$, $R^{18}$ and $R^9$ are as defined herein and Y is —$CH_2$— or —CO—; or a pharmaceutically acceptable salt thereof.

In a particular embodiment of the present invention $X^1$ is N or $CR^{11}$; particularly N, CH or C-halo; more particularly N, CH or CF; most particularly CH.

In a particular embodiment of the present invention $X^2$ is N or $CR^{12}$; particularly N, CH, C-halo, C—$CH_2$—$NH_2$, C-aryl or C-heteroaryl; particularly N, CH, CF, CBr, C—$CH_2$—$NH_2$, C-phenyl or C-pyridinyl; more particularly CH or CF; most particularly CH.

In a particular embodiment of the present invention $X^3$ is N or $CR^{13}$; particularly N, CH, C-halo or C-aryl; more particularly N, CH, CBr, C-phenyl; most particularly CH.

In a particular embodiment of the present invention $X^4$ is N or $CR^{14}$, particularly N or CH, most particularly CH.

In a particular embodiment of the present invention $X^5$ is N or $CR^{15}$; particularly N, CH, C-halo, C—$C_{1-7}$-alkyl, C—$C_{1-7}$-haloalkyl, C-heterocycloalkyl, C-aryl, C-heteroaryl, C-heteroaryl substituted with one $C_{1-7}$-haloalkyl or C-heteroaryl substituted with one $C_{1-7}$-alkoxy; more particularly N, CH, CF, CCl, $CCH_3$, $CF_3$, C-morpholinyl, C-phenyl, C-pyridinyl, C-pyridinyl substituted with $CF_3$ or C-pyridinyl substituted with methoxy; even more particularly CH, CCl, $CCH_3$ or $CCF_3$; most particularly CH or CCl.

In a particular embodiment of the present invention $X^6$ is N or $CR^{16}$; particularly CH, C-halo, C—$C_{1-7}$-alkyl, C—$C_{1-7}$-haloalkyl, C-aryl or C-heterocycloalkyl; more particularly N, CH, CF, CCl, $CCH_3$, $CCF_3$, C-phenyl or C-morpholinyl; most particularly CH.

In a particular embodiment of the present invention $X^6$ is N.

In a particular embodiment of the present invention $X^7$ is N or $CR^{17}$.

In a particular embodiment of the present invention $X^7$ is N, CH, C-halo, C-cyano, C—$C_{1-7}$-alkyl, C—$C_{1-2}$-haloalkyl, C—$NH_2$, C—$C_{1-7}$-alkoxy, C—$B(OH)_2$, C—C≡C—$CH_2$—O—$CH_2$-aryl, C-aryl, C-heteroaryl, or C-heterocycloalkyl; wherein aryl is optionally substituted with one substituent selected from halo, cyano, $SO_2$—$C_{1-7}$-alkyl and $SO_2$—$NH_2$; wherein heteroaryl is optionally substituted with one or two substituents selected from halo, cyano, $C_{1-7}$-alkyl, $NH_2$, hydroxy, $C_{1-7}$-alkoxy, $SO_2$—$C_{1-7}$-alkyl, heterocycloalkyl and $C_{1-7}$-alkyl-heterocycloalkyl; and wherein heterocycloalkyl is optionally substituted with one $NH_2$.

In a particular embodiment of the present invention $X^7$ is N, CH, CF, Cl, CBr, C-cyano, C-methyl, C-ethyl, C-isopropyl, C-tert-butyl, $CCF_3$, $CNH_2$, C-methoxy, C—$B(OH)_2$, C—C≡C—$CH_2$—O—$CH_2$-phenyl, C-phenyl, C-heteroaryl, or C-heterocycloalkyl;
  wherein phenyl is optionally substituted with one substituent selected from halo, cyano, $SO_2$—$C_{1-7}$-alkyl and $SO_2$—$NH_2$;
  wherein heteroaryl is selected from the list of imidazolyl, pyrazolyl, pyrrolyl, isoxazolyl, pyridinyl, pyrazinyl, pyridazinyl and pyrimidinyl and wherein heteroaryl is optionally substituted with one or two substituents selected from halo, cyano, $C_{1-7}$-alkyl, $NH_2$, hydroxy, $C_{1-7}$-alkoxy, $SO_2$—$C_{1-7}$-alkyl, heterocycloalkyl and $C_{1-7}$-alkyl-heterocycloalkyl; and
  wherein heterocycloalkyl is pyrrolidinyl optionally substituted with one $NH_2$, morpholinyl 2-oxa-5-aza-bicyclo[2.2.1]heptyl, and 3,6-dihydro-2H-pyranyl.

In a particular embodiment of the present invention $X^7$ is CH, C-halo, C—$C_{1-7}$-haloalkyl, or C—$C_{1-7}$-alkoxy.

In a particular embodiment of the present invention $X^7$ is CH, CCl, $CCF_3$ or C-methoxy.

In a particular embodiment of the present invention $X^8$ is N or $CR^{18}$.

In a particular embodiment of the present invention $X^8$ is N, CH, C-halo, C—$C_{1-7}$-haloalkyl, C-di$C_{1-7}$-alkylamino, C-aryl, C-heteroaryl, or C-heterocycloalkyl; wherein aryl is optionally substituted with one substituent selected from $C_{1-7}$-alkyl-$NH_2$, —CO—NH—$(CH_2)_2$—$N(CH_3)_2$, —CO—NH—$(CH_2)_2$—OH, —CO—NH—$(CH_2)_2$-heterocycloalkyl, —CO—OH, —O—$C_{1-7}$-hydroxyalkyl, —O—$CH_2$—CO—OH, —$SO_2$—$C_{1-7}$-alkyl, —$SO_2$—$NH_2$, —$SO_2$—NH($CH_2CH_2OH$), heterocycloalkyl, and —O—heterocycloalkyl; and wherein heteroaryl is optionally substituted with one substituent selected from halo, $C_{1-7}$-alkyl, $NH_2$ and hydroxy.

In a particular embodiment of the present invention $X^8$ is N, CH, CF, CCl, CBr, $CCF_3$, $CN(CH_3)_2$, C-phenyl, C-pyridinyl, or C-morpholinyl; wherein phenyl is optionally substituted with one substituent selected from —$CH_2$—$NH_2$, —$CH_2$—$CH_2$—$NH_2$, —CO—NH—$(CH_2)_2$—$N(CH_3)_2$, —CO—NH—$(CH_2)_2$—OH, —CO—NH—$(CH_2)_2$-morpholinyl, —CO—OH, —O-(2,3-dihydroxy-propoxy), —O—$CH_2$—CO—OH, —$SO_2$—$CH_3$, —$SO_2$—$NH_2$, —$SO_2$—NH($CH_2CH_2OH$), piperidinyl, piperazinyl, and —O— piperidinyl; and wherein pyridinyl is optionally substituted with one substituent selected from fluoro, methyl, $NH_2$ and hydroxy.

In a particular embodiment of the present invention $X^8$ is CH, C-halo, C—$C_{1-7}$-haloalkyl, C-aryl or C-heteroaryl; wherein aryl is optionally substituted with one substituent selected from —CO—OH, —O—$CH_2$—CO—OH, —$SO_2$—$C_{1-7}$-alkyl, —$SO_2$—$NH_2$ and —$SO_2$—NH($CH_2CH_2OH$); and wherein heteroaryl is optionally substituted with one substituent selected from $NH_2$ and hydroxy.

In a particular embodiment of the present invention $X^8$ is CH, CCl, $CCF_3$, C-phenyl or C-pyridinyl; wherein phenyl is optionally substituted with one substituent selected from —CO—OH, —O—$CH_2$—CO—OH, —$SO_2$—$CH_3$ and —$SO_2$—$NH_2$; and wherein pyridinyl is optionally substituted with one substituent selected from $NH_2$ and hydroxy.

In a particular embodiment of the present invention $R^1$ is —$(CH_2)_m$-heteroaryl or —$(CH_2)_m$-heterocycloalkyl, wherein heteroaryl is monocyclic or bicyclic, particularly bicyclic, and is optionally substituted with one or more halo, cyano, $C_{1-7}$-alkyl, $C_{1-7}$-haloalkyl, $C_{3-7}$-cycloalkyl or $C_{1-7}$-alkoxy; and wherein heterocycloalkyl is partly unsaturated.

In a particular embodiment of the present invention $R^1$ is —$(CH_2)_m$-indolyl, —$(CH_2)_m$-quinolyl, or —$(CH_2)_m$-dihydroindolyl, wherein indolyl, quinolyl and dihydroindolyl are optionally substituted with one or more halo or $C_{1-7}$-alkyl.

In a particular embodiment of the present invention $R^1$ is indolylmethyl optionally substituted with one or two substituents selected from fluoro, chloro and methyl or $R^1$ is 2,3-dihydro-indolmethyl or $R^1$ is quinolylmethyl.

In a particular embodiment of the present invention $R^1$ is 1H-indol-3-ylmethyl, 1-methyl-1H-indol-3-ylmethyl, 2-methyl-1H-indol-3-ylmethyl, 5-fluoro-1H-indol-3-ylmethyl, 5-chloro-1H-indol-3-ylmethyl, 6-chloro-1H-indol-3-ylmethyl, 6-chloro-1-methyl-1H-indol-3-ylmethyl, quinolin-2-ylmethyl or 2,3-dihydro-1H-indol-3-ylmethyl.

In a particular embodiment of the present invention $R^1$ is 1H-indol-3-ylmethyl or 2-methyl-1H-indol-3-ylmethyl.

In a particular embodiment of the present invention $R^2$ is hydrogen or $C_{1-7}$-alkyl, more particularly hydrogen, methyl or ethyl; most particularly methyl or ethyl.

In a particular embodiment of the present invention $R^3$ is butyl, amino-propyl, amino-butyl, methylamino-butyl, propionamide or amino-ethoxymethyl.

In a particular embodiment of the present invention $R^3$ is butyl, 3-amino-propyl, 4-amino-butyl, 4-methylamino-butyl, propionamide or 2-amino-ethoxymethyl.

In a particular embodiment of the present invention $R^3$ is 3-amino-propyl or 4-amino-butyl; most particularly 4-amino-butyl.

In a particular embodiment of the present invention $R^4$ is hydrogen.

In a particular embodiment of the present invention $R^5$ is hydrogen, $C_{1-7}$-alkyl, hydroxy-$C_{1-7}$-alkyl, —$(CH_2)_o$—$NR^{22}R^{23}$, —$(CH_2)_o$—C(O)—$NR^{22}R^{23}$, —$(CH_2)_o$—O—$(CH_2)_q$—$NR^{20}R^{21}$, —$(CH_2)_o$—NH—C(NH)—$NR^{22}R^{23}$, —$(CH_2)O$—NH—C(O)—$NR^{22}R^{23}$, —$(CH_2)O$—NH—C(O)—$OR^{26}$, —$(CH_2)_o$-heterocycloalkyl, —$(CH_2)_o$-heteroaryl, —$(CH_2)_o$-aryl, wherein heterocycloalkyl, heteroaryl and aryl are optionally substituted by halo, cyano, $C_{1-7}$-alkyl, $C_{1-7}$-haloalkyl, $C_{1-7}$-alkoxy or aryl.

In a particular embodiment of the present invention $R^5$ is hydrogen, methyl, isopropyl, isobutyl, hydroxy-methyl, hydroxy-ethyl, hydroxy-propyl, amino-propyl, amino-butyl, methylamino-butyl, acetamide, propionamide, N-methyl-propionamide, amino-ethoxymethyl, ureyl-methyl, guanidiyl-methyl, benzylcarboxy-amino-propyl, piperidinyl, pyridinyl-methyl, methylimidazolyl-methyl, biphenyl-methyl or naphthalenyl-methyl.

In a particular embodiment of the present invention $R^5$ is —$(CH_2)_o$—$NR^{22}R^{23}$ or —$(CH_2)_o$—C(O)—$NR^{22}R^{23}$.

In a particular embodiment of the present invention $R^5$ is 3-amino-propyl or propionamide.

In a particular embodiment of the present invention $R^{5'}$ is hydrogen or methyl, most particularly hydrogen.

In a particular embodiment of the present invention $R^6$ is hydrogen or methyl, most particularly hydrogen.

In a particular embodiment of the present invention $R^7$ is hydrogen or methyl, most particularly hydrogen.

In a particular embodiment of the present invention $R^8$ is hydrogen or $C_{1-7}$-alkyl; more particularly hydrogen or methyl; most particularly hydrogen.

In a particular embodiment of the present invention $R^9$ is hydrogen or $C_{1-7}$-alkyl; more particularly hydrogen or methyl; most particularly hydrogen.

In a particular embodiment of the present invention $R^{10}$ is hydrogen or $C_{1-7}$-alkyl; more particularly hydrogen or methyl; most particularly hydrogen.

In a particular embodiment of the present invention $R^{11}$ is hydrogen or halo; more particularly hydrogen or fluoro; most particularly hydrogen.

In a particular embodiment of the present invention $R^{12}$ is hydrogen, halo, $C_{1-7}$-alkyl-$NR^{24}R^{25}$, aryl or heteroaryl; more particularly hydrogen, fluoro, bromo, aminomethyl, phenyl or pyridinyl; most particularly hydrogen.

In a particular embodiment of the present invention $R^{13}$ is hydrogen, halo or aryl; more particularly hydrogen, bromo or phenyl; most particularly hydrogen.

In a particular embodiment of the present invention $R^{14}$ is hydrogen.

In a particular embodiment of the present invention $R^{15}$ is hydrogen, halo, $C_{1-7}$-alkyl, halo-$C_{1-7}$-alkyl, heterocycloalkyl, aryl or heteroaryl, wherein heteroaryl is optionally substituted with one $C_{1-7}$-haloalkyl or $C_{1-7}$-alkoxy.

In a particular embodiment of the present invention $R^{15}$ is hydrogen, fluoro, chloro, methyl, $CF_3$, morpholinyl, phenyl or pyridinyl, wherein pyridinyl is optionally substituted with $CF_3$ or methoxy.

In a particular embodiment of the present invention $R^{15}$ is hydrogen,

In a particular embodiment of the present invention $R^{16}$ is hydrogen, halo, $C_{1-7}$-alkyl, halo-$C_{1-7}$-alkyl, heterocycloalkyl or aryl.

In a particular embodiment of the present invention $R^{16}$ is hydrogen, fluoro, chloro, bromo, methyl, $CF_3$, morpholinyl or phenyl.

In a particular embodiment of the present invention $R^{16}$ is hydrogen,

In a particular embodiment of the present invention $R^{17}$ is hydrogen, halogen, cyano, $C_{1-7}$-alkyl, $C_{1-7}$-haloalkyl, —$NR^{24}R^{25}$, $C_{1-7}$-alkyl-$NR^{24}R^{25}$, hydroxy, $C_{1-7}$-alkoxy, —$B(OH)_2$, benzyloxy-propynyl, heterocycloalkyl, aryl or heteroaryl, wherein heterocycloalkyl is optionally substituted with one amino, wherein aryl is optionally substituted with one halo, cyano, —$SO_2$—$C_{1-7}$-alkyl, or —$SO_2$—$NR^{24}R^{25}$, and wherein heteroaryl is optionally substituted with one or two substituents selected from the list of halogen, cyano, $C_{1-7}$-alkyl, $C_{1-7}$-hydroxyalkyl, hydroxy, $C_{1-7}$-alkoxy, —$NR^{24}R^{25}$, —$SO_2$—$C_{1-7}$-alkyl, heterocycloalkyl and heterocycloalkyl substituted with $C_{1-7}$-alkyl.

In a particular embodiment of the present invention $R^{17}$ is hydrogen, fluoro, chloro, bromo, cyano, methyl, ethyl, isopropyl, tertbutyl, $CF_3$, amino, methoxy, $B(OH)_2$, benzyloxy-propynyl, pyrrolidinyl, amino-pyrrolidinyl, morpholinyl, 2-oxa-5-aza-bicyclo[2.2.1]hept-5-yl, dihydropyranyl, phenyl, chloro-phenyl, cyano-phenyl, methylsulfonyl-phenyl, aminosulfonylphenyl, imidazolyl, methyl-imidazolyl, methyl-pyrazolyl, dimethyl-pyrazolyl, pyrrolyl, dimethyl-isoxazolyl, pyridinyl, fluoro-pyridinyl, difluoro-pyridinyl, chloro-pyridinyl, cyano-pyridinyl, methyl-pyridinyl, amino-pyridinyl, dimethylamino-pyridinyl, hydroxy-pyridinyl, methoxy-pyridinyl, methylsulfonyl-pyridinyl, morpholinyl-pyridinyl, methylpiperazinyl-pyridinyl, pyrazinyl, pyridazinyl, or pyrimidinyl.

In a particular embodiment of the present invention $R^{17}$ is hydrogen, halogen, $C_{1-7}$-haloalkyl, or $C_{1-7}$-alkoxy.

In a particular embodiment of the present invention $R^{17}$ is hydrogen, chloro, $CF_3$, or methoxy.

In a particular embodiment of the present invention $R^{18}$ is hydrogen, halogen, $C_{1-7}$-haloalkyl, —NR$^{24}$R$^{25}$, heterocycloalkyl, aryl or heteroaryl,
  wherein aryl is optionally substituted with one substituent selected from the list of $C_{1-7}$-alkyl-NR$^{24}$R$^{25}$, —CO—NH—(CH$_2$)$_r$—NR$^{24}$R$^{25}$, —CO—NH—(CH$_2$)$_r$—OH, —CO—NH—(CH$_2$)$_r$-heterocycloalkyl, —CO—OH, —O—C$_{1-7}$-hydroxyalkyl, —O—(CH$_2$)$_r$—CO—OH, —SO$_2$—C$_{1-7}$-alkyl, —SO$_2$—NR$^{24}$R$^{25}$, heterocycloalkyl, and —O-heterocycloalkyl,
  and wherein heteroaryl is optionally substituted with one substituent selected from halo, $C_{1-7}$-alkyl, amino and hydroxy.

In a particular embodiment of the present invention $R^{18}$ is hydrogen, fluoro, chloro, bromo, CF$_3$, dimethyl amino, morpholinyl, phenyl or pyridinyl,
  wherein phenyl is optionally substituted with one substituent selected from the list of aminomethyl, aminoethyl, —CO—NH—(CH$_2$)$_2$—N(CH$_3$)$_2$, —CO—NH—(CH$_2$)$_2$—OH, —CO—NH—(CH$_2$)$_2$-morpholinyl, —CO—OH, 2,3-dihydroxy-propoxy, —O—CH$_2$—CO—OH, —SO$_2$-methyl, —SO$_2$—NH$_2$, —SO$_2$—NH(hydroxyethyl), piperidinyl, piperazinyl, and piperidinyloxy,
  and wherein heteroaryl is optionally substituted with one substituent selected from fluoro, methyl, amino and hydroxy.

In a particular embodiment of the present invention $R^{18}$ is hydrogen, chloro, CF$_3$, phenyl or pyridinyl,
  wherein phenyl is optionally substituted with one substituent selected from the list of —CO—OH, —O—CH$_2$—CO—OH, —SO$_2$-methyl, —SO$_2$—NH$_2$, and —SO$_2$—NH(hydroxyethyl),
  and wherein heteroaryl is optionally substituted with one substituent selected from amino and hydroxy.

In a particular embodiment of the present invention $R^{19}$ is hydrogen or halo, more particularly hydrogen or chloro; most particularly hydrogen.

In a particular embodiment of the present invention $R^{20}$ is hydrogen or methyl, particularly hydrogen.

In a particular embodiment of the present invention $R^{21}$ is hydrogen.

In a particular embodiment of the present invention $R^{22}$ is hydrogen, $C_{1-7}$-alkyl and —C(=NH)—NH$_2$; more particularly hydrogen, methyl or —C(=NH)—NH$_2$; most particularly hydrogen.

In a particular embodiment of the present invention $R^{23}$ is hydrogen.

In a particular embodiment of the present invention $R^{24}$ is hydrogen.

In a particular embodiment of the present invention $R^{25}$ is hydrogen.

In a particular embodiment of the present invention $R^{26}$ is hydrogen, methyl or benzyl.

In a particular embodiment of the present invention m is 1.

In a particular embodiment of the present invention n is 1, 3 or 4, particularly 4.

In a particular embodiment of the present invention o is 0, 1, 3 or 4, particularly 3.

In a particular embodiment of the present invention p is 1, 2, 3 or 4.

In a particular embodiment of the present invention q is 2.

In a particular embodiment of the present invention r is 1 or 2, particularly 2.

A particular embodiment of the present invention relates to a compound of formula (I), (I'), (Ia), (Ib) or (Ic), wherein:
  $X^1$ is CR$^{11}$;
  $X^2$ is CR$^{12}$;
  $X^3$ is CR$^{13}$;
  $X^4$ is N;
  $X^5$ is CR$^{15}$;
  $X^6$ is CR$^{16}$ or $X^6$ is N;
  $R^1$ is —(CH$_2$)$_m$-indolyl, wherein indolyl is optionally substituted with one or more halo or $C_{1-7}$-alkyl;
  $R^2$ is hydrogen or $C_{1-7}$-alkyl;
  $R^3$ is 3-amino-propyl or 4-amino-butyl;
  $R^4$ is hydrogen;
  $R^5$ is —(CH$_2$)O—NR$^{22}$R$^{23}$ or piperidinyl;
  $R^6$ is hydrogen;
  $R^7$ is hydrogen;
  $R^8$ is hydrogen or $C_{1-7}$-alkyl;
  $R^9$ is hydrogen or $C_{1-7}$-alkyl;
  $R^{10}$ is hydrogen or $C_{1-7}$-alkyl;
  $R^{11}$ is hydrogen or halo;
  $R^{12}$ is hydrogen or halo;
  $R^{13}$ is hydrogen;
  $R^{14}$ is hydrogen;
  $R^{15}$ is hydrogen, halo, $C_{1-7}$-alkyl or halo-$C_{1-7}$-alkyl;
  $R^{16}$ is hydrogen, halo, $C_{1-7}$-alkyl or halo-$C_{1-7}$-alkyl;
  $R^{17}$ is hydrogen, halo, $C_{1-7}$-alkyl, halo-$C_{1-7}$-alkyl, $C_{1-7}$-alkoxy or aryl;
  $R^{18}$ is hydrogen, halo or halo-$C_{1-7}$-alkyl;
  $R^{19}$ is hydrogen or halo;
  $R^{20}$ is hydrogen;
  $R^{21}$ is hydrogen;
  $R^{22}$ is hydrogen, $C_{1-7}$-alkyl and —C(=NH)—NH$_2$;
  $R^{23}$ is hydrogen;
  m is 1;
  n is 3 or 4; and
  is 1, 3 or 4;
  or a pharmaceutically acceptable salt thereof.

A particular embodiment of the present invention relates to a compound of formula (Ia),
  wherein
  $X^1$ is CH or C-halo;
  $X^2$ is CH or C-halo;
  $X^3$ is CH;
  $X^4$ is CH or N;
  $X^5$ is CH, C-halo, C—$C_{1-7}$-alkyl or C—$C_{1-7}$-haloalkyl;
  $X^6$ is N, CH, C-halo, C—$C_{1-7}$-alkyl or C—$C_{1-7}$-haloalkyl;
  $X^7$ is CH, C-halo, C—$C_{1-7}$-alkyl, C—$C_{1-7}$-haloalkyl, C—$C_{1-7}$-alkoxy or C-aryl;
  $X^8$ is CH, C-halo or C—$C_{1-7}$-haloalkyl;
  $R^1$ is indolylmethyl optionally substituted with one or two substituents selected from chloro and methyl;
  $R^2$ is hydrogen or $C_{1-7}$-alkyl;
  $R^3$ is 3-amino-propyl or 4-amino-butyl;
  $R^4$ is hydrogen;
  $R^5$ is 3-amino-propyl, 4-methylamino-butyl, guanidinylmethyl or piperidinyl;
  $R^6$ is hydrogen;
  $R^7$ is hydrogen;
  $R^8$ is hydrogen or $C_{1-7}$-alkyl;
  $R^9$ is hydrogen or $C_{1-7}$-alkyl;
  $R^{10}$ is hydrogen or $C_{1-7}$-alkyl;
  $R^{19}$ is hydrogen or halo;
  or a pharmaceutically acceptable salt thereof.

Particular compounds of formula (I), (I'), (Ia), (Ib) or (Ic) of the present invention are those selected from the group consisting of:
  (12S,15S,18S)-15-(4-Amino-butyl)-18-(3-amino-propyl)-12-(1H-indol-3-ylmethyl)-13-methyl-2-thia-10, 13,16,19-tetraaza-tricyclo[19.4.0.0*3,8*]pentacosa-1 (21),3,5,7,22,24-hexaene-11,14,17-trione;

(12S,15S,18S)-15,18-Bis-(3-amino-propyl)-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-12-(1H-indol-3-ylmethyl)-13-methyl-18-piperidin-4-yl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

N-[(11S,14S,17S)-14-(4-Amino-butyl)-17-(1H-indol-3-ylmethyl)-16-methyl-12,15,18-trioxo-2-thia-10,13,16,19-tetraaza-tricyclo[19.4.0.0*3,8*]pentacosa-1(25),3(8),4,6,21,23-hexaen-11-ylmethyl]-guanidine;

(12S,15S,18S)-15-(4-Amino-butyl)-18-(3-amino-propyl)-5-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-6-methoxy-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-4,13-dimethyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-5,13-dimethyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-6,13-dimethyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-13-methyl-4-trifluoromethyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-13-methyl-5-trifluoromethyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-13-methyl-6-trifluoromethyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(6-chloro-1-methyl-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-chloro-13-methyl-12-(1-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-chloro-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-chloro-12-(6-chloro-1-methyl-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(9S,12S,15S,18S)-15-(4-Amino-butyl)-18-(3-amino-propyl)-6-chloro-12-(1H-indol-3-ylmethyl)-9,13-dimethyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-6,7-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-7-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4,7-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-7-trifluoromethyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-6-trifluoromethyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-7-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4,6-dichloro-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(12S,15S,18S)-15-(4-Amino-butyl)-18-(3-amino-propyl)-4,7-difluoro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4-fluoro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-chloro-12-(1H-indol-3-ylmethyl)-13-methyl-4-trifluoromethyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(11S,14S,17S)-14-(4-Amino-butyl)-11-(3-amino-propyl)-23-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-22-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(12S,15S,18S)-15-(4-Amino-butyl)-18-(3-amino-propyl)-22-fluoro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione;

(11S,14S,17S)-14-(4-Amino-butyl)-11-(3-amino-propyl)-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-22,23-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-22,25-dichloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-22,25-difluoro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(12S,15S,18S)-15-(4-Amino-butyl)-18-(3-amino-propyl)-4-chloro-12-(1H-indol-3-ylmethyl)-6,13-dimethyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-6-chloro-13-ethyl-12-(1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-13-ethyl-12-(1H-indol-3-ylmethyl)-6-methoxy-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4-chloro-13-ethyl-12-(1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-13-ethyl-12-(1H-indol-3-ylmethyl)-4-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-6-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-4-chloro-12-(1H-indol-3-ylmethyl)-13-methyl-18-(4-methylamino-butyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4-chloro-12-(1H-indol-3-ylmethyl)-6-methoxy-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-12-(1H-indol-3-ylmethyl)-6-methoxy-4,13-dimethyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-17-(1H-indol-3-ylmethyl)-16,25-dimethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-23-chloro-22-fluoro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-22-fluoro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(12S,15S,18S)-15-(4-Amino-butyl)-18-(3-amino-propyl)-6-chloro-12-(1H-indol-3-ylmethyl)-4,13-dimethyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-6-chloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4,13-dimethyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4,6-dichloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(9S,12S,15S,18S)-15-(4-Amino-butyl)-18-(3-amino-propyl)-4-chloro-12-(1H-indol-3-ylmethyl)-9,13-dimethyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-17-(1H-indol-3-ylmethyl)-23-methoxy-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-trifluoromethyl-2-thia-4,10,13,16,19-pentaaza-tricyclo[19.4.0.0*3,8*]pentacosa-1(25),3,5,7,21,23-hexaene-12,15,18-trione;

(12S,15S,18S)-15-(4-Amino-butyl)-18-(3-amino-propyl)-12-(1H-indol-3-ylmethyl)-13-methyl-2-thia-5,10,13,16,19-pentaaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-23-fluoro-12-(1H-indol-3-ylmethyl)-4,13-dimethyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-6-ethyl-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-23,25-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-22-chloro-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione;

(12S,15S,18S)-15-(4-Amino-butyl)-18-(3-amino-propyl)-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-6-tert-butyl-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-6-methoxy-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-6-isopropyl-13-methyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-25-chloro-22-fluoro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23,25-dichloro-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-ethyl-17-(1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-22,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-ethyl-17-(1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23,25-dichloro-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-22,25-dichloro-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-ethyl-17-(1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23-bromo-16-ethyl-17-(1H-indol-3-ylmethyl)-25-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-25-chloro-17-(1H-indol-3-ylmethyl)-16-methyl-11-(3-methyl-3H-imidazol-4-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-25-chloro-17-(1H-indol-3-ylmethyl)-16-methyl-11-pyridin-3-ylmethyl-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-17-(1H-indol-3-ylmethyl)-16-methyl-23-phenyl-25-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-23-bromo-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-23-bromo-25-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-22-bromo-25-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-17-(1H-indol-3-ylmethyl)-16-methyl-23,25-bis-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-morpholin-4-yl-2-thia-4,10,13,16,19-pentaaza-tricyclo[19.4.0.0*3,8*]pentacosa-1(25),3,5,7,21,23-hexaene-12,15,18-trione;

(14S,17S)-14-(4-Amino-butyl)-23,25-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-23,25-dichloro-17-(1H-indol-3-ylmethyl)-11,16-dimethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-23,25-dichloro-17-(1H-indol-3-ylmethyl)-11-isopropyl-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-23,25-dichloro-11-hydroxymethyl-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-trifluoromethyl-2-thia-4,7,10,13,16,19-hexaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-25-chloro-17-(1H-indol-3-ylmethyl)-16-methyl-22-trifluoromethyl-2-thia-4,7,10,13,16,19-hexaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-25-chloro-17-(1H-indol-3-ylmethyl)-16-methyl-23-pyridin-3-yl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-pyridin-4-yl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-23,25-dichloro-17-(1H-indol-3-ylmethyl)-11-isobutyl-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-23-(2-methoxy-pyridin-4-yl)-16-methyl-2-thia-4,10,13,16,19-pentaaza-tricyclo[19.4.0.0*3,8*]pentacosa-1(25),3,5,7,21,23-hexaene-12,15,18-trione;

3-[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3,5,7,21,23-hexaen-11-yl]-propionamide;

(11S,14S,17S)-14-(4-Amino-butyl)-11-(3-amino-propyl)-22,25-dichloro-17-(1H-indol-3-ylmethyl)-16-methyl-2-thia-7,10,13,16,19-pentaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-25-chloro-17-(1H-indol-3-ylmethyl)-16-methyl-23-(2-methyl-pyridin-4-yl)-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-23,25-dichloro-11-((S)-1-hydroxy-ethyl)-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(14S,17S)-14-(4-Amino-butyl)-23,25-dichloro-17-(1H-indol-3-ylmethyl)-11,11,16-trimethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-23,25-dichloro-17-(1H-indol-3-ylmethyl)-16-methyl-11-naphthalen-2-yl-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-23-(6-amino-pyridin-3-yl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-22,25-dichloro-17-(1H-indol-3-ylmethyl)-16-methyl-2-thia-4,7,10,13,16,19-hexaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-16-methyl-22-trifluoromethyl-2-thia-7,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-trifluoromethyl-2-thia-7,10,13,16,19-pentaaza-tricyclo[19.4.0.0*3,8*]pentacosa-1(25),3,5,7,21,23-hexaene-12,15,18-trione;

(12S,15S,18S)-15-(4-Amino-butyl)-18-(3-amino-propyl)-4-chloro-12-(1H-indol-3-ylmethyl)-13-methyl-2-thia-5,10,13,16,19-pentaaza-tricyclo[19.4.0.0*3,8*]pentacosa-1(25),3,5,7,21,23-hexaene-11,14,17-trione;

(11S,14S,17S)-14-(4-Amino-butyl)-23,25-dichloro-17-(1H-indol-3-ylmethyl)-16-methyl-11-naphthalen-1-yl-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-[2-(4-methyl-piperazin-1-yl)-pyridin-4-yl]-2-thia-4,10,13,16,19-pentaaza-tricyclo[19.4.0.0*3,8*]pentacosa-1(25),3,5,7,21,23-hexaene-12,15,18-trione;

{(7S,10S,13S)-10-(4-aminobutyl)-7-(3-aminopropyl)-20-chloro-13-[(1H-indol-3-yl)methyl]-12-methyl-8,11,14-trioxo-5,6,7,8,9,10,11,12,13,14,15,16-dodecahydro-pyrido[2,3-b][1,5,8,11,14]benzothiatetraazacycloheptadecin-18-yl}boronic acid;

(12S,15S,18S)-15-(3-Amino-propyl)-18-biphenyl-4-ylmethyl-12-(1H-indol-3-ylmethyl)-19-methyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(2-amino-ethoxymethyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-11,14-Bis-(2-amino-ethoxymethyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(2-Amino-ethoxymethyl)-11-(3-amino-propyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

3-[(11S,14S,17S)-14-(4-Amino-butyl)-22,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3,5,7,21,23-hexaen-11-yl]-propionamide;

(11S,14S,17S)-14-(4-Amino-butyl)-11-(3-amino-propyl)-25-chloro-17-(1H-indol-3-ylmethyl)-16-methyl-22-trifluoromethyl-2-thia-5,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-trifluoromethyl-2-thia-5,10,13,16,19-pentaaza-tricyclo[19.4.0.0*3,8*]pentacosa-1(25),3,5,7,21,23-hexaene-12,15,18-trione;

(11R,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[19.4.0.0*3,8*]pentacosa-1(25),3,5,7,21,23-hexaene-12,15,18-trione;

(11R,14S,17S)-14-(4-Amino-butyl)-11-(3-amino-propyl)-25-chloro-17-(1H-indol-3-ylmethyl)-16-methyl-24-phenyl-2-thia-4,10,13,16,19-pentaaza-tricyclo[19.4.0.0*3,8*]pentacosa-1(25),3,5,7,21,23-hexaene-12,15,18-trione;

2-[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-acetamide;

(12S,15S,18S)-15-(4-Amino-butyl)-18-(3-amino-propyl)-12-(1H-indol-3-ylmethyl)-13-methyl-6-phenyl-4-trifluoromethyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-25-chloro-17-(1H-indol-3-ylmethyl)-16-methyl-22-phenyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-pyrrolidin-1-yl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(5-fluoro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-16-methyl-17-quinolin-2-ylmethyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(12S,15S,18S)-15,18-Bis-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

3-[(11S,14S,17S)-14-(4-Amino-butyl)-25-chloro-17-(1H-indol-3-ylmethyl)-23-(2-methoxy-pyridin-4-yl)-16-methyl-12,15,18-trioxo-2-thia-4,10,13,16,19-pentaaza-tricyclo[19.4.0.0*3,8*]pentacosa-1(25),3(8),4,6,21,23 exaen-11-yl]-propionamde;

(11S,14S,17S)-14-(4-Amino-butyl)-11-(3-amino-propyl)-25-chloro-17-(5-chloro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-17-(2,3-dihydro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

3-[(11S,14S,17S)-14-(4-Amino-butyl)-25-chloro-17-(1H-indol-3-ylmethyl)-16-methyl-23-morpholin-4-yl-12,15,18-trioxo-2-thia-4,10,13,16,19-pentaaza-tricyclo[19.4.0.0*3,8*]pentacosa-1(25),3(8),4,6,21,23-hexaen-11-yl]-propionamide;

(11S,14S,17S)-14-(4-Amino-butyl)-11-(3-amino-propyl)-25-chloro-23-(3,6-dihydro-2H-pyran-4-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

{3-[(11S,14S,17S)-14-(4-Amino-butyl)-22,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-propyarbamic acid benzyl ester;

(12S,15S,18S)-15-(4-Amino-butyl)-18-(3-amino-propyl)-4-chloro-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-6-(2-chloro-phenyl)-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-6-pyridin-3-yl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-6- pyridin-4-yl-2-thia-10,13,16,19-tetraaza-tricyclo [19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-6-(1-methyl-1H-pyrazol-3-yl)-2-thia-10,13,16,19-tetraaza-tricyclo[19.4.0.0*3,8*]pentacosa-1(25),3,5,7,21, 23-hexaene-11,14,17-trione;

3-[(11S,14S,17S)-14-(4-Amino-butyl)-25-chloro-17-(1H-indol-3-ylmethyl)-16-methyl-23-(2-methyl-pyridin-4-yl)-12,15,18-trioxo-2-thia-4,10,13,16,19-pentaaza-tricyclo[19.4.0.0*3,8*]pentacosa-1(25),3(8),4,6, 21,23-hexaen-11-yl]-propionamide;

(11S,14S,17S)-14-(4-Amino-butyl)-11-(3-amino-propyl)-25-chloro-17-(1H-indol-3-ylmethyl)-16-methyl-23-pyrazin-2-yl-2-thia-4,10,13,16,19-pentaaza-tricyclo [19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-22-morpholin-4-yl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-pyridazin-4-yl-2-thia-4,10,13,16,19-pentaaza-tricyclo[19.4.0.0*3,8*]pentacosa-1(25),3(8),4,6,21,23-hexaene-12,15,18-trione;

11-(3-amino-propyl)-25-chloro-17-(1H-indol-3-ylmethyl)-16-methyl-23-phenyl-2-thia-4,10,13,16,19-pentaaza-tricyclo[19.4.0.0*3,8*]pentacosa-1(25),3(8),4,6, 21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-pyridin-2-yl-2-thia-4,10,13,16,19-pentaaza-tricyclo [19.4.0.0*3,8*]pentacosa-1(25),3(8),4,6,21,23-hexaene-12,15-18-trione;

(12S,15S,18S)-15-(4-Amino-butyl)-18-(3-amino-propyl)-6-bromo-4-chloro-12-(1H-indol-3-ylmethyl)-13-methyl-2-thia-10,13,16,19-tetraaza-tricyclo [19.4.0.0*3,8*]pentacosa-1(25),3,5,7,21,23-hexaene-11,14,17-trione;

(8S,11S,14S)-8-((1H-Indol-3-yl)methyl)-11-(4-aminobutyl)-14-(3-aminopropyl)-1,4-dichloro-9-methyl-5, 6,8,9,11,12,15,16-octahydrobenzo[b]pyrido[4,3-p][1, 5,8,11,14]thiatetraazacycloheptadecine-7,10,13(14H)-trione;

(8S,11S,14S)-8-((1H-Indol-3-yl)methyl)-11-(4-aminobutyl)-14-(3-aminopropyl)-3-chloro-9-methyl-5,6,8, 9,11,12,15,16-octahydrobenzo[b]pyrido[4,3-p][1,5,8, 11,14]thiatetraazacycloheptadecine-7,10,13(14H)-trione;

(12S,15S,18S)-15-(4-Amino-butyl)-18-(3-amino-propyl)-4-chloro-12-(1H-indol-3-ylmethyl)-13-methyl-6-(1-methyl-1H-imidazol-4-yl)-2-thia-10,13,16,19-tetraaza-tricyclo[19.4.0.0*3,8*]pentacosa-1(25),3,5,7,21, 23-hexaene-11,14,17-trione;

3-[(11S,14S,17S)-14-(4-Amino-butyl)-17-(1H-indol-3-ylmethyl)-16-methyl-12,15,18-tri oxo-23-phenyl-25-trifluoromethyl-2-thia-10,13,16,19-tetraaza-tricyclo [19.4.0.0*3,8*]pentacosa-1(25),3,5,7,21,23-hexaen-11-yl]-propionamide;

(7S,10S,13S)-13-((1H-Indol-3-yl)methyl)-10-(4-aminobutyl)-7-(3-aminopropyl)-20-chloro-12-methyl-18-(trifluoromethyl)-6,7,9,10,12,13,15,16-octahydrobenzo[b]pyrido[3,4-p][1,5,8,11,14] thiatetraazacycloheptadecine-8,11,14(5H)-trione;

(7S,10S,13S)-13-((1H-Indol-3-yl)methyl)-10-(4-aminobutyl)-7-(3-aminopropyl)-20-chloro-12-methyl-6,7, 9,10,12,13,15,16-octahydrodipyrido[2,3-b:3',4'-p][1,5, 8,11,14]thiatetraazacycloheptadecine-8,11,14(5H)-trione;

(8S,11S,14S)-8-((1H-Indol-3-yl)methyl)-11-(4-aminobutyl)-14-(3-aminopropyl)-1-chloro-9-methyl-5,6,8, 9,11,12,15,16-octahydrobenzo[b]pyrido[3,4-p][1,5,8, 11,14]thiatetraazacycloheptadecine-7,10,13 (14H)-trione;

(7S,10S,13S)-13-((1H-Indol-3-yl)methyl)-10-(4-aminobutyl)-7-(3-aminopropyl)-18-chloro-12-methyl-6,7, 9,10,12,13,15,16-octahydrodipyrido[2,3-b:4',3'-p][1,5, 8,11,14]thiatetraazacycloheptadecine-8,11,14(5H)-trione;

3-[(11S,14S,17S)-14-(3-Amino-propyl)-23,25-dichloro-17-(1H-indol-3-ylmethyl)-16-methyl-12,15,18-trioxo-2-thia-4,10,13,16,19-pentaaza-tricyclo[19.4.0.0*3,8*] pentacosa-1(25),3(8),4,6,21,23-hexaen-11-yl]-propionamide;

3-[(11S,14S,17S)-11-(3-Amino-propyl)-17-(1H-indol-3-ylmethyl)-16-methyl-12,15,18-tri oxo-23-phenyl-25-trifluoromethyl-2-thia-10,13,16,19-tetraaza-tricyclo [19.4.0.0*3,8*]pentacosa-1(25),3,5,7,21,23-hexaen-14-yl]-propionamide;

(11S,14S,17S)-14-(4-Amino-butyl)-11-(3-amino-propyl)-25-chloro-17-(1H-indol-3-ylmethyl)-16-methyl-23-(2-morpholin-4-yl-pyridin-4-yl)-2-thia-4,10,13,16, 19-pentaaza-tricyclo[19.4.0.0*3,8*]pentacosa-1(25),3 (8),4,6,21,23-hexaene-12,15,18-trione;

3-[(11S,14S,17S)-14-(4-Amino-butyl)-25-chloro-17-(1H-indol-3-ylmethyl)-16-methyl-12,15,18-trioxo-23-pyridin-2-yl-2-thia-4,10,13,16,19-pentaaza-tricyclo [19.4.0.0*3,8*]pentacosa-1(25),3(8),4,6,21,23-hexaen-11-yl]-propionamide;

(11S,14S,17S)-14-(4-Amino-butyl)-11-(3-amino-propyl)-25-chloro-23-(2-chloro-pyridin-4-yl)-17-(1H-indol-3-ylmethyl)-16-methyl-2-thia-4,10,13,16,19-pentaaza-tricyclo[19.4.0.0*3,8*]pentacosa-1(21),3,5,7,22, 24-hexaene-12,15,18-trione;

(11S,14S,17S)-14-(4-Amino-butyl)-11-(3-amino-propyl)-25-chloro-23-(6-hydroxy-pyridin-3-yl)-17-(1H-indol-3-ylmethyl)-16-methyl-2-thia-4,10,13,16,19-pentaaza-tricyclo[19.4.0.0*3,8*]pentacosa-1(25),3(8), 4,6,21,23-hexaene-12,15,18-trione;

(11S,14S,17S)-14-(4-Amino-butyl)-11-(3-amino-propyl)-25-chloro-23-(6-dimethylamino-pyridin-3-yl)-17-(1H-indol-3-ylmethyl)-16-methyl-2-thia-4,10,13,16, 19-pentaaza-tricyclo[19.4.0.0*3,8*]pentacosa-1(25),3 (8),4,6,21,23-hexaene-12,15,18-trione;

(7S,10S,13S)-13-((1H-Indol-3-yl)methyl)-10-(4-aminobutyl)-7-(3-aminopropyl)-12-methyl-18-(2-methylpyridin-4-yl)-6,7,9,10,12,13,15,16-octahydrodipyrido[2,3-b:4',3'-p][1,5,8,11,14] thiatetraazacycloheptadecine-8,11,14(5H)-trione;

(12S,15S,18S)-15-(4-Amino-butyl)-18-(3-amino-propyl)-5-bromo-4-chloro-12-(1H-indol-3-ylmethyl)-13-methyl-2-thia-10,13,16,19-tetraaza-tricyclo [19.4.0.0*3,8*]pentacosa-1(25),3,5,7,21,23-hexaene-11,14,17-trione;

3-[(11S,14S,17S)-14-(4-Amino-butyl)-25-chloro-23-(3, 5-dimethyl-isoxazol-4-yl)-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6, 21,23-hexaen-11-yl]-propionamide;

(11S,14S,17S)-14-(4-Amino-butyl)-11-(3-amino-propyl)-25-chloro-16-methyl-17-(2-methyl-1H-indol-3- ylmethyl)-23-(2-methyl-pyridin-4-yl)-2-thia-4,10,13, 16,19-pentaaza-tricyclo[19.4.0.0*3,8*]pentacosa-1 (25),3(8),4,6,21,23-hexaene-12,15,18-trione;

(11S,14S,17S)-14-(4-Amino-butyl)-11-(3-amino-propyl)-25-chloro-23-(2-methoxy-pyridin-4-yl)-16-methyl-17-(2-methyl-1H-indol-3-ylmethyl)-2-thia-4, 10,13,16,19-pentaaza-tricyclo[19.4.0.0*3,8*] pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-23-(4-methanesulfonyl-phenyl)-16-methyl-2-thia-4,10,13,16,19-pentaaza-tricyclo[19.4.0.0*3,8*]pentacosa-1(25),3(8), 4,6,21,23-hexaene-12,15,18-trione;

(11S,14S,17S)-14-(4-Amino-butyl)-11-(3-amino-propyl)-25-chloro-17-(1H-indol-3-ylmethyl)-23-(5-methanesulfonyl-pyridin-3-yl)-16-methyl-2-thia-4,10,13, 16,19-pentaaza-tricyclo[19.4.0.0*3,8*]pentacosa-1 (25),3(8),4,6,21,23-hexaene-12,15,18-trione;

(11S,14S,17S)-14-(4-Amino-butyl)-11-(3-amino-propyl)-23-(3-amino-pyrrolidin-1-yl)-25-chloro-17-(1H-indol-3-ylmethyl)-16-methyl-2-thia-4,10,13,16,19-pentaaza-tricyclo[19.4.0.0*3,8*]pentacosa-1(25),3(8), 4,6,21,23-hexaene-12,15,18-trione;

(11S,14S,17S)-14-(4-Amino-butyl)-11-(3-amino-propyl)-25-chloro-23-(3,5-dimethyl-1H-pyrazol-4-yl)-17-(1H-indol-3-ylmethyl)-16-methyl-2-thia-4,10,13,16, 19-pentaaza-tricyclo[19.4.0.0*3,8*]pentacosa-1(25),3 (8),4,6,21,23-hexaene-12,15,18-trione;

(12S,15S,18S)-15-(4-Amino-butyl)-18-(3-amino-propyl)-4-chloro-12-(1H-indol-3-ylmethyl)-13-methyl-5-phenyl-2-thia-10,13,16,19-tetraaza-tricyclo [19.4.0.0*3,8*]pentacosa-1(25),3,5,7,21,23-hexaene-11,14,17-trione;

(11S,14S,17S)-14-(4-Amino-butyl)-11-(3-amino-propyl)-25-chloro-23-(2-fluoro-pyridin-4-yl)-17-(1H-indol-3-ylmethyl)-16-methyl-2-thia-4,10,13,16,19-pentaaza-tricyclo[19.4.0.0*3,8*]pentacosa-1(25),3(8),4,6, 21,23-hexaene-12,15,18-trione;

(7S,10S,13S)-13-((1H-Indol-3-yl)methyl)-10-(4-aminobutyl)-7-(3-aminopropyl)-12-methyl-18-(6-methylpyridin-3-yl)-6,7,9,10,12,13,15,16-octahydrodipyrido[2,3-b:4',3'-p][1,5,8,11,14] thiatetraazacycloheptadecine-8,11,14(5H)-trione;

(8S,11S,14S)-8-((1H-Indol-3-yl)methyl)-11-(4-aminobutyl)-14-(3-aminopropyl)-3-chloro-9-methyl-5,6,8, 9,11,12,15,16-octahydrobenzo[b]pyrido[3,2-p][1,5,8, 11,14]thiatetraazacycloheptadecine-7,10,13(14H)-trione;

[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*] pentacosa-1(25),3(8),4,6,21,23-hexaen-11-ylmethyl]-urea;

(11S,14S,17S)-14-(4-Amino-butyl)-11-(3-amino-propyl)-25-chloro-16-methyl-17-(2-methyl-1H-indol-3-ylmethyl)-23-pyridin-4-yl-2-thia-4,10,13,16,19-pentaaza-tricyclo[19.4.0.0*3,8*]pentacosa-1(25),3(8),4,6, 21,23-hexaene-12,15,18-trione;

(11S,14S,17S)-14-(4-Amino-butyl)-11-(3-amino-propyl)-25-chloro-23-(2-chloro-pyridin-4-yl)-16-methyl-17-(2-methyl-1H-indol-3-ylmethyl)-2-thia-4,10,13,16, 19-pentaaza-tricyclo[19.4.0.0*3,8*]pentacosa-1(25),3 (8),4,6,21,23-hexaene-12,15,18-trione;

(11S,14S,17S)-14-(4-Amino-butyl)-11-(3-amino-propyl)-25-chloro-23-(2-fluoro-pyridin-4-yl)-16-methyl-17-(2-methyl-1H-indol-3-ylmethyl)-2-thia-4,10,13,16, 19-pentaaza-tricyclo[19.4.0.0*3,8*]pentacosa-1(25),3 (8),4,6,21,23-hexaene-12,15,18-trione;

3-[(11S,14S,17S)-14-(4-Amino-butyl)-25-chloro-17-(1H-indol-3-ylmethyl)-16-methyl-12,15,18-trioxo-23-phenyl-2-thia-4,10,13,16,19-pentaaza-tricyclo [19.4.0.0*3,8*]pentacosa-1(25),3(8),4,6,21,23-hexaen-11-yl]-propionamide;

(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo [19.4.0.0*3,8*]pentacosa-1(25),3(8),4,6,21,23-hexaene-23-carbonitrile;

(11S,14S,17S)-14-(4-Amino-butyl)-11-(3-amino-propyl)-25-chloro-23-(3,5-dimethyl-isoxazol-4-yl)-17-(1H-indol-3-ylmethyl)-16-methyl-2-thia-4,10,13,16, 19-pentaaza-tricyclo[19.4.0.0*3,8*]pentacosa-1(25),3 (8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-(2-oxa-5-aza-bicyclo[2.2.1]hept-5-yl)-2-thia-4,10, 13,16,19-pentaaza-tricyclo[19.4.0.0*3,8*]pentacosa-1 (25),3(8),4,6,21,23-hexaene-12,15,18-trione;

(11S,14S,17S)-14-(4-Amino-butyl)-11-(3-amino-propyl)-23-(3-benzyl oxy-prop-1-ynyl)-25-chloro-17-(1H-indol-3-ylmethyl)-16-methyl-2-thia-4,10,13,16, 19-pentaaza-tricyclo[19.4.0.0*3,8*]pentacosa-1(25),3 (8),4,6,21,23-hexaene-12,15,18-trione;

(8S,11S,14S)-8-((1H-Indol-3-yl)methyl)-11-(4-aminobutyl)-14-(3-aminopropyl)-4-chloro-9-methyl-1-phenyl-5,6,8,9,11,12,15,16-octahydrobenzo[b]pyrido [4,3-p][1,5,8,11,14]thiatetraazacycloheptadecine-7,10, 13(14H)-trione;

(11S,14S,17S)-14-(4-Amino-butyl)-11-(3-amino-propyl)-25-chloro-17-(1H-indol-3-ylmethyl)-16-methyl-22-pyridin-4-yl-2-thia-4,10,13,16,19-pentaaza-tricyclo [19.4.0.0*3,8*]pentacosa-1(21),3,5,7,22,24-hexaene-12,15,18-trione;

(11S,14S,17S)-14-(4-Amino-butyl)-11-(3-amino-propyl)-25-chloro-17-(1H-indol-3-ylmethyl)-16-methyl-22-pyridin-3-yl-2-thia-4,10,13,16,19-pentaaza-tricyclo [19.4.0.0*3,8*]pentacosa-1(25),3(8),4,6,21,23-hexaene-12,15,18-trione;

(8S,11S,14S)-8-((1H-Indol-3-yl)methyl)-11-(4-aminobutyl)-14-(3-aminopropyl)-9-methyl-2-morpholino-5,6,8,9,11,12,15,16-octahydrobenzo[b]pyrido[3,2-p] [1,5,8,11,14]thiatetraazacycloheptadecine-7,10,13 (14H)-trione;

(8S,11S,14S)-8-((1H-Indol-3-yl)methyl)-11-(4-aminobutyl)-14-(3-aminopropyl)-9-methyl-4-morpholino-5,6,8,9,11,12,15,16-octahydrobenzo[b]pyrido[3,4-p] [1,5,8,11,14]thiatetraazacycloheptadecine-7,10,13 (14H)-trione;

(8S,11S,14S)-8-((1H-Indol-3-yl)methyl)-11-(4-aminobutyl)-14-(3-aminopropyl)-4-chloro-9-methyl-1-(pyridin-3-yl)-5,6,8,9,11,12,15,16-octahydrobenzo[b] pyrido[4,3-p][1,5,8,11,14] thiatetraazacycloheptadecine-7,10,13(14H)-trione;

(8S,11S,14S)-8-((1H-Indol-3-yl)methyl)-11-(4-aminobutyl)-14-(3-aminopropyl)-4-chloro-9-methyl-1-(pyridin-4-yl)-5,6,8,9,11,12,15,16-octahydrobenzo[b] pyrido[4,3-p][1,5,8,11,14] thiatetraazacycloheptadecine-7,10,13 (14H)-trione;

(8S,11S,14S)-8-((1H-Indol-3-yl)methyl)-11-(4-aminobutyl)-14-(3-aminopropyl)-4-chloro-1-(2-methoxypyridin-4-yl)-9-methyl-5,6,8,9,11,12,15,16-octahydrobenzo[b]pyrido[4,3-p][1,5,8,11,14] thiatetraazacycloheptadecine-7,10,13(14H)-trione;

(7S,10S,13S)-13-((1H-Indol-3-yl)methyl)-10-(4-aminobutyl)-7-(3-aminopropyl)-18-bromo-12-methyl-6,7,9,10,12,13,15,16-octahydrodipyrido[2,3-b:2',3'-p][1,5,8,11,14]thiatetraazacycloheptadecine-8,11,14(5H)-trione;

(8S,11S,14S)-8-((1H-Indol-3-yl)methyl)-11-(4-aminobutyl)-14-(3-aminopropyl)-4-chloro-9-methyl-1-(2-(trifluoromethyl)pyridin-4-yl)-5,6,8,9,11,12,15,16-octahydrobenzo[b]pyrido[4,3-p][1,5,8,11,14]thiatetraazacycloheptadecine-7,10,13(14H)-trione;

(11S,14S,17S)-14-(4-Amino-butyl)-11-(3-amino-propyl)-25-chloro-23-(5-methanesulfonyl-pyridin-3-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-22-pyridin-3-yl-2-thia-4,10,13,16,19-pentaaza-tricyclo[19.4.0.0*3,8*]pentacosa-1(25),3(8),4,6,21,23-hexaene-12,15,18-trione;

(8S,11S,14S)-8-((1H-Indol-3-yl)methyl)-11-(4-aminobutyl)-14-(3-aminopropyl)-4-chloro-9-methyl-1-morpholino-5,6,8,9,11,12,15,16-octahydrobenzo[b]pyrido[4,3-p][1,5,8,11,14]thiatetraazacycloheptadecine-7,10,13(14H)-trione;

(11S,14S,17S)-14-(4-Amino-butyl)-11-(3-amino-propyl)-25-chloro-16-methyl-17-(2-methyl-1H-indol-3-ylmethyl)-22-pyridin-4-yl-2-thia-4,10,13,16,19-pentaaza-tricyclo[19.4.0.0*3,8*]pentacosa-1(25),3(8),4,6,21,23-hexaene-12,15,18-trione;

(7S,10S,13S)-10-(4-aminobutyl)-7-(3-aminopropyl)-20-chloro-6,7,9,10,12,13,15,16-octahydro-12-methyl-13-[(2-methyl-1H-indol-3-yl)methyl]-18-[2-(4-methyl-1-piperazinyl)-4-pyridinyl]pyrido[2,3-b][1,5,8,11,14]benzothiatetraazacycloheptadecine-8,11,14(5H)-trione;

(7S,10S,13S)-13-((1H-Indol-3-yl)methyl)-10-(4-aminobutyl)-7-(3-aminopropyl)-12-methyl-18-morpholino-6,7,9,10,12,13,15,16-octahydrodipyrido[2,3-b:4',3'-p][1,5,8,11,14]thiatetraazacycloheptadecine-8,11,14(5H)-trione;

(7S,10S,13S)-13-((1H-Indol-3-yl)methyl)-10-(4-aminobutyl)-7-(3-aminopropyl)-18-(2-methoxypyridin-4-yl)-12-methyl-6,7,9,10,12,13,15,16-octahydrodipyrido[2,3-b:4',3'-p][1,5,8,11,14]thiatetraazacycloheptadecine-8,11,14(5H)-trione;

(12S,15S,18S)-15-(4-Amino-butyl)-18-(3-amino-propyl)-23-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-23-phenyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-23-pyridin-3-yl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-25-chloro-23-(2,6-difluoro-pyridin-4-yl)-17-(1H-indol-3-ylmethyl)-16-methyl-2-thia-4,10,13,16,19-pentaaza-tricyclo[19.4.0.0*3,8*]pentacosa-1(21),3(8),4,6,22,24-hexaene-12,15,18-trione;

3-[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-N-methyl-propionamide;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-23-yl]-benzonitrile;

(11S,14S,17S)-14-(4-Amino-butyl)-11-(3-amino-propyl)-25-chloro-17-(1H-indol-3-ylmethyl)-16-methyl-22-(2-methyl-pyridin-4-yl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-pyrimidin-4-yl-2-thia-4,10,13,16,19-pentaaza-tricyclo[19.4.0.0*3,8*]pentacosa-1(21),3,5,7,22,24-hexaene-12,15,18-trione;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-23-yl]-benzenesulfonamide;

(7S,10S,13S)-13-((1H-Indol-3-yl)methyl)-10-(4-aminobutyl)-7-(3-aminopropyl)-12-methyl-18-(2-methylpyridin-4-yl)-6,7,9,10,12,13,15,16-octahydrodipyrido[2,3-b:2',3'-p][1,5,8,11,14]thiatetraazacycloheptadecine-8,11,14(5H)-trione;

(12S,15S,18S)-15-(4-Amino-butyl)-23-(4-aminomethyl-phenyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(7S,10S,13S)-13-((1H-Indol-3-yl)methyl)-10-(4-aminobutyl)-7-(3-aminopropyl)-18-(2-methoxypyridin-4-yl)-12-methyl-6,7,9,10,12,13,15,16-octahydrodipyrido[2,3-b:2',3'-p][1,5,8,11,14]thiatetraazacycloheptadecine-8,11,14(5H)-trione;

(7S,10S,13S)-13-((1H-Indol-3-yl)methyl)-10-(4-aminobutyl)-7-(3-aminopropyl)-12-methyl-18-morpholino-6,7,9,10,12,13,15,16-octahydrodipyrido[2,3-b:2',3'-p][1,5,8,11,14]thiatetraazacycloheptadecine-8,11,14(5H)-trione;

(12S,15S,18S)-15-(4-Amino-butyl)-18-(3-amino-propyl)-24-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-4-chloro-12-(1H-indol-3-ylmethyl)-13-methyl-24-phenyl-2-thia-10,13,16,19-tetraaza-tricyclo[19.4.0.0*3,8*]pentacosa-1(25),3,5,7,21,23-hexaene-11,14,17-trione;

3-[(11S,14S,17S)-14-(4-Amino-butyl)-25-chloro-17-(1H-indol-3-ylmethyl)-16-methyl-12,15,18-trioxo-22-pyridin-3-yl-2-thia-4,10,13,16,19-pentaaza-tricyclo[19.4.0.0*3,8*]pentacosa-1(25),3(8),4,6,21,23-hexaen-11-yl]-propionamide;

(11S,14S,17S)-14-(4-Amino-butyl)-11-(3-amino-propyl)-25-chloro-22-(2-fluoro-pyridin-4-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23hexaene-12,15,18-trione;

(11S,14S,17S)-14-(4-Amino-butyl)-11-(3-amino-propyl)-23-(2-amino-pyridin-4-yl)-25-chloro-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-22-yl]-benzenesulfonamide;

(11S,14S,17S)-14-(4-Amino-butyl)-11-(3-amino-propyl)-25-chloro-17-(1H-indol-3-ylmethyl)-22-(4-methanesulfonyl-phenyl)-16-methyl-2-thia-4,10,13,16,19-pentaaza-tricyclo[19.4.0.0*3,8*]pentacosa-1(21),3,5,7,22,24-hexaene-12,15,18-trione;

(7S,10S,13S)-13-((1H-Indol-3-yl)methyl)-10-(4-aminobutyl)-7-(3-aminopropyl)-3-fluoro-12-methyl-6,7,9,10,12,13,15,16-octahydrobenzo[b]pyrido[3,2-p][1,5,8,11,14]thiatetraazacycloheptadecine-8,11,14(5H)-trione;

(11S,14S,17S)-14-(4-Amino-butyl)-11-(3-amino-propyl)-25-chloro-23-imidazol-1-yl-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-22-(6-amino-pyridin-3-yl)-25-chloro-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-23-yl]-pyridine-2-carbonitrile;

(11S,14S,17S)-14-(4-Amino-butyl)-11-(3-amino-propyl)-25-chloro-22-(6-hydroxy-pyridin-3-yl)-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;

3-[(11S,14S,17S)-14-(4-Amino-butyl)-25-chloro-22-(2-fluoro-pyridin-4-yl)-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-11-yl]-propionamide;

(11S,14S,17S)-14-(4-Amino-butyl)-11-(3-amino-propyl)-25-chloro-17-(1H-indol-3-ylmethyl)-16-methyl-23-(1H-pyrrol-3-yl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-12,15,18-trioxo-2-thia-4,10,13,16,19-pentaaza-tricyclo[19.4.0.0*3,8*]pentacosa-1(25),3(8),4,6,21,23-hexaene-23-carbonitrile;

(11S,14S,17S)-14-(4-Amino-butyl)-11-(3-amino-propyl)-25-chloro-23-(4-methanesulfonyl-phenyl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

4-[(11S,14S,17S)-14-(4-Amino-butyl)-11-(3-amino-propyl)-25-chloro-16-methyl-17-(2-methyl-1H-indol-3-ylmethyl)-12,15,18-trioxo-2-thia-4,10,13,16,19-pentaaza-tricyclo[19.4.0.0*3,8*]pentacosa-1(25),3(8),4,6,21,23-hexaen-23-yl]-benzenesulfonamide;

(7S,10S,13S)-13-((1H-Indol-3-yl)methyl)-10-(4-aminobutyl)-7-(3-aminopropyl)-3-bromo-12-methyl-6,7,9,10,12,13,15,16-octahydrobenzo[b]pyrido[3,2-p][1,5,8,11,14]thiatetraazacycloheptadecine-8,11,14(5H)-trione;

(7S,10S,13S)-13-((1H-Indol-3-yl)methyl)-10-(4-aminobutyl)-7-(3-aminopropyl)-17-(dimethylamino)-12-methyl-6,7,9,10,12,13,15,16-octahydrodipyrido[2,3-b:3',4'-p][1,5,8,11,14]thiatetraazacycloheptadecine-8,11,14(5H)-trione;

(7S,10S,13S)-13-((1H-Indol-3-yl)methyl)-10-(4-aminobutyl)-7-(3-aminopropyl)-12-methyl-17-(pyridin-3-yl)-6,7,9,10,12,13,15,16-octahydrodipyrido[2,3-b:3',4'-p][1,5,8,11,14]thiatetraazacycloheptadecine-8,11,14(5H)-trione;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-benzoic acid;

(11S,14S,17S)-14-(4-Amino-butyl)-11-(3-amino-propyl)-25-chloro-22-[4-(2,3-dihydroxy-propoxy)-phenyl]-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

{4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-phenoxy}-acetic acid;

(11S,14S,17S)-14-(4-Amino-butyl)-11-(3-amino-propyl)-25-chloro-17-(1H-indol-3-ylmethyl)-16-methyl-22-[4-(piperidin-4-yloxy)-phenyl]-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-22-(4-aminomethyl-phenyl)-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-22-[3-(2-amino-ethyl)-phenyl]-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-22-(4-piperazin-1-yl-phenyl)-2-thia-4,10,13,16,19-pentaaza-tricyclo[19.4.0.0*3,8*]pentacosa-1(25),3(8),4,6,21,2-hexaene-12,15,18-trione;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-hydroxy-ethyl)-benzenesulfonamide;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-hydroxy-ethyl)-benzamide;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-dimethylamino-ethyl)-benzamide;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo

[19.4.0.0*3,8*]pentacosa-1(25),3(8),4,6,21,23-hexaen-22-yl]-N-(2-morpholin-4-yl-ethyl)-benzamide;

(11S,14S,17S)-14-(4-Amino-butyl)-11-(3-amino-propyl)-25-chloro-17-(1H-indol-3-ylmethyl)-16-methyl-22-(4-piperidin-4-yl-phenyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-11-(3-Amino-propyl)-23,25-dichloro-17-(1H-indol-3-ylmethyl)-16-methyl-14-(4-methylamino-butyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-23,25-dichloro-11-(3-hydroxy-propyl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-11-(3-Amino-propyl)-14-butyl-23,25-dichloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

and pharmaceutically acceptable salts thereof.

More particular compounds of formula (I), (I'), (Ia), (Ib) or (Ic) of the present invention are those selected from the group consisting of:

(12S,15S,18S)-15-(4-Amino-butyl)-18-(3-amino-propyl)-12-(1H-indol-3-ylmethyl)-6-methoxy-13-methyl-2-thia-10,13,16,19-tetraaza-tri cyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-4,13-dimethyl-2-thia-10,13,16,19-tetraaza-tricyclo[19.4.0.0*3,8*]pentacosa-1(21),3,5,7,22,24-hexaene-11,14,17-trione;

(11S,14S,17S)-14-(4-Amino-butyl)-11-(3-amino-propyl)-22,25-dichloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(12S,15S,18S)-15-(4-Amino-butyl)-18-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-13-ethyl-12-(1H-indol-3-ylmethyl)-6-methoxy-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-13-ethyl-12-(1H-indol-3-ylmethyl)-4-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-4,6-dichloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione;

(11S,14S,17S)-14-(4-Amino-butyl)-11-(3-amino-propyl)-25-chloro-17-(1H-indol-3-ylmethyl)-16-methyl-23-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-23,25-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-22-chloro-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23,25-dichloro-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-ethyl-17-(1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-22,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-ethyl-17-(1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-23-trifluoromethyl-2-thia-4,7,10,13,16,19-hexaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-25-chloro-17-(1H-indol-3-ylmethyl)-16-methyl-22-trifluoromethyl-2-thia-4,7,10,13,16,19-hexaaza-tricyclo[19.4.0.0*3,8*]pentacosa-1(21),3,5,7,22,24-hexaene-12,15,18-trione;

3-[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3,5,7,21,23-hexaen-11-yl]-propionamide;

(11S,14S,17S)-14-(4-Amino-butyl)-11-(3-amino-propyl)-25-chloro-17-(1H-indol-3-ylmethyl)-16-methyl-22-pyridin-4-yl-2-thia-4,10,13,16,19-pentaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-25-chloro-17-(1H-indol-3-ylmethyl)-16-methyl- 22-pyridin-3-yl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-22-pyridin-3-yl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-22-pyridin-4-yl-2-thia-4,10,13,16,19-pentaaza-tricyclo[19.4.0.0*3,8*]pentacosa-1(25),3(8),4,6,21,23-hexaene-12,15,18-trione;

3-[(11S,14S,17S)-14-(4-Amino-butyl)-25-chloro-17-(1H-indol-3-ylmethyl)-16-methyl-12,15,18-trioxo-22-pyridin-3-yl-2-thia-4,10,13,16,19-pentaaza-tricyclo[19.4.0.0*3,8*]pentacosa-1(25),3(8),4,6,21,23-hexaen-11-yl]-propionamide;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-22-yl]-benzenesulfonamide;

(11S,14S,17S)-14-(4-Amino-butyl)-11-(3-amino-propyl)-25-chloro-17-(1H-indol-3-ylmethyl)-22-(4-methanesulfonyl-phenyl)-16-methyl-2-thia-4,10,13,16,19-pentaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-22-(6-amino-pyridin-3-yl)-25-chloro-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;

(11S,14S,17S)-14-(4-Amino-butyl)-11-(3-amino-propyl)-25-chloro-22-(6-hydroxy-pyridin-3-yl)-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-benzoic acid;

{4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-phenoxy}-acetic acid;

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-hydroxy-ethyl)-benzenesulfonamide;

and pharmaceutically acceptable salts thereof.

Most particular compounds of formula (I), (I'), (Ia), (Ib) or (Ic) of the present invention are those selected from the group consisting of:

(12S,15S,18S)-15-(4-Amino-butyl)-18-(3-amino-propyl)-12-(1H-indol-3-ylmethyl)-6-methoxy-4,13-dimethyl-2-thia-10,13,16,19-tetraaza-tricyclo[19.4.0.0*3,8*]pentacosa-1(25),3,5,7,21,23-hexaene-11,14,17-trione;

(11S,14S,17S)-14-(4-Amino-butyl)-11-(3-amino-propyl)-25-chloro-17-(1H-indol-3-ylmethyl)-16-methyl-23-trifluoromethyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-23,25-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-methyl-17-(2-methyl-1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23,25-dichloro-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-22,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-16-ethyl-17-(1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-23,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;

and pharmaceutically acceptable salts thereof.

Further particular compounds of formula (I), (I'), (Ia), (Ib) or (Ic) of the present invention are those selected from the group consisting of:

(12S,15S,18S)-15-(4-Amino-butyl)-18-(3-amino-propyl)-12-(1H-indol-3-ylmethyl)-6-methoxy-13-methyl-2-thia-10,13,16,19-tetraaza-tricyclo[19.4.0.0*3,8*]pentacosa-1(21),3,5,7,22,24-hexaene-11,14,17-trione;

(12S,15S,18S)-15-(4-Amino-butyl)-18-(3-amino-propyl)-12-(1H-indol-3-ylmethyl)-4,13-dimethyl-2-thia-10,13,16,19-tetraaza-tricyclo[19.4.0.0*3,8*]pentacosa-1(21),3,5,7,22,24-hexaene-11,14,17-trione;

(11S,14S,17S)-14-(4-Amino-butyl)-11-(3-amino-propyl)-22,25-dichloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione;

(11S,14S,17S)-14-(4-Amino-butyl)-11-(3-amino-propyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione;

(12S,15S,18S)-15-(4-Amino-butyl)-18-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione;

(12S,15S,18S)-15-(4-Amino-butyl)-18-(3-amino-propyl)-13-ethyl-12-(1H-indol-3-ylmethyl)-6-methoxy-2- thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-13-ethyl-12-(1H-indol-3-ylmethyl)-4-methyl-2-thia-10,13,16,19-tetraaza-tricyclo[19.4.0.0*3,8*]pentacosa-1(21),3,5,7,22,24-hexaene-11,14,17-trione;
(12S,15S,18S)-15-(4-Amino-butyl)-18-(3-amino-propyl)-4,6-dichloro-13-methyl-12-(2-methyl-1H-indol-3-ylmethyl)-2-thia-10,13,16,19-tetraaza-tri cyclo[19.4.0.0*3,8*]pentacosa-1(21),3,5,7,22,24-hexaene-11,14,17-trione;
(11S,14S,17S)-14-(4-Amino-butyl)-11-(3-amino-propyl)-25-chloro-17-(1H-indol-3-ylmethyl)-16-methyl-23-trifluoromethyl-2-thia-4,10,13,16,19-pentaaza-tricyclo[19.4.0.0*3,8*]pentacosa-1(25),3,5,7,21,23-hexaene-12,15,18-trione;
(11S,14S,17S)-14-(4-Amino-butyl)-11-(3-amino-propyl)-23,25-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione;
(11S,14S,17S)-14-(4-Amino-butyl)-11-(3-amino-propyl)-22-chloro-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione;
(11S,14S,17S)-14-(4-Amino-butyl)-11-(3-amino-propyl)-25-chloro-16-methyl-17-(2-methyl-1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;
(11S,14S,17S)-14-(4-Amino-butyl)-11-(3-amino-propyl)-25-chloro-16-methyl-17-(2-methyl-1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;
(11S,14S,17S)-14-(4-Amino-butyl)-11-(3-amino-propyl)-23,25-dichloro-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;
(11S,14S,17S)-14-(4-Amino-butyl)-11-(3-amino-propyl)-25-chloro-16-ethyl-17-(1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione;
(11S,14S,17S)-14-(4-Amino-butyl)-11-(3-amino-propyl)-22,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;
(11S,14S,17S)-14-(4-Amino-butyl)-11-(3-amino-propyl)-25-chloro-16-ethyl-17-(1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione;
(11S,14S,17S)-14-(4-Amino-butyl)-11-(3-amino-propyl)-23,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione;
and pharmaceutically acceptable salts thereof.

Manufacturing Processes

Compounds of formula (I), (I'), (Ia), (Ib) or (Ic) and pharmaceutically acceptable salts thereof as defined above can be prepared following standard methods known in the art.

1. General Synthesis of the Tether

The tether intermediate of formula (III) can be prepared following standard methods known in the art, particularly according to methods as described in the examples (e.g. PG=Fmoc).

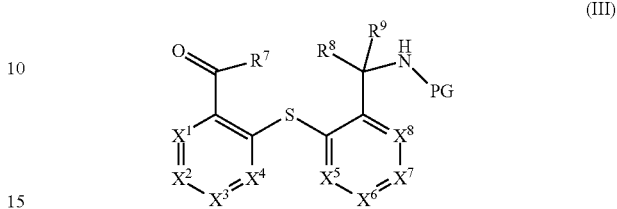

(III)

2. General Synthesis of the Tripeptide

The tripeptide of formula (IV) can be prepared following standard methods known in the art.

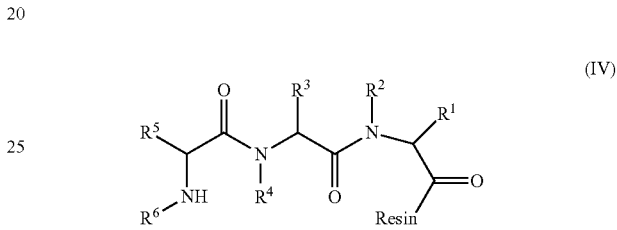

(IV)

The tripeptide sequence can for example be synthesized via state-of-the-art solid-phase peptide synthesis (SPPS) protocols (e.g. Fmoc-chemistry) as follows:

a) A resin (e.g. 2-Cl-Trityl resin) as solid support is loaded with the first N-protected amino acid and Hünig's base (N,N-Diisopropylethylamine or DIPEA) followed by cleavage of the protecting group.

b) A second N-protected amino acid is coupled with a coupling reagent and Hünig's base followed by cleavage of the protecting group (e.g. Fmoc).

c) A third N-protected amino acid is coupled with a coupling reagent and Hünig's base followed by cleavage of the protecting group.

In case N-methylated amino acids are present in the compound of formula (IV), the alkylation may be performed on the solid phase. After the appropriate step of the SPPS, the terminal amine is protected in a first step e.g. by swelling the resin in tetrahydrofurane (THF) and addition of Hünig's base and 2-nitrobenzene-1-1sulfonylchloride (Nbs). In the second step, methyl-4-nitrobenzenesulfonate together with 7-methyl-1,5,7-triazabicyclo[4.4.0]dec-5-ene can be added to the resin in dimethylfurane (DMF). For removal of the 2-nitrobenzene-1-1sulfonamide protecting group, 1,8-diazabicyclo[5.4.0]undec-7-ene (DBU) can be added to the resin in DMF followed by addition of mercaptoethanol.

In a particular embodiment, the solid support is a 2-Chlortritylchloride resin.

In a particular embodiment, the N-protected amino acids are protected with 9-fluorenylmethyloxycarbonyl (Fmoc).

In a particular embodiment, the resin is loaded in step a) with 0.1-1.0 eq of the first amino acid and excess Hünig's base in dichloromethane (DCM).

In a particular embodiment, the resin is thoroughly washed after the coupling reaction in step a) with dimethylformamide (DMF) and dichloromethane (DCM).

In a particular embodiment, the Fmoc protecting group is cleaved off in step a) with a mixture of 50% Piperidine in DCM/DMF (1:1).

In a particular embodiment, the resin is thoroughly washed after the deprotection in step a) with DMF, DCM and Methanol (MeOH) followed by drying under vacuum and weighing.

In a particular embodiment, the coupling reagent in step b) is Mukaiyama's reagent (2-chloro-1-methylpyridinium iodide).

In a particular embodiment, the second amino acid in step b) is coupled with 4 eq of Mukaiyama's reagent as coupling reagent and 6 eq of Hünig's base in DMF/DCM (1:1).

In a particular embodiment, the resin is thoroughly washed after the coupling reaction in step b) with dimethylformamide (DMF) and dichloromethane (DCM).

In a particular embodiment, the Fmoc protecting group is cleaved off in step b) with a mixture of 50% Piperidine in DCM/DMF (1:1).

In a particular embodiment, the resin is thoroughly washed after the deprotection in step b) with DMF and DCM followed by drying under vacuum and weighing.

In a particular embodiment, the coupling reagent in step c) is HATU (1-[bis(dimethyl-amino)methylene]-1H-1,2,3-triazolo[4,5-b]pyridinium 3-oxid hexafluorophosphate).

In a particular embodiment, the third amino acid in step c) is coupled with 4 eq of HATU as coupling reagent and 6 eq of Hünig's base in DMF/DCM (1:1).

In a particular embodiment, the resin is thoroughly washed after the coupling reaction in step c) with dimethylformamide (DMF) and dichloromethane (DCM).

In a particular embodiment, the Fmoc protecting group is cleaved off in step c) with a mixture of 20% Piperidine in DMF.

In a particular embodiment, the resin is thoroughly washed after the deprotection in step c) with DMF and DCM followed by drying under vacuum and weighing.

3. General Synthesis for the Coupling of the Tripeptide to the Tether

The compound of formula (I) can be obtained starting from the compounds of formula (III) and of formula (IV) according to Scheme 1.

Scheme 1.

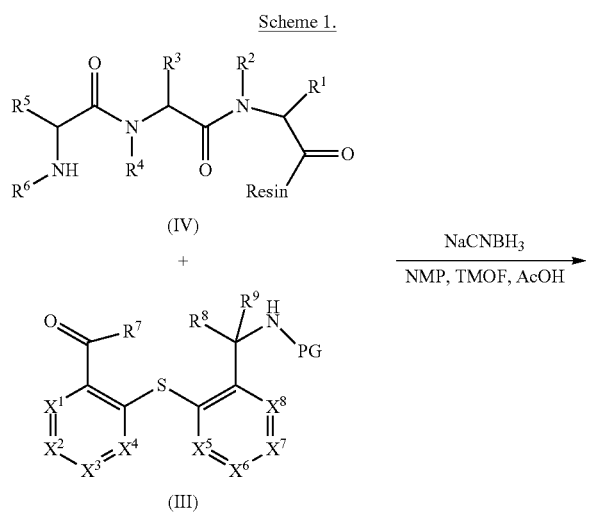

(IV)

+

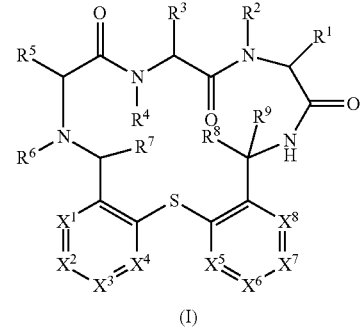

(III)

NaCNBH₃
―――――――→
NMP, TMOF, AcOH

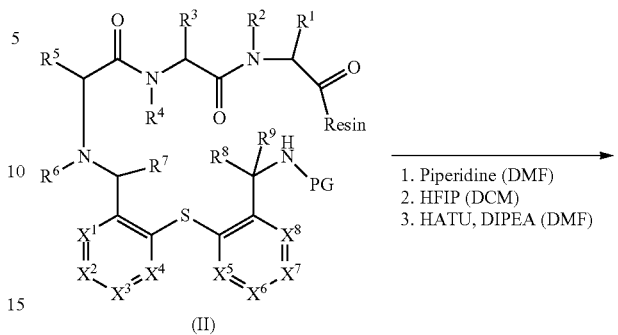

(II)

1. Piperidine (DMF)
2. HFIP (DCM)
3. HATU, DIPEA (DMF)

-continued (I)

The tether aldehyde or ketone of formula (III) is dissolved in a mixture of N-methyl-2-pyrrolidone (NMP), trimethyl orthoformate (TMOF) and acetic acid (AcOH) and the resin comprising the tripeptide of formula (IV) is added to the solution. After agitation of the mixture, sodium cyanoborohydride (NaCNBH₃) is added to provide a compound of formula (II).

After the Borch reaction, the protecting group (PG) on the tether is cleaved off, e.g. with a mixture of 20% Piperidine in DMF. The resin on the tripeptide can be cleaved e.g. by addition of 20% hexafluoroisopropanol (HFIP) in DCM and filtered off. The compound of formula (I) is finally obtained through cyclisation of the cleaved compound of formula (II) using HATU and Hünig's base followed by global deprotection of remaining protected amine groups.

A particular embodiment of the invention relates to a process for the manufacture of a compound of formula (I) comprising the steps of:

a) reacting a compound of formula (III) with a compound of formula (IV) using sodium cyanoborohydride (NaCNBH₃) to provide a compound of formula (II);

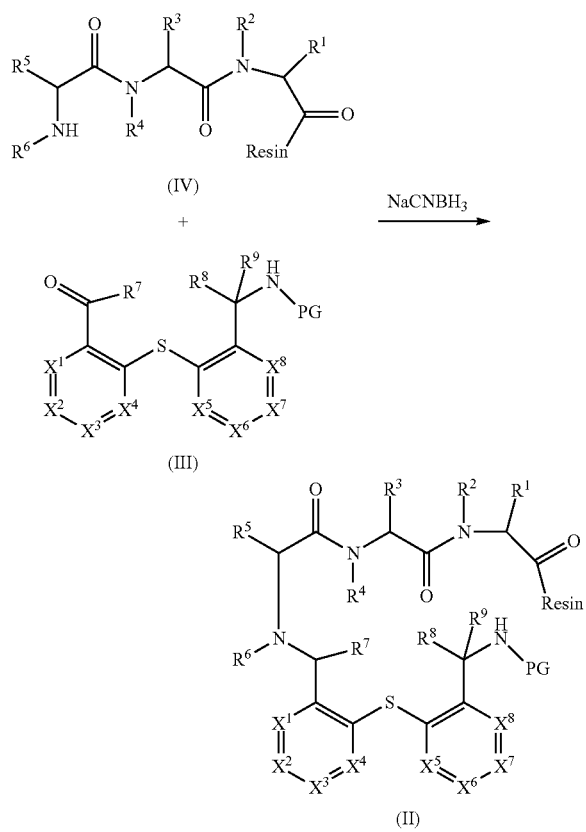

b) cleaving off the protecting group (PG) and the resin from the compound of formula (II);

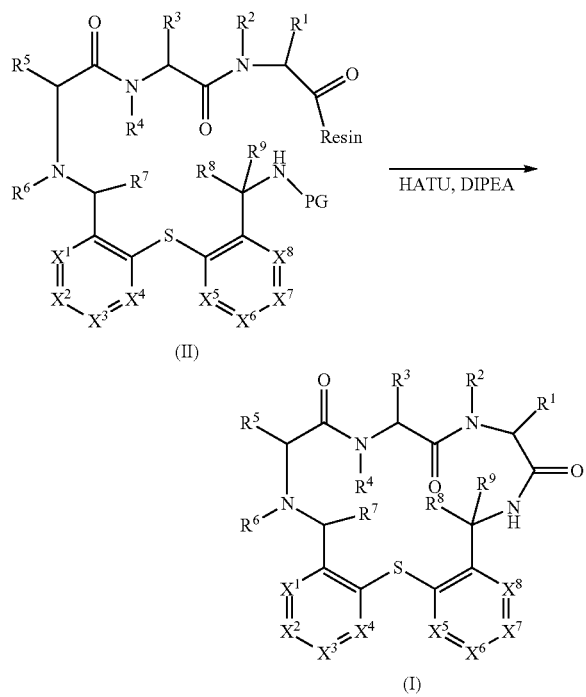

c) followed by cyclisation of the cleaved compound of formula (II) using HATU and Hünig's base.

In particular embodiment, the tripeptide of formula (IV) is washed with DCM prior to adding it to the tether aldehyde or ketone of formula (III).

In a particular embodiment, the solvent of the tether aldehyde of formula (III) consists of a mixture of N-methyl-2-pyrrolidone (NMP), trimethyl orthoformate (TMOF) and acetic acid (AcOH).

In a particular embodiment, the reaction mixture is washed after the Borch reaction with DMF, DCM, MeOH/DCM and/or DMF.

In a particular embodiment, the cyclization of the deprotected and cleaved compound of formula (II) takes place using HATU and DIPEA in DMF.

In a particular embodiment, the global BOC-deprotection is achieved by treatment with TFA in a solvent, particularly DCM, at RT.

Pharmaceutical Compositions

Another embodiment provides pharmaceutical compositions or medicaments comprising the compounds of the invention and a therapeutically inert carrier, diluent or pharmaceutically acceptable excipient, as well as methods of using the compounds of the invention to prepare such compositions and medicaments.

Compositions are formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

The compounds of the invention may be administered by any suitable means, including oral, topical (including buccal and sublingual), rectal, vaginal, transdermal, parenteral, subcutaneous, intraperitoneal, intrapulmonary, intradermal, intrathecal and epidural and intranasal, and, if desired for local treatment, intralesional administration. Parenteral infusions include intramuscular, intravenous, intraarterial, intraperitoneal, or subcutaneous administration.

The compounds of the present invention may be administered in any convenient administrative form, e.g., tablets, powders, capsules, solutions, dispersions, suspensions, syrups, sprays, suppositories, gels, emulsions, patches, etc. Such compositions may comprise components conventional in pharmaceutical preparations, e.g., diluents, carriers, pH modifiers, preservatives, solubilizers, stabilizers, wetting agents, emulsifiers, sweeteners, colorants, flavorants, salts for varying the osmotic pressure, buffers, masking agents, antioxidants, and further active agents. They can also comprise still other therapeutically valuable substances.

A typical formulation is prepared by mixing a compound of the present invention and a carrier or excipient. Suitable carriers and excipients are well known to those skilled in the art and are described in detail in, e.g., Ansel H. C. et al., *Ansel's Pharmaceutical Dosage Forms and Drug Delivery Systems* (2004) Lippincott, Williams & Wilkins, Philadelphia; Gennaro A. R et al., *Remington; The Science and Practice of Pharmacy* (2000) Lippincott, Williams & Wilkins, Philadelphia; and Rowe R C, *Handbook of Pharmaceutical Excipients* (2005) Pharmaceutical Press, Chicago. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents, diluents and other known additives to provide an elegant presentation of the drug (i.e., a compound of the present invention or pharmaceutical composition thereof) or aid in the manufacturing of the pharmaceutical product (i.e., medicament).

The dosage at which compounds of the invention can be administered can vary within wide limits and will, of course, be fitted to the individual requirements in each particular case. In general, in the case of oral administration a daily dosage of about 0.01 to 1000 mg per person of a compound of general formula (I) should be appropriate, although the above upper limit can also be exceeded when necessary.

An example of a suitable oral dosage form is a tablet comprising about 100 mg to 500 mg of the compound of the invention compounded with about 30 to 90 mg anhydrous lactose, about 5 to 40 mg sodium croscarmellose, about 5 to 30 mg polyvinylpyrrolidone (PVP) K30, and about 1 to 10 mg magnesium stearate. The powdered ingredients are first mixed together and then mixed with a solution of the PVP. The resulting composition can be dried, granulated, mixed with the magnesium stearate and compressed to tablet form using conventional equipment.

An example of an aerosol formulation can be prepared by dissolving the compound, for example 10 to 100 mg, of the invention in a suitable buffer solution, e.g. a phosphate buffer, adding a tonicifier, e.g. a salt such as sodium chloride, if desired. The solution may be filtered, e.g., using a 0.2 μm filter, to remove impurities and contaminants.

Uses

As described above, the compounds of formula (I), (I'), (Ia), (Ib) or (Ic) and their pharmaceutically acceptable salts possess valuable pharmacological properties for the treatment or prevention of infections and resulting diseases, particularly bacteremia, pneumonia, meningitis, urinary tract infection, and wound infection, caused by pathogens, particularly by bacteria, more particularly by *Acinetobacter* species, most particularly by *Acinetobacter baumannii*.

The compounds of formula (I), (I'), (Ia), (Ib) or (Ic) and their pharmaceutically acceptable salts exhibit activity as antibiotics, particularly as antibiotics against *Acinetobacter* species, more particularly as antibiotics against *Acinetobacter baumannii*, most particularly as pathogen-specific antibiotics against *Acinetobacter baumannii*.

The compounds of formula (I), (I'), (Ia), (Ib) or (Ic) and their pharmaceutically acceptable salts can be used as antibiotics, i.e. as antibacterial pharmaceutical ingredients suitable in the treatment and prevention of bacterial infections, particularly in the treatment and prevention of bacterial infections caused by *Acinetobacter* species, more particularly in the treatment and prevention of bacterial infections caused by *Acinetobacter baumannii*.

The compounds of the present invention can be used, either alone or in combination with other drugs, for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to pharmaceutical compositions comprising compounds of formula (I), (I'), (Ia), (Ib) or (Ic) as defined above or their pharmaceutically acceptable salts as defined above and one or more pharmaceutically acceptable excipients.

A particular embodiment of the present invention relates to pharmaceutical compositions comprising compounds of formula (I), (I'), (Ia), (Ib) or (Ic) or their pharmaceutically acceptable salts as defined above and one or more pharmaceutically acceptable excipients for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to compounds of formula (I), (I'), (Ia), (Ib) or (Ic) or their pharmaceutically acceptable salts as defined above for use as therapeutically active substances, especially for use as therapeutically active substances for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to compounds of formula (I), (I'), (Ia), (Ib) or (Ic) or their pharmaceutically acceptable salts as defined above for the use in the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to a method for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*, which method comprises administering compounds of formula (I), (I'), (Ia), (Ib) or (Ic) or their pharmaceutically acceptable salts as defined above to a subject.

A particular embodiment of the present invention relates to the use of compounds of formula (I), (I'), (Ia), (Ib) or (Ic) or their pharmaceutically acceptable salts as defined above for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*.

A particular embodiment of the present invention relates to the use of compounds of formula (I), (I'), (Ia), (Ib) or (Ic) or their pharmaceutically acceptable salts as defined above for the preparation of medicaments for the treatment or prevention of infections and resulting diseases, particularly bacteremia, pneumonia, meningitis, urinary tract infection, and wound infection, caused by pathogens, particularly by bacteria, more particularly caused by *Acinetobacter* species, most particularly by *Acinetobacter baumannii*. Such medicaments comprise compounds of formula (I), (I'), (Ia), (Ib) or (Ic) or their pharmaceutically acceptable salts as defined above.

EXAMPLES

The invention will be more fully understood by reference to the following examples. They should however not be construed as limiting the scope of the invention.

Abbreviations Used

Agp: 2-amino-3-guanidino-propionic acid
Boc: tert. Butyloxycarbonyl
DCM: Dichlormethane
DIPEA: N,N-Diisopropylamine
DMF: N,N-Dimethylformamide EA: Ethyl acetate
EtOAc: Ethyl acetate
EtOH: Ethanol
Fmoc: 9-Fluorenylmethoxycarbonyl
Fmoc-OSu: N-(9-Fluorenylmethoxycarbonyloxy)succinimide
HATU: O-(7-Azabenzotriazol-1-yl)-N,N,N',N'-tetramethyluronium-hexafluorophosphate
HFIP: Hexafluoroisopropanol
HOBt: Hydroxy-benzotriazole
LAH: Lithium aluminium hydride
Lys: Lysine
MeCN: Acetonitrile
Mukaiyama's reagent: 2-Chloro-1-methyl-pyridinium iodide
MTBD: 7-Methyl-1,5,7-triazabicyclo[4.4.0]dec-5-ene
NMP: N-Methylprolidone
Orn: Ornithine
Pd$_2$(dba)$_3$: Tris(dibenzylideneacetone)dipalladium(0)
THF: tetrahydrofurane
TLC: Thin layer chromatography
TMOF: Trimethyl-orthoformiate
Trp: Tryptophane
p-TSA: p-Toluenesulfonic acid or tosylic acid
HMPA: Hexamethylphosphoramide Intermediate 1

9H-fluoren-9-ylmethyl N-[[3-chloro-2-(2-formylphenyl)sulfanyl-phenyl]methyl]carbamate

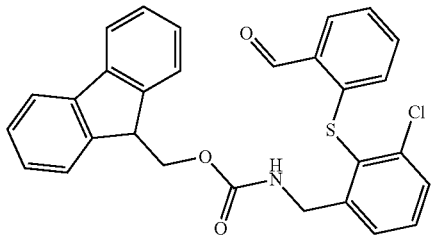 [SMILES: O=Cc1ccccc1Sc1c(Cl)cccc1CNC(=O)OCC1c2ccccc2-c2ccccc21]

To a suspension of 3-Chloro-2-fluoro-benzaldehyde (2.8 g, 16.64 mmol) and K$_2$CO$_3$ (4.5 g, 33.29 mmol) in DMF (15 mL) was added 2-Mercapto-benzoic acid methyl ester (7.9 g, 49.93 mmol) and the reaction mixture was stirred for 2 h at room temperature. Progress of the reaction was monitored by TLC. After completion, the reaction mixture was diluted with water (100 mL) and extracted with (3×100 mL) ethyl acetate. Combined organic layer was dried over sodium sulphate and concentrated under reduced pressure to get the crude compound which was purified by silica gel column chromatography (20% ethyl acetate and hexane) to afford methyl 2-(2-chloro-6-formyl-phenyl)sulfanylbenzoate (4.4 g, 86.17%) as white solid. LC-MS: 307.2 [M+H]$^+$.

To a solution of methyl 2-(2-chloro-6-formyl-phenyl)sulfanylbenzoate (4.4 g, 14.37 mmol) and tert-butyl sulphinamide (2.61 g, 21.56 mmol) in THF (50 mL) was added titanium tetra ethoxide (4.92 g, 21.56 mmol) and the reaction mixture was heated to 80° C. for 3 h. Progress of the reaction was monitored by TLC. After completion, the reaction mixture was diluted with water (100 mL) and extracted with ethyl acetate (3×100 mL). Combined organic layers were dried over sodium sulphate and concentrated under reduced pressure to get the crude compound which was purified by silica gel column chromatography (20% ethyl acetate and hexane) to afford methyl 2-[2-[(E)-tert-butylsulfinyliminomethyl]-6-chloro-phenyl]sulfanylbenzoate (4.2 g, 71.25%) as brown solid. LC-MS: =409.8 [M+H]$^+$.

To an ice cooled solution of methyl 2-[2-[(E)-tert-butylsulfinyliminomethyl]-6-chloro-phenyl]sulfanylbenzoate (4.2 g, 10.26 mmol) in THF (50 mL) was added LAH (1.1 g, 37.95 mmol) portion wise and the reaction mixture was stirred for 1 h at the same temperature. Progress of the reaction was monitored by TLC. After completion, the reaction mixture was diluted with aq. sodium sulphate solution (50 mL) and extracted with ethyl acetate (3×100 mL). Combined organic layers were dried over sodium sulphate and concentrated under reduced pressure to get crude compound which was purified by triturating with hexane followed by pentane to get N-[[3-chloro-2-[2-(hydroxymethyl)phenyl]sulfanyl-phenyl]methyl]-2-methyl-propane-2-sulfinamide (3.7 g, 94.06%) as brown solid. LC-MS: 383.8 [M+H].

To a solution of N-[[3-chloro-2-[2-(hydroxymethyl)phenyl]sulfanyl-phenyl]methyl]-2-methyl-propane-2-sulfinamide (3.7 g, 9.64 mmol) in DCM (100 mL) was added Dess-Martin periodinane (1,1,1-Triacetoxy-1,1-dihydro-1,2-benziodoxol-3(1H)-one) (12.26 g, 28.90 mmol) and the reaction mixture was stirred at room temperature for 4 h. Progress of the reaction was monitored by TLC. After completion, the reaction mixture was diluted with water (100 mL) and extracted with DCM (3×100 mL). Combined organic layer was dried over sodium sulphate and concentrated under reduced pressure to get the crude compound. The crude compound was purified by silica gel column chromatography (ethyl acetate) to get N-[[3-chloro-2-(2-formylphenyl)sulfanyl-phenyl]methyl]-2-methyl-propane-2-sulfinamide (0.7 g, 19.02%) as white solid. LC-MS: 381.8 [M+H]$^+$.

To an ice cooled solution of N-[[3-chloro-2-(2-formylphenyl)sulfanyl-phenyl]methyl]-2-methyl-propane-2-sulfinamide (0.800 g, 2.09 mmol) in dioxane (10 mL) was added 4M HCl in dioxane (0.9 mL) and the resulting reaction mixture was stirred at room temperature for 2 h. Progress of the reaction was monitored by TLC. Volatiles were removed under reduced pressure to obtain 2-[2-(aminomethyl)-6-chloro-phenyl]sulfanylbenzaldehyde (0.660 g, quantitative) as off white solid. LC-MS: 278.0 [M+H]$^+$.

To a solution of 2-[2-(aminomethyl)-6-chloro-phenyl]sulfanylbenzaldehyde (0.660 g, 2.09 mmol) in 5% aqueous NaHCO$_3$ (6 mL) was added Fmoc-OSu (0.754 g, 2.24 mmol) in CH$_3$CN (20 mL) and the reaction mixture was stirred at room temperature for 3 h. Progress of the reaction mixture was monitored by TLC. After completion, the reaction mixture was diluted with ethyl acetate and washed with water followed by brine. Organic layer was dried over sodium sulfate and evaporated under reduced pressure to get the crude compound which was purified by flash-chromatography (5-7% ethyl acetate in hexane) to afford 9H-fluoren-9-ylmethyl N-[[3-chloro-2-(2-formylphenyl)sulfanyl-phenyl]methyl]carbamate (0.460 g, 44%) as off white solid. LC-MS: 500.3 [M+H]

$^1$H-NMR: (400 MHz, DMSO-d6): δ 4.22-4.19 (1H, m), 4.33-4.29 (4H, m), 6.47 (1H, d, J=8.00 Hz), 7.37-7.28 (4H, m), 7.47-7.40 (3H, m), 7.57 (1H, t, J=7.8 Hz), 7.64 (1H, d, J=7.6 Hz), 7.68 (2H, d, J=7.4 Hz), 7.90-7.81 (3H, m), 8.00 (1H, d, J=7.5 Hz), 10.20 (1H, s).

Intermediate 2

9H-fluoren-9-ylmethyl N-[[4-chloro-2-(2-form-ylphenyl)sulfanyl-phenyl]methyl]carbamate

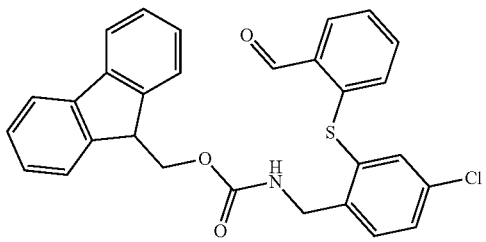 [SMILES: O=Cc1ccccc1Sc1cc(Cl)ccc1CNC(=O)OCC1c2ccccc2-c2ccccc21]

Intermediate 2 was generated in analogy to Intermediate 1 starting from the accordingly substituted benzaldehyde.

$^1$H-NMR: (400 MHz, DMSO-d6) δ 4.20-4.22 (m; 3H); 4.32 (2H; d; J=6.8 Hz); 7.6 (1H; d; J=7.6 Hz); 7.31-7.36 (m; 4H); 7.40 (3H; t; J=7.4 Hz); 7.46 (1H; br s); 7.54 (2H; t; J=8.4 Hz); 7.69 (2H; d; J=7.6 Hz); 7.82-7.84 (m; 1H); 7.90 (2H; d; J=7.2 Hz); 7.99 (1H; d; J=7.2 Hz); 10.21 (1H; s).

Intermediate 3

9H-fluoren-9-ylmethyl N-[[5-chloro-2-(2-form-ylphenyl)sulfanyl-phenyl]methyl]carbamate

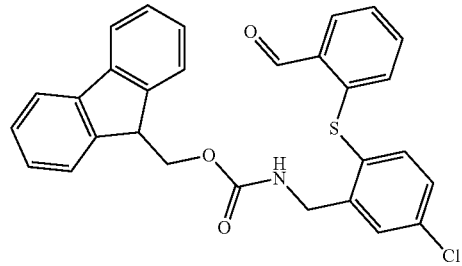 [SMILES: O=Cc1ccccc1Sc1ccc(Cl)cc1CNC(=O)OCC1c2ccccc2-c2ccccc21]

Intermediate 3 was generated in analogy to Intermediate 1 starting from the accordingly substituted benzaldehyde.

1H-NMR: (400 MHz, DMSO-d6) δ 4.23-4.25 (m; 3H); 4.32 (2H; d; J=6.8 Hz); 6.7 (1H; d; J=8.0 Hz); 7.31 (2H; t; J=7.4 Hz); 7.39-7.43 (4H; m); 7.44-7.54 (2H; m); 7.70 (2H; d; J=7.6 Hz); 7.82-7.84 (m; 2H); 7.98 (2H; d; J=7.2 Hz); 10.20 (1H; s).

Intermediate 4

9H-fluoren-9-ylmethyl N-[[2-(2-formylphenyl)sulfa-nylphenyl]methyl]carbamate

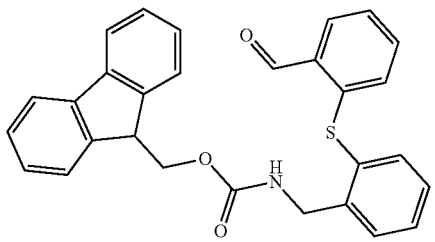 [SMILES: O=Cc1ccccc1Sc1ccccc1CNC(=O)OCC1c2ccccc2-c2ccccc21]

Intermediate 4 was generated accordingly from commercially available [2-[2-(aminomethyl)phenyl]sulfanylphenyl]methanol.

1H NMR (600 MHz, CHCl3-d6) δ ppm 4.15-4.22 (m, 1H) 4.38 (d, J=6.9 Hz, 2H) 4.48 (d, J=6.3 Hz, 2H) 5.12-5.20 (m, 1H) 6.77 (d, J=7.8 Hz, 1H) 7.17-7.25 (m, 1H) 7.27-7.58 (m, 12H) 7.76 (d, J=7.6 Hz, 2H) 7.86 (d, J=7.6 Hz, 1H) 10.13-10.40 (m, 1H).

Intermediate 5

9H-fluoren-9-ylmethyl N-[[2-(2-formylphenyl)sulfa-nyl-5-methoxy-phenyl]methyl]carbamate

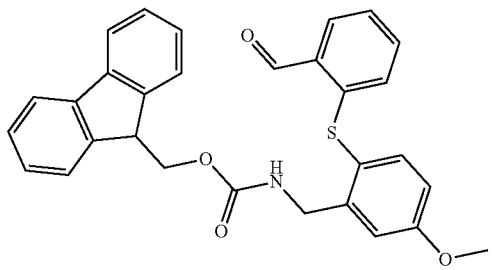 [SMILES: COc1ccc(Sc2ccccc2C=O)c(CNC(=O)OCC2c3ccccc3-c3ccccc32)c1]

A suspension of Na$_2$S·H$_2$O (2.43 g, 31.16 mmol) and MgSO$_4$ (7.79 g, 64.93 mmol) in NMP (80 mL) was heated to 80° C. for 30 min under N$_2$ atmosphere. To the resulting reaction mixture was added 2-Fluoro-5-methoxy-benzaldehyde (4.0 g, 25.97 mmol) drop-wise at same temperature and heated to 80° C. for 1 h. Then the reaction mixture was cooled to 0° C., acetic anhydride (3.42 mL, 36.36 mmol) was added drop-wise and stirring was continued for 1 h. The reaction mixture partitioned between water and ethyl acetate, organic layer was separated off, dried over anhydrous sodium sulphate and concentrated under reduced pressure to get crude compound which was purified by flash chromatography (30% ethyl acetate in hexane) to afford S-(2-formyl-4-methoxy-phenyl) ethanethioate (2.5 g, 45%) as viscous oil. LC-MS: 210.9 (M+H).

To a stirred solution of S-(2-formyl-4-methoxy-phenyl) ethanethioate (2.5 g, 11.90 mmol) in anhydrous THF (70 mL) was added tert-butyl sulphinamide (1.44 g, 11.90 mmol) followed by Titanium (IV) ethoxide (2.49 mL, 11.90 mmol). The resultant reaction mixture was heated to 60° C. for 1 h under argon atmosphere. Progress of the reaction was monitored by TLC. Then the reaction mixture was poured onto water (50 mL), filtered through celite and washed with ethyl acetate. Organic layer was separated, washed with brine, dried over anhydrous sodium sulphate and concentrated under reduced pressure to get the crude compound which was purified by flash column chromatography (25% ethyl acetate in hexane) to get S-[2-[(E)-tert-butylsulfi-nyliminomethyl]-4-methoxy-phenyl] ethanethioate (1.56 g, 42%) as reddish oil. LC-MS: 313.7 (M+H).

A solution of S-[2-[(E)-tert-butylsulfinyliminomethyl]-4-methoxy-phenyl] ethanethioate (1.9 g, 6.07 mmol) in THF/EtOH (4:1; 50 mL) was degassed with argon for 10 min and NaBH$_4$ (1.61 g, 42.5 mmol) was added portion-wise at 0° C. The reaction mixture was stirred for 1 h. The reaction mixture was then quenched with acetone/ethanol (1:1; degassed with argon) and stirred for 1 h at room temperature. Volatiles were evaporated under reduced pressure and released under argon to afford N-[(5-methoxy-2-sulfanylphenyl)methyl]-2-methyl-propane-2-sulfinamide (1.65 g, crude) as yellow solid which was used as such in next step without further purification. LC-MS: 273.9 (M+H).

To a solution of N-[(5-methoxy-2-sulfanyl-phenyl)methyl]-2-methyl-propane-2-sulfinamide (1.6 g, 2.05 mmol) in DMF (40 mL, degassed with argon prior to addition for about 10 min) were added $K_2CO_3$ (1.61 g, 11.72 mmol) and 2-Fluorobenzaldehyde (0.93 ml, 8.79 mmol) sequentially and the reaction mixture was stirred at 70° C. for 5 h. Then the reaction mixture was diluted with ethyl acetate, washed with water followed by brine, dried over sodium sulfate and concentrated under reduced pressure to get the crude compound. The crude compound thus obtained was purified by flash column chromatography (50% EtOAc in hexane) to afford N-[[2-(2-formylphenyl)sulfanyl-5-methoxy-phenyl]methyl]-2-methyl-propane-2-sulfinamide (0.64 g, 24.3% over two steps) as off-white solid. LC-MS: 378.1 (M+H).

To an ice cooled solution of N-[[2-(2-formylphenyl)sulfanyl-5-methoxy-phenyl]methyl]-2-methyl-propane-2-sulfinamide (0.64 g, 1.69 mmol) in dioxane (3 mL) was added 4M HCl in dioxane (10 mL) and the reaction mixture was allowed to stir at room temperature for 1 h. Progress of the reaction was monitored by TLC. Volatiles were evaporated under reduced pressure to obtain 2-[2-(aminomethyl)-4-methoxy-phenyl]sulfanylbenzaldehyde (0.52 g, 99%) as off-white solid. LC-MS: 274.1 (M+H).

To an ice cooled suspension of 2-[2-(aminomethyl)-4-methoxy-phenyl]sulfanylbenzaldehyde (0.52 g, 1.68 mmol) in acetonitrile (20 mL) and 5% aqueous $NaHCO_3$ solution (2 mL) was added Fmoc-OSu (0.57 g, 1.68 mmol) in $CH_3CN$ (20 mL) and the reaction mixture was stirred at room temperature for 3 h. Progress of the reaction was monitored by TLC. After completion, the reaction mixture was diluted with ethyl acetate (50 mL) and organic layer was separated off. Organic layer was washed with water followed by brine and dried over anhydrous sodium sulfate. Organic layer was concentrated under reduced pressure to get the crude compound which was purified by flash-chromatography (10% EtOAc in hexane) to afford 9H-fluoren-9-ylmethyl N-[[2-(2-formylphenyl)sulfanyl-5-methoxy-phenyl]methyl]carbamate (0.50 g, 60%) as off-white solid. LC-MS: 496.4 (M+H).

$^1$H-NMR: (400 MHz, $CDCl_3$): δ 3.84 (3H, s), 4.15 (1H, t, J=7.00 Hz), 4.34 (2H, d, J=7.1 Hz), 4.41 (2H, d, J=6.4 Hz), 5.16 (1H, t, J=5.8 Hz), 6.65 (1H, d, J=8.0 Hz), 6.90 (1H, dd, J=8.5, 2.6 Hz), 7.11 (1H, d, J=2.5 Hz), 7.31-7.17 (4H, m), 7.39-7.36 (2H, m), 7.53-7.47 (3H, m), 7.74 (2H, d, J=7.5 Hz), 7.81 (1H, d, J=7.6 Hz), 10.27 (1H, s).

Intermediate 6

9H-fluoren-9-ylmethyl N-[[2-(2-formylphenyl)sulfanyl-3-methyl-phenyl]methyl]carbamate

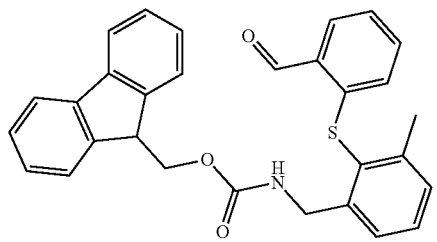

A suspension of $Na_2S·9H_2O$ (4.79 g, 61.41 mmol) and $MgSO_4$ (10.87 g, 90.31 mmol) in NMP (100 mL) was stirred at 80° C. for a period of 30 min under argon atmosphere. To the resulting reaction mixture was added a solution of 2-Fluoro-3-methyl benzaldehyde (5 g, 36.12 mmol) in NMP (25 mL) drop-wise at 80° C. and stirring was continued for 30 min at 80° C. Then the reaction mixture was cooled in an ice-bath. To the resulting reaction mixture was added acetic anhydride (6 mL) drop wise and the reaction mixture was stirred for 30 min. Progress of the reaction was monitored by TLC. Reaction mixture was then partitioned between water and ethyl acetate; organic layer was separated off, dried over anhydrous sodium sulfate and concentrated under reduced pressure to get the crude compound. The crude compound was purified by flash-chromatography (25% ethyl acetate in hexane) to afford S-(2-formyl-6-methyl-phenyl) ethanethioate (3.2 g, 45.64%) as brown color solid. LC-MS: 194.25 (M+H).

To a solution of S-(2-formyl-6-methyl-phenyl) ethanethioate (3.2 g, 16.47 mmol) in anhydrous THF (100 mL) were added 2-methylpropane-2-sulfinamide (1.99 g, 16.47 mmol) and titanium tetra ethoxide (3.76 g, 16.474 mmol) sequentially. The resultant reaction mixture was stirred for a period of 2 h under argon atmosphere at 60° C. Then the reaction mixture was cooled to ambient temperature, poured onto ice-water and filtered through a short pad of celite. Filtrate was extracted with ethyl acetate (100 mL×2) and the combined organic layer was washed with brine (100 mL×2), dried over anhydrous sodium sulfate and concentrated under reduced pressure to get the crude compound which was purified by flash-chromatography (10-20% ethyl acetate in hexane) to afford S-[2-[(E)-tert-butylsulfinyliminomethyl]-6-methyl-phenyl]ethanethioate (2.9 g, 59.30%) as viscous oil. LC-MS: 297.44 (M+H).

A solution of S-[2-[(E)-tert-butylsulfinyliminomethyl]-6-methyl-phenyl] ethanethioate (2.7 g, 9.091 mmol) in THF-Ethanol (4:1; 75 mL) was degassed with Argon for 15 min and then sodium borohydride (2.75 g, 72.727 mmol) was added portion wise at 0° C. The resulting reaction mixture was stirred for 30 min at 0° C. and 30 min at room temperature. Then the reaction mixture was quenched with acetone/ethanol (1:1; 30 mL) (degassed with argon) and stirred for 1 hour at 0° C. Volatiles were evaporated under reduced pressure and released under argon to afford 2-methyl-N-[(3-methyl-2-sulfanyl-phenyl)methyl]propane-2-sulfinamide (crude) as yellow solid. This compound was used as such in next step without further purification. LC-MS: 257.41 (M+H).

To a solution of 2-methyl-N-[(3-methyl-2-sulfanyl-phenyl)methyl]propane-2-sulfinamide (2.31 g, 8.98 mmol) in DMF (80 mL) (degassed with argon prior to addition for 10 min) were added potassium carbonate (2.48 g, 17.947 mmol) and 2-Fluorobenzaldehyde (3.34 g, 26.92 mmol) and the reaction mixture was heated to 70° C. for 5 h. Then the reaction mixture was diluted with ethyl acetate (50 mL), washed with water (50 mL) followed by brine (50 mL×2), dried over sodium sulfate and concentrated under reduced pressure to get the crude compound. The crude compound thus obtained was purified by silica gel (100-200 mesh) column chromatography (3% methanol in DCM) to get N-[[2-(2-formylphenyl)sulfanyl-3-methyl-phenyl]methyl]-2-methyl-propane-2-sulfinamide (1.0 g, 25% over two steps) as brown color viscous oil. LC-MS: 361.53 (M+H).

To an ice cooled solution of N-[[2-(2-formylphenyl)sulfanyl-3-methyl-phenyl]methyl]-2-methyl-propane-2-sulfinamide (0.950 g, 2.63 mmol) in dioxane (10 mL) was added 4M HCl in dioxane (0.95 mL) and the resultant reaction mixture was stirred at room temperature for 2 h. Progress of the reaction was monitored by TLC. Volatiles were evaporated under reduced pressure to obtain crude compound which was washed with diethyl ether and dried to get 2-[2-(aminomethyl)-6-methyl-phenyl]sulfanylbenzaldehyde (0.670 g, 87.10%) as white solid. This compound was used as such in next step without further purification. LC-MS: 257.36 (M+H).

To a stirred suspension of 2-[2-(aminomethyl)-6-methyl-phenyl]sulfanylbenzaldehyde (0.670 g, 2.607 mmol) in 5% sodium bicarbonate (5 mL) was added a solution of Fmoc-OSU (0.879 g, 2.607 mmol) in acetonitrile (10 mL) and the reaction mixture was stirred at room temperature for 3 h. The reaction mixture was then diluted with ethyl acetate (50 mL) and washed with brine (50 mL), dried over anhydrous sodium sulfate and concentrated under reduced pressure to get the crude compound. The crude thus obtained was purified by flash-chromatography (25% ethyl acetate in hexane) to afford 9H-fluoren-9-ylmethyl N-[[2-(2-formylphenyl)sulfanyl-3-methyl-phenyl]methyl]carbamate (0.48 g, 44.12%) as white solid. LC-MS: 479.60 (M+H).

¹H-NMR: (400 MHz, DMSO-d6): δ 2.29 (3H, s), 4.20 (1H, t, J=6.7 Hz), 4.26 (2H, d, J=6.00 Hz), 4.30 (2H, t, J=6.8 Hz), 6.45 (1H, d, J=8.00 Hz), 7.21 (1H, d, J=7.56 Hz), 7.35-7.29 (4H, m), 7.48-7.38 (4H, m), 7.69 (2H, d, J=7.52 Hz), 7.78 (1H, t, J=6.00 Hz), 7.89 (2H, d, J=7.5 Hz), 7.97 (1H, d, J=6.2 Hz), 10.22 (1H, s).

Intermediate 7

9H-fluoren-9-ylmethyl N-[[2-(2-formylphenyl)sulfanyl-4-methyl-phenyl]methyl]carbamate

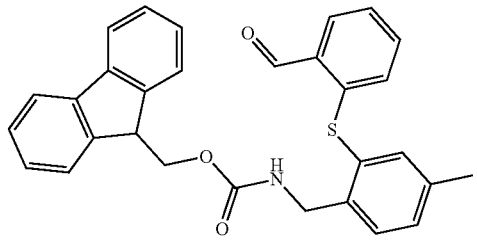 [SMILES: Cc1ccc(CNC(=O)OCC2c3ccccc3-c3ccccc32)c(Sc2ccccc2C=O)c1]

A suspension of sodium sulfide (4.8 g, 78.04 mmol) and MgSO₄ (10.8 g, 90.48 mmol) in NMP (100 mL) was stirred at 80° C. for a period of 30 min under argon atmosphere. To the resulting reaction mixture was added a solution of 2-Fluoro-4-methyl benzaldehyde (5 g, 36.19 mmol) in NMP (25 mL) drop wise at 80° C. and stirring was continued for 30 min at 80° C. Then the reaction mixture was cooled in an ice-bath. To the resulting reaction mixture was added acetic anhydride (5.1 mL, 54.29 mmol) drop wise and the reaction mixture was stirred for 30 min. Progress of the reaction was monitored by TLC. Then the reaction mixture was partitioned between water (150 mL) and ethyl acetate (150 mL), organic layer was separated off, dried over anhydrous sodium sulfate and concentrated under reduced pressure to get the crude compound. The crude compound thus obtained was purified by combiflash (30% ethyl acetate in hexane) to afford S-(2-formyl-5-methyl-phenyl) ethanethioate (4.8 g, 68%) as cherry color solid. LC-MS: 195.0 (M+H).

To a solution of S-(2-formyl-5-methyl-phenyl) ethanethioate (4.8 g, 24.71 mmol) in anhydrous THF (100 mL) were added 2-methylpropane-2-sulfinamide (2.9 g, 24.71 mmol) followed by titanium tetra ethoxide (5.6 g, 24.71 mmol) and the resultant reaction mixture was stirred for a period of 30 min under argon atmosphere at 60° C. Then the reaction mixture was cooled to room temperature, poured onto ice-water and filtered through a short pad of celite. Filtrate was extracted with ethyl acetate (100 mL×2), washed with brine (100 mL×2), dried over anhydrous sodium sulfate and concentrated under reduced pressure to get the crude compound which was purified by combiflash (10-20% ethyl acetate in hexane) to afford S-[2-[(E)-tert-butylsulfinyliminomethyl]-5-methyl-phenyl] ethanethioate (4.5 g, 61%) as pale orange color solid. LC-MS: 313.6 (M+H).

A solution of S-[2-[(E)-tert-butylsulfinyliminomethyl]-5-methyl-phenyl] ethanethioate (1.5 g, 4.78 mmol) in THF-Ethanol (4:1; 40 mL) was degassed with Argon for 15 min and then sodium borohydride (1.4 g, 38.28 mmol) was added portion wise at 0° C. and the reaction mixture was stirred for 30 min at 0° C. and 30 min at room temperature. Then the reaction mixture was quenched with acetone/ethanol (1:1; 30 mL) (degassed with argon) and stirring continued for 1 h at 0° C. Volatiles were evaporated under reduced pressure and released under argon to afford 2-methyl-N-[(4-methyl-2-sulfanyl-phenyl)methyl]propane-2-sulfinamide as yellow solid. This compound was used as such in next step without further purification. LC-MS: 258 (M+H).

To a solution of 2-methyl-N-[(4-methyl-2-sulfanyl-phenyl)methyl]propane-2-sulfinamide (3 g, crude) in DMF (60 mL) (degassed with argon prior to addition for about 10 min) were added potassium carbonate (1.2 g, 9.32 mmol) and 2-Fluorobenzaldehyde (1.7 g, 13.98 mmol) and the reaction mixture was heated to 70° C. for 5 h. Then the reaction mixture was diluted with ethyl acetate (50 mL), washed with water (50 mL) followed by brine (50 mL×2), dried over sodium sulfate and concentrated under reduced pressure to get the crude compound. The crude compound thus obtained was purified by silica gel (100-200 mesh) column chromatography (5% methanol in DCM) to get N-[[2-(2-formylphenyl)sulfanyl-4-methyl-phenyl]methyl]-2-methyl-propane-2-sulfinamide (0.6 g, 16% over two steps) as colorless liquid. LC-MS: 362.1 (M+H).

To an ice cooled solution of N-[[2-(2-formylphenyl)sulfanyl-4-methyl-phenyl]methyl]-2-methyl-propane-2-sulfinamide (0.8 g, 2.216 mmol) in dioxane (10 mL) was added 4M HCl in dioxane (0.8 mL) and the resultant reaction mixture was stirred at room temperature for 2 h. Progress of the reaction was monitored by TLC. Volatiles were evaporated under reduced pressure to obtain crude compound which was washed with diethyl ether and dried to get 2-(2-ethyl-5-methyl-phenyl)sulfanylbenzaldehyde (0.56 g, 98%) as pale yellow solid. This compound was used as such in next step without further purification. LC-MS: 258.0 (M+H).

To a stirred suspension of 2-(2-ethyl-5-methyl-phenyl)sulfanylbenzaldehyde (0.56 g, 2.17 mmol) in 5% sodium bicarbonate (5 mL) was added a solution of Fmoc-OSU (0.73 g, 2.18 mmol) in acetonitrile (2 mL) and the reaction mixture was stirred at room temperature for 3 h. Then the reaction mixture was diluted with ethyl acetate (50 mL) and washed with brine (50 mL). Organic layer was dried over anhydrous sodium sulfate and evaporated under reduced pressure to get the crude compound. The crude compound thus obtained was purified by combiflash (30% ethyl acetate in hexane) to afford 9H-fluoren-9-ylmethyl N-[[2-(2-formylphenyl)sulfanyl-4-methyl-phenyl]methyl]carbamate (0.51 g, 56%) as off white solid. LC-MS: 480.5 (M+H).

$^1$H-NMR: (400 MHz, CDCl$_3$): δ 2.33 (3H, s), 4.16 (1H, t, J=7.0 Hz), 4.35 (2H, d, J=7.0 Hz), 4.41 (2H, d, J=6.0 Hz), 5.12 (1H, br t, J=5.3 Hz), 6.75 (1H, d, J=7.7 Hz), 7.33-7.23 (5H, m), 7.42-7.35 (4H, m), 7.52 (2H, d, J=7.6 Hz), 7.74 (2H, d, J=7.5 Hz), 7.84 (1H, d, J=7.6 Hz), 10.29 (1H, s).

Intermediate 8

9H-fluoren-9-ylmethyl N-[[2-(2-formylphenyl)sulfanyl-5-methyl-phenyl]methyl]carbamate

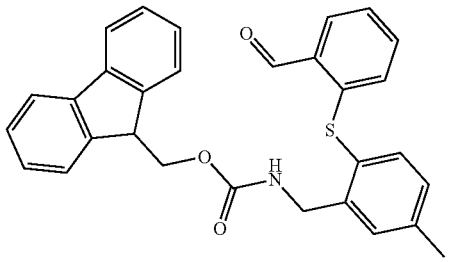 [SMILES: Cc1ccc(Sc2ccccc2C=O)c(CNC(=O)OCC2c3ccccc3-c3ccccc32)c1]

A suspension of Na$_2$S·H$_2$O (4.79 g, 61.41 mmol) and MgSO$_4$ (10.87 g, 90.31 mmol) in NMP (100 mL) was stirred at 80° C. for a period of 30 min under argon atmosphere. To the resulting reaction mixture was added a solution of 2-Fluoro-5-methyl benzaldehyde (5 g, 36.12 mmol) in NMP (25 mL) drop wise at 80° C. and stirring was continued for 30 min at 80° C. Then the reaction mixture was cooled in an ice-bath gradually. To the resulting reaction mixture was added acetic anhydride (6 mL) drop wise and the reaction mixture was stirred for 30 min. Progress of the reaction was monitored by TLC. Then the reaction mixture was partitioned between water and ethyl acetate, organic layer was separated off, dried over anhydrous sodium sulfate and concentrated under reduced pressure to get the crude compound. The crude compound thus obtained was purified by flash-chromatography (30% ethyl acetate in hexane) to afford S-(2-formyl-4-methyl-phenyl) ethanethioate (3.3 g, 47%) as brown color solid. LC-MS: 194.25 (M+H).

To a stirred solution of S-(2-formyl-4-methyl-phenyl) ethanethioate (3.3 g, 17.01 mmol) in anhydrous THF (100 mL) were added tert-butyl sulphinamide (2.06 g, 17.01 mmol) followed by titanium tetra ethoxide (3.88 g, 17.01 mmol) and the resultant reaction mixture was stirred for a period of 2 h under argon atmosphere at 60° C. Then the reaction mixture was poured onto ice-water and filtered through a short pad of celite. Filtrate was extracted with ethyl acetate (100 mL×2), washed with brine (100 mL×2), dried over anhydrous sodium sulfate and concentrated under reduced pressure to get the crude compound which was purified by combiflash (10-20% ethyl acetate in hexane) to afford S-[2-[(E)-tert-butylsulfinyliminomethyl]-4-methyl-phenyl]ethanethioate (3.0 g, 59.40%) as viscous oil. LC-MS: 297.44 (M+H).

A solution of thioacetic acid S-[2-[(E)-tert-butylsulfinyliminomethyl]-4-methyl-phenyl]ethanethioate (2.0 g, 6.73 mmol) in THF-Ethanol (4:1; 75 mL) was degassed with argon for 15 min and then sodium borohydride (2.03 g, 53.87 mmol) was added portion wise at 0° C. and the reaction mixture was stirred for 30 min at 0° C. and 30 min at room temperature. The reaction mixture was then quenched with acetone/ethanol (1:1; 30 mL) (degassed with argon) and stirred for 1 h at 0° C. Volatiles were evaporated under reduced pressure and released under argon to afford 2-methyl-N-[(5-methyl-2-sulfanyl-phenyl)methyl]propane-2-sulfinamide (crude) as yellow solid. This compound was used as such in next step without further purification. LC-MS: 257.41 (M+H).

To a solution of 2-methyl-N-[(5-methyl-2-sulfanyl-phenyl)methyl]propane-2-sulfinamide (1.73 g, 6.7 mmol) in DMF (80 mL) (degassed with argon prior to addition for about 10 min) were added potassium carbonate (1.86 g, 13.463 mmol) and 2-fluorobenzaldehyde (2.50 g, 20.194 mmol) sequentially and the reaction mixture was heated to 70° C. for 5 h. Progress of the reaction was monitored by TLC. Then the reaction mixture was diluted with ethyl acetate (50 mL), washed with water (50 mL) followed by brine (50 mL×2), dried over sodium sulfate and concentrated under reduced pressure to get the crude compound. The crude compound thus obtained was purified by silica gel (100-200 mesh) chromatography (3% methanol in DCM) to get N-[[2-(2-formylphenyl)sulfanyl-5-methyl-phenyl]methyl]-2-methyl-propane-2-sulfinamide (0.840 g, 21% over two steps) as brown viscous oil. LC-MS: 361.5 (M+H).

To a solution of N-[[2-(2-formylphenyl)sulfanyl-5-methyl-phenyl]methyl]-2-methyl-propane-2-sulfinamide (0.840 g, 3.26 mmol) in dioxane (10 mL) was added 4M HCl in dioxane (0.87 mL) and the reaction mixture was stirred at room temperature for 2 h. Progress of the reaction was monitored by TLC. Volatiles were evaporated under reduced pressure to obtain crude compound which was washed with diethyl ether and dried to get 2-(2-ethyl-4-methyl-phenyl) sulfanylbenzaldehyde (0.600 g, 88.10%) as white solid. This compound was used as such in next step without further purification. LC-MS: 257.36 (M+H).

To a stirred suspension of 2-(2-ethyl-4-methyl-phenyl) sulfanylbenzaldehyde hydrochloride (0.600 g, 2.33 mmol) in 5% sodium bicarbonate (5 mL) was added Fmoc-OSU (0.787 g, 2.334 mmol) in acetonitrile (10 mL) and the reaction mixture was stirred at room temperature for 3 h. Then the reaction mixture was diluted with ethyl acetate (50 mL) followed by brine (50 mL), dried over anhydrous sodium sulfate and evaporated under reduced pressure to get the crude compound. The crude compound thus obtained was purified by flash-chromatography (25% ethyl acetate in hexane) to afford 9H-fluoren-9-ylmethyl N-[[2-(2-formylphenyl)sulfanyl-5-methyl-phenyl]methyl]carbamate (0.5 g, 51%) as off white solid. LC-MS: 480.1 (M+H).

$^1$H-NMR: (400 MHz, DMSO-d6): δ 2.36 (3H, s), 4.23-4.21 (3H, br m), 4.30-4.28 (2H, br m), 6.64 (1H, d, J=8.0 Hz), 7.24-7.20 (2H, m), 7.37-7.30 (3H, m), 7.47-7.38 (4H, m), 7.70 (2H, d, J=7.4 Hz), 7.81 (1H, t, J=5.7 Hz), 7.90 (2H, d, J=7.5 Hz), 7.95 (1H, d, J=7.6 Hz), 10.20 (1H, s).

Intermediate 9

9H-fluoren-9-ylmethyl N-[[2-(2-formylphenyl)sulfanyl-3-(trifluoromethyl)phenyl]methyl]carbamate

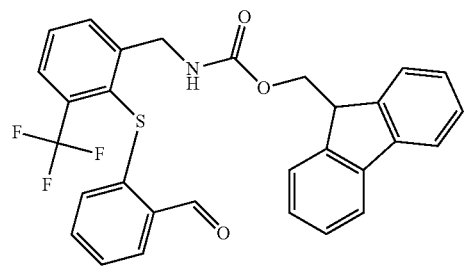 [SMILES: O=Cc1ccccc1Sc1c(CNC(=O)OCC2c3ccccc3-c3ccccc32)cccc1C(F)(F)F]

To a solution of 2-Fluoro-3-trifluoromethyl-benzaldehyde (2.0 g, 10.41 mmol) in DMF (4 mL) was added K$_2$CO$_3$ (2.8 g, 20.82 mmol) followed by 2-Mercapto-benzoic acid methyl ester (2.62 g, 15.61 mmol) and the reaction mixture was stirred for 6 h at room temperature. Progress of the reaction was monitored by TLC. After completion, the reaction mixture was diluted with water (30 mL) and extracted with ethyl acetate (70 mL). Organic layer was dried over sodium sulphate and concentrated under reduced pressure to obtain methyl 2-[2-formyl-6-(trifluoromethyl) phenyl]sulfanylbenzoate (3.0 g, 84.67%) as off white solid. LC-MS: 341.0 (M+H).

To a solution of methyl 2-[2-formyl-6-(trifluoromethyl) phenyl]sulfanylbenzoate (3 g, 8.81 mmol) in anhydrous THF (50 mL) was added tert butylsulphinamide (1.6 g, 13.22 mmol) followed by titanium (IV) ethoxide (3.49 mL, 16.6 mmol) and the reaction mixture was heated to 80° C. for 1 h under argon atmosphere. Progress of the reaction was monitored by TLC. After completion, the reaction mixture was diluted with water (30 mL) and extracted with ethyl acetate (70 mL). Organic layer was separated off, dried over anhydrous sodium sulphate and concentrated under reduced pressure to get methyl 2-[2-[(E)-tert-butylsulfinyliminomethyl]-6-methyl-phenyl]sulfanylbenzoate (3.8 g, 97.19%) as pale yellow viscous oil. LC-MS: 443.8 (M+H).

To an ice cooled suspension of LAH (0.977 g, 25.73 mmol) in THF (30 mL) was added methyl 2-[2-[(E)-tert-butylsulfinyliminomethyl]-6-methyl-phenyl]sulfanylbenzoate (3.8 g, 8.57 mmol) in THF (30 mL) and the reaction mixture was stirred for 2h at 0° C. Progress of the reaction was monitored by TLC. After completion, the reaction mixture was quenched with saturated sodium sulphate solution (3 mL) and filtered through celite. Residue was washed with ethyl acetate (80 mL) and filtrate was concentrated to get N-[[2-[2-(hydroxymethyl)phenyl]sulfanyl-3-methyl-phenyl]methyl]-2-methyl-propane-2-sulfinamide (2.6 g, 72.6%) as off white solid. LC-MS: 418.1 (M+H).

To an ice cooled solution of N-[[2-[2-(hydroxymethyl) phenyl]sulfanyl-3-methyl-phenyl]methyl]-2-methyl-propane-2-sulfinamide (2.6 g, 6.235 mmol) in DCM (100 mL) was added Dess-Martin periodinane (7.931 g, 18.70 mmol) and the reaction mixture was stirred at room temperature for 1 h. Progress of the reaction was monitored by TLC. After completion, the reaction mixture was poured onto saturated sodium bicarbonate solution and extracted with DCM (3×100 mL). Combined organic layer was washed with sodium thiosulphate, dried over sodium sulphate and concentrated under reduced pressure to get the crude compound. The crude compound was purified by using combiflash (ethyl acetate) to afford N-[[2-(2-formylphenyl)sulfanyl-3-methyl-phenyl]methyl]-2-methyl-propane-2-sulfinamide (1.2 g, 46%) as off white solid. LC-MS: 415.9 (M+H).

To an ice cooled solution of N-[[2-(2-formylphenyl)sulfanyl-3-methyl-phenyl]methyl]-2-methyl-propane-2-sulfinamide (1.2 g, 2.88 mmol) in dioxane (12 mL) was added 4M HCl in dioxane (1.2 mL) and the reaction mixture was stirred at room temperature for 1 h. Progress of the reaction was monitored by TLC. After completion, volatiles were evaporated under reduced pressure to obtain 2-[2-(aminomethyl)-6-methyl-phenyl]sulfanylbenzaldehyde (0.88 g, 97.87%) as yellow solid. LC-MS: 311.9 (M+H).

To an ice cooled suspension of 2-[2-(aminomethyl)-6-methyl-phenyl]sulfanylbenzaldehyde (0.88 g, 2.82 mmol) in acetonitrile (15 mL) and 5% aqueous NaHCO$_3$ solution (8 mL) was added a solution of Fmoc-OSu (0.953 g, 2.82 mmol) in CH$_3$CN (15 mL) and the reaction mixture was stirred at room temperature for 3 h. Progress of the reaction was monitored by TLC. After completion, the reaction mixture was diluted with ethyl acetate (50 mL) and organic layer was separated off. Organic layer was washed with water followed by brine and dried over anhydrous sodium sulfate and evaporated under reduced pressure to get the crude compound. The crude compound was purified by flash-chromatography (5-7% EtOAc in hexane) to afford 9H-fluoren-9-ylmethyl N-[[2-(2-formylphenyl)sulfanyl-3-methyl-phenyl]methyl]carbamate (1.1 g, 82%) as white solid. LC-MS: 533.9 (M+H).

$^1$H-NMR: (400 MHz, DMSO-d6): δ 4.20 (3H, br), 4.33 (2H, d, J=6.6 Hz), 6.36 (1H, d, J=7.9 Hz), 7.44-7.31 (6H, m), 7.61 (1H, d, J=7.4 Hz), 7.68 (2H, d, J=7.4 Hz), 7.86-7.76 (2H, m), 7.92-7.88 (3H, m), 8.01 (1H, d, J=7.4 Hz), 10.17 (1H, s).

Intermediate 10

9H-fluoren-9-ylmethyl N-[[2-(2-formylphenyl)sulfanyl-4-(trifluoromethyl)phenyl]methyl]carbamate

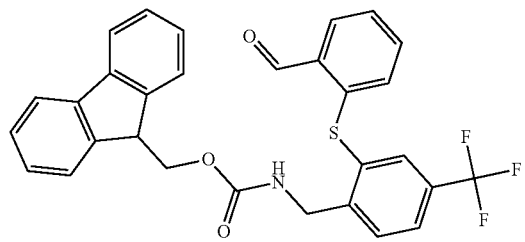 [SMILES: O=Cc1ccccc1Sc1cc(C(F)(F)F)ccc1CNC(=O)OCC1c2ccccc2-c2ccccc21]

To a solution of 2-Fluoro-4-trifluoromethyl-benzaldehyde (2.0 g, 10.41 mmol) in DMF (4 mL) was added K$_2$CO$_3$ (2.8 g, 20.82 mmol) followed by 2-Mercapto-benzoic acid methyl ester (2.62 g, 15.61 mmol) and the reaction mixture was stirred for 6 h at room temperature. Progress of the reaction was monitored by TLC. After completion, the reaction mixture was diluted with water (30 mL) and extracted with ethyl acetate (70 mL). Organic layer was dried over sodium sulphate and concentrated under reduced pressure to obtain methyl 2-[2-formyl-5-(trifluoromethyl) phenyl]sulfanylbenzoate (3.0 g, 84.67%) as off white solid. LC-MS: 341.1 (M+H).

To a solution of methyl 2-[2-formyl-5-(trifluoromethyl) phenyl]sulfanylbenzoate (3 g, 8.81 mmol) in anhydrous THF (50 mL) was added tert butylsulphinamide (1.6 g, 13.22 mmol) followed by titanium (IV) ethoxide (2.77 g, 13.22 mmol) and the reaction mixture was heated to 80° C. for 1 h under argon atmosphere. Progress of the reaction was monitored by TLC. After completion, the reaction mixture was diluted with water (30 mL) and extracted with ethyl acetate (70 mL). Organic layer was dried over anhydrous sodium sulphate and concentrated under reduced pressure to get methyl 2-[2-[(E)-tert-butylsulfinyliminomethyl]-5-(trifluoromethyl)phenyl]sulfanylbenzoate (3.8 g, 97.19%) as pale yellow viscous oil. LC-MS: 443.9 (M+H).

To an ice cooled suspension of LAH (0.977 g, 25.73 mmol) in THF (30 mL) was added methyl 2-[2-[(E)-tert-butylsulfinyliminomethyl]-5-(trifluoromethyl)phenyl]sulfanylbenzoate (3.8 g, 8.57 mmol) in THF (30 mL) and the reaction mixture was stirred for 2h at 0° C. Progress of the reaction was monitored by TLC. After completion, the reaction mixture was quenched with saturated sodium sulphate solution (3 mL) and filtered through celite. Residue was washed with ethyl acetate (80 mL) and filtrate was concentrated to get N-[[2-[2-(hydroxymethyl)phenyl]sulfanyl-4-(trifluoromethyl)phenyl]methyl]-2-methyl-propane-2-sulfinamide (3.5 g, 99%) as yellow oil. LC-MS: 418.1 (M+H).

To an ice cooled solution of N-[[2-[2-(hydroxymethyl)phenyl]sulfanyl-4-(trifluoromethyl)phenyl]methyl]-2-methyl-propane-2-sulfinamide (3.5 g, 8.39 mmol) in DCM (100 mL) was added Dess-Martin periodinane (10.67 g, 25.18 mmol) and the reaction mixture was stirred at room temperature for 1 h. Progress of the reaction was monitored by TLC. After completion, the reaction mixture was poured onto saturated sodium bicarbonate solution and extracted with DCM (3×100 mL). Combined organic layer was washed with sodium thiosulphate, dried over sodium sulphate and concentrated under reduced pressure to get the crude compound. The crude compound was purified by using combiflash (ethyl acetate) to afford N-[[2-(2-formylphenyl)sulfanyl-4-(trifluoromethyl)phenyl]methyl]-2-methyl-propane-2-sulfinamide (1.7 g, 48.75%) as yellow viscous oil. LC-MS: 415.9 (M+H).

To an ice cooled solution of N-[[2-(2-formylphenyl)sulfanyl-4-(trifluoromethyl)phenyl]methyl]-2-methyl-propane-2-sulfinamide (1.7 g, 4.091 mmol) in dioxane (17 mL) was added 4M HCl in dioxane (1.7 mL) and the reaction mixture was stirred at room temperature for 1 h. Progress of the reaction was monitored by TLC. After completion, volatiles were evaporated under reduced pressure to obtain 2-[2-(aminomethyl)-5-(trifluoromethyl)phenyl]sulfanylbenzaldehyde (1.1 g, 86%) as off white solid. LC-MS: 311.9 (M+H).

To an ice cooled suspension of 2-[2-(aminomethyl)-5-(trifluoromethyl)phenyl]sulfanylbenzaldehyde (1.1 g, 3.53 mmol) in acetonitrile (15 mL) and 5% aqueous NaHCO₃ solution (8 mL) was added a solution of Fmoc-OSu (1.19 g, 3.53 mmol) in CH₃CN (15 mL) and the reaction mixture was stirred at room temperature for 3 h. Progress of the reaction was monitored by TLC. After completion, the reaction mixture was diluted with ethyl acetate (50 mL) and organic layer was separated off. Organic layer was washed with water followed by brine, dried over anhydrous sodium sulfate and evaporated under reduced pressure to get the crude compound. The crude compound was purified by flash-chromatography (5-7% EtOAc in hexane) to afford 9H-fluoren-9-ylmethyl N-[[2-(2-formylphenyl)sulfanyl-4-methyl-phenyl]methyl]carbamate (0.530 g, 31%) as off white solid. LC-MS: 534.2 (M+H).

¹H-NMR: (400 MHz, DMSO-d6): δ 4.22 (1H, t, J=6.7 Hz), 4.29 (2H, d, J=5.7 Hz), 4.35 (2H, d, J=6.7 Hz), 6.76 (1H, d, J=7.9 Hz), 7.35-7.31 (2H, m), 7.46-7.40 (3H, m), 7.52 (1H, d, J=7.2 Hz), 7.56 (1H, d, J=7.8 Hz), 7.69 (2H, d, J=7.4 Hz), 7.91-7.85 (3H, m), 7.73 (1H, s), 7.94 (1H, t, J=8.00 Hz), 8.00 (1H, d, J=7.4 Hz), 10.22 (1H, s).

Intermediate 11

9H-fluoren-9-ylmethyl N-[[2-(2-formylphenyl)sulfanyl-5-(trifluoromethyl)phenyl]methyl]carbamate

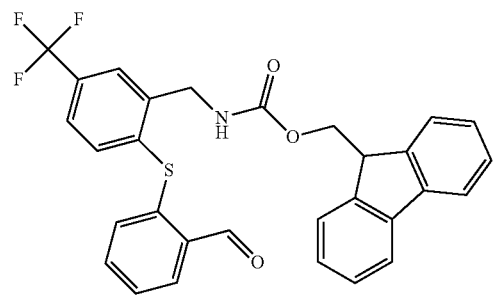 [SMILES: O=Cc1ccccc1Sc1ccc(C(F)(F)F)cc1CNC(=O)OCC1c2ccccc2-c2ccccc21]

To a solution of 2-fluoro-5-trifluoromethyl-benzaldehyde (2.0 g, 10.41 mmol) in DMF (4 mL) was added K₂CO₃ (2.8 g, 20.82 mmol) followed by 2-Mercapto-benzoic acid methyl ester (2.67 g, 15.61 mmol) and the reaction mixture was stirred for 4 h at room temperature. Progress of the reaction was monitored by TLC. After completion, the reaction mixture was diluted with water (100 mL) and extracted with ethyl acetate (3×100 mL). Combined organic layer was dried over sodium sulphate and concentrated under reduced pressure to obtain methyl 2-[2-formyl-4-(trifluoromethyl)phenyl]sulfanylbenzoate (3.5 g, 98.78%) as off white solid. LC-MS: 340.7 (M+H).

To a solution of methyl 2-[2-formyl-4-(trifluoromethyl)phenyl]sulfanylbenzoate (3.5 g, 16.6 mmol) in anhydrous THF (20 mL) was added tert butylsulphinamide (2.01 g, 16.6 mmol) followed by titanium (IV) ethoxide (3.49 mL, 16.6 mmol) and the reaction mixture was heated to 80° C. for 2 h under argon atmosphere. Progress of the reaction was monitored by TLC. After completion, the reaction mixture was diluted with water (50 mL), filtered through celite and washed with ethyl acetate. Organic layer was separated off, washed with brine, dried over anhydrous sodium sulphate and concentrated under reduced pressure to get methyl 2-[2-[(E)-tert-butylsulfinyliminomethyl]-4-(trifluoromethyl)phenyl]sulfanylbenzoate (4.0 g, 54.11%) as off white solid. LC-MS: 444.0 (M+H).

To an ice cooled suspension of LAH (1.02 g, 27.0 mmol) in THF (60 mL) was added methyl 2-[2-[(E)-tert-butylsulfinyliminomethyl]-4-(trifluoromethyl)phenyl]sulfanylbenzoate (4.0 g, 9.02 mmol) in THF (40 mL) and the reaction mixture was stirred for 30 min at 0° C. Progress of the reaction was monitored by TLC. After completion, the reaction mixture was quenched with saturated sodium sulphate solution (5 mL) and filtered through celite. The residue was washed with ethyl acetate (3×50 mL) and filtrate was concentrated to get N-[[2-[2-(hydroxymethyl)phenyl]sulfanyl-5-(trifluoromethyl)phenyl]methyl]-2-methyl-propane-2-sulfinamide (3.0 g, 79.58%) as off white solid. LC-MS: 418 (M+H).

To an ice cooled solution of N-[[2-[2-(hydroxymethyl)phenyl]sulfanyl-5-(trifluoromethyl)phenyl]methyl]-2-methyl-propane-2-sulfinamide (3.0 g, 7.1 mmol) in DCM (100 mL) was added Dess-Martin periodinane (9.1 g, 21.5 mmol) and the reaction mixture was stirred at room temperature for 1 h. Progress of the reaction was monitored by TLC. After completion, the reaction mixture was poured onto saturated sodium bicarbonate solution and extracted with DCM (3×100 mL). Combined organic layer was washed with sodium thiosulphate, dried over sodium sulphate and concentrated under reduced pressure to get the crude compound. The crude compound was purified by using flash-chromatography (ethyl acetate) to afford N-[[2-(2-formylphenyl)sulfanyl-5-(trifluoromethyl)phenyl]methyl]-2-methyl-propane-2-sulfinamide (1.7 g, 56.87%) as off white solid. LC-MS: 415.7 (M+H).

To an ice cooled solution of N-[[2-(2-formylphenyl)sulfanyl-5-(trifluoromethyl)phenyl]methyl]-2-methyl-propane-2-sulfinamide (1.7 g, 4.09 mmol) in dioxane (20 mL) was added 4M HCl in dioxane (1.7 mL) and the reaction mixture was stirred at room temperature for 1 h. Progress of the reaction was monitored by TLC. After completion, volatiles were evaporated under reduced pressure to obtain 2-[2-(aminomethyl)-4-(trifluoromethyl)phenyl]sulfanylbenzaldehyde (1.1 g, 86.36%) as off white solid. LC-MS: 312.1 (M+H).

To a suspension of 2-[2-(aminomethyl)-4-(trifluoromethyl)phenyl]sulfanylbenzaldehyde (1.0 g, 3.53 mmol) in 5% aqueous $NaHCO_3$ solution (8 mL) was added Fmoc-OSu (1.19 g, 3.53 mmol) in $CH_3CN$ (10 mL) and the reaction mixture was stirred at room temperature for 3 h. Progress of the reaction was monitored by TLC. After completion, the reaction mixture was diluted with ethyl acetate (50 mL) and organic layer was separated off. Organic layer was washed with water followed by brine, dried over anhydrous sodium sulfate and evaporated under reduced pressure to get the crude compound. The crude compound was purified by flash-chromatography (30% EtOAc in hexane) to afford 9H-fluoren-9-ylmethyl N-[[2-(2-formylphenyl)sulfanyl-5-(trifluoromethyl)phenyl]methyl]carbamate (0.410 g, 26.79%) as off white solid. LC-MS: 533.9 (M+H).

$^1$H-NMR: (400 MHz, $CDCl_3$): δ 4.19 (1H, t, J=6.7 Hz), 4.41 (2H, d, J=6.9 Hz), 4.53 (2H, d, J=6.2 Hz), 5.22 (1H, br), 6.93 (1H, d, J=7.6 Hz), 7.31-7.27 (1H, m), 7.47-7.33 (6H, m), 7.56-7.51 (3H, m), 7.76-7.74 (3H, m), 7.91 (1H, d, J=8.5 Hz), 10.29 (1H, s).

Intermediate 12

9H-fluoren-9-ylmethyl N-[(1S)-1-[5-chloro-2-(2-formylphenyl)sulfanyl-phenyl]ethyl]carbamate

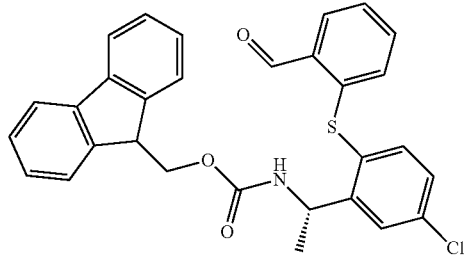 [SMILES: C[C@H](NC(=O)OCC1c2ccccc2-c2ccccc21)c1cc(Cl)ccc1Sc1ccccc1C=O]

A solution of 1-(5-chloro-2-fluorophenyl)ethan-1-one (2.0 g, 11.588 mmol), (2-sulfanylphenyl)methanol (1.625 g, 11.588 mmol), 63% aq. NaOH (0.7 mL) and HMPA (5 mL) was heated to 100° C. for 5h. Reaction mixture was diluted with water and extracted with EtOAc. The combined organic layers were washed with brine, dried over anhydrous sodium sulfate and concentrated under vacuum. The crude thus obtained was purified by normal silica column using 20% EtOAc in hexane to get 1-[5-chloro-2-[2-(hydroxymethyl)phenyl]sulfanyl-phenyl]ethanone (2.67 g, 78%) as a colorless sticky liquid.

To the stirred solution of 1-[5-chloro-2-[2-(hydroxymethyl)phenyl]sulfanyl-phenyl]ethanone (1.0 g, 3.425 mmol) in THF (7 mL) were added (S) 2-methyl 2-propane sulfinamide (415 mg, 3.425 mmol) and Ti(OEt)$_4$ (3.59 ml, 17.123 mmol) and heated to 70° C. for 48 h. Reaction mixture was quenched with brine solution and extracted with ethyl acetate. The separated organic layer was dried over sodium sulfate and concentrated under vacuum to afford N-[(1S)-1-[5-chloro-2-[2-(hydroxymethyl)phenyl]sulfanyl-phenyl]ethyl]-2-methyl-propane-2-sulfinamide (1.0 g, crude) as sticky liquid.

To a stirred solution of N-[(1S)-1-[5-chloro-2-[2-(hydroxymethyl)phenyl]sulfanyl-phenyl]ethyl]-2-methyl-propane-2-sulfinamide (2.5 g, 6.925 mmol) in THF (30 ml) was added L-selectride (lithium tri-sec-butyl(hydrido)borate) (10 ml) at −78° C. and stirred at the same condition for 2 h. Then the reaction mixture was quenched with saturated $NH_4Cl$ solution and extracted with ethyl acetate, dried over $Na_2SO_4$ and concentrated under vacuum to afford the crude which was purified by normal silica column (30% EtOAc-Hexane) to get N-[(1S)-1-[5-chloro-2-[2-(hydroxymethyl)phenyl]sulfanyl-phenyl]ethyl]-2-methyl-propane-2-sulfinamide (1.9 g, 68%) as off white sticky solid. MS found: 398.2 (M+H).

To a stirred solution of N-[(1S)-1-[5-chloro-2-[2-(hydroxymethyl)phenyl]sulfanyl-phenyl]ethyl]-2-methyl-propane-2-sulfinamide (1.0 g, 2.513 mmol) in MeOH (10 mL), was added 4M HCl/dioxane (5 mL) at 0° C. and reaction mixture was stirred at 25° C. for 1 h. After completion of reaction, reaction mixture was concentrated under reduced pressure to get [2-[2-[(1S)-1-aminoethyl]-4-chloro-phenyl]sulfanylphenyl]methanol (900 mg, crude) as a colorless liquid. MS found: 294.1 (M+H).

To a stirred suspension of [2-[2-[(1S)-1-aminoethyl]-4-chloro-phenyl]sulfanylphenyl]methanol (900 mg, 2.727 mmol) in 5% $NaHCO_3$(20 mL) was added Fmoc OSU (919.636 mg, 2.727 mmol) in $CH_3CN$ (20 mL) at 25° C. and reaction mass was stirred at 25° C. for 2h. Then reaction mass was diluted with water and extracted with ethyl acetate. The separated organic layer was washed with brine solution, dried over sodium sulfate and evaporated under reduced pressure. The crude thus obtained was then purified by normal silica column (20% ethyl acetate-hexane) to afford 9H-fluoren-9-ylmethyl N-[(1R)-1-[5-chloro-2-[2-(hydroxymethyl)phenyl]sulfanyl-phenyl]ethyl]carbamate as sticky solid (800 mg, 56%). MS found: 516.3 (M+H).

To a stirred solution of 9H-fluoren-9-ylmethyl N-[(1R)-1-[5-chloro-2-[2-(hydroxymethyl)phenyl]sulfanyl-phenyl]ethyl]carbamate (540 mg, 1.046 mmol) in DCM/THF (1:1, 24 mL) was added $MnO_2$ (1.819 g, 20.928 mmol) and reaction mass was stirred at 25° C. for 2h. The reaction mass was filtered through celite pad, filtrate was evaporated under reduced pressure. The crude thus obtained was purified by normal silica column using 5-20% EA/Hexane to get 9H-fluoren-9-ylmethyl N-[(1S)-1-[5-chloro-2-(2-formylphenyl)sulfanyl-phenyl]ethyl]carbamate (300 mg, 55%) as a light yellow solid.

$^1$H-NMR: (400 MHz, DMSO-d6) δ 1.26 (3H; d; J=6.92 Hz); 4.21-4.23 (2H; m); 5.08-5.12 (1H; m); 6.83 (1H; d; J=7.8 Hz); 7.31-7.33 (2H; m); 7.39-7.40 (4H; m); 7.45-7.46 (m; 2H); 7.66-7.69 (3H; m); 7.90 (2H; d; J=7.4 Hz); 7.96 (1H; d; J=7.4 Hz); 8.03 (1H; d; J=7.36 Hz); 10.21 (1H; s).

Intermediate 13

9H-fluoren-9-ylmethyl N-[[3,6-dichloro-2-(2-formylphenyl)sulfanyl-phenyl]methyl]carbamate

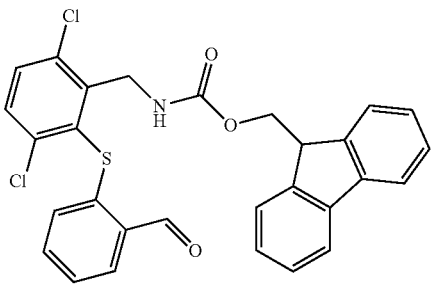 [SMILES: O=Cc1ccccc1Sc1c(Cl)ccc(Cl)c1CNC(=O)OCC1c2ccccc2-c2ccccc21]

To an ice-cooled suspension of 3,6-Dichloro-2-fluoro-benzaldehyde (3 g, 15.54 mmol) and K$_2$CO$_3$ in DMF (10 mL) was added 2-Mercapto-benzoic acid methyl ester and the reaction mixture was stirred for 1 h at room temperature. Progress of the reaction was monitored by TLC. After completion, the reaction mixture was poured onto water and extracted with ethyl acetate (50 mL×3). Combined organic layer was washed with brine, dried over sodium sulphate and evaporated under reduced pressure to get crude compound which was triturated with hexane to get methyl 2-(3,6-dichloro-2-formyl-phenyl)sulfanylbenzoate (4.5 g, 85%) as off-white solid.

To a stirred solution of 2-(3,6-dichloro-2-formyl-phenyl)sulfanylbenzoate (4.5 g, 13.19 mmol) in anhydrous THF (100 mL) was added tert-butyl sulphinamide (2.39 g, 19.79 mmol) followed by titanium (IV) ethoxide (4.51 mL, 19.79 mmol) and the reaction mixture was heated to 60° C. for 1 h under argon atmosphere. Progress of the reaction was monitored by TLC. After completion, the reaction mixture was poured onto water (200 mL), filtered through celite and washed with ethyl acetate (200 mL). Organic layer was separated off, washed with brine, dried over anhydrous sodium sulphate and concentrated under reduced pressure to get the crude compound which was triturated with hexane to get methyl 2-[2-[(E)-tert-butylsulfinyliminomethyl]-3,6-dichloro-phenyl]sulfanylbenzoate (5.6 g, 96%) as white solid.

To an ice-cooled suspension of LAH (1.43 g, 37.95 mmol) in THF (50 mL) was added methyl 2-[2-[(E)-tert-butylsulfinyliminomethyl]-3,6-dichloro-phenyl]sulfanylbenzoate (5.6 g, 12.61 mmol) in THF (50 mL) and the reaction mixture was stirred for 30 min. Then the reaction mixture was quenched with saturated sodium sulphate (15 mL) solution and filtered through celite. Filtrate was concentrated to get crude compound which was triturated with hexane to get N-[[3,6-dichloro-2-[2-(hydroxymethyl)phenyl]sulfanyl-phenyl]methyl]-2-methyl-propane-2-sulfinamide (2.0 g, 96%) as an off-white solid. LC-MS: 418.0 (M+H).

To an ice-cooled solution of N-[[3,6-dichloro-2-[2-(hydroxymethyl)phenyl]sulfanyl-phenyl]methyl]-2-methyl-propane-2-sulfinamide (4.2 g, 10.76 mmol) in DCM (100 mL) was added Dess-Martin periodinane (6.84 g 16.14 mmol) and the reaction mixture was stirred at ambient temperature for overnight. Then the reaction mixture was poured onto saturated sodium bicarbonate solution and extracted with DCM (100 mL×3). Combined organic layer was washed with sodium thiosulphate solution, dried over anhydrous sodium sulphate and concentrated under reduced pressure to get the crude compound. The crude compound thus obtained was purified by flash column chromatography (10% EtOAc in hexane) to get N-[[3,6-dichloro-2-(2-formylphenyl)sulfanyl-phenyl]methyl]-2-methyl-propane-2-sulfinamide (1.6 g, 36%) as sticky solid which was used as such in next step without further purification. MS calculated: 415 MS found 416.0 (M+H).

To an ice-cooled solution of N-[[3,6-dichloro-2-(2-formylphenyl)sulfanyl-phenyl]methyl]-2-methyl-propane-2-sulfinamide (1.6 g, 3.84 mmol) in dioxane (12 mL) was added 4M HCl in dioxane (4 mL) and the reaction mixture was stirred at ambient temperature for 6 h. Volatiles were evaporated under reduced pressure to obtain 2-[2-(aminomethyl)-3,6-dichloro-phenyl]sulfanylbenzaldehyde (1.1 g, 92%) as pale yellow solid. LC-MS: 311.9 (M+H).

To an ice-cooled suspension of 2-[2-(aminomethyl)-3,6-dichloro-phenyl]sulfanylbenzaldehyde (1.1 g, 3.52 mmol) in acetonitrile (25 mL) was added 5% aqueous NaHCO$_3$ solution (10 mL) followed by a solution of Fmoc-OSu (1.18 g, 3.52 mmol) in CH$_3$CN (15 mL) and the reaction mixture was stirred at ambient temperature for 4 h. Then the reaction mixture was diluted with ethyl acetate (80 mL) and water (50 mL). Organic layer was separated off, washed with brine and dried over anhydrous sodium sulfate. Organic layer was concentrated under reduced pressure and the crude compound thus obtained was purified by flash chromatography (20% EtOAc in hexane) to obtain 9H-fluoren-9-ylmethyl N-[[3,6-dichloro-2-(2-formylphenyl)sulfanyl-phenyl]methyl]carbamate (0.83 g, 44%) as white solid. LC-MS: 534.2 (M+H).

$^1$H-NMR: (400 MHz, CDCl$_3$): δ 4.10 (1H, t, J=7.2 Hz), 4.26 (2H, d, J=7.1 Hz), 4.80 (2H, d, J=6.0 Hz), 5.10 (1H, br), 6.53 (1H, d, J=7.6 Hz), 7.31-7.27 (4H, m), 7.37 (2H, t, J=7.4 Hz), 7.52-7.46 (4H, m), 7.73 (2H, d, J=7.5 Hz), 7.84 (1H, d, J=6.2 Hz), 10.28 (1H, s).

Intermediate 14

9H-fluoren-9-ylmethyl N-[[2,3-dichloro-6-(2-formylphenyl)sulfanyl-phenyl]methyl]carbamate

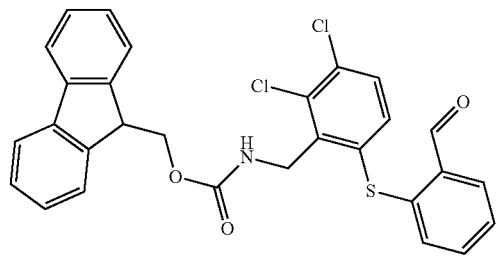 [SMILES: O=Cc1ccccc1Sc1ccc(Cl)c(Cl)c1CNC(=O)OCC1c2ccccc2-c2ccccc21]

To an ice-cooled suspension of 2,3-Dichloro-6-fluoro-benzaldehyde (3 g, 15.54 mmol) and K$_2$CO$_3$ (4.29 g, 31.08 mmol) in DMF (10 mL) was added 2-Mercapto-benzoic acid methyl ester (2.12 mL, 15.54 mmol) and the reaction mixture was stirred for 1 h. Progress of the reaction was monitored by TLC. After completion, the reaction mixture was poured onto water and extracted with ethyl acetate (50 mL×3). Combined organic layer was washed with brine, dried over sodium sulphate and evaporated under reduced pressure to get crude compound which was purified by flash column chromatography (10% EtOAc in hexane) to get methyl 2-(3,4-dichloro-2-formyl-phenyl)sulfanylbenzoate (3 g, 57%) as an off-white solid.

To a solution of methyl 2-(3,4-dichloro-2-formyl-phenyl)sulfanylbenzoate (3 g, 8.79 mmol) in anhydrous THF (100 mL) were added tert-butyl sulphinamide (1.60 g, 13.19 mmol) and titanium (IV) ethoxide (3 mL, 13.19 mmol) sequentially and the resulting reaction mixture was heated to 60° C. for 1 h under argon atmosphere. Progress of the reaction was monitored by TLC. After completion, the reaction mixture was poured onto water (100 mL) filtered through celite and celite bed was washed with ethyl acetate. Organic layer was separated off and washed with brine. Organic layer was dried over anhydrous sodium sulphate and concentrated under reduced pressure to get the crude compound which was triturated with hexane to get methyl 2-[2-[(E)-tert-butylsulfinyliminomethyl]-3,4-dichloro-phenyl]sulfanylbenzoate (3.8 g, 92%) as an off-white solid.

To an ice-cooled suspension of LAH (0.97 g, 25.67 mmol) in THF (40 mL) was added methyl 2-[2-[(E)-tert-butylsulfinyliminomethyl]-3,4-dichloro-phenyl]sulfanylbenzoate (3.8 g, 8.56 mmol) in THF (30 mL) and the reaction mixture was stirred for 30 min. Then the reaction mixture was quenched with saturated sodium sulphate (5 mL) solution, filtered through celite and celite bed was washed with ethyl acetate (3×50 mL). Filtrate was concentrated and the crude compound thus obtained was triturated with hexane to get N-[[2,3-dichloro-6-[2-(hydroxymethyl)phenyl]sulfanyl-phenyl]methyl]-2-methyl-propane-2-sulfinamide (2.5 g, 70%) as an off-white solid. LC-MS: 417.8 (M+H).

To an ice-cooled solution of N-[[2,3-dichloro-6-[2-(hydroxymethyl)phenyl]sulfanyl-phenyl]methyl]-2-methyl-propane-2-sulfinamide (2.5 g, 5.98 mmol) in DCM (100 mL) was added Dess-Martin periodinane (3.80 g, 8.97 mmol) and the resulting reaction mixture was stirred at ambient temperature for 1 h. After completion, the reaction mixture was poured onto saturated sodium bicarbonate solution and extracted with DCM (100 mL×3). Combined organic layer was washed with sodium thiosulphate solution and dried over anhydrous sodium sulphate. Organic layer was concentrated under reduced pressure and the crude compound thus obtained was purified by flash column chromatography (10% EtOAc in hexane) to get N-[[2,3-dichloro-6-(2-formylphenyl)sulfanyl-phenyl]methyl]-2-methyl-propane-2-sulfinamide (1.7 g, 69%) as an off-white solid. LC-MS: 416.0 (M+H).

To an ice-cooled solution of N-[[2,3-dichloro-6-(2-formylphenyl)sulfanyl-phenyl]methyl]-2-methyl-propane-2-sulfinamide (1.7 g, 4.08 mmol) in dioxane (25 mL) was added 4M HCl in dioxane (10 mL) and the resultant reaction mixture was allowed to stir at ambient temperature for 6 h. Volatiles were evaporated under reduced pressure to obtain crude compound which was triturated with diethyl ether to get 2-[2-(aminomethyl)-3,4-dichloro-phenyl]sulfanylbenzaldehyde (1.27 g, 99%) as white solid. LC-MS: 311.9 (M+H).

To an ice-cooled suspension of 2-[2-(aminomethyl)-3,4-dichloro-phenyl]sulfanylbenzaldehyde (1.3 g, 4.16 mmol) in acetonitrile (40 mL) was added 5% aqueous NaHCO$_3$ solution (10 mL) followed by a solution of Fmoc-OSu (1.40 g, 4.16 mmol) in CH$_3$CN (15 mL) and the reaction mixture was stirred at ambient temperature for 3 h. Then the reaction mixture was diluted with ethyl acetate (100 mL) and water (100 mL). Organic layer was separated off and washed with brine. Organic layer was dried over anhydrous sodium sulfate and evaporated under reduced pressure to get the crude compound. The crude compound thus obtained was purified by flash column chromatography (20% EtOAc in hexane) to afford 9H-fluoren-9-ylmethyl N-[[2,3-dichloro-6-(2-formylphenyl)sulfanyl-phenyl]methyl]carbamate (0.610 g, 28%) as white solid. LC-MS: 534.1 (M+H).

$^1$H-NMR: (400 MHz, CDCl$_3$): δ 4.17-4.15 (1H, m), 4.22-4.21 (2H, m), 4.50 (2H, d, J=4.4 Hz), 6.89 (1H, d, J=7.8 Hz), 7.30 (2H, t, J=7.4 Hz), 7.42-7.38 (4H, m), 7.51 (2H, t, J=7.5 Hz), 7.70-7.64 (3H, m), 7.88 (2H, d, J=7.6 Hz), 7.97 (1H, d, J=7.8 Hz), 10.19 (1H, s).

Intermediate 15

9H-fluoren-9-ylmethyl N-[[2-chloro-6-(2-formylphenyl)sulfanyl-phenyl]methyl]carbamate

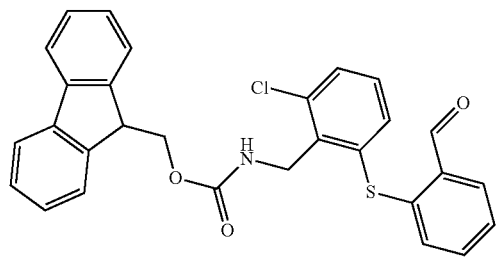

To an ice-cooled suspension of 2-chloro-6-fluoro-benzaldehyde (3 g, 18.92 mmol) and K$_2$CO$_3$ in DMF (10 mL) was added 2-mercapto-benzoic acid methyl ester (2.6 mL, 18.92 mmol) and the reaction mixture was stirred for 1 h at room temperature. Progress of the reaction was monitored by TLC. After completion, the reaction mixture was poured onto water and extracted with ethyl acetate (3×50 mL). Combined organic layer was washed with brine, dried over sodium sulphate and evaporated under reduced pressure to get crude compound which was purified by flash column chromatography (10% EtOAc in hexane) to get methyl 2-(3-chloro-2-formyl-phenyl)sulfanylbenzoate (3.4 g, 59%) as white solid.

To a stirred solution of methyl 2-(3-chloro-2-formyl-phenyl)sulfanylbenzoate (3.4 g, 11.11 mmol) in anhydrous THF (100 mL) was added tert-butyl sulphinamide (2.01 g, 16.66 mmol) followed by titanium (IV) ethoxide (3.8 mL, 16.66 mmol). The resultant reaction mixture was heated to 60° C. for 1 h under argon atmosphere. Progress of the reaction was monitored by TLC. After completion, the reaction mixture was poured onto water (150 mL) and filtered through celite, washed with ethyl acetate (150 mL). Organic layer was separated off, washed with brine, dried over anhydrous sodium sulphate and concentrated under reduced pressure to get the crude compound which was triturated using hexane to get methyl 2-[2-[(E)-tert-butylsulfinyliminomethyl]-3-chloro-phenyl]sulfanylbenzoate (4.4 g, 97%) as an off-white solid.

To an ice-cooled slurry of LAH (1.05 g, 27.87 mmol) in THF (30 mL) was added methyl 2-[2-[(E)-tert-butylsulfinyliminomethyl]-3-chloro-phenyl]sulfanylbenzoate (3.8 g, 9.29 mmol) in THF (40 mL) and the reaction mixture was stirred at room temperature for 0.5 h. Then the reaction mixture was quenched with saturated sodium sulphate (10 mL), filtered through celite and washed with ethyl acetate (3×75 mL). Filtrate was concentrated to get crude compound which was triturated with hexane to get N-[[2-chloro-6-[2-(hydroxymethyl)phenyl]sulfanyl-phenyl]methyl]-2-methyl-propane-2-sulfinamide (3.2 g, 90%) as white solid. LC-MS: 384.0 (M+H).

To an ice-cooled solution of N-[[2-chloro-6-[2-(hydroxymethyl)phenyl]sulfanyl-phenyl]methyl]-2-methyl-propane-2-sulfinamide (3.2 g, 8.35 mmol) in DCM (100 mL) was added Dess-Martin periodinane (5.31 g, 12.53 mmol) and the reaction mixture was stirred at ambient temperature for 1 h. After completion, the reaction mixture was poured onto saturated sodium bicarbonate solution and extracted with DCM (100 mL×3). Combined organic layer was washed with sodium thiosulphate solution, dried over anhydrous sodium sulphate and concentrated under reduced pressure to get the crude compound. Crude compound was purified by flash column chromatography (10% EtOAc in hexane) to get N-[[2-chloro-6-(2-formylphenyl)sulfanyl-phenyl]methyl]-2-methyl-propane-2-sulfinamide (2.1 g, 66%) as an off-white solid. LC-MS: 382.1 (M+H).

To an ice-cooled solution of N-[[2-chloro-6-(2-formylphenyl)sulfanyl-phenyl]methyl]-2-methyl-propane-2-sulfinamide (2.1 g, 5.51 mmol) in dioxane (30 mL) was added 4M in HCl in dioxane (10 mL) and the reaction mixture was allowed to stir at room temperature for 6 h. Volatiles were evaporated under reduced pressure to obtain 2-[2-(aminomethyl)-3-chloro-phenyl]sulfanylbenzaldehyde (1.5 g, 98%) as white solid which was used as such in next step without further purification. LC-MS: 277.9 (M+H).

To an ice-cooled suspension of 2-[2-(aminomethyl)-3-chloro-phenyl]sulfanylbenzaldehyde (1.5 g, 4.90 mmol) in acetonitrile (40 mL) was added 5% aqueous NaHCO$_3$ (15 mL) followed by a solution of Fmoc-OSu (1.65 g, 4.90 mmol) in CH$_3$CN (10 mL) and the reaction mixture was stirred at ambient temperature for 4 h. Then the reaction mixture was diluted with ethyl acetate (100 mL) and water (50 mL). Organic layer was separated off and washed with brine. Organic layer was dried over anhydrous sodium sulfate and evaporated under reduced pressure to get the crude compound which was purified by combiflash chromatography (20% EtOAc in hexane) to afford 9H-fluoren-9-ylmethyl N-[[2-chloro-6-(2-formylphenyl)sulfanyl-phenyl]methyl]carbamate (0.93 g, 39%) as white solid. LC-MS: 499.9 (M+H).

1H-NMR: (400 MHz, DMSO-d6): δ 4.20-4.14 (3H, m), 4.47 (2H, d, J=4.4 Hz), 6.86 (1H, d, J=7.9 Hz), 7.32-7.28 (2H, m), 7.43-7.36 (5H, m), 7.53-7.49 (1H, m), 7.62-7.59 (2H, m), 7.68 (2H, d, J=7.4 Hz), 7.87 (2H, d, J=7.5 Hz), 7.96 (1H, d, J=6.6 Hz), 10.20 (1H, s).

Intermediate 16

9H-fluoren-9-ylmethyl N-[[3-chloro-2-(2-formylphenyl)sulfanyl-6-(trifluoromethyl)-phenyl]methyl]carbamate

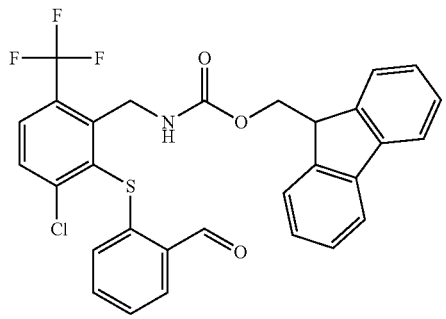 [SMILES: O=Cc1ccccc1Sc1c(Cl)ccc(C(F)(F)F)c1CNC(=O)OCC1c2ccccc2-c2ccccc21]

To a stirred solution of methyl 2-mercapto-benzoic acid methyl ester (2 g, 11.89 mmol) and 2,3-dichloro-6-(trifluoromethyl)benzaldehyde (2.89 g, 11.889 mmol) in DMF (20 mL) was added K$_2$CO$_3$ (1.64 g, 11.89 mmol) and reaction mass was stirred at 25° C. for 30 min. Reaction mixture was diluted with ethyl acetate and washed with water. The separated organic layer was washed with brine solution, dried over anhydrous sodium sulfate and evaporated under reduced pressure. The crude thus obtained was purified by normal silica column using 0-5% ethyl acetate in hexane to get methyl 2-[6-chloro-2-formyl-3-(trifluoromethyl)phenyl]sulfanylbenzoate (2.3 g, 51%) as a white solid. MS found: 375 (M+H).

To a stirred solution of methyl 2-[6-chloro-2-formyl-3-(trifluoromethyl)phenyl]sulfanyl-benzoate (4.5 g, 12.007 mmol) in THF (50 mL) was added 2-methylpropane-2-sulfinamide (1.45 g, 12.0 mmol), Ti(OEt)$_4$ (12.68 mL, 60.04 mmol) and reaction mass was heated to 70° C. for 16h. The reaction mass was quenched with saturated sodium chloride solution, solid obtained was filtered through celite pad, washed with ethyl acetate. The separated organic layer was dried over anhydrous sodium sulfate and evaporated under reduced pressure to get ethyl 2-[2-[(E)-tert-butylsulfinyliminomethyl]-6-chloro-3-(trifluoromethyl)phenyl]sulfanylbenzoate (5.8 g crude) which was directly used for next step without further purification. MS found: 491.8 (M+H).

To a stirred solution of ethyl 2-[2-[(E)-tert-butylsulfinyliminomethyl]-6-chloro-3-(trifluoromethyl)phenyl]sulfanylbenzoate (5.8 g, 15.185 mmol) in THF (60 mL) was added LiBH$_4$ (3.2 g, 151.85 mmol) and reaction mass was heated to 50° C. for 4h. Reaction mixture was quenched with saturated ammonium chloride solution and extracted with ethyl acetate. The separated organic layer was washed with water, brine solution, dried over anhydrous sodium sulfate and evaporated under reduced pressure. The crude thus obtained was purified by normal silica column using 5-40% ethyl acetate in hexane to get N-[[3-chloro-2-[2-(hydroxymethyl)phenyl]sulfanyl-6-(trifluoromethyl)phenyl]methyl]-2-methyl-propane-2-sulfinamide (3.7 g, 69%, 2 steps) as a off white solid. MS found: 452.2 (M+H).

To a stirred solution of N-[[3-chloro-2-[2-(hydroxymethyl)phenyl]sulfanyl-6-(trifluoromethyl)phenyl]methyl]-2-methyl-propane-2-sulfinamide (3.7 g, 8.18 mmol) in MeOH (40 mL), was added 4M HCl in dioxane (20 mL) at 0° C. and reaction mixture was stirred at 25° C. for 1 h. After completion of reaction, reaction mixture was concentrated under reduced pressure to get [2-[2-(aminomethyl)-6-chloro-3-(trifluoromethyl)phenyl]sulfanylphenyl]methanol (3.6 g, crude) which was directly used for next step without further purification. MS found: 347.8 (M+H).

To a stirred suspension of [2-[2-(aminomethyl)-6-chloro-3-(trifluoromethyl)phenyl]sulfanylphenyl]methanol (3.6 g, 9.368 mmol) in 5% NaHCO$_3$ (35 mL) was added Fmoc OSU (3.1 g, 9.368 mmol) in CH$_3$CN (35 mL) at 25° C. and reaction mixture was stirred at 25° C. for 2h. Then reaction mass was diluted with water and extracted with ethyl acetate. The separated organic layer was washed with brine solution, dried over anhydrous sodium sulfate and evaporated under reduced pressure. The crude thus obtained was purified by normal silica column using 5-30% ethyl acetate in hexane to get 9H-fluoren-9-ylmethyl N-[[3-chloro-2-[2-(hydroxymethyl)phenyl]sulfanyl-6-(trifluoromethyl)phenyl]methyl]carbamate (2.96 g, 63%, 2 steps) as a off white solid. MS found: 569.9 (M+H).

To a stirred solution of get 9H-fluoren-9-ylmethyl N-[[3-chloro-2-[2-(hydroxymethyl)phenyl]sulfanyl-6-(trifluoromethyl)phenyl]methyl]carbamate (2.9 g, 5.087 mmol) in DCM/THF (1:1, 60 mL) was added MnO$_2$ (8.84 g, 101.749 mmol) and reaction mixture was stirred at 25° C. for 2h. The reaction mass was filtered through celite pad, filtrate was evaporated under reduced pressure. The crude thus obtained was purified by normal silica column using 5-20% ethyl acetate in hexane to get 9H-fluoren-9-ylmethyl N-[[3-chloro-2-(2-formylphenyl)sulfanyl-6-(trifluoromethyl)phenyl]methyl]carbamate (2 g, 69%) as a off white solid. MS found: 567.9 (M+H).

$^1$H-NMR: (400 MHz, DMSO-d6) δ 4.01-4.03 (1H; m); 4.22-4.28 (2H; m); 4.41 (2H; d; J=5.6 Hz); 6.53 (1H; d; J=7.76 Hz); 7.30 (2H; t; J=7.4 Hz); 7.42 (3H; t; J=7.4 Hz); 7.49-7.51 (1H; m); 7.67 (2H; d; J=7.36 Hz); 7.74 (1H; br s); 7.89 (2H; d; J=7.8 Hz); 7.99-8.03 (2H; m); 8.07 (1H; s); 10.20 (1H; s).

Intermediate 17

9H-fluoren-9-ylmethyl N-[[3,6-difluoro-2-(2-formylphenyl)sulfanyl-phenyl]methyl]carbamate

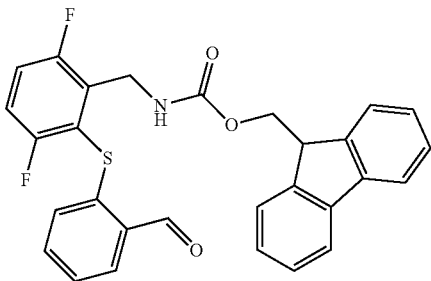

To a stirred solution of methyl 2-Mercapto-benzoic acid methyl ester (1.37 g, 8.153 mmol) and 2-chloro-3,6-difluorobenzaldehyde (1.43 g, 8.153 mmol) in DMF (12 mL) was added K$_2$CO$_3$ (1.12 g, 8.153 mmol) and reaction mass was stirred at 25° C. for 30 min. Reaction mixture was diluted with ethyl acetate and washed with water. The separated organic layer was washed with brine solution, dried over anhydrous sodium sulfate and evaporated under reduced pressure. The crude thus obtained was purified by normal silica column using 0-2% ethyl acetate in hexane to get methyl 2-(3,6-difluoro-2-formyl-phenyl)sulfanylbenzoate (1 g, 40%) as a yellow solid. MS found: 309.3 (M+H).

To a stirred solution of methyl 2-(3,6-difluoro-2-formylphenyl)sulfanylbenzoate (1.7 g, 5.519 mmol) in THF (20 mL) was added 2-methylpropane-2-sulfinamide (0.669 g, 5.519 mmol), Ti(OEt)$_4$ (5.786 mL, 27.597 mmol) and reaction mass was heated to 70° C. for 4h. The reaction mass was quenched with saturated sodium chloride solution, solid obtained was filtered through celite pad, washed with ethyl acetate. The separated organic layer was dried over anhydrous sodium sulfate and evaporated under reduced pressure to get ethyl 2-[2-[(E)-tert-butylsulfinyliminomethyl]-3,6-difluoro-phenyl]sulfanylbenzoate (2.4 g crude) which was directly used for next step without further purification. MS found: 425.7 (M+H).

To a stirred solution of ethyl 2-[2-[(E)-tert-butylsulfinyliminomethyl]-3,6-difluoro-phenyl]sulfanylbenzoate (2.4 g, 5.647 mmol) in THF (30 mL) was added LiBH$_4$ (1.23 g, 56.471 mmol) and reaction mass was heated to 70° C. for 2h. Reaction mixture was quenched with saturated ammonium chloride solution and extracted with ethyl acetate. The separated organic layer was washed with water, brine solution, dried over anhydrous sodium sulfate and evaporated under reduced pressure. The crude thus obtained was purified by normal silica column using 5-50% ethyl acetate in hexane to get N-[[3,6-difluoro-2-[2-(hydroxymethyl)phenyl]sulfanyl-phenyl]methyl]-2-methyl-propane-2-sulfinamide (1.6 g, 75%, 2 steps) as a off white solid. MS found: 385.9 (M+H).

To a stirred solution of N-[[3,6-difluoro-2-[2-(hydroxymethyl)phenyl]sulfanyl-phenyl]methyl]-2-methyl-propane-2-sulfinamide (1.6 g, 3.855 mmol) in MeOH (25 mL), was added 4M HCl in dioxane (12 mL) at 0° C. and reaction mixture was stirred at 25° C. for 1 h. After completion of reaction, reaction mixture was concentrated under reduced pressure to get [2-[2-(aminomethyl)-3,6-difluoro-phenyl]sulfanylphenyl]methanol (1.6 g, crude) which was directly used for next step without further purification. MS found: 281.9 (M+H).

To a stirred suspension of [2-[2-(aminomethyl)-3,6-difluoro-phenyl]sulfanylphenyl]methanol (1.6 g, 5.112 mmol) in 5% NaHCO$_3$(20 mL) was added Fmoc OSU (1.724 g, 5.112 mmol) in CH$_3$CN (20 mL) at 25° C. and reaction mixture was stirred at 25° C. for 3h. Then reaction mass was diluted with water and extracted with ethyl acetate. The separated organic layer was washed with brine solution, dried over sodium sulfate and evaporated under reduced pressure. The crude thus obtained was purified by normal silica column using 30% ethyl acetate in hexane to get 9H-fluoren-9-ylmethyl N-[[3,6-difluoro-2-[2-(hydroxymethyl)phenyl]sulfanyl-phenyl]methyl]carbamate (2 g, 95%, 2 steps) as a off white solid. MS found: 503.9 (M+H).

To a stirred solution of 9H-fluoren-9-ylmethyl N-[[3,6-difluoro-2-[2-(hydroxymethyl)phenyl]sulfanyl-phenyl]methyl]carbamate (2 g, 3.976 mmol) in DCM/THF (1:1, 50 mL) was added MnO$_2$ (6.913 g, 79.523 mmol) and reaction mixture was stirred at 25° C. for 2h.

The reaction mass was filtered through celite pad, filtrate was evaporated under reduced pressure. The crude thus obtained was purified by normal silica column using 0-12% ethyl acetate in hexane to get 9H-fluoren-9-ylmethyl N-[[3,6-difluoro-2-(2-formylphenyl)sulfanyl-phenyl]methyl]carbamate (1 g, 50%) as a off white solid. MS found: 502.1 (M+H).

$^1$H-NMR: (400 MHz, DMSO-d6) δ 4.12-4.14 (3H; m); 4.40 (2H; d; J=3.68 Hz); 6.70 (1H; d; J=7.76 Hz); 7.20-7.31 (2H; m); 7.33-7.45 (4H; m); 7.49-7.53 (1H; m); 7.64 (2H; d; J=7.44 Hz); 7.69 (1H; m); 7.82 (2H; d; J=7.52 Hz); 7.99 (1H; d; J=7.4 Hz); 10.19 (1H; s).

Intermediate 18

9H-fluoren-9-ylmethyl N-[[2-(2-fluoro-6-formylphenyl)sulfanylphenyl]methyl]carbamate

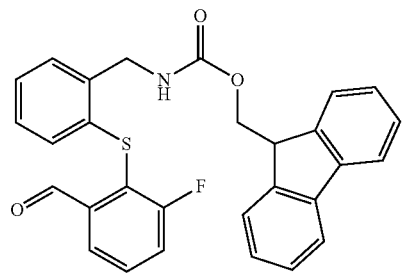 [SMILES: O=Cc1cccc(F)c1Sc1ccccc1CNC(=O)OCC1c2ccccc2-c2ccccc21]

To an ice cooled suspension of 2,3-Difluoro-benzaldehyde (4.0 g, 28.16 mmol) and $K_2CO_3$ (7.77 g, 56.33 mmol) in DMF (15 mL) was added 2-Mercapto-benzoic acid methyl ester (4.7 g, 28.16 mmol) and the reaction mixture was stirred for 1 h at 0° C. Progress of the reaction was monitored by TLC. After completion, the reaction mixture was diluted with water (100 mL) and extracted with ethyl acetate (2×100 mL). Combined organic layers were dried over sodium sulphate and concentrated under reduced pressure to get crude compound which was triturated with hexane to get methyl 2-(2-fluoro-6-formyl-phenyl)sulfanyl-benzoate (5.5 g, 67%) as off-white solid. LCMS: 290.9 (M+H).

To a solution of methyl 2-(2-fluoro-6-formyl-phenyl)sulfanylbenzoate (i.e. 3d) (3 g, 10.34 mmol) in toluene (50 mL) were added ethylene glycol (1.2 mL, 20.68 mmol) and p-TSA (0.19 g, 1.03 mmol) and the reaction mixture was heated to 140° C. using Dean-Stark condenser for 3 h. Progress of the reaction was monitored by TLC. Then the reaction mixture was poured onto saturated sodium bicarbonate solution and extracted with ethyl acetate (2×50 mL). Combined organic layer was dried over anhydrous sodium sulfate, filtered and concentrated to get methyl 2-[2-(1,3-dioxolan-2-yl)-6-fluoro-phenyl]sulfanylbenzoate (3 g, 86%) which was used as such in next step without purification. LC-MS: 334.7 (M+H).

To an ice cooled suspension of LAH (1.19 g, 31.43 mmol) in THF (40 mL) was added a solution of get methyl 2-[2-(1,3-dioxolan-2-yl)-6-fluoro-phenyl]sulfanylbenzoate (3.5 g, 10.47 mmol) in THF (40 mL) and the reaction mixture was stirred for 30 min. Then the reaction mixture was quenched with saturated sodium sulphate solution (20 mL), stirred for 30 min and filtered through celite, washed with ethyl acetate (3×100 mL). Filtrate was concentrated to get [2-[2-(1,3-dioxolan-2-yl)-6-fluoro-phenyl]sulfanylphenyl]methanol (3 g, 93%) as viscous oil. LC-MS: 324 (M+NH_4).

To an ice cooled solution of [2-[2-(1,3-dioxolan-2-yl)-6-fluoro-phenyl]sulfanylphenyl]methanol (3 g, 9.80 mmol) in DCM (50 mL) were added $Et_3N$ (4.08 mL, 29.41 mmol) and methanesulfonyl chloride (1.13 g, 14.70 mmol) and the resultant reaction mixture was stirred for 30 min. Then the reaction mixture was diluted by water (100 mL) and extracted with DCM (50 mL). Organic layer was dried over anhydrous sodium sulphate and concentrated under reduced pressure to afford [2-[2-(1,3-dioxolan-2-yl)-6-fluoro-phenyl]sulfanylphenyl]methyl methanesulfonate (3.5 g, 93%) as pale yellow liquid which was used as such in next step without further purification. LC-MS: 384.9 (M+H).

To a solution of [2-[2-(1,3-dioxolan-2-yl)-6-fluoro-phenyl]sulfanylphenyl]methyl methanesulfonate (3.5 g, 9.11 mmol) in THF (40 mL) was added liquid ammonia (15 mL) at −78° C. Then the reaction mixture gradually heated to 55° C. for 4 h. Volatiles were removed under reduced pressure to afford [2-[2-(1,3-dioxolan-2-yl)-6-fluoro-phenyl]sulfanylphenyl]methanamine (2.5 g, 94%) as viscous oil. LCMS: 305.8 (M+H).

To an ice cooled suspension of [2-[2-(1,3-dioxolan-2-yl)-6-fluoro-phenyl]sulfanylphenyl]methanamine (2.5 g, 8.19 mmol) in acetonitrile (60 mL) was added 5% aqueous $NaHCO_3$ (5 mL) followed by a solution of Fmoc-OSu (2.76 g, 8.19 mmol) in $CH_3CN$ (40 mL) and the reaction mixture was stirred at ambient temperature for 4 h. It was then diluted with ethyl acetate (200 mL) and water (200 mL). Organic layer was separated off, washed with water, brine, dried over anhydrous sodium sulfate and evaporated under reduced pressure to get the crude compound. The crude compound thus obtained was purified by flash-chromatography (20% EtOAc in hexane) to get 9H-fluoren-9-ylmethyl N-[[2-[2-(1,3-dioxolan-2-yl)-6-fluoro-phenyl]sulfanylphenyl]methyl]carbamate (1.5 g, 39%) as white solid. LC-MS: 527.6 (M+H).

To an ice cooled solution of 9H-fluoren-9-ylmethyl N-[[2-[2-(1,3-dioxolan-2-yl)-6-fluoro-phenyl]sulfanylphenyl]methyl]carbamate (1.5 g, 2.84 mmol) in acetone (50 mL) was added of conc. HCl solution (8 mL) and the reaction mixture was stirred at RT for 1 h. Progress of the reaction was monitored by TLC. After completion, volatiles were removed under reduced pressure and the crude reaction mixture was dissolved in sodium bicarbonate solution. The aq. layer was extracted with ethyl acetate, dried over anhydrous sodium sulphate, filtered and concentrated to get crude compound which was further purified by flash column chromatography (20% EtOAc in hexane) to get 9H-fluoren-9-ylmethyl N-[[2-(2-fluoro-6-formyl-phenyl)sulfanylphenyl]methyl]carbamate (1.0 g, 72%) as white solid. LC-MS: 483.9 (M+H).

$^1$H-NMR: (400 MHz, DMSO-d6): δ 4.26-4.23 (1H, m), 4.38-4.35 (4H, m), 6.86 (1H, d, J=7.7 Hz), 7.19-7.14 (1H, m), 7.23-7.22 (2H, m), 7.33 (2H, t, J=7.3 Hz), 7.42 (2H, t, J=7.3 Hz), 7.79-7.64 (5H, m), 7.93-7.88 (3H, m), 10.44 (1H, s).

Intermediate 19

9H-fluoren-9-ylmethyl N-[[3-fluoro-2-(2-formylphenyl)sulfanyl-phenyl]methyl]carbamate

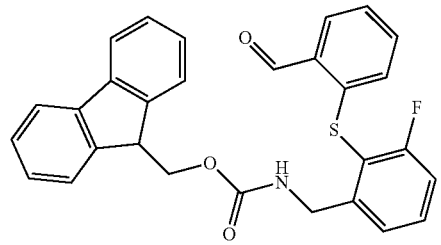 [SMILES: O=Cc1ccccc1Sc1c(F)cccc1CNC(=O)OCC1c2ccccc2-c2ccccc21]

To an ice cooled suspension of 2,3-Difluoro-benzaldehyde (4.7 g, 28.16 mmol) and $K_2CO_3$ (7.77 g, 56.33 mmol) in DMF (15 mL) was added 2-Mercapto-benzoic acid methyl ester (4 g, 28.16 mmol) and the reaction mixture was stirred for 1 h at 0° C. Progress of the reaction was monitored by TLC. After completion, the reaction mixture was diluted with water (100 mL) and extracted with ethyl acetate (2×100 mL). Combined organic layers were dried over sodium sulphate and concentrated under reduced pressure to get crude compound which was triturated with hexane to get methyl 2-(2-fluoro-6-formyl-phenyl)sulfanyl-benzoate (5.5 g, 67%) as off-white solid. LCMS: 290.9 (M+H).

To a solution of methyl 2-(2-fluoro-6-formyl-phenyl)sulfanylbenzoate (3 g, 10.34 mmol) in dry THF (50 mL) under argon atmosphere at room temperature was added tert-butyl sulphinamide (1.87 g, 15.51 mmol) followed by titanium (IV) ethoxide (3.53 g, 15.51 mmol) and the reaction mixture was heated to 70° C. for 3 h. After completion, the reaction mixture was cooled to room temperature, poured onto water (10 mL) and filtered through celite bed. Celite bed was washed with ethyl acetate (100 mL). Organic layer was separated off, washed with water (100 mL) and dried over anhydrous sodium sulfate. Organic layer was concentrated under reduced pressure to get methyl 2-[2-[(E)-tert-butylsulfinyliminomethyl]-6-fluoro-phenyl]sulfanylbenzoate (2.5 g, 61%) as yellow solid. LCMS: 393.8 (M+H).

To an ice cooled suspension of LAH (0.72 g, 19.04 mmol) in THF (30 mL) was methyl 2-[2-[(E)-tert-butylsulfinyliminomethyl]-6-fluoro-phenyl]sulfanylbenzoate (2.5 g, 6.36 mmol) in THF (40 mL) and the reaction mixture was stirred at that temperature for 30 min. Then the reaction mixture was quenched with saturated sodium sulphate solution (15 mL) and filtered through celite. Filtrate was concentrated to get N-[[3-fluoro-2-[2-(hydroxymethyl)phenyl]sulfanyl-phenyl]methyl]-2-methyl-propane-2-sulfinamide (2.2 g, 94%) as off-white solid. LCMS: 367.8 (M+H).

To an ice cooled solution of N-[[3-fluoro-2-[2-(hydroxymethyl)phenyl]sulfanyl-phenyl]methyl]-2-methyl-propane-2-sulfinamide (2.2 g, 5.99 mmol) in DCM (100 mL) was added Dess-Martin periodinane (3.81 g, 8.99 mmol) and the reaction mixture was stirred at RT for 1 h. Progress of the reaction was monitored by TLC. After completion, the reaction mixture was diluted with NaHCO₃ (100 mL) and extracted with DCM (2×100 mL). Combined organic layer was washed with saturated sodium thiosulphate solution, dried over anhydrous sodium sulphate, filtered and concentrated to get crude compound which was purified by flash column chromatography (50% EtOAc in hexane) to get N-[[3-fluoro-2-(2-formylphenyl)sulfanyl-phenyl]methyl]-2-methyl-propane-2-sulfinamide (1.8 g, 82%) as white solid. LCMS: 365.8 (M+H).

To an ice cooled solution of N-[[3-fluoro-2-(2-formylphenyl)sulfanyl-phenyl]methyl]-2-methyl-propane-2-sulfinamide (1.8 g, 2.88 mmol) in dioxane (40 mL) was added HCl in dioxane (20 mL, 4M) and the reaction mixture was stirred at RT for 3h. Progress of the reaction was monitored by TLC. Volatiles were removed under reduced pressure and the crude compound was triturated with diethyl ether followed by drying under reduced pressure to get 2-[2-(aminomethyl)-6-fluoro-phenyl]sulfanylbenzaldehyde (1 g, 88%) as white solid. LCMS: 261.7 (M+H).

To a stirred suspension of 2-[2-(aminomethyl)-6-fluoro-phenyl]sulfanylbenzaldehyde (1.0 g, 3.83 mmol) in acetonitrile (50 mL) and 5% aqueous was added a solution of Fmoc-OSu (1.29 g, 3.83 mmol) in acetonitrile (30 mL) and the reaction mixture was stirred at ambient temperature for 4 h. It was then diluted with ethyl acetate (200 mL) and water (200 mL). Organic layer was separated off, washed with water, brine, dried over anhydrous sodium sulfate and evaporated under reduced pressure to get crude compound. The crude compound thus obtained was purified by flash-chromatography (10% ethyl acetate in hexane) to afford 9H-fluoren-9-ylmethyl N-[[3-fluoro-2-(2-formylphenyl)sulfanyl-phenyl]methyl]carbamate (0.65 g, 22% over two steps) as white solid. LCMS: 484.0 (M+H).

¹H-NMR: (400 MHz, DMSO-d6): δ 4.21 (1H, t, J=6.6 Hz), 4.33-4.28 (4H, m), 6.60 (1H, d, J=8.0), 7.23 (1H, d, J=7.7 Hz), 7.48-7.30 (7H, m), 7.64-7.58 (1H, m), 7.68 (2H, d, J=7.4 Hz), 7.90-7.85 (3H, m), 8.00 (1H, d, J=6.9 Hz), 10.19 (1H, s).

Intermediate 20

9H-fluoren-9-ylmethyl N-[[5-chloro-2-(2-formylphenyl)sulfanyl-3-(trifluoromethyl)phenyl]methyl] carbamate

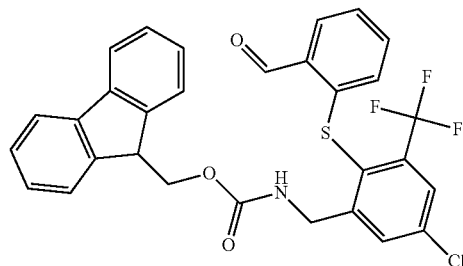 [SMILES: O=Cc1ccccc1Sc1c(CNC(=O)OCC2c3ccccc3-c3ccccc32)cc(Cl)cc1C(F)(F)F]

To a suspension of 5-Chloro-2-fluoro-3-trifluoromethyl-benzaldehyde (1.5 g, 6.62 mmol) and K₂CO₃ (1.8 g, 13.24 mmol) in DMF (15 mL) was added 2-Mercapto-benzoic acid methyl ester (1.1 g, 6.62 mmol) added and the reaction mixture was stirred for 2 h at room temperature. Progress of the reaction was monitored by TLC. After completion, the reaction mixture was diluted with water (100 mL) and extracted with (3×250 mL) ethyl acetate. Combined organic layer was dried over sodium sulphate and concentrated under reduced pressure to get crude compound which was purified by silica gel (100-200 mesh) column chromatography (20% ethyl acetate and hexane) to get methyl 2-[4-chloro-2-formyl-6-(trifluoromethyl)phenyl]sulfanylbenzoate (2.3 g, 93%) as brown solid.

To a solution of methyl 2-[4-chloro-2-formyl-6-(trifluoromethyl)phenyl]sulfanylbenzoate (2.6 g, 6.95 mmol) and tert-butyl sulphinamide (1.8 g, 15.29 mmol) in THF (50 mL) was added titanium tetraethoxide (3.48 g, 15.29 mmol) and the reaction mixture was heated to 60° C. for 3h. Progress of the reaction was monitored by TLC. After completion, the reaction mixture was diluted with water (100 mL) and extracted with ethyl acetate (3×100 mL). Combined organic layer was dried over sodium sulphate and concentrated to get crude compound which was purified by silica gel (100-200 mesh) column chromatography (30% ethyl acetate and hexane) to get methyl 2-[2-[(E)-tert-butylsulfinyliminomethyl]-4-chloro-6-(trifluoromethyl)phenyl]sulfanylbenzoate (1.9 g, 57%) as brown solid. LC-MS: 477.9 (M+H).

To an ice cooled suspension LAH (0.45 g, 11.95 mmol) in THF (20 mL) was added a solution of methyl 2-[2-[(E)-tert-butylsulfinyliminomethyl]-4-chloro-6-(trifluoromethyl)phenyl]sulfanylbenzoate (1.9 g, 3.98 mmol) in THF (30 mL) and the reaction mixture was stirred for 1 h. Progress of the reaction was monitored by TLC. After completion, the reaction mixture was quenched with aq. sodium sulphate solution (50 mL) and extracted with ethyl acetate (3×100 mL). Combined organic layer was dried over sodium sulphate and concentrated under reduced pressure to get crude compound which was washed with hexane followed by pentane to get N-[[5-chloro-2-[2-(hydroxymethyl)phenyl]sulfanyl-3-(trifluoromethyl)phenyl]methyl]-2-methyl-propane-2-sulfinamide (1.6 g, 89%) as off white solid. LC-MS: 452.0 (M+H).

To a suspension of N-[[5-chloro-2-[2-(hydroxymethyl)phenyl]sulfanyl-3-(trifluoromethyl)phenyl]methyl]-2-methyl-propane-2-sulfinamide (1.6 g, 3.54 mmol) in DCM (50 mL) was added Dess-Martin periodinane (3.7 g, 8.86 mmol) and the reaction mixture was stirred at RT for 2 h. Progress the reaction mass was monitored by TLC. After completion, the reaction mixture was diluted with water (100 mL) and extracted with DCM (3×100 mL). Combined organic layer was dried over sodium sulphate and concentrated under reduced pressure to get crude compound. The crude compound thus obtained was purified by silica gel (100-200 mesh) column chromatography (ethyl acetate) and concentrated under reduced pressure to get N-[[5-chloro-2-(2-formylphenyl)sulfanyl-3-(trifluoromethyl)phenyl]methyl]-2-methyl-propane-2-sulfinamide (0.900 g, 56%) as white solid. LC-MS: 449.7 (M+H).

To an ice cooled solution of N-[[5-chloro-2-(2-formylphenyl)sulfanyl-3-(trifluoromethyl)phenyl]methyl]-2-methyl-propane-2-sulfinamide (0.9 g, 0.0020 mol) in 1,4 dioxane (20 mL) was added 4M HCl in dioxane (4 mL) and the reaction mixture was stirred at ambient temperature for 2 h. Volatiles were removed under reduced pressure to obtain 2-[2-(aminomethyl)-4-chloro-6-(trifluoromethyl)phenyl]sulfanylbenzaldehyde (0.65 g, 94%) as off white solid. LC-MS: 346.0 (M+H).

To a solution of N-[[5-chloro-2-(2-formylphenyl)sulfanyl-3-(trifluoromethyl)phenyl]methyl]-2-methyl-propane-2-sulfinamide (0.9 g, 0.0020 mol) in 5% aqueous NaHCO$_3$ solution (12 mL) was added Fmoc-OSu (0.558 g, 0.0020 mol) in CH$_3$CN (50 mL) and the reaction mixture was stirred at room temperature for 3 h. Then the reaction mixture was diluted with ethyl acetate and washed with water followed by brine. Organic layer was separated off, dried over sodium sulfate and evaporated under reduced pressure to get the crude compound which was purified by flash-chromatography to get 9H-fluoren-9-ylmethyl N-[[5-chloro-2-(2-formylphenyl)sulfanyl-3-(trifluoromethyl)phenyl]methyl]carbamate (0.435 g, 32%) as off white solid. LC-MS: 568.0 (M+H).

$^1$H-NMR: (400 MHz, DMSO-d6): δ 4.23-4.20 (3H, m), 4.32-4.30 (2H, m), 6.43 (1H, d, J=8.0 Hz), 7.34-7.30 (2H, m), 7.44-7.37 (4H, m), 7.67 (2H, d, J=7.4 Hz), 7.70 (1H, br s), 7.89 (3H, d, J=7.5 Hz), 8.03-8.00 (2H, m), 10.15 (1H, s).

Intermediate 21

9H-fluoren-9-ylmethyl N-[[3-chloro-2-(2-formylphenyl)sulfanyl-5-(trifluoromethyl)phenyl]methyl] carbamate

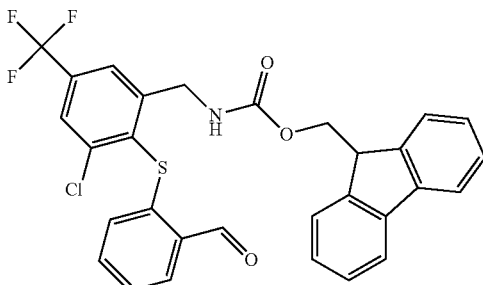

A suspension of 3-Chloro-2-fluoro-5-trifluoromethyl-benzaldehyde (2.5 g, 11.06 mmol) and K$_2$CO$_3$ (3.0 g, 22.12 mmol) in DMF (15 mL) was added 2-Mercapto-benzoic acid methyl ester (1.8 g, 11.06 mmol) and the reaction mixture was stirred for 2 h at room temperature. Progress of the reaction was monitored by TLC. After completion, the reaction mixture was diluted with water (100 mL) and extracted with ethyl acetate (3×250 mL). Combined organic layer was dried over sodium sulphate and concentrated under reduced pressure to get crude compound. The crude compound thus obtained was purified by silica gel column chromatography (100-200 mesh) using 20% ethyl acetate and hexane as eluent to get methyl 2-[2-chloro-6-formyl-4-(trifluoromethyl)phenyl]sulfanylbenzoate (3.5 g, 85%) as brown solid.

To a suspension of methyl 2-[2-chloro-6-formyl-4-(trifluoromethyl)phenyl]sulfanylbenzoate (3.5 g, 9.36 mmol) and tert-butyl sulphinamide (1.6 g, 14.03 mmol) in THF (50 mL) was added titanium tetraethoxide (3.2 g, 14.03 mmol) and the reaction mixture was heated to 60° C. for 3 h. Progress of the reaction was monitored by TLC. After completion, the reaction mixture was diluted water (100 mL) and extracted with ethyl acetate (3×100 mL). Combined organic layer was dried over sodium sulphate and concentrated under reduced pressure to get crude compound. The crude compound thus obtained was purified by silica gel (100-200 mesh) column chromatography (30% ethyl acetate and hexane) to get methyl 2-[2-[(E)-tert-butylsulfinyliminomethyl]-6-chloro-4-(trifluoromethyl)phenyl]sulfanylbenzoate (4 g, 89%) as brown solid. LC-MS: 477.9 (M+H).

To an ice cooled suspension of LAH (0.955 g, 25.15 mmol) in THF (25 mL) was added a solution of 2-[2-[(E)-tert-butylsulfinyliminomethyl]-6-chloro-4-(trifluoromethyl)phenyl]sulfanylbenzoate (4 g, 8.38 mmol) in THF (25 mL) and the reaction mixture was stirred for 1 h. Progress of the reaction was monitored by TLC. After completion, the reaction mixture was diluted with aq. sodium sulphate solution (100 mL) and extracted with ethyl acetate (3×250 ml). Combined organic layer was dried over sodium sulphate and concentrated under reduced pressure to get crude compound which was purified by washing with hexane followed by pentane to get N-[[3-chloro-2-[2-(hydroxymethyl)phenyl]sulfanyl-5-(trifluoromethyl)phenyl]methyl]-2-methyl-propane-2-sulfinamide (3.9 g, 95%) as brown solid. LC-MS: 452.1 (M+H).

To a solution of N-[[3-chloro-2-[2-(hydroxymethyl)phenyl]sulfanyl-5-(trifluoromethyl)phenyl]methyl]-2-methyl-propane-2-sulfinamide (3.9 g, 8.64 mmol) in DCM (100 mL) was added Dess-Martin periodinane (9.17 g, 21.62 mmol) and the reaction mixture was stirred at RT for 3 h. Progress of the reaction was monitored by TLC. After completion, the reaction mixture was diluted with NaHCO$_3$ solution (100 mL) and extracted with DCM (3×100 mL). Combined organic layer was dried over sodium sulphate and concentrated under reduced pressure to get crude compound. The crude compound thus obtained was purified by silica gel (100-200 mesh) column chromatography (ethyl acetate) to get N-[[3-chloro-2-(2-formylphenyl)sulfanyl-5-(trifluoromethyl)phenyl]methyl]-2-methyl-propane-2-sulfinamide (2 g, 51%) as white solid. LC-MS: 449.7 (M+H).

To an ice cooled solution of N-[[3-chloro-2-(2-formylphenyl)sulfanyl-5-(trifluoromethyl)phenyl]methyl]-2-methyl-propane-2-sulfinamide (2 g, 4.45 mmol) in 1,4 dioxane (50 mL) was added 4M HCl in dioxane (4 mL) and the resultant reaction mixture was stirred at ambient temperature for 2 h. Volatiles were evaporated under reduced pressure to obtain 2-[2-(aminomethyl)-6-chloro-4-(trifluoromethyl)phenyl]sulfanylbenzaldehyde (1.5 g, 98%) as off white solid. LC-MS: 346.1 (M+H).

To a solution of 2-[2-(aminomethyl)-6-chloro-4-(trifluoromethyl)phenyl]sulfanylbenzaldehyde (2 g, 5.24 mmol) in 5% aqueous NaHCO$_3$ solution (12 mL) was added Fmoc-OSu (1.42 g, 4.19 mmol) in CH$_3$CN (50 mL) and the reaction mixture was stirred at ambient temperature for 3 h. Progress of the reaction was monitored by TLC. After completion, the reaction mixture was diluted with ethyl acetate and washed with water followed by brine. Combined organic layer was dried over sodium sulfate and evaporated under reduced pressure to get crude compound which was purified by flash-chromatography to get 9H-fluoren-9-ylmethyl N-[[3-chloro-2-(2-formylphenyl)sulfanyl-5-(trifluoromethyl)phenyl]methyl]carbamate (0.700 g, 34%) as off white solid. LC-MS: 568.1 (M+H).

$^1$H-NMR: (400 MHz, CDCl$_3$): δ 4.15 (1H, t, J=6.9 Hz), 4.37 (2H, d, J=6.9 Hz), 4.55 (2H, d, J=6.4 Hz), 5.29-5.26 (1H, br), 6.52 (1H, d, J=7.0 Hz), 7.29-7.27 (2H, m), 7.34-7.30 (2H, m), 7.41-7.36 (2H, m), 7.51 (2H, d, J=7.4 Hz), 7.76-7.73 (4H, m), 7.87-7.85 (1H, m), 10.25 (1H, s).

Intermediate 22

9H-fluoren-9-ylmethyl N-[[3-chloro-6-fluoro-2-(2-formylphenyl)sulfanyl-phenyl]methyl]carbamate

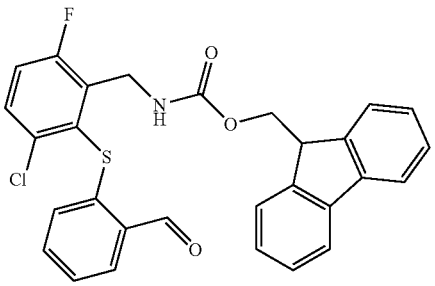

To a solution of 2,3 dichloro 6-fluoro benzaldehyde (1.0 g, 5.208 mmol) in DMF (7.0 ml) were added K$_2$CO$_3$ (720 mg, 5.208 mmol) and methyl 2-sulfanylbenzoate (876 mg, 5.208 mmol) and stirred at 25° C. for 30 min. Reaction mixture was diluted with water and extracted with EtOAc. The combined organic layer was washed with brine, dried over anhydrous sodium sulfate and concentrated under vacuum to get the compound which was purified by normal silica column using 0-2% ethyl acetate in hexane to get methyl 2-(6-chloro-3-fluoro-2-formyl-phenyl)sulfanylbenzoate (354 mg, 21%) as a yellow solid.

To the stirred solution of methyl 2-(6-chloro-3-fluoro-2-formyl-phenyl)sulfanylbenzoate (1.7 g, 5.247 mmol) in THF (25 mL) were added 2-methyl 2-propane sulfinamide (0.636 g, 5.247 mmol) and Ti(OEt)$_4$ (5.5 mL, 26.235 mmol) and reaction mixture was heated to 70° C. for 4 h. Reaction mixture was quenched with brine solution and extracted with ethyl acetate, dried over sodium sulphate and concentrated under vacuum to afford ethyl 2-({6-chloro-3-fluoro-2-[(1Z)-[(2-methylpropane-2-sulfinyl)imino]methyl]phenyl}sulfanyl)benzoate (2.2 g, crude) as a yellow liquid. MW found: 442.3 (M+H).

To a stirred solution of ethyl 2-({6-chloro-3-fluoro-2-[(1Z)-[(2-methylpropane-2-sulfinyl)imino]methyl]phenyl}sulfanyl)benzoate (2.4 g, 5.442 mmol) in THF (25 mL) was added LiBH$_4$ (1.185 g, 54.422 mmol) at 0° C. and reaction mass was heated to 70° C. for 4h. The solvent was evaporated and the reaction mixture was quenched with NH$_4$Cl and extracted with ethyl acetate. The separated organic layer was washed with brine solution, dried over sodium sulfate and evaporated under reduced pressure. The crude thus obtained was purified by normal silica column using 0-50% ethyl acetate in hexane to get N-[[3-chloro-6-fluoro-2-[2-(hydroxymethyl)phenyl]sulfanyl-phenyl]methyl]-2-methyl-propane-2-sulfinamide (1.4 g, 64%) as a off-white solid. MS found: 402.2 (M+H).

To a stirred solution of N-[[3-chloro-6-fluoro-2-[2-(hydroxymethyl)phenyl]sulfanyl-phenyl]methyl]-2-methyl-propane-2-sulfinamide (1.4 g, 3.373 mmol) in MeOH (25 mL), was added 4M HCl in dioxane (12 mL) at 0° C. and reaction mixture was stirred at 25° C. for 1 h. After completion of reaction, reaction mixture was concentrated under reduced pressure to get [2-[2-(aminomethyl)-6-chloro-3-fluoro-phenyl]sulfanylphenyl]methanol (1.4 g, crude) as a white solid. MS found: 298.2 (M+H).

To a stirred suspension of [2-[2-(aminomethyl)-6-chloro-3-fluoro-phenyl]sulfanylphenyl]methanol (1.4 g, 4.714 mmol) in 5% NaHCO$_3$(20 mL) was added Fmoc OSU (1.589 g, 4.714 mmol) in CH$_3$CN (20 mL) at 25° C. and reaction mixture was stirred at 25° C. for 3h. Then reaction mixture was diluted with water and extracted with ethyl acetate. The separated organic layer was washed with brine solution, dried over sodium sulfate and evaporated under reduced pressure. The crude thus obtained was purified by normal silica column using 5-50% ethyl acetate in hexane to get 9H-fluoren-9-ylmethyl N-[[3-chloro-6-fluoro-2-[2-(hydroxymethyl)phenyl]sulfanyl-phenyl]methyl]carbamate (1.6 g, 88%, 2 steps) as off-white solid. MS found: 520 (M+H).

To a stirred solution of 9H-fluoren-9-ylmethyl N-[[3-chloro-6-fluoro-2-[2-(hydroxymethyl)phenyl]sulfanyl-phenyl]methyl]carbamate (1.6 g, 3.083 mmol) in DCM/THF (1:1, 50 mL) was added MnO$_2$ (5.36 g, 61.657 mmol) and reaction mixture was stirred at 25° C. for 2h. The reaction mass was filtered through celite pad, filtrate was evaporated under reduced pressure The crude thus obtained was purified by normal silica column using 0-13% ethyl acetate in hexane to afford 9H-fluoren-9-ylmethyl N-[[3-chloro-6-fluoro-2-(2-formylphenyl)sulfanyl-phenyl]methyl]carbamate (1.0 g, 63%) as a off-white solid. MS found: 517.8 (M+H).

$^1$H-NMR: (400 MHz, DMSO-d6) δ 4.12-4.14 (3H; m); 4.40 (2H; br s); 6.55 (1H; d; J=7.92 Hz); 7.28-7.31 (2H; m); 7.33-7.45 (4H; m); 7.51 (1H; t; J=8.96 Hz); 7.62 (2H; d; J=7.44 Hz); 7.70-7.72 (1H; m); 7.82 (2H; d; J=7.52 Hz); 7.99 (1H; d; J=7.4 Hz); 10.19 (1H; s)

Intermediate 23

9H-fluoren-9-ylmethyl N-[[2-[(3-formyl-2-pyridyl)sulfanyl]-3-(trifluoromethyl)phenyl]methyl]carbamate

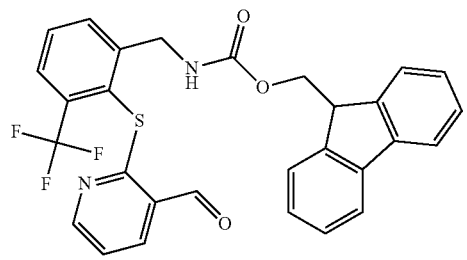 [SMILES: O=Cc1cccnc1Sc1c(CNC(=O)OCC2c3ccccc3-c3ccccc32)cccc1C(F)(F)F]

To an ice-cooled solution of 2-Fluoro-3-trifluoromethyl-benzaldehyde (3.2 g, 20.87 mmol) in DMF (30 mL) was added sodium hydride portion-wise (1.663 g, 9.16 mmol) and the reaction mixture was stirred for 30 min. To the resulting reaction mixture was added a solution of 2-Mercapto-nicotinic acid methyl ester (2.2 g, 13.87 mmol) in DMF (10 mL) dropwise and the reaction mixture was heated to 90° C. for 9 h. Progress of the reaction was monitored by TLC. After completion, the reaction mixture was cooled at 0° C. and potassium carbonate (3.83 g, 27.742 mmol) followed by methyl iodide (5.90 g, 27.74 mmol) were added. The reaction mixture was stirred at room temperature for 16 h. After completion, the reaction mixture was diluted with ice cold water (100 mL) and extracted with (3×100 mL) ethyl acetate. Combined organic layer was dried over sodium sulphate and concentrated under reduced pressure to obtain crude compound. The crude compound was purified by flash-chromatography (30% EtOAc in hexane) to afford methyl 2-[2-formyl-6-(trifluoromethyl)phenyl]sulfanylpyridine-3-carboxylate (1.3 g, 33%) as an off-white solid. LC-MS: 341.7 (M+H).

To a solution of afford methyl 2-[2-formyl-6-(trifluoromethyl)phenyl]sulfanylpyridine-3-carboxylate (1.3 g, 3.81 mmol) in anhydrous THF (50 mL) was added tert butylsulphinamide (2.31 g, 19.06 mmol) followed by titanium (IV) ethoxide (4.34 g, 19.06 mmol) and the reaction mixture was heated to 60° C. for 2 h under argon atmosphere. Progress of the reaction was monitored by TLC. After completion, the reaction mixture was diluted with water (50 mL), filtered through celite and washed with ethyl acetate. Organic layer was separated off, washed with brine, dried over anhydrous sodium sulphate and concentrated under reduced pressure to get crude compound which was purified by flash-chromatography (30% EtOAc in hexane) to afford methyl 2-[2-[(Z)-tert-butylsulfinyliminomethyl]-6-(trifluoromethyl)phenyl]sulfanylpyridine-3-carboxylate (1.3 g, 77%) as an off-white solid. LC-MS: 444.9 (M+H).

To an ice-cooled suspension of LAH (0.277 g, 7.32 mmol) in THF (50 mL) was added 2-[2-[(Z)-tert-butylsulfinyliminomethyl]-6-(trifluoromethyl)phenyl]sulfanylpyridine-3-carboxylate (1.3 g, 2.93 mmol) in THF (30 mL) and the reaction mixture was stirred for 30 min at 0° C. Progress of the reaction was monitored by TLC. After completion, the reaction mixture was quenched with saturated sodium sulphate (5 mL) and filtered through celite. The residue was washed with ethyl acetate (3×50 mL) and the filtrate was concentrated to get N-[[2-[[3-(hydroxymethyl)-2-pyridyl]sulfanyl]-3-(trifluoromethyl)phenyl]methylene]-2-methyl-propane-2-sulfinamide (1.1 g, 90%) as sticky mass. LC-MS: 418.7 (M+H).

To an ice-cooled solution of N-[[2-[[3-(hydroxymethyl)-2-pyridyl]sulfanyl]-3-(trifluoromethyl)phenyl]methylene]-2-methyl-propane-2-sulfinamide (1.1 g, 2.63 mmol) in DCM (100 mL) was added Dess-Martin periodinane (1.45 g, 3.421 mmol) and the reaction mixture was stirred at room temperature for 2h. Progress of the reaction was monitored by TLC. After completion, the reaction mixture was poured onto saturated sodium bicarbonate solution and extracted with DCM (3×100 mL). Combined organic layer was washed with sodium thiosulphate, dried over sodium sulphate and concentrated under reduced pressure to get the crude compound. The crude compound was purified by flash-chromatography (30% EtOAc in hexane) to afford N-[[2-[(3-formyl-2-pyridyl)sulfanyl]-3-(trifluoromethyl)phenyl]methyl]-2-methyl-propane-2-sulfinamide (0.750 g, 69%) as an off-white solid. LC-MS: 416.9 (M+H).

To an ice-cooled solution of N-[[2-[(3-formyl-2-pyridyl)sulfanyl]-3-(trifluoromethyl)phenyl]methyl]-2-methyl-propane-2-sulfinamide (0.750 g, 1.80 mmol) in dioxane (20 mL) was added 4M HCl in dioxane (1.0 mL) and the reaction mixture was stirred at room temperature for 1 h.

Progress of the reaction was monitored by TLC. After completion, volatiles were evaporated under reduced pressure to obtain 2-[2-(aminomethyl)-6-(trifluoromethyl)phenyl]sulfanylpyridine-3-carbaldehyde (0.620 g, 100%) as an off-white solid. LC-MS: 313.0 (M+H).

To a suspension of 2-[2-(aminomethyl)-6-(trifluoromethyl)phenyl]sulfanylpyridine-3-carbaldehyde (0.620 g, 1.9808 mmol) in 5% aqueous NaHCO₃ solution (5 mL) was added Fmoc-OSu (0.534 g, 1.5846 mmol) in CH₃CN (10 mL) and the reaction mixture was stirred at room temperature for 4 h. Progress of the reaction was monitored by TLC. After completion, the reaction mixture was diluted with ethyl acetate (50 mL) and organic layer was separated off. Organic layer was washed with water followed by brine and dried over anhydrous sodium sulfate and evaporated under reduced pressure to get the crude compound. The crude compound was purified by flash-chromatography (30% EtOAc in hexane) to afford 9H-fluoren-9-ylmethyl N-[[2-[(3-formyl-2-pyridyl)sulfanyl]-3-(trifluoromethyl)phenyl]methyl]carbamate (0.635 g, 60%) as white solid. LC-MS: 534.8 (M+H).

¹H-NMR: (400 MHz, DMSO-d6): δ 4.21 (3H, m), 4.34 (2H, d, J=8.8 Hz), 7.44-7.29 (5H, m), 7.58 (1H, d, J=7.6 Hz), 7.72-7.67 (3H, m), 7.83-7.81 (2H, m), 7.89 (2H, d, J=7.5 Hz), 8.40-8.36 (2H, m), 10.18 (1H, s).

Intermediate 24

9H-fluoren-9-ylmethyl N-[[5-chloro-2-[(3-formyl-2-pyridyl)sulfanyl]phenyl]methyl]carbamate

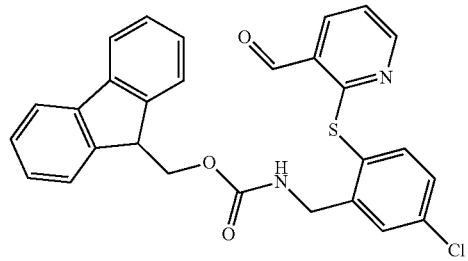 [SMILES: O=Cc1cccnc1Sc1ccc(Cl)cc1CNC(=O)OCC1c2ccccc2-c2ccccc21]

To an ice-cooled solution of 5-Chloro-2-fluoro-benzaldehyde (5.14 g, 33.10 mmol) in DMF (80 mL) was added sodium hydride portion-wise (1.52 g, 66.20 mmol) and the reaction mixture was stirred for 30 min. To the resulting reaction mixture was added 2-Mercapto-nicotinic acid methyl ester (3.5 g, 22.06 mmol) in DMF (20 mL) and the reaction mixture was heated at 90° C. for 9 h. Progress of the reaction was monitored by TLC. After completion, the reaction mixture was cooled at 0° C. and potassium carbonate (6.1 g, 44.14 mmol) and methyl iodide (9.39 g, 66.20 mmol) were added. Then the reaction mixture was stirred at room temperature for 16 h. After completion, the reaction mixture was diluted with ice cold water (100 mL) and extracted with (3×100 mL) ethyl acetate. Combined organic layer was dried over sodium sulphate and concentrated under reduced pressure to obtain crude compound. The crude compound was purified by flash-chromatography (30% EtOAc in hexane) to afford methyl 2-(4-chloro-2-formyl-phenyl)sulfanylpyridine-3-carboxylate (2.5 g, 37%) as viscous oil. LC-MS: 308.0 (M+H).

To a solution of methyl 2-(4-chloro-2-formyl-phenyl)sulfanylpyridine-3-carboxylate (2.5 g, 8.14 mmol) in anhydrous THF (50 mL) was added tert-butylsulphinamide (4.93 g, 40.72 mmol) followed by titanium (IV) ethoxide (9.28 g, 40.72 mmol) and the reaction mixture was heated to 60° C. for 2 h under argon atmosphere. Progress of the reaction was monitored by TLC. After completion, the reaction mixture was diluted with water (50 mL), filtered through celite and washed with ethyl acetate. Organic layer was separated off, washed with brine, dried over anhydrous sodium sulphate and concentrated under reduced pressure to get crude compound which was purified by flash-chromatography (30% EtOAc in hexane) to afford methyl 2-[4-chloro-2-[(Z)-trifluoromethylsulfinyliminomethyl]phenyl]sulfanylpyridine-3-carboxylate (1.5 g, 45%) as an off-white solid. LC-MS: 411.1 (M+H).

To an ice-cooled suspension of LAH (0.277 g, 7.32 mmol) in THF (50 mL) was added crude methyl 2-[4-chloro-2-[(Z)-trifluoromethylsulfinyliminomethyl]phenyl]sulfanylpyridine-3-carboxylate (1.5 g, 4.39 mmol) in THF (70 mL) and the reaction mixture was stirred for 30 min at 0° C. Progress of the reaction was monitored by TLC. After completion, the reaction mixture was quenched with saturated sodium sulphate solution (5 mL) and filtered through celite. The residue was washed with ethyl acetate (3×50 mL) and the filtrate was concentrated to get N-[[5-chloro-2-[[3-(hydroxymethyl)-2-pyridyl]sulfanyl]phenyl]methyl]-1,1,1-trifluoro-methanesulfinamide (1.1 g, 65%) as an off-white solid. LC-MS: 385.0 (M+H).

To an ice-cooled solution of N-[[5-chloro-2-[[3-(hydroxymethyl)-2-pyridyl]sulfanyl]phenyl]methyl]-1,1,1-trifluoro-methanesulfinamide (1.1 g, 2.86 mmol) in DCM (100 mL) was added Dess-Martin periodinane (1.57 g, 3.72 mmol) and the reaction mixture was stirred at room temperature for 1 h. Progress of the reaction was monitored by TLC. After completion, the reaction mixture was poured onto saturated sodium bicarbonate solution and extracted with DCM (3×100 mL). Combined organic layers were washed with sodium thiosulphate, dried over sodium sulphate and concentrated under reduced pressure to get the crude N-[[5-chloro-2-[(3-formyl-2-pyridyl)sulfanyl]phenyl]methyl]-1,1,1-trifluoro-methanesulfinamide (0.750 g, 68%) as an off-white solid. LC-MS: 382.7 (M+H).

To an ice-cooled solution of N-[[5-chloro-2-[(3-formyl-2-pyridyl)sulfanyl]phenyl]methyl]-1,1,1-trifluoro-methanesulfinamide (0.750 g, 1.96 mmol) in dioxane (20 mL) was added 4M HCl in dioxane (1.0 mL) and the reaction mixture was stirred at room temperature for 1 h. Progress of the reaction was monitored by TLC. After completion, volatiles were evaporated under reduced pressure to obtain hydrochloride salt of 2-[2-(aminomethyl)-4-chloro-phenyl]sulfanylpyridine-3-carbaldehyde (0.650 g, 66%) as sticky mass. LC-MS: 279.1 (M+H).

To a suspension of 2-[2-(aminomethyl)-4-chloro-phenyl]sulfanylpyridine-3-carbaldehyde (0.650 g, 2.34 mmol) in 5% aqueous NaHCO₃ solution (5 mL) was added Fmoc-OSu (0.788 g, 2.34 mmol) in CH₃CN (10 mL) and the reaction mixture was stirred at room temperature for 4 h. Progress of the reaction was monitored by TLC. After completion, the reaction mixture was diluted with ethyl acetate (50 mL) and organic layer was separated off. Organic layer was washed with water followed by brine and dried over anhydrous sodium sulfate. Organic layer was concentrated under reduced pressure to get the crude compound. The crude compound was purified by flash-chromatography (30% EtOAc in hexane) to afford 9H-fluoren-9-ylmethyl N-[[5-chloro-2-[(3-formyl-2-pyridyl)sulfanyl]phenyl]methyl]carbamate (0.390 g, 36%) as white solid. LC-MS: 501.0 (M+H).

¹H-NMR: (400 MHz, DMSO-d6): δ 4.24-4.18 (3H, m), 4.30 (2H, d, J=6.9 Hz), 7.43-7.31 (7H, m), 7.54 (1H, d, J=7.9 Hz), 7.69 (2H, d, J=7.4 Hz), 7.90-7.84 (3H, m), 8.34 (1H, dd, J=7.6, 1.7 Hz), 8.44 (1H, dd, J=4.7, 1.7 Hz), 10.18 (1H, s).

Intermediate 25

9H-fluoren-9-ylmethyl N-[[2-chloro-6-[(3-formyl-2-pyridyl)sulfanyl]phenyl]methyl]carbamate

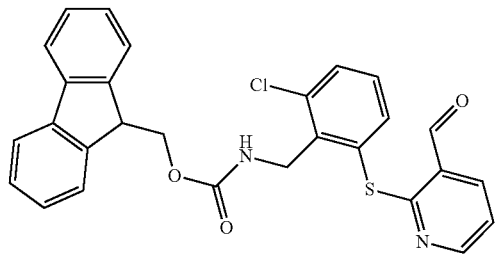 [SMILES: O=Cc1cccnc1Sc1cccc(Cl)c1CNC(=O)OCC1c2ccccc2-c2ccccc21]

To a solution 2-Chloro-6-fluoro-benzaldehyde (2.0 g, 12.89 mmol) in ethanol (80 mL, argon purged) was added sodium ethoxide (2.19 g, 32.22 mmol) and 2-Mercaptonicotinic acid (2.04 g, 12.89 mmol) at room temperature. The reaction mixture was heated to reflux for 4h. Progress of the reaction was monitored by TLC. After completion, volatiles were removed under reduced pressure to afford 2-(3-chloro-2-formyl-phenyl)sulfanylpyridine-3-carboxylic acid (6 g, crude) as brown solid which was used as such in next step without further purification. LC-MS: 294.1 (M+H).

To an ice-cooled solution of 2-(3-chloro-2-formyl-phenyl)sulfanylpyridine-3-carboxylic acid (6.0 g, crude) in DMF (25 mL) under argon atmosphere was added K₂CO₃ (2.827 g, 20.46 mmol) and the reaction mixture was stirred at 0° C. for 30 min. To the resulting reaction mixture was added MeI (1.27 mL, 20.46 mmol) and the reaction mixture was stirred at room temperature for 16 h. Then the reaction mixture was diluted with water (100 mL) and the aqueous phase was extracted with ethyl acetate (50 mL×3). Combined organic layer was washed with brine, dried over sodium sulfate and evaporated under reduced pressure to get crude compound. The crude compound thus obtained was purified by flash-chromatography (10% ethyl acetate in hexane) to afford methyl 2-(3-chloro-2-formyl-phenyl)sulfanylpyridine-3-carboxylate (1.6 g, 40% over two steps) as yellow solid. LC-MS: 307.7 (M+H).

To a stirred solution of methyl 2-(3-chloro-2-formyl-phenyl)sulfanylpyridine-3-carboxylate (1.6 g, 5.20 mmol) in dry THF (100 mL) under argon atmosphere was added titanium (IV) ethoxide (2.96 g, 13.00 mmol) followed by tert-butyl sulphinamide (1.57 g, 13.00 mmol) and the resulting reaction mixture was heated to 60° C. for 4h. Then the reaction mixture was cooled to room temperature, poured onto water (100 mL) and filtered through celite bed.

Celite bed was washed with ethyl acetate. Organic layer was separated off and the aqueous layer was extracted with ethyl acetate (50 mL×3). Combined organic layer was dried over sodium sulfate and concentrated under reduced pressure to get the crude compound. The crude compound thus obtained was purified by flash-chromatography (25% ethyl acetate in hexane) to afford methyl 2-[2-[(E)-tert-butylsulfinyliminomethyl]-3-chloro-phenyl]sulfanylpyridine-3-carboxylate (1.8 g, 84%) as viscous oil. LC-MS: 410.6 (M+H). As per ¹H-NMR, this compound is a mixture of ethyl and methyl ester. MS found: 424.9 (M+H).

To an ice-cooled solution of methyl 2-[2-[(E)-tert-butylsulfinyliminomethyl]-3-chloro-phenyl]sulfanylpyridine-3-carboxylate (1.8 g, 4.38 mmol) in THF (50 mL) under argon atmosphere was added LAH (0.416 g, 10.95 mmol) portion-wise and the reaction mixture was stirred at 0° C. for 1 h. Progress of the reaction was monitored by TLC. After completion, the reaction mixture was quenched with ethyl acetate and saturated sodium sulfate solution. Then the reaction mixture was filtered through celite and washed with EtOAc. Filtrate was concentrated to get N-[[2-chloro-6-[[3-(hydroxymethyl)-2-pyridyl]sulfanyl]phenyl]methyl]-2-methyl-propane-2-sulfinamide (1.6 g, 95%) as an off-white solid. LC-MS: 384.9 (M+H).

To an ice-cooled solution of N-[[2-chloro-6-[[3-(hydroxymethyl)-2-pyridyl]sulfanyl]phenyl]methyl]-2-methyl-propane-2-sulfinamide (1.6 g, 4.15 mmol) in DCM (50 mL) was added Dess Martin periodinane (2.227 g, 5.40 mmol) portion-wise and the reaction mixture was stirred at room temperature for 2h under argon atmosphere. Progress of the reaction was monitored by TLC. After completion, the reaction mixture was diluted with DCM (50 mL) and saturated solution of sodium bicarbonate (50 mL). Organic layer was separated off and the aqueous layer was extracted with DCM (50 mL×2). Combined organic layer was washed with sodium thiosulphate solution followed by brine. Volatiles were removed under reduced pressure to get N-[[2-fluoro-6-[(3-formyl-2-pyridyl)sulfanyl]phenyl]methyl]-2-methyl-propane-2-sulfinamide (1.6 g) as viscous oil. LC-MS: 382.9 (M+H).

To an ice-cooled solution of N-[[2-fluoro-6-[(3-formyl-2-pyridyl)sulfanyl]phenyl]methyl]-2-methyl-propane-2-sulfinamide (2.0 g, crude) in dioxane (20 mL) was added 4M HCl in dioxane (30 mL) and the reaction mixture was stirred at room temperature for a period of 2 h. Progress of the reaction was monitored by LCMS. Volatiles were removed under reduced pressure to get the crude compound which was washed with diethyl ether (30 mL×2) and dried well to get 2-[2-(aminomethyl)-3-chloro-phenyl]sulfanylpyridine-3-carbaldehyde (2.0 g, crude) as yellow solid. LC-MS: 279.1 (M+H).

To a stirred suspension of crude 2-[2-(aminomethyl)-3-chloro-phenyl]sulfanylpyridine-3-carbaldehyde (2.0 g, crude) in 5% sodium bicarbonate solution and acetonitrile (30 mL, 1:1) was added Fmoc-OSu (1.08 g, 3.21 mmol) in acetonitrile (15 mL) and the reaction mixture was stirred at room temperature for 3 h. Progress of the reaction was monitored by TLC. After completion, volatiles were removed under reduced pressure and the crude reaction mixture was diluted with water (50 mL). The aqueous phase was extracted with ethyl acetate (50 mL×3). Combined organic layer was washed with brine (50 mL×1), dried over anhydrous sodium sulfate and evaporated under reduced pressure to get crude compound. The crude compound thus obtained was purified by flash-chromatography (30% ethyl acetate in hexane) to afford desired compound which was further washed with ethyl acetate (5 mL) and dried to get 9H-fluoren-9-ylmethyl N-[[2-chloro-6-[(3-formyl-2-pyridyl)sulfanyl]phenyl]methyl]carbamate (0.515 g, 20% over two steps) as white solid. LC-MS: 500.9 (M+H).

¹H-NMR: (400 MHz, DMSO-d6): δ 4.19-4.15 (3H, m), 4.36 (2H, d, J=4.6 Hz), 7.30 (2H, t, J=7.4 Hz), 7.42-7.34 (4H, m), 7.47 (1H, t, J=4.5 Hz), 7.53 (1H, d, J=7.0 Hz), 7.61 (1H, d, J=7.9 Hz), 7.67 (2H, s, J=7.4 Hz), 7.88 (2H, d, J=7.5 Hz), 8.33 (1H, dd, J=7.6, 1.7 Hz), 8.44 (1H, dd, J=4.7, 1.7 Hz), 10.18 (1H, s).

Intermediate 26

9H-fluoren-9-ylmethyl N-[[3,5-dichloro-2-(4-fluoro-2-formyl-phenyl)sulfanyl-phenyl]methyl]carbamate

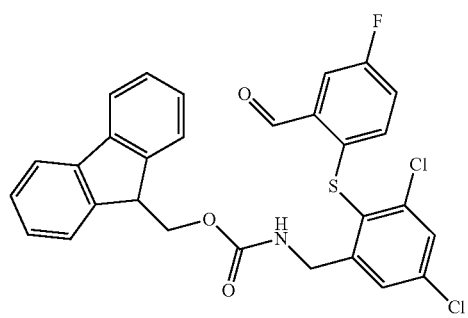 [SMILES: O=Cc1cc(F)ccc1Sc1c(Cl)cc(Cl)cc1CNC(=O)OCC1c2ccccc2-c2ccccc21]

To a stirred solution of 5-Fluoro-2-mercapto-benzoic acid (1 g, 5.808 mmol) in THF (20 mL), was added 2,2,2-Trichloro-acetimidic acid tert-butyl ester (3.6 mL, 20.328 mmol) followed by slow addition of BF₃·OEt₂ (0.615 mL, 5.808 mmol) at 0° C. and stirred at 25° C. for 2 h. After completion of reaction, reaction mixture was quenched with water and extracted with ethyl acetate. The combined organic layer was washed with brine, dried over anhydrous sodium sulfate and concentrated under reduced pressure to get crude which was purified by normal silica column using 2% ethyl acetate in hexane to afford tert-butyl 5-fluoro-2-sulfanyl-benzoate (620 mg, 47%) as a colourless liquid.

To a stirred solution tert-butyl 5-fluoro-2-sulfanyl-benzoate (600 mg, 2.628 mmol) in DMF (10 mL) were added 2,3,5-Trichloro-benzaldehyde (660 mg, 3.154 mmol), Cs₂CO₃ (2.13 g, 6.571 mmol) and reaction mixture was heated 60° C. for 3 h. After completion of reaction, reaction mixture was quenched with water and extracted with ethyl acetate. The combined organic layer was washed with brine, dried over anhydrous sodium sulfate and concentrated under reduced pressure to get crude which was purified by normal silica column using 2% ethyl acetate in hexane to afford tert-butyl 2-(2,4-dichloro-6-formyl-phenyl)sulfanyl-5-fluoro-benzoate (660 mg, 62%) as a colorless liquid.

To a stirred solution of 2-(2,4-dichloro-6-formyl-phenyl)sulfanyl-5-fluoro-benzoate (900 mg, 2.243 mmol) in THF (20 mL) were added 2-methyl 2-propane sulfonamide (271 mg, 2.243 mmol) and Ti(OEt)₄ (2.3 mL, 11.214 mmol) and heated to 70° C. for 16h. Reaction mixture was quenched with brine solution and extracted with ethyl acetate. The separated organic layer was dried over anhydrous sodium sulfate and concentrated under vacuum to afford tert-butyl 2-[2-[(E)-tert-butylsulfinyliminomethyl]-4,6-dichloro-phenyl]sulfanyl-5-fluoro-benzoate (1 g, crude) as a yellow liquid. MS found: 504.1 (M+H).

To a stirred solution of tert-butyl 2-[2-[(E)-tert-butylsulfinyliminomethyl]-4,6-dichloro-phenyl]sulfanyl-5-fluoro-benzoate (1 g, 1.982 mmol) in THF (20 mL) was added LiBH₄ (215 mg, 9.911 mmol) and reaction mass was heated to 50° C. for 4h. Reaction mass was quenched with saturated ammonium chloride and extracted with ethyl acetate. The separated organic layer washed with brine solution, dried over anhydrous sodium sulfate and evaporated under reduced pressure to get N-[[3,5-dichloro-2-[4-fluoro-2-(hydroxymethyl)phenyl]sulfanyl-phenyl]methyl]-2-methyl-propane-2-sulfinamide (1.2 g, crude) as a off white solid. MS found: 435.7 (M+H).

To a stirred solution of N-[[3,5-dichloro-2-[4-fluoro-2-(hydroxymethyl)phenyl]sulfanyl-phenyl]methyl]-2-methyl-propane-2-sulfinamide (1.2 g, 2.75 mmol) in MeOH (20 mL), was added 4M HCl/dioxane (10 mL) at 0° C. and reaction mixture was stirred at 25° C. for 1 h. After completion of reaction, reaction mixture was concentrated under reduced pressure to get [2-[2-(aminomethyl)-4,6-dichloro-phenyl]sulfanyl-5-fluoro-phenyl]methanol (1 g, crude) as a off white solid. MS found: 332 (M+H).

To a stirred suspension of [2-[2-(aminomethyl)-4,6-dichloro-phenyl]sulfanyl-5-fluoro-phenyl]methanol (1 g, 2.712 mmol) in 5% NaHCO₃ (20 mL) was added Fmoc OSU (914 mg, 2.712 mmol) in CH₃CN (20 mL) at 25° C. and reaction was stirred at 25° C. for 2h. Then reaction mass was diluted with water and extracted with ethyl acetate. The separated organic layer was washed with brine solution, dried over sodium sulfate and evaporated under reduced pressure. The crude thus obtained was purified by normal silica column using 5-30% ethyl acetate in hexane to get 9H-fluoren-9-ylmethyl N-[[3,5-dichloro-2-[4-fluoro-2-(hydroxymethyl)phenyl]sulfanyl-phenyl]methyl]carbamate (800 mg, 64%, 4 steps) as a off white solid. MS found: 554 (M+H).

To a stirred solution of 9H-fluoren-9-ylmethyl N-[[3,5-dichloro-2-[4-fluoro-2-(hydroxymethyl)phenyl]sulfanyl-phenyl]methyl]carbamate (800 mg, 1.661 mmol) in DCM/THF (1:1, 20 mL) was added MnO₂ (2.88 g, 33.221 mmol) and reaction mixture was stirred at 25° C. for 2h. The reaction mixture was filtered through celite pad; filtrate was evaporated under reduced pressure. The crude thus obtained was purified by normal silica column using 5-20% ethyl acetate in hexane to get 9H-fluoren-9-ylmethyl N-[[3,5-dichloro-2-(4-fluoro-2-formyl-phenyl)sulfanyl-phenyl]methyl]carbamate (700 mg, 76%) as an off white solid. MS found: 552.3 (M+H).

¹H-NMR: (400 MHz, DMSO-d6): δ 4.17-4.12 (3H, m), 4.35 (2H, d, J=5.1 Hz), 7.45-7.28 (6H, m), 7.67-7.60 (4H, m), 7.88 (2H, d, J=7.5 Hz), 8.35 (1H, dd, J=7.6, 1.8 Hz), 8.41 (1H, dd, J=4.8, 1.8 Hz), 10.19 (1H, s).

Intermediate 27 and Intermediate 28

9H-fluoren-9-ylmethyl N-[[3-chloro-6-fluoro-2-[(3-formyl-2-pyridyl)sulfanyl]phenyl]methyl]carbamate

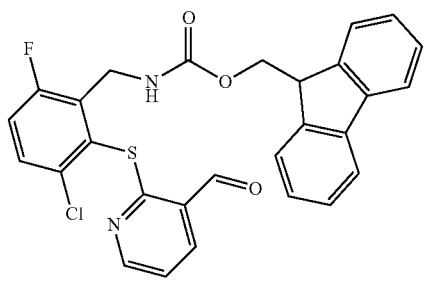 [SMILES: O=Cc1cccnc1Sc1c(Cl)ccc(F)c1CNC(=O)OCC1c2ccccc2-c2ccccc21]

and 9H-fluoren-9-ylmethyl N-[[3-chloro-2-fluoro-6-[(3-formyl-2-pyridyl)sulfanyl]phenyl]methyl]carbamate

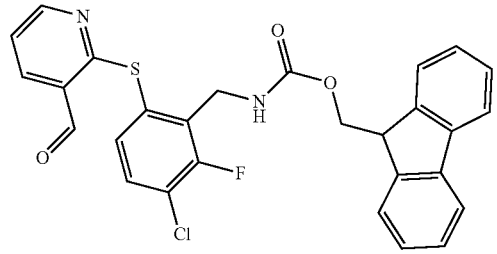 [SMILES: O=Cc1cccnc1Sc1ccc(Cl)c(F)c1CNC(=O)OCC1c2ccccc2-c2ccccc21]

To a solution 3-chloro-2,6-difluoro-benzaldehyde (2.0 g, 12.88 mmol) in ethanol (80 mL, argon purged) was added sodium ethoxide (2.192 g, 32.21 mmol) and 2-Mercapto-nicotinic acid (2.26 g, 12.88 mmol) at room temperature and the reaction mixture was heated to reflux for 4h. Progress of the reaction was monitored by TLC. After completion, volatiles were removed under reduced pressure to afford a mixture of 2-(6-chloro-3-fluoro-2-formyl-phenyl)sulfanylpyridine-3-carboxylic acid and 2-(4-chloro-3-fluoro-2-formyl-phenyl)sulfanylpyridine-3-carboxylic acid (6 g, crude) as brown solid which was used as such in next step without further purification. LC-MS: 312.1 (M+H).

To an ice-cooled solution of above mentioned mixture (6.0 g, crude) in DMF (25 mL) under argon atmosphere was added K₂CO₃ (2.66 g, 19.24 mmol) and the reaction mixture was stirred at 0° C. for 30 min. To the resulting reaction mixture was added MeI (1.198 mL, 19.248 mmol) and the reaction mixture was stirred at room temperature for 16 h. Then the reaction mixture was diluted with water (100 mL) and the aqueous phase was extracted with ethyl acetate (50 mL×3). Combined organic layer was washed with brine, dried over sodium sulfate and evaporated under reduced pressure to get crude compound. The crude compound thus obtained was purified by flash-chromatography (10% ethyl acetate in hexane) to afford a mixture of methyl 2-(4-chloro-3-fluoro-2-formyl-phenyl)sulfanylpyridine-3-carboxylate and methyl 2-(4-chloro-3-fluoro-2-formyl-phenyl)sulfanylpyridine-3-carboxylate (2.3 g, 57% over two steps) as yellow solid. LC-MS: 325.7 (M+H).

To a stirred solution of above mentioned mixture (2.3 g, 7.06 mmol) in dry THF (100 mL) under argon atmosphere was added titanium(IV) ethoxide (4.027 g, 17.65 mmol) followed by tert-butyl sulphinamide (2.139 g, 17.65 mmol) and the resulting reaction mixture was stirred at room temperature for 1 h and heated to 60° C. for 4h. Then the reaction mixture was cooled to room temperature, poured onto water (100 mL) and filtered through celite bed. Celite bed was washed with ethyl acetate. Organic layer was separated off and the aqueous layer was extracted with ethyl acetate (50 mL×3). Combined organic layer was dried over sodium sulfate and concentrated under reduced pressure to get the crude compound. The crude compound thus obtained was purified by flash-chromatography (25% ethyl acetate in hexane) to afford a mixture of methyl 2-[2-[(E)-tert-butylsulfinyliminomethyl]-4-chloro-3-fluoro-phenyl]sulfanylpyridine-3-carboxylate and methyl 2-[2-[(E)-tert-butylsulfinyliminomethyl]-4-chloro-3-fluoro-phenyl]sulfanylpyridine-3-carboxylate (1.9 g, 63%) as viscous oil. LC-MS: 428.6 (M+H).

To an ice-cooled solution of above mentioned mixture (1.9 g, 4.43 mmol) in THF (50 mL) under argon atmosphere was added LAH (0.42 g, 11.07 mmol) portion wise and the reaction mixture was stirred at 0° C. for 1 h. Progress of the reaction was monitored by TLC. After completion, the reaction mixture was quenched with ethyl acetate and saturated sodium sulfate solution. Then the reaction mixture was filtered through celite and washed with EtOAc. Filtrate was concentrated to get a mixture of N-[[3-chloro-2-fluoro-6-[[3-(hydroxymethyl)-2-pyridyl]sulfanyl]phenyl]methyl]-2-methyl-propane-2-sulfinamide and N-[[3-chloro-2-fluoro-6-[[3-(hydroxymethyl)-2-pyridyl]sulfanyl]phenyl]methyl]-2-methyl-propane-2-sulfinamide (1.6 g, 90%) as an off-white solid. LC-MS: 402.9 (M+H).

To an ice-cooled solution of above mentioned mixture (1.6 g, 3.97 mmol) in DCM (50 mL) was added Dess Martin periodinane (2.128 g, 5.162 mmol) portion-wise and the reaction mixture was stirred at room temperature for 2h under argon atmosphere. Progress of the reaction was monitored by TLC. After completion, the reaction mixture was diluted with DCM (50 mL) and saturated solution of sodium bicarbonate (50 mL). Organic layer was separated off and the aqueous layer was extracted with DCM (50 mL×2). Combined organic layer was washed with sodium thiosulphate solution followed by brine. Volatiles were removed under reduced pressure to get a mixture of N-[[2-fluoro-6-[(3-formyl-2-pyridyl)sulfanyl]-3-methyl-phenyl]methyl]-2-methyl-propane-2-sulfinamide and N-[[3-chloro-2-fluoro-6-[(3-formyl-2-pyridyl)sulfanyl]phenyl]methyl]-2-methyl-propane-2-sulfinamide (1.6 g, quan) as viscous oil. LC-MS: 400.8 (M+H).

To an ice-cooled solution of above mentioned mixture (2.0 g, crude) in dioxane (20 mL) was added 4M HCl in dioxane (30 mL) and the reaction mixture was stirred at room temperature for a period of 2 h. Progress of the reaction was monitored by LCMS. Volatiles were removed under reduced pressure to get the crude compound which was washed with diethyl ether (30 mL×2) and dried to get a mixture of 2-[2-(aminomethyl)-4-chloro-3-fluoro-phenyl]sulfanylpyridine-3-carbaldehyde and 2-[2-(aminomethyl)-4-chloro-3-fluoro-phenyl]sulfanylpyridine-3-carbaldehyde (2.0 g, crude) as yellow solid. LC-MS: 297.1 (M+H).

To a stirred suspension of above mentioned mixture (2.0 g, crude) in 5% sodium bicarbonate solution and acetonitrile (30 mL, 1:1) was added Fmoc-OSu (1.422 g, 4.21 mmol) in acetonitrile (15 mL) and the reaction mixture was stirred at room temperature for 3 h. Progress of the reaction was monitored by TLC. After completion, volatiles were removed under reduced pressure and the crude reaction mixture was diluted with water (50 mL). The aqueous phase was extracted with ethyl acetate (50 mL×3). Combined organic layer was washed with brine (50 mL×1), dried over anhydrous sodium sulfate and evaporated under reduced pressure to get crude compound. The crude compound thus obtained was purified by flash-chromatography (20% ethyl acetate in hexane) to afford a mixture of two isomers 1.6 g. The mixture of isomers was purified by prep HPLC to get 9H-fluoren-9-ylmethyl N-[[3-chloro-2-fluoro-6-[(3-formyl-2-pyridyl)sulfanyl]phenyl]methyl]carbamate (0.910 g, 35% over two steps) as white solid and 9H-fluoren-9-ylmethyl N-[[3-chloro-2-fluoro-6-[(3-formyl-2-pyridyl)sulfanyl]phenyl]methyl]carbamate (0.210 g, 8% over two steps) as white solid. LC-MS: 518.9 (M+H). and LC-MS: 519.0 (M+H).

¹H-NMR 9H-fluoren-9-ylmethyl N-[[3-chloro-2-fluoro-6-[(3-formyl-2-pyridyl)sulfanyl]phenyl]methyl]carbamate: (400 MHz, DMSO-d6): δ 4.17-4.12 (3H, m), 4.35 (2H, d, J=5.1 Hz), 7.45-7.28 (6H, m), 7.67-7.60 (4H, m), 7.88 (2H, d, J=7.5 Hz), 8.35 (1H, dd, J=7.6, 1.8 Hz), 8.41 (1H, dd, J=4.8, 1.8 Hz), 10.19 (1H, s).

¹H-NMR 9H-fluoren-9-ylmethyl N-[[3-chloro-2-fluoro-6-[(3-formyl-2-pyridyl)sulfanyl]phenyl]methyl]carbamate: (400 MHz, DMSO-d6): δ 4.18-4.13 (3H, m), 4.27 (2H, d, J=4.2 Hz), 7.30 (2H, t, J=7.4 Hz), 7.42-7.34 (4H, m), 7.66-7.60 (4H, m), 7.9 (2H, d, J=7.5 Hz), 8.34 (1H, dd, J=7.6, 1.8 Hz), 8.44 (1H, dd, J=4.8, 1.8 Hz), 10.18 (1H, s).

Intermediate 29

9H-fluoren-9-ylmethyl N-[[2,3-dichloro-6-[(3-formyl-2-pyridyl)sulfanyl]phenyl]methyl]carbamate

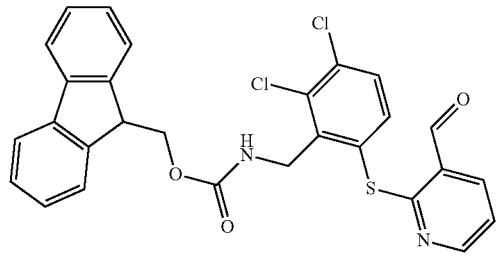

To an ice-cooled solution of 2,3-Dichloro-6-fluoro-benzaldehyde (2 g, 12.88 mmol) in ethanol (20 mL) were added sodium ethoxide (2.1 g, 32.22 mmol) and 2-Mercaptonicotinic acid (2.7 g, 14.17 mmol) sequentially and the reaction mixture was heated to 90° C. for 5 h. Progress of the reaction was monitored by TLC. Volatiles were removed under reduced pressure to get 2-(3,4-dichloro-2-formyl-phenyl)sulfanylpyridine-3-carboxylic acid (6.8 g, crude) as pale yellow solid which was used as such in next step without further purification.

To an ice-cooled solution of 2-(3,4-dichloro-2-formyl-phenyl)sulfanylpyridine-3-carboxylic acid (4.2 g, crude) in DMF (30 mL) were added potassium carbonate (4.4 g, 32.10 mmol) and methyl iodide (2.3 mL, 38.52 mmol) sequentially and the reaction mixture was stirred at room temperature for 15 h. Progress of the reaction was monitored by TLC. Then the reaction mixture was diluted with water (50 mL) and the aqueous phase was extracted with ethyl acetate (50 mL×2). Combined organic layer was washed with brine solution (50 mL×2), dried over anhydrous sodium sulfate and solvent distilled-off under reduced pressure to get crude compound which was purified by flash-chromatography to get methyl 2-(3,4-dichloro-2-formyl-phenyl)sulfanylpyridine-3-carboxylate (2.5 g, 56% over two steps) as pale yellow solid.

To a stirred solution of methyl 2-(3,4-dichloro-2-formyl-phenyl)sulfanylpyridine-3-carboxylate (2.5 g, 7.30 mmol) in anhydrous THF (40 mL) were added 2-methylpropane-2-sulfinamide (1.7 g, 14.61 mmol) and titanium tetraethoxide (3.33 g, 14.61 mmol). The resultant reaction mixture was heated to 60° C. for a period of 1 h under argon atmosphere. Then the reaction mixture was cooled to ambient temperature, poured onto ice-water and filtered through a short pad of celite. Filtrate was extracted with ethyl acetate (100 mL×2), washed with brine (100 mL×2), dried over sodium sulfate and concentrated under reduced pressure to get the crude compound which was purified by flash-chromatography (gradient 10-20% ethyl acetate in hexane) to afford methyl 2-[2-[(E)-tert-butylsulfinyliminomethyl]-3,4-dichloro-phenyl]sulfanylpyridine-3-carboxylate (1.9 g, 58%) as pale orange solid. LC-MS: 444.6 (M+H).

To an ice-cooled solution of methyl 2-[2-[(E)-tert-butylsulfinyliminomethyl]-3,4-dichloro-phenyl]sulfanylpyridine-3-carboxylate (2.2 g, 4.93 mmol) in THF (30 mL) under argon atmosphere was added LAH (0.375 g, 9.879 mmol) portion-wise and the reaction mixture was stirred at room temperature for 45 min. Progress of the reaction was monitored by TLC. After completion, the reaction mixture was quenched with saturated ammonium chloride solution (~5 mL), filtered through celite bed and bed was washed with ethyl acetate. Filtrate was concentrated to get N-[[2,3-dichloro-6-[[3-(hydroxymethyl)-2-pyridyl]sulfanyl]phenyl]methyl]-2-methyl-propane-2-sulfinamide (2.0 g, 96%) as off-white solid. LC-MS: 418.6 (M+H).

To an ice-cooled solution of N-[[2,3-dichloro-6-[[3-(hydroxymethyl)-2-pyridyl]sulfanyl]phenyl]methyl]-2-methyl-propane-2-sulfinamide (2.1 g, 5.01 mmol) in DCM (20 mL) was added Dess-Martin periodinane (2.7 g, 6.51 mmol) portion-wise and the reaction mixture was stirred at room temperature for a period of 2 h under argon atmosphere. Progress of the reaction was monitored by TLC. The resulting reaction mixture was diluted with diethyl ether (25 mL) and poured into a saturated solution of sodium bicarbonate (30 mL) containing sodium thiosulphate (4 g) and stirred until two distinct layers were observed. Organic layer was separated off and the aqueous phase was extracted with ethyl acetate (50 mL×2). Combined organic layer was washed with saturated aqueous sodium bicarbonate solution (50 mL×2) followed by brine (25 mL×2). Organic layer dried over anhydrous sodium sulfate and concentrated under reduced pressure to get N-[[2,3-dichloro-6-[(3-formyl-2-pyridyl)sulfanyl]phenyl]methyl]-2-methyl-propane-2-sulfinamide (2.0 g, 95%) as pale yellow solid which was used as such in next step without further purification. LC-MS: 416.7 (M+H).

To a solution of N-[[2,3-dichloro-6-[(3-formyl-2-pyridyl)sulfanyl]phenyl]methyl]-2-methyl-propane-2-sulfinamide (2.0 g, 4.79 mmol) in dioxane (10 mL) was added 4M HCl in dioxane (2.0 mL) slowly and the resultant reaction mixture was stirred at ambient temperature for 2 h. Progress of the reaction was monitored by TLC. Volatiles were removed under reduced pressure to get crude compound which was washed with diethyl ether and dried to get 2-[2-(aminomethyl)-3,4-dichloro-phenyl]sulfanylpyridine-3-carbaldehyde (1.6 g, crude) as pale yellow solid. This compound was used as such in the next step without further purification. LC-MS: 313.1 (M+H).

To a stirred suspension of 2-[2-(aminomethyl)-3,4-dichloro-phenyl]sulfanylpyridine-3-carbaldehyde (1.6 g, crude) in 5% sodium bicarbonate (15 mL) was added Fmoc-OSU (1.8 g, 5.62 mmol) in acetonitrile (2 mL) and the reaction mixture was stirred at room temperature for 3 h. Then the reaction mixture was diluted with ethyl acetate (50 mL) and washed with brine (50 mL×1), dried over anhydrous sodium sulfate and evaporated under reduced pressure. The crude compound thus obtained was purified by combiflash (30% ethyl acetate in hexane) to afford 9H-fluoren-9-ylmethyl N-[[2,3-dichloro-6-[(3-formyl-2-pyridyl)sulfanyl]phenyl]methyl]carbamate (1.0 g, 40% over two steps) as an off-white solid. LC-MS: 534.9 (M+H).

¹H-NMR: (400 MHz, DMSO-d6): δ 4.33-4.13 (3H, m), 4.39 (2H, d, J=4.5 Hz), 7.30 (2H, t, J=7.4 Hz), 7.42-7.35 (3H, m), 7.55-7.53 (2H, m), 7.69-7.66 (3H, m), 7.88 (2H, d, J=7.5 Hz), 8.34 (1H, dd, J=7.6, 1.4 Hz), 8.45 (1H, dd, J=4.8, 1.7 Hz), 10.17 (1H, s).

Intermediate 30

9H-fluoren-9-ylmethyl N-[[3,6-dichloro-2-[(3-formyl-2-pyridyl)sulfanyl]phenyl]methyl]carbamate

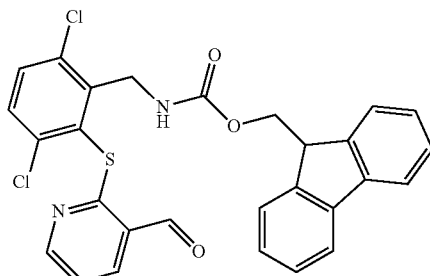

To an ice-cooled solution of 3,6-Dichloro-2-fluoro-benzaldehyde (2 g, 12.88 mmol) in ethanol (30 mL) was added sodium ethoxide (2.1 g, 32.22 mmol) and 2-Mercaptonicotinic acid (2.7 g, 14.17 mmol) sequentially and the reaction mixture was heated to 90° C. for 5 h. Progress of the reaction was monitored by TLC. Volatiles were removed under reduced pressure to get 2-(3,6-dichloro-2-formyl-phenyl)sulfanylpyridine-3-carboxylic acid (6.8 g, crude) as pale yellow solid which was used as such in next step without further purification.

To a solution of 2-(3,6-dichloro-2-formyl-phenyl)sulfanylpyridine-3-carboxylic acid (4.2 g, crude) in DMF (30 mL) was added potassium carbonate (4.42 g, 31.99 mmol) and methyl iodide (2.3 mL, 38.39 mmol) sequentially and the reaction mixture was stirred at room temperature for 15 h. Progress of the reaction was monitored by TLC. Then the reaction mixture was diluted with water (50 mL) and extracted with ethyl acetate (50 mL×2). Combined organic layers were washed with brine solution (50 mL×2), dried over anhydrous sodium sulfate and solvent distilled-off under reduced pressure to get crude compound which was purified by flash-chromatography to get methyl 2-(3,6-dichloro-2-formyl-phenyl)sulfanylpyridine-3-carboxylate (2.6 g, 60% over two steps) as pale yellow oil.

To a stirred solution of methyl 2-(3,6-dichloro-2-formyl-phenyl)sulfanylpyridine-3-carboxylate (2.6 g, 7.598 mmol) in anhydrous THF (40 mL) were added 2-methylpropane-2-sulfinamide (1.8 g, 15.19 mmol) and titanium tetraethoxide (3.4 g, 15.19 mmol). The resultant reaction mixture was heated to 60° C. for 1 h under argon atmosphere. Then the reaction mixture was then cooled to ambient temperature, poured onto ice-water and filtered through a short pad of celite. Filtrate was extracted with ethyl acetate (100 mL×2), washed with brine (100 mL×2), dried over sodium sulfate and concentrated under reduced pressure to get the crude compound which was purified by flash-chromatography (gradient 10-20% ethyl acetate in hexane) to afford methyl 2-[2-[(E)-tert-butylsulfinyliminomethyl]-3,6-dichloro-phenyl]sulfanylpyridine-3-carboxylate (2 g, 59%) as pale orange solid. LC-MS: 444.9 (M+H).

To an ice-cooled solution of methyl 2-[2-[(E)-tert-butylsulfinyliminomethyl]-3,6-dichloro-phenyl]sulfanylpyridine-3-carboxylate (2.2 g, 4.93 mmol) in THF (40 mL) under argon atmosphere was added LAH (0.37 g, 9.87 mmol) portion-wise and the reaction mixture was stirred at room temperature for 1 h. Progress of the reaction was monitored by TLC. After completion, the reaction mixture was quenched with saturated Ammonium chloride solution (~5 mL), filtered through celite bed and bed was washed with EtOAc. Filtrate was concentrated to get N-[[3,6-dichloro-2-[(3-formyl-2-pyridyl)sulfanyl]phenyl]methyl]-2-methyl-propane-2-sulfinamide (2.0 g, 96%) as off-white solid. LC-MS: 418.9 (M+H).

To an ice-cooled solution of N-[[3,6-dichloro-2-[(3-formyl-2-pyridyl)sulfanyl]phenyl]methyl]-2-methyl-propane-2-sulfinamide (2.1 g, 5.01 mmol) in DCM (20 mL) was added Dess-Martin periodinane (2.7 g, 6.50 mmol) portion-wise and the reaction mixture was stirred at room temperature for 2 h under argon atmosphere. Progress of the reaction was monitored by TLC. The resulting reaction mixture was diluted with diethyl ether (25 mL) and poured onto a solution of saturated solution of sodium bicarbonate (30 mL) containing sodium thiosulphate (4 g) and stirred until two distinct layers were observed. Organic layer was separated off and the aqueous phase was extracted with ethyl acetate (50 mL×2). Combined organic layer was washed with saturated aqueous sodium bicarbonate solution (50 mL×2) followed by brine (25 mL×2). Organic layer was dried over anhydrous sodium sulfate and concentrated under reduced pressure to get N-[[3,6-dichloro-2-[(3-formyl-2-pyridyl)sulfanyl]phenyl]methyl]-2-methyl-propane-2-sulfinamide (2.0 g, 95%) as pale brown oil which was used as such in next step without further purification. LC-MS: 416.7 (M+H).

To a solution of N-[[3,6-dichloro-2-[(3-formyl-2-pyridyl)sulfanyl]phenyl]methyl]-2-methyl-propane-2-sulfinamide (2.0 g, crude) in dioxane (20 mL) was added 4 M HCl in dioxane (2.0 mL) dropwise and the reaction mixture was stirred at room temperature for 2 h. Progress of the reaction was monitored by TLC. Volatiles were removed under reduced pressure to get crude compound which was washed with diethyl ether and dried to get 2-[2-(aminomethyl)-3,6-dichloro-phenyl]sulfanylpyridine-3-carbaldehyde (1.8 g, crude) as pale yellow solid. This compound was used as such in next step without further purification. LC-MS: 313.0 (M+H).

To a stirred suspension of 2-[2-(aminomethyl)-3,6-dichloro-phenyl]sulfanylpyridine-3-carbaldehyde (1.8 g, crude) in 5% sodium bicarbonate (15 mL) was added Fmoc-OSU (2.1 g, 6.322 mmol) in acetonitrile (25 mL) and the reaction mixture was stirred at room temperature for 3 h. Then the reaction mixture was diluted with ethyl acetate (50 mL) and washed with brine (50 mL×1), dried over anhydrous sodium sulfate and evaporated under reduced pressure to get the crude compound. The crude compound thus obtained was purified by flash-chromatography (30% ethyl acetate in hexane) to afford 9H-fluoren-9-ylmethyl N-[[3,6-dichloro-2-[(3-formyl-2-pyridyl)sulfanyl]phenyl]methyl] carbamate (0.98 g, 38% over two steps) as an off-white solid. LC-MS: 534.8 (M+H).

¹H-NMR: (400 MHz, DMSO-d6): δ 4.21-4.14 (3H, m), 4.45 (2H, d, J=4.4 Hz), 7.31 (2H, t, J=7.32 Hz), 7.42-7.35 (3H, m), 7.55 (1H, t, J=4.4 Hz), 7.68-7.62 (4H, m), 7.88 (2H, d, J=7.52 Hz), 8.36 (1H, dd, J=7.52, 1.48 Hz), 8.43 (1H, dd, J=4.8, 1.76 Hz), 10.19 (1H, s).

Intermediate 31

9H-fluoren-9-ylmethyl N-[[3-chloro-2-[(3-formyl-2-pyridyl)sulfanyl]-6-(trifluoromethyl)phenyl]methyl] carbamate

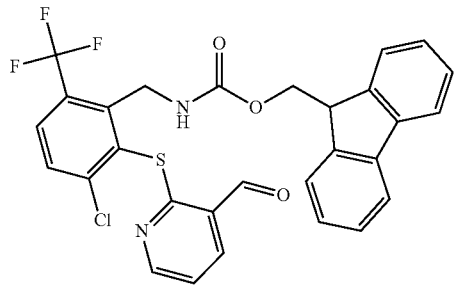 [SMILES: O=Cc1cccnc1Sc1c(Cl)ccc(C(F)(F)F)c1CNC(=O)OCC1c2ccccc2-c2ccccc21]

To an ice-cooled solution of NaH (1.13 g, 27.80 mmol) in DMF (10 mL) was added 2-thionicotinic acid (2.15 g, 13.90 mmol) in DMF (10 mL) and the reaction mixture was stirred for 15 min. To the resulting reaction mixture was added a solution of 3-Chloro-2-fluoro-6-methyl-benzaldehyde (2.1 g, 9.26 mmol) in DMF (10 mL) and the reaction mixture was stirred at room temperature for 9h. Then the reaction mixture was cooled to 0° C. and $K_2CO_3$ (3.84 g, 27.80 mmol) followed by methyl iodide (3.10 mL, 27.80 mmol) were added. The resulting reaction mixture was stirred at room temperature for 16h. Then the reaction mixture was quenched by saturated $NH_4Cl$ solution (20 mL) and extracted with ethyl acetate (60 mL). Organic layer was separated off, washed with water (2×30 mL) followed by brine (2×30 mL) and dried over anhydrous sodium sulfate. Organic layer was concentrated under reduced pressure and the crude compound was purified by flash-chromatography to afford methyl 2-[6-chloro-2-formyl-3-(trifluoromethyl)phenyl]sulfanylpyridine-3-carboxylate (1.3 g, 37%) as an off-white solid. LC-MS: 375.7 (M+H).

To a degassed solution of methyl 2-[6-chloro-2-formyl-3-(trifluoromethyl)phenyl]sulfanylpyridine-3-carboxylate (1.4 g, 3.72 mmol) in THF (30 mL) was added titanium (IV) ethoxide (8.49 g, 37.25 mmol) followed by tert-butyl sulphinamide (4.50 g, 37.25 mmol) and the resulting reaction mixture was heated to 60° C. for 2 h. Then the reaction mixture was diluted with water (30 mL) and extracted with EtOAc (70 mL). Organic layer was dried over anhydrous sodium sulfate and concentrated under reduced pressure to afford methyl 2-[2-[(E)-tert-butylsulfinyliminomethyl]-6-chloro-3-(trifluoromethyl)phenyl]sulfanylpyridine-3-carboxylate (1.25 g, 70%) as an off-white solid. It's a mixture of ethyl and methyl ester. MS found: 478.7 (M+H).

To an ice-cooled solution of LAH (0.297 g, 7.83 mmol) in THF (10 mL) was added methyl 2-[2-[(E)-tert-butylsulfinyliminomethyl]-6-chloro-3-(trifluoromethyl)phenyl]sulfanylpyridine-3-carboxylate (1.25 g, 2.61 mmol) in THF (15 mL) and the reaction mixture was stirred for 0.5h at same temperature. Then the reaction mixture was quenched by saturated sodium sulfate solution (2 mL) and EtOAc (80 mL). The reaction mixture was filtered through celite and filtrate was concentrated under reduced pressure to afford N-[[3-chloro-2-[[3-(hydroxymethyl)-2-pyridyl]sulfanyl]-6-(trifluoromethyl)phenyl]methyl]-2-methyl-propane-2-sulfinamide (1.1 g, 93%) as an off-white solid. MS found: 452.8 (M+H).

To an ice-cooled solution of N-[[3-chloro-2-[[3-(hydroxymethyl)-2-pyridyl]sulfanyl]-6-(trifluoromethyl)phenyl]methyl]-2-methyl-propane-2-sulfinamide (1.1 g, 2.42 mmol) in DCM (30 mL) was added Dess-Martin periodinane (2.06 g, 4.85 mmol) and the reaction mixture was allowed to stir at ambient temperature for 1 h. Progress of the reaction was monitored by TLC. After completion, the reaction mixture was poured onto saturated sodium bicarbonate solution and extracted with DCM (3×50 mL). Combined organic layer was washed with sodium thiosulphate, dried over sodium sulfate and concentrated under reduced pressure to afford N-[[3-chloro-2-[(3-formyl-2-pyridyl)sulfanyl]-6-(trifluoromethyl)phenyl]methyl]-2-methyl-propane-2-sulfinamide (1.0 g, 91%) as an off-white solid. MS found: 450.8 (M+H).

To an ice-cooled solution of N-[[3-chloro-2-[(3-formyl-2-pyridyl)sulfanyl]-6-(trifluoromethyl)phenyl]methyl]-2-methyl-propane-2-sulfinamide (1.2 g, 2.66 mmol) in dioxane (20 mL) was added 4 M HCl in dioxane (15 mL) and the reaction mixture was allowed to stir at ambient temperature for 1 h. TLC showed consumption of starting material. Volatiles were evaporated under reduced pressure to obtain 2-[2-(aminomethyl)-6-chloro-3-(trifluoromethyl)phenyl]sulfanylpyridine-3-carbaldehyde (0.91 g, 99%) as an off-white solid.

To an ice-cooled suspension of 2-[2-(aminomethyl)-6-chloro-3-(trifluoromethyl)phenyl]sulfanylpyridine-3-carbaldehyde (0.91 g, 2.62 mmol) in acetonitrile (15 mL) were added 5% aqueous NaHCO₃ solution (12 mL) and Fmoc-OSu (0.708 g, 2.09 mmol) in CH₃CN (15 mL) and the reaction mixture was stirred at ambient temperature for 4h. It was then diluted with ethyl acetate (80 mL) and water (30 mL). Organic layer was separated off, washed with water, brine and dried over anhydrous sodium sulfate. Organic layer was concentrated under reduced pressure to get the crude compound which was purified by flash-chromatography to afford 9H-fluoren-9-ylmethyl N-[[3-chloro-2-[(3-formyl-2-pyridyl)sulfanyl]-6-(trifluoromethyl)phenyl]methyl]carbamate (0.590 g, 40%) as an off-white solid. LC-MS: 569.0 (M+H).

¹H-NMR: (400 MHz, CDCl₃): δ 4.21-4.16 (3H, m), 4.43 (2H, br s), 7.33-7.29 (2H, m), 7.43-7.36 (3H, m), 7.56 (1H, br s), 7.66 (2H, m), 7.94-7.84 (4H, m), 8.38 (1H, d, J=7.4 Hz), 8.43 (1H, d, J=3.8 Hz), 10.19 (1H, s).

Intermediate 32

9H-fluoren-9-ylmethyl N-[[3,6-difluoro-2-[(3-formyl-2-pyridyl)sulfanyl]phenyl]methyl]carbamate

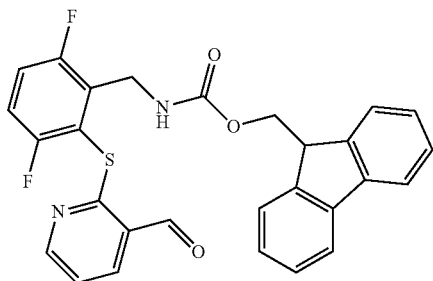

To a solution 2-thionicotinic acid (4.0 g, 25.77 mmol) in ethanol (80 mL, argon purged) were added sodium ethoxide (4.385 g, 64.437 mmol) and 2,3,6-Trifluoro-benzaldehyde (4.95 g, 30.93 mmol) sequentially and the reaction mixture was heated to reflux for 4h. Progress of the reaction was monitored by TLC. After completion, volatiles were removed under reduced pressure to afford 2-(3,6-difluoro-2-formyl-phenyl)sulfanylpyridine-3-carboxylic acid (12 g, crude) as brown solid which was used as such in next step without further purification. LC-MS: 296.1 (M+H).

To an ice-cooled solution of 2-(3,6-difluoro-2-formyl-phenyl)sulfanylpyridine-3-carboxylic acid (12.0 g, crude) in DMF (25 mL) under argon atmosphere was added K₂CO₃ (5.617 g, 40.64 mmol) and the reaction mixture was stirred at 0° C. for 30 min. To the resulting reaction mixture was added MeI (2.53 mL, 40.64 mmol) and the reaction mixture was stirred at room temperature for 16 h. Then the reaction mixture was diluted with water (100 mL) and the aqueous phase was extracted with ethyl acetate (50 mL×3). Combined organic layer was washed with brine, dried over sodium sulfate and evaporated under reduced pressure to get crude compound. The crude compound thus obtained was purified by combiflash (10% ethyl acetate in hexane) to afford methyl 2-(3,6-difluoro-2-formyl-phenyl)sulfanylpyridine-3-carboxylate (2.3 g, 29% over two steps) as yellow solid. LC-MS: 311.1 (M+2H), MS found: 310.1 (M+H).

To a stirred solution of methyl 2-(3,6-difluoro-2-formyl-phenyl)sulfanylpyridine-3-carboxylate (2.3 g, 7.43 mmol) in dry THF (100 mL) under argon atmosphere was added titanium(IV) ethoxide (4.24 g, 18.59 mmol) followed by tert-butyl sulphinamide (2.25 g, 18.59 mmol). The resulting reaction mixture was stirred at room temperature for 1 h and heated to 60° C. for 4h. Then the reaction mixture was cooled to room temperature, poured onto water (100 mL) and filtered through celite bed. Celite bed was washed with ethyl acetate. Organic layer was separated off and the aqueous layer was extracted with ethyl acetate (50 mL×3). Combined organic layer was dried over sodium sulfate and concentrated under reduced pressure to get the crude compound. The crude compound thus obtained was purified by combiflash (25% ethyl acetate in hexane) to afford methyl 2-[2-[(E)-tert-butylsulfinyliminomethyl]-3,6-difluoro-phenyl]sulfanylpyridine-3-carboxylate (1.6 g, 52%) as viscous oil. LC-MS: 412.6 (M+H).

To an ice-cooled solution of methyl 2-[2-[(E)-tert-butylsulfinyliminomethyl]-3,6-difluoro-phenyl]sulfanylpyridine-3-carboxylate (1.6 g, 3.88 mmol) in THF (30 mL) under argon atmosphere was added LAH (0.368 g, 9.70 mmol) portion wise and the reaction mixture was stirred at 0° C. for 1 h. Progress of the reaction was monitored by TLC. After completion, the reaction mixture was quenched with ethyl acetate and saturated sodium sulfate solution. Then the reaction mixture was filtered through celite and washed with EtOAc. Filtrate was concentrated to get N-[[3,6-difluoro-2-[[3-(hydroxymethyl)-2-pyridyl]sulfanyl]phenyl]methyl]-2-methyl-propane-2-sulfinamide (1.4 g, 94%) as an off-white solid. LC-MS: 387.0 (M+H).

To an ice-cooled solution of N-[[3,6-difluoro-2-[[3-(hydroxymethyl)-2-pyridyl]sulfanyl]phenyl]methyl]-2-methyl-propane-2-sulfinamide (1.4 g, 3.62 mmol) in DCM (50 mL) was added Dess-Martin periodinane (2.239 g, 5.43 mmol) portion-wise and the reaction mixture was stirred at room temperature for 2h under argon atmosphere. Progress of the reaction was monitored by TLC. After completion, the reaction mixture was diluted with DCM (50 mL) and saturated solution of sodium bicarbonate (50 mL). Organic layer was separated off and the aqueous layer was extracted with DCM (50 mL×2). Combined organic layers were washed with sodium thiosulfate solution followed by brine. Volatiles were removed under reduced pressure to get N-[[3, 6-difluoro-2-[(3-formyl-2-pyridyl)sulfanyl]phenyl]methyl]-2-methyl-propane-2-sulfinamide (1.4 g, quant) as viscous oil. LC-MS: 384.9 (M+H).

To an ice-cooled solution of N-[[3,6-difluoro-2-[(3-formyl-2-pyridyl)sulfanyl]phenyl]methyl]-2-methyl-propane-2-sulfinamide (1.4 g, 4.14 mmol) in dioxane (20 mL) was added 4M HCl in dioxane (30 mL) and the reaction mixture was stirred at room temperature for a period of 2 h. Progress of the reaction was monitored by LC-MS. Volatiles were removed under reduced pressure to get the crude compound which was washed with diethyl ether (30 mL×2) and dried well to get 2-[2-(aminomethyl)-3,6-difluoro-phenyl]sulfanylpyridine-3-carbaldehyde (1.6 g, crude) as yellow solid. LC-MS: 281.0 (M+H).

To a stirred suspension of 2-[2-(aminomethyl)-3,6-difluoro-phenyl]sulfanylpyridine-3-carbaldehyde (1.6 g, crude) in 5% sodium bicarbonate solution and acetonitrile (30 mL, 1:1) was added Fmoc-OSu (1.08 g, 3.21 mmol) in acetonitrile (15 mL) and the reaction mixture was stirred at room temperature for 3 h. Progress of the reaction was monitored by TLC. After completion, volatiles were removed under reduced pressure and the crude reaction mixture was diluted with water (50 mL). The aqueous phase was extracted with ethyl acetate (50 mL×3). Combined organic layer was washed with brine (50 mL×1), dried over anhydrous sodium sulfate and evaporated under reduced pressure to get crude compound. The crude compound thus obtained was purified by flash-chromatography (20% ethyl acetate in hexane) to afford desired compound which was further washed with n-pentane (5 mL) and dried to get 9H-fluoren-9-ylmethyl N-[[3,6-difluoro-2-[(3-formyl-2-pyridyl)sulfanyl]phenyl]methyl]carbamate (0.85 g, 47% over two steps) as white solid. LC-MS: 502.9 (M+H).

$^1$H-NMR: (400 MHz, DMSO-d6): δ 4.20-4.11 (3H, m), 4.32 (2H, d, J=4.2 Hz), 7.30 (2H, m), 7.47-7.35 (5H, m), 7.66-7.64 (3H, m), 7.87 (2H, d, J=7.5 Hz), 8.35 (1H, dd, J=7.6, 1.8 Hz), 8.42 (1H, dd, J=4.8, 1.8 Hz), 10.18 (1H, s).

Intermediate 33

9H-fluoren-9-ylmethyl N-[[3-chloro-2-(2-formylphenyl)sulfanyl-5-methoxy-phenyl]methyl]carbamate

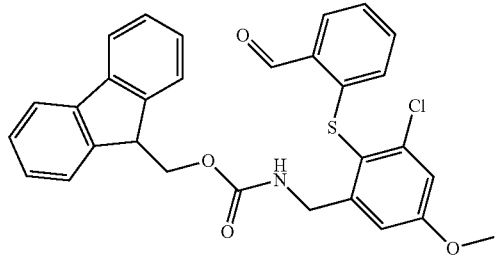 [SMILES: COc1cc(Cl)c(Sc2ccccc2C=O)c(CNC(=O)OCC2c3ccccc3-c3ccccc32)c1]

To a stirred solution of 3-Chloro-2-hydroxy-5-methoxy-benzaldehyde (2.4 g, 12.903 mmol) in DCM (25 mL) was added Et$_3$N (2.72 ml, 19.355 mmol), triflic anhydride (3.27 ml, 19.355 mmol) at −5° C. and reaction mass was stirred at −5° C. for 30 min. Reaction mass was diluted with DCM and washed with saturated sodium bicarbonate solution. The separated organic layer was washed with brine solution, dried over anhydrous sodium sulfate and evaporated under reduced pressure. The crude thus obtained was purified by normal silica column using 0-8% ethyl acetate in hexane to get (2-chloro-6-formyl-4-methoxy-phenyl) trifluoromethanesulfonate (2.4 g, 58%) as a colorless liquid.

To a stirred and degassed solution of (2-chloro-6-formyl-4-methoxy-phenyl) trifluoromethanesulfonate (2.915 g, 9.167 mmol) in dioxan (25 mL) were added DIPEA (3.159 ml, 18.333 mmol), Xanthphos (165.205 mg, 0.458 mmol), Pd$_2$(dba)$_3$ (209.848 mg, 0.229 mmol), methyl 2-sulfanylbenzoate (770 mg, 4.583 mmol) and reaction mass was heated to 110° C. for 2.5h. Reaction mixture was filtered through celite pad, washed with ethyl acetate and filtrate evaporated under reduced pressure. The crude thus obtained was purified by normal silica column using 0-3% ethyl acetate and hexane to get methyl 2-(2-chloro-6-formyl-4-methoxy-phenyl)sulfanylbenzoate (1.2 g, 78%) as a light yellow solid.

To a stirred solution of methyl 2-(2-chloro-6-formyl-4-methoxy-phenyl)sulfanylbenzoate (1.2 g, 3.571 mmol) in THF (25 mL) was added 2-methylpropane-2-sulfinamide (433 mg, 3.571 mmol), Ti(OEt)$_4$ (3.74 mL, 17.857 mmol) and reaction mass was heated to 70° C. for 4h. The reaction mass was quenched with saturated sodium chloride solution, solid obtained was filtered through celite pad, washed with ethyl acetate. The separated organic layer was dried over anhydrous sodium sulfate and evaporated under reduced pressure to get ethyl 2-[2-[(E)-tert-butylsulfinyliminomethyl]-6-chloro-4-methoxy-phenyl]sulfanylbenzoate (1.8 g crude) which was directly used for next step without further purification. MS found: 453.8 (M+H).

To a stirred solution of ethyl 2-[2-[(E)-tert-butylsulfinyliminomethyl]-6-chloro-4-methoxy-phenyl]sulfanylbenzoate (1.8 g, 3.974 mmol) in THF (25 mL) was added LiBH$_4$ (0.865 g, 39.735 mmol) at 0° C. and reaction mass was heated to 50° C. for 4h. The solvent was evaporated and the reaction mass was quenched with NH$_4$Cl and extracted with ethyl acetate. The separated organic layer was washed with brine solution, dried over sodium sulfate and evaporated under reduced pressure to get N-[[3-chloro-2-[2-(hydroxymethyl)phenyl]sulfanyl-5-methoxy-phenyl]methyl]-2-methyl-propane-2-sulfinamide (1,4 g crude) which was directly used for next step without further purification. MS found: 413.9 (M+H).

To a stirred solution of N-[[3-chloro-2-[2-(hydroxymethyl)phenyl]sulfanyl-5-methoxy-phenyl]methyl]-2-methyl-propane-2-sulfinamide (1.4 g, 3.39 mmol) in MeOH (25 mL), was added 4M HCl in dioxane (12 mL) at 0° C. and reaction mixture was stirred at 25° C. for 1 h. After completion of reaction, reaction mixture was concentrated under reduced pressure to [2-[2-(aminomethyl)-6-chloro-4-methoxy-phenyl]sulfanylphenyl]methanol (1.4 g, crude) which was directly used for next step without further purification. MS found: 310.0 (M+H).

To a stirred suspension of [2-[2-(aminomethyl)-6-chloro-4-methoxy-phenyl]sulfanylphenyl]methanol (1.4 g, 4.531 mmol) in 5% NaHCO$_3$(20 mL) was added Fmoc OSU (1.528 g, 4.531 mmol) in CH$_3$CN (20 mL) at 25° C. and reaction mixture was stirred at 25° C. for 2h. Then reaction mass was diluted with water and extracted with ethyl acetate. The separated organic layer was washed with brine solution, dried over anhydrous sodium sulfate and evaporated under reduced pressure to 9H-fluoren-9-ylmethyl N-[[3-chloro-2-[2-(hydroxymethyl)phenyl]sulfanyl-5-methoxy-phenyl]methyl]carbamate (1.4 g, crude) as a off white solid. MS found: 531.8 (M+H).

To a stirred solution of N-[[3-chloro-2-[2-(hydroxymethyl)phenyl]sulfanyl-5-methoxy-phenyl]methyl]carbamate (1.4 g, 2.637 mmol) in DCM/THF (1:1, 50 mL) was added MnO₂ (4.584 g, 52.731 mmol) and reaction mixture was stirred at 25° C. for 2h. The reaction mass was filtered through celite pad, filtrate was evaporated under reduced pressure. The crude thus obtained was purified by normal silica column using 0-13% ethyl acetate in hexane to OH-fluoren-9-ylmethyl N-[[3-chloro-2-(2-formylphenyl)sulfanyl-5-methoxy-phenyl]methyl]carbamate (600 mg, 32%, 5 steps) as a off white solid.

¹H-NMR: (400 MHz, DMSO-d6) δ 3.84 (3H; s); 4.20-4.29 (5H; m); 6.51 (1H; d; J=8.0 Hz); 6.97 (1H; br s); 7.26 (1H; br s); 7.33-7.36 (3H; m); 7.399-7.44 (2H; m); 7.69 (2H; d; J=7.40 Hz); 7.80 (1H; m); 7.89 (2H; d; J=7.52 Hz); 7.99 (1H; d; J=7.4 Hz); 10.18 (1H; s)

Intermediate 34

9H-fluoren-9-ylmethyl N-[[2-(2-formylphenyl)sulfanyl-5-methoxy-3-methyl-phenyl]methyl]carbamate

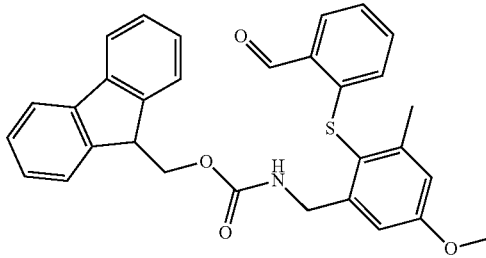

To a stirred and degassed solution of 2-formyl-4-methoxy-6-methylphenyl trifluoromethanesulfonate (3.01 g, 10.106 mmol) in dioxan (10 mL) were added DIPEA (3.53 mL, 20.212 mmol), Xanthphos (292 mg, 0.505 mmol), Pd₂(dba)₃ (231 mg, 0.253 mmol), methyl 2-sulfanylbenzoate (850 mg, 5.053 mmol) and reaction mass was heated to 110° C. for 2h. Reaction mixture was filtered through celite pad, washed with ethyl acetate and filtrate evaporated under reduced pressure. The crude thus obtained was purified by normal silica column using 0-5% ethyl acetate and hexane to get methyl 2-(2-formyl-4-methoxy-6-methyl-phenyl)sulfanylbenzoate (1.3 g, 81%) as a off white solid.

To a stirred solution of methyl 2-(2-formyl-4-methoxy-6-methyl-phenyl)sulfanylbenzoate (1.3 g, 4.109 mmol) in THF (10 mL) was added 2-methylpropane-2-sulfinamide (498 mg, 4.109 mmol), Ti(OEt)₄ (4.33 mL, 20.545 mmol) and reaction mass was heated to 70° C. for 16h. The reaction mass was quenched with saturated sodium chloride solution, solid obtained was filtered through celite pad, washed with ethyl acetate. The separated organic layer was dried over anhydrous sodium sulfate and evaporated under reduced pressure to get ethyl 2-[2-[(E)-tert-butylsulfinyliminomethyl]-4-methoxy-6-methyl-phenyl]sulfanylbenzoate (1.5 g crude) which was directly used for next step without further purification. MS found: 434 (M+H).

To a stirred solution of ethyl 2-[2-[(E)-tert-butylsulfinyliminomethyl]-4-methoxy-6-methyl-phenyl]sulfanylbenzoate (1.5 g, 3.459 mmol) in THF (15 mL) was added LiBH₄ (751 mg, 34.595 mmol) at 0° C. and reaction mass was heated to 50° C. for 4h. The solvent was evaporated and the reaction mass was quenched with NH₄Cl and extracted with ethyl acetate. The separated organic layer was washed with brine solution, dried over sodium sulfate and evaporated under reduced pressure to get N-[[2-[2-(hydroxymethyl)phenyl]sulfanyl-5-methoxy-3-methyl-phenyl]methyl]-2-methyl-propane-2-sulfinamide (1.3 g crude) which was directly used for next step without further purification. MS found: 394 (M+H).

To a stirred solution of N-[[2-[2-(hydroxymethyl)phenyl]sulfanyl-5-methoxy-3-methyl-phenyl]methyl]-2-methyl-propane-2-sulfinamide (1.3 g, 3.303 mmol) in MeOH (20 mL), was added 4M HCl in dioxane (10 mL) at 0° C. and reaction mixture was stirred at 25° C. for 1 h. After completion of reaction, reaction mixture was concentrated under reduced pressure to get [2-[2-(aminomethyl)-4-methoxy-6-methyl-phenyl]sulfanylphenyl]methanol (1.1 g, crude) which was directly used for next step without further purification. MS found: 290 (M+H).

To a stirred suspension of [2-[2-(aminomethyl)-4-methoxy-6-methyl-phenyl]sulfanylphenyl]methanol (1.1 g, 3.375 mmol) in 5% NaHCO₃(20 mL) was added Fmoc OSU (1.1 g, 3.375 mmol) in CH₃CN (20 mL) at 25° C. and reaction mixture was stirred at 25° C. for 2h. Then reaction mass was diluted with water and extracted with ethyl acetate. The separated organic layer was washed with brine solution, dried over anhydrous sodium sulfate and evaporated under reduced pressure. The crude thus obtained was purified by normal silica column using 5-30% ethyl acetate in hexane to get 9H-fluoren-9-ylmethyl N-[[2-[2-(hydroxymethyl)phenyl]sulfanyl-5-methoxy-3-methyl-phenyl]methyl]carbamate (1,2 g, 57%, 4 steps) as a off white solid. MS found: 511.9 (M+H).

To a stirred solution of 9H-fluoren-9-ylmethyl N-[[2-[2-(hydroxymethyl)phenyl]sulfanyl-5-methoxy-3-methyl-phenyl]methyl]carbamate (1,2 g, 2.345 mmol) in DCM/THF (1:1, 20 mL) was added MnO₂ (4.07 g, 46.907 mmol) and reaction mixture was stirred at 25° C. for 2h. The reaction mass was filtered through celite pad, filtrate was evaporated under reduced pressure. The crude thus obtained was purified by normal silica column using 5-20% ethyl acetate in hexane to 9H-fluoren-9-ylmethyl N-[[2-(2-formylphenyl)sulfanyl-5-methoxy-3-methyl-phenyl]methyl]carbamate (800 mg, 67%) as an off white solid.

¹H-NMR: (400 MHz, DMSO-d6) δ 2.13 (3H; s); 3.79 (3H; s); 4.20-4.29 (5H; m); 6.42 (1H; d; J=8.0 Hz); 6.87 (1H; br s); 6.99 (1H; br s); 6.29-6.33 (3H; m); 6.42 (3H; t; J=5.4 Hz); 7.69 (2H; d; J=7.40 Hz); 7.77-7.82 (1H; m); 7.89 (2H; d; J=7.52 Hz); 7.96 (1H; d; J=7.4 Hz); 10.21 (1H; s)

Intermediate 35

9H-fluoren-9-ylmethyl N-[[5-fluoro-2-(2-formylphenyl)sulfanyl-phenyl]methyl]carbamate

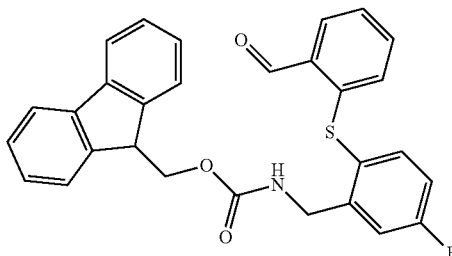

To an ice cooled solution of 2,5-Difluoro-benzaldehyde (5.21 g, 30.98 mmol) and 2-Mercapto-benzoic acid methyl ester (4.0 g, 28.17 mmol) in DMF (20 mL, purged with argon for 10 min) was added potassium carbonate (7.78 g, 56.33 mmol) and the reaction mixture was stirred at 0° C. for 30 min. Then the reaction mixture was diluted with water (100 mL) and the aq. phase was extracted with ethyl acetate (3×50 mL). Combined organic layer was washed with brine, dried over sodium sulfate and concentrated under reduced pressure to get crude compound. The crude compound thus obtained was purified by flash-chromatography (5% ethyl acetate in hexane) to afford methyl 2-(4-fluoro-2-formyl-phenyl)sulfanylbenzoate (2.4 g, 27%) as off white solid. MS found: 291.1 (M+H).

To a stirred solution of methyl 2-(4-fluoro-2-formyl-phenyl)sulfanylbenzoate (2.9 g, 10 mmol) in dry THF (50 mL) under argon atmosphere was added titanium(IV) ethoxide (4.56 g, 20 mmol) followed by tert-butyl sulphinamide (2.42 g, 20 mmol) and the resulting reaction mixture was heated to 70° C. for 4h. Then the reaction mixture was cooled to room temperature, poured onto water (100 mL), gelatinous white mass was filtered through celite. Celite bed was washed thoroughly with ethyl acetate (50 mL). Organic layer was separated off. Aqueous layer was extracted with ethyl acetate (3×50 mL). Combined organic layer was dried over sodium sulfate and concentrated under reduced pressure to get methyl 2-[2-[(E)-tert-butylsulfinyliminomethyl]-4-fluoro-phenyl]sulfanylbenzoate (3.9 g, 99%) as white solid. MS found: 394.1 (M+H).

To an ice cooled suspension of LAH (1.15 g, 30.53 mmol) was added a solution of methyl 2-[2-[(E)-tert-butylsulfinyliminomethyl]-4-fluoro-phenyl]sulfanylbenzoate (4.0 g, 10.17 mmol) in THF (50 mL) and the reaction mixture was stirred at 0° C. for 1 h. Progress of the reaction was monitored by TLC. After completion, the reaction mixture was quenched with ethyl acetate and saturated solution of sodium sulfate. Reaction mixture was filtered through celite and washed thoroughly with EtOAc (50 mL). Filtrate was concentrated to get N-[[5-fluoro-2-[2-(hydroxymethyl)phenyl]sulfanyl-phenyl]methyl]-2-methyl-propane-2-sulfinamide (3.6 g, 96%) as off white solid. MS found: 367.8 (M+H).

To an ice cooled solution of N-[[5-fluoro-2-[2-(hydroxymethyl)phenyl]sulfanyl-phenyl]methyl]-2-methyl-propane-2-sulfinamide (3.0 g, 8.17 mmol) in DCM (150 mL) was added Dess-Martin periodinane (5.2 g, 12.26 mmol) portion-wise and the reaction mixture was stirred at room temperature for 2h under argon atmosphere. Progress of the reaction was monitored by TLC. After completion, the reaction mixture was diluted with DCM (50 mL) and saturated sodium bicarbonate solution (50 mL). Organic layer was separated off and the aqueous layer was extracted with DCM (2×50 mL). Combined organic layer was washed with saturated sodium bicarbonate followed by brine. Organic layer was dried over Na$_2$SO$_4$, and evaporated under reduced pressure. Compound was purified by flash-chromatography (50% EtOAc in hexane) to get N-[[5-fluoro-2-(2-formylphenyl)sulfanyl-phenyl]methyl]-2-methyl-propane-2-sulfinamide (2.0 g, 67%) as white solid. MS found: 365.9 (M+H).

To an ice cooled solution of N-[[5-fluoro-2-(2-formylphenyl)sulfanyl-phenyl]methyl]-2-methyl-propane-2-sulfinamide (2.0 g, crude) in dioxane (20 mL) was added 4M HCl in dioxane (30 mL) and the reaction mixture was stirred at room temperature for a period of 2 h. Progress of the reaction was monitored by LCMS. Volatiles were removed under reduced pressure to get the crude compound which was washed with diethyl ether (2×30 mL) and dried to get 2-[2-(aminomethyl)-4-fluoro-phenyl]sulfanylbenzaldehyde (1.37 g, crude) as yellow solid.

To a stirred suspension of 2-[2-(aminomethyl)-4-fluoro-phenyl]sulfanylbenzaldehyde (1.37 g, crude) in 5% sodium bicarbonate solution and acetonitrile (30 mL, 1:1) was added a solution of Fmoc-OSu (1.047 g, 3.05 mmol) in acetonitrile (15 mL) and the reaction mixture was stirred at room temperature for 3 h. Progress of the reaction was monitored by TLC. After completion, volatiles were removed under reduced pressure and the crude reaction mixture was diluted with water (50 mL). The aq. phase was extracted with ethyl acetate (50 mL×3). Combined organic layers were washed with brine (50 mL), dried over anhydrous sodium sulfate and evaporated under reduced pressure to get crude compound. The crude compound thus obtained was purified by flash-chromatography (20% ethyl acetate in hexane) to afford desired compound which was further washed with n-pentane (5 mL) and dried to get 9H-fluoren-9-ylmethyl N-[[5-fluoro-2-(2-formylphenyl)sulfanyl-phenyl]methyl]carbamate (0.6 g, 23% over two steps) as white solid. LC-MS: 484.2 (M+H).

$^1$H-NMR: (400 MHz, DMSO-d6): δ 4.23-4.21 (3H, m), 4.33 (2H, d, J=6.9 Hz), 6.63 (1H, d, J=8.0 Hz), 7.17 (1H, dd, J=10.0, 2.7 Hz), 7.35-7.24 (4H, m), 7.45-7.36 (3H, m), 7.48 (1H, t, J=6.3 Hz), 7.58 (1H, dd, J=8.5, 5.9 Hz), 7.69 (2H, d, J=7.4 Hz), 7.89 (2H, d, J=7.8 Hz), 7.98 (1H, dd, J=7.5, 1.3 Hz), 10.19 (1H, s).

Intermediate 36

9H-fluoren-9-ylmethyl N-[[3-chloro-2-(2-formylphenyl)sulfanyl-5-methyl-phenyl]methyl]carbamate

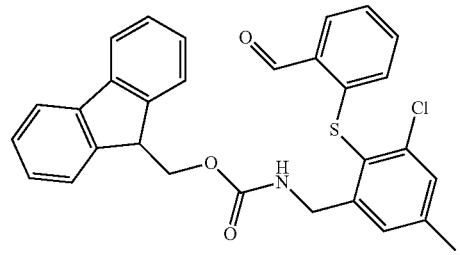 [SMILES: Cc1cc(Cl)c(Sc2ccccc2C=O)c(CNC(=O)OCC2c3ccccc3-c3ccccc32)c1]

To an ice cooled solution of 3-Chloro-2-fluoro-5-methyl-benzaldehyde (4 g, 23.25 mmol) and 2-Mercapto-benzoic acid methyl ester (3.91 g, 23.25 mmol) in DMF (30 mL) under argon atmosphere was added potassium carbonate (6.4 g, 46.51 mmol) and the reaction was stirred at room temperature for 3 h. Progress of the reaction was monitored by TLC. After completion the reaction mixture was diluted with water (50 mL) and extracted with ethyl acetate (30 mL×3). Combined organic layer was washed with brine (15 mL×3), dried over sodium sulfate and concentrated under reduced pressure to get crude compound. The crude compound thus obtained was purified by flash-chromatography chromatography using 10% Ethyl acetate in hexane as eluent to get methyl 2-(2-chloro-6-formyl-4-methyl-phenyl)sulfanylbenzoate (4.5 g, 61%) as pale yellow solid. LC-MS: 321.0 (M+H).

To a solution of methyl 2-(2-chloro-6-formyl-4-methyl-phenyl)sulfanylbenzoate (3 g, 9.375 mmol) in anhydrous THF (100 mL) was added tert butylsulphinamide (1.7 g, 14.062 mmol) followed by titanium (IV) ethoxide (3.2 g, 14.062 mmol) and the reaction mixture was heated to 70° C. for 2 h under argon atmosphere. Progress of the reaction was monitored by TLC. After completion, the reaction mixture was diluted with water (100 mL), filtered through celite and washed with ethyl acetate. Organic layer was separated off, washed with brine, dried over anhydrous sodium sulphate and concentrated under reduced pressure to get methyl 2-[2-[(E)-tert-butylsulfinyliminomethyl]-6-chloro-4-methyl-phenyl]sulfanylbenzoate (3 g, 76%) as off white solid. LC-MS: 424.0 (M+H).

To an ice cooled suspension of LAH (0.807 g, 21.27 mmol) in THF (50 mL) was added methyl 2-[2-[(E)-tert-butylsulfinyliminomethyl]-6-chloro-4-methyl-phenyl]sulfanylbenzoate (3 g, 7.092 mmol) in THF (30 mL) and the reaction mixture was stirred for 30 min at 0° C. Progress of the reaction was monitored by TLC. After completion, the reaction mixture was quenched with saturated sodium sulphate (5 mL) and filtered through celite. Residue was washed with ethyl acetate (3×50 mL) and filtrate was concentrated to get N-[[3-chloro-2-[2-(hydroxymethyl)phenyl]sulfanyl-5-methyl-phenyl]methyl]-2-methyl-propane-2-sulfinamide (2.5 g, 90%) as white solid. LC-MS: 397.8 (M+H).

To an ice cooled solution of N-[[3-chloro-2-[2-(hydroxymethyl)phenyl]sulfanyl-5-methyl-phenyl]methyl]-2-methyl-propane-2-sulfinamide (2.0 g, 5.04 mmol) in DCM (100 mL) was added Dess-Martin periodinane (2.34 g, 5.54 mmol) and the reaction mixture was stirred at room temperature for 2 h. Progress of the reaction was monitored by TLC. After completion, the reaction mixture was poured onto saturated sodium bicarbonate solution and extracted with DCM (3×100 mL). Combined organic layer was washed with sodium thiosulphate, dried over sodium sulphate and concentrated under reduced pressure to get the crude compound. The crude compound was purified by combiflash (30% EtOAc in hexane) to afford N-[[3-chloro-2-(2-formylphenyl)sulfanyl-5-methyl-phenyl]methyl]-2-methyl-propane-2-sulfinamide (1.5 g, 76%) as off white solid. LC-MS: 396.1 (M+H).

To an ice cooled solution of N-[[3-chloro-2-(2-formylphenyl)sulfanyl-5-methyl-phenyl]methyl]-2-methyl-propane-2-sulfinamide (1.5 g, 3.79 mmol) in dioxane (20 mL) was added 4M HCl in dioxane (2 mL) and the reaction mixture was stirred at room temperature for 1 h. Progress of the reaction was monitored by TLC. After completion, volatiles were evaporated under reduced pressure to obtain 2-[2-(aminomethyl)-6-chloro-4-methyl-phenyl]sulfanylbenzaldehyde (1.2 g, crude) as off white solid. LC-MS: 292.1 (M+H).

To a suspension of 2-[2-(aminomethyl)-6-chloro-4-methyl-phenyl]sulfanylbenzaldehyde (1.2 g, 4.12 mmol) in 5% aqueous NaHCO₃ solution (5 mL) was added a solution of Fmoc-OSu (0.973 g, 2.88 mmol) in CH₃CN (20 mL) and the reaction mixture was stirred at room temperature for 3 h. Progress of the reaction was monitored by TLC. After completion, the reaction mixture was diluted with ethyl acetate (50 mL) and organic layer was separated off. Organic layer was washed with water followed by brine and dried over anhydrous sodium sulfate. Organic layer was concentrated under reduced pressure to get the crude compound. The crude compound was purified by flash-chromatography (17% EtOAc in hexane) to afford OH-fluoren-9-ylmethyl N-[[3-chloro-2-(2-formylphenyl)sulfanyl-5-methyl-phenyl]methyl]carbamate (1.0 g, 53%) as white solid. LC-MS: 513.9 (M+H).

¹H-NMR: (400 MHz, DMSO-d6): δ 2.37 (3H, s), 4.22-4.18 (1H, m), 4.32-4.28 (4H, m), 6.48 (1H, d, J=8.0 Hz), 7.22 (1H, s), 7.38-7.31 (3H, m), 7.46-7.40 (3H, m), 7.54 (1H, s), 7.69 (2H, d, J=7.4 Hz), 7.85 (1H, t, J=6.1 Hz), 7.89 (2H, d, J=7.5 Hz), 7.99 (1H, dd, J=7.52, 1.16 Hz), 10.19 (1H, s).

Intermediate 37

9H-fluoren-9-ylmethyl N-[[3,5-dichloro-2-(2-formylphenyl)sulfanyl-phenyl]methyl]carbamate

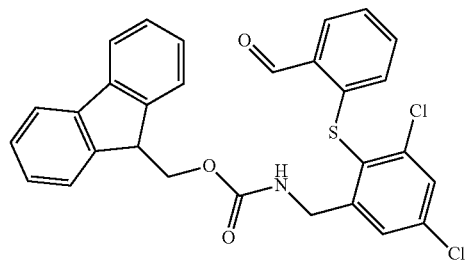

To an ice cooled solution of 3,5-Dichloro-2-fluoro-benzaldehyde (2.78 g, 16.57 mmol) in DMF (20 mL, purged with argon for 10 min) under argon atmosphere were added 2-Mercapto-benzoic acid methyl ester (4.0 g, 20.72 mmol) and potassium carbonate (8.59 g, 62.17 mmol) slowly and the reaction mixture was stirred at 0° C. for 30 min. Then the reaction mixture was diluted with water (100 mL) and the aq. phase was extracted with ethyl acetate (50 mL×3). Combined organic layer was washed with brine, dried over sodium sulfate and concentrated under reduced pressure to get crude compound. The crude compound thus obtained was purified by flash-chromatography (5% ethyl acetate in hexane) to afford methyl 2-(2,4-dichloro-6-formyl-phenyl)sulfanylbenzoate (1.6 g, 23%) as off white solid. LC-MS: 339.8 (M+H).

To a stirred solution of methyl 2-(2,4-dichloro-6-formyl-phenyl)sulfanylbenzoate (1.6 g, 4.69 mmol) in dry THF (50 mL) under argon atmosphere was added titanium (IV) ethoxide (2.14 g, 9.38 mmol) followed by tert-butyl sulphinamide (1.137 g, 9.38 mmol). The resulting reaction mixture was stirred at room temperature for 1 h and heated to 60° C. for 4h. Then the reaction mixture was cooled to room temperature, poured onto water (100 mL) and filtered through celite bed. Celite bed was washed with ethyl acetate. Organic layer was separated off and the aqueous layer was extracted with ethyl acetate (50 mL×3). Combined organic layer was dried over sodium sulfate and concentrated under reduced pressure to get the crude compound. The crude compound thus obtained was purified by combiflash (25% ethyl acetate in hexane) to afford methyl 2-[2-[(E)-tert-butylsulfinyliminomethyl]-4,6-dichloro-phenyl]sulfanylbenzoate (2.0 g, 95%) as viscous oil. LC-MS: 443.9 (M+H).

To an ice cooled solution of methyl 2-[2-[(E)-tert-butylsulfinyliminomethyl]-4,6-dichloro-phenyl]sulfanylbenzoate (2.0 g, 4.5 mmol) in THF (50 mL) under argon atmosphere was added LAH (0.512 g, 13.50 mmol) portion wise and the reaction mixture was stirred at 0° C. for 1 h. Progress of the reaction was monitored by TLC. After completion, the reaction mixture was quenched with ethyl acetate and saturated sodium sulfate solution. Then the reaction mixture was filtered through celite and washed with EtOAc. Filtrate was concentrated to get N-[[3,5-dichloro-2-[2-(hydroxymethyl)phenyl]sulfanyl-phenyl]methyl]-2-methyl-propane-2-sulfinamide (1.8 g, 95%) as off white solid. LC-MS: 417.7 (M+H).

To an ice cooled solution of N-[[3,5-dichloro-2-[2-(hydroxymethyl)phenyl]sulfanyl-phenyl]methyl]-2-methyl-propane-2-sulfinamide (1.8 g, 4.30 mmol) in DCM (50 mL) was added Dess-Martin periodinane (2.24 g, 6.45 mmol) portion-wise and the reaction mixture was stirred at room temperature for 2h under argon atmosphere. Progress of the reaction was monitored by TLC. After completion, the reaction mixture was diluted with DCM (50 mL) and saturated solution of sodium bicarbonate (50 mL). Organic layer was separated off and the aqueous layer was extracted with DCM (50 mL×2). Combined organic layer was washed with sodium thiosulphate solution followed by brine. Volatiles were removed under reduced pressure to get N-[[3,5-dichloro-2-(2-formylphenyl)sulfanyl-phenyl]methyl]-2-methyl-propane-2-sulfinamide (2.0 g, crude) as viscous oil which was used as such in next step without further purification. LC-MS: 416.0 (M+H).

To an ice cooled solution of N-[[3,5-dichloro-2-(2-formylphenyl)sulfanyl-phenyl]methyl]-2-methyl-propane-2-sulfinamide (2.0 g, crude) in dioxane (20 mL) was added 4M HCl in dioxane (30 mL) and the reaction mixture was stirred at room temperature for a period of 2 h. Progress of the reaction was monitored by LCMS. Volatiles were removed under reduced pressure to get the crude compound which was washed with diethyl ether (30 mL×2) and dried well to get 2-[2-(aminomethyl)-4,6-dichloro-phenyl]sulfanylbenzaldehyde (1.2 g, crude) as yellow solid. LC-MS: 312.1 (M+H)

To a stirred suspension of 2-[2-(aminomethyl)-4,6-dichloro-phenyl]sulfanylbenzaldehyde (1.2 g, crude) in 5% sodium bicarbonate solution and acetonitrile (30 mL, 1:1) was added a solution of Fmoc-OSu (1.047 g, 3.10 mmol) in acetonitrile (15 mL) and the reaction mixture was stirred at room temperature for 3 h. Progress of the reaction was monitored by TLC. After completion, volatiles were removed under reduced pressure and the crude reaction mixture was diluted with water (50 mL). The aq. phase was extracted with ethyl acetate (50 mL×3). Combined organic layer was washed with brine (50 mL×1), dried over anhydrous sodium sulfate and evaporated under reduced pressure to get crude compound. The crude compound thus obtained was purified by flash-chromatography (20% ethyl acetate in hexane) to afford desired compound which was further washed with n-pentane (5 mL) and dried to get 9H-fluoren-9-ylmethyl N-[[3,5-dichloro-2-(2-formylphenyl)sulfanyl-phenyl]methyl]carbamate (0.75 g, 33% over three steps) as white solid. LC-MS: 533.7 (M+H).

¹H-NMR: (400 MHz, DMSO-d6): δ 4.22-4.19 (2H, m), 4.31-4.29 (3H, m), 6.51 (1H, d, J=7.9 Hz), 7.37-7.31 (3H, m), 7.47-7.38 (4H, m), 7.68 (2H, d, J=7.4 Hz), 7.85 (1H, d, J=2.0 Hz), 7.89 (2H, d, J=7.5 Hz), 7.94 (1H, t, J=5.9 Hz), 8.01 (1H, d, J=7.4 Hz), 10.18 (1H, s).

Intermediate 38

9H-fluoren-9-ylmethyl N-[[5-chloro-2-(2-formylphenyl)sulfanyl-3-methyl-phenyl]methyl]carbamate

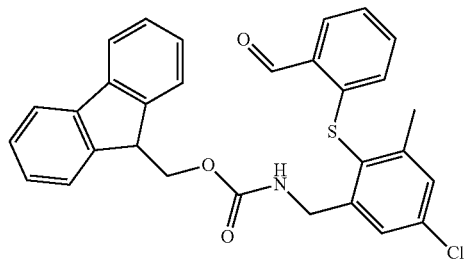 [SMILES: Cc1cc(Cl)cc(CNC(=O)OCC2c3ccccc3-c3ccccc32)c1Sc1ccccc1C=O]

To a stirred solution of 5-chloro-2-fluoro-3-methylbenzoic acid (2.0 g, 10.605 mmol) in THF (20 mL) was added LiAlH4 (21.0 ml, 21.0 mmol) drop-wise in ice cold condition and stirred at 25° C. for 30 min. It was then quenched with saturated Na₂SO₄ solution and extracted with ethyl acetate, washed with brine and dried over Na₂SO₄ and concentrated under vacuum to get (5-chloro-2-fluoro-3-methyl-phenyl)methanol (1.8 g, crude) as a light yellow liquid. To a stirred solution of (5-chloro-2-fluoro-3-methyl-phenyl)methanol (1.8 g, 10.345 mmol) in DCM/THF (1:1.40 mL) was added MnO₂ (8.993 g, 103.448 mmol) and reaction mass was stirred at 25° C. for 2h. The reaction mass was filtered through celite pad, filtrate was evaporated under reduced pressure The crude thus obtained was purified by normal silica column using 2% ethyl acetate in hexane to afford 5-chloro-2-fluoro-3-methyl-benzaldehyde (1.2 g, 64.86%, 2 steps) as yellow liquid.

To a solution of 5-chloro-2-fluoro-3-methyl-benzaldehyde (1.0 g, 5.814 mmol) in DMF (15.0 ml) were added Cs₂CO₃ (4.727 g, 14.535 mmol) and methyl 2-sulfanylbenzoate (0.978 g, 5.814 mmol) and stirred at 60° C. for 2.5 h. Reaction mixture was diluted with water and extracted with EtOAc. The combined organic layer was washed with brine, dried over anhydrous sodium sulfate and concentrated under vacuum to get the compound which was purified by normal silica column using 0-2% ethyl acetate in hexane to methyl 2-(4-chloro-2-formyl-6-methyl-phenyl)sulfanylbenzoate (1.5 g, 80.43%) as a yellow solid. MS found: 321.2 (M+H).

To a stirred solution of methyl 2-(4-chloro-2-formyl-6-methyl-phenyl)sulfanylbenzoate (1.5 g, 4.688 mmol) in THF (25 mL) was added 2-methylpropane-2-sulfinamide (568 mg, 4.688 mmol), Ti(OEt)₄ (4.914 ml, 23.438 mmol) and reaction mass was heated to 70° C. for 16h. The reaction mass was quenched with saturated sodium chloride solution, solid obtained was filtered through celite pad, washed with ethyl acetate. The separated organic layer was dried over anhydrous sodium sulfate and evaporated under reduced pressure to get ethyl 2-[2-[(Z)-tert-butylsulfinyliminomethyl]-4-chloro-6-methyl-phenyl]sulfanylbenzoate (2.0 g, crude) which was directly used for next step without further purification. MS found: 438.2 (M+H).

To a stirred solution of ethyl 2-[2-[(Z)-tert-butylsulfinyliminomethyl]-4-chloro-6-methyl-phenyl]sulfanylbenzoate (2.0 g, 4.577 mmol) in THF (25 mL) was added LiBH₄ (0.997 g, 45.767 mmol) at 0° C. and reaction mass was heated to 50° C. for 4h. The solvent was evaporated and the reaction mass was quenched with NH₄Cl and extracted with ethyl acetate. The separated organic layer was washed with brine solution, dried over sodium sulfate and evaporated under reduced pressure to get N-[[5-chloro-2-[2-(hydroxymethyl)phenyl]sulfanyl-3-methyl-phenyl]methyl]-2-methyl-propane-2-sulfinamide (1.8 g crude) which was directly used for next step without further purification. MS found: 398.1 (M+H).

To a stirred solution of N-[[5-chloro-2-[2-(hydroxymethyl)phenyl]sulfanyl-3-methyl-phenyl]methyl]-2-methyl-propane-2-sulfinamide (1.8 g, 4.534 mmol) in MeOH (40 mL), was added 4M HCl in dioxane (20 mL) at 0° C. and reaction mixture was stirred at 25° C. for 1 h. After completion of reaction, reaction mixture was concentrated under reduced pressure to get [2-[2-(aminomethyl)-4-chloro-6-methyl-phenyl]sulfanylphenyl]methanol (1.6 g, crude) which was directly used for next step without further purification. MS found: 293.8 (M+H).

To a stirred suspension of [2-[2-(aminomethyl)-4-chloro-6-methyl-phenyl]sulfanylphenyl]methanol (1.6 g, 5.461 mmol) in 5% NaHCO$_3$(20 mL) was added Fmoc OSU (1.841 g, 5.461 mmol) in CH$_3$CN (20 mL) at 25° C. and reaction mixture was stirred at 25° C. for 2h. Then reaction mass was diluted with water and extracted with ethyl acetate. The separated organic layer was washed with brine solution, dried over anhydrous sodium sulfate and evaporated under reduced pressure. The crude thus obtained was purified by normal silica column using 5-30% ethyl acetate in hexane to 9H-fluoren-9-ylmethyl N-[[5-chloro-2-[2-(hydroxymethyl)phenyl]sulfanyl-3-methyl-phenyl]methyl]carbamate (1.4 g, 72%, 4 steps) as a off white solid. MS found: 516.2 (M+H).

To a stirred solution of 9H-fluoren-9-ylmethyl N-[[5-chloro-2-[2-(hydroxymethyl)phenyl]sulfanyl-3-methyl-phenyl]methyl]carbamate (1.6 g, 3.107 mmol) in DCM/THF (1:1, 50 mL) was added MnO$_2$ (5.401 g, 62.136 mmol) and reaction mixture was stirred at 25° C. for 2h. The reaction mass was filtered through celite pad, filtrate was evaporated under reduced pressure. The crude thus obtained was purified by normal silica column using 5-20% ethyl acetate in hexane to 9H-fluoren-9-ylmethyl N-[[5-chloro-2-(2-formylphenyl)sulfanyl-3-methyl-phenyl]methyl]carbamate (1.1 g, 68%) as a off white solid. MS found: 514.4 (M+H).

$^1$H-NMR: (400 MHz, DMSO-d6) δ 2.32 (3H; s); 4.19-4.29 (5H; m); 6.47 (1H; d; J=7.8 Hz); 6.29-6.37 (4H; m); 7.37-7.44 (3H; m); 7.51 (1H; br s); 7.69 (2H; d; J=7.36 Hz); 7.87 (1H; m); 7.96 (2H; d; J=7.4 Hz); 7.99 (1H; d; J=7.6 Hz); 10.20 (1H; s)

Intermediate 39

9H-fluoren-9-ylmethyl N-[[2-(4-fluoro-2-formyl-phenyl)sulfanylphenyl]methyl]carbamate

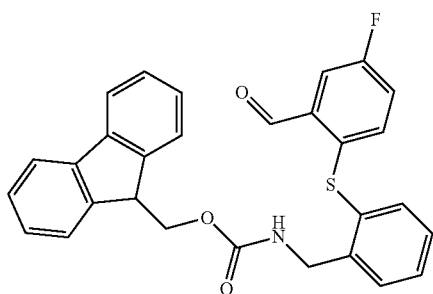 [SMILES: O=Cc1cc(F)ccc1Sc1ccccc1CNC(=O)OCC1c2ccccc2-c2ccccc21]

To an ice cooled solution of 2,5-Difluoro-benzaldehyde (5.21 g, 30.98 mmol) and methyl 2-sulfanylbenzoate (4.0 g, 28.17 mmol) in DMF (20 mL, purged with argon for 10 min) was added potassium carbonate (7.78 g, 56.33 mmol) and the reaction mixture was stirred at 0° C. for 30 min. Then the reaction mixture was diluted with water (100 mL) and the aq. phase was extracted with ethyl acetate (3×50 mL). Combined organic layer was washed with brine, dried over sodium sulfate and concentrated under reduced pressure to get crude compound. The crude compound thus obtained was purified by flash-chromatography (5% ethyl acetate in hexane) to afford methyl 2-(4-fluoro-2-formyl-phenyl)sulfanylbenzoate (2.4 g, 27%) as off white solid. MS found: 291.1 (M+H).

A solution of methyl 2-(4-fluoro-2-formyl-phenyl)sulfanylbenzoate (i.e. 3a) (2.0 g, 6.89 mmol), ethylene glycol (1.28 g, 20.69 mmol), p-TSA (0.131 g, 0.69 mmol) in toluene (100.0 mL) was heated to 140° C. for 6 h. Progress of the reaction was monitored by TLC. After completion, the reaction mixture was diluted with water (100 mL) and organic layer was separated off. Aq. layer was further extracted with ethyl acetate (50 mL×2). Combined organic layer was dried over anhydrous sodium sulfate and solvent distilled-off under reduced pressure to get methyl 2-[2-(1,3-dioxolan-2-yl)-4-fluoro-phenyl]sulfanylbenzoate (1.70 g, 74%) as off white solid. LC-MS: 335.0 (M+NH$_4$)

To an ice cooled suspension of LAH (0.454 g, 11.97 mmol) in THF (50 mL) was added methyl 2-[2-(1,3-dioxolan-2-yl)-4-fluoro-phenyl]sulfanylbenzoate (1.6 g, 4.79 mmol) in THF (30 mL) and the reaction mixture was stirred for 30 min at 0° C. Progress of the reaction was monitored by TLC. After completion, the reaction mixture was quenched with saturated sodium sulphate solution (5 mL) and filtered through celite. Residue was washed with ethyl acetate (3×50 mL) and filtrate was concentrated under reduced pressure to get [2-[2-(1,3-dioxolan-2-yl)-4-fluoro-phenyl]sulfanylphenyl]methanol (1.4 g, 96%) as white solid. MS found: 324.1 (M+18)

A suspension of [2-[2-(1,3-dioxolan-2-yl)-4-fluoro-phenyl]sulfanylphenyl]methanol (2.56 g, 9.80 mmol), sodium azide (0.486 g, 7.84 mmol) in carbon tetrachloride (5.0 mL) and DMF (15.0 mL) was heated to 80° C. for 5 h. Progress of the reaction was monitored by TLC. Reaction mixture was diluted with water (20 mL) and compound was extracted with ethyl acetate (30 mL×2). Combined organic layer was dried over anhydrous sodium sulfate and concentrated under reduced pressure to get crude compound which was purified by silica gel column chromatography (30% ethyl acetate in hexane) to get 2-[2-[2-(azidomethyl)phenyl]sulfanyl-5-fluoro-phenyl]-1,3-dioxolane (0.9 g, 70%) as viscous oil. MS found: 349.1 (M+NH$_4$)

To a solution of 2-[2-[2-(azidomethyl)phenyl]sulfanyl-5-fluoro-phenyl]-1,3-dioxolane (0.9 g, 2.71 mmol) in ethanol (20 mL) was added Pd—C (0.3 g) and the reaction mixture was agitated under hydrogen balloon pressure for 16h. Then the reaction mixture was filtered through celite. Filtrate was concentrated under reduced pressure to get [2-[2-(1,3-dioxolan-2-yl)-4-fluoro-phenyl]sulfanylphenyl]methanamine (0.800 g, 96%) as viscous oil. MS found: 305.9 (M+H).

To a suspension of [2-[2-(1,3-dioxolan-2-yl)-4-fluoro-phenyl]sulfanylphenyl]methanamine (0.800 g, 2.62 mmol) in 5% sodium bicarbonate (3 mL) was added Fmoc-OSu (0.619 g, 1.84 mmol) in acetonitrile (20 mL) and the reaction mixture was stirred at ambient temperature for 3h. Volatiles were removed under reduced pressure and the crude reaction mixture was diluted with water (50 mL). The aq. phase was extracted with ethyl acetate (50 mL×3). Combined organic layer was washed with brine (50 mL×1), dried over anhydrous sodium sulfate and evaporated under reduced pressure to get crude compound. The crude compound thus obtained was purified by flash-chromatography (19% ethyl acetate in hexane) followed by washing with diethyl ether:pentane (5 mL, 1:1) afforded 9H-fluoren-9-ylmethyl N-[[2-[2-(1,3-dioxolan-2-yl)-4-fluoro-phenyl]sulfanylphenyl]methyl]carbamate (0.750 g, 54%) as white solid. MS found: 528.1 (M+H).

To a solution of 9H-fluoren-9-ylmethyl N-[[2-[2-(1,3-dioxolan-2-yl)-4-fluoro-phenyl]sulfanylphenyl]methyl]carbamate (0.750 g, 1.42 mmol) in acetone (40 mL) was added 5N HCl (15 mL) and the reaction mixture was stirred at room temperature for 2h. Volatiles were removed under reduced pressure and extracted with ethyl acetate (30 mL×3). Combined organic layer was washed with 5% NaHCO$_3$ solution (50 mL) followed by water (50 mL). Organic layer was concentrated under reduced pressure to get crude compound which was purified by flash-chromatography (17% ethyl acetate in hexane) followed by washing with diethyl ether-pentane (5 mL, 1:1) afforded 9H-fluoren-9-ylmethyl N-[[2-(4-fluoro-2-formyl-phenyl)sulfanylphenyl]methyl]carbamate (0.550 g, 80%) as off white solid. LC-MS: 483.8 (M+H).

$^1$H-NMR: (400 MHz, DMSO-d6): δ 4.26-4.19 (3H, m), 4.33 (2H, d, J=6.8 Hz), 6.86 (1H, dd, J=8.8, 5.0 Hz), 7.48-7.31 (9H, m), 7.70 (2H, d, J=7.4 Hz), 7.86-7.79 (2H, m), 7.89 (2H, d, J=7.5 Hz), 10.21 (1H, s).

Intermediate 40

9H-fluoren-9-ylmethyl N-[[2-[(3-formyl-2-pyridyl)sulfanyl]-3-methyl-phenyl]methyl]carbamate

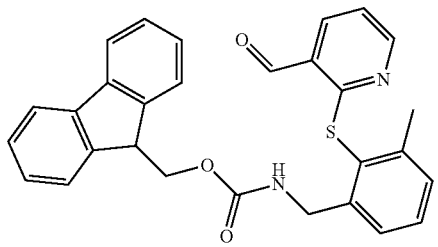 [SMILES: Cc1cccc(CNC(=O)OCC2c3ccccc3-c3ccccc32)c1Sc1ncccc1C=O]

A suspension of Na$_2$S·xH$_2$O (1.35 g, 17.374 mmmol) and MgSO$_4$ (4 g) in N,N-dimethyl acetamide (40 mL) was stirred at 80° C. for a period of 30 minutes under nitrogen atmosphere followed by the addition of 2-Fluoro-3-methyl-benzaldehyde (2 g, 14.478 mmmol) at the same temperature. Stirring was continued for another 30 min at 80° C. The reaction mixture was cooled to 0° C., acetic anhydride (1.9 mL, 20.269 mmmol) was added drop wise and the mixture was stirred at 0° C. for another 30 min. The reaction mixture was diluted with ethyl acetate and washed with water. The separated organic layer was washed with brine solution, dried over anhydrous sodium sulfate and evaporated under reduced pressure. The crude thus obtained was purified by normal silica column using 0-5% ethyl acetate in hexane to get S-(2-formyl-6-methyl-phenyl) ethanethioate (830 mg, 29%) as an off white solid.

To the stirred solution of get S-(2-formyl-6-methyl-phenyl) ethanethioate (800 mg, 4.118 mmol) in THF (20 mL) were added 2-methyl 2-propane sulfinamide (499 mg, 4.118 mmol) and Ti(OEt)$_4$ (4.349 mL, 20.592 mmol) and heated to 70° C. for 45 min. Reaction mixture was quenched with brine solution and extracted with ethyl acetate. The separated organic layer was dried over anhydrous sodium sulfate and concentrated under reduced pressure. The crude thus obtained was purified by normal silica column using 0-10% ethyl acetate in hexane to get S-[2-[(Z)-tert-butylsulfinyliminomethyl]-6-methyl-phenyl] ethanethioate (800 mg, 65%) as a colorless sticky liquid. MS found: 298.2 (M+H).

A solution of S-[2-[(Z)-tert-butylsulfinyliminomethyl]-6-methyl-phenyl] ethanethioate (800 mg, 2.69 mmol) in THF (30 mL) was degassed with Argon for about 10 minutes and then NaBH$_4$ (1017 mg, 26.896 mmol) was added portionwise under cooling condition and stirred for 30 min. The reaction was then quenched with acetone (10 mL) (degassed with argon) and stirred under the cooling condition for 1 hr. Reaction mass was concentrated under reduced pressure and released in Argon to get 2-methyl-N-[(3-methyl-2-sulfanyl-phenyl)methyl]propane-2-sulfinamide (650 mg, crude) whish was directly used for next step without further purification. MS found: 258.0 (M+H).

To a stirred solution of 2-methyl-N-[(3-methyl-2-sulfanyl-phenyl)methyl]propane-2-sulfinamide (1.4 g, 5.439 mmol) and 2-Chloro-nicotinic acid tert-butyl ester (1.16 g, 5.439 mmol) in acetonitrile (20 mL) was added K$_2$CO$_3$ (1.5 g, 10.877 mmol) and reaction mixture was heated to 70° C. for 4h. Reaction mixture was diluted with ethyl acetate and washed with water. The separated organic layer was washed with brine solution, dried over anhydrous sodium sulfate and evaporated under reduced pressure. The crude thus obtained was purified by silica chromatography using 5-40% ethyl acetate in hexane to get tert-butyl 2-[2-[(tert-butylsulfinylamino)methyl]-6-methyl-phenyl]sulfanylpyridine-3-carboxylate (700 mg, 30%, 2 steps) as a off white solid. MS found: 435 (M+H).

To a stirred solution of tert-butyl 2-[2-[(tert-butylsulfinylamino)methyl]-6-methyl-phenyl]sulfanylpyridine-3-carboxylate (1.4 g, 3.665 mmol) in THF (20 mL) was added LiBH$_4$ (795 mg, 36.654 mmol) and reaction mixture was heated to 70° C. for 4h. Reaction mixture was quenched with saturated ammonium chloride solution and extracted with ethyl acetate. The separated organic layer was washed with water, brine solution, dried over anhydrous and evaporated under reduced pressure. The crude thus obtained was purified by normal silica column using 5-60% ethyl acetate in hexane to get N-[[2-[[3-(hydroxymethyl)-2-pyridyl]sulfanyl]-3-methyl-phenyl]methyl]-2-methyl-propane-2-sulfinamide (800 mg, 57%) as a off white solid. MS found: 364.8 (M+H).

To a stirred solution of N-[[2-[[3-(hydroxymethyl)-2-pyridyl]sulfanyl]-3-methyl-phenyl]methyl]-2-methyl-propane-2-sulfinamide (800 mg, 2.195 mmol) in MeOH (15 mL), was added 4M HCl/dioxane (30 mL) at 0° C. and reaction mixture was stirred at 25° C. for 1 h. After completion of reaction, reaction mixture was concentrated under reduced pressure to get [2-[2-(aminomethyl)-6-methyl-phenyl]sulfanyl-3-pyridyl]methanol (650 mg, crude) as a off white solid. MS found: 260.9 (M+H).

To a stirred suspension of [2-[2-(aminomethyl)-6-methyl-phenyl]sulfanyl-3-pyridyl]methanol (650 mg, 2.19 mmol) in 5% NaHCO$_3$(20 mL) was added Fmoc OSU (738 mg, 2.19 mmol) in CH$_3$CN (30 mL) at 25° C. and reaction was stirred at 25° C. for 2h. Then reaction mixture was diluted with water and extracted with ethyl acetate. The separated organic layer was washed with brine solution, dried over sodium sulfate and evaporated under reduced pressure. The crude thus obtained was purified by normal silica column using 5-30% ethyl acetate in hexane to get 9H-fluoren-9- ylmethyl N-[[2-[[3-(hydroxymethyl)-2-pyridyl]sulfanyl]-3-methyl-phenyl]methyl]carbamate (700 mg, 66%, 2 steps) as a off white solid. MS found: 482.9 (M+H).

To a stirred solution of 9H-fluoren-9-ylmethyl N-[[2-[[3-(hydroxymethyl)-2-pyridyl]sulfanyl]-3-methyl-phenyl] methyl]carbamate (700 mg, 1.45 mmol) in DCM/THF (1:1, 20 mL) was added MnO$_2$ (2.52 g, 29.009 mmol 1) and reaction mixture was stirred at 25° C. for 2h. The reaction mixture was filtered through celite pad; filtrate was evaporated under reduced pressure. The crude thus obtained was purified by silica chromatography using 5-30% ethyl acetate in hexane to get 9H-fluoren-9-ylmethyl N-[[2-[(3-formyl-2-pyridyl)sulfanyl]-3-methyl-phenyl]methyl]carbamate (490 mg, 70%) as a off white solid. NMR complies.

$^1$H-NMR: (400 MHz, DMSO-d6) δ 2.32 (3H; s); 4.18-4.29 (5H; m); 7.16 (1H; d; J=7.48 Hz); 7.28-7.37 (5H; m); 7.40-7.44 (3H; m); 7.69 (2H; d; J=7.20 Hz); 7.87 (1H; m); 7.96 (2H; d; J=7.48 Hz); 8.31 (1H; d; J=7.32 Hz); 8.40 (1H; br d; J=4.04 Hz); 10.23 (1H; s)

Intermediate 41

9H-fluoren-9-ylmethyl N-[(1S)-1-[3-chloro-2-(2-formylphenyl)sulfanyl-phenyl]ethyl]carbamate

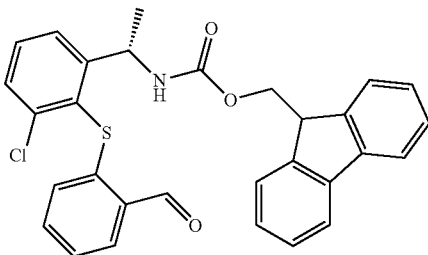

A solution of 1-(3-chloro-2-fluorophenyl)ethan-1-one (4 g, 23.176 mmol), (2-sulfanylphenyl)methanol (3.25 g, 23.176 mmol), 63% aq. NaOH (1.2 mL) and HMPA (40 mL) was heated to 100° C. for 5h. The reaction mixture was diluted with water and extracted with EtOAc. The combined organic layers were washed with brine, dried over anhydrous sodium sulfate and concentrated under vacuum. The crude material obtained was purified by silica chromatography (100-200 mesh) using 0-20% EtOAc in hexane to get 1-[3-chloro-2-[2-(hydroxymethyl)phenyl]sulfanyl-phenyl] ethanone (4 g, 59%) as a colourless sticky liquid.

To the stirred solution of 1-[3-chloro-2-[2-(hydroxymethyl)phenyl]sulfanyl-phenyl]ethanone (4 g, 13.662 mmol) in THF (40 mL) were added (S) 2-methyl 2-propane sulfinamide (1.65 g, 13.662 mmol) and Ti(OEt)$_4$ (14.4 mL, 68.308 mmol) and heated to 70° C. for 16h. The reaction mixture was quenched with brine solution and extracted with ethyl acetate. The separated organic layers were dried over anhydrous sodium sulfate and concentrated under reduced pressure. The crude material obtained was purified by normal silica column using 0-30% ethyl acetate in hexane to afford N-[1-[3-chloro-2-[2-(hydroxymethyl)phenyl]sulfanyl-phenyl]ethylidene]-2-methyl-propane-2-sulfinamide (3.2 g, 59%) as a yellow solid. MS found: 395.9 (M+H).

To a stirred solution of N-[1-[3-chloro-2-[2-(hydroxymethyl)phenyl]sulfanyl-phenyl]ethylidene]-2-methyl-propane-2-sulfinamide (600 mg, 1.515 mmol) in THF (20 mL) was added L-selectride (7.5 mL, 7.5 mmol) at 25° C. and stirred at the same temperature for 16 h. Then the reaction mixture was quenched with saturated NH$_4$Cl solution and extracted with ethyl acetate, dried over Na$_2$SO$_4$ and concentrated under vacuum to get N-[(1S)-1-[3-chloro-2-[2-(hydroxymethyl)phenyl]sulfanyl-phenyl]ethyl]-2-methyl-propane-2-sulfinamide (600 mg, crude) as off white sticky solid. MS found: 398.0 (M+H).

To a stirred solution of N-[(1S)-1-[3-chloro-2-[2-(hydroxymethyl)phenyl]sulfanyl-phenyl]ethyl]-2-methyl-propane-2-sulfinamide (500 mg, 1.256 mmol) in MeOH (20 mL), was added 4M HCl/dioxane (10 mL) at 0° C. and reaction mixture was stirred at 25° C. for 1 h. After completion of reaction, reaction mixture was concentrated under reduced pressure to get [2-[2-[(1S)-1-aminoethyl]-6-chloro-phenyl]sulfanylphenyl]methanol (400 mg, crude) as a off white solid. MS found: 294.0 (M+H).

To a stirred suspension of [2-[2-[(1S)-1-aminoethyl]-6-chloro-phenyl]sulfanylphenyl]methanol (480 mg, 1.453 mmol) in 5% NaHCO$_3$(10 mL) was added Fmoc OSU (489 mg, 1.453 mmol) in CH$_3$CN (10 mL) at 25° C. and reaction was stirred at 25° C. for 2h. Then reaction mixture was diluted with water and extracted with ethyl acetate. The separated organic layers were washed with brine solution, dried over sodium sulfate and evaporated under reduced pressure. The crude thus obtained was purified by normal silica column using 5-30% ethyl acetate in hexane to get 9H-fluoren-9-ylmethyl N-[(1S)-1-[3-chloro-2-[2-(hydroxymethyl)phenyl]sulfanyl-phenyl]ethyl]carbamate (420 mg, 54%, 3 steps) as a off white solid. MS found: 516.2 (M+H).

To a stirred solution of 9H-fluoren-9-ylmethyl N-[(1S)-1-[3-chloro-2-[2-(hydroxymethyl)phenyl]sulfanyl-phenyl] ethyl]carbamate (420 mg, 0.814 mmol) in DCM/THF (1:1, 20 mL) was added MnO$_2$ (1.414 g, 16.277 mmol) and reaction mass was stirred at 25° C. for 2h. The reaction mass was filtered through celite pad; filtrate was evaporated under reduced pressure. The crude thus obtained was purified by normal silica column using 5-20% ethyl acetate in hexane to get 9H-fluoren-9-ylmethyl N-[(1S)-1-[3-chloro-2-(2-formylphenyl)sulfanyl-phenyl]ethyl]carbamate (350 mg, 83%) as a off white solid. $^1$H-NMR: (400 MHz, DMSO-d6) δ 1.26 (3H; d; J=6.76 Hz); 4.18-4.23 (3H; m); 5.23 (1H; m); 6.59 (1H; d; J=8.04 Hz); 7.31-7.43 (5H; m); 7.58 (2H; m); 7.68 (2H; m); 7.90 (2H; d; J=7.4 Hz); 7.96 (1H; d; J=7.4 Hz); 8.03 (1H; d; J=7.36 Hz); 10.21 (1H; s)

Intermediate 42

9H-fluoren-9-ylmethyl N-[[3-chloro-2-(4-fluoro-2-formyl-phenyl)sulfanyl-phenyl]methyl]carbamate

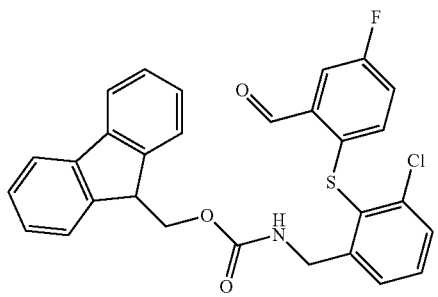 [SMILES: O=Cc1cc(F)ccc1Sc1c(Cl)cccc1CNC(=O)OCC1c2ccccc2-c2ccccc21]

To a stirred solution of 4-fluoro-3-formyl-benzoic acid (2.5 g, 14.535 mmol) in THF (20 mL), was added tert-butyl 2,2,2-trichloroethanecarboximidate (9.112 mL, 50.872 mmol) followed by slow addition of BF$_3$·OEt$_2$ (1.54 mL, 14.535 mmol) at 0° C. and stirred at room temperature for 2 h. After completion of reaction, reaction mixture was quenched with water and extracted with ethyl acetate. The combined organic layers were washed with brine, dried over anhydrous sodium sulfate and concentrated under reduced pressure to get crude material which was purified by normal silica column using 1% ethyl acetate in hexane to get tert-butyl 5-fluoro-2-sulfanyl-benzoate (1.7 g, 51%) as yellow solid.

To a stirred solution of tert-butyl 5-fluoro-2-sulfanylbenzoate (2 g, 8.761 mmol) and 3-chloro-2-fluoro-benzaldehyde (1.38 g, 8.761 mmol) in DMF (12 mL) was added K$_2$CO$_3$ (2.4 g, 17.522 mmol) and reaction mass was stirred at 25° C. for 1 h. Reaction mixture was diluted with ethyl acetate and washed with water. The separated organic layer was washed with brine solution, dried over anhydrous sodium sulfate and evaporated under reduced pressure. The crude thus obtained was purified by normal silica column using 0-2% ethyl acetate in hexane to get tert-butyl 2-(2-chloro-6-formyl-phenyl)sulfanyl-5-fluoro-benzoate (1.8 g, 56%) as a yellow solid.

To the stirred solution of tert-butyl 2-(2-chloro-6-formyl-phenyl)sulfanyl-5-fluoro-benzoate (1.8 g, 4.907 mmol) in THF (20 mL) were added 2-methyl 2-propane sulfinamide (595 mg, 4.907 mmol) and Ti(OEt)$_4$ (5.18 mL, 24.534 mmol) and heated to 70° C. for 1 h. The reaction mixture was quenched with brine solution and extracted with ethyl acetate. The separated organic layers were dried over anhydrous sodium sulfate and concentrated under vacuum to afford tert-butyl 2-[2-[(Z)-tert-butylsulfinyliminomethyl]-6-chloro-phenyl]sulfanyl-5-fluoro-benzoate (2 g, crude) as a yellow solid. MS found: 470.2 (M+H).

To a stirred solution of tert-butyl 2-[2-[(Z)-tert-butylsulfinyliminomethyl]-6-chloro-phenyl]sulfanyl-5-fluoro-benzoate (2 g, 4.255 mmol) in THF (30 mL) was added LiBH$_4$ (923 mg, 42.55 mmol) and reaction mixture was heated to 70° C. for 8h. The reaction mixture was quenched with saturated ammonium chloride solution and extracted with ethyl acetate. The separated organic layer was washed with water, brine solution, dried over anhydrous sodium sulfate and evaporated under reduced pressure to get N-[[3-chloro-2-[4-fluoro-2-(hydroxymethyl)phenyl]sulfanyl-phenyl]methyl]-2-methyl-propane-2-sulfinamide (1,7 g, crude) which was directly used for next step. MS found: 401.7 (M+H).

To a stirred solution of N-[[3-chloro-2-[4-fluoro-2-(hydroxymethyl)phenyl]sulfanyl-phenyl]methyl]-2-methyl-propane-2-sulfinamide (1.7 g, 4.2229 mmol) in MeOH (24 mL), was added 4M HCl/dioxane (12 mL) at 0° C. and reaction mixture was stirred at 25° C. for 20 min. After completion of reaction, reaction mixture was concentrated under reduced pressure to get [2-[2-(aminomethyl)-6-chloro-phenyl]sulfanyl-5-fluoro-phenyl]methanol (1.4 g, crude) as a sticky liquid. MS found: 298.1 (M+H).

To a stirred suspension of [2-[2-(aminomethyl)-6-chloro-phenyl]sulfanyl-5-fluoro-phenyl]methanol (1.4 g, 4.188 mmol) in 5% NaHCO$_3$(20 mL) was added Fmoc OSU (1.41 g, 4.188 mmol) in CH$_3$CN (20 mL) at 25° C. and reaction was stirred at 25° C. for 2h. Then reaction mass was diluted with water and extracted with ethyl acetate. The separated organic layers were washed with brine solution, dried over sodium sulfate and evaporated under reduced pressure to get 9H-fluoren-9-ylmethyl N-[[3-chloro-2-[4-fluoro-2-(hydroxymethyl)phenyl]sulfanyl-phenyl]methyl]carbamate (2 g, crude) which was directly used for next step without further purification. MS found: 520.1 (M+H).

To a stirred solution of 9H-fluoren-9-ylmethyl N-[[3-chloro-2-[4-fluoro-2-(hydroxymethyl)phenyl]sulfanyl-phenyl]methyl]carbamate (1 g, 1.923 mmol) in DCM/THF (1:1, 20 mL) was added MnO$_2$ (3.3 g, 38.459 mmol) and reaction mass was stirred at 25° C. for 2h. The reaction mixture was filtered through celite pad; filtrate was evaporated under reduced pressure. The crude thus obtained was purified by normal silica column using 5-40% ethyl acetate in hexane to get 9H-fluoren-9-ylmethyl N-[[3-chloro-2-(4-fluoro-2-formyl-phenyl)sulfanyl-phenyl]methyl]carbamate (420 mg, 42%, 5 steps) as a off white solid. $^1$H-NMR: (400 MHz, DMSO-d6) δ 4.12-4.33 (5H; m); 6.55-6.59 (1H; m); 7.30-7.41 (5H; m); 7.56 (1H; t; J=7.72 Hz); 7.61-7.66 (3H; m); 7.84-7.90 (4H; m); 10.19 (1H; s)

Intermediate 43

9H-fluoren-9-ylmethyl N-[[2-[(3-formyl-2-pyridyl)sulfanyl]-5-methoxy-phenyl]methyl]carbamate

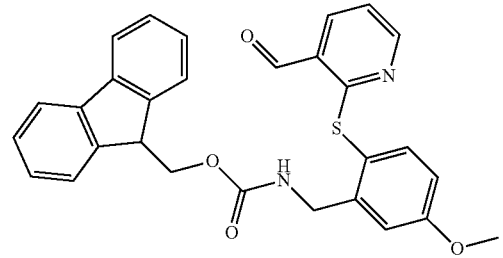 [SMILES: COc1ccc(Sc2ncccc2C=O)c(CNC(=O)OCC2c3ccccc3-c3ccccc32)c1]

A suspension of Na$_2$S·xH$_2$O (1.2 g, 15.57 mmmol) and MgSO$_4$(4 g) in N,N-dimethyl acetamide (40 mL) was stirred at 90° C. for a period of 90 minutes under nitrogen atmosphere followed by the addition of 2-Fluoro-5-methoxy-benzaldehyde (2 g, 12.975 mmmol) at the same temperature. Stirring was continued for another 5h at 90° C. The reaction mixture was cooled to 0° C., acetic anhydride (12.2 mL, 129.752 mmmol) was added drop-wise and the mixture was stirred at 0° C. for 30 min and 25° C. for 16h. The reaction mixture was diluted with ethyl acetate and washed with water. The separated organic layer was washed with brine solution, dried over anhydrous sodium sulfate and evaporated under reduced pressure to get S-(2-formyl-4-methoxy-phenyl) ethanethioate (2 g, crude) which was directly used for next step without further purification. MS found: 211.0 (M+H).

To the stirred solution of S-(2-formyl-4-methoxy-phenyl) (2.8 g, 13.333 mmol) in THF (20 mL) were added 2-methyl 2-propane sulfinamide (1.616 g, 13.333 mmol) and Ti(OEt)$_4$ (2.795 ml, 13.333 mmol) and heated to 70° C. for 45 min. The reaction mixture was quenched with brine solution and extracted with ethyl acetate. The separated organic layer was dried over anhydrous sodium sulfate and concentrated under reduced pressure. The crude thus obtained was purified by normal silica column using 0-10% ethyl acetate in hexane to get S-[2-[(Z)-tert-butylsulfinyliminomethyl]-4-methoxy-phenyl] ethanethioate (980 mg, 17%, 2 steps) as a colorless sticky liquid. MS found: 313.8 (M+H).

A solution of S-[2-[(Z)-tert-butylsulfinyliminomethyl]-4-methoxy-phenyl] ethanethioate (980 mg, 3.131 mmol) in THF (15 mL) was degassed with argon for about 10 minutes and then NaBH$_4$ (1.184 g, 31.31 mmol) was added portionwise under cooling condition and stirred for 30 min at 0° C. The reaction was then quenched with acetone (10 mL) (degassed with argon) and stirred under the cooling condition for 1 hr. Reaction mass was concentrated under reduced pressure and released in Argon to get N-[(5-methoxy-2-sulfanyl-phenyl)methyl]-2-methyl-propane-2-sulfinamide (855 mg, crude) whish was directly used for next step without further purification.

To a stirred solution of N-[(5-methoxy-2-sulfanyl-phenyl)methyl]-2-methyl-propane-2-sulfinamide (854 mg, 3.128 mmol) and 2-Chloro-nicotinic acid tert-butyl ester (668.497 mg, 3.128 mmol) in acetonitrile (15 mL) was added K₂CO₃ (1.08 g, 7.821 mmol) and reaction mass was heated to 70° C. for 4h. Reaction mass was diluted with ethyl acetate and washed with water. The separated organic layer was washed with brine solution, dried over anhydrous sodium sulfate and evaporated under reduced pressure. The crude thus obtained was purified by normal silica column using 10-60% ethyl acetate in hexane to get tert-butyl 2-[2-[(tert-butylsulfinylamino)methyl]-4-methoxy-phenyl]sulfanylpyridine-3-carboxylate (420 mg, 30%, 2 steps) as a white sticky solid. MS found: 450.8 (M+H).

To a stirred solution of tert-butyl 2-[2-[(tert-butylsulfinylamino)methyl]-4-methoxy-phenyl]sulfanylpyridine-3-carboxylate (470 mg, 1.044 mmol) in THF (12 mL) was added LiBH₄ (227.48 mg, 10.44 mmol) and reaction mass was heated to 70° C. for 4h. Reaction mass was quenched with saturated ammonium chloride solution and extracted with ethyl acetate. The separated organic layer was washed with water, brine solution, dried over anhydrous and evaporated under reduced pressure to get N-[[2-[[3-(hydroxymethyl)-2-pyridyl]sulfanyl]-5-methoxy-phenyl]methyl]-2-methyl-propane-2-sulfinamide (370 mg, crude) as a off white sticky solid. MS found: 380.9 (M+H).

To a stirred solution of N-[[2-[[3-(hydroxymethyl)-2-pyridyl]sulfanyl]-5-methoxy-phenyl]methyl]-2-methyl-propane-2-sulfinamide (370.0 mg, 0.974 mmol) in MeOH (10 mL), was added 4M HCl/dioxane (5 mL) at 0° C. and reaction mixture was stirred at 25° C. for 1 h. After completion of reaction, reaction mixture was concentrated under reduced pressure to get [2-[2-(aminomethyl)-4-methoxy-phenyl]sulfanyl-3-pyridyl]methanol (300 mg, crude) as an off white solid. MS found: 276.9 (M+H).

To a stirred suspension [2-[2-(aminomethyl)-4-methoxy-phenyl]sulfanyl-3-pyridyl]methanol (300 mg, 1.087 mmol) in 5% NaHCO₃(5 mL) was added Fmoc OSU (366.522 mg, 1.087 mmol) in CH₃CN (5 mL) at 25° C. and reaction was stirred at 25° C. for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[[2-[[3-(hydroxymethyl)-2-pyridyl]sulfanyl]-5-methoxy-phenyl]methyl]carbamate (350 mg, crude) as a off white solid. MS found: 498.8 (M+H).

To a stirred solution of 9H-fluoren-9-ylmethyl N-[[2-[[3-(hydroxymethyl)-2-pyridyl]sulfanyl]-5-methoxy-phenyl]methyl]carbamate (350 mg, 0.703 mmol) in DCM/THF (1:1, 20 mL) was added MnO₂ (610.954 mg, 7.028 mmol) and reaction mass was stirred at 25° C. for 2h. The reaction mass was filtered through celite pad; filtrate was evaporated under reduced pressure. The crude material obtained was purified by normal silica column using 5-30% ethyl acetate in hexane to get 9H-fluoren-9-ylmethyl N-[[2-[(3-formyl-2-pyridyl)sulfanyl]-5-methoxy-phenyl]methyl]carbamate (250 mg, 48%, 4 steps) as a off white solid.

¹H-NMR: (400 MHz, DMSO-d6) δ 3.79 (3H; s); 4.17-4.21 (3H; m); 4.26-4.28 (2H; m); 6.90-6.92 (1H; m); 6.96 (1H; m); 7.30-7.36 (3H; m); 7.39-7.44 (3H; m); 7.69 (2H; d; J=7.48 Hz); 7.84 (1H; m); 7.90 (2H; d; J=7.4 Hz); 8.30 (1H; d; J=7.4 Hz); 8.4 (1H; d; J=3.56 Hz); 10.19 (1H; s)

Intermediate 44

9H-fluoren-9-ylmethyl N-[[2-(4-fluoro-2-formyl-phenyl)sulfanyl-3-methyl-phenyl]methyl]carbamate

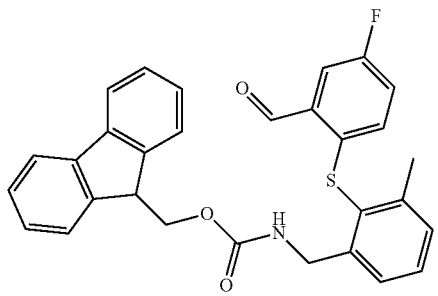 [SMILES: Cc1cccc(CNC(=O)OCC2c3ccccc3-c3ccccc32)c1Sc1ccc(F)cc1C=O]

To a stirred solution of tert-butyl 5-fluoro-2-sulfanylbenzoate (1.2 g, 5.256 mmol) and 2-fluoro-3-methyl-benzaldehyde (726 mg, 5.256 mmol) in DMF (12 mL) was added Cs₂CO₃ (3.4 g, 10.513 mmol) and reaction mass was heated to 70° C. for 3h. Reaction mixture was diluted with ethyl acetate and washed with water. The separated organic layer was washed with brine solution, dried over anhydrous sodium sulfate and evaporated under reduced pressure. The crude material obtained was purified by silica chromatography using 0-2% ethyl acetate in hexane to get tert-butyl 5-fluoro-2-(2-formyl-6-methyl-phenyl)sulfanyl-benzoate (600 mg, 33%) as a colorless sticky liquid.

To the stirred solution of tert-butyl 5-fluoro-2-(2-formyl-6-methyl-phenyl)sulfanyl-benzoate (1.2 g, 3.464 mmol) in THF (20 mL) were added 2-methyl 2-propane sulfinamide (420 mg, 3.464 mmol) and Ti(OEt)₄ (3.65 mL, 17.32 mmol) and heated to 70° C. for 1 h. Reaction mixture was quenched with brine solution and extracted with ethyl acetate. The separated organic layer was dried over anhydrous sodium sulfate and concentrated under vacuum to tert-butyl 2-[2-[(Z)-tert-butylsulfinyliminomethyl]-6-methyl-phenyl]sulfanyl-5-fluoro-benzoate (1.3 g, crude) as a yellow solid. MS found: 449.7 (M+H).

To a stirred solution of tert-butyl 2-[2-[(Z)-tert-butylsulfinyliminomethyl]-6-methyl-phenyl]sulfanyl-5-fluoro-benzoate (1.3 g, 2.891 mmol) in THF (20 mL) was added LiBH₄ (627 mg, 28.914 mmol) and reaction mass was heated to 70° C. for 8h. Reaction mixture was quenched with saturated ammonium chloride solution and extracted with ethyl acetate. The separated organic layer was washed with water, brine solution, dried over anhydrous sodium sulfate and evaporated under reduced pressure. The crude thus obtained was purified by normal silica column using 5-50% EA/Hex to get N-[[2-[4-fluoro-2-(hydroxymethyl)phenyl]sulfanyl-3-methyl-phenyl]methyl]-2-methyl-propane-2-sulfinamide (1 g, 75%, 2 steps) as a off white solid. MS found: 382.0 (M+H).

To a stirred solution of N-[[2-[4-fluoro-2-(hydroxymethyl)phenyl]sulfanyl-3-methyl-phenyl]methyl]-2-methyl-propane-2-sulfinamide (1 g, 2.62 mmol) in MeOH (10 mL), was added 4M HCl/dioxane (5 mL) at 0° C. and reaction mixture was stirred at 25° C. for 1 h. After completion of reaction, reaction mixture was concentrated under reduced pressure to get [2-[2-(aminomethyl)-6-methyl-phenyl]sulfanyl-5-fluoro-phenyl]methanol (800 mg, crude) as a sticky liquid. MS found: 277.9 (M+H).

To a stirred suspension of [2-[2-(aminomethyl)-6-methyl-phenyl]sulfanyl-5-fluoro-phenyl]methanol (800 mg, 2.549 mmol) in 5% NaHCO$_3$(10 mL) was added Fmoc OSU (859 mg, 2.549 mmol) in CH$_3$CN (10 mL) at 25° C. and reaction was stirred at 25° C. for 2h. Then reaction mass was diluted with water and extracted with ethyl acetate. The separated organic layer was washed with brine solution, dried over sodium sulfate and evaporated under reduced pressure. The crude material obtained was purified by silica chromatography using 5-30% ethyl acetate in hexane to get 9H-fluoren-9-ylmethyl N-[[2-[4-fluoro-2-(hydroxymethyl)phenyl]sulfanyl-3-methyl-phenyl]methyl]carbamate (800 mg, 61%, 2 steps) as a off white solid. MS found: 500.1 (M+H).

To a stirred solution of 9H-fluoren-9-ylmethyl N-[[2-[4-fluoro-2-(hydroxymethyl)phenyl]sulfanyl-3-methyl-phenyl]methyl]carbamate (800 mg, 1.661 mmol) in DCM/THF (1:1, 20 mL) was added MnO$_2$ (2.88 g, 33.221 mmol) and reaction mixture was stirred at 25° C. for 2h. The reaction mixture was filtered through celite pad; filtrate was evaporated under reduced pressure. The crude thus obtained was purified by silica chromatography using 5-20% ethyl acetate in hexane to get 9H-fluoren-9-ylmethyl N-[[2-(4-fluoro-2-formyl-phenyl)sulfanyl-3-methyl-phenyl]methyl]carbamate (510 mg, 61%) as a off white solid. MS found: 498.1 (M+H).

$^1$H-NMR: (400 MHz, DMSO-d6) δ 2.2 (3H; s); 4.19-4.21 (1H; m); 4.23-4.30 (4H; m); 6.45 (1H; m); 7.23 (1H; br s; J=6.88 Hz); 7.32-7.45 (7H; m); 7.67 (1H; d; J=7.04 Hz); 7.78-7.90 (4H; m); 10.20 (1H; s).

Intermediate 45

9H-fluoren-9-ylmethyl N-[[3-chloro-2-[(3-formyl-2-pyridyl)sulfanyl]-5-(trifluoromethyl)phenyl]methyl] carbamate

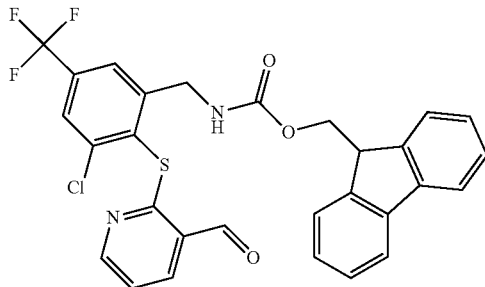

To a stirred solution of 2-mercapto-nicotinic acid methyl ester (1.23 g, 7.283 mmol), in DMF (15 mL) was added KOtBu (817 mg, 7.283 mmol) and reaction mass was stirred at 25° C. for 30 min. Then 3-chloro-2-fluoro-5-trifluoromethyl-benzaldehyde (1.5 g, 6.621 mmol) was added to the reaction mass and it was heated to 80° C. for 1 h. The reaction mixture was quenched with water and extracted with ethyl acetate. The separated organic layer was washed with brine solution, dried over anhydrous sodium sulfate and evaporated under reduced pressure to get methyl 2-[2-chloro-6-formyl-4-(trifluoromethyl)phenyl]sulfanylpyridine-3-carboxylate (2.3 g, crude) which was directly used for next step without further purification. MS found: 375.5 (M+H).

To a stirred solution of methyl 2-[2-chloro-6-formyl-4-(trifluoromethyl)phenyl]sulfanylpyridine-3-carboxylate (2.3 g, 6.121 mmol) in THF (20 mL) were added 2-methylpropane-2-sulfinamide (742 mg, 6.121 mmol) and Ti(OEt)$_4$ (6.4 mL, 30.605 mmol) and heated to 70° C. for 1 h. Reaction mixture was quenched with brine solution and extracted with ethyl acetate. The separated organic layer was dried over anhydrous sodium sulfate and concentrated under vacuum to afford ethyl 2-[2-[(Z)-tert-butylsulfinyliminomethyl]-6-chloro-4-(trifluoromethyl)phenyl]sulfanylpyridine-3-carboxylate (2.8 g, crude) which was directly used for next step without further purification. MS found: 492.6 (M+H).

To a stirred solution of ethyl 2-[2-[(Z)-tert-butylsulfinyliminomethyl]-6-chloro-4-(trifluoromethyl)phenyl]sulfanylpyridine-3-carboxylate (2.8 g, 5.68 mmol) in THF (20 mL) was added LAH (1M in THF, 11.36 mL, 11.36 mmol) at 0° C. and reaction mass was stirred at 25° C. for 2h. The reaction mixture was quenched with saturated sodium sulfate solution and extracted with ethyl acetate. The separated organic layers were washed with water, brine solution, dried over anhydrous sodium sulfate and evaporated under reduced pressure. The crude material obtained was purified by silica chromatography using 10-60% ethyl acetate in hexane to get N-[[3-chloro-2-[[3-(hydroxymethyl)-2-pyridyl]sulfanyl]-5-(trifluoromethyl)phenyl]methyl]-2-methyl-propane-2-sulfinamide (1.4 g, 47%, 3 steps) as an off white solid. MS found: 452.8 (M+H).

To a stirred solution of N-[[3-chloro-2-[[3-(hydroxymethyl)-2-pyridyl]sulfanyl]-5-(trifluoromethyl)phenyl]methyl]-2-methyl-propane-2-sulfinamide (1.4 g, 3.091 mmol) in MeOH (40 mL), was added 4M HCl in dioxane (20 mL) at 0° C. and reaction mixture was stirred at 25° C. for 1 h. After completion of reaction, the mixture was concentrated under reduced pressure to get [2-[2-(aminomethyl)-6-chloro-4-(trifluoromethyl)phenyl]sulfanyl-3-pyridyl]methanol (1 g, crude) as off white solid which was directly used for next step. MS found: 348.7 (M+H).

To a stirred suspension of [2-[2-(aminomethyl)-6-chloro-4-(trifluoromethyl)phenyl]sulfanyl-3-pyridyl]methanol (1 g, 2.596 mmol) in 5% NaHCO$_3$(20 mL) was added Fmoc OSU (875 mg, 2.596 mmol) in CH$_3$CN (20 mL) at 25° C. and reaction mixture was stirred at 25° C. for 2h. Then reaction mixture was diluted with water and extracted with ethyl acetate. The separated organic layer was washed with brine solution, dried over sodium sulfate and evaporated under reduced pressure to get the crude which was purified by normal silica column using 5-30% ethyl acetate in hexane to 9H-fluoren-9-ylmethyl N-[[3-chloro-2-[[3-(hydroxymethyl)-2-pyridyl]sulfanyl]-5-(trifluoromethyl)phenyl]methyl]carbamate (1.1 g, 62%, 2 steps) as off-white solid. MS found: 570.8 (M+H).

To a stirred solution of N-[[3-chloro-2-[[3-(hydroxymethyl)-2-pyridyl]sulfanyl]-5-(trifluoromethyl)phenyl]methyl]carbamate (1.1 g, 1.926 mmol) in DCM/THF (1:1, 40 mL) was added MnO$_2$ (3.34 g, 38.528 mmol)) and reaction mass was stirred at 25° C. for 2h. The reaction mass was filtered through celite pad, filtrate was evaporated under reduced pressure to get the crude which was purified by normal silica column using 5-20% ethyl acetate in hexane to afford the 9H-fluoren-9-ylmethyl N-[[3-chloro-2-[(3-formyl-2-pyridyl)sulfanyl]-5-(trifluoromethyl)phenyl]methyl]carbamate as off-white solid (650 mg, 59%)

$^1$H-NMR: (400 MHz, DMSO-d6) δ 4.20-4.21 (1H; m); 4.22-4.28 (2H; m); 4.34-4.35 (2H; m); 7.28-7.32 (2H; m);

7.39-7.43 (3H; m); 7.66-7.68 (3H; m); 7.89 (2H; d; J=7.4 Hz); 7.96-7.97 (1H; m); 7.99 (1H; br s); 8.39-8.43 (2H; m); 10.19 (1H; s)

Intermediate 46

9H-fluoren-9-ylmethyl N-[[3-(2-formylphenyl)sulfanyl-4-pyridyl]methyl]carbamate

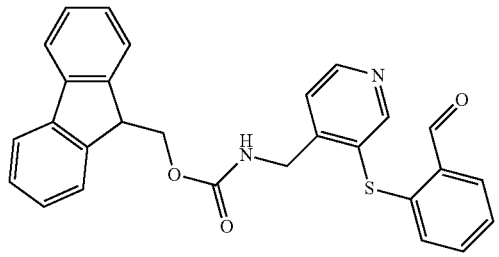 [SMILES: O=Cc1ccccc1Sc1cnccc1CNC(=O)OCC1c2ccccc2-c2ccccc21]

To a stirred solution of 2-chloro-pyridine-3-carbaldehyde (2.0 g, 14.124 mmol) and methyl thio salicylate (2.376 g, 14.124 mmol) in DMF (20 mL) was added $Cs_2CO_3$ (9.181 g, 28.249 mmol) and reaction mass was heated to 70° C. for 2h. The reaction mixture was diluted with ethyl acetate and washed with water. The separated organic layers were washed with brine solution, dried over anhydrous sodium sulfate and evaporated under reduced pressure. The crude thus obtained was purified by silica chromatography using 10-50% ethyl acetate in hexane to get methyl 2-[(3-formyl-2-pyridyl)sulfanyl]benzoate (3 g, 77%) as a yellow solid.

To the stirred solution of methyl 2-[(3-formyl-2-pyridyl)sulfanyl]benzoate (3.02 g, 11.062 mmol) in THF (25 mL) were added 2-methyl 2-propane sulfinamide (1.341 g, 11.062 mmol) and $Ti(OEt)_4$ (11.597 mL, 55.311 mmol) and heated to 70° C. for 90 min. The reaction mixture was quenched with brine solution and extracted with ethyl acetate. The separated organic layers were dried over anhydrous sodium sulfate and concentrated under vacuum to afford ethyl 2-[[3-[(Z)-tert-butylsulfinyliminomethyl]-2-pyridyl]sulfanyl]benzoate (3.5 g, crude) as a yellow solid. MS found: 390.7 (M+H).

To a stirred solution of ethyl 2-[[3-[(Z)-tert-butylsulfinyliminomethyl]-2-pyridyl]sulfanyl]benzoate (3.5 g, 8.974 mmol) in THF (25 mL) was added $LiBH_4$ (1.955 g, 89.744 mmol) and reaction mixture was heated to 70° C. for 3h. The reaction mixture was quenched with saturated ammonium chloride solution and extracted with ethyl acetate. The separated organic layers were washed with water, brine solution, dried over anhydrous sodium sulfate and evaporated under reduced pressure to get N-[[2-[2-(hydroxymethyl)phenyl]sulfanyl-3-pyridyl]methyl]-2-methyl-propane-2-sulfinamide (3 g, crude) as a off white solid. MS found: 350.8 (M+H).

To a stirred solution of N-[[2-[2-(hydroxymethyl)phenyl]sulfanyl-3-pyridyl]methyl]-2-methyl-propane-2-sulfinamide (3.0 g, 8.571 mmol) in MeOH (30 mL), was added 4M HCl/dioxane (15 mL) at 0° C. and reaction mixture was stirred at 25° C. for 1 h. After completion of reaction, the mixture was concentrated under reduced pressure to get [2-[[3-(aminomethyl)-2-pyridyl]sulfanyl]phenyl]methanol (2.5 g, crude) as a sticky liquid. MS found: 247.1 (M+H).

To a stirred suspension of [2-[[3-(aminomethyl)-2-pyridyl]sulfanyl]phenyl]methanol (2.5 g, 10.163 mmol) in 5% $NaHCO_3$ (20 mL) was added Fmoc OSU (3.427 g, 10.163 mmol) in $CH_3CN$ (20 mL) at 25° C. and reaction was stirred at 25° C. for 3h. Then reaction mixture was diluted with water and extracted with ethyl acetate. The separated organic layers were washed with brine solution, dried over sodium sulfate and evaporated under reduced pressure. The crude thus obtained was purified by silica chromatography using 5-50% ethyl acetate in hexane to get 9H-fluoren-9-ylmethyl N-[[2-[2-(hydroxymethyl)phenyl]sulfanyl-3-pyridyl]methyl]carbamate (1.6 g, 31%, 4 steps) as a off a white solid. MS found: 468.8 (M+H).

To a stirred solution of 9H-fluoren-9-ylmethyl N-[[2-[2-(hydroxymethyl)phenyl]sulfanyl-3-pyridyl]methyl]carbamate (2.0 g, 4.274 mmol) in DCM/THF (1:1, 50 mL) was added $MnO_2$ (7.43 g, 85.47 mmol) and reaction mixture was stirred at 25° C. for 2h. The reaction mixture was filtered through celite pad; filtrate was evaporated under reduced pressure. The crude material obtained was purified by normal silica column using 10-70% ethyl acetate in hexane to get 9H-fluoren-9-ylmethyl N-[[3-(2-formylphenyl)sulfanyl-4-pyridyl]methyl]carbamate (600 mg, 28%, 3 steps) as an off white solid.

$^1$H-NMR: (400 MHz, DMSO-d6) δ 4.11-4.24 (3H; m); 4.37-4.38 (2H; m); 6.62 (2H; d; J=7.52 Hz); 7.25 (1H; m); 7.32-7.35 (3H; m); 7.42-7.47 (3H; m); 7.47-7.49 (1H; m); 7.70 (2H; d; J=7.16 Hz); 7.92 (2H; br d; J=6.88 Hz); 8.01 (1H; br d; J=6.92 Hz); 8.5 (1H; br s); 8.66 (1H; d; J=4.76 Hz); 10.21 (1H; s)

Intermediate 47

9H-fluoren-9-ylmethyl N-[[3,5-dichloro-2-[(3-formyl-2-pyridyl)sulfanyl]phenyl]methyl]carbamate

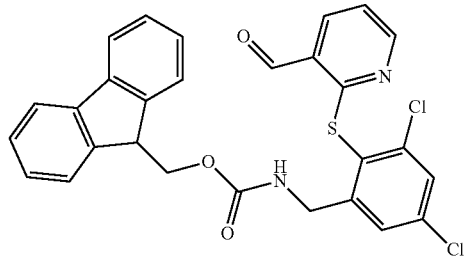 [SMILES: O=Cc1cccnc1Sc1c(Cl)cc(Cl)cc1CNC(=O)OCC1c2ccccc2-c2ccccc21]

To a stirred solution of 2-mercapto-nicotinic acid (2.44 g, 15.755 mmol), in DMF (30 mL) was added KOtBu (3.2 g, 28.645 mmol) and reaction mixture was stirred at 25° C. for 30 min. Then 2,3,5-trichloro-benzaldehyde (3 g, 14.323 mmol) was added to the reaction mass and it was heated to 80° C. for 4h. Then $K_2CO_3$ (5.93 g, 42.968 mmol) was added followed by addition of MeI (2.67 mL, 42.968 mmmol) and reaction mass was stirred at 25° C. for 16h. The reaction mixture was quenched with water and extracted with ethyl acetate. The separated organic layer was washed with brine solution, dried over anhydrous sodium sulfate and evaporated under reduced pressure. The crude thus obtained was purified by normal silica column using 5-15% ethyl acetate in hexane to get methyl 2-(2,4-dichloro-6-formyl-phenyl)sulfanylpyridine-3-carboxylate (2.3 g, 46%) as a yellow solid. MS found: 341.8 (M+H).

To a stirred solution of methyl 2-(2,4-dichloro-6-formyl-phenyl)sulfanylpyridine-3-carboxylate (2.3 g, 6.721 mmol) in THF (20 mL) were added 2-methylpropane-2-sulfinamide (815 mg, 6.721 mmol) and $Ti(OEt)_4$ (7.09 mL, 33.606 mmol) and reaction mass heated to 70° C. for 1 h. Reaction mixture was quenched with brine solution and extracted with ethyl acetate. The separated organic layer was dried over anhydrous sodium sulfate and concentrated under reduced pressure to afford ethyl 2-[2-[(Z)-tert-butylsulfinyliminomethyl]-4,6-dichloro-phenyl]sulfanylpyridine-3-carboxylate (2.6 g, crude) which was directly used for next step without further purification. MS found: 458.7 (M+H).

To a stirred solution of methyl 2-[2-[(Z)-tert-butylsulfinyliminomethyl]-4,6-dichloro-phenyl]sulfanylpyridine-3-carboxylate (2.6 g, 5.659 mmol) in THF (25 mL) was added LAH (1M in THF, 11.31 mL, 11.31 mmol) at 0° C. and reaction mass was stirred at 25° C. for 2h. Reaction mixture was quenched with saturated sodium sulfate solution and extracted with ethyl acetate. The separated organic layer was washed with water, brine solution, dried over anhydrous sodium sulfate and evaporated under reduced pressure. The crude thus obtained was purified by normal silica column using 10-60% ethyl acetate in hexane to get N-[[3,5-dichloro-2-[[3-(hydroxymethyl)-2-pyridyl]sulfanyl]phenyl]methyl]-2-methyl-propane-2-sulfinamide (1.5 g, 53%, 2 steps) as off white solid. MS found: 418.8 (M+H).

To a stirred solution of N-[[3,5-dichloro-2-[[3-(hydroxymethyl)-2-pyridyl]sulfanyl]phenyl]methyl]-2-methyl-propane-2-sulfinamide (1.9 g, 11.429 mmol) in MeOH (20 mL), was added 4M HCl in dioxane (12 mL) at 0° C. and reaction mixture was stirred at 25° C. for 1 h. After completion of reaction, the mixture was concentrated under reduced pressure to get [2-[2-(aminomethyl)-4,6-dichloro-phenyl]sulfanyl-3-pyridyl]methanol (1.9 g, crude) as off white solid which was directly used for next step. MS found: 315.1 (M+H).

To a stirred suspension of [2-[2-(aminomethyl)-4,6-dichloro-phenyl]sulfanyl-3-pyridyl]methanol (1.9 g, 6.051 mmol) in 5% NaHCO₃ (25 mL) was added Fmoc OSU (2.04 g, 6.051 mmol) in CH₃CN (25 mL) at 25° C. and reaction mass was stirred at 25° C. for 3h. Then reaction mass was diluted with water and extracted with ethyl acetate. The separated organic layer was washed with brine solution, dried over sodium sulfate and evaporated under reduced pressure to get 9H-fluoren-9-ylmethyl N-[[3,5-dichloro-2-[[3-(hydroxymethyl)-2-pyridyl]sulfanyl]phenyl]methyl]carbamate (2.5 g, crude) which was directly used for next step. MS found: 537.0 (M+H).

To a stirred solution of 9H-fluoren-9-ylmethyl N-[[3,5-dichloro-2-[[3-(hydroxymethyl)-2-pyridyl]sulfanyl]phenyl]methyl]carbamate (2.5 g, 4.664 mmol) in DCM/THF (1:1, 70 mL) was added MnO₂ (4.055 g, 46.642 mmol) and reaction mass was stirred at 25° C. for 3h. The reaction mass was filtered through celite pad, filtrate was evaporated under reduced pressure to get the crude which was purified by silica chromatography using 5-40% ethyl acetate in hexane to afford 9H-fluoren-9-ylmethyl N-[[3,5-dichloro-2-[(3-formyl-2-pyridyl)sulfanyl]phenyl]methyl]carbamate as off-white solid (1.7 g, 69%, 3 steps).

¹H-NMR: (400 MHz, DMSO-d6) δ 4.21-4.30 (5H; m); 7.25-7.43 (6H; m); 7.67 (2H; d; J=7.26 Hz); 7.79 (1H; s); 7.90 (2H; br d; J=7.16 Hz); 8.36 (1; br d; J=7.36 Hz); 8.40 (1H; br s); 10.18 (1H; s)

Intermediate 48

9H-fluoren-9-ylmethyl N-[[6-chloro-2-[(3-formyl-2-pyridyl)sulfanyl]-3-(trifluoromethyl)phenyl]methyl] carbamate

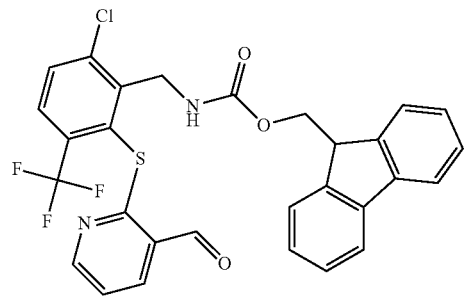 [SMILES: O=Cc1cccnc1Sc1c(C(F)(F)F)ccc(Cl)c1CNC(=O)OCC1c2ccccc2-c2ccccc21]

To a stirred solution of ethyl 2-mercapto-nicotinic acid (2.116 g, 13.636 mmol), in DMF (30 mL) was added KOtBu (2.782 g, 24.793 mmol) and reaction mass was stirred at 25° C. for 30 min. Then 2,6-dichloro-3-trifluoromethyl-benzaldehyde (3.0 g, 12.397 mmol) was added to the reaction mass and it was heated to 80° C. for 4h. Then K₂CO₃ (5.14 g, 37.19 mmol) was added followed by addition of MeI (2.325 mL, 39.19 mmol) and reaction mixture was stirred at 25° C. for 16h. The reaction mixture was quenched with water and extracted with ethyl acetate. The separated organic layer was washed with brine solution, dried over anhydrous sodium sulfate and evaporated under reduced pressure. The crude thus obtained was purified by silica chromatography using 0-10% methyl acetate in hexane to get methyl 2-[3-chloro-2-formyl-6-(trifluoromethyl)phenyl]sulfanylpyridine-3-carboxylate (3.3 g, 71%) as a yellow solid.

To a stirred solution of methyl acetate in hexane to get methyl 2-[3-chloro-2-formyl-6-(trifluoromethyl)phenyl]sulfanylpyridine-3-carboxylate (3.5 g, 9.314 mmol) in THF (30 mL) were added 2-methylpropane-2-sulfinamide (1.12 g, 9.314 mmol) and Ti(OEt)₄ (9.837 mL, 46.572 mmol) and reaction mass heated to 70° C. for 1 h. The reaction mixture was quenched with brine solution and extracted with ethyl acetate. The separated organic layer was dried over anhydrous sodium sulfate and concentrated under reduced pressure to afford methyl 2-[2-[(E)-tert-butylsulfinyliminomethyl]-3-chloro-6-(trifluoromethyl)phenyl]sulfanylpyridine-3-carboxylate (4.2 g, crude) which was directly used for next step without further purification. MS found: 492.5 (M+H).

To a stirred solution of methyl 2-[2-[(E)-tert-butylsulfinyliminomethyl]-3-chloro-6-(trifluoromethyl)phenyl]sulfanylpyridine-3-carboxylate (4.2 g, 8.52 mmol) in THF (40 mL) was added LAH (1M in THF, 17.04 mL, 17.04 mmol) at 0° C. and reaction mixture was stirred at 25° C. for 2h. The reaction mixture was quenched with saturated sodium sulfate solution and extracted with ethyl acetate. The separated organic layer was washed with water, brine solution, dried over anhydrous sodium sulfate and evaporated under reduced pressure. The crude thus obtained was purified by normal silica column using 10-60% ethyl acetate in hexane to get N-[[6-chloro-2-[[3-(hydroxymethyl)-2-pyridyl]sulfanyl]-3-(trifluoromethyl)phenyl]methyl]-2-methyl-propane-2-sulfinamide (1.7 g, 52%, 2 steps) as off white solid. MS found: 452.9 (M+H).

To a stirred solution of N-[[6-chloro-2-[[3-(hydroxymethyl)-2-pyridyl]sulfanyl]-3-(trifluoromethyl)phenyl]

methyl]-2-methyl-propane-2-sulfinamide (1.5 g, 3.319 mmol) in MeOH (20 mL), was added 4M HCl in dioxane (10 mL) at 0° C. and reaction mixture was stirred at 25° C. for 1 h. After completion of reaction, reaction mixture was concentrated under reduced pressure to get [2-[2-(aminomethyl)-3-chloro-6-(trifluoromethyl)phenyl]sulfanyl-3-pyridyl]methanol (1.5 g, crude) as a yellow sticky solid which was directly used for next step. MS found: 348.7 (M+H).

To a stirred solution of [2-[2-(aminomethyl)-3-chloro-6-(trifluoromethyl)phenyl]sulfanyl-3-pyridyl]methanol (2.0 g, 3.509 mmol) in DCM/THF (1:1, 60 mL) was added MnO$_2$ (3.05 g, 35.088 mmol) and reaction mass was stirred at 25° C. for 3h. The reaction mass was filtered through celite pad, filtrate was evaporated under reduced pressure to get the crude material which was purified by silica chromatography using 5-40% ethyl acetate in hexane to afford 9H-fluoren-9-ylmethyl N-[[6-chloro-2-[(3-formyl-2-pyridyl)sulfanyl]-3-methyl-phenyl]methyl]carbamate as off-white solid (1.1 g, 58%, 3 steps).

$^1$H-NMR: (400 MHz, DMSO-d6) δ 4.16-4.22 (3H; m); 4.32-4.45 (2H; m); 7.32 (2H; br t; J=7.28 Hz); 7.40 (3H; br t; J=7.28 Hz); 7.60 (1H; m); 7.67 (2H; br d; J=7.24 Hz); 7.73 (2H; br d; J=7.96 Hz); 7.86 (3H; m); 8.32 (1H; br d; J=6.56 Hz); 8.46 (1H; m); 10.18 (1H; s).

Intermediate 49

9H-fluoren-9-ylmethyl N-[[5-ethyl-2-(2-formylphenyl)sulfanyl-phenyl]methyl]carbamate

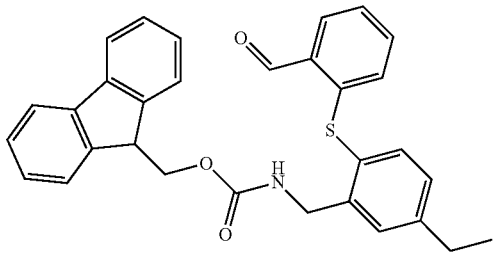 [SMILES: CCc1ccc(Sc2ccccc2C=O)c(CNC(=O)OCC2c3ccccc3-c3ccccc32)c1]

To a solution of 2-Fluoro-5-iodo-benzaldehyde (2.0 g, 8 mmol) in dioxane:water (30 mL) were added vinyl boronic acid pinacol ester (1.6 mL, 9.6 mmol) and Cs$_2$CO$_3$ (3.9 g, 12 mmol) sequentially. Then the reaction mixture was degassed with argon and Pd(PPh$_3$)$_4$ (0.184 g, 0.16 mmol) was added. The resulting reaction mixture was heated to 70° C. for 2h. Progress of the reaction was monitored by TLC. After completion, the reaction mixture was extracted with EtOAc (3×50 mL). Combined organic layer was washed with water followed by brine and dried over anhydrous sodium sulfate. Solvent was evaporated under reduced pressure to get crude compound which was further purified by flash-chromatography (hexane) to get 2-fluoro-5-vinyl-benzaldehyde (0.83 g, 69%) as colorless oil.

To a degassed solution of 2-fluoro-5-vinyl-benzaldehyde (0.83 g, 5.5 mmol) in dry DMF (4 mL) were added K$_2$CO$_3$ (1.2 g, 13.8 mmol) and methyl thiosalicylate (0.91 mL, 0.66 mmol). Then the reaction mixture was stirred for 1 h. Progress of the reaction was monitored by TLC. After completion the reaction mixture was diluted with water (30 mL) and extracted with EtOAc (3×20 mL). Combined organic layer was washed with water followed by brine and dried over Na$_2$SO$_4$. Solvent was evaporated under reduced pressure to get crude compound which was purified by combiflash (20% ethyl acetate in hexane) to afford methyl 2-(2-formyl-4-vinyl-phenyl)sulfanylbenzoate (1.4 g, 85%) as yellow oil. MS found: 299.2 (M+H).

To a degassed solution of methyl 2-(2-formyl-4-vinyl-phenyl)sulfanylbenzoate (1.4 g, 4.6 mmol) in ethyl acetate (25 mL) was added PtO$_2$ (0.05 g) and the reaction mixture was stirred under hydrogen atmosphere for 3h. Progress of the reaction was monitored by TLC. After completion, the reaction mixture was filtered through celite and the filtrate was concentrated under reduced pressure to get methyl 2-(4-ethyl-2-formyl-phenyl)sulfanylbenzoate (1.4 g, 99%) as white solid. MS found: 301.0 (M+H).

To a solution of methyl 2-(4-ethyl-2-formyl-phenyl)sulfanylbenzoate (1.4 g, 4.6 mmol) in THF (30 mL) was added 2-methylpropane-2-sulfinamide (1.4 g, 11.66 mmol) followed by titanium ethoxide (2.4 mL, 11.66 mmol) and the reaction mixture was heated at 55° C. for 2 h. Progress of the reaction was monitored by TLC. After completion the reaction mixture was diluted with water (30 mL) and filtered through celite. Organic layer was separated off, dried over sodium sulphate and concentrated under reduced pressure to get methyl 2-[2-[(Z)-tert-butylsulfinyliminomethyl]-4-ethyl-phenyl]sulfanylbenzoate (1.6 g, 85%) as colorless oil. MS found: 404.3 (M+H).

To an ice-cooled solution of LAH (0.471 g, 12.40 mmol) in dry THF (10 mL) was added a solution of methyl 2-[2-[(Z)-tert-butylsulfinyliminomethyl]-4-ethyl-phenyl]sulfanylbenzoate (2.5 g, 6.20 mmol) in THF (20 mL) and the resulting reaction mixture was stirred for 0.5h. Progress of the reaction was monitored by TLC. After completion, the reaction was quenched with saturated sodium sulphate solution (5 mL) and ethyl acetate. Then the reaction mixture was filtered through celite and washed with ethyl acetate (50 mL). The filtrate was concentrated under reduced pressure to get N-[[5-ethyl-2-[2-(hydroxymethyl)phenyl]sulfanyl-phenyl]methyl]-2-methyl-propane-2-sulfinamide (2.0 g, 93%) which was used as such in next step. MS found: 378.1 (M+H).

To an ice cold solution of N-[[5-ethyl-2-[2-(hydroxymethyl)phenyl]sulfanyl-phenyl]methyl]-2-methyl-propane-2-sulfinamide (1.2 g, 4.23 mmol) in acetonitrile (20 mL) was added 5% sodium bicarbonate solution (12 mL) followed by a solution of Fmoc-Osu (1.4 g, 4.29 mmol) in acetonitrile (10 mL) and the reaction mixture was stirred at ambient temperature for 4h. Progress of the reaction was monitored by TLC. After completion, the reaction mixture was diluted with water (50 mL) and ethyl acetate (80 mL). Organic layer was separated from which volatiles were removed under reduced pressure to get crude compound which was then purified by flash-chromatography (20% ethyl acetate in hexane) to 9H-fluoren-9-ylmethyl N-[[5-ethyl-2-(2-formylphenyl)sulfanyl-phenyl]methyl]carbamate (0.670 g, 35%) as white solid. LC-MS: 494.0 (M+H).

$^1$H-NMR: (400 MHz, DMSO-d6): δ 1.20 (3H, t, J=7.6 Hz), 2.65 (2H, q, J=7.6 Hz), 4.30-4.23 (5H, m), 6.66 (1H, d, J=8.0 Hz), 7.36-7.23 (5H, m), 7.48-7.38 (4H, m), 7.70 (2H, d, J=7.4 Hz), 7.83 (1H, t, J=5.9 Hz), 7.89 (2H, d, J=7.5 Hz), 7.95 (1H, d, J=7.6 Hz), 10.21 (1H, s).

Intermediate 50

9H-fluoren-9-ylmethyl N-[[2-(2-formylphenyl)sulfanyl-5-phenyl-phenyl]methyl]carbamate

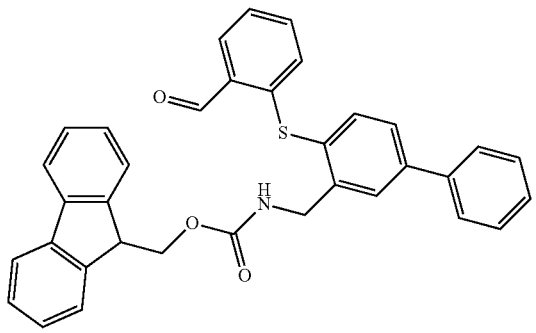 [SMILES: O=Cc1ccccc1Sc1ccc(-c2ccccc2)cc1CNC(=O)OCC1c2ccccc2-c2ccccc21]

A solution of 4-Fluoro-biphenyl (2 g, 11.61 mmol) and PMDTA (3 mL) in THF (50 mL) was cooled to −78° C. and 1.6 M nBuLi (10.88 mL, 17.42 mmol) was added drop wise. The resultant reaction mixture was stirred for 40 min at −60° C. The reaction mixture was cooled to −78° C. again and DMF (2.12 mL, 29.03 mmol) was added. Then the reaction mixture was stirred at −78° C. for 30 min before allowing the mixture to warm up to room temperature. The reaction mixture was quenched with aqueous $NH_4Cl$ and the whole mixture was extracted with diethyl ether (30 mL). Combined organic layer was washed with brine (30 mL) and concentrated under reduced pressure to afford crude compound which was purified by flash-chromatography (10% ethylacetate in hexane) to get 2-fluoro-5-phenyl-benzaldehyde (1.8 g, 77%) as viscous oil.

To a solution of 2-fluoro-5-phenyl-benzaldehyde (2.5 g, 10 mmol) in dioxane-water (1:1) (30 mL) was added phenyl boronic ester (1.45 g, 12 mmol) and $Cs_2CO_3$ (4.87 g, 15 mmol) sequentially. The solution was then degassed with argon for 30 min. To this solution was added $Pd(PPh_3)_4$ (0.23 g, 0.2 mmol) and heated to 70° C. for 2h. Then the reaction mixture was filtered, filtrate was concentrated and diluted with water (50 mL). The aq. layer was extracted with ethyl acetate (100 mL×2). Combined organic layer was washed with brine (50 mL) and dried over anhydrous sodium sulphate. Organic layer was concentrated to get the crude compound which was purified by flash-chromatography (10% ethyl acetate in hexane) to afford 2-fluoro-5-phenyl-benzaldehyde (1.7 g, 85%) as viscous oil.

To a solution of 2-fluoro-5-phenyl-benzaldehyde (1.7 g, 8.5 mmol) and methyl thiosalicylate (1.43 g, 8.5 mmol) in DMF (20 mL) was added $K_2CO_3$ (2.35 g, 17 mmol) and the reaction mixture was heated to 60° C. for 16h. Then the reaction mixture was diluted with water and extracted with ethyl acetate (100 mL×2). Combined organic layer was washed with brine (40 mL×2), dried over sodium sulphate and concentrated to afford crude compound which was further purified by combiflash (30% ethyl acetate in hexane) to afford methyl 2-(2-formyl-4-phenyl-phenyl)sulfanylbenzoate (1.8 g, 60%) as an off-white solid. LCMS: 349.1 (M+H).

To a stirred solution of methyl 2-(2-formyl-4-phenyl-phenyl)sulfanylbenzoate (1.7 g, 4.88 mmol) in anhydrous THF (50 mL) were added 2-methylpropane-2-sulfinamide (1.18 g, 9.77 mmol) and titanium tetraethoxide (2.23 g, 9.77 mmol) sequentially and the resultant reaction mixture was heated at 60° C. for 5h. Then the reaction mixture was poured onto ice-water and filtered through a short pad of celite. Filtrate was extracted with ethyl acetate (100 mL×2), washed with brine (100 mL×2), dried over anhydrous sodium sulfate and concentrated under reduced pressure to get the crude compound which was purified by flash-chromatography column (10-20% ethyl acetate in hexane) to afford methyl 2-[2-[(Z)-tert-butylsulfinyliminomethyl]-4-phenyl-phenyl]sulfanylbenzoate (1.8 g, crude) as sticky mass. MS found: 452.1 (M+H).

To an ice-cooled suspension of LAH (0.279 g, 7.54 mmol) in THF (50 mL) was added a solution of methyl 2-[2-[(Z)-tert-butylsulfinyliminomethyl]-4-phenyl-phenyl]sulfanyl-benzoate (1.7 g, crude) in THF (50 mL) and the reaction mixture was stirred at 0° C. for 30 min. Progress of the reaction was monitored by TLC. After completion, the reaction mixture was quenched with saturated sodium sulphate solution (5 mL) and diluted with ethyl acetate (20 mL). The reaction mixture was filtered through celite and filtrate was concentrated to get N-[[2-[2-(hydroxymethyl)phenyl]sulfanyl-5-phenyl-phenyl]methyl]-2-methyl-propane-2-sulfinamide (1.4 g, crude) as white solid. MS found: 426.1 (M+H).

To an ice-cooled solution of N-[[2-[2-(hydroxymethyl)phenyl]sulfanyl-5-phenyl-phenyl]methyl]-2-methyl-propane-2-sulfinamide (2 g, crude) in DCM (50 mL) was added Dess-Martin periodinane (2.59 g, 6.12 mmol) portion wise and the reaction mixture was stirred at room temperature for 2h under argon atmosphere. Progress of the reaction was monitored by TLC. After completion, the reaction mixture was diluted with DCM (50 mL) and saturated sodium bicarbonate solution (50 mL). Organic layer was separated off and the aqueous layer was extracted with DCM (50 mL×2). Combined organic layer was washed with sodium thiosulphate solution followed by brine. Volatiles were removed under reduced pressure to get N-[[2-(2-formylphenyl)sulfanyl-5-phenyl-phenyl]methyl]-2-methyl-propane-2-sulfinamide (0.8 g, 40% over four steps) as viscous oil. MS found: 423.9 (M+H).

To an ice-cooled solution of N-[[2-(2-formylphenyl)sulfanyl-5-phenyl-phenyl]methyl]-2-methyl-propane-2-sulfinamide (1.5 g, 3.5 mmol) in dioxane (20 mL) was added 4M HCl in dioxane and the reaction mixture was stirred at same temperature for 1 h. Volatiles were removed under reduced pressure to get the crude compound which was triturated with diethyl ether to get 2-[2-(aminomethyl)-4-phenyl-phenyl]sulfanylbenzaldehyde (0.9 g, 79%) as white solid. MS found: 320.0 (M+H).

To a stirred suspension of 2-[2-(aminomethyl)-4-phenyl-phenyl]sulfanylbenzaldehyde (0.7 g, 1.88 mmol) in 5% sodium bicarbonate solution (12 mL) was added a solution of Fmoc-OSu (0.443 g, 1.314 mmol) in acetonitrile (30 mL) and the reaction mixture was stirred at room temperature for 3 h. Volatiles were removed under reduced pressure and the crude reaction mixture was diluted with water (10 mL). Then the aq. phase was extracted with ethyl acetate (50 mL×3) and washed with brine (50 mL), dried over anhydrous sodium sulfate and evaporated under reduced pressure to get the crude compound which was purified by flash-chromatography (10% ethyl acetate in hexane) to 9H-fluoren-9-ylmethyl N-[[2-(2-formylphenyl)sulfanyl-5-phenyl-phenyl]methyl]carbamate (0.45 g, 44%) as white solid. LC-MS: 542.2 (M+H).

$^1$H-NMR: (400 MHz, DMSO-d6): δ 4.22-4.19 (1H, m), 4.28 (2H, d, J=7.0 Hz), 4.35 (2H, d, J=5.6 Hz), 6.82 (1H, d, J=7.9 Hz), 7.25 (2H, t, J=7.4 Hz), 7.44-7.36 (4H, m), 7.55-7.47 (4H, m), 7.69-7.67 (5H, m), 7.76 (1H, s), 7.87 (2H, d, J=7.4 Hz), 7.99-7.96 (2H, m), 10.24 (1H, s).

Intermediate 51

9H-fluoren-9-ylmethyl N-[[5-tert-butyl-2-(2-formylphenyl)sulfanyl-phenyl]methyl]carbamate

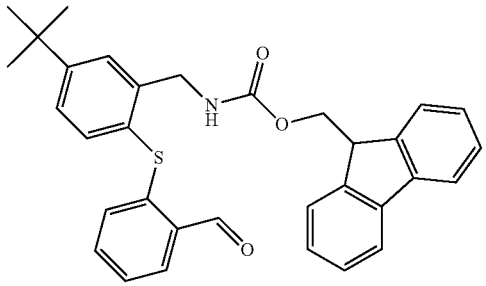 [SMILES: CC(C)(C)c1ccc(Sc2ccccc2C=O)c(CNC(=O)OCC2c3ccccc3-c3ccccc32)c1]

To a stirred solution of 1-tert-butyl-4-flurobenzene (2.0 g, 13.15 mmol) in dry THF (20 mL) was added PMDTA (3.4 mL, 19.73 mmol) and n-BuLi (1.6 M in THF, 12.3 mL, 26.31 mmol) at −78° C. and the resulting reaction mixture was stirred at the same temperature for 1 h. To the reaction mixture was added DMF (2.6 mL, 32.89 mmol) at −78° C. and stirred further at the same temperature for 1 h. Then the reaction mixture was quenched by the addition of saturated NH$_4$Cl (20 mL) and extracted with diethyl ether (2×25 mL). Combined organic layer was washed with water (20 mL), brine (20 mL), dried over anhydrous Na$_2$SO$_4$ and concentrated under reduced pressure. The crude compound thus obtained was purified by flash-chromatography (1% ethyl acetate in hexane) to afford 5-tert-butyl-2-fluoro-benzaldehyde (2.1 g, 88%) as a pale yellow oil.

To a stirred solution of 5-tert-butyl-2-fluoro-benzaldehyde (1.3 g, 7.22 mmol) in dry DMF (20 mL) were added methyl thiosalicylate (2.0 mL, 14.44 mmol) and KOtBu (1.6 g, 14.44 mmol) sequentially and the resulting reaction mixture was heated to 50° C. for 16 h. Then the reaction mixture was cooled to room temperature, diluted with water (30 mL) and extracted with ethyl acetate (2×25 mL). Combined organic layer was washed with water (30 mL), brine (30 mL), dried over anhydrous Na$_2$SO$_4$ and concentrated under reduced pressure. The crude compound thus obtained was purified by flash-chromatography (1.8% ethyl acetate in hexane) to afford methyl 2-(4-tert-butyl-2-formyl-phenyl)sulfanylbenzoate (0.7 g, 30%) as a pale yellow oil. MS found: 329.3 (M+H).

To a stirred solution of methyl 2-(4-tert-butyl-2-formyl-phenyl)sulfanylbenzoate (0.7 g, 2.13 mmol) in dry THF (20 mL) was added 2-methylpropane-2-sulfinamide (0.6 g, 5.33 mmol) followed by titanium (IV) ethoxide (1.1 mL, 5.33 mmol) and the resulting reaction mixture was heated to 70° C. for 2 h. Then the reaction mixture was cooled to room temperature, diluted with water, filtered through celite. The filtrate was extracted with ethyl acetate (2×20 mL). Combined organic layer was washed with water (10 mL) followed by brine (10 mL) and dried over anhydrous Na$_2$SO$_4$. Organic layer was concentrated under reduced pressure to get the crude compound which was purified by flash-chromatography (18% ethyl acetate in hexane) to afford methyl 2-[4-tert-butyl-2-[(E)-tert-butylsulfinyliminomethyl]phenyl]sulfanylbenzoate (0.9 g, 97%) as a pale yellow oil.

To an ice cooled solution of LAH (0.2 g, 6.26 mmol) in dry THF (20 mL) was added a solution of methyl 2-[4-tert-butyl-2-[(E)-tert-butylsulfinyliminomethyl]phenyl]sulfanylbenzoate (0.9 g, 2.08 mmol) in dry THF (20 mL) and the resulting reaction mixture was stirred at room temperature for 2 h. Then reaction mixture was quenched with ethyl acetate (30 mL), filtered through celite and concentrated under reduced pressure to afford N-[[5-tert-butyl-2-[2-(hydroxymethyl)phenyl]sulfanyl-phenyl]methyl]-2-methyl-propane-2-sulfinamide (0.7 g, 82%) as a white solid.

To an ice-cooled solution of N-[[5-tert-butyl-2-[2-(hydroxymethyl)phenyl]sulfanyl-phenyl]methyl]-2-methyl-propane-2-sulfinamide (0.7 g, 1.72 mmol) in dry DCM (10 mL) was added Dess-Martin periodinane (0.8 g, 1.90 mmol) and the resulting reaction mixture was stirred at room temperature for 2 h. The reaction mixture was quenched with saturated NaHCO$_3$ solution (25 mL) and extracted with DCM (2×25 mL). Combined organic layer was washed with water (15 mL), dried over anhydrous Na$_2$SO$_4$ and concentrated under reduced pressure. The crude compound thus obtained was purified by flash-chromatography (50% ethyl acetate in hexane) to afford N-[[5-tert-butyl-2-(2-formylphenyl)sulfanyl-phenyl]methyl]-2-methyl-propane-2-sulfinamide (0.55 g, 78%) as an off-white solid.

To an ice-cooled solution of N-[[5-tert-butyl-2-(2-formylphenyl)sulfanyl-phenyl]methyl]-2-methyl-propane-2-sulfinamide (0.55 g, 1.36 mmol) in dioxane (2 mL) was added 4M dioxane in HCl (2 mL) and the resulting reaction mixture was stirred at room temperature for 3 h. Volatiles were reduced under reduced pressure to afford 2-[2-(aminomethyl)-4-tert-butyl-phenyl]sulfanylbenzaldehyde (0.45 g, 100%) as a yellow solid. The crude was used as such for the next step.

To an ice-cooled solution of 2-[2-(aminomethyl)-4-tert-butyl-phenyl]sulfanylbenzaldehyde (0.45 g, 1.34 mmol) in acetonitrile (10 mL) was added 5% NaHCO$_3$ solution (3 mL) followed by Fmoc-OSu (0.3 g, 0.94 mmol) and the resulting reaction mixture was stirred at room temperature for 5h. Then the reaction mixture was diluted with water (10 mL) and extracted with ethyl acetate (2×20 mL). Combined organic layer was washed with water (10 mL) followed by brine (10 mL), dried over anhydrous Na$_2$SO$_4$ and concentrated under reduced pressure. The crude compound thus obtained was purified by flash-chromatography (15% ethyl acetate in hexane) to afford 9H-fluoren-9-ylmethyl N-[[5-tert-butyl-2-(2-formylphenyl)sulfanyl-phenyl]methyl]carbamate (0.45 g, 64%) as a yellow solid. LC-MS: 522.4 (M+H).

$^1$H-NMR: (400 MHz, CDCl$_3$): δ 1.34 (9H, s), 4.17 (1H, t, J=7.1 Hz), 4.34 (2H, d, J=7.1 Hz), 4.46 (2H, d, J=6.2 Hz), 5.14 (1H, br), 6.76 (1H, d, J=8.2 Hz), 7.30-7.27 (3H, m), 7.42-7.32 (5H, m), 7.55-7.51 (3H, m), 7.74 (2H, d, J=7.4 Hz), 7.84 (1H, d, J=7.9 Hz), 10.30 (1H, s).

Intermediate 52

9H-fluoren-9-ylmethyl N-[[2-(2-formylphenyl)sulfanyl-5-isopropyl-phenyl]methyl]carbamate

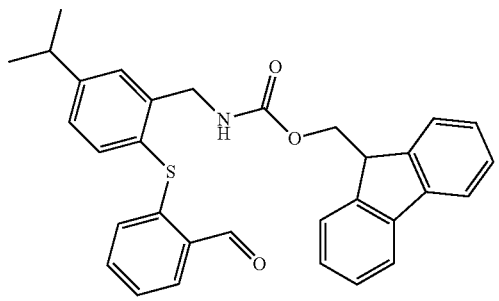 [SMILES: CC(C)c1ccc(Sc2ccccc2C=O)c(CNC(=O)OCC2c3ccccc3-c3ccccc32)c1]

To a solution of 5-Bromo-2-fluoro-benzaldehyde (2 g, 9.85 mmol) in dioxane:water (1:1) (40 mL, 1:1) was added isoprenylboronic ester (1.98 g, 11.82 mmol) and Cs$_2$CO$_3$ (8 g, 24.63 mmol) sequentially. The reaction mixture was then degassed with argon for 0.5 h and to it was added Pd(PPh$_3$)$_4$ (0.22 g, 0.19 mmol). The reaction mixture was then heated at 70° C. for 2h. Progress of the reaction was monitored by TLC. After completion, the reaction mixture was filtered. The filtrate was concentrated and diluted with ethyl acetate (100 mL). Organic layer was washed with water followed by brine and dried over anhydrous sodium sulfate. Organic layer was concentrated to get the crude compound which was purified by flash-chromatography (20% ethyl acetate in hexane) to afford 2-fluoro-5-isopropenyl-benzaldehyde (1.2 g, 74%) as viscous oil.

To an ice-cooled solution of 2-fluoro-5-isopropenyl-benzaldehyde (1.3 g, 7.92 mmol) and methyl thiosalicylate (1.59 g, 9.51 mmol) in DMF (30 mL) under argon atmosphere was added potassium carbonate (2.73 g, 19.81 mmol) and the reaction mixture was heated at 60° C. for 3 h. Then the reaction mixture was diluted with water (50 mL) and extracted with ethyl acetate (40 mL×3). The organic layer was washed with brine (40 mL×3), dried over sodium sulfate and concentrated under reduced pressure to get crude compound which was purified by flash-chromatography (30% ethyl acetate in hexane) to afford methyl 2-(2-formyl-4-isopropenyl-phenyl)sulfanylbenzoate (2.2 g, 89%) as pale yellow solid. MS found: 313.1 (M+H).

To a degassed solution of methyl 2-(2-formyl-4-isopropenyl-phenyl)sulfanylbenzoate (1.6 g, 5.12 mmol) in THF (50 mL) was added Raney Ni (0.2 g) and the reaction mixture was then stirred under hydrogen atmosphere for 16h. Then the reaction mixture was filtered through celite, washed with THF and concentrated under reduced pressure to get crude compound which was purified by flash-chromatography (60% ethyl acetate in hexane) to afford methyl 2-[2-(hydroxymethyl)-4-isopropyl-phenyl]sulfanylbenzoate (1.4 g, 87%) as viscous oil. MS found: 317.1 (M+H).

To an ice-cooled solution of methyl 2-[2-(hydroxymethyl)-4-isopropyl-phenyl]sulfanylbenzoate (1.4 g, 4.43 mmol) in DCM (50 mL) was added Dess-Martin periodinane (2.25 g, 5.31 mmol) portion wise and the reaction mixture was stirred at room temperature for 2h under argon atmosphere. Progress of the reaction was monitored by TLC. After completion, the reaction mixture was diluted with DCM (50 mL) and saturated sodium bicarbonate solution (50 mL×2). Organic layer was separated off and the aqueous layer was extracted with DCM (50 mL×2). Combined organic layer was washed with sodium thiosulphate solution followed by brine. Volatiles were removed under reduced pressure to get the crude compound which was purified by flash-chromatography (30% ethyl acetate in hexane) to afford methyl 2-(2-formyl-4-isopropyl-phenyl)sulfanylbenzoate (1.2 g, 86%) as viscous oil. MS found: 314.9 (M+H).

To a stirred solution of methyl 2-(2-formyl-4-isopropyl-phenyl)sulfanylbenzoate (1.2 g, 3.82 mmol) in anhydrous THF (50 mL) were added 2-methylpropane-2-sulfinamide (1.15 g, 9.55 mmol) and titanium tetraethoxide (2.17 g, 9.77 mmol) sequentially. The resultant reaction mixture was heated to 60° C. for 5 h under argon atmosphere. Then the reaction mixture was poured onto ice-water and filtered through celite. Filtrate was extracted with ethyl acetate (100 mL×2), washed with brine (100 mL×2), dried over anhydrous sodium sulfate and concentrated under reduced pressure to get the crude compound which was purified by flash column (10-20% ethyl acetate in hexane) to afford methyl 2-[2-[(E)-tert-butylsulfinyliminomethyl]-4-isopropyl-phenyl]sulfanylbenzoate (1.45 g, 91%) as brown solid. MS found: 418.2 (M+H).

To an ice-cooled suspension of LAH (0.25 g, 6.95 mmol) in THF (30 mL) was added a solution of afford methyl 2-[2-[(E)-tert-butylsulfinyliminomethyl]-4-isopropyl-phenyl]sulfanylbenzoate (1.45 g, 3.47 mmol) in THF (20 mL) and the reaction mixture was stirred for 30 min at 0° C. Progress of the reaction was monitored by TLC. After completion, the reaction mixture was quenched with saturated sodium sulphate solution (5 mL) and diluted with ethyl acetate (20 mL). The reaction mixture was filtered through celite. The filtrate was concentrated to afford N-[[2-[2-(hydroxymethyl)phenyl]sulfanyl-5-isopropyl-phenyl]methyl]-2-methyl-propane-2-sulfinamide (1.1 g, 81%) as white solid. MS found: 392.0 (M+H).

To an ice-cooled solution of N-[[2-[2-(hydroxymethyl)phenyl]sulfanyl-5-isopropyl-phenyl]methyl]-2-methyl-propane-2-sulfinamide (1 g, 2.55 mmol) in dioxane (20 mL) was added 4M HCl in dioxane and the resulting reaction mixture was stirred at room temperature for 1 h. Volatiles were removed under reduced pressure to get crude compound which was triturated with diethyl ether and dried to get [2-[2-(aminomethyl)-4-isopropyl-phenyl]sulfanylphenyl]methanol (0.735 g, 87%) as white solid. MS found: 287.9 (M+H).

To a stirred suspension of [2-[2-(aminomethyl)-4-isopropyl-phenyl]sulfanylphenyl]methanol (0.7 g, 2.16 mmol) in 5% sodium bicarbonate solution (12 mL) was added Fmoc-OSu (0.51 g, 1.51 mmol) in acetonitrile (30 mL) and the reaction mixture was stirred at ambient temperature for 3 h. Volatiles were concentrated under vacuum then diluted with water (50 mL) and extracted with ethyl acetate (50 mL×3) and washed with brine (50 mL), dried over anhydrous sodium sulfate and evaporated under reduced pressure to get crude compound. Crude compound was purified by flash-chromatography (20% ethyl acetate in hexane) to afford [2-(2-ethyl-4-isopropyl-phenyl)sulfanylphenyl]methanol (0.7 g, 63%) as white solid. MS found: 510.2 (M+H).

To an ice-cooled solution of [2-(2-ethyl-4-isopropyl-phenyl)sulfanylphenyl]methanol (0.7 g, 1.38 mmol) in DCM (30 mL) was added Dess-Martin periodinane (0.75 g, 1.78 mmol) portion wise and the reaction mixture was stirred at room temperature for 2h under argon atmosphere. Progress of the reaction was monitored by TLC. After completion, the reaction mixture was diluted with DCM (50 mL) and saturated sodium bicarbonate solution (50 mL×2). Organic layer was separated off and the aqueous layer was extracted with DCM (50 mL×2). Combined organic layer was washed with sodium thiosulfate solution followed by brine. Volatiles were removed under reduced pressure to get crude compound which was purified by flash-chromatography (30% ethyl acetate in hexane) to afford 9H-fluoren-9-ylmethyl N-[[2-(2-formylphenyl)sulfanyl-5-isopropyl-phenyl]methyl]carbamate (0.530 g, 76%) as white solid. LC-MS: 508.1 (M+H).

$^1$H-NMR: (400 MHz, DMSO-d6): δ 1.21 (6H, d, J=6.9 Hz), 2.92 (1H, sep, J=6.9 Hz), 4.28-4.19 (5H, m), 6.67 (1H, d, J=8.0 Hz), 7.49-7.25 (9H, m), 7.70 (2H, d, J=7.4 Hz), 7.85 (1H, t, J=5.7 Hz), 7.89 (2H, d, J=7.5 Hz), 7.96 (1H, d, J=7.3 Hz), 10.21 (1H, s).

Intermediate 53

9H-fluoren-9-ylmethyl N-[[2-fluoro-6-(2-formylphenyl)sulfanyl-phenyl]methyl]carbamate

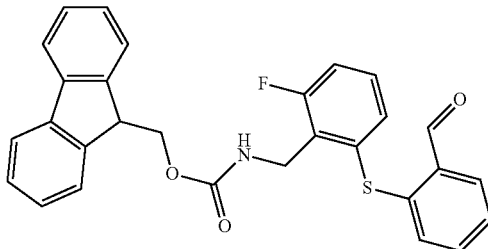

To a suspension methyl 2-sulfanylbenzoate (3 g, 21.11 mmol) and K$_2$CO$_3$ (5.8 g, 42.22 mmol) in DMF (50 mL) was added 2,6-difluorobenzaldehyde (3.5 g, 21.11 mmol) and the reaction mixture was stirred for 2h at room temperature. Progress of the reaction was monitored by TLC. After completion, the reaction mixture was diluted with water (100 mL) and extracted with ethyl acetate (3×250 ml). Combined organic layer was dried over sodium sulfate and concentrated under reduced pressure to get crude compound which was purified by flash-chromatography (20% ethyl acetate in hexane) to get compound methyl 2-(3-fluoro-2-formyl-phenyl)sulfanylbenzoate (4.1 g, 67%) as brown solid.

To a solution of methyl 2-(3-fluoro-2-formyl-phenyl)sulfanylbenzoate (2.5 g, 8.62 mmol) and 2-methylpropane-2-sulfinamide (2.60 g, 21.55 mmol) in THF (100 mL) was added titanium tetraethoxide (4.9 g, 21.52 mmol) and the reaction mixture was heated to 70° C. for 3h. Progress of the reaction was monitored by TLC. After completion, the reaction mixture was diluted with water (100 mL) and extracted with ethyl acetate (3×250 mL). Combined organic layers were dried over sodium sulphate and concentrated under reduced pressure to get crude methyl 2-[2-[(E)-tert-butylsulfinyliminomethyl]-3-fluoro-phenyl]sulfanylbenzoate (3.2 g, 94%) which was used as such in next step without purification. LC-MS: 393.8 (M+H).

To an ice cooled suspension of LAH (0.9 g, 25.95 mmol) was added a solution of methyl 2-[2-[(E)-tert-butylsulfinyliminomethyl]-3-fluoro-phenyl]sulfanylbenzoate (3.4 g, 8.65 mmol) in THF (50 mL) and the reaction mixture was stirred for 1 h at same temperature. Progress of the reaction was monitored by TLC. After completion, the reaction mixture was diluted with aq. sodium sulfate solution (50 mL) and extracted with ethyl acetate (3×100 mL). Combined organic layers were dried over sodium sulfate and concentrated under reduced pressure to get crude compound which was washed with hexane and pentane to get N-[[2-fluoro-6-[2-(hydroxymethyl)phenyl]sulfanyl-phenyl]methyl]-2-methyl-propane-2-sulfinamide (2.8 g, 88%) as brown solid. LC-MS: 367.7 (M+H).

To a solution of N-[[2-fluoro-6-[2-(hydroxymethyl)phenyl]sulfanyl-phenyl]methyl]-2-methyl-propane-2-sulfinamide (2.8 g, 7.62 mmol) in DCM (50 mL) was added Dess-Martin periodinane (8.07 g, 19.04 mmol) and the reaction mixture was stirred at RT for 2 h. Progress of the reaction was monitored by TLC. After completion, the reaction mixture was diluted with sodium bicarbonate solution (100 mL) and extracted with DCM (3×100 mL). Combined organic layers were dried over sodium sulphate and concentrated under reduced pressure to get crude compound which was purified by silica-gel column chromatography to get solid N-[[2-fluoro-6-(2-formylphenyl)sulfanyl-phenyl]methyl]-2-methyl-propane-2-sulfinamide (2 g, 72%) as white solid. LC-MS: 365.7 (M+H).

To an ice cooled solution of N-[[2-fluoro-6-(2-formylphenyl)sulfanyl-phenyl]methyl]-2-methyl-propane-2-sulfinamide (1.8 g, 2.88 mmol) in dioxane (40 mL) was added 4M HCl in dioxane (20 mL) and the reaction mixture was stirred for 2h at room temperature. Progress of the reaction was monitored by TLC. Volatiles were removed under reduced pressure and the crude compound was triturated with diethyl ether to get 2-[2-(aminomethyl)-3-fluoro-phenyl]sulfanyl-benzaldehyde (2 g, crude) as white solid. LC-MS: 361.7 (M+H).

To a suspension of 2-[2-(aminomethyl)-3-fluoro-phenyl]sulfanylbenzaldehyde (2 g, 4.96 mmol) in 5% aqueous NaHCO$_3$ (15 mL) was added a solution of Fmoc-OSu (1.1 g, 3.47 mmol) in acetonitrile (50 mL) and the reaction mixture was stirred at ambient temperature for 3 h. Then the reaction mixture was diluted with ethyl acetate and washed with water followed by brine. Organic layer was dried over sodium sulfate and evaporated under reduced pressure to get crude compound which was purified by flash-chromatography to get 9H-fluoren-9-ylmethyl N-[[2-fluoro-6-(2-formylphenyl)sulfanyl-phenyl]methyl]carbamate (0.550 g, 16% over two steps) as off white solid. LC-MS: 483.9 (M+H).

Intermediate 54

9H-fluoren-9-ylmethyl N-[[3-chloro-2-[(3-formyl-2-pyridyl)sulfanyl]phenyl]methyl]carbamate

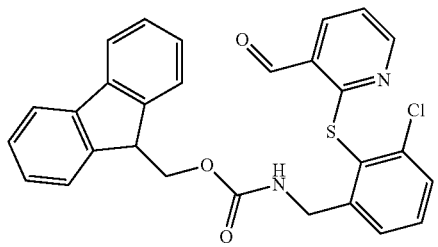 [SMILES: O=Cc1cccnc1Sc1c(Cl)cccc1CNC(=O)OCC1c2ccccc2-c2ccccc21]

To an ice-cooled solution of sodium chlorite (6.81 g, 75.68 mmol) in water (30 mL) was added a solution of 3-Chloro-2-fluoro-benzaldehyde (3 g, 18.92 mmol) in acetone (75 mL) and the reaction mixture was stirred for 5 min. To the resulting reaction mixture was added sulphamic acid (5.50 g, 56.761 mmol) in one lot at 0° C. and stirring continued for 30 min. Progress of the reaction was monitored by TLC. After completion, the reaction mixture was diluted with water (5 mL) and filtered. Filtrate was extracted with ethyl acetate (3×50 mL), combined organic layer was dried over anhydrous sodium sulphate, filtered and concentrated under reduced pressure to get 3-chloro-2-fluoro-benzoic acid (3.2 g, 97%) as white solid. LC-MS: 172.9 (M–H).

To a solution of 3-chloro-2-fluoro-benzoic acid (0.55 g, 3.151 mmol) in methanol (20 mL) was added conc. sulfuric acid (1 mL) and the reaction mixture was heated to 80° C. for 16 h. Volatiles were concentrated under reduced pressure and the crude reaction mixture was diluted with ethyl acetate. Then the reaction mixture was washed with saturated sodium bicarbonate solution followed by brine. Organic layers were dried over anhydrous sodium sulphate, filtered and concentrated to get methyl 3-chloro-2-fluoro-benzoate (0.5 g, 84%) as colorless liquid.

To a stirred solution of methyl 3-chloro-2-fluoro-benzoate (0.05 g, 0.265 mmol) in DMF (2 mL) was added $Na_2S$ (0.05 g) and the reaction mixture was heated to 70° C. for 5 h. Then the reaction mixture was acidified with 10% HCl and extracted with EtOAc (3×25 mL). Combined organic layers were washed with water followed by brine, dried over anhydrous sodium sulphate and concentrated to get methyl 3-chloro-2-sulfanyl-benzoate (0.035 g, crude) as yellow solid. LC-MS: 201.1 (M–H).

To a stirred solution of methyl 3-chloro-2-sulfanyl-benzoate (0.05 g, 0.247 mmol) in DMF (2 mL) were added $K_2CO_3$ (136 mg, 0.987 mmol) and 2-fluoro-pyridine-3-carbaldehyde (61 mg, 0.493 mmol) sequentially and the reaction mixture was heated to 70° C. for 16 h. Then the reaction mixture was diluted with EtOAc and washed with brine. The organic layer was dried over anhydrous sodium sulphate, filtered and concentrated to get the crude compound which was purified by column chromatography (25% ethyl acetate in hexane) to get methyl 3-chloro-2-[(3-formyl-2-pyridyl)sulfanyl]benzoate (0.015 g, 12% over two steps) as white solid. LC-MS: 308.0 (M+H).

A mixture of methyl 3-chloro-2-[(3-formyl-2-pyridyl)sulfanyl]benzoate (1.3 g, 4.23 mmol), ethylene glycol (0.789 g, 12.70 mmol), p-TSA (0.081 g, 0.423 mmol) in toluene (30.0 mL) was heated to 140° C. for 2 h. Progress of the reaction was monitored by TLC. Then the reaction mixture was diluted with water (100 mL) and the aqueous phase was extracted with ethyl acetate (50 mL×2). Combined organic layers were dried over anhydrous sodium sulfate and solvent distilled-off under reduced pressure to get crude methyl 3-chloro-2-[[3-(1,3-dioxolan-2-yl)-2-pyridyl]sulfanyl]benzoate (1.4 g, 94%) as colorless oil which was used as such in next step. LC-MS: 351.9 (M+H).

To an ice-cooled solution of methyl 3-chloro-2-[[3-(1,3-dioxolan-2-yl)-2-pyridyl]sulfanyl]benzoate (1.4 g, crude) in THF (25 mL) was added LAH powder in batches (0.302 g, 7.96 mmol) and the reaction mixture was stirred for 30 min at RT. Then the reaction mixture was quenched with ethyl acetate and saturated sodium sulphate solution. Then the reaction mixture was filtered through celite and filtrate was extracted with ethyl acetate. The organic layer was washed with brine solution and dried over sodium sulphate, filtered and concentrated to get the crude compound which was further purified by column chromatography (50% ethyl acetate in hexane) to get [3-chloro-2-[[3-(1,3-dioxolan-2-yl)-2-pyridyl]sulfanyl]phenyl]methanol (1.2 g, 93%) as white solid. LC-MS: 324.1 (M+H).

A solution of [3-chloro-2-[[3-(1,3-dioxolan-2-yl)-2-pyridyl]sulfanyl]phenyl]methanol (1 g, crude), triphenyl phosphine (2.5 g, 0.040 mmol), sodium azide (2 g, 0.007 mmol) in carbon tetrachloride (0.1 mL) and DMF (5.0 ml) was heated to 70° C. for 3 h. Progress of the reaction was monitored by TLC. The reaction mixture was diluted with water (20 mL) and the aqueous phase was extracted with ethyl acetate (30 mL×2). Combined organic layers were dried over anhydrous sodium sulfate and solvent distilled-off under reduced pressure to get the crude compound which was purified by column chromatography (30% ethyl acetate in hexane) to get 2-[2-(azidomethyl)-6-chloro-phenyl]sulfanyl-3-(1,3-dioxolan-2-yl)pyridine (0.12 g, 11%) as viscous oil. LC-MS: 348.9 (M+H).

To a stirred solution of 2-[2-(azidomethyl)-6-chloro-phenyl]sulfanyl-3-(1,3-dioxolan-2-yl)pyridine (0.45 g, 1.29 mmol) in ethanol (20 mL) was added Pd—C (0.138 g, 7.96 mmol) and the reaction mixture was agitated under hydrogen pressure for 16h. Then the reaction mixture was filtered through celite and the filtrate was concentrated in vacuo to get [3-chloro-2-[[3-(1,3-dioxolan-2-yl)-2-pyridyl]sulfanyl]phenyl]methanamine (0.350 g, 83%) as viscous oil which was used as such in next step without further purification. LC-MS: 322.9 (M+H).

To a solution of [3-chloro-2-[[3-(1,3-dioxolan-2-yl)-2-pyridyl]sulfanyl]phenyl]methanamine (0.35 g, crude) in 5% sodium bicarbonate (0.5 mL) was added Fmoc-OSu (0.31 g, 0.93 mmol) in acetonitrile (10 mL) and the reaction mixture was stirred at room temperature for 3 h. Progression of the reaction was monitored by TLC. After completion, volatiles were removed under reduced pressure and the crude reaction mixture was diluted with water (10 mL). The aqueous phase was extracted with ethyl acetate (10 mL×3). Combined organic layers were washed with brine (10 mL), dried over anhydrous sodium sulfate and evaporated under reduced pressure to get crude compound. The crude compound was purified by combiflash (30% ethyl acetate in hexane) to afford desired compound which was further washed with diethyl ether (5 mL) followed by pentane (5 mL) and dried to get 9H-fluoren-9-ylmethyl N-[[3-chloro-2-[[3-(1,3-dioxolan-2-yl)-2-pyridyl]sulfanyl]phenyl]methyl]carbamate (0.300 g, 59%) as an off-white solid. LC-MS: 544.9 (M+H).

To a solution of 9H-fluoren-9-ylmethyl N-[[3-chloro-2-[[3-(1,3-dioxolan-2-yl)-2-pyridyl]sulfanyl]phenyl]methyl] carbamate (0.3 g, 0.642 mmol) in of acetone (10 mL) was added conc. HCl (2 mL) and the reaction mixture was stirred for 4 h at room temperature. After completion, volatiles were removed under reduced pressure and the crude reaction mixture was quenched with saturated sodium bicarbonate solution. Then the resulting reaction mixture was extracted with ethyl acetate (3×25 mL). Combined organic layers were washed with brine solution, dried over anhydrous sodium sulphate, filtered and concentrated to get crude compound which was purified by flash-chromatography (50% ethyl acetate in hexane) to get 9H-fluoren-9-ylmethyl N-[[3-chloro-2-[(3-formyl-2-pyridyl)sulfanyl]phenyl]methyl]carbamate (0.115 g, 36%) as an off-white solid. LC-MS: 500.9 (M+H).

$^1$H-NMR (400 MHz, CDCl-3): δ 4.13-4.16 (1H; m); 4.39 (2H; d; J=6.76 Hz); 4.57 (2H; d; J=6.76 Hz); 7.18-7.20 (1H; m); 7.26-7.29 (1H; m): 7.35-7.39 (3H; m); 7.37-7.50 (4H; m); 7.74 (2H; d; J=7.56 Hz); 7.74-7.79 (1H; m); 8.29-8.30 (1H; m); 10.45 (1H: s).

Intermediate 55

3-{(S)-2-Carboxy-2-[ethyl-(9H-fluoren-9-yl-methoxycarbonyl)-amino]-ethyl}-indole-1-carboxylic Acid Tert-Butyl Ester

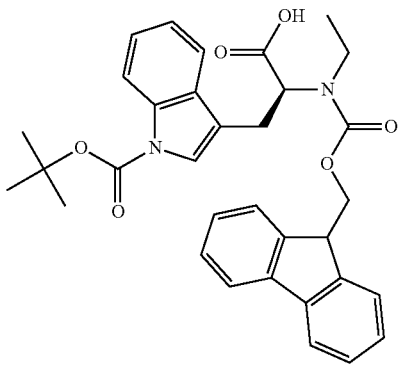 [SMILES: CCN(C(=O)OCC1c2ccccc2-c2ccccc21)[C@@H](Cc1cn(C(=O)OC(C)(C)C)c2ccccc12)C(=O)O]

A solution of (2S)-2-amino-3-(1-tert-butoxycarbonylindol-3-yl)propanoic acid (2 g, 6.57 mmol), o-nitrobenzenesulfonylchloride (1.64 g, 7.42 mmol) in saturated sodium carbonate solution and dioxane (132 mL, 1:1) was stirred for 18h. Then the pH of the solution was adjusted to 7.0 with 0.5 M HCl. Solvent was removed under reduced pressure and the crude reaction mixture was extracted with ether (3×50 mL). Combined organic layer was washed with water, dried over sodium sulfate and concentrated to afford (2S)-3-(1-tert-butoxycarbonylindol-3-yl)-2-[(2-nitrophenyl)sulfonylamino] propanoic acid (2.4 g, 75%) as a yellow solid. To a solution of (2S)-3-(1-tert-butoxycarbonylindol-3-yl)-2-[(2-nitrophenyl)sulfonylamino]propanoic acid (1.6 g, 3.26 mmol) in dry DMF (25 mL) were added potassium carbonate (1.5 g, 11.44 mmol) and ethyl iodide (1.5, 9.8 mmol) sequentially and the reaction mixture was stirred for 8 h. Then the reaction mixture was poured onto water (25 mL) and the aqueous layer was extracted with ether (3×30 mL). Combined organic layers were washed with water, dried over sodium sulfate and concentrated under reduced pressure to get the crude compound which was purified by flash-chromatography (20% ethyl acetate in hexane) to afford tert-butyl 3-[(2S)-3-ethoxy-2-[ethyl-(2-nitrophenyl)sulfonyl-amino]-3-oxo-propyl]indole-1-carboxylate (0.3 g, 17%) as viscous oil. LC-MS: 544.1 (M–H).

To a solution of tert-butyl 3-[(2S)-3-ethoxy-2-[ethyl-(2-nitrophenyl)sulfonyl-amino]-3-oxo-propyl]indole-1-carboxylate (3.4 g, 6.2 mmol) in dry DMF (50 mL) were added K$_2$CO$_3$ (2.5 g, 18.72 mmol) and thiophenol (0.825 g, 7.4 mmol) sequentially and the reaction mixture was stirred for 2h at RT. After completion, the reaction mixture was quenched with water (50 mL) and extracted with ethyl acetate (100 mL×3). Organic layer was separated off, washed with water (50 mL×2) and dried over Na$_2$SO$_4$. The organic layer was evaporated under reduced pressure and the crude compound thus obtained was purified by – chromatography (20% ethyl acetate in hexane) to afford tert-butyl 3-[(2S)-3-ethoxy-2-(ethylamino)-3-oxo-propyl]indole-1-carboxylate (1.5 g, 67%) as viscous mass. LC-MS: 361.0 (M+H).

To a solution of tert-butyl 3-[(2S)-3-ethoxy-2-(ethyl-amino)-3-oxo-propyl]indole-1-carboxylate (1.5 g, 4.17 mmol) in THF-water (40 mL, 3:1) was added LiOH (0.21 g 5.0 mmol) and the reaction mixture was stirred for 24h at room temperature. After completion, the reaction mixture was neutralized with 0.5 N HCl and evaporated under reduced pressure. The crude compound obtained was washed with water (50 mL) and dried well to afford (2S)-3-(1-tert-butoxycarbonylindol-3-yl)-2-(ethylamino)propanoic acid (1.3 g, 96%) as white solid. LC-MS: 332.9 (M+H).

To a solution of (2S)-3-(1-tert-butoxycarbonylindol-3-yl)-2-(ethylamino)propanoic acid (1.4 g, 4.2 mmol) in THF: water (40 mL, 1:1) was added 5% NaHCO$_3$ followed by Fmoc-OSU (1.4 g, 4.2 mmol) and the reaction mixture was stirred for 5 h at room temperature. Then the reaction mixture was diluted with water and extracted with ethyl acetate (50 mL×3). Organic layer was separated off, dried over sodium sulfate and concentrated under reduced pressure to get the crude compound which was purified by flash-chromatography (50% ethyl acetate in hexane) to afford desired compound. The compound thus obtained was dried by adding toluene to it and distilling the toluene (10 mL×5). The resulting solid was washed with diethyl ether-n-pentane (20 mL, 1:4) and dried to get (2S)-3-(1-tert-butoxycarbonylindol-3-yl)-2-[ethyl(9H-fluoren-9-yl-methoxycarbonyl)amino]propanoic acid (0.48 g, 21%) as an off-white solid. LC-MS: 554.9 (M+H).

Intermediate 56

[5-Bromo-2-(3-formyl-pyridin-2-ylsulfanyl)-3-methyl-benzyl]-carbamic Acid 9H-fluoren-9-ylmethyl Ester

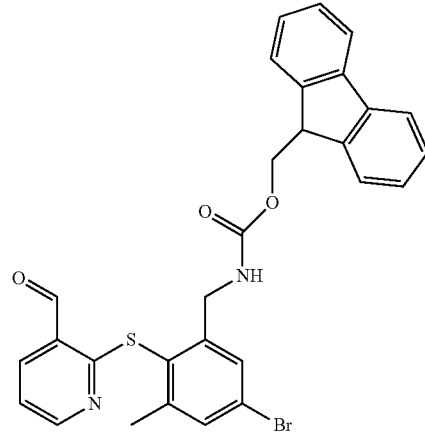 [SMILES: Cc1cc(Br)cc(CNC(=O)OCC2c3ccccc3-c3ccccc32)c1Sc1ncccc1C=O]

To a stirred solution of 2-Mercapto-nicotinic acid (3.94 g, 25.3 mmol) in DMF (60 mL) was added NaH (1.844 g, 46.076 mmol) at 0° C. and the resulting reaction mixture was stirred at 25° C. for 1 h. Then 5-Bromo-2-fluoro-3-methyl-benzaldehyde (5 g, 23 mmol) was added to the reaction mass and it was heated to 80° C. for 32h. After completion of starting material, the reaction mixture was cooled to room temperature, were added K$_2$CO$_3$ (9.6 g, 69.1 mmol) and methyl iodide (4.4 ml, 69.1 mol), stirred at 25° C. for 16 h. The reaction mixture was diluted with water, extracted with EtOAc. The separated organic layer was washed with brine, dried over anhydrous sodium sulfate and concentrated under reduced pressure to get crude material, which was purified by normal silica-gel (100-200 mesh) column chromatography eluting with 12% EtOAc in hexane to get 2-(4-Bromo- 2-formyl-6-methyl-phenylsulfanyl)-nicotinic acid methyl ester (2.5 g, 29%) as yellow solid. LC-MS: 366.0 [M+H]⁺

To a stirred solution of 2-(4-Bromo-2-formyl-6-methyl-phenylsulfanyl)-nicotinic acid methyl ester (2.55 g, 6.9 mmol) in THF (15 mL), 2-methylpropane-2-sulfinamide (770 mg, 6.9 mmol) and Ti(OEt)₄ (7.3 ml, 34.8 mmol) were added at room temperature and the reaction mixture was heated to 70° C. for 16h. The reaction mixture was quenched with brine, filtered through celite bed and washed with ethyl acetate. The organic layer was separated, dried on anhydrous Na₂SO₄, concentrated to get crude material, which was purified by column chromatography eluting with 10% EtOAc in hexane to get the desired compound 2-(4-Bromo-2-methyl-6-{[(Z)-2-methyl-propane-2-sulfinylimino]-methyl}-phenylsulfanyl)-nicotinic acid ethyl ester (2.75 g, 82%) as off-white solid. LC-MS: 485.0 [M+H]⁺

To a stirred and degassed solution of 2-(4-Bromo-2-methyl-6-{[(Z)-2-methyl-propane-2-sulfinylimino]-methyl}-phenylsulfanyl)-nicotinic acid ethyl ester (3.11 g, 6.6 mmol) in THF (15 mL), was added LAH (1M in THF, 13 ml, 13.3 mmol) at 0° C. and reaction mass was stirred at 25° C. for 1 h. The reaction mixture was quenched with saturated Na₂SO₄ solution and extracted with EtOAc. The separated organic layer was washed with water, brine and dried (Na₂SO₄) and concentrated to get 2-Methyl-propane-2-sulfinic acid 5-bromo-2-(3-hydroxymethyl-pyridin-2-ylsulfanyl)-3-methyl-benzylamide (2.3 g, 78%) as off white solid. LC-MS: 445.0[M+H]⁺

To a stirred solution of 2-Methyl-propane-2-sulfinic acid 5-bromo-2-(3-hydroxymethyl-pyridin-2-ylsulfanyl)-3-methyl-benzylamide (3 g, 6.8 mmol) in Methanol (20 mL) was added 4M HCl in 1,4-dioxane (20 mL) at 0° C., and stirred for 2h at the same temperature. After completion of starting material, reaction mixture was concentrated to get [2-(2-Aminomethyl-4-bromo-6-methyl-phenylsulfanyl)-pyridin-3-yl]-methanol HCl salt (2.6 g, crude) as off white solid. This crude was used for the next step with out further purification.

To a stirred solution of [2-(2-Aminomethyl-4-bromo-6-methyl-phenylsulfanyl)-pyridin-3-yl]-methanol (2.6 g, 6.9 mmol) in 5% NaHCO₃ solution (15 mL) Fmoc-OSU (2.4 g, 6.9 mmol) in CH₃CN (15 ml) was added at 25° C., and stirring was continued at the same temperature for 3h. Then reaction mass was diluted with water and extracted with ethyl acetate. The separated organic layer was washed with brine, dried over sodium sulfate and evaporated under reduced pressure to get crude material which was purified by washing with n-pentane to get the desired compound [5-Bromo-2-(3-hydroxymethyl-pyridin-2-ylsulfanyl)-3-methyl-benzyl]-carbamic acid 9H-fluoren-9-ylmethyl ester (3.6 g, 92%) as off white solid. LC-MS: 561.1[M+H]⁺

To a stirred solution of [5-Bromo-2-(3-hydroxymethyl-pyridin-2-ylsulfanyl)-3-methyl-benzyl]-carbamic acid 9H-fluoren-9-ylmethyl ester (6.4 g, 11.4 mmol) in DCM: THF (1:1, 60 ml), MnO₂ (20 g, 228 mmol) was added at room temperature, and stirring was continued at the same temperature for 2h. After consuming of starting material as monitored by silica gel TLC, the reaction mixture was filtered through celite pad, the filtrate was evaporated under reduced pressure. The crude material obtained was washed with n-Pentane and n-Hexane to get [5-Bromo-2-(3-formyl-pyridin-2-ylsulfanyl)-3-methyl-benzyl]-carbamic acid 9H-fluoren-9-ylmethyl ester (5.5 g, 86%). LC-MS: 560.1 [M+H]⁺

¹H-NMR: (400 MHz, DMSO-d6): δ 2.36 (3H, s), 4.22-4.26 (5H, m), 7.33-7.39 (7H, m), 7.54 (1H, brs), 7.63 (2H, d, J=7.2 Hz), 7.81 (1H, m), 7.90 (2H, d, J=7.3 Hz), 8.32 (1H, m), 8.41 (1H, m), 10.20 (1H, s).

Intermediate 57

9H-fluoren-9-ylmethyl N-({2-[(3-formylpyridin-2-yl)sulfanyl]-5-phenyl-3-(trifluoromethyl) phenyl}methyl)carbamate

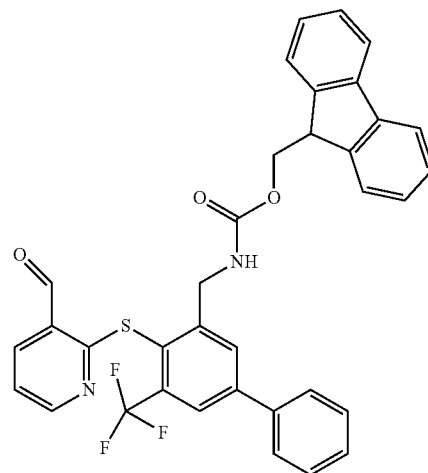

To a stirred solution of 2-mercapto nicotinic acid (3.2 g, 20.3 mmol) in DMF (50 mL) was added NaH (60%, 1.47 g, 36.9 mmol) and reaction mass was stirred at 25° C. for 30 min. Then 5-bromo-2-fluoro-3-trifluoromethyl-benzaldehyde (5.0 gm, 18.5 mmol) was added and reaction mixture was stirred at 80° C. for 1 h. Then K₂CO₃ (7.6 g, 55.3 mmol) was added followed by addition of MeI (3.4 mL, 55.3 mmmol) and reaction mass was stirred at 25° C. for 2h. Reaction mass was quenched with water and extracted with ethyl acetate. The separated organic layer was washed with brine, dried over anhydrous sodium sulfate and evaporated under reduced pressure. The crude material obtained was purified by normal silica column using 0-30% ethyl acetate in hexane to get methyl 2-{[4-bromo-2-formyl-6-(trifluoromethyl)phenyl]sulfanyl}pyridine-3-carboxylate (5 g, 64%) as a yellow solid.

To a stirred solution of methyl 2-{[4-bromo-2-formyl-6-(trifluoromethyl)phenyl]sulfanyl}pyridine-3-carboxylate (4.5 g, 10.7 mmol) in THF (100 mL) were added 2-methylpropane-2-sulfinamide (2.6 g, 21.4 mmol), Ti(OEt)₄ (6.7 mL, 32.1 mmol) and reaction mass was heated to 70° C. for 1 h. The reaction mass was quenched with saturated sodium chloride solution, solid obtained was filtered through celite pad, washed with ethyl acetate. The separated organic layer was dried over anhydrous sodium sulfate and concentrated under reduced pressure to afford methyl 2-({4-bromo-2-[(1E)-[(2-methylpropane-2-sulfinyl)imino]methyl]-6-(trifluoromethyl)phenyl}sulfanyl)pyridine-3-carboxylate (5.5 g, crude) which was directly used for next step without further purification. LC-MS: 523.0 [M+H]⁺

To a stirred solution of methyl 2-({4-bromo-2-[(1E)-[(2-methylpropane-2-sulfinyl)imino]methyl]-6-(trifluoromethyl)phenyl}sulfanyl)pyridine-3-carboxylate (5.5 g, 10.5 mmol) in THF (100 mL) was added LAH (2M in THF, 10.5 mL, 21 mmol) at 0° C. and reaction mass was stirred at 0° C. for 1 h. Reaction mixture was quenched with saturated sodium sulfate solution and extracted with ethyl acetate. The separated organic layer was washed with water, brine, dried over anhydrous sodium sulfate and evaporated under reduced pressure to get N-[(5-bromo-2-{[3-(hydroxymethyl)pyridin-2-yl]sulfanyl}-3-(trifluoromethyl)phenyl)methyl]-2-methylpropane-2-sulfinamide (5.0 g, crude) which was directly used for next step without further purification. LC-MS: 496.7 [M+H]$^+$ To a stirred solution of N-[(5-bromo-2-{[3-(hydroxymethyl)pyridin-2-yl]sulfanyl}-3-(trifluoromethyl)phenyl)methyl]-2-methylpropane-2-sulfinamide (3.6 g, 7.2 mmol) in DCM (50 mL) were added imidazole (1.5 g, 21.7 mmol) and TBDMSCl (1.6 gm, 10.9 mmol) at 0° C. and stirred at 25° C. for 2h. Reaction mass was quenched with aq NaHCO$_3$ solution and extracted with ethyl acetate. The separated organic layer was washed with water, brine solution, dried over sodium sulfate and evaporated under reduced pressure. The crude thus obtained was purified by combiflash column chromatography using 20% ethyl acetate in hexane to get N-({5-bromo-2-[(3-{[(tert-butyldimethylsilyl)oxy]methyl}pyridin-2-yl)sulfanyl]-3-(trifluoromethyl)phenyl}methyl)-2-methylpropane-2-sulfinamide (3.1 g, 70%, 3 steps) as off white solid. LC-MS: 611.1 [M+H]$^+$ To a stirred solution of compound N-({5-bromo-2-[(3-{[(tert-butyldimethylsilyl)oxy]methyl}pyridin-2-yl)sulfanyl]-3-(trifluoromethyl)phenyl}methyl)-2-methylpropane-2-sulfinamide (250 mg, 0.4 mmol) in toluene (8 mL) were added phenyl boronic acid (140.5 mg, 0.7 mmol), Na$_2$CO$_3$ (129.9 mg, 1.2 mmol), water (2.0 ml) and degassed for 10 min in argon atmosphere. Then to it was added Pd(PPh$_3$)$_4$ (47.23 mg, 0.04 mmol) and again degassed for 5 min. The reaction mass was heated to 100° C. for 12 h. Reaction mixture was then cooled to 25° C., filtered through celite pad and washed with EtOAc. The separated organic layer was washed with brine, dried over sodium sulfate and concentrated under vacuum to get the crude material which was purified by combiflash column chromatography using 0-25% ethyl acetate in hexane to get N-({2-[(3-{[(tert-butyldimethylsilyl)oxy]methyl}pyridin-2-yl)sulfanyl]-5-phenyl-3-(trifluoromethyl)phenyl}methyl)-2-methylpropane-2-sulfinamide (200 mg, 80%) as colourless sticky liquid. LC-MS: 609.0 [M+H]$^+$ To a stirred solution of N-({2-[(3-{[(tert-butyldimethylsilyl)oxy]methyl}pyridin-2-yl)sulfanyl]-5-phenyl-3-(trifluoromethyl)phenyl}methyl)-2-methylpropane-2-sulfinamide (2.2 g, 3.6 mmol) in MeOH (20 mL), was added 4M HCl in dioxane (10 mL) at 0° C. and reaction mixture was stirred at 25° C. for 1 h. Reaction mass was evaporated under reduced pressure to get (2-{[2-(aminomethyl)-4-phenyl-6-(trifluoromethyl)phenyl]sulfanyl}pyridin-3-yl)methanol HCl salt (1.2 g, crude) which was directly used for next step. LC-MS: 390.7 [M+H]$^+$ To a stirred suspension of (2-{[2-(aminomethyl)-4-phenyl-6-(trifluoromethyl)phenyl]sulfanyl}pyridin-3-yl)methanol HCl salt (1.2 g, 3.1 mmol) in 5% NaHCO$_3$ (30 mL) was added Fmoc-OSU (1.13 g, 3.35 mmol) in dioxan (30 mL) at 25° C. and reaction mass was stirred at the same temperature for 3h. Then reaction mass was diluted with water and extracted with ethyl acetate. The separated organic layer was washed with brine, dried over sodium sulfate and evaporated under reduced pressure. The crude material obtained was purified by column chromatography (10%-30% ethylacetate-hexane) to get 9H-fluoren-9-ylmethyl N-[(2-{[3-(hydroxymethyl)pyridin-2-yl]sulfanyl}-5-phenyl-3-(trifluoromethyl)phenyl)methyl]carbamate (1.5 g, 79%, 2 steps) as white solid.

To a stirred solution of 9H-fluoren-9-ylmethyl N-[(2-{[3-(hydroxymethyl)pyridin-2-yl]sulfanyl}-5-phenyl-3-(trifluoromethyl)phenyl)methyl]carbamate (1.5 g, 2.45 mmol) in DCM:THF (1:1, 50 mL) was added MnO$_2$ (3.15 g, 36.7 mmol) and reaction mass was stirred at 25° C. for 4 h. The reaction mass was filtered through celite pad and filtrate was evaporated under reduced pressure. The crude material obtained was purified by combiflash chromatography (10%-30% ethylacetate-hexane) to get 9H-fluoren-9-ylmethyl N-({2-[(3-formylpyridin-2-yl)sulfanyl]-5-phenyl-3-(trifluoromethyl)phenyl}methyl)carbamate (1.0 g, 66%) as white solid with 95.56% purity. LC-MS: 611.2 [M+H]$^+$ 1H NMR (400 MHz, DMSO-d6): δ 3.98-4.08 (1H, m), 4.21 (1H, d, J=5.9 Hz), 4.27 (3H, d, J=6.6 Hz), 7.24 (2H, t, J=6.3 Hz), 7.36-7.40 (3H, m), 7.51 (4H, dq, J=13.3, 6.8 Hz), 7.67 (2H, d, J=7.1 Hz), 7.78 (3H, d, J=7.4 Hz), 7.87 (2H, d, J=7.5 Hz), 7.89-7.97 (1H, m), 8.00 (2H, d, J=17.9 Hz), 8.37-8.47 (2H, m), 10.20 (1H, s)

Intermediate 58

9H-fluoren-9-ylmethyl N-({5-bromo-2-[(3-formylpyridin-2-yl)sulfanyl]-3-(trifluoromethyl)phenyl}methyl)carbamate To a stirred solution of 2-mercapto nicotinic acid (3.2 g, 20.3 mmol) in DMF (50 mL) was added NaH (60%, 1.47 g, 36.9 mmol) and reaction mass was stirred at 25° C. for 30 min. Then 5-bromo-2-fluoro-3-trifluoromethyl-benzaldehyde (5.0 gm, 18.5 mmol) was added and reaction mixture was stirred at 80° C. for 1 h. Then K$_2$CO$_3$ (7.6 g, 55.3 mmol) was added followed by addition of MeI (3.4 mL, 55.3 mmmol) and reaction mass was stirred at 25° C. for 2 h. Reaction mass was quenched with water and extracted with ethyl acetate. The separated organic layer was washed with brine, dried over anhydrous sodium sulfate and evaporated under reduced pressure. The crude material obtained was purified by normal silica column using 0-30% ethyl acetate in hexane to get methyl 2-{[4-bromo-2-formyl-6-(trifluoromethyl)phenyl]sulfanyl}pyridine-3-carboxylate (5 g, 64%) as a yellow solid.

To a stirred solution of methyl 2-{[4-bromo-2-formyl-6-(trifluoromethyl)phenyl]sulfanyl}pyridine-3-carboxylate (4.5 g, 10.7 mmol) in THF (100 mL) were added 2-methylpropane-2-sulfinamide (2.6 g, 21.4 mmol), Ti(OEt)$_4$ (6.7 mL, 32.1 mmol) and reaction mass was heated to 70° C. for 1 h. The reaction mass was quenched with saturated sodium chloride solution, solid obtained was filtered through celite pad, washed with ethyl acetate. The separated organic layer was dried over anhydrous sodium sulfate and concentrated under reduced pressure to afford methyl 2-({4-bromo-2-[(1E)-[(2-methylpropane-2-sulfinyl)imino]methyl]-6-(trifluoromethyl)phenyl}sulfanyl)pyridine-3-carboxylate (5.5 g, crude) which was directly used for next step without further purification. LC-MS: 523.0 [M+H]$^+$ To a stirred solution of methyl 2-({4-bromo-2-[(1E)-[(2-methylpropane-2-sulfinyl)imino]methyl]-6-(trifluoromethyl)phenyl}sulfanyl)pyridine-3-carboxylate (5.5 g, 10.5 mmol) in THF (100 mL) was added LAH (2M in THF, 10.5 mL, 21.0 mmol) at 0° C. and reaction mass was stirred at 0° C. for 1 h. Reaction mixture was quenched with saturated sodium sulfate solution and extracted with ethyl acetate. The separated organic layer was washed with water, brine, dried over anhydrous sodium sulfate and evaporated under reduced pressure to get N-[(5-bromo-2-{[3-(hydroxymethyl)pyridin-2-yl]sulfanyl}-3-(trifluoromethyl)phenyl)methyl]-2-methylpropane-2-sulfinamide (5.0 g, crude) which was directly used for next step without further purification. LC-MS: 496.7 [M+H]$^+$ To a stirred solution of N-[(5-bromo-2-{[3-(hydroxymethyl)pyridin-2-yl]sulfanyl}-3-(trifluoromethyl)phenyl)methyl]-2-methylpropane-2-sulfinamide (1.5 g, 3.0 mmol) in MeOH (50 mL), was added 4M HCl in dioxane (8 mL) at 0° C. and reaction mixture was stirred at 25° C. for 1 h. Reaction mass was evaporated under reduced pressure to get (2-{[2-(aminomethyl)-4-bromo-6-(trifluoromethyl)phenyl]sulfanyl}pyridin-3-yl)methanol HCl salt (1 g) which was directly used for next step. LC-MS: 392.7 [M+H]$^+$ To a stirred suspension of (2-{[2-(aminomethyl)-4-bromo-6-(trifluoromethyl)phenyl]sulfanyl}pyridin-3-yl)methanol HCl salt (1.2 g, 2.8 mmol) in 5% NaHCO$_3$ (120 mL) was added Fmoc OSU (1.04 g, 3.1 mmol) in dioxan (50 mL) at 25° C. and reaction mass was stirred at the same temperature for 3h. Then reaction mass was diluted with water and extracted with ethyl acetate. The separated organic layer was washed with brine, dried over sodium sulfate and evaporated under reduced pressure. The crude thus obtained was purified by normal silica column 10%-30% ethyl acetate-hexane to get 9H-fluoren-9-ylmethyl N-[(5-bromo-2-{[3-(hydroxymethyl)pyridin-2-yl]sulfanyl}-3-(trifluoromethyl)phenyl)methyl]carbamate (1.2 g, 68%, 2 steps) as off white solid. LC-MS: 617.0 [M+H]$^+$ To a stirred solution of 9H-fluoren-9-ylmethyl N-[(5-bromo-2-{[3-(hydroxymethyl)pyridin-2-yl]sulfanyl}-3-(trifluoromethyl)phenyl)methyl]carbamate (1.5 g, 2.4 mmol) in DCM:THF (1:1, 50 mL) was added MnO$_2$ (3.14 g, 36.6 mmol) and reaction mass was stirred at 25° C. for 4 h. The reaction mass was filtered through celite pad; filtrate was evaporated under reduced pressure. The crude material obtained was purified by combiflash chromatography eluting with 10%-30% ethyl acetate in hexane to get 9H-fluoren-9-ylmethyl N-({5-bromo-2-[(3-formylpyridin-2-yl)sulfanyl]-3-(trifluoromethyl)phenyl}methyl)carbamate (700 mg, 46%) as white solid with 95.13% purity. LC-MS: 615.1 [M+H]$^+$ 1H NMR (400 MHz, DMSO-d6): δ 4.21-4.30 (5H, m), 7.31-7.34 (2H, m), 7.40-7.41 (3H, m), 7.68 (3H, m), 7.69 (2H, d, J=7.0 Hz), 7.81 (1H, m), 7.80-7.90 (3H, m), 8.01 (1H, m), 8.37-8.39 (2H, m), 10.16 (1H, s)

Intermediate 59

9H-fluoren-9-ylmethyl N-({5-bromo-3-chloro-2-[(3-formylpyridin-2-yl)sulfanyl]phenyl}methyl) carbamate

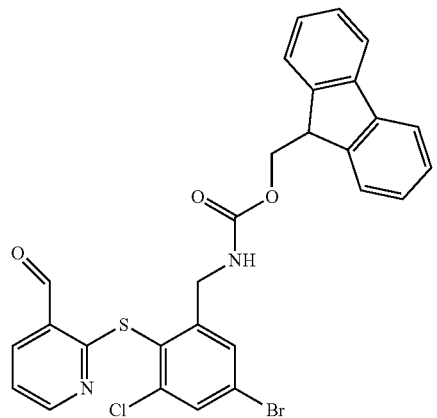 [SMILES: O=Cc1cccnc1Sc1c(Cl)cc(Br)cc1CNC(=O)OCC1c2ccccc2-c2ccccc21]

To a stirred solution of 2-mercapto nicotinic acid (10.7 g, 69.5 mmol) in DMF (150 mL) was added NaH (60%, 5.1 g, 126.3 mmol) and reaction mass was stirred at 25° C. for 30 min. Then 5-bromo-3-chloro-2-fluoro-benzaldehyde (15 g, 63.1 mmol) was added and reaction mixture was stirred at 70° C. for 4h. Then K$_2$CO$_3$ (26.1 g, 189.5 mmol) was added followed by addition of MeI (11.8 mL, 189.5 mmol) and reaction mass was stirred at 25° C. for 16h. Reaction mass was quenched with water and extracted with ethyl acetate. The separated organic layer was washed with brine, dried over anhydrous sodium sulfate and evaporated under reduced pressure. The crude thus obtained was purified by normal silica column using 0-8% ethyl acetate in hexane to get methyl 2-[(4-bromo-2-chloro-6-formylphenyl)sulfanyl]pyridine-3-carboxylate (12 g, 49%) as a yellow solid.

To a stirred solution of methyl 2-[(4-bromo-2-chloro-6-formylphenyl)sulfanyl]pyridine-3-carboxylate (15 g, 38.9 mmol) in THF (80 mL) were added 2-methylpropane-2-sulfinamide (4.71 g, 38.9 mmol), Ti(OEt)$_4$ (40.7 mL, 194.3 mmol) and reaction mass was heated to 70° C. for 2h. The reaction mass was quenched with saturated sodium chloride solution, solid obtained was filtered through celite pad, washed with ethyl acetate. The separated organic layer was dried over anhydrous sodium sulfate and concentrated under reduced pressure to afford ethyl 2-({4-bromo-2-chloro-6-[(1Z)-[(2-methylpropane-2-sulfinyl)imino]methyl]phenyl}sulfanyl)pyridine-3-carboxylate (17 g, crude) which was directly used for next step without further purification. LC-MS: 502.7 [M+H]$^+$ To a stirred solution of ethyl 2-({4-bromo-2-chloro-6-[(1Z)-[(2-methylpropane-2-sulfinyl)imino]methyl]phenyl}sulfanyl)pyridine-3-carboxylate (17 g, 33.8 mmol) in THF (80 mL) was added LAH (2M in THF, 25.3 mL, 50.7 mmol) at 0° C. and reaction mass was stirred at 0° C. for 1 h. Reaction mixture was quenched with saturated sodium sulfate solution and extracted with ethyl acetate. The separated organic layer was washed with water, brine, dried over anhydrous sodium sulfate and evaporated under reduced pressure to get N-[(5-bromo-3-chloro-2-{[3-(hydroxymethyl)pyridin-2-yl]sulfanyl}phenyl)methyl]-2-methylpropane-2-sulfinamide (16 g) as off-white solid. LC-MS: 464.8 [M+H]$^+$ To a stirred solution of N-[(5-bromo-3-chloro-2-{[3-(hydroxymethyl)pyridin-2-yl]sulfanyl}phenyl)methyl]-2-methylpropane-2-sulfinamide (12 g, 12.9 mmol) in MeOH (30 mL), was added 4M HCl in dioxane (30 mL) at 0° C. and reaction mixture was stirred at 25° C. for 1 h. Reaction mass was evaporated under reduced pressure to get (5-bromo-3-chloro-2-{[3-(hydroxymethyl)pyridin-2-yl] sulfanyl}phenyl)methanaminium HCl salt (4.5 g) which was directly used for next step.

To a stirred suspension of (2-{[2-(aminomethyl)-3-bromo-6-chlorophenyl]sulfanyl}pyridin-3-yl)methanol HCl salt (2.5 g, 6.5 mmol) in 5% NaHCO₃ (100 mL) was added Fmoc OSU (2.4 g, 7.1 mmol) in dioxan (50 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure. The crude thus obtained was purified by normal silica column using 0-50% ethyl acetate in hexane to get 9H-fluoren-9-ylmethyl N-[(5-bromo-3-chloro-2-{[3-(hydroxymethyl)pyridin-2-yl] sulfanyl}phenyl)methyl]carbamate (1.9 g, 50%, 4 steps) as off white solid. LC-MS: 583.0 [M+H]⁺

To a stirred solution of 9H-fluoren-9-ylmethyl N-[(5-bromo-3-chloro-2-{[3-(hydroxymethyl)pyridin-2-yl] sulfanyl}phenyl)methyl]carbamate (2.3 g, 3.9 mmol) in DCM:THF (1:1, 40 mL) was added MnO₂ (3.4 g, 39.6 mmol) and reaction mass was stirred at 25° C. for 16 h. The reaction mass was filtered through celite pad; filtrate was evaporated under reduced pressure. The crude thus obtained was purified by normal silica column using 0-30% ethyl acetatel in hexane to get 9H-fluoren-9-ylmethyl N-({5-bromo-3-chloro-2-[(3-formylpyridin-2-yl)sulfanyl] phenyl}methyl) carbamate (1.9 g, 82%) as off white solid with 97.5% purity. LC-MS: 580.8 [M+H]⁺

1H NMR (400 MHz, DMSO-d6): δ 4.26 (2H, d, J=5.8 Hz), 4.29 (2H, d, J=6.8 Hz), 7.33 (2H, t, J=7.3 Hz), 7.41 (3H, q, J=5.8, 4.4 Hz), 7.51 (1H, s), 7.68 (2H, d, J=7.4 Hz), 7.86-7.91 (4H, m), 8.38 (1H, d, J=7.4 Hz), 8.43 (1H, d, J=3.3 Hz), 10.18 (1H, s).

Intermediate 60

9H-fluoren-9-ylmethyl N-({6-bromo-3-chloro-2-[(3-formylpyridin-2-yl)sulfanyl]phenyl}methyl)carbamate

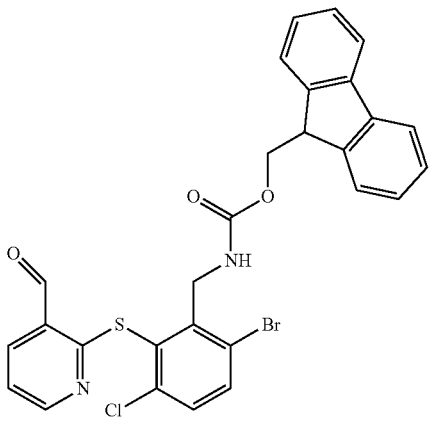 [SMILES: O=Cc1cccnc1Sc1c(Cl)ccc(Br)c1CNC(=O)OCC1c2ccccc2-c2ccccc21]

To a stirred solution of 2-mercapto nicotinic acid (2.4 g, 15.5 mmol) in DMF (25 mL) was added NaH (60%, 1.23 g, 30.95 mmol) and reaction mass was stirred at 25° C. for 30 min. Then 6-bromo-3-chloro-2-fluoro-benzaldehyde (4.05 g, 17.05 mmol) was added and reaction mixture was stirred at 90° C. for 16h. Then K₂CO₃ (6.4 g, 46.4 mmol) was added followed by addition of MeI (2.9 mL, 46.4 mmol) and reaction mass was stirred at 25° C. for 5h. Reaction mass was quenched with water and extracted with ethyl acetate. The separated organic layer was washed with brine solution, dried over anhydrous sodium sulfate and evaporated under reduced pressure. The crude material obtained was purified by normal silica column using 0-30% ethyl acetate in hexane to get methyl 2-[(3-bromo-6-chloro-2-formylphenyl)sulfanyl]pyridine-3-carboxylate (4 g, 67%) as a yellow solid. LC-MS: 387.9 [M+H]⁺

To a stirred solution of methyl 2-[(3-bromo-6-chloro-2-formylphenyl)sulfanyl]pyridine-3-carboxylate (5.0 g, 12.9 mmol) in THF (50 mL) were added 2-methylpropane-2-sulfinamide (1.57 g, 12.9 mmol), Ti(OEt)₄ (8.147 ml, 38.9 mmol) and reaction mass was heated to 70° C. for 45 min. The reaction mass was quenched with saturated sodium chloride solution, solid obtained was filtered through celite pad, washed with ethyl acetate. The separated organic layer was dried over anhydrous sodium sulfate and concentrated under reduced pressure to afford ethyl 2-({3-bromo-6-chloro-2-[(1E)-[(2-methylpropane-2-sulfinyl)imino]methyl] phenyl}sulfanyl)pyridine-3-carboxylate (6 g, crude) which was directly used for next step without further purification. LC-MS: 504.6 [M+H]⁺

To a stirred solution of ethyl 2-({3-bromo-6-chloro-2-[(1E)-[(2-methylpropane-2-sulfinyl)imino]methyl] phenyl}sulfanyl)pyridine-3-carboxylate (6.0 g, 11.9 mmol) in THF (50 mL) was added LAH (2M in THF, 8.9 mL, 17.9 mmol) at 0° C. and reaction mass was stirred at 0° C. for 1 h. Reaction mixture was quenched with saturated sodium sulfate solution and extracted with ethyl acetate. The separated organic layer was washed with water, brine, dried over anhydrous sodium sulfate and evaporated under reduced pressure. The crude thus obtained was purified by normal silica column using 50-90% ethyl acetate in hexane to get N-[(6-bromo-3-chloro-2-{[3-(hydroxymethyl)pyridin-2-yl] sulfanyl}phenyl)methyl]-2-methylpropane-2-sulfinamide (4.0 g) as off-white solid. LC-MS: 464.9 [M+H]⁺

To a stirred solution of N-[(6-bromo-3-chloro-2-{[3-(hydroxymethyl)pyridin-2-yl]sulfanyl}phenyl)methyl]-2-methylpropane-2-sulfinamide (4.0 g, 8.6 mmol) in MeOH (40 mL), was added 4M HCl in dioxane (20 mL) at 0° C. and reaction mixture was stirred at 25° C. for 20 min. Reaction mass was evaporated under reduced pressure to get (2-{[2-(aminomethyl)-3-bromo-6-chlorophenyl]sulfanyl}pyridin-3-yl)methanol HCl salt (4 g) which was directly used for next step.

To a stirred suspension of (2-{[2-(aminomethyl)-3-bromo-6-chlorophenyl]sulfanyl}pyridin-3-yl)methanol HCl salt (4.0 g, 11.1 mmol) in 5% NaHCO₃ (25 mL) was added Fmoc-OSU (3.7 g, 11.1 mmol) in CH₃CN (25 mL) at 25° C. and reaction mass was stirred at the same temperature for 3h. Then reaction mass was diluted with water and extracted with ethyl acetate. The separated organic layer was washed with brine solution, dried over sodium sulfate and evaporated under reduced pressure to get 9H-fluoren-9-ylmethyl N-[(6-bromo-3-chloro-2-{[3-(hydroxymethyl)pyridin-2-yl] sulfanyl}phenyl)methyl]carbamate (4.5 g) which was directly used for next step. LC-MS: 582.8 [M+H]⁺

To a stirred solution of 9H-fluoren-9-ylmethyl N-[(6-bromo-3-chloro-2-{[3-(hydroxymethyl)pyridin-2-yl]

sulfanyl}phenyl)methyl]carbamate (2.0 g, 3.4 mmol) in DCM:THF (1:1, 40 mL) was added MnO₂ (3 g, 34.4 mmol) and reaction mass was stirred at 25° C. for 1 h. The reaction mass was filtered through celite pad, the filtrate was evaporated under reduced pressure. The crude material obtained was purified by normal silica column using 0-10% methanol in DCM to get 9H-fluoren-9-ylmethyl N-({6-bromo-3-chloro-2-[(3-formylpyridin-2-yl)sulfanyl]phenyl}methyl) carbamate (1.3 g) as off white solid with 90.7% LCMS purity. LC-MS: 581.1 [M+H]⁺

1H NMR (400 MHz, DMSO-d6): δ 4.14-4.25 (3H, m), 4.46 (2H, d, J=3.9 Hz), 7.31 (2H, t, J=7.5 Hz), 7.34-7.45 (3H, m), 7.48-7.54 (1H, m), 7.56 (1H, d, J=8.5 Hz), 7.67 (2H, d, J=7.4 Hz), 7.81 (1H, d, J=8.6 Hz), 7.88 (2H, d, J=7.6 Hz), 8.37 (1H, d, J=7.5 Hz), 8.44 (1H, dd, J=4.8, 1.8 Hz), 10.19 (1H, s).

Intermediate 61

9H-fluoren-9-ylmethyl N-({2-[(3-formylpyridin-2-yl)sulfanyl]-3,5-bis(trifluoromethyl)phenyl}methyl) carbamate

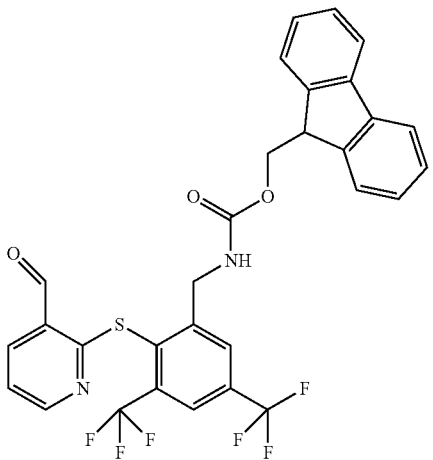 [SMILES: O=Cc1cccnc1Sc1c(CNC(=O)OCC2c3ccccc3-c3ccccc32)cc(C(F)(F)F)cc1C(F)(F)F]

To a stirred solution of 1-fluoro-2,4-bis(trifluoromethyl) benzene (3 g, 12.9 mmol), TMEDA (2.3 mL, 15.5 mmol) in THF (30 mL) was added nBuLi (2.2M in THF, 6.4 mL, 14.2 mmol) at −78 deg C. and reaction mass was stirred at −78° C. for 1 h. Then 1-formylpiperidine (2.2 mL, 19.4 mmol) was added to the reaction mass at −78° C. and it was stirred at −78° C. for 1 h and then at 25° C. for 1 h. Reaction mass was quenched with saturated ammonium chloride solution and extracted with pentane. The separated organic layer was washed with brine solution, dried over anhydrous sodium sulfate and evaporated under reduced pressure to get 2-fluoro-3,5-bis(trifluoromethyl) benzaldehyde (2.2 g).

To a stirred solution of 2-mercapto nicotinic acid (3.9 g, 25.4 mmol) in DMF (50 mL) was added NaH (60%, 1.8 g, 46.1 mmol) and reaction mass was stirred at 25° C. for 30 min. Then 2-fluoro-3,5-bis(trifluoromethyl)benzaldehyde (6 g, 23.1 mmol) was added and reaction mixture was stirred at 70° C. for 4h. Then K₂CO₃ (9.6 g, 69.2 mmol) was added followed by addition of MeI (4.3 mL, 69.2 mmmol) and reaction mass was stirred at 25° C. for 16h. Reaction mass was quenched with water and extracted with ethyl acetate. The separated organic layer was washed with brine solution, dried over anhydrous sodium sulfate and evaporated under reduced pressure. The crude thus obtained was purified by normal silica column using 0-8% ethyl acetate in hexane to get methyl 2-{[2-formyl-4,6-bis(trifluoromethyl)phenyl] sulfanyl}pyridine-3-carboxylate (1.4 g, 11%, 2 steps) as a yellow solid. LC-MS: 409.5

To a stirred solution of methyl 2-{[2-formyl-4,6-bis(trifluoromethyl)phenyl]sulfanyl}pyridine-3-carboxylate (1.4 g, 3.4 mmol) in THF (10 mL) were added 2-methylpropane-2-sulfinamide (415 mg, 3.4 mol), Ti(OEt)₄ (3.6 mL, 17.1 mmol) and reaction mass was heated to 70° C. for 1 h. The reaction mass was quenched with saturated sodium chloride solution. The solid obtained was filtered through celite pad and washed with ethyl acetate. The separated organic layer was dried over anhydrous sodium sulfate and concentrated under reduced pressure to afford ethyl 2-({2-[(1E)-[(2-methylpropane-2-sulfinyl)imino]methyl]-4,6-bis(trifluoromethyl)phenyl}sulfanyl)pyridine-3-carboxylate (1.6 g, crude) which was directly used for next step without further purification. LC-MS: 527.1 [M+H]⁺

To a stirred solution of ethyl 2-({2-[(1E)-[(2-methylpropane-2-sulfinyl)imino]methyl]-4,6-bis(trifluoromethyl) phenyl}sulfanyl)pyridine-3-carboxylate (1.5 g, 2.8 mmol) in THF (15 mL) was added LAH (2M in THF, 2.13 mL, 4.3 mmol) at 0° C. and reaction mass was stirred at 0° C. for 2h. Reaction mixture was quenched with saturated sodium sulfate solution and extracted with ethyl acetate. The separated organic layer was washed with water, brine solution, dried over anhydrous sodium sulfate and evaporated under reduced pressure. The crude thus obtained was purified by normal silica column using 5-60% ethyl acetate in hexane to get N-[(2-{[3-(hydroxymethyl)pyridin-2-yl]sulfanyl}-3,5-bis(trifluoromethyl)phenyl)methyl]-2-methylpropane-2-sulfinamide (800 mg, 48%, 2 steps) as off-white solid. LC-MS: 486.7 [M+H]⁺

To a stirred solution of N-[(2-{[3-(hydroxymethyl)pyridin-2-yl]sulfanyl}-3,5-bis(trifluoromethyl)phenyl)methyl]-2-methylpropane-2-sulfinamide (800 mg, 1.6 mmol) in MeOH (8 mL), was added 4M HCl in dioxan (4 mL) at 0° C. and reaction mixture was stirred at 25° C. for 1 h. Reaction mass was evaporated under reduced pressure to get (2-{[2-(aminomethyl)-4,6-bis(trifluoromethyl)phenyl] sulfanyl}pyridin-3-yl)methanol HCl salt (650 mg, crude) which was directly used for next step. LC-MS: 382.8 [M+H]⁺

To a stirred suspension of (2-{[2-(aminomethyl)-4,6-bis(trifluoromethyl)phenyl]sulfanyl}pyridin-3-yl)methanol HCl salt (650 mg, 1.6 mmol) in 5% NaHCO₃ (100 mL) was added Fmoc-OSU (523 mg, 1.6 mmol) in acetonitrile (20 mL) at 25° C. and reaction mass was stirred at the same temperature for 2h. Then reaction mass was diluted with water and extracted with ethyl acetate. The separated organic layer was washed with brine, dried over sodium sulfate and evaporated under reduced pressure to get 9H-fluoren-9-ylmethyl N-[(2-{[3-(hydroxymethyl)pyridin-2-yl]sulfanyl}-3,5-bis(trifluoromethyl)phenyl)methyl]carbamate (950 mg) as off white solid. LC-MS: 605.2 [M+H]⁺

To a stirred solution of 9H-fluoren-9-ylmethyl N-[(2-{[3-(hydroxymethyl)pyridin-2-yl]sulfanyl}-3,5-bis(trifluoromethyl)phenyl)methyl]carbamate (950 mg, 1.6 mmol) in DCM/THF (1:1, 20 mL) was added MnO₂ (2.7 g, 31.46 mmol) and reaction mass was stirred at 25° C. for 2 h. The reaction mass was filtered through celite pad. The filtrate was evaporated under reduced pressure. The crude material obtained was purified by normal silica column using 5-20% ethyl acetate in hexane to get 9H-fluoren-9-ylmethyl N-({2-[(3-formylpyridin-2-yl)sulfanyl]-3,5-bis(trifluoromethyl)

phenyl}methyl)carbamate (600 mg) as off white solid with 95% LCMS purity. LC-MS: 602.9 [M+H]⁺

1H NMR (400 MHz, DMSO-d6): δ 4.22 (1H, d, J=6.8 Hz), 4.29 (4H, d, J=6.8 Hz), 7.31 (2H, t, J=7.4 Hz), 7.41 (3H, t, J=6.0 Hz), 7.67 (2H, d, J=7.5 Hz), 7.89 (2H, d, J=7.4 Hz), 7.94 (1H, s), 8.01 (1H, s), 8.12 (1H, s), 8.41 (2H, d, J=7.2 Hz), 10.18 (1H, s).

Intermediate 62

9H-fluoren-9-ylmethyl N-({3-chloro-2-[(3-formylpyridin-2-yl)sulfanyl]-5-(morpholin-4-yl)phenyl}methyl)carbamate

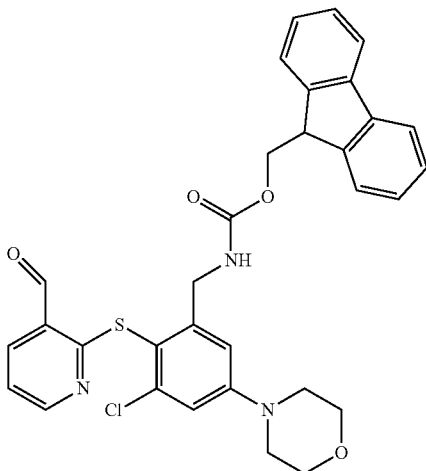

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in toluene (10 mL) were added morpholine (272 mg, 3.1 mmol) and sodium tertiary butoxide (675 mg, 7.0 mmol) and degassed in argon atmosphere for 5 min. Then to it were added 2-ditertiary butyl phosphino biphenyl (70 mg, 0.2 mmol) and Pd(dba)₂ (120 mg, 0.21 mmol) and heated to 110° C. for 16h. Reach on mass was filtered through celite pad and the filtrate was evaporated under reduced pressure. The crude thus obtained was purified by combiflash column chromatography using 20-80% ethyl acetate in hexane to get N-({2-[(3-{[(tert-butyldimethylsilyl)oxy]methyl}pyridin-2-yl)sulfanyl]-3-chloro-5-(morpholin-4-yl)phenyl}methyl)-2-methylpropane-2-sulfinamide (530 mg) as brown sticky solid. LC-MS: 584.3 [M+H]⁺

To a stirred solution of N-({2-[(3-{[(tert-butyldimethylsilyl)oxy]methyl}pyridin-2-yl)sulfanyl]-3-chloro-5-(morpholin-4-yl)phenyl}methyl)-2-methylpropane-2-sulfinamide (530 mg, 0.9 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(aminomethyl)-6-chloro-4-(morpholin-4-yl)phenyl]sulfanyl}pyridin-3-yl)methanol HCl salt (500 mg) which was directly used for next step. LC-MS: 365.8 [M+H]⁺

To a stirred suspension of (2-{[2-(aminomethyl)-6-chloro-4-(morpholin-4-yl)phenyl]sulfanyl}pyridin-3-yl)methanol HCl salt (500 mg, 1.4 mmol) in 5% NaHCO₃ (10 mL) was added Fmoc-OSU (461 mg, 1.4 mmol) in acetonitrile (10 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(morpholin-4-yl)phenyl)methyl]carbamate (530 mg) as off white solid. LC-MS: 588.2 [M+H]⁺

To a stirred solution of 9H-fluoren-9-ylmethyl N-[(3-chloro-2-{[3-(hydroxymethyl)pyridin-2-yl]sulfanyl}-5-(morpholin-4-yl)phenyl)methyl]carbamate (530 mg, 0.90 mmol) in DCM:THF (1:1, 40 mL) was added MnO₂ (1.18 g, 13.5 mmol) and reaction mass was stirred at 25° C. for 2 h. The reaction mass was filtered through celite pad; filtrate was evaporated under reduced pressure. The crude material obtained was purified by column chromatography using 30-80% ethyl acetate in hexane to get 9H-fluoren-9-ylmethyl N-({3-chloro-2-[(3-formylpyridin-2-yl)sulfanyl]-5-(morpholin-4-yl)phenyl}methyl)carbamate (230 mg, 42%, 3 steps) as off white solid. LC-MS: 585.8 [M+H]⁺

1H NMR (400 MHz, DMSO-d6): δ 3.19 (4H, s), 3.70 (4H, s), 4.18-4.28 (5H, m), 6.91 (1H, s), 7.07 (1H, s), 7.27-7.36 (3H, m), 7.41 (2H, d, J=7.2 Hz), 7.69 (2H, d, J=6.9 Hz), 7.79 (1H, s), 7.90 (2H, d, J=7.7 Hz), 8.32 (1H, d, J=6.5 Hz), 8.42 (1H, s), 10.20 (1H, s).

Intermediate 63

(9H-Fluoren-9-yl)methyl 3-chloro-2-((3-formylpyrazin-2-yl)thio)-5-(trifluoromethyl)benzylcarbamate

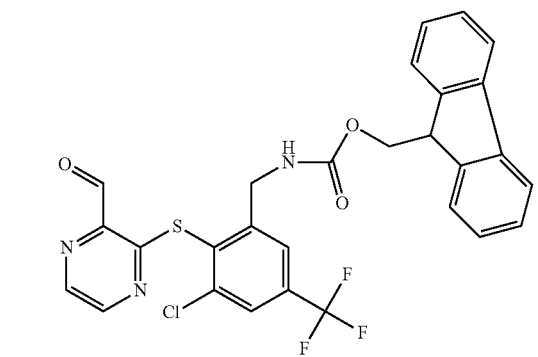 [SMILES: O=Cc1nccnc1Sc1c(Cl)cc(C(F)(F)F)cc1CNC(=O)OCC1c2ccccc2-c2ccccc21]

A mixture of 3-mercaptopyrazine-2-carboxylic acid (1 g, 6.4 mmol, Eq: 1), 3-chloro-2-fluoro-5-(trifluoromethyl)benzaldehyde (1.45 g, 942 µl, 6.4 mmol, Eq: 1) and K₂CO₃ (1.77 g, 12.8 mmol, Eq: 2) in DMF (10.7 ml) was stirred at 60° C. for 2 h. The reaction mixture was cooled to room temperature. Then iodomethane (4.54 g, 2 ml, 32 mmol, Eq: 5) was added and stirring at room temperature continued for 2 h. The reaction mixture was concentrated in vacuo. The residue was treated with water and extracted with EtOAc. The organic layers were washed with water and brine, dried over Na₂SO₄ and concentrated in vacuo. Methyl 3-((2-chloro-6-formyl-4-(trifluoromethyl)phenyl)thio)pyrazine-2-carboxylate was obtained as brown solid (1.84 g) and was used without further purification. MS ESI (m/z): 377.0 [(M+H)⁺]

To a mixture of methyl 3-((2-chloro-6-formyl-4-(trifluoromethyl)phenyl)thio)pyrazine-2-carboxylate (1.84 g, 4.88 mmol, Eq: 1), 2-methylpropane-2-sulfinamide (592 mg, 4.88 mmol, Eq: 1) in THF (20.4 ml) was added titanium(IV) ethoxide (5.57 g, 5.12 ml, 24.4 mmol, Eq: 5). The reaction mixture was heated to 70° C. and stirred for 2 h. The mixture was quenched with brine, filtered through glass fiber paper and washed multiple times with EtOAc. The organic layers were washed with brine, dried over Na$_2$SO$_4$ and concentrated in vacuo. Ethyl 3-((2-(((tert-butylsulfinyl)imino)methyl)-6-chloro-4-(trifluoromethyl)phenyl)thio)pyrazine-2-carboxylate was obtained as light brown solid (2.26 g) and was used without further purification. MS ESI (m/z): 494.2 [(M+H)$^+$]

To a mixture of ethyl 3-((2-(((tert-butylsulfinyl)imino)methyl)-6-chloro-4-(trifluoromethyl)phenyl)thio)pyrazine-2-carboxylate (2.2 g, 3.56 mmol, Eq: 1) and calcium chloride (1.38 g, 12.5 mmol, Eq: 3.5) in ethanol (14.8 ml) and THF (20.8 ml) was added NaBH$_4$ (607 mg, 16 mmol, Eq: 4.5) at 0° C. reaction mixture stirred at 0° C. for 1 h, then at room temperature for 1 h. The mixture was quenched at 0° C. with sat. aq. NH$_4$Cl slt., extracted with ethyl acetate and the organic layers washed with water. The combined organic layers were dried with Na$_2$SO$_4$, filtered and concentrated in vacuo. N-(3-chloro-2-((3-(hydroxymethyl)pyrazin-2-yl)thio)-5-(trifluoromethyl)benzyl)-2-methylpropane-2-sulfinamide was obtained as light brown foam (2.0 g) and was used without further purification. MS ESI (m/z): 454.2 [(M+H)$^+$]

To a mixture of N-(3-chloro-2-((3-(hydroxymethyl)pyrazin-2-yl)thio)-5-(trifluoromethyl)benzyl)-2-methylpropane-2-sulfinamide (2 g, 3.52 mmol, Eq: 1) in MeOH (17.6 ml) was added 4M HCl in dioxane (8.81 ml, 35.2 mmol, Eq: 10) and the reaction mixture stirred at room temperature for 2 h. The reaction mixture was concentrated in vacuo. (3-((2-(Aminomethyl)-6-chloro-4-(trifluoromethyl)phenyl)thio)pyrazin-2-yl)methanol hydrochloride was obtained as dark brown foam (2.3 g) and was used without further purification. MS ESI (m/z): 350.1 [(M+H)$^+$]

To a mixture of (3-((2-(aminomethyl)-6-chloro-4-(trifluoromethyl)phenyl)thio)pyrazin-2-yl)methanol hydrochloride (2.3 g, 3.57 mmol, Eq: 1) and sodium bicarbonate (600 mg, 7.15 mmol, Eq: 2) in acetonitrile (11.9 ml) and water (11.9 ml) was added Fmoc-OSu (1.21 g, 3.57 mmol, Eq: 1). The reaction mixture was stirred at room temperature for 1 h. Again Fmoc-OSu (120 mg, 0.1 eq) was added and the mixture stirred for another 1 h. The mixture was then diluted with EtOAc and water, extracted with ethyl acetate and the organic layers washed with water. The combined organic layers were dried with Na$_2$SO$_4$, filtered and concentrated in vacuo. (9H-Fluoren-9-yl)methyl 3-chloro-2-((3-(hydroxymethyl)pyrazin-2-yl)thio)-5-(trifluoromethyl)benzylcarbamate was obtained as yellow foam (2.7 g) and was used without further purification. MS ESI (m/z): 572.2 [(M+H)$^+$]

To a solution of (9H-fluoren-9-yl)methyl 3-chloro-2-((3-(hydroxymethyl)pyrazin-2-yl)thio)-5-(trifluoromethyl)benzylcarbamate (2.7 g, 3.54 mmol, Eq: 1) in DCM (50.6 ml) was added dess-martin periodinane (1.8 g, 4.25 mmol, Eq: 1.2) at 0° C. The cooling bath was removed and the mixture stirred 30 min at room temperature. The mixture was diluted with sat. aq. NaHCO$_3$ slt. and extracted with EtOAc. The organic layers were washed with sat. aq. Na$_2$S$_2$O$_3$ slt. combined, dried over Na$_2$SO$_4$ and concentrated in vacuo. The crude material was purified by silica gel chromatography using heptane/EtOAc as eluent. The obtained material was triturated with EtOAc. The title compound (9H-fluoren-9-yl)methyl 3-chloro-2-((3-formylpyrazin-2-yl)thio)-5-(trifluoromethyl)benzylcarbamate was obtained as light yellow solid (1.02 g). MS ESI (m/z): 570.2 [(M+H)$^+$]

Intermediate 64

(9H-Fluoren-9-yl)methyl 3-chloro-2-((3-formylpyrazin-2-yl)thio)-6-(trifluoromethyl)benzylcarbamate

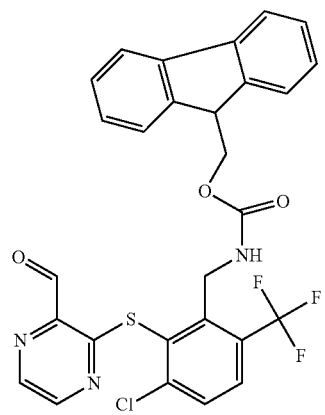 [SMILES: O=Cc1nccnc1Sc1c(Cl)ccc(C(F)(F)F)c1CNC(=O)OCC1c2ccccc2-c2ccccc21]

This material was prepared in analogy to Intermediate 63 starting from 3-chloro-2-fluoro-6-(trifluoromethyl)benzaldehyde and 3-mercaptopyrazine-2-carboxylic acid. The title compound was obtained as light yellow foam (0.454 g). MS ESI (m/z): 570.2 [(M+H)$^+$]

Intermediate 65

9H-fluoren-9-ylmethyl N-({3-chloro-2-[(3-formylpyridin-2-yl)sulfanyl]-5-(pyridin-3-yl)phenyl}methyl)carbamate

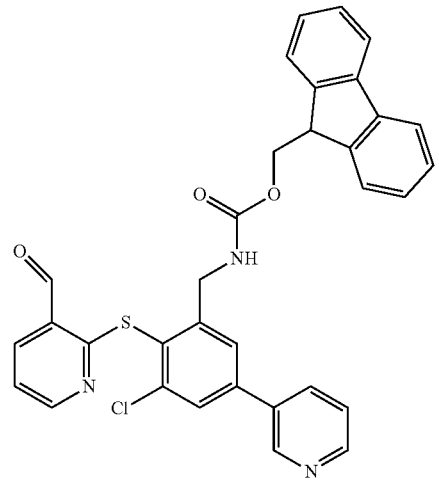 [SMILES: O=Cc1cccnc1Sc1c(Cl)cc(-c2cccnc2)cc1CNC(=O)OCC1c2ccccc2-c2ccccc21]

To a stirred solution of 2-mercapto nicotinic acid (10.8 g, 69.5 mmol) in DMF (150 mL) was added NaH (60%, 5.1 g, 126.3 mmol) and reaction mass was stirred at 25° C. for 30 min. Then 5-bromo-3-chloro-2-fluoro-benzaldehyde (15 g, 63.2 mmol) was added and reaction mixture was stirred at 70° C. for 4h. Then K$_2$CO$_3$ (26.2 g, 189.5 mmol) was added followed by addition of MeI (11.8 mL, 189.58 mmol) and reaction mass was stirred at 25° C. for 16h. Reaction mass was quenched with water and extracted with ethyl acetate. The separated organic layer was washed with brine solution, dried over anhydrous sodium sulfate and evaporated under reduced pressure. The crude material obtained was purified by normal silica column using 0-8% ethyl acetate in hexane to get methyl 2-[(4-bromo-2-chloro-6-formylphenyl)sulfanyl]pyridine-3-carboxylate (12 g, 49%) as a yellow solid.

To a stirred solution of methyl 2-[(4-bromo-2-chloro-6-formylphenyl)sulfanyl]pyridine-3-carboxylate (15 g, 38.9 mmol) in THF (80 mL) were added 2-methylpropane-2-sulfinamide (4.7 g, 38.9 mmol), Ti(OEt)$_4$ (40.7 mL, 194.3 mmol) and reaction mass was heated to 70° C. for 2h. The reaction mass was quenched with saturated sodium chloride solution, solid obtained was filtered through celite pad and washed with ethyl acetate. The separated organic layer was dried over anhydrous sodium sulfate and concentrated under reduced pressure to afford ethyl 2-({4-bromo-2-chloro-6-[(1Z)-[(2-methylpropane-2-sulfinyl)imino]methyl]phenyl}sulfanyl)pyridine-3-carboxylate (17 g) which was directly used for next step without further purification. LC-MS: 502.7 [M+H]$^+$ To a stirred solution of ethyl 2-({4-bromo-2-chloro-6-[(1Z)-[(2-methylpropane-2-sulfinyl)imino]methyl]phenyl}sulfanyl)pyridine-3-carboxylate (17 g, 33.8 mmol) in THF (80 mL) was added LAH (2M in THF, 25.3 mL, 50.7 mmol) at 0° C. and reaction mass was stirred at 0° C. for 1 h. Reaction mixture was quenched with saturated sodium sulfate solution and extracted with ethyl acetate. The separated organic layer was washed with water, brine, dried over anhydrous sodium sulfate and evaporated under reduced pressure to get N-[(5-bromo-3-chloro-2-{3-(hydroxymethyl)pyridin-2-yl]sulfanyl}phenyl)methyl]-2-methylpropane-2-sulfinamide (16 g) as off-white solid. LC-MS: 464.8 [M+H]$^+$ To a stirred solution of compound N-[(5-bromo-3-chloro-2-{[3-(hydroxymethyl)pyridin-2-yl]sulfanyl}phenyl)methyl]-2-methylpropane-2-sulfinamide (6 g, 12.9 mmol) in DCM (60 mL) were added imidazole (2.6 g, 38.8 mmol) and TBDMSCl (2.9 g, 19.4 mmol) at 0° C. and stirred at 25° C. for 3h. Reaction mass was quenched with aq NaHCO$_3$ solution and extracted with ethyl acetate. The separated organic layer was washed with water, brine, dried over sodium sulfate and evaporated under reduced pressure. The crude thus obtained was purified by combiflash column chromatography using 5-20% ethyl acetate in hexane to get N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (6 g, 69%) as off white solid. LC-MS: 578.8 [M+H]$^+$ To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2 g, 3.5 mmol) in dioxan (20 mL) were added pyridine-3-boronic acid (553 mg, 4.5 mmol), Na$_2$CO$_3$ (1.1 g, 10.4 mmol), water (10 mL) and degassed for 10 min in argon atmosphere. Then to it was added Pd(PPh$_3$)$_4$ (200 mg, 0.17 mmol) and again degassed for 5 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under vacuum to get the crude which was purified by normal silica column using 5-80% ethyl acetate in hexane to get N-({2-[(3-{[(tert-butyldimethylsilyl)oxy]methyl}pyridin-2-yl)sulfanyl]-3-chloro-5-(pyridin-3-yl)phenyl}methyl)-2-methylpropane-2-sulfinamide (1.3 g, 65%) as yellow solid. LC-MS: 576.2 [M+H]$^+$ To a stirred solution of N-({2-[(3-{[(tert-butyldimethylsilyl)oxy]methyl}pyridin-2-yl)sulfanyl]-3-chloro-5-(pyridin-3-yl)phenyl}methyl)-2-methylpropane-2-sulfinamide (1.3 g, 2.2 mmol) in MeOH (20 mL), was added 4M HCl in dioxan (10 mL) at 0° C. and reaction mixture was stirred at 25° C. for 1 h. Reaction mass was evaporated under reduced pressure to get (2-{[2-(aminomethyl)-6-chloro-4-(pyridin-3-yl)phenyl]sulfanyl}pyridin-3-yl)methanol HCl salt (900 mg, crude) which was directly used for next step. LC-MS: 358.0 [M+H]$^+$ To a stirred suspension of (2-{[2-(aminomethyl)-6-chloro-4-(pyridin-3-yl)phenyl]sulfanyl}pyridin-3-yl)methanol HCl salt (900 mg, 2.3 mmol) in 5% NaHCO$_3$ (20 mL) was added Fmoc-OSU (769 mg, 2.3 mmol) in acetonitrile (30 mL) at 25° C. and reaction mass was stirred at the same temperature for 2h. Then reaction mass was diluted with water and extracted with ethyl acetate. The separated organic layer was washed with brine, dried over sodium sulfate and evaporated under reduced pressure to get 9H-fluoren-9-ylmethyl N-[(3-chloro-2-{[3-(hydroxymethyl)pyridin-2-yl]sulfanyl}-5-(pyridin-3-yl)phenyl)methyl]carbamate (1.2 g, crude) as off white solid. LC-MS: 580.0 [M+H]$^+$ To a stirred solution of 9H-fluoren-9-ylmethyl N-[(3-chloro-2-{[3-(hydroxymethyl)pyridin-2-yl]sulfanyl}-5-(pyridin-3-yl)phenyl)methyl]carbamate (1.2 g, 2.1 mmol) in DCM:THF (1:1, 40 mL) was added MnO$_2$ (3.6 g, 41.4 mmol) and reaction mass was stirred at 25° C. for 2 h. The reaction mass was filtered through celite pad; filtrate was evaporated under reduced pressure. The crude thus obtained was purified by normal silica column using 5-20% ethyl acetate in hexane to get 9H-fluoren-9-ylmethyl N-({3-chloro-2-[(3-formylpyridin-2-yl)sulfanyl]-5-(pyridin-3-yl)phenyl}methyl)carbamate (700 mg, 53%, 3 steps) as off white solid with 93.6% purity. LC-MS: 577.9 [M+H]$^+$ 1H NMR (400 MHz, DMSO-d6): δ 4.21 (1H, d, J=7.0 Hz), 4.28 (2H, d, J=6.9 Hz), 4.37 (2H, d, J=5.5 Hz), 7.25 (2H, t, J=7.4 Hz), 7.33-7.44 (3H, m), 7.55 (1H, dd, J=7.7, 4.9 Hz), 7.67 (2H, d, J=7.6 Hz), 7.73 (1H, s), 7.87 (2H, d, J=7.8 Hz), 7.96 (1H, s), 8.15 (1H, d, J=7.2 Hz), 8.38 (1H, d, J=6.7 Hz), 8.45 (1H, d, J=3.3 Hz), 8.67 (1H, d, J=3.9 Hz), 8.98 (1H, s), 10.22 (1H, s).

Intermediate 66

9H-fluoren-9-ylmethyl N-({3-chloro-2-[(3-form-ylpyridin-2-yl)sulfanyl]-5-(pyridin-4-yl)phenyl}methyl)carbamate

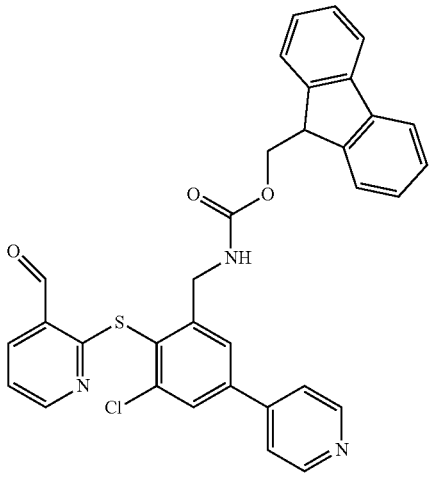 [SMILES: O=Cc1cccnc1Sc1c(Cl)cc(-c2ccncc2)cc1CNC(=O)OCC1c2ccccc2-c2ccccc21]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2 g, 3.5 mmol) in dioxan (20 mL) were added pyridine-4-boronic acid (553 mg, 4.5 mmol), Na$_2$CO$_3$ (1.1 g, 10.4 mmol), water (10 mL) and degassed for 10 min in argon atmosphere. Then to it was added Pd(PPh$_3$)$_4$ (200 mg, 0.17 mmol) and again degassed for 5 min. The reaction mass was heated to 120° C. for 16 h. Reaction mixture was then cooled to 25° C., filtered through celite pad, washed with EtOAc. The separated organic layer was washed with brine, dried over sodium sulfate and concentrated under vacuum to get the crude which was purified by normal silica column using 5-80% ethyl acetate in hexane to get N-({2-[(3-{[(tert-butyldimethylsilyl)oxy]methyl}pyridin-2-yl)sulfanyl]-3-chloro-5-(pyridin-4-yl)phenyl}methyl)-2-methylpropane-2-sulfinamide (1.2 g, 60%) as yellow solid. LC-MS: 576.1 [M+H]$^+$ To a stirred solution of N-({2-[(3-{[(tert-butyldimethylsilyl)oxy]methyl}pyridin-2-yl)sulfanyl]-3-chloro-5-(pyridin-4-yl)phenyl}methyl)-2-methylpropane-2-sulfinamide (1,2 g, 2.1 mmol) in MeOH (20 mL), was added 4M HCl in dioxan (10 mL) at 0° C. and reaction mixture was stirred at 25° C. for 1 h. Reaction mass was evaporated under reduced pressure to get (2-{[2-(aminomethyl)-6-chloro-4-(pyridin-4-yl)phenyl]sulfanyl}pyridin-3-yl)methanol HCl salt (850 mg, crude) which was directly used for next step. LC-MS: 357.8 [M+H]$^+$ To a stirred suspension of (2-{[2-(aminomethyl)-6-chloro-4-(pyridin-4-yl)phenyl]sulfanyl}pyridin-3-yl)methanol HCl salt (850 mg, 2.1 mmol) in 5% NaHCO$_3$ (20 mL) was added Fmoc-OSU (726 mg, 2.1 mmol) in acetonitrile (30 mL) at 25° C. and reaction mass was stirred at the same temperature for 2h. Then reaction mass was diluted with water and extracted with ethyl acetate. The separated organic layer was washed with brine, dried over sodium sulfate and evaporated under reduced pressure to get 9H-fluoren-9-ylmethyl N-[(3-chloro-2-{[3-(hydroxymethyl)pyridin-2-yl]sulfanyl}-5-(pyridin-4-yl)phenyl)methyl]carbamate (1.1 g, crude) as off white solid. LC-MS: 579.9 [M+H]$^+$ To a stirred solution of 9H-fluoren-9-ylmethyl N-[(3-chloro-2-{[3-(hydroxymethyl)pyridin-2-yl]sulfanyl}-5-(pyridin-4-yl)phenyl)methyl]carbamate (1.1 g, 1.9 mmol) in DCM:THF (1:1, 40 mL) was added MnO$_2$ (3.3 g, 37.9 mmol) and reaction mass was stirred at 25° C. for 2 h. The reaction mass was filtered through celite pad; filtrate was evaporated under reduced pressure. The crude material obtained was purified by normal silica column using 5-20% ethyl acetate in hexane to get 9H-fluoren-9-ylmethyl N-({3-chloro-2-[(3-formylpyridin-2-yl)sulfanyl]-5-(pyridin-4-yl)phenyl}methyl)carbamate (650 mg) as off white solid with 95% LCMS purity. LC-MS: 578.0 [M+H]$^+$ 1H NMR (400 MHz, DMSO-d6): δ 4.16-4.25 (1H, m), 4.28 (2H, d, J=6.5 Hz), 4.34-4.40 (2H, m), 7.26 (2H, t, J=7.4 Hz), 7.39 (3H, t, J=7.3 Hz), 7.67 (2H, d, J=7.3 Hz), 7.75 (3H, d, J=5.3 Hz), 7.88 (2H, d, J=7.4 Hz), 8.01 (1H, s), 8.38 (1H, d, J=6.9 Hz), 8.44 (1H, d, J=4.6 Hz), 8.69 (2H, d, J=5.6 Hz), 10.22 (1H, s).

Intermediate 67

9H-fluoren-9-ylmethyl N-({3-chloro-2-[(3-form-ylpyridin-2-yl)sulfanyl]-5-(2-methoxypyridin-4-yl)phenyl}methyl)carbamate

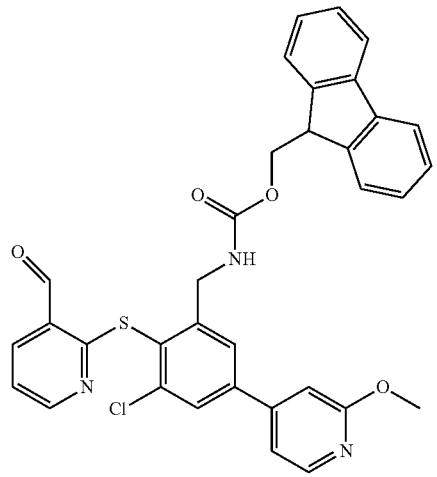 [SMILES: COc1cc(-c2cc(Cl)c(Sc3ncccc3C=O)c(CNC(=O)OCC3c4ccccc4-c4ccccc43)c2)ccn1]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (10 mL) were added (2-methoxypyridin-4-yl)boronic acid (516 mg, 3.4 mmol), Na$_2$CO$_3$ (825 mg, 7.8 mmol), water (5 mL) and degassed for 10 min in argon atmosphere. Then to it was added Pd(PPh$_3$)$_4$ (150 mg, 0.13 mmol) and again degassed for 5 min. The reaction mass was heated to 120° C. for 16 h. Reaction mixture was then cooled to 25° C., filtered through celite pad and washed with EtOAc. The separated organic layer was washed with brine solution, dried over sodium sulfate and concentrated under reduced pressure to get N-({2-[(3-{[(tert-butyldimethylsilyl)oxy]methyl}pyridin-2-yl)sulfanyl]-3-chloro-5-(2-methoxypyridin-4-yl)phenyl}methyl)-2-methylpropane-2-sulfinamide (1.5 g) as yellow solid. LC-MS: 605.8 [M+H]$^+$ To a stirred solution of N-({2-[(3-{[(tert-butyldimethylsilyl)oxy]methyl}pyridin-2-yl)sulfanyl]-3-chloro-5-(2-methoxypyridin-4-yl)phenyl}methyl)-2-methylpropane-2-sulfinamide (1.5 g, 2.5 mmol) in MeOH (30 mL), was added 4M HCl in dioxan (15 mL) at 0° C. and reaction mixture was stirred at 25° C. for 2h. Reaction mass was evaporated under reduced pressure to get (2-{[2-(aminomethyl)-6-chloro-4-(2-methoxypyridin-4-yl)phenyl]sulfanyl}pyridin-3-yl)methanol HCl salt (950 mg) which was directly used for next step. LC-MS: 388.8 [M+H]+

To a stirred suspension of (2-{[2-(aminomethyl)-6-chloro-4-(2-methoxypyridin-4-yl)phenyl]sulfanyl}pyridin-3-yl)methanol HCl salt (950 mg, 2.2 mmol) in 5% NaHCO$_3$ (20 mL) was added Fmoc-OSU (754 mg, 2.2 mmol) in acetonitrile (30 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(2-methoxypyridin-4-yl)phenyl)methyl]carbamate (1.3 g) as off white solid. LC-MS: 609.9 [M+H]+

To a stirred solution of 9H-fluoren-9-ylmethyl N-[(3-chloro-2-{[3-(hydroxymethyl)pyridin-2-yl]sulfanyl}-5-(2-methoxypyridin-4-yl)phenyl)methyl]carbamate (1.3 g, 2.1 mmol) in DCM:THF (1:1, 40 mL) was added MnO$_2$ (3.7 g, 42.6 mmol) and reaction mass was stirred at 25° C. for 2 h. The reaction mass was filtered through celite pad and the filtrate was evaporated under reduced pressure. The crude material obtained was purified by normal silica column using 5-20% ethyl acetate in hexane to get 9H-fluoren-9-ylmethyl N-({3-chloro-2-[(3-formylpyridin-2-yl)sulfanyl]-5-(2-methoxypyridin-4-yl)phenyl}methyl)carbamate (650 mg) as off white solid with 96.9% LCMS purity. LC-MS: 608 [M+H]+

1H NMR (400 MHz, DMSO-d6): δ 3.92 (3H, s), 4.21 (1H, d, J=6.3 Hz), 4.27 (2H, d, J=6.7 Hz), 4.36 (2H, d, J=5.8 Hz), 7.20 (1H, s), 7.26 (2H, t, J=7.3 Hz), 7.37 (4H, dd, J=16.2, 7.0 Hz), 7.67 (2H, d, J=7.3 Hz), 7.76 (1H, s), 7.84-7.93 (3H, m), 7.98 (1H, s), 8.28 (1H, d, J=5.3 Hz), 8.38 (1H, d, J=7.8 Hz), 8.44 (1H, d, J=5.6 Hz), 10.21 (1H, s).

Intermediate 68

(9H-Fluoren-9-yl)methyl 3,6-dichloro-2-((2-formylpyridin-3-yl)thio)benzylcarbamate

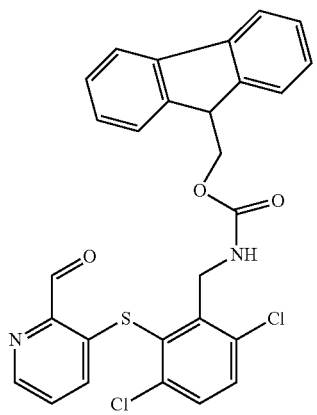 [SMILES: O=Cc1ncccc1Sc1c(Cl)ccc(Cl)c1CNC(=O)OCC1c2ccccc2-c2ccccc21]

This material was prepared in analogy to Intermediate 63 starting from 3,6-dichloro-2-fluorobenzaldehyde and 3-mercaptopicolinic acid up to the second last step. Last step: A mixture of (9H-fluoren-9-yl)methyl 3,6-dichloro-2-((2-(hydroxymethyl)pyridin-3-yl)thio)benzylcarbamate (18 mg, 33.5 μmol, Eq: 1) and manganese dioxide (58.2 mg, 670 μmol, Eq: 20) in THF (335 μl) and DCM (335 μl) was stirred at room temperature for 1 h. The resulting mixture was filtered through glass fiber paper and washed with DCM. The filtrate was concentrated in vacuo. The title compound was obtained as white solid. MS ESI (m/z): 535.2 [(M+H)+]

Intermediate 69

9H-fluoren-9-ylmethyl N-({3-chloro-2-[(3-formylpyridin-2-yl)sulfanyl]-5-(2-methylpyridin-4-yl)phenyl}methyl)carbamate

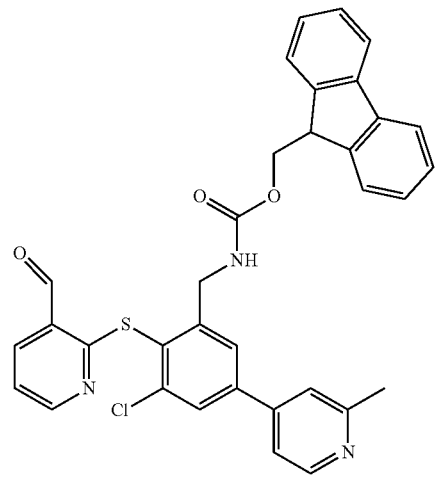 [SMILES: Cc1cc(-c2cc(Cl)c(Sc3ncccc3C=O)c(CNC(=O)OCC3c4ccccc4-c4ccccc43)c2)ccn1]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (10 mL) were added (2-methylpyridin-4-yl)boronic acid (462 mg, 3.4 mmol), Na$_2$CO$_3$ (825 mg, 7.8 mmol), water (5 mL) and degassed for 10 min in argon atmosphere. Then it was added Pd(PPh$_3$)$_4$ (150 mg, 0.13 mmol) and again degassed for 5 min. The reaction mass was heated to 120° C. for 16 h. Reaction mixture was then cooled to 25° C., filtered through celite pad and washed with EtOAc. The separated organic layer was washed with brine, dried over sodium sulfate and concentrated under reduced pressure to get N-({2-[(3-{[(tert-butyldimethylsilyl)oxy]methyl}pyridin-2-yl)sulfanyl]-3-chloro-5-(2-methylpyridin-4-yl)phenyl}methyl)-2-methylpropane-2-sulfinamide (1.5 g, crude) as yellow solid. LC-MS: 589.8 [M+H]+

To a stirred solution of N-({2-[(3-{[(tert-butyldimethylsilyl)oxy]methyl}pyridin-2-yl)sulfanyl]-3-chloro-5-(2-methylpyridin-4-yl)phenyl}methyl)-2-methylpropane-2-sulfinamide (1.5 g, 2.5 mmol) in MeOH (30 mL), was added 4M HCl in dioxan (15 mL) at 0° C. and reaction mixture was stirred at 25° C. for 2h. Reaction mass was evaporated under reduced pressure to get (2-{[2-(aminomethyl)-6-chloro-4-(2-methylpyridin-4-yl)phenyl]sulfanyl}pyridin-3-yl)methanol HCl salt (940 mg) which was directly used for next step. LC-MS: 371.8 [M+H]+

To a stirred suspension of (2-{[2-(aminomethyl)-6-chloro-4-(2-methylpyridin-4-yl)phenyl]sulfanyl}pyridin-3-yl)methanol HCl salt (940 mg, 2.3 mmol) in 5% NaHCO₃ (20 mL) was added Fmoc-OSU (776 mg, 2.2 mmol) in acetonitrile (30 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(2-methylpyridin-4-yl)phenyl)methyl]carbamate (1.3 g, crude) as off white solid. LC-MS: 593.8 [M+H]⁺

To a stirred solution of 9H-fluoren-9-ylmethyl N-[(3-chloro-2-{[3-(hydroxymethyl)pyridin-2-yl]sulfanyl}-5-(2-methylpyridin-4-yl)phenyl)methyl]carbamate (1.3 g, 2.19 mmol) in DCM/THF (1:1, 40 mL) was added MnO₂ (3.8 g, 43.8 mmol) and reaction mass was stirred at 25° C. for 2 h. The reaction mass was filtered through celite pad; filtrate was evaporated under reduced pressure. The crude thus obtained was purified by normal silica column using 5-20% ethyl acetate in hexane to get 9H-fluoren-9-ylmethyl N-({3-chloro-2-[(3-formylpyridin-2-yl)sulfanyl]-5-(2-methylpyridin-4-yl)phenyl}methyl)carbamate (600 mg) as off white solid with 86% LCMS purity. LC-MS: 592.0 [M+H]⁺

1H NMR (400 MHz, DMSO-d6): δ 2.50 (3H, s), 4.21 (1H, d, J=6.7 Hz), 4.28 (2H, d, J=6.6 Hz), 4.37 (2H, d, J=5.1 Hz), 7.25 (2H, t, J=7.5 Hz), 7.34-7.43 (3H, m), 7.50-7.60 (3H, m), 7.57-7.71 (6H, m), 7.76 (1H, s), 7.84-7.95 (3H, m), 7.98 (1H, s), 8.39 (1H, d, J=7.5 Hz), 8.44 (1H, d, J=3.3 Hz), 8.55 (1H, d, J=5.2 Hz), 10.22 (1H, s).

Intermediate 70

9H-fluoren-9-ylmethyl N-{[5-(6-{[(tert-butoxy)carbonyl]amino}pyridin-3-yl)-3-chloro-2-[(3-formylpyridin-2-yl)sulfanyl]phenyl]methyl}carbamate

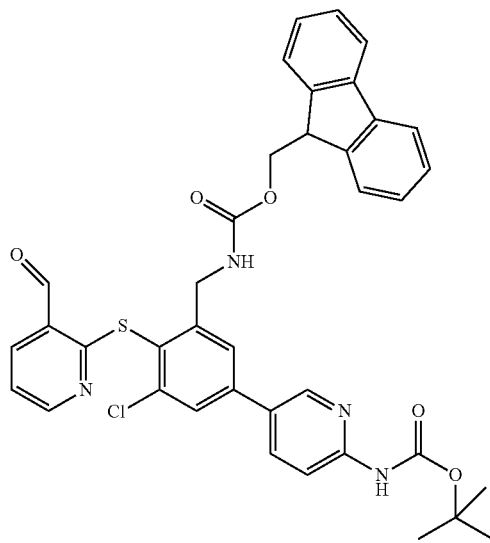 [SMILES: CC(C)(C)OC(=O)Nc1ccc(-c2cc(Cl)c(Sc3ncccc3C=O)c(CNC(=O)OCC3c4ccccc4-c4ccccc43)c2)cn1]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (600 mg, 1.0 mmol) in dioxan (5 mL) were added 5-(tetramethyl-1,3,2-dioxaborolan-2-yl)pyridin-2-amine (296 mg, 1.3 mmol), Na₂CO₃ (330 mg, 3.1 mmol), water (2.5 mL) and degassed for 10 min in argon atmosphere. Then to it was added Pd(PPh₃)₄ (60 mg, 0.05 mmol) and again degassed for 5 min. The reaction mass was heated to 120° C. for 16 h. Reaction mixture was then cooled to 25° C., filtered through celite pad and washed with EtOAc. The separated organic layer was washed with brine, dried over sodium sulfate and concentrated under reduced pressure. The crude thus obtained was purified by normal silica column using 10-70% ethyl acetate in hexane to get N-{[5-(6-aminopyridin-3-yl)-2-[(3-{[(tert-butyldimethylsilyl)oxy]methyl}pyridin-2-yl)sulfanyl]-3-chlorophenyl]methyl}-2-methylpropane-2-sulfinamide (500 mg) as yellow solid. LC-MS: 590.8 [M+H]⁺

To a stirred solution of N-{[5-(6-aminopyridin-3-yl)-2-[(3-{[(tert-butyldimethylsilyl)oxy]methyl}pyridin-2-yl)sulfanyl]-3-chlorophenyl]methyl}-2-methylpropane-2-sulfinamide (500 mg, 1.1 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(aminomethyl)-4-(6-aminopyridin-3-yl)-6-chlorophenyl]sulfanyl}pyridin-3-yl)methanol HCl salt (450 mg) which was directly used for next step. LC-MS: 372.8 [M+H]⁺

To a stirred suspension of (2-{[2-(aminomethyl)-4-(6-aminopyridin-3-yl)-6-chlorophenyl]sulfanyl}pyridin-3-yl)methanol HCl salt (450 mg, 1.1 mmol) in 5% NaHCO₃ (10 mL) was added Fmoc-OSU (370 mg, 1.1 mmol) in acetonitrile (15 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-{[5-(6-aminopyridin-3-yl)-3-chloro-2-{[3-(hydroxymethyl)pyridin-2-yl]sulfanyl}phenyl]methyl}carbamate (600 mg) as off white solid. LC-MS: 594.9 [M+H]⁺

To a stirred solution of 9H-fluoren-9-ylmethyl N-{[5-(6-aminopyridin-3-yl)-3-chloro-2-{[3-(hydroxymethyl)pyridin-2-yl]sulfanyl}phenyl]methyl}carbamate (550 mg, 0.9 mmol) in tertiary butanol (30 mL) was added boc anhydride (242 mg, 1.1 mmol) and reaction mass was stirred at 25° C. for 16h. Reaction mass was evaporated under reduced pressure and crude thus obtained was purified by normal silica column using 5-40% ethyl acetate in hexane to get 9H-fluoren-9-ylmethyl N-{[5-(6-{[(tert-butoxy)carbonyl]amino}pyridin-3-yl)-3-chloro-2-{[3-(hydroxymethyl)pyridin-2-yl]sulfanyl}phenyl]methyl}carbamate (330 mg) as yellow solid. LC-MS: 695.2 [M+H]⁺

To a stirred solution of 9H-fluoren-9-ylmethyl N-{[5-(6-{[(tert-butoxy)carbonyl]amino}pyridin-3-yl)-3-chloro-2-{[3-(hydroxymethyl)pyridin-2-yl]sulfanyl}phenyl]methyl}carbamate (350 mg, 0.50 mmol) in DCM:THF (1:1, 10 mL) was added MnO₂ (875 mg, 10.1 mmol) and reaction mass was stirred at 25° C. for 2 h. The reaction mass was filtered through celite pad and the filtrate was evaporated under reduced pressure. The crude thus obtained was purified by normal silica column using 5-30% ethyl acetate in hexane to get 9H-fluoren-9-ylmethyl N-{[5-(6-{[(tert-butoxy)carbonyl]amino}pyridin-3-yl)-3-chloro-2-[(3-formylpyridin-2-yl)sulfanyl]phenyl]methyl}carbamate (220 mg, 63%) as off white solid with 94.7% LCMS purity. LC-MS: 693.1 [M+H]⁺

1H NMR (400 MHz, DMSO-d6): δ 1.50 (9H, s), 4.21 (1H, d, J=6.9 Hz), 4.27 (2H, d, J=7.7 Hz), 4.35 (2H, d, J=5.3 Hz), 7.27 (2H, t, J=7.8 Hz), 7.38 (3H, t, J=7.1 Hz), 7.67 (3H, d, J=7.8 Hz), 7.85-7.92 (5H, m), 8.11 (1H, d, J=9.5 Hz), 8.33-8.41 (1H, m), 8.44 (1H, d, J=4.2 Hz), 8.66 (1H, s), 10.02 (1H, s), 10.21 (1H, s).

Intermediate 71

(9H-Fluoren-9-yl)methyl 3,6-dichloro-2-((3-formylpyrazin-2-yl)thio)benzylcarbamate

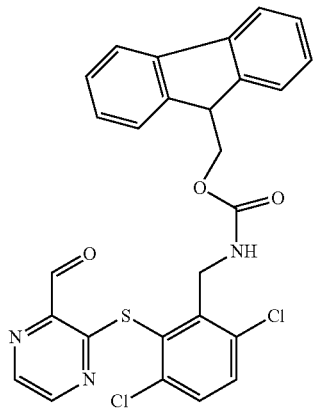 [SMILES: O=Cc1nccnc1Sc1c(Cl)ccc(Cl)c1CNC(=O)OCC1c2ccccc2-c2ccccc21]

This material was prepared in analogy to Intermediate 68 starting from 3,6-dichloro-2-fluorobenzaldehyde and 3-mercaptopyrazine-2-carboxylic acid. The title compound was obtained as light yellow foam (500 mg). MS ESI (m/z): 536.2 [(M+H)$^+$]

Intermediate 72

(9H-Fluoren-9-yl)methyl 3-chloro-2-((2-formylpyridin-3-yl)thio)-6-(trifluoromethyl)benzylcarbamate

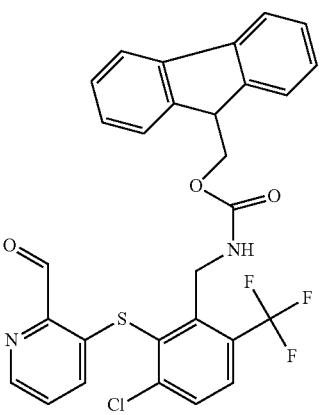 [SMILES: O=Cc1ncccc1Sc1c(Cl)ccc(C(F)(F)F)c1CNC(=O)OCC1c2ccccc2-c2ccccc21]

This material was prepared in analogy to Intermediate 63 starting from 3-chloro-2-fluoro-6-(trifluoromethyl)benzaldehyde and 3-mercaptopicolinic acid. The title compound was obtained as light brown solid (618 mg). MS ESI (m/z): 569.1 [(M+H)$^+$]

Intermediate 73

(9H-Fluoren-9-yl)methyl 3-chloro-2-((2-formylpyridin-3-yl)thio)-5-(trifluoromethyl)benzylcarbamate

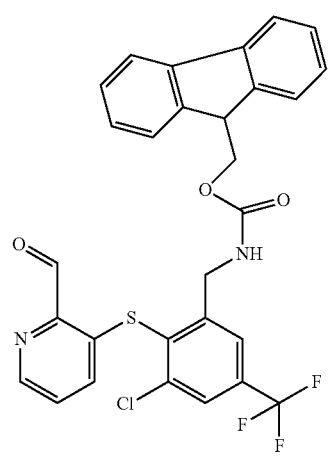 [SMILES: O=Cc1ncccc1Sc1c(Cl)cc(C(F)(F)F)cc1CNC(=O)OCC1c2ccccc2-c2ccccc21]

This material was prepared in analogy to Intermediate 63 starting from 3-chloro-2-fluoro-5-(trifluoromethyl)benzaldehyde and 3-mercaptopicolinic acid. The title compound was obtained as brown solid (183 mg). MS ESI (m/z): 569.1 [(M+H)$^+$]

Intermediate 74

(9H-Fluoren-9-yl)methyl ((2-chloro-3-((2-formylphenyl)thio)pyridin-4-yl)methyl)carbamate

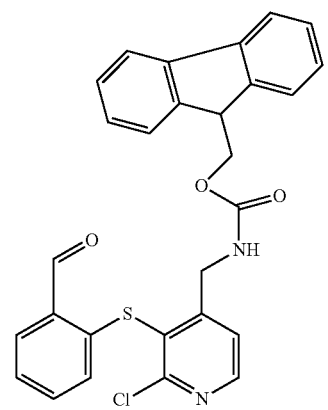 [SMILES: O=Cc1ccccc1Sc1c(CNC(=O)OCC2c3ccccc3-c3ccccc32)ccnc1Cl]

To a mixture of 2-mercaptobenzoate (2 g, 1.64 ml, 11.5 mmol, Eq: 1) in DMF (19.2 ml) were added 2-chloro-3-fluoroisonicotinaldehyde (1.86 g, 11.6 mmol, Eq: 1.01) und K₂CO₃ (3.17 g, 23 mmol, Eq: 1.99) and the mixture stirred at room temperature over night. The reaction mixture was diluted with water and extracted with EtOAc. The organic layers were washed with brine, combined, dried over Na₂SO₄, filtered and concentrated in vacuo. The crude material was purified by silica gel chromatography using heptane/EtOAc as solvent. Methyl 2-((2-chloro-4-formylpyridin-3-yl)thio)benzoate was obtained as yellow solid (2.12 g) and used without further purification. MS ESI (m/z): 308.1 [(M+H)⁺]

A mixture of methyl 2-((2-chloro-4-formylpyridin-3-yl)thio)benzoate (1.28 g, 4.16 mmol, Eq: 1), sodium acetate (478 mg, 5.82 mmol, Eq: 1.4) and hydroxylamine hydrochloride (376 mg, 5.41 mmol, Eq: 1.3) in acetic acid (16.6 ml) was stirred at room temperature for 30 min. Then zinc (1.36 g, 20.8 mmol, Eq: 5) was added and the reaction mixture was stirred at room temperature for 30 min. The reaction mixture was quenched with water and extracted with EtOAc. The organic layers were dried over Na₂SO₄ and concentrated in vacuo. Methyl 2-((4-(aminomethyl)-2-chloropyridin-3-yl)thio)benzoate was obtained as white solid (935 mg) and was used without further purification. MS ESI (m/z): 309.1 [(M+H)⁺]

To a mixture of methyl 2-((4-(aminomethyl)-2-chloropyridin-3-yl)thio)benzoate (1 g, 3.24 mmol, Eq: 1) and sodium bicarbonate (1.36 g, 16.2 mmol, Eq: 5) in THF (10.8 ml) and water (10.8 ml) was added Fmoc-OSu (1.09 g, 3.24 mmol, Eq: 1) and the reaction mixture stirred at room temperature for 2 h. The reaction mixture was filtered through sintered glass and washed with diisopropylether, the solid collected and dried. Methyl 2-((4-(((((9H-fluoren-9-yl)methoxy)carbonyl)amino)methyl)-2-chloropyridin-3-yl)thio)benzoate was obtained as white solid (1.9 g) and was used without further purification. MS ESI (m/z): 531.2 [(M+H)⁺], To a suspension of methyl 2-((4-(((((9H-fluoren-9-yl)methoxy)carbonyl)amino)methyl)-2-chloropyridin-3-yl)thio)benzoate (1.9 g, 3.58 mmol, Eq: 1) in tetrahydrofuran (24.6 ml) was added LiBH₄ (390 mg, 17.9 mmol, Eq: 5) and the reaction mixture was stirred at room temperature for 5 h. The reaction was quenched with sat. aq. NH₄Cl sit and diluted with water. The mixture was extracted with EtOAc. The combined organic layers were dried over Na₂SO₄ and concentrated in vacuo. The crude material was purified by silica gel chromatography using heptane/EtOAc as eluent. (9H-fluoren-9-yl)methyl ((2-chloro-3-((2-(hydroxymethyl)phenyl)thio)pyridin-4-yl)methyl)carbamate was obtained as white foam (716 mg) and was used without further purification. MS ESI (m/z): 503.2 [(M+H)⁺], A mixture of (9H-fluoren-9-yl)methyl ((2-chloro-3-((2-(hydroxymethyl)phenyl)thio)pyridin-4-yl)methyl)carbamate (280 mg, 557 μmol, Eq: 1) and manganese dioxide (484 mg, 5.57 mmol, Eq: 10) in THF (3.98 ml) and DCM (3.98 ml) was stirred at room temperature for 3 h. The reaction mixture was filtered through sintered glass and concentrated in vacuo. The title compound was obtained as white solid (265 mg). MS ESI (m/z): 501.2 [(M+H)⁺]

Intermediate 75

9H-fluoren-9-ylmethyl N-({3-chloro-2-[(3-formylpyridin-2-yl)sulfanyl]-5-[2-(4-methylpiperazin-1-yl)pyridin-4-yl]phenyl}methyl)carbamate

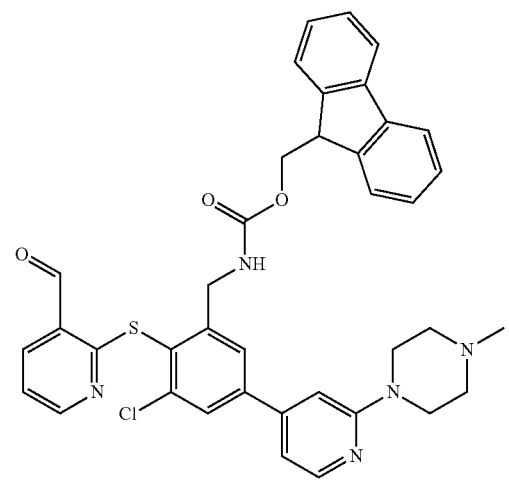 [SMILES: CN1CCN(c2cc(-c3cc(Cl)c(Sc4ncccc4C=O)c(CNC(=O)OCC4c5ccccc5-c5ccccc54)c3)ccn2)CC1]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (10 mL) were added [2-(4-methylpiperazin-1-yl)pyridin-4-yl]boronic acid (746 mg, 3.4 mmol), Na₂CO₃ (825 mg, 7.8 mmol), water (5 mL) and degassed for 10 min in argon atmosphere. Then it was added Pd(PPh₃)₄ (150 mg, 0.13 mmol) and again degassed for 5 min. The reaction mass was heated to 120° C. for 16 h. Reaction mixture was then cooled to 25° C., filtered through celite pad and washed with ethyl acetate. The separated organic layer was washed with brine, dried over sodium sulfate and concentrated under reduced pressure to get N-({2-[(3-{[(tert-butyldimethylsilyl)oxy]methyl}pyridin-2-yl)sulfanyl]-3-chloro-5-[2-(4-methylpiperazin-1-yl)pyridin-4-yl]phenyl}methyl)-2-methylpropane-2-sulfinamide (1.6 g) as yellow solid. LC-MS: 674.1 [M+H]⁺

To a stirred solution of N-({2-[(3-{[(tert-butyldimethylsilyl)oxy]methyl}pyridin-2-yl)sulfanyl]-3-chloro-5-[2-(4-methylpiperazin-1-yl)pyridin-4-yl]phenyl}methyl)-2-methylpropane-2-sulfinamide (1.6 g, 2.4 mmol) in MeOH (30 mL), was added 4M HCl in dioxan (15 mL) at 0° C. and reaction mixture was stirred at 25° C. for 2h. Reaction mass was evaporated under reduced pressure to get (2-{[2-(aminomethyl)-6-chloro-4-[2-(4-methylpiperazin-1-yl)pyridin-4-yl]phenyl]sulfanyl}pyridin-3-yl) methanol HCl salt (1 g) which was directly used for next step. LC-MS: 456.1 [M+H]⁺

To a stirred suspension of (2-{[2-(aminomethyl)-6-chloro-4-[2-(4-methylpiperazin-1-yl)pyridin-4-yl]phenyl]sulfanyl}pyridin-3-yl) methanol HCl salt (1 g, 2.0 mmol) in 5% NaHCO₃ (20 mL) was added Fmoc-OSU (685 mg, 2.0 mmol) in acetonitrile (30 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-[2-(4-methylpiperazin-1-yl)pyridin-4-yl]phenyl)methyl]carbamate (1.3 g) as off white solid. LC-MS: 678.1 [M+H]$^+$ To a stirred solution of 9H-fluoren-9-ylmethyl N-[(3-chloro-2-{[3-(hydroxymethyl)pyridin-2-yl]sulfanyl}-5-[2-(4-methylpiperazin-1-yl)pyridin-4-yl]phenyl)methyl]carbamate (1.0 g, 1.5 mmol) in DCM:THF (1:1, 20 mL) was added MnO$_2$ (2.5 g, 29.5 mmol) and reaction mass was stirred at 25° C. for 2 h. The reaction mass was filtered through celite pad and the filtrate was evaporated under reduced pressure. The crude thus obtained was purified by normal silica column using 0-5% methanol in DCM to get 9H-fluoren-9-ylmethyl N-({3-chloro-2-[(3-formylpyridin-2-yl)sulfanyl]-5-[2-(4-methylpiperazin-1-yl)pyridin-4-yl]phenyl}methyl)carbamate (600 mg) as off white solid with 96.5% purity. LC-MS: 675.8 [M+H]$^+$ 1H NMR (400 MHz, DMSO-d6): δ 2.22 (3H, s), 2.39 (4H, s), 3.56 (4H, s), 4.26 (3H, d, J=6.0 Hz), 4.36 (2H, d, J=4.9 Hz), 6.95 (1H, d, J=5.4 Hz), 7.11 (1H, s), 7.26 (2H, t, J=5.9 Hz), 7.34-7.42 (3H, m), 7.67 (2H, d, J=7.3 Hz), 7.72 (1H, s), 7.88 (3H, d, J=7.8 Hz), 7.98 (1H, s), 8.20 (1H, d, J=4.9 Hz), 8.38 (1H, d, J=6.9 Hz), 8.44 (1H, d, J=2.8 Hz), 10.22 (1H, s).

Intermediate 76

3-chloro-5-({[(9H-fluoren-9-ylmethoxy)carbonyl]amino}methyl)-4-[(3-formylpyridin-2-yl)sulfanyl]phenyl]boronic Acid

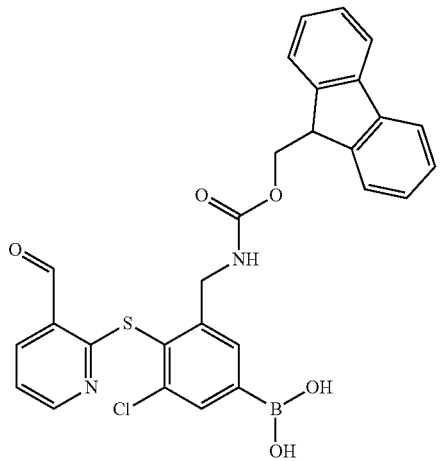 [SMILES: O=Cc1cccnc1Sc1c(Cl)cc(B(O)O)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (12.0 ml) were added bispinacolate diborane (1.6 g, 6.2 mmol) and potassium acetate (1.0 g, 10.4 mmol) and degassed in argon atmosphere for 5 min. Then to it was added PdCl2(dppf) (424 mg, 0.52 mmol) and heated to 110° C. for 16h. Reaction mass was filtered through celite pad and the filtrate was evaporated under reduced pressure and the filtrate was then extracted with ethyl acetate. The separated organic layer was washed with brine solution, dried over sodium sulfate and evaporated under reduced pressure to get N-({2-[(3-{[(tert-butyldimethylsilyl)oxy]methyl}pyridin-2-yl)sulfanyl]-3-chloro-5-(4,4,5,5-tetramethyl-1,3,2-dioxaborolan-2-yl)phenyl}methyl)-2-methylpropane-2-sulfinamide (1.6 g) which was directly used for next step. LC-MS: 625.3 [M+H]$^+$ To a stirred solution N-({2-[(3-{[(tert-butyldimethylsilyl)oxy]methyl}pyridin-2-yl)sulfanyl]-3-chloro-5-(4,4,5,5-tetramethyl-1,3,2-dioxaborolan-2-yl)phenyl}methyl)-2-methylpropane-2-sulfinamide (1.6 g, 2.6 mmol) in MeOH (24 mL), was added 4M HCl in dioxan (12 mL) at 0° C. and reaction mixture was stirred at 25° C. for 2h. Reaction mass was evaporated under reduced pressure to get (2-{[2-(aminomethyl)-6-chloro-4-(4,4,5,5-tetramethyl-1,3,2-dioxaborolan-2-yl)phenyl]sulfanyl}pyridin-3-yl) methanol as HCl salt (1.6 g) which was directly used for next step. LC-MS: =407 [M+H]$^+$ To a stirred suspension of (2-{[2-(aminomethyl)-6-chloro-4-(4,4,5,5-tetramethyl-1,3,2-dioxaborolan-2-yl)phenyl]sulfanyl}pyridin-3-yl)methanol HCl salt (1.6 g, 3.9 mmol) in 5% NaHCO$_3$ (25 mL) was added Fmoc OSU (1.329 g, 3.9 mmol) in acetonitrile (25 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure to 9H-fluoren-9-ylmethyl N-[(3-chloro-2-{[3-(hydroxymethyl)pyridin-2-yl]sulfanyl}-5-(4,4,5,5-tetramethyl-1,3,2-dioxaborolan-2-yl)phenyl)methyl]carbamate (1.8 g) as brown sticky solid; which was used for next step without further purification. LC-MS: 629.1 [M+H]

To a stirred solution of 9H-fluoren-9-ylmethyl N-[(3-chloro-2-{[3-(hydroxymethyl)pyridin-2-yl]sulfanyl}-5-(4,4,5,5-tetramethyl-1,3,2-dioxaborolan-2-yl)phenyl)methyl]carbamate (1.0 g, 1.59 mmol) in DCM:THF (1:1, 20 mL) was added MnO$_2$ (3.74 g, 43 mmol) and reaction mass was stirred at 25° C. for 2 h. The reaction mass was filtered through celite pad and the filtrate was evaporated under reduced pressure. The crude thus obtained was purified by washing with ethyl acetate to get [3-chloro-5-({[(9H-fluoren-9-ylmethoxy)carbonyl]amino}methyl)-4-[(3-formylpyridin-2-yl)sulfanyl]phenyl]boronic acid (270 mg) as an off white sticky solid. LC-MS: 544.9 [M+H]$^+$ $^1$H-NMR: (400 MHz, DMSO-d6): δ 4.02-4.08 (2H, m), 4.15-4.22 (2H, m), 4.28-4.29 (2H, m) 7.27-7.32 (4H, m), 7.39-7.40 (2H, m), 7.57-7.69 (2H, m), 7.80-7.81 (2H, m), 7.85-7.95 (2H, m); 8.20-8.40 (m; 2H); 10.19 (1H, s).

Intermediate 77

(9H-Fluoren-9-yl)methyl 3-chloro-2-((4-formylpyridin-3-yl)thio)-6-(trifluoromethyl)benzylcarbamate

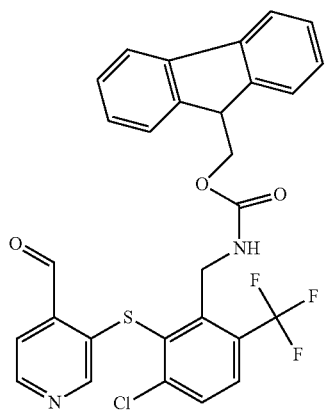 [SMILES: O=Cc1ccncc1Sc1c(Cl)ccc(C(F)(F)F)c1CNC(=O)OCC1c2ccccc2-c2ccccc21]

This material was prepared in analogy to Intermediate 63 starting from 3-chloro-2-fluoro-6-(trifluoromethyl)benzaldehyde and 3-mercaptoisonicotinic acid hydrochloride. Only the reduction step was carried out as follows:

To a solution of ethyl 3-((2-(((tert-butylsulfinyl)imino)methyl)-6-chloro-3-(trifluoromethyl)phenyl)thio)isonicotinate (295 mg, 598 μmol, Eq: 1) in DCM (6 ml) was added dropwise 1M DIBAL-H in THF (1.8 ml, 1.8 mmol, Eq: 3) at room temperature and stirred for 2 h. The reaction mixture was quenched at 0° C. with sat. aq. NH$_4$Cl slt., diluted with water and extracted with EtOAc. The combined organic layers were dried over Na2SO4, filtered and concentrated in vacuo. The title compound was obtained as light brown foam (183 mg). MS ESI (m/z): 569.1 [(M+H)$^+$]

Intermediate 78

(9H-Fluoren-9-yl)methyl 3-chloro-2-((4-formylpyridin-3-yl)thio)-5-(trifluoromethyl)benzylcarbamate

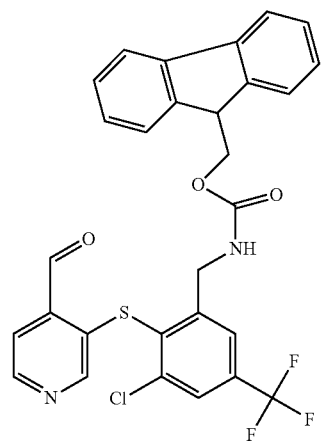 [SMILES: O=Cc1ccncc1Sc1c(Cl)cc(C(F)(F)F)cc1CNC(=O)OCC1c2ccccc2-c2ccccc21]

This material was prepared in analogy to Intermediate 77 starting from 3-chloro-2-fluoro-5-(trifluoromethyl)benzaldehyde and 3-mercaptoisonicotinic acid hydrochloride, except for the last step which was done in analogy to RO7117947-000. The title compound was obtained as white solid (110 mg). MS ESI (m/z): 569.1 [(M+H)$^+$]

Intermediate 79

9H-fluoren-9-ylmethyl N-[[3-chloro-2-[(3-formyl-2-pyridyl)sulfanyl]-4-phenyl-phenyl]methyl]carbamate

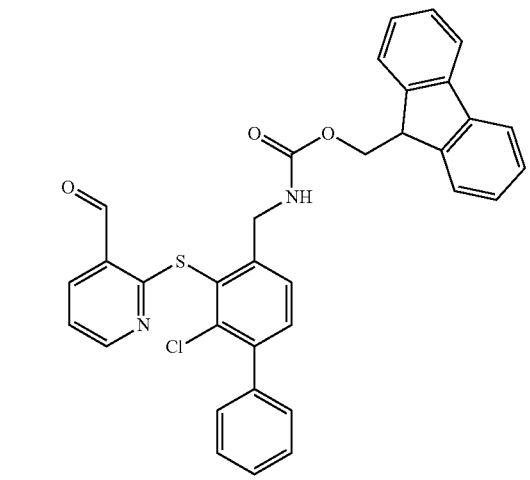 [SMILES: O=Cc1cccnc1Sc1c(CNC(=O)OCC2c3ccccc3-c3ccccc32)ccc(-c2ccccc2)c1Cl]

To a stirred solution of 1-bromo-2-chloro-3-fluoro benzene (1.0 g, 4.79 mmol) in toluene (20 mL) were added phenyl boronic acid (875 mg, 7.18 mmol), Na2CO3 (1.52 g, 14.35 mmol), water (5 mL) and degassed for 10 min in argon atmosphere. Then to it was added Pd(PPh3)4 (553 mg, 0.48 mmol) and again degassed for 5 min. The reaction was heated to 100° C. for 16 h. The reaction mixture was then cooled to 25° C., filtered through celite and washed with ethyl acetate. The separated organic layer was washed with brine solution, dried over sodium sulfate and concentrated under reduced pressure to get the crude product which was purified by combiflash column chromatography using hexane to get 2-chloro-1-fluoro-3-phenylbenzene (920 mg, 93%) as yellow, sticky liquid.

To the stirred solution of 2-chloro-1-fluoro-3-phenylbenzene (4.0 g, 19.42 mmol) in THF (25 ml) was added LDA (2M in THF, 14.4 mL) at −78° C. and reaction mass was stirred at the same condition for 1 h. Then to the reaction mixture was added DMF (5 mL) at −78° C. and stirred at room temperature for 2h. The reaction was quenched with water and extracted with ethyl acetate. The separated organic layer was washed with brine solution, dried over sodium sulfate and evaporated under reduced pressure to get the crude product which was purified by silica column chromatography using 0-10% ethyl acetate in hexane to get 3-chloro-2-fluoro-4-phenylbenzaldehyde as light yellow solid (2.5 g, 54%).

To a stirred solution of 2-mercapto nicotinic acid (3.6 g, 23.2 mmol) in DMF (30 mL) was added NaH (60%, 1.11 g, 46.4 mmol) and the reaction was stirred at 25° C. for 30 min. Then 3-chloro-2-fluoro-4-phenylbenzaldehyde (5.971 g, 25.519 mmol) was added and the reaction mixture was stirred at 90° C. for 6h. Then K2CO3 (9.62 g, 69.6 mmol) was added followed by addition of methyliodide (4.33 ml, 69.597 mmol) and the reaction was stirred at 25° C. for 16h. The Reaction was quenched with water and extracted with ethyl acetate. The separated organic layer was washed with brine solution, dried over anhydrous sodium sulfate and evaporated under reduced pressure. The crude product was purified by normal silica column using 0-20% ethyl acetate in hexane to get methyl 2-[(2-chloro-6-formyl-3-phenylphenyl)sulfanyl]pyridine-3-carboxylate (4.5 g, 50%) as a sticky solid.

LC-MS: m/z=383.9 (M+H)+ for monoisotopic mass 383.04

To a stirred solution of methyl 2-[(2-chloro-6-formyl-3-phenylphenyl)sulfanyl]pyridine-3-carboxylate (4.5 g, 11.75 mmol) in THF (40 mL) were added 2-methylpropane-2-sulfinamide (1.42 g, 11.75 mmol), Ti(OEt)4 (12.317 ml, 58.747 mmol) and the reaction was heated to 70° C. for 45 min. The reaction was quenched with saturated sodium chloride solution, the obtained solid was filtered through celite, washed with ethyl acetate. The separated organic layer was dried over anhydrous sodium sulfate and concentrated under reduced pressure to afford methyl 2-({2-chloro-6-[(1Z)-[(2-methylpropane-2-sulfinyl)imino]methyl]-3-phenylphenyl}sulfanyl)pyridine-3-carboxylate (4.8 g, crude) which was directly used for next step without further purification.

LC-MS: m/z=486.8 (M+H)+ for monoisotopic mass 486.08

To a stirred solution of methyl 2-({2-chloro-6-[(1Z)-[(2-methylpropane-2-sulfinyl)imino]methyl]-3-phenylphenyl}sulfanyl)pyridine-3-carboxylate (4.8 g, 9.88 mmol) in THF (40 mL) was added LAH (2M in THF, 7.4 mL, 14.81 mmol) at 0° C. and the reaction was stirred at 0° C. for 1 h. The reaction mixture was quenched with saturated sodium sulfate solution and extracted with ethyl acetate. The separated organic layer was washed with water, brine solution, dried over anhydrous sodium sulfate and evaporated under reduced pressure. The crude obtained product was purified by normal silica column using 50-90% ethyl acetate in hexane to get N-[(3-chloro-2-{[3-(hydroxymethyl)pyridin-2-yl]sulfanyl}-4-phenylphenyl)methyl]-2-methylpropane-2-sulfinamide (4.0 g, 74% 2 steps) as off-white solid.

LC-MS: m/z=460.8 (M+H)+ for monoisotopic mass 460.10

To a stirred solution of N-[(3-chloro-2-{[3-(hydroxymethyl)pyridin-2-yl]sulfanyl}-4-phenylphenyl)methyl]-2-methylpropane-2-sulfinamide (4.0 g, 8.7 mmol) in MeOH (40 mL), was added 4M HCl in dioxane (20 mL) at 0° C. and the reaction mixture was stirred at 25° C. for 3h. The solvent was evaporated under reduced pressure to yield (2-{[6-(aminomethyl)-2-chloro-3-phenylphenyl]sulfanyl}pyridin-3-yl)methanol HCl salt (3.5 g, crude) which was directly used for next step.

LC-MS: m/z=356.9 (M+H)+ for monoisotopic mass 356.08

To a stirred suspension of (2-{[6-(aminomethyl)-2-chloro-3-phenylphenyl]sulfanyl}pyridin-3-yl)methanol HCl salt (3.5 g, 9.831 mmol) in 5% NaHCO3 (25 mL) was added Fmoc OSU (3.32 g, 9.83 mmol) in CH3CN (25 mL) at 25° C. and the reaction was stirred at the same temperature for 16h. Then the reaction was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-4-phenylphenyl)methyl]carbamate (3,7 g, crude) which was directly used for next step.

LC-MS: m/z=579.1 (M+H)+ for monoisotopic mass 578.14

To a stirred solution of 9H-fluoren-9-ylmethyl N-[(3-chloro-2-{[3-(hydroxymethyl)pyridin-2-yl]sulfanyl}-4-phenylphenyl)methyl]carbamate (3.7 g, 6.40 mmol) in DCM/THF (1:1, 60 mL) was added MnO2 (5.57 g, 64.01 mmol) and the reaction was stirred at 25° C. for 1 h. The reaction was filtered through a pad of celite; the filtrate was evaporated under reduced pressure. The crude product was purified by normal silica column using 10-30% ethyl acetate in hexane to get 9H-fluoren-9-ylmethyl N-({3-chloro-2-[(3-formylpyridin-2-yl)sulfanyl]-4-phenylphenyl}methyl)carbamate (3.5 g, 70%) as a off white solid.

LC-MS: m/z=577.0 (M+H)+ for monoisotopic mass 576.13

1H NMR (400 MHz, DMSO-d6) δ 10.20 (s, 1H), 8.47 (d, 1H), 8.36 (d, 1H), 7.89 (d, 2H), 7.69 (d, 2H), 7.51-7.31 (m, 12H), 4.33-4.29 (m, 4H), 4.22 (m, 1H)

Intermediate 80

9H-fluoren-9-ylmethyl N-[[2-(2-formylphenyl)sulfanyl-5-phenyl-3-(trifluoromethyl)phenyl]methyl]carbamate

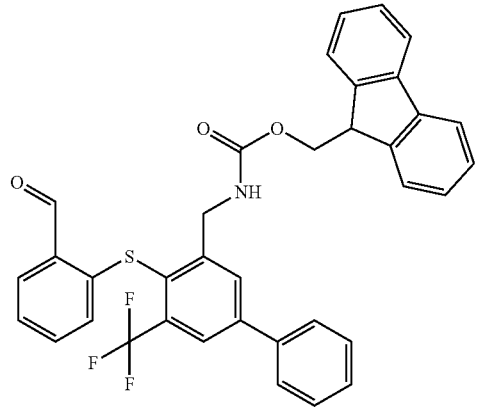 [SMILES: O=Cc1ccccc1Sc1c(CNC(=O)OCC2c3ccccc3-c3ccccc32)cc(-c2ccccc2)cc1C(F)(F)F]

To a stirred solution of 5-bromo-2-fluoro-3-trifluoromethylbenzaldehyde (4.63 g, 21.4 mmol) and methyl 2-sulfanylbenzoate (3.0 g, 17.9 mmol) in DMF (30 mL) was added K2CO3 (4.93 g, 35.7 mmol) and the reaction was stirred at 25° C. for 1 h. Reaction mixture was diluted with ethyl acetate and washed with water. The separated organic layer was washed with sat. NaCl solution, dried over anhydrous sodium sulfate and evaporated under reduced pressure. The obtained crude product was purified by combiflash column chromatography using 10% EA/Hexane to get methyl 2-{[4-bromo-2-formyl-6-(trifluoromethyl)phenyl]sulfanyl}benzoate (6 g, 80%) as off white solid.

To a stirred solution of methyl 2-{[4-bromo-2-formyl-6-(trifluoromethyl)phenyl]sulfanyl}benzoate (0.5 g, 1.19 mmol) in THF (5 mL) were added 2-methylpropane-2-sulfinamide (288.6 mg, 2.38 mol), Ti(OEt)4 (0.75 mL, 3.57 mmol) and reaction mass was heated to 70° C. for 2h. The reaction was quenched with saturated sodium chloride solution, the obtained solid was filtered through celite, washed with ethyl acetate. The separated organic layer was dried over anhydrous sodium sulfate and concentrated under reduced pressure to afford ethyl 2-({4-bromo-2-[(1Z)-[(2-methylpropane-2-sulfinyl)imino]methyl]-6-(trifluoromethyl)phenyl}sulfanyl)benzoate (0.6 g, crude) which was directly used for next step without further purification.

LC-MS: mixture of methyl- and ethyl-ester, ratio ca. 3:1; m/z=522.2 (M+H)+ for methyl ester (MW 520.99 for monoisotopic mass) and 536.2 (M+H)+ for ethyl ester (MW 535.01 for monoisotopic mass)

To a stirred solution of ethyl 2-({4-bromo-2-[(1Z)-[(2-methylpropane-2-sulfinyl)imino]methyl]-6-(trifluoromethyl)phenyl}sulfanyl)benzoate (0.9 g, 1.724 mmol) in THF (20 mL) was added LiAlH4(2M in THF, 1.7 mL, 3.44 mmol) at 0° C. and the reaction was stirred at 0° C. for 1 h. Reaction mixture was quenched with saturated sodium sulfate solution and extracted with ethyl acetate. The separated organic layer was washed with water, brine solution, dried over anhydrous sodium sulfate and evaporated under reduced pressure to get N-[[5-bromo-2-[2-(hydroxymethyl)phenyl]sulfanyl-3-(trifluoromethyl)phenyl]methyl]-2-methyl-propane-2-sulfinamide (0.8 g, crude) which was directly used for next step without further purification.

LC-MS: m/z=495.9 (M+H)+ for monoisotopic mass 495.01

To a stirred solution of N-[[5-bromo-2-[2-(hydroxymethyl)phenyl]sulfanyl-3-(trifluoromethyl)phenyl]methyl]-2-methyl-propane-2-sulfinamide (1 g, 2 mmol) in DCM (30 mL) were added imidazole (0.41 g, 6 mmol) and TBDMSCl (0.455 g, 3. mmol) at 0° C. and stirred at 25° C. for 1 h. Reaction mass was quenched with aq NaHCO3 solution and extracted with ethyl acetate. The separated organic layer was washed with water, brine solution, dried over sodium sulfate and evaporated under reduced pressure. The crude product was purified by normal silica gel column chromatography using 10% ethyl acetate in hexane to get N-({5-bromo-2-[(2-{[(tert-butyldimethylsilyl)oxy]methyl}phenyl)sulfanyl]-3-(trifluoromethyl)phenyl}methyl)-2-methylpropane-2-sulfinamide (0.95 g, 77%) as colorless sticky liquid.

LC-MS: m/z=611.8 (M+H)+ for monoisotopic mass 609.10

To a stirred solution of N-({5-bromo-2-[(2-{[(tert-butyldimethylsilyl)oxy]methyl}phenyl)sulfanyl]-3-(trifluoromethyl)phenyl}methyl)-2-methylpropane-2-sulfinamide (5.5 g, 9.55 mmol) in toluene (88 mL) were added phenyl boronic acid (1.75 g, 14.3 mmol), Na2CO3 (3.03 g, 28.6 mmol), water (22 mL), the mixture was degassed for 10 min under argon atmosphere. Then to it was added Pd(PPh3)4 (1.1 g, 0.955 mmol) and again degassed for 5 min. The reaction mass was heated to 110° C. for 16h. Reaction mixture was then cooled to 25° C., filtered through celite, washed with ethyl acetate. The separated organic layer was washed with brine solution, dried over sodium sulfate and concentrated under reduced pressure. Crude product was purified by normal silica gel column chromatography, eluted with 50% ethylacetate in hexane to get N-({2-[(2-{[(tert-butyldimethylsilyl)oxy]methyl}phenyl) sulfanyl]-5-phenyl-3-(trifluoromethyl)phenyl}methyl)-2-methylpropane-2-sulfinamide (4.7 g, 81%) as yellow solid.

To a stirred solution of N-({2-[(2-{[(tert-butyldimethylsilyl)oxy]methyl}phenyl)sulfanyl]-5-phenyl-3-(trifluoromethyl)phenyl}methyl)-2-methylpropane-2-sulfinamide (1.5 g, 2.47 mmol) in MeOH (20 mL), was added 4M HCl in dioxane (6 mL) at 0° C. and reaction mixture was stirred at 25° C. for 2h. The solvent was evaporated under reduced pressure to get (2-{[2-(aminomethyl)-4-phenyl-6-(trifluoromethyl)phenyl]sulfanyl}phenyl) methanol hydrochloride (1.1 g, crude) which was directly used for next step.

LC-MS: m/z=390.2 (M+H)+ for monoisotopic mass 389.11

To a stirred suspension of (2-{[2-(aminomethyl)-4-phenyl-6-(trifluoromethyl)phenyl]sulfanyl}phenyl) methanol hydrochloride (3.5 g, 9 mmol) in 5% NaHCO3 (250 mL) was added Fmoc N-hydroxysuccinimide ester (3.03 g, 9 mmol) in CH3CN (70 mL) at 25° C. and reaction was stirred at the same temperature for 16h. Then the reaction was diluted with water and extracted with ethyl acetate. The separated organic layer was washed with brine solution, dried over sodium sulfate and evaporated under reduced pressure to yield 9H-fluoren-9-ylmethyl N-[[2-[2-(hydroxymethyl)phenyl]sulfanyl-5-phenyl-3-(trifluoromethyl) phenyl]methyl]carbamate (3.7 g, crude) which was directly used for next step.

LC-MS: m/z=594.3 (M+H–H2O)+ for monoisotopic mass 611.17

To a stirred solution of 9H-fluoren-9-ylmethyl N-[(2-{[2-(hydroxymethyl)phenyl]sulfanyl}-5-phenyl-3-(trifluoromethyl)phenyl)methyl]carbamate (3.5 g, 5.7 mmol) in DCM/THF (1:1, 160 mL) was added MnO2 (7.47 g, 85.9 mmol) and the reaction was stirred at 25° C. for 1 h. The reaction mixture was filtered through celite; filtrate was evaporated under reduced pressure. The crude product was purified by normal silica column using 10% ethyl acetate in hexane to get 9H-fluoren-9-ylmethyl N-({2-[(2-formylphenyl)sulfanyl]-5-phenyl-3-(trifluoromethyl)phenyl}methyl)carbamate (3.2 g, 91%) as off white solid.

LC-MS: m/z=592.4 (M+H–H2O)+ for monoisotopic mass 609.16

1H NMR (400 MHz, DMSO-d$_6$) δ 10.19 (s, 1H), 8.11 (s, 1H), 8.03-7.93 (m, 3H), 7.86 (d, 2H), 7.78 (d, 2H), 7.66 (d, 2H), 7.56-7.43 (m, 4H), 7.38 (t, 3H), 7.23 (t, 2H), 6.50 (d, 1H), 4.33-4.26 (m, 4H), 4.20 (m, 1H)

Intermediate 81

9H-fluoren-9-ylmethyl N-({3-chloro-2-[(3-formylpyridin-2-yl)sulfanyl]-6-phenylphenyl}methyl) carbamate

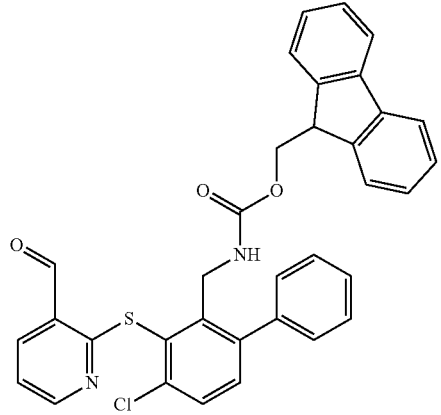 [SMILES: O=Cc1cccnc1Sc1c(Cl)ccc(-c2ccccc2)c1CNC(=O)OCC1c2ccccc2-c2ccccc21]

To a stirred solution of N-[(6-bromo-3-chloro-2-{[3-(hydroxymethyl)pyridin-2-yl]sulfanyl}phenyl)methyl]-2-methylpropane-2-sulfinamide (8.9 g, 19.2 mmol) in DCM (50 mL) were added imidazole (3.9 g, 57.6 mmol) and TBDMSCl (4.33 g, 28.8 mmol) at 0° C. and stirred at 25° C. for 2h. Reaction mass was quenched with aq NaHCO3 solution and extracted with ethyl acetate. The separated organic layer was washed with water, brine, dried over sodium sulfate and evaporated under reduced pressure. The crude thus obtained was purified by combiflash column chromatography using 0-20% ethyl acetate in hexane to get N-({6-bromo-2-[(3-{[(tert-butyldimethylsilyl)oxy]

methyl}pyridin-2-yl)sulfanyl]-3-chlorophenyl}methyl)-2-methylpropane-2-sulfinamide (9 g) as off white solid. LC-MS: 578.6 [M+H]⁺

To a stirred solution of compound N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (10 mL) were added phenyl boronic acid (411 mg, 3.4 mmol), Na₂CO₃ (825 mg, 7.8 mmol), water (5 mL) and degassed for 10 min in argon atmosphere. Then to it was added Pd(PPh₃)₄ (150 mg, 0.13 mmol) and again degassed for 5 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under reduced pressure to get N-({2-[(3-{[(tert-butyldimethylsilyl)oxy]methyl}pyridin-2-yl)sulfanyl]-3-chloro-6-phenylphenyl}methyl)-2-methylpropane-2-sulfinamide (1.3 g) as yellow solid. LC-MS: 575.0 [M+H]⁺

To a stirred solution of N N-({2-[(3-{[(tert-butyldimethylsilyl)oxy]methyl}pyridin-2-yl)sulfanyl]-3-chloro-6-phenylphenyl}methyl)-2-methylpropane-2-sulfinamide (1.3 g, 2.26 mmol) in MeOH (20 mL), was added 4M HCl in dioxan (10 mL) at 0° C. and reaction mixture was stirred at 25° C. for 2h. Reaction mass was evaporated under reduced pressure to get (2-{[2-(aminomethyl)-6-chloro-3-phenylphenyl]sulfanyl}pyridin-3-yl)methanol HCl salt (890 mg, crude) which was directly used for next step.

To a stirred suspension of (2-{[2-(aminomethyl)-6-chloro-3-phenylphenyl]sulfanyl}pyridin-3-yl)methanol HCl salt (890 mg, 2.3 mmol) in 5% NaHCO₃ (10 mL) was added Fmoc OSU (762 mg, 2.3 mmol) in acetonitrile (20 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-6-phenylphenyl)methyl]carbamate (1,2 g) as off white solid. LC-MS: 578.8 [M+H]⁺

To a stirred solution of 9H-fluoren-9-ylmethyl N-[(3-chloro-2-{[3-(hydroxymethyl)pyridin-2-yl]sulfanyl}-6-phenylphenyl)methyl]carbamate (1.2 g, 2.1 mmol) in DCM/THF (1:1, 40 mL) was added MnO₂ (3.6 g, 41.4 mmol) and reaction mass was stirred at 25° C. for 2 h. The reaction mass was filtered through celite, filtrate was evaporated under reduced pressure to get crude mass that was purified by normal silica column using 10-40% ethyl acetate in hexane to get 9H-fluoren-9-ylmethyl N-({3-chloro-2-[(3-formylpyridin-2-yl)sulfanyl]-6-phenylphenyl}methyl) carbamate (710 mg) as off white solid with 98% purity. LC-MS: 576.8 [M+H]⁺

1H NMR (400 MHz, DMSO-d6): δ 4.08-4.15 (5H, m), 7.34 (4H, q, J=7.3, 6.2 Hz), 7.42 (7H, d, J=8.1 Hz), 7.58 (1H, s), 7.64-7.71 (3H, m), 7.89 (2H, d, J=7.5 Hz), 8.33 (1H, d, J=7.7 Hz), 8.48 (1H, d, J=3.2 Hz), 10.21 (1H, s).

Intermediate 82

9H-Fluoren-9-ylmethyl N-{[5-(3-{[(tert-butoxy)carbonyl]amino}pyrrolidin-1-yl)-3-chloro-2-[(3-formylpyridin-2-yl)sulfanyl]phenyl]methyl}carbamate

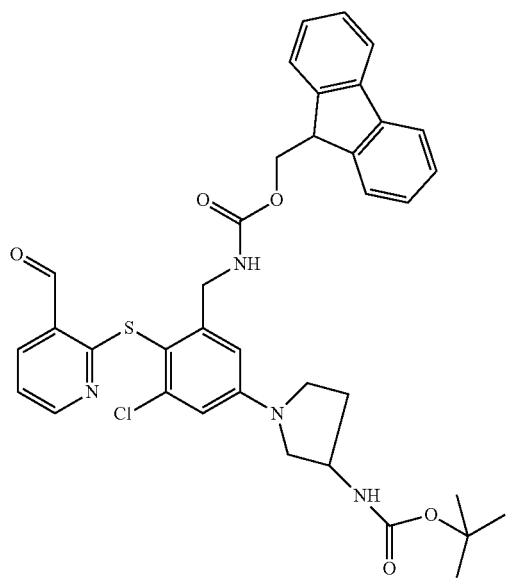 [SMILES: CC(C)(C)OC(=O)NC1CCN(c2cc(Cl)c(Sc3ncccc3C=O)c(CNC(=O)OCC3c4ccccc4-c4ccccc43)c2)C1]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (750 mg, 1.3 mmol) in toluene (7 mL) were added tert-butyl pyrrolidine-3-carboxylate (290.5 mg, 1.5 mmol) and sodium tertiary butoxide (337.3 mg, 3.5 mmol) and degassed in argon atmosphere for 5 min. Then to it were added 2-ditertiary butyl phosphino biphenyl (34.9 mg, 0.12 mmol) and Pd(dba)₂ (59.8 mg, 0.1 mmol) and heated to 110° C. for 16h. Reaction mass was filtered through celite pad and the filtrate was evaporated under reduced pressure. The crude thus obtained was purified by combiflash column chromatography using 60% ethylacetate in hexane to get tert-butyl N-(1-{4-[(3-{[(tert-butyldimethylsilyl)oxy]methyl}pyridin-2-yl) sulfanyl]-3-chloro-5-{[(2-methylpropane-2-sulfinyl)amino]methyl}phenyl}pyrrolidin-3-yl)carbamate (450 mg) as off-white solid. LC-MS: 683.1 [M+H]⁺

To a stirred solution of tert-butyl N-(1-{4-[(3-{[(tert-butyldimethylsilyl)oxy]methyl}pyridin-2-yl)sulfanyl]-3-chloro-5-{[(2-methylpropane-2-sulfinyl)amino]methyl}phenyl}pyrrolidin-3-yl) carbamate (900 mg, 1.3 mmol) in THF (10 mL) was added TBAF in 1(M) THF (1.9 mL) and reaction mixture was stirred at 25° C. for 1 h. After completion of reaction, reaction mixture was extracted with ethyl acetate, washed with water, brine solution, dried over Na2SO4 and evaporated under reduced pressure to get tert-butyl N-[1-(3-chloro-4-{[3-(hydroxymethyl)pyridin-2- yl]sulfanyl}-5-{[(2-methylpropane-2-sulfinyl)amino]methyl}phenyl)pyrrolidin-3-yl]carbamate (700 mg) which was directly used for next step. LC-MS: 568.6 [M+H]+

To a stirred solution of tert-butyl N-[1-(3-chloro-4-{[3-(hydroxymethyl)pyridin-2-yl]sulfanyl}-5-{[(2-methylpropane-2-sulfinyl)amino]methyl}phenyl)pyrrolidin-3-yl]carbamate (700 mg, 1.2 mmol) in MeOH (8 mL), was added 4M HCl in dioxan (4 mL) at 0° C. and reaction mixture was stirred at 25° C. for 15 mins. Reaction mass was evaporated under reduced pressure to get tert-butyl N-{1-[3-(amino methyl)-5-chloro-4-{[3-(hydroxymethyl)pyridin-2-yl]sulfanyl}phenyl]pyrrolidin-3-yl}carbamate hydrochloride (600 mg) which was directly used for next step. LC-MS: 464.9 [M+H]+

To a stirred suspension of tert-butyl N-{1-[3-(aminomethyl)-5-chloro-4-{[3-(hydroxymethyl)pyridin-2-yl]sulfanyl}phenyl]pyrrolidin-3-yl}carbamateHCl salt (600 mg, 1.3 mmol) in 5% NaHCO₃ (10 mL) was added Fmoc-OSU (436.0 mg, 1.3 mmol) in dioxan (10 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-Fluoren-9-ylmethyl N-{[5-(3-{[(tert-butoxy) carbonyl]amino}pyrrolidin-1-yl)-3-chloro-2-{[3-(hydroxymethyl)pyridin-2-yl]sulfanyl}phenyl]methyl}carbamate (700 mg) as off white solid; which was used for next step without further purification. LC-MS: 687.0 [M+H]+

To a stirred solution of 9H-fluoren-9-ylmethyl N-{[5-(3-{[(tert-butoxy)carbonyl]amino}pyrrolidin-1-yl)-3-chloro-2-{[3-(hydroxymethyl)pyridin-2-yl]sulfanyl}phenyl]methyl}carbamate (700 mg, 1.02 mmol)) in DCM:THF (1:1, 20 mL) was added MnO₂ (18 g, 20.4 mmol) and reaction mass was stirred at 25° C. for 2 h. The reaction mass was filtered through celite pad and the filtrate was evaporated under reduced pressure. The crude material obtained was purified by normal silica column using 30%-80% ethylacetate in hexane to get 9H-Fluoren-9-ylmethyl N-{[5-(3-{[(tert-butoxy) carbonyl]amino}pyrrolidin-1-yl)-3-chloro-2-[(3-formylpyridin-2-yl)sulfanyl]phenyl]methyl}carbamate (250 mg) as off white solid with 96% LCMS purity. LC-MS: 685.1 [M+H]+

1H NMR (400 MHz, DMSO-d6): δ 1.40 (9H, s), 1.87-1.96 (1H, m), 2.14 (1H, dd, J=12.4, 7.0 Hz), 3.09 (1H, dd, J=8.4, 3.6 Hz), 3.26 (1H, dd, J=8.6, 7.0 Hz), 3.34-3.42 (1H, m), 3.49 (1H, dd, J=9.6, 7.0 Hz), 4.24 (5H, dd, J=18.9, 6.4 Hz), 6.51 (1H, s), 6.60 (1H, s), 7.32 (4H, q, J=5.8 Hz), 7.41 (2H, t, J=5.8 Hz), 7.68 (2H, d, J=7.1 Hz), 7.78 (1H, s), 7.89 (2H, d, J=7.2 Hz), 8.29 (1H, d, J=7.2 Hz), 8.42 (1H, d, J=3.7 Hz), 10.21 (1H, s).

Intermediate 83

9H-Fluoren-9-ylmethyl N-{[3-chloro-5-(3,6-dihydro-2H-pyran-4-yl)-2-[(3-formylpyridin-2-yl)sulfanyl]phenyl]methyl}carbamate

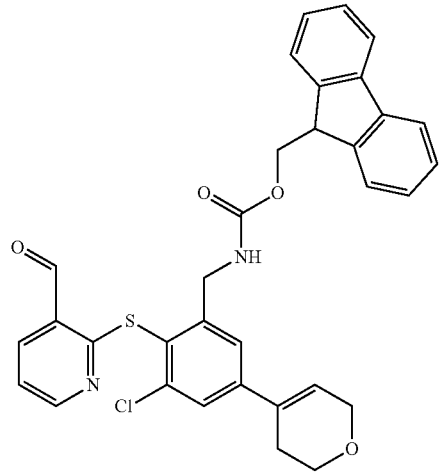 [SMILES: O=Cc1cccnc1Sc1c(Cl)cc(C2=CCOCC2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.2 g, 2.1 mmol) in dioxan (10 mL) were added 2-(3,6-dihydro-2H-pyran-4-yl)-4,4,5,5-tetramethyl-1,3,2-dioxaborolane (567 mg, 2.7 mmol), Na₂CO₃ (660 mg, 6.2 mmol), water (5 mL) and degassed for 10 min in argon atmosphere. Then to it was added Pd(PPh₃)₄ (120 mg, 0.1 mmol) and again degassed for 5 min. The reaction mass was heated to 120° C. for 16 h. Reaction mixture was then cooled to 25° C., filtered through celite pad and washed with ethyl acetate. The separated organic layer was washed with brine solution, dried over sodium sulfate and concentrated under reduced pressure to get N-({2-[(3-{[(tert-butyldimethylsilyl)oxy]methyl}pyridin-2-yl)sulfanyl]-3-chloro-5-(3,6-dihydro-2H-pyran-4-yl)phenyl}methyl)-2-methylpropane-2-sulfinamide (1.2 g) as yellow sticky solid; which was used for next step without further purification. LC-MS: 580.9 [M+H]+

To a stirred solution of N-({2-[(3-{[(tert-butyldimethylsilyl)oxy]methyl}pyridin-2-yl)sulfanyl]-3-chloro-5-(3,6-dihydro-2H-pyran-4-yl)phenyl}methyl)-2-methylpropane-2-sulfinamide (1.2 g, 2.0 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(amino methyl)-6-chloro-4-(3,6-dihydro-2H-pyran-4-yl)phenyl]sulfanyl}pyridin-3-yl)methanol hydrochloride (820 mg) which was directly used for next step. LC-MS: 362.8 [M+H]+

To a stirred suspension of (2-{[2-(amino methyl)-6-chloro-4-(3,6-dihydro-2H-pyran-4-yl)phenyl]sulfanyl}pyridin-3-yl)methanol hydrochloride (820 mg, 2.0 mmol) in 5% NaHCO₃ (10 mL) was added Fmoc-OSU (692 mg, 2.0 mmol) in acetonitrile (20 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to give 9H-Fluoren-9-ylmethyl N-{[3-chloro-5-(3,6-dihydro-2H-pyran-4-yl)-2-{[3-(hydroxymethyl)pyridin-2-yl]sulfanyl}phenyl]methyl}carbamate (1 g) as off white solid, which was used for next step without further purification. LC-MS: 584.9 [M+H]+

To a stirred solution of 9H-fluoren-9-ylmethyl N-{[3-chloro-5-(3,6-dihydro-2H-pyran-4-yl)-2-{[3-(hydroxymethyl)pyridin-2-yl]sulfanyl}phenyl]methyl}carbamate (1.0 g, 1.7 mmol) in DCM:THF (1:1, 40 mL) was added MnO₂ (2.97 g, 34.2 mmol) and reaction mass was stirred at 25° C. for 2 h. The reaction mass was filtered through celite pad and the filtrate was evaporated under reduced pressure. The crude thus obtained was purified by normal silica column using 10%-40% ethyl acetate in hexane to get 9H-fluoren-9-ylmethyl N-{[3-chloro-5-(3,6-dihydro-2H-pyran-4-yl)-2-[(3-formylpyridin-2-yl)sulfanyl]phenyl]methyl}carbamate (550 mg) as a off white solid with 94% LCMS purity. LC-MS: 582.8 [M+H]+

1H NMR (400 MHz, DMSO-d6): δ 2.39-2.48 (3H, m), 3.80 (2H, t, J=4.6 Hz), 4.22 (3H, s), 4.27 (3H, d, J=6.7 Hz), 6.39 (1H, s), 7.31 (2H, t, J=7.0 Hz), 7.37-7.47 (4H, m), 7.60 (1H, s), 7.69 (2H, d, J=7.5 Hz), 7.89 (3H, t, J=7.1 Hz), 8.36 (1H, d, J=7.6 Hz), 8.42 (1H, d, J=4.8 Hz), 10.20 (1H, s).

Intermediate 84

9H-fluoren-9-ylmethyl N-({3-chloro-2-[(3-formylpyridin-2-yl)sulfanyl]-5-(pyrazin-2-yl)phenyl}methyl)carbamate

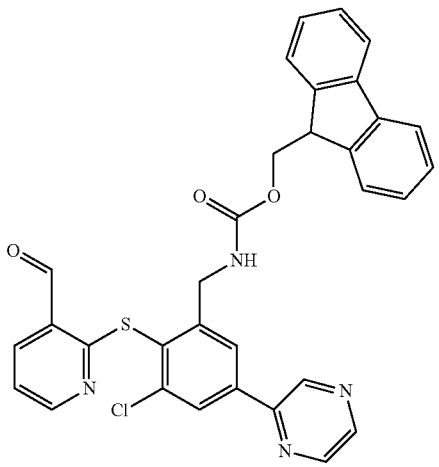 [SMILES: O=Cc1cccnc1Sc1c(Cl)cc(-c2cnccn2)cc1CNC(=O)OCC1c2ccccc2-c2ccccc21]

To a stirred and degassed solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (12 mL) were added 4,4,5,5-tetramethyl-2-(tetramethyl-1,3,2-dioxaborolan-2-yl)-1,3,2-dioxaborolane (1.6 g, 6.2 mmol) and potassium acetate (1.0 g, 10.4 mmol), PdCl₂dppf (424 mg, 0.52 mmol) and reaction mass was heated to 110° C. for 16h. Reaction mass was filtered through celite pad and the filtrate was evaporated under reduced pressure to get N-({2-[(3-{[(tert-butyldimethylsilyl)oxy]methyl}pyridin-2-yl)sulfanyl]-3-chloro-5-(4,4,5,5-tetramethyl-1,3,2-dioxaborolan-2-yl)phenyl}methyl)-2-methylpropane-2-sulfinamide (1.6 g) which was directly used for next step. LC-MS: 625.3 [M+H]+

To a stirred solution of 2-bromopyrazin (500 mg, 3.1 mmol) in dioxan (5 mL) were added N-({2-[(3-{[(tert-butyldimethylsilyl)oxy]methyl}pyridin-2-yl)sulfanyl]-3-chloro-5-(4,4,5,5-tetramethyl-1,3,2-dioxaborolan-2-yl)phenyl}methyl)-2-methylpropane-2-sulfinamide (2.3 g, 3.7 mmol), Na₂CO₃ (1.0 g, 9.4 mmol), water (2 mL) and degassed for 10 min in argon atmosphere. Then to it was added Pd(PPh₃)₄ (363 mg, 0.31 mmol) and again degassed for 5 min. The reaction mass was heated to 120° C. for 16 h. Reaction mixture was then cooled to 25° C., filtered through celite pad and washed with EtOAc. The separated organic layer was washed with brine solution, dried over sodium sulfate and concentrated under reduced pressure. The crude thus obtained was purified by normal silica column using 0-10% methanol in DCM to get N-({2-[(3-{[(tert-butyldimethylsilyl)oxy]methyl}pyridin-2-yl)sulfanyl]-3-chloro-5-(pyrazin-2-yl)phenyl}methyl)-2-methylpropane-2-sulfinamide (450 mg) as off white solid. LC-MS: 577.1 [M+H]+

To a stirred solution of N-({2-[(3-{[(tert-butyldimethylsilyl)oxy]methyl}pyridin-2-yl)sulfanyl]-3-chloro-5-(pyrazin-2-yl)phenyl}methyl)-2-methylpropane-2-sulfinamide (450 mg, 0.781 mmol) in MeOH (8 mL), was added 4M HCl in dioxan (4 mL) at 0° C. and reaction mixture was stirred at 25° C. for 2h. Reaction mass was evaporated under reduced pressure to get (2-{[2-(aminomethyl)-6-chloro-4-(pyrazin-2-yl)phenyl]sulfanyl}pyridin-3-yl)methanol HCl salt (400 mg) which was directly used for next step. LC-MS: 358.9 [M+H]+

To a stirred suspension of (2-{[2-(aminomethyl)-6-chloro-4-(pyrazin-2-yl)phenyl]sulfanyl}pyridin-3-yl) methanol HCl salt (400 mg, 1.1 mmol) in 5% NaHCO₃ (6 mL) was added Fmoc-OSU (376 mg, 1.1 mmol) in dioxan (6 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(pyrazin-2-yl)phenyl)methyl]carbamate (500 mg, crude) as off white solid. LC-MS: 581.1 [M+H]+

To a stirred solution of 9H-fluoren-9-ylmethyl N-[(3-chloro-2-{[3-(hydroxymethyl)pyridin-2-yl]sulfanyl}-5-(pyrazin-2-yl)phenyl)methyl]carbamate (500 mg, 0.86 mmol) in DCM:THF (1:1, 20 mL) was added MnO₂ (1.49 g, 17.24 mmol) and reaction mass was stirred at 25° C. for 2 h. The reaction mass was filtered through celite pad and filtrate was evaporated under reduced pressure. The crude thus obtained was purified by normal silica column using 10-80% ethyl acetate in hexane to get 9H-fluoren-9-ylmethyl N-({3-chloro-2-[(3-formylpyridin-2-yl)sulfanyl]-5-(pyrazin-2-yl)phenyl}methyl)carbamate (130 mg) as off white solid. LC-MS: 578.8 [M+H]+

1H NMR (400 MHz, DMSO-d6): δ 4.24-4.32 (3H, m), 4.34-4.41 (2H, m), 7.28 (2H, t, J=6.9 Hz), 7.37-7.42 (3H, m), 7.69 (2H, d, J=7.7 Hz), 7.88 (2H, d, J=7.5 Hz), 7.92-8.00 (1H, m), 8.17-8.22 (1H, m), 8.28-8.34 (1H, m), 8.35-8.42 (1H, m), 8.41-8.47 (1H, m), 8.68-8.75 (2H, m), 9.35 (1H, s), 10.22 (1H, s).

Intermediate 85

9H-fluoren-9-ylmethyl N-({3-chloro-2-[(3-form-ylpyridin-2-yl)sulfanyl]-6-(morpholin-4-yl)phenyl}methyl)carbamate

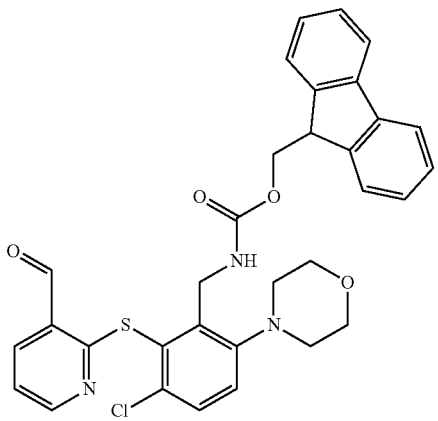 [SMILES: O=Cc1cccnc1Sc1c(Cl)ccc(N2CCOCC2)c1CNC(=O)OCC1c2ccccc2-c2ccccc21]

To a stirred solution of 2-mercapto nicotinic acid (719 mg, 4.6 mmol) in DMF (10 mL) was added NaH (60%, 336 mg, 8.4 mmol) and reaction mass was stirred at 25° C. for 30 min. Then 6-Bromo-3-chloro-2-fluoro-benzaldehyde (1 g, 4.2 mmol) was added and reaction mixture was stirred at 90° C. for 4h. Then $K_2CO_3$ (1.74 g, 12.6 mmol) was added followed by addition of MeI (0.8 mL, 12.6 mmmol) and reaction mass was stirred at 25° C. for 16h. The reaction was quenched with water and extracted with ethyl acetate. The separated organic layer was washed with brine, dried over anhydrous sodium sulfate and evaporated under reduced pressure. The crude thus obtained was purified by normal silica column using 5-15% ethyl acetate in hexane to get methyl 2-[(3-bromo-6-chloro-2-formylphenyl)sulfanyl]pyridine-3-carboxylate (800 mg, 49%) as yellow solid. LC-MS: 388.0 $[M+H]^+$ To the stirred solution of compound methyl 2-[(3-bromo-6-chloro-2-formylphenyl)sulfanyl]pyridine-3-carboxylate (1.3 g, 3.4 mmol) in toluene (10 mL) were added Morpholine (352 mg, 4.0 mmol) and $Cs_2CO_3$ (2.9 g, 9.1 mmol) and degassed in argon atmosphere for 5 min. Then to it were added Xanthphos (175 mg, 0.3 mmol), $Pd_2(dba)_3$ (247 mg, 0.27 mmol) and heated to 110° C. for 16h. Reaction mass was filtered through celite pad and the filtrate was evaporated under reduced pressure. The crude thus obtained was purified by combiflash column chromatography using 20-60% ethyl acetate in hexane to get the methyl 2-{[6-chloro-2-formyl-3-(morpholin-4-yl)phenyl]sulfanyl}pyridine-3-carboxylate (260 mg) as brown sticky solid. LC-MS: 393.0 $[M+H]^+$ To a stirred solution of methyl 2-{[6-chloro-2-formyl-3-(morpholin-4-yl)phenyl]sulfanyl}pyridine-3-carboxylate (550 mg, 1.4 mmol) in THF (10 mL) were added 2-methylpropane-2-sulfinamide (170 mg, 1.40 mmol), $Ti(OEt)_4$ (1.5 mL, 7.0 mmol) and reaction mass was heated to 70° C. for 45 min. The reaction mass was quenched with saturated sodium chloride solution, solid obtained was filtered through celite pad, washed with ethyl acetate. The separated organic layer was dried over anhydrous sodium sulfate and concentrated under reduced pressure to afford ethyl 2-[(6-chloro-2-{[(2-methylpropane-2-sulfinyl)imino]methyl}-3-(morpholin-4-yl)phenyl)sulfanyl]pyridine-3-carboxylate (600 mg, crude) which was directly used for next step without further purification. LC-MS: 509.6 $[M+H]^+$ To a stirred solution of 2-[(6-chloro-2-{[(2-methylpropane-2-sulfinyl)imino]methyl}-3-(morpholin-4-yl)phenyl)sulfanyl]pyridine-3-carboxylate (600 mg, 1.2 mmol) in THF (30 mL) was added LAH (2M in THF, 1.2 mL, 2.3 mmol) at 0° C. and reaction mass was stirred at 0° C. for 1 h. Reaction mixture was quenched with saturated sodium sulfate solution and extracted with ethyl acetate. The separated organic layer was washed with water, brine, dried over anhydrous sodium sulfate and evaporated under reduced pressure to get N-[(3-chloro-2-{3-(hydroxymethyl)pyridin-2-yl]sulfanyl}-6-(morpholin-4-yl)phenyl)methyl]-2-methylpropane-2-sulfinamide (530 mg, crude) as of white solid. LC-MS: 469.6 $[M+H]^+$ To a stirred solution of N-[(3-chloro-2-{[3-(hydroxymethyl)pyridin-2-yl]sulfanyl}-6-(morpholin-4-yl)phenyl)methyl]-2-methylpropane-2-sulfinamide (530 mg, 1.1 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(aminomethyl)-6-chloro-3-(morpholin-4-yl)phenyl]sulfanyl}pyridin-3-yl)methanol HCl salt (450 mg) which was directly used for next step. LC-MS: 365.8 $[M+H]^+$ To a stirred suspension of (2-{[2-(aminomethyl)-6-chloro-3-(morpholin-4-yl)phenyl]sulfanyl}pyridin-3-yl)methanol HCl salt (450 mg, 1.2 mmol) in 5% $NaHCO_3$ (10 mL) was added Fmoc-OSU (415.7 mg, 1.2 mmol) in dioxan (10 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure. The crude thus obtained was purified by normal silica column using 20-60% ethyl acetate in hexane to get to get 9H-fluoren-9-ylmethyl N-[(3-chloro-2-{[3-(hydroxymethyl)pyridin-2-yl]sulfanyl}-6-(morpholin-4-yl)phenyl)methyl]carbamate (300 mg) as off white solid. LC-MS: 588.0 $[M+H]^+$ To a stirred solution of 9H-fluoren-9-ylmethyl N-[(3-chloro-2-{[3-(hydroxymethyl)pyridin-2-yl]sulfanyl}-6-(morpholin-4-yl)phenyl)methyl]carbamate (300 mg, 0.51 mmol) in DCM:THF (1:1, 12 mL) was added $MnO_2$ (888 mg, 10.2 mmol) and reaction mass was stirred at 25° C. for 2 h. The reaction mass was filtered through celite pad and the filtrate was evaporated under reduced pressure. The crude material obtained was purified by normal silica column using 30-50% ethyl acetate in hexane to get 9H-fluoren-9-ylmethyl N-({3-chloro-2-[(3-formylpyridin-2-yl)sulfanyl]-6-(morpholin-4-yl)phenyl}methyl)carbamate (160 mg) as off white solid with 97% LCMS purity. LC-MS: 585.8 $[M+H]^+$ 1H NMR (400 MHz, DMSO-d6): δ 2.79-2.94 (4H, m), 3.66 (4H, s), 4.12-4.23 (3H, m), 4.43 (2H, d, J=3.9 Hz), 7.27-7.41 (7H, m), 7.57 (1H, d, J=8.6 Hz), 7.63 (2H, d, J=7.3 Hz), 7.88 (2H, d, J=7.1 Hz), 8.30-8.37 (1H, m), 8.37-8.44 (1H, m), 10.21 (1H, s).

Intermediate 86

9H-fluoren-9-ylmethyl N-({3-chloro-2-[(3-form-ylpyridin-2-yl)sulfanyl]-5-(pyridazin-4-yl)phenyl}methyl)carbamate

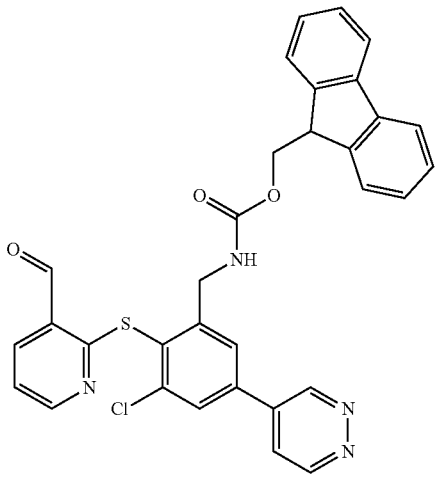 [SMILES: O=Cc1cccnc1Sc1c(Cl)cc(-c2ccnnc2)cc1CNC(=O)OCC1c2ccccc2-c2ccccc21]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.2 g, 2.1 mmol) in dioxan (10 mL) were added (pyridazin-4-yl)boronic acid (514 mg, 2.5 mmol), Na$_2$CO$_3$ (661 mg, 6.4 mmol), water (5 mL) and degassed for 10 min in argon atmosphere. Then to it was added Pd(PPh$_3$)$_4$ (240 mg, 0.21 mmol) and again degassed for 5 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under reduced pressure. The crude thus obtained was purified by normal silica column using 1-5% methanol in DCM to get N-({2-[(3-{[(tert-butyldimethylsilyl)oxy]methyl}pyridin-2-yl)sulfanyl]-3-chloro-5-(pyridazin-4-yl)phenyl}methyl)-2-methylpropane-2-sulfinamide (400 mg) as light yellow solid. LC-MS: 576.8 [M+H]$^+$ To a stirred solution of N-({2-[(3-{[(tert-butyldimethylsilyl)oxy]methyl}pyridin-2-yl)sulfanyl]-3-chloro-5-(pyridazin-4-yl)phenyl}methyl)-2-methylpropane-2-sulfinamide (400 mg, 0.7 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(aminomethyl)-6-chloro-4-(pyridazin-4-yl)phenyl]sulfanyl}pyridin-3-yl)methanol HCl salt (250 mg) which was directly used for next step. LC-MS: 358.7 [M+H]$^+$ To a stirred suspension of (2-{[2-(aminomethyl)-6-chloro-4-(pyridazin-4-yl)phenyl]sulfanyl}pyridin-3-yl)methanol HCl salt (250 mg, 0.7 mmol) in 5% NaHCO$_3$ (5 mL) was added Fmoc-OSU (235 mg, 0.7 mmol) in acetonitrile (5 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(pyridazin-4-yl)phenyl)methyl]carbamate (300 mg, crude) as off white solid. LC-MS: 581.1 [M+H]$^+$ To a stirred solution of 9H-fluoren-9-ylmethyl N-[(3-chloro-2-{[3-(hydroxymethyl)pyridin-2-yl]sulfanyl}-5-(pyridazin-4-yl)phenyl)methyl]carbamate (300 mg, 0.5 mmol) in DCM/THF (1:1, 10 mL) was added MnO$_2$ (900 mg, 10.4 mmol) and reaction mass was stirred at 25° C. for 2 h. The reaction mass was filtered through celite pad; filtrate was evaporated under reduced pressure. The crude thus obtained was purified by normal silica column using 30-80% ethyl acetate in hexane to get 9H-fluoren-9-ylmethyl N-({3-chloro-2-[(3-formylpyridin-2-yl)sulfanyl]-5-(pyridazin-4-yl)phenyl}methyl)carbamate (130 mg) as a off white solid with 95.2% LCMS purity. LC-MS: 578.7 [M+H]$^+$ 1H NMR (400 MHz, DMSO-d6): δ 4.21 (1H, d, J=7.0 Hz), 4.28 (2H, d, J=6.8 Hz), 4.38 (2H, d, J=5.3 Hz), 7.27 (2H, d, J=7.4 Hz), 7.34-7.45 (4H, m), 7.67 (2H, d, J=7.1 Hz), 7.87 (4H, d, J=6.5 Hz), 8.03-8.09 (1H, m), 8.16 (1H, s), 8.39 (1H, d, J=6.5 Hz), 8.44 (1H, d, J=3.3 Hz), 9.36 (1H, d, J=5.1 Hz), 9.69 (1H, s), 10.21 (1H, s).

Intermediate 87

9H-fluoren-9-ylmethyl N-({3-chloro-2-[(3-form-ylpyridin-2-yl)sulfanyl]-5-phenyl phenyl}methyl)carbamate

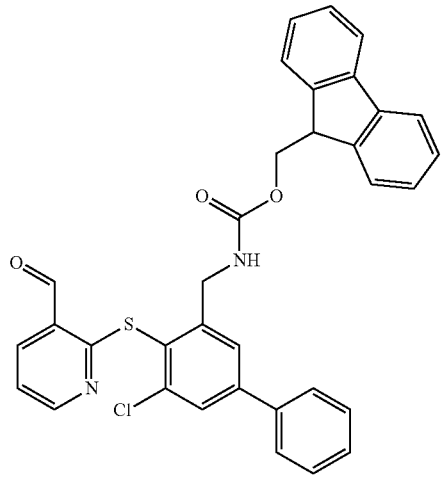 [SMILES: O=Cc1cccnc1Sc1c(Cl)cc(-c2ccccc2)cc1CNC(=O)OCC1c2ccccc2-c2ccccc21]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.2 g, 1.9 mmol) in toluene (10 mL) were added phenyl boronic acid (311 mg, 2.5 mmol), Na$_2$CO$_3$ (625 mg, 5.9 mmol), water (5 mL) and degassed for 15 min in argon atmosphere. Then to it was added Pd(PPh$_3$)$_4$ (114 mg, 0.1 mmol) and again degassed for 5 min. The reaction mass was heated to 110° C. for 16 h. Reaction mixture was then cooled to 25° C., filtered through celite pad, washed with ethyl acetate. The separated organic layer was washed with brine solution, dried over sodium sulfate and concentrated under reduced pressure to get N-({2-[(3-{[(tert-butyldimethylsilyl)oxy]methyl}pyridin-2-yl)sulfanyl]-3-chloro-5-phenylphenyl}methyl)-2-methylpropane-2-sulfinamide (1.2 g) as colourless sticky liquid. LC-MS: 575.3 [M+H]$^+$ To a stirred solution of N-({2-[(3-{[(tert-butyldimethylsilyl)oxy]methyl}pyridin-2-yl)sulfanyl]-3-chloro-5-phenylphenyl}methyl)-2-methylpropane-2-sulfinamide (1.2 g, 2.1 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(aminomethyl)-6-chloro-4-phenylphenyl]sulfanyl}pyridin-3-yl)methanol HCl salt (800 mg) which was directly used for next step. LC-MS: 356.9 [M+H]+

To a stirred suspension of (2-{[2-(aminomethyl)-6-chloro-4-phenylphenyl]sulfanyl}pyridin-3-yl)methanol HCl salt (800 mg, 2.0 mmol) in 5% NaHCO₃ (20 mL) was added Fmoc-OSU (685 mg, 2.0 mmol) in acetonitrile (40 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-phenylphenyl)methyl]carbamate (1.1 g) as off white solid. LC-MS: 579.3 [M+H]+

To a stirred solution of 9H-fluoren-9-ylmethyl N-[(3-chloro-2-{[3-(hydroxymethyl)pyridin-2-yl]sulfanyl}-5-phenylphenyl)methyl]carbamate (1.1 g, 1.9 mmol) in DCM:THF (1:1, 40 mL) was added MnO₂ (3.3 g, 38 mmol) and reaction mass was stirred at 25° C. for 2 h. The reaction mass was filtered through celite pad and the filtrate was evaporated under reduced pressure. The crude thus obtained was purified by normal silica column using 0-20% ethyl acetate in hexane to get 9H-fluoren-9-ylmethyl N-({3-chloro-2-[(3-formylpyridin-2-yl)sulfanyl]-5-phenylphenyl}methyl) carbamate (800 mg) as off white solid with 96% LCMS purity. LC-MS: 577.0 [M+H]+

1H NMR (400 MHz, DMSO-d6): δ 4.16-4.24 (1H, m), 4.27 (2H, d, J=7.0 Hz), 4.36 (2H, d, J=5.6 Hz), 7.25 (2H, t, J=7.5 Hz), 7.36-7.42 (3H, m), 7.49 (3H, dt, J=15.5, 7.1 Hz), 7.70 (5H, dd, J=23.8, 7.0 Hz), 7.83-7.89 (3H, m), 7.92 (1H, t, J=6.1 Hz), 8.38 (1H, d, J=6.1 Hz), 8.45 (1H, d, J=4.6 Hz), 10.22 (1H, s).

Intermediate 88

9H-fluoren-9-ylmethyl N-({3-chloro-2-[(3-formylpyridin-2-yl)sulfanyl]-5-(pyridin-2-yl)phenyl}methyl)carbamate

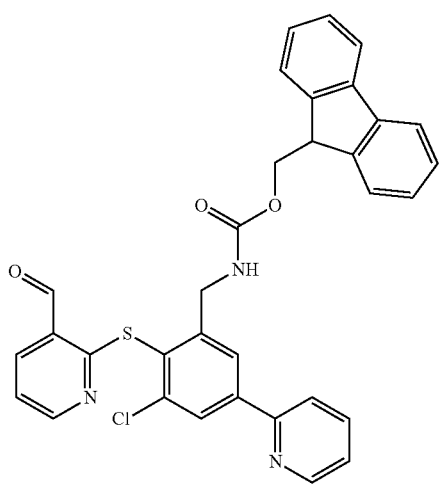 [SMILES: O=Cc1cccnc1Sc1c(Cl)cc(-c2ccccn2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2 g, 3.5 mmol) in toluene (20 mL) were added 2-(tributylstannyl)pyridine (1.9 g, 5.2 mmol) and LiCl (44 mg, 1.0 mmol) and degassed in argon atmosphere for 10 min. Then to it was added Pd(PPh3)4 (400 mg, 0.34 mmol) and reaction mass was heated to 110° C. for 16h. Reach on mixture was then filtered through celite pad and evaporated under reduced pressure. The crude thus obtained was purified by normal silica column using 0-60% ethyl acetate in hexane to get N-({2-[(3-{[(tert-butyldimethylsilyl)oxy]methyl}pyridin-2-yl)sulfanyl]-3-chloro-5-(pyridin-2-yl)phenyl}methyl)-2-methylpropane-2-sulfinamide (1.4 g) as colourless sticky liquid. LC-MS: 576.2 [M+H]+

To a stirred solution of N-({2-[(3-{[(tert-butyldimethylsilyl)oxy]methyl}pyridin-2-yl)sulfanyl]-3-chloro-5-(pyridin-2-yl)phenyl}methyl)-2-methylpropane-2-sulfinamide (1.4 g, 2.4 mmol) in MeOH (12 mL), was added 4M HCl in dioxan (6 mL) at 0° C. and reaction mixture was stirred at 25° C. for 2h. Reaction mass was evaporated under reduced pressure to get (2-{[2-(aminomethyl)-6-chloro-4-(pyridin-2-yl)phenyl]sulfanyl}pyridin-3-yl)methanol HCl salt (850 mg) which was directly used for next step. LC-MS: 357.8 [M+H]+

To a stirred suspension of ((2-{[2-(aminomethyl)-6-chloro-4-(pyridin-2-yl)phenyl]sulfanyl}pyridin-3-yl)methanol HCl salt (850 mg, 2.2 mmol) in 5% NaHCO₃ (20 mL) was added Fmoc-OSU (727 mg, 2.2 mmol) in acetonitrile (40 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(pyridin-2-yl)phenyl)methyl]carbamate (1.2 g) as off white solid. LC-MS: 580.2 [M+H]+

To a stirred solution of 9H-fluoren-9-ylmethyl N-[(3-chloro-2-{[3-(hydroxymethyl)pyridin-2-yl]sulfanyl}-5-(pyridin-2-yl)phenyl)methyl]carbamate (1.2 g, 2.1 mmol) in DCM:THF (1:1, 40 mL) was added MnO₂ (3.6 g, 41.4 mmol) and reaction mass was stirred at 25° C. for 2 h. The reaction mass was filtered through celite pad and the filtrate was evaporated under reduced pressure. The crude thus obtained was purified by normal silica column using 10-50% ethyl acetate in hexane to get 9H-fluoren-9-ylmethyl N-({3-chloro-2-[(3-formylpyridin-2-yl)sulfanyl]-5-(pyridin-2-yl)phenyl}methyl)carbamate (800 mg) as off white solid with 98.0% LCMS purity. LC-MS: 578.1 [M+H]+

1H NMR (400 MHz, DMSO-d6): δ 4.24-4.30 (3H, m), 4.33-4.39 (2H, m), 7.27 (2H, t, J=7.4 Hz), 7.35-7.49 (4H, m), 7.69 (2H, d, J=7.1 Hz), 7.88 (2H, d, J=7.1 Hz), 7.96 (2H, dd, J=10.0, 2.1 Hz), 8.05 (1H, d, J=7.1 Hz), 8.16 (1H, s), 8.22 (1H, s), 8.34-8.42 (1H, m), 8.44 (1H, d, J=2.7 Hz), 8.68 (1H, d, J=3.3 Hz), 10.22 (1H, s).

Intermediate 89

(9H-fluoren-9-yl)methyl 5-bromo-3-chloro-2-((2-formylphenyl)thio)benzylcarbamate

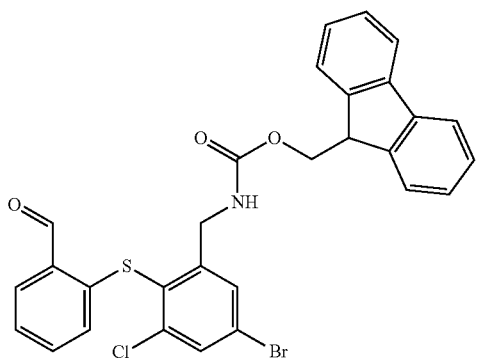 [SMILES: O=Cc1ccccc1Sc1c(Cl)cc(Br)cc1CNC(=O)OCC1c2ccccc2-c2ccccc21]

To a solution of diisopropylamine (4.02 g, 5.66 ml, 39.7 mmol, Eq: 1.04) in THF (28 ml) was added dropwise (10 min) at −20° C. n-butyllithium, 1.6 M in hexane (24.8 ml, 39.7 mmol, Eq: 1.04) and stirred at 0° C. for 20 minutes. The mixture was cooled to −78° C. followed by dropwise addition (20 minutes) of 4-bromo-2-chloro-1-fluorobenzene (8 g, 38.2 mmol, Eq: 1) and the yellow suspension was stirred at −78° C. for 45 min. Then was added dropwise (5 minutes—exotherm) N,N-dimethylformamide (4.19 g, 4.44 ml, 57.3 mmol, Eq: 1.5), the cooling bath was removed and the mixture was allowed to warm to −20° C. to give complete conversion. At −20° C. the clear solution was quenched with sat $NH_4Cl$ (80 ml) and extracted with TBME (80 ml). The aqueous layer was extracted again with TBME (40 ml). The organic layers were dried and evaporated. The residue (9.03 g, 100%) was purified by flash chromatography (silica gel) to give 5-bromo-3-chloro-2-fluorobenzaldehyde (6.88 g, 76%) as a white solid.

GC-MS: m/z=236.9 (M+H)+(monoisotopic mass 235.90)

To a solution of 5-bromo-3-chloro-2-fluorobenzaldehyde (1.19 g, 5 mmol, Eq: 1) in DMF (12 ml) was added at 22° C. methyl 2-mercaptobenzoate (867 mg, 709 μl, 5 mmol, Eq: 1) followed by potassium carbonate (691 mg, 5 mmol, Eq: 1) and stirred at 22° C. for 5 min to give nearly complete conversion. After total 30 minutes the thick suspension was quenched with water (25 ml) and extracted with ethyl acetate (2×25 ml). The organic layers—containing solid—were combined, the solid was filtered, washed with ethyl acetate (2×6 ml) and dried in HV to give methyl 2-((4-bromo-2-chloro-6-formylphenyl)thio)benzoate (1.5 g, 3.89 mmol, 77.8% yield) as light yellow solid.

GC-MS: m/z=325.9 (M+H−HCOOMe)+ for monoisotopic mass 383.92 for P1

To a suspension of methyl 2-((4-bromo-2-chloro-6-formylphenyl)thio)benzoate (1.43 g, 3.71 mmol, Eq: 1) and 2-methylpropane-2-sulfinamide (449 mg, 3.71 mmol, Eq: 1) in THF (16 ml) was added at 22° C. Titanium(IV)ethoxide (4.23 g, 3.84 ml, 18.5 mmol, Eq: 5) to give a clear yellow solution followed by heating to reflux and stirred at 70° C. for 1 h to give nearly complete conversion. After total 3 h the clear yellow solution was cooled to 22° C. and quenched with sat NaCl (20 ml). The mixture was filtered through dicalite and washed with ethyl acetate (2×20 ml). The filtrate was dried and evaporated to give (E)-methyl 2-((4-bromo-2-(((tert-butylsulfinyl)imino)methyl)-6-chlorophenyl)thio)benzoate (1.73 g, 3.54 mmol, 95.4% yield) (1.73 g, 95%) as light yellow foam.

NMR: mixture of ethyl- and methyl-ester P2/P1 ca. 3:2→yield has to be corrected (ca. 94%)

LC-MS: m/z=488.0 and 490.0 (M+H)+ for P1 and second main peak with 502.0 and 504.0 (M+H)+ for P2

To a solution of (E)-methyl 2-((4-bromo-2-(((tert-butylsulfinyl)imino)methyl)-6-chlorophenyl)thio)benzoate (1.679 g, 3.43 mmol, Eq: 1) in THF (17 ml) was added at 22° C. LiBH4 (748 mg, 34.3 mmol, Eq: 10) while color changed immediately to intensive green and temperature rised up to 31° C. Mixture was stirred for 10 min to 22° C. to give nearly full reduction of double bond, but still ester. The meanwhile yellow reaction mixture was warmed to 50° C. and stirred at 50° C. for total 20 h: complete conversion. Mixture cooled to 22° C., quenched dropwise with sat $NH_4Cl$ (50 ml) and completely extr. with EtOAc (1×50 ml). The organic layer was washed with sat NaCl (50 ml), dried and evaporated to give 1.53 g (96%) crude product as off-white solid; suspended in 3 ml DCM, solid filtered off, washed with DCM (1×2 ml) and Hep/EtOAc-mixture of 4:1 (2×4 ml), dried in HV to give the compound P-1.1 (811 mg, 51%) as white solid. NMR: OK, but contains borane-signals; LC-MS: m/z=462.0 (M+H)+ For destroying borane-complex P-1.1 was dissolved in THF/EtOAc 2:5 (70 ml) and extracted with 5% KH2PO4 (75 ml-pH 5) and sat NaCl (75 ml); org layer dried and evap to give N-(5-bromo-3-chloro-2-((2-(hydroxymethyl)phenyl)thio)benzyl)-2-methylpropane-2-sulfinamide (P-1.1=766 mg, 48%) as white solid. NMR: OK; LC-MS: m/z=462.1 (M+H)+ The previously obtained filtrate was purified by flash chrom (silica gel, 40 g, EtOAc in heptane 30% to 90%, then MeOH in DCM 9%) to give the additional product P-1.2 (363 mg, 23%) as white solid. NMR: OK—pure; LC-MS: m/z=462.0 (M+H)+ for monoisotopic mass 460.99 Remarks: total yield of pure product: P-1.1+P-1.2=1.129 g=71%

To a suspension of N-(5-bromo-3-chloro-2-((2-(hydroxymethyl)phenyl)thio)benzyl)-2-methylpropane-2-sulfinamide (330 mg, 713 μmol, Eq: 1) in Methanol (3.3 ml) was added at 0° C. HCl, 4 M in dioxane (1.78 ml, 7.13 mmol, Eq: 10), allowed to warm to 22° C., the solid dissolved completely and it was stirred at 22° C. for 30 min to give complete conversion. The solvent was removed under reduced pressure and dried in HV to give (2-((2-(aminomethyl)-4-bromo-6-chlorophenyl)thio)phenyl)methanol hydrochloride. (334 mg, 119%) off-white solid.

LC-MS: m/z=358.0 (M+H)+(free amine MW 358.68; 356.96 for monoisotopic mass)

To a solution of (2-((2-(aminomethyl)-4-bromo-6-chlorophenyl)thio)phenyl)methanol hydrochloride (267 mg, 676 μmol, Eq: 1) in Methanol (15 ml) was added at 22° C. pyridine (214 mg, 219 μl, 2.7 mmol, Eq: 4) followed by a suspension of (9H-fluoren-9-yl)methyl (2,5-dioxopyrrolidin-1-yl) carbonate (239 mg, 709 μmol, Eq: 1.05) in Methanol (3 ml) and stirred at 22° C. for 1 h, but still educt was observed. After total 16 h more solid had precipitated and conversion was nearly complete. The solid was filtered off, washed with methanol (2×3 ml) and dried in high vacuum to give (9H-fluoren-9-yl)methyl 5-bromo-3-chloro-2-((2-(hydroxymethyl)phenyl)thio)benzylcarbamate (230 mg, 59%) as white solid.

LC-MS: m/z=562.0 (M+H−H2O)+ for monoisotopic mass 579.03

To a solution of (9H-fluoren-9-yl)methyl 5-bromo-3-chloro-2-((2-(hydroxymethyl)phenyl)thio)benzylcarbamate (205 mg, 353 μmol, Eq: 1) in THF (7 ml) and DCM (7 ml)

(slightly warmed to dissolve all solid) was added at 22° C. manganese dioxide (614 mg, 7.06 mmol, Eq: 20) and stirred at 22° C. for 3 h to give conversion complete. The mixture was filtered (0.45 RC syringe-filter), washed with THF/DCM 1:1 (2×2 ml) and the filtrate was evaporated to give 193 mg crude product. The crude product was suspended in 6 ml DCM/MeOH 1:1, the solid was filtered off and washed with MeOH (1×2 ml) and DCM (1×2 ml), dried in HV to give the title compound (99 mg, 49%) as white solid.

The filtrate was concentrated (DCM was removed) and the resulting suspension again filtered. The solid was washed with MeOH (2×2 ml), dried in HV to give the title compound (60 mg, 29%) as white solid.

LC-MS: m/z=560.0 (M+H−H2O)+ for monoisotopic mass 577.01 (weak ionisation for molecular mass; main signal for benzyl cation after loss of water) total yield: 159 mg=78%

1H NMR (600 MHz, CDCl$_3$) δ 10.26 (s, 1H), 7.86 (br d, J=7.4 Hz, 1H), 7.76 (br d, J=7.5 Hz, 3H), 7.70 (d, J=2.1 Hz, 1H), 7.65 (s, 1H), 7.52 (br d, J=7.3 Hz, 2H), 7.28-7.45 (m, 8H), 6.56 (br d, J=8.0 Hz, 1H), 5.16-5.26 (m, 1H), 4.48 (br d, J=6.3 Hz, 2H), 4.38 (br d, J=6.7 Hz, 2H), 4.16 (br t, J=6.9 Hz, 1H)

Intermediate 90

(9H-Fluoren-9-yl)methyl ((2,5-dichloro-3-((2-formylphenyl)thio)pyridin-4-yl)methyl)carbamate

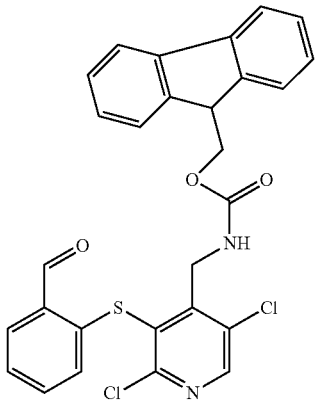 [SMILES: O=Cc1ccccc1Sc1c(Cl)ncc(Cl)c1CNC(=O)OCC1c2ccccc2-c2ccccc21]

This material was prepared in analogy to Intermediate 68 starting from 2,3,5-trichloroisonicotinaldehyde and methyl 2-mercaptobenzoate. The title compound was obtained as white solid (2.7 g). NMR (300 MHz, CHLOROFORM-d) δ=10.27 (s, 1H), 8.52 (s, 1H), 7.94-7.83 (m, 1H), 7.75 (d, J=1.1 Hz, 2H), 7.53-7.28 (m, 8H), 6.56 (br d, J=7.5 Hz, 1H), 5.24 (br s, 1H), 4.76 (br d, J=6.0 Hz, 2H), 4.30 (br d, J=6.4 Hz, 2H), 4.10 (br s, 1H)

Intermediate 91

(9H-Fluoren-9-yl)methyl ((2-chloro-5-((2-formylphenyl)thio)pyridin-4-yl)methyl)carbamate

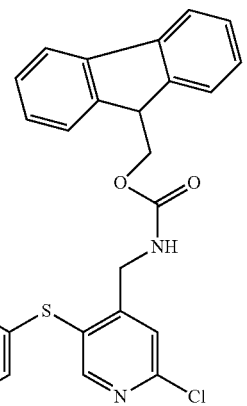

This material was prepared in analogy to Intermediate 68 starting from 2-chloro-5-fluoroisonicotinaldehyde and methyl 2-mercaptobenzoate. The title compound was obtained as white solid (220 mg). MS ESI (m/z): 501.2 [(M+H)$^+$]

Intermediate 92

(9H-Fluoren-9-yl)methyl 3-chloro-2-((3-formylpyridin-4-yl)thio)-5-(trifluoromethyl)benzylcarbamate

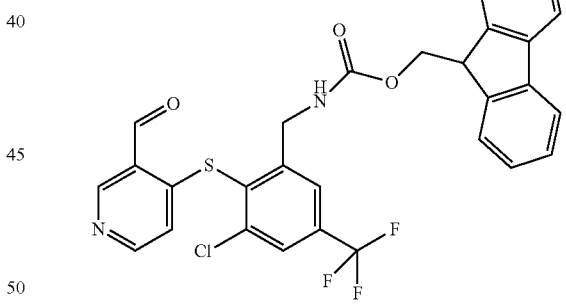

To a stirred solution of 3-chloro-2-fluoro-5-(trifluoromethyl)benzaldehyde (5 g, 22.07 mmol) in THF (100 ml) were added 2-methylpropane-2-sulfinamide (2.675 g, 22.07 mmol) and Ti(OEt)$_4$ (23.3 ml, 110.35 mmol) and heated at 70° C. for 2 h. The reaction mixture was quenched with brine solution, ethyl acetate was added and filtered. The layers were separated and the aqueous layer was extracted with ethyl acetate. The combined organic layers were dried over anhydrous sodium sulfate and concentrated under vacuum. The crude, thus obtained was purified by silica gel chromatography using ethyl acetate in hexane (0-5%) as eluting solvent to afford N-[(1Z)-[3-chloro-2-fluoro-5-(trifluoromethyl)phenyl]methylidene]-2-methyl propane-2-sulfinamide (5.54 g, 76.13%) as yellow liquid. LC-MS: 330.1 [M+H]$^+$.

To a suspension of Na₂S·xH₂O (0.473 g, 6.07 mmol) in DMA (30 ml) was added MgSO₄ (4 g) and heated at 105° C. for 1 h. Then N-[(1Z)-[3-chloro-2-fluoro-5-(trifluoromethyl)phenyl]methylidene]-2-methyl propane-2-sulfinamide (1 g, 3.03 mmol) in DMA (2 ml), MgSO₄ (0.2 g) was added to the reaction mixture at the same temperature and continued heating for another 1 h. Reaction mixture was then cooled to 0° C., Ac₂O (1.2 ml, 6.07 mmol) was added slowly and stirred at 0° C. for another 30 min. The reaction mixture was then quenched with water (50 ml) and extracted with ethyl acetate. The combined organic layers were washed with water, dried over anhydrous sodium sulfate and concentrated under vacuum to afford crude, which was purified (combined with another parallel batch) by silica gel chromatography using ethyl acetate in n-hexane (0-6%) as eluting solvent to afford N-[(1Z)-[2-(acetylsulfanyl)-3-chloro-5-(trifluoromethyl)phenyl]methylidene]-2-methyl-propane-2-sulfinamide (1.12 g, 48%) as brown liquid. LC-MS: 385.7 [M+H]⁺.

A solution of N-[(1Z)-[2-(acetylsulfanyl)-3-chloro-5-(trifluoromethyl)phenyl]methylidene]-2-methyl propane-2-sulfinamide (160 mg, 0.42 mmol) in THF (5 ml) was degassed with argon and then DTT (64 mg, 0.42 mmol) was added. Then reaction mixture was cooled to 0° C., NaBH₄ (156.9 mg, 4.15 mmol) was added portion wise into the reaction mixture and stirred at the same temperature for 30 min. The reaction mixture was then quenched with water (degassed with argon) and extracted with ethyl acetate (degassed with argon) at 0° C. The organic layer was separated, dried over anhydrous sodium sulfate and concentrated under vacuum (all processes done under argon atmosphere) to afford N-{[3-chloro-2-sulfanyl-5-(trifluoromethyl)phenyl]methyl}-2-methyl propane-2-sulfinamide (130 mg, crude) as light yellow solid, which was used as such in the next step. LC-MS: 344.2 [M−H]⁻.

To a stirred solution of N-{[3-chloro-2-sulfanyl-5-(trifluoromethyl)phenyl]methyl}-2-methylpropane-2-sulfinamide (crude, 100 mg, 0.29 mmol) in dioxane (degassed with argon, 3 ml) were added DTT (44.6 mg, 0.29 mmol), 4-chloropyridine-3-carbaldehyde (49.1 mg, 0.35 mmol), DIPEA (0.2 ml, 1.16 mmol) and purged with argon. Then xantphos (16.7 mg, 0.03 mmol), Pd₂(dba)₃ (13.2 mg, 0.01 mmol) were added to the reaction mixture, again purged with argon and heated at 110° C. for 1.5 h. The reaction mixture was quenched with water (20 ml) and extracted with ethyl acetate. The combined organic layers were dried over anhydrous sodium sulfate and concentrated under vacuum. The crude, thus obtained was purified by silica gel chromatography using ethyl acetate in n-hexane (0-50%) as eluting solvent to afford N-({3-chloro-2-[(3-formylpyridin-4-yl)sulfanyl]-5-(trifluoromethyl)phenyl}methyl)-2-methylpropane-2-sulfinamide (61 mg, 42%, over 2 steps) as brown solid. LC-MS: 451.02 [M+H]⁺.

To a stirred solution of N-({3-chloro-2-[(3-formylpyridin-4-yl)sulfanyl]-5-(trifluoromethyl)phenyl}methyl)-2-methylpropane-2-sulfinamide (700 mg, 1.55 mmol) in THF (10 ml) was added NaBH₄ (88.1 mg, 2.33 mmol) portion wise at 0° C. and stirred at 25° C. for 30 min. The reaction mixture was then quenched with aqueous saturated ammonium chloride solution (15 ml) and extracted with ethyl acetate. The combined organic layers were dried over anhydrous sodium sulfate and concentrated under vacuum to afford N-[(3-chloro-2-{[3-(hydroxymethyl)pyridin-4-yl]sulfanyl}-5-(trifluoromethyl)phenyl)methyl]-2-methylpropane-2-sulfinamide (685 mg, crude) and was used without further purification. LC-MS: 452.8 [M+H]⁺.

To a stirred solution of N-[(3-chloro-2-{[3-(hydroxymethyl)pyridin-4-yl]sulfanyl}-5-(trifluoromethyl)phenyl)methyl]-2-methyl propane-2-sulfinamide (crude, 680 mg, 1.5 mmol) in MeOH (10 ml), was added 4N HCl in dioxan (20 ml) at 0° C. and stirred at 25° C. for 30 min. After completion, reaction mixture was concentrated under vacuum to afford (4-{[2-(aminomethyl)-6-chloro-4-(trifluoromethyl)phenyl]sulfanyl}pyridin-3-yl)methanol hydrochloride (566 mg, crude) as brown solid and used without further purification. LC-MS: 348.6 [M+H]⁺.

To a stirred suspension of (4-{[2-(aminomethyl)-6-chloro-4-(trifluoromethyl)phenyl]sulfanyl}pyridin-3-yl)methanol hydrochloride (crude, 560 mg, 1.45 mmol) in 5% aqueous NaHCO₃ (15 ml) was added Fmoc-OSu (490.3 mg, 1.45 mmol) in acetonitrile (25 ml) and stirred at 25° C. for 30 min. The reaction mixture was diluted with water (25 ml) and extracted with ethyl acetate. The combined organic layers were dried over anhydrous sodium sulfate and concentrated under vacuum. The crude, thus obtained was purified by silica gel chromatography using ethyl acetate in n-hexane (0-80%) as eluting solvent to afford 9H-fluoren-9-ylmethyl N-[(3-chloro-2-{[3-(hydroxymethyl)pyridin-4-yl]sulfanyl}-5-(trifluoromethyl)phenyl)methyl]carbamate (305 mg, 49% over 3 steps). LC-MS: 570.6 [M+H]⁺.

To a stirred solution of 9H-fluoren-9-ylmethyl N-[(3-chloro-2-{[3-(hydroxymethyl)pyridin-4-yl]sulfanyl}-5-(trifluoromethyl)phenyl)methyl]carbamate (410 mg, 0.72 mmol) in DCM (10 ml) and THF (10 ml) was added MnO₂ (624.2 mg, 7.18 mmol) and stirred at 25° C. for 1 h. After completion of reaction, reaction mixture was filtered and concentrated under vacuum to afford crude, which was purified by silica gel column chromatography using ethyl acetate in n-hexane (0-20%) as eluting solvent to afford 9H-fluoren-9-ylmethyl N-({3-chloro-2-[(3-formylpyridin-4-yl)sulfanyl]-5-(trifluoromethyl)phenyl}methyl) carbamate (151 mg, 37%) as white solid. LC-MS: 569.2 [M+H]⁺.

1H NMR: (400 MHz, Chloroform-d) δ 4.11-4.21 (1H, m), 4.40 (2H, d, J=6.8 Hz), 4.48-4.55 (2H, m), 5.24 (1H, ddt, J=6.1, 3.5, 1.0 Hz), 6.36-6.44 (1H, m), 7.26-7.34 (2H, m), 7.39 (2H, t, J=6.6 Hz), 7.48-7.56 (2H, m), 7.71-7.77 (3H, m), 7.80 (1H, s), 8.35-8.44 (1H, m), 8.94 (1H, s), 10.24 (1H, s).

Intermediate 93

(9H-Fluoren-9-yl)methyl ((5-chloro-4-((3-formylpyridin-2-yl)thio)pyridin-3-yl)methyl)carbamate

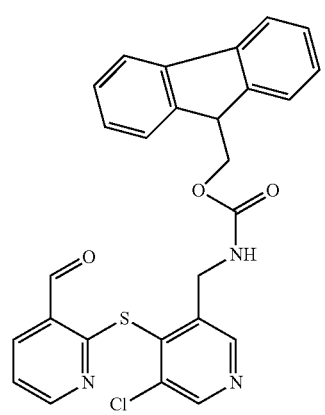 [SMILES: O=Cc1cccnc1Sc1c(Cl)cncc1CNC(=O)OCC1c2ccccc2-c2ccccc21]

This material was prepared in analogy to Intermediate 78 starting from 4,5-dichloronicotinaldehyde and 2-mercaptonicotinic acid. The title compound was obtained as light yellow foam (151 mg). MS ESI (m/z): 502.1 [(M+H)$^+$]

Intermediate 94

(9H-Fluoren-9-yl)methyl ((5-chloro-4-((2-formylphenyl)thio)pyridin-3-yl)methyl)carbamate

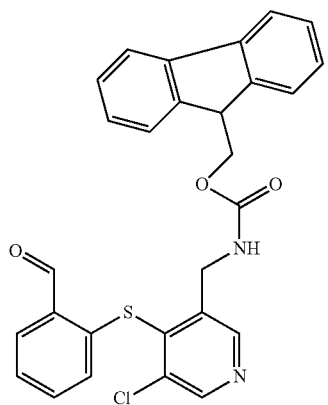 [SMILES: O=Cc1ccccc1Sc1c(Cl)cncc1CNC(=O)OCC1c2ccccc2-c2ccccc21]

This material was prepared in analogy to Intermediate 77 starting from 4,5-dichloronicotinaldehyde and methyl 2-mercaptobenzoate. The title compound was obtained as light yellow foam (361 mg). MS ESI (m/z): 501.1 [(M+H)$^+$]

Intermediate 95

(9H-Fluoren-9-yl)methyl ((2-chloro-5-((3-formylpyridin-2-yl)thio)pyridin-4-yl)methyl)carbamate

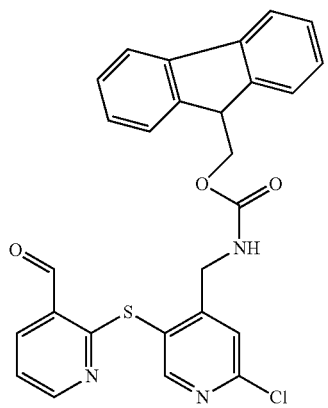 [SMILES: O=Cc1cccnc1Sc1cnc(Cl)cc1CNC(=O)OCC1c2ccccc2-c2ccccc21]

A mixture of 2-mercaptonicotinic acid (2.5 g, 16.1 mmol, Eq: 1) and Na$_2$CO$_3$ (5.12 g, 48.3 mmol, Eq: 3) in DMSO (53.7 ml) in a pressure tube was sparged with argon. Then 2-chloro-5-fluoroisonicotinaldehyde (2.57 g, 1.79 ml, 16.1 mmol, Eq: 1) was added, the tube sealed and the reaction mixture stirred at 90° C. for 1.5 h. The mixture was cooled to room temperature, then dimethyl sulfate (6.1 g, 4.62 ml, 48.3 mmol, Eq: 3) was added slowly and the mixture stirred at room temperature for 1 h. Then a solution of 25% aq. ammonia (4.5 g, 5 ml, 66.1 mmol, Eq: 4.1) and 5 ml water was added slowly at max. 24° C. and the mixture stirred at room temperature for 1 h. The reaction mixture was poured into water and extracted with EtOAc. The organic layers were dried over Na$_2$SO$_4$ and concentrated in vacuo. The crude material was purified by silica gel chromatography using heptane/ethyl acetate as eluent. Methyl 2-((6-chloro-4-formylpyridin-3-yl)thio)nicotinate was obtained as yellow solid (848 mg). MS ESI (m/z): 309.0 [(M+H)$^+$]

Intermediate 96

9H-Fluoren-9-ylmethyl N-({3-chloro-2-[(3-formylpyridin-2-yl) sulfanyl]-5-[2-(morpholin-4-yl)pyridin-4-yl]phenyl}methyl) carbamate

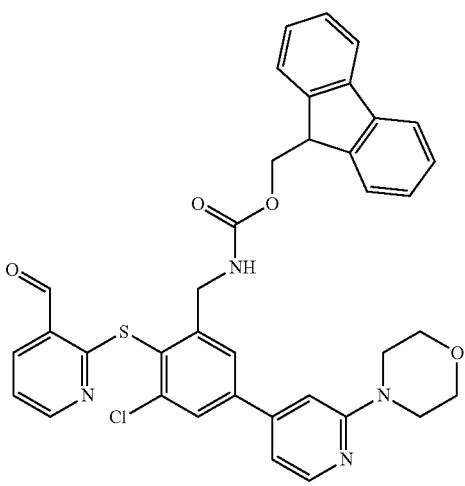 [SMILES: O=Cc1cccnc1Sc1c(Cl)cc(-c2ccnc(N3CCOCC3)c2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (1.5 g, 2.6 mmol) in dioxan (10 mL) were added 4-[4-(tetramethyl-1,3,2-dioxaborolan-2-yl)pyridin-2-yl]morpholine (905 mg, 3.12 mmol), Na$_2$CO$_3$ (827 mg, 7.8 mmol), water (5 mL) and degassed for 10 min in argon atmosphere. Then to it was added Pd(PPh$_3$)$_4$ (300 mg, 0.26 mmol) and again degassed for 5 min. The reaction mass was heated to 120° C. for 16 h. Reaction mixture was then cooled to 25° C., filtered through celite pad and washed with EtOAc. The separated organic layer was washed with brine solution, dried over sodium sulfate and concentrated under reduced pressure to get the crude which was purified by column chromatography (SiO$_2$; 100-200 mesh; 50-90% EtOAc/Hexanes) to get N-({2-[(3-{[(tert-butyldimethylsilyl)oxy] methyl}pyridin-2-yl) sulfanyl]-3-chloro-5-[2-(morpholin-4-yl)pyridin-4-yl]phenyl}methyl)-2-methylpropane-2-sulfinamide (1.1 g, 63%) as off white solid. LC-MS: 661.5 [M+H]$^+$ To a stirred solution of N-({2-[(3-{[(tert-butyldimethylsilyl)oxy]methyl}pyridin-2-yl)sulfanyl]-3-chloro-5-[2-(morpholin-4-yl)pyridin-4-yl]phenyl}methyl)-2-methylpropane-2-sulfinamide (1.1 g, 1.7 mmol) in MeOH (20 mL), was added 4M HCl in dioxan (10 mL) at 0° C. and reaction mixture was stirred at 25° C. for 2h. Reaction mass was evaporated under reduced pressure to get (2-{[2-(aminomethyl)-6-chloro-4-[2-(morpholin-4-yl)pyridin-4-yl]phenyl]sulfanyl}pyridin-3-yl) methanol hydrochloride (900 mg) which was directly used for next step without further purification. LC-MS: 443.2 [M+H]$^+$ To a stirred suspension of (2-{[2-(amino methyl)-6-chloro-4-[2-(morpholin-4-yl)pyridin-4-yl]phenyl]sulfanyl}pyridin-3-yl) methanol hydrochloride (900 mg, 1.98 mmol) in 5% NaHCO$_3$ (15 mL) was added Fmoc-OSU (0.667 g, 1.98 mmol) in dioxan (15 mL) at 25° C. and reaction mass was stirred at the same temperature for 16h. Then reaction mass was diluted with water and extracted with 10% methanol in dichloromethane. The separated organic layer was washed with brine solution, dried over sodium sulfate and evaporated under reduced pressure to give 9H-fluoren-9-ylmethyl N-[(3-chloro-2-{[3-(hydroxymethyl)pyridin-2-yl]sulfanyl}-5-[2-(morpholin-4-yl)pyridin-4-yl]phenyl)methyl]carbamate (1.0 g) as sticky solid, which was used for next step without further purification. LC-MS: 665.3 [M+H]$^+$ To a stirred solution of 9H-fluoren-9-ylmethyl N-[(3-chloro-2-{[3-(hydroxymethyl)pyridin-2-yl]sulfanyl}-5-[2-(morpholin-4-yl)pyridin-4-yl]phenyl)methyl]carbamate in DCM:THF (1:1, 20 mL) was added MnO$_2$ (2.62 g, 30.1 mmol) and reaction mass was stirred at 25° C. for 2 h. The reaction mass was filtered through celite pad and the filtrate was evaporated under reduced pressure. The crude material obtained was purified by column chromatography (SiO$_2$; 100-200 mesh; 40-70% EtOAc/Hexanes) to get 9H-fluoren-9-ylmethyl N-({3-chloro-2-[(3-formylpyridin-2-yl)sulfanyl]-5-[2-(morpholin-4-yl)pyridin-4-yl]phenyl}methyl)carbamate (290 mg) as off-white solid with 88.5% purity. LC-MS: 663.2 [M+H]$^+$ 1H NMR (400 MHz, DMSO-d6): δ 3.53 (4H, s), 3.69 (4H, s), 4.21 (1H, d, J=5.9 Hz), 4.26 (2H, d, J=6.4 Hz), 4.36 (2H, d, J=5.1 Hz), 6.99 (1H, d, J=4.5 Hz), 7.13 (1H, s), 7.27 (1H, d, J=7.3 Hz), 7.39 (3H, t, J=7.0 Hz), 7.61 (1H, d, J=11.7 Hz), 7.67 (2H, d, J=7.4 Hz), 7.73 (1H, s), 7.88 (3H, d, J=7.5 Hz), 7.99 (1H, s), 8.22 (1H, d, J=5.0 Hz), 8.38 (1H, d, J=7.1 Hz), 8.43 (1H, s), 10.22 (1H, s).

Intermediate 97

9H-Fluoren-9-ylmethyl N-{[3-chloro-5-(2-chloropyridin-4-yl)-2-[(3-formylpyridin-2-yl)sulfanyl]phenyl]methyl}carbamate

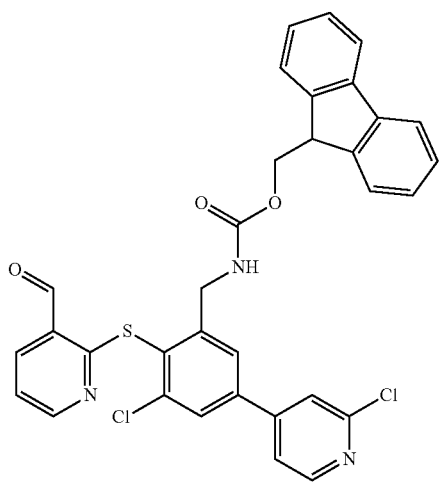 [SMILES: O=Cc1cccnc1Sc1c(Cl)cc(-c2ccnc(Cl)c2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2.5 g, 4.3 mmol) in dioxan (20 mL) were added (2-chloropyridin-4-yl)boronic acid (818 mg, 5.2 mmol), Na$_2$CO$_3$ (1.4 g, 13 mmol), water (10 mL) and degassed for 10 min in argon atmosphere. To this was added Pd(PPh$_3$)$_4$ (501 mg, 0.43 mmol) and again degassed for 5 min. The reaction mass was heated to 120° C. for 16 h. Reaction mixture was cooled to 25° C., filtered through celite pad and washed with EtOAc. The separated organic layer was washed with brine solution, dried over anhydrous sodium sulfate and concentrated under reduced pressure. The crude thus obtained was purified by silica column chromatography (SiO$_2$; 100-200 mesh; 50-90% EtOAC/Hexanes) to get N-({2-[(3-{[(tert-butyldimethylsilyl)oxy]methyl}pyridin-2-yl)sulfanyl]-3-chloro-5-(2-chloropyridin-4-yl)phenyl}methyl)-2-methylpropane-2-sulfinamide (2.8 g) as off white solid. LC-MS: 609.8 [M+H]$^+$ To a stirred solution of N-({2-[(3-{[(tert-butyldimethylsilyl)oxy]methyl}pyridin-2-yl)sulfanyl]-3-chloro-5-(2-chloropyridin-4-yl)phenyl}methyl)-2-methylpropane-2-sulfinamide (2.8 g, 4.6 mmol) in MeOH (30 mL), was added 4M HCl in dioxan (15 mL) at 0° C. and reaction mixture was stirred at 25° C. for 2h. Reaction mass was evaporated under reduced pressure to get (2-{[2-(aminomethyl)-6-chloro-4-(2-chloropyridin-4-yl)phenyl]sulfanyl}pyridin-3-yl) methanol hydrochloride (1.5 g) as off white sticky solid, which was directly used for next step without further purification. LC-MS: 392.2 [M+H]$^+$ To a stirred suspension of (2-{[2-(aminomethyl)-6-chloro-4-(2-chloropyridin-4-yl)phenyl]sulfanyl}pyridin-3-yl)methanol hydrochloride (1.5 g, 3.8 mmol) in 5% NaHCO$_3$ (20 mL) was added Fmoc-OSU (1.3 g, 3.8 mmol) in dioxan (20 mL) at 25° C. and reaction mass was stirred at the same temperature for 16h. Then reaction mass was diluted with water and extracted with EtOAc. The separated organic layer was washed with brine, dried over sodium sulfate and evaporated under reduced pressure to get 9H-fluoren-9-ylmethyl N-{[3-chloro-5-(2-chloropyridin-4-yl)-2-{[3-(hydroxymethyl)pyridin-2-yl]sulfanyl}phenyl]methyl}carbamate (2.7 g) as off white solid; which was used for next step without further purification. LC-MS: 614.3 [M+H]$^+$ To a stirred solution 9H-fluoren-9-ylmethyl N-{[3-chloro-5-(2-chloropyridin-4-yl)-2-{[3-(hydroxymethyl)pyridin-2-yl]sulfanyl}phenyl]methyl}carbamate in DCM:THF (1:1, 40 mL) was added MnO$_2$ (7.66 g, 88.1 mmol) and reaction mass was stirred at 25° C. for 2 h. The reaction mass was filtered through celite pad and the filtrate was evaporated under reduced pressure. The crude thus obtained was purified by column chromatography (SiO$_2$; 100-200 mesh; 40-80% EtOAc/Hexanes) to 9H-fluoren-9-ylmethyl N-{[3-chloro-5-(2-chloropyridin-4-yl)-2-[(3-formylpyridin-2-yl)sulfanyl]phenyl]methyl}carbamate (1.5 g) as off-white solid with 96.46% purity. LC-MS: 612.2 [M+H]$^+$ 1H NMR (400 MHz, DMSO-d6): δ 4.19-4.37 (5H, m), 7.27 (2H, t, J=7.36 Hz), 7.36-7.39 (3H, m), 7.67 (2H, d, J=7.2 Hz), 7.81 (3H, m), 7.88 (2H, d, J=7.21 Hz), 7.94 (1H, m), 8.37 (1H, d, J=7.31 Hz), 8.34 (1H, m), 8.54 (1H, d, J=5.12 Hz), 10.21 (1H, s)

Intermediate 98

9H-fluoren-9-ylmethyl N-({3-chloro-2-[(3-formylpyridin-2-yl)sulfanyl]-5-(6-hydroxypyridin-3-yl)phenyl}methyl)carbamate

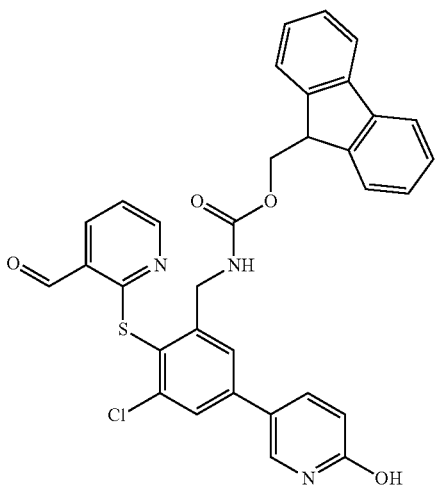 [SMILES: O=Cc1cccnc1Sc1c(Cl)cc(-c2ccc(O)nc2)cc1CNC(=O)OCC1c2ccccc2-c2ccccc21]

A solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2.5 g, 4.3 mmol), (6-hydroxypyridin-3-yl)boronic acid (0.79 g, 5.6 mmol) and sodium carbonate (1.38 g, 13 mmol) in 1,4-dioxane (20 mL) and water (5 mL) in a sealed tube was degassed with argon for 10 min and Pd(PPh$_3$)$_4$ (0.25 g, 0.22 mmol) was added. The reaction mixture was heated at 120° C. for 16 h. Progress of the reaction was monitored by TLC. Crude mixture was diluted with water and extracted with EtOAc (100 mL×2). Combined organic layer was washed with brine and dried over sodium sulphate, evaporated under reduced pressure to get the crude compound which was purified by combiflash (70% ethyl acetate in hexane) to afford N-({2-[(3-{[(tert-butyldimethylsilyl)oxy]methyl}pyridin-2-yl)sulfanyl]-3-chloro-5-(6-hydroxypyridin-3-yl)phenyl}methyl)-2-methylpropane-2-sulfinamide (1.0 g) as a brown-orange solid. LC-MS: 592.1 [M+H]$^+$ To an ice-cooled solution of N-({2-[(3-{[(tert-butyldimethylsilyl)oxy]methyl}pyridin-2-yl)sulfanyl]-3-chloro-5-(6-hydroxypyridin-3-yl)phenyl}methyl)-2-methylpropane-2-sulfinamide (1.0 g, 1.69 mmol) in MeOH (20 mL) was added 4M HCl/dioxane (10 mL) and the reaction mixture was stirred at 25° C. for 2h. Volatiles were removed under reduced pressure to get crude compound which was washed with diethyl ether (50 mL×2) to get 5-(3-chloro-5-ethyl-4-{[3-(hydroxymethyl)pyridin-2-yl]sulfanyl}phenyl)pyridin-2-ol hydrochloride (1.0 g, crude) as yellow solid. LC-MS: 373.8 [M+H]$^+$ To a stirred solution of 5-(3-chloro-5-ethyl-4-{[3-(hydroxymethyl)pyridin-2-yl]sulfanyl}phenyl)pyridin-2-ol hydrochloride (1.0 g, 2.69 mmol) in CH$_3$CN (20 mL) was added 5% NaHCO$_3$ solution (20 mL) followed by Fmoc-OSu (0.9 g, 2.69 mmol) in CH$_3$CN (10 mL) drop-wise and the reaction mixture was stirred at 25° C. for 2h. Then the reaction mixture was diluted with water (50.0 mL) and extracted with ethyl acetate (3×50 mL). Combined organic layer was washed with brine solution (3×20 mL), dried over anhydrous sodium sulphate and evaporated under reduced pressure to get 9H-fluoren-9-ylmethyl N-[(3-chloro-2-{[3-(hydroxymethyl)pyridin-2-yl]sulfanyl}-5-(6-hydroxypyridin-3-yl)phenyl)methyl]carbamate (1.0 g) as white solid. LC-MS: 593.8 [M+H]$^+$ To an ice-cooled solution of 9H-fluoren-9-ylmethyl N-[(3-chloro-2-{[3-(hydroxymethyl)pyridin-2-yl]sulfanyl}-5-(6-hydroxypyridin-3-yl)phenyl)methyl]carbamate (1.2 g) in DCM (30 mL) was added Dess-Martin periodinane (1.28 g, 3.02 mmol) portion-wise. The resulting mixture was then stirred at ambient temperature for 2 h. Progress of the reaction was monitored by TLC. After completion the reaction mixture was poured onto saturated sodium bicarbonate solution (100 mL) and organic layer was separated off. Organic layer was washed with sodium thiosulphate solution (2×50 mL), dried over sodium sulphate and concentrated under reduced pressure and the resulting crude compound was purified by combiflash (70% ethyl acetate in hexane) to afford 9H-fluoren-9-ylmethyl N-({3-chloro-2-[(3-formylpyridin-2-yl)sulfanyl]-5-(6-hydroxypyridin-3-yl)phenyl}methyl)carbamate (0.25 g) as brown-orange solid with 92% LCMS purity. LC-MS: 594.3 [M+H]$^+$ 1H NMR (400 MHz, DMSO-d6) δ 4.21 (1H, d, J=6.1 Hz), 4.26 (2H, d, J=6.7 Hz), 4.32 (2H, d, J=5.8 Hz), 6.45 (1H, d, J=9.5 Hz), 7.28 (2H, t, J=7.4 Hz), 7.34-7.44 (3H, m), 7.57 (1H, d, J=1.5 Hz), 7.67 (2H, d, J=7.5 Hz), 7.78-7.92 (7H, m), 8.36 (1H, dd, J=7.6, 1.7 Hz), 8.43 (1H, dd, J=4.7, 1.7 Hz), 10.20 (1H, s), 12.04 (1H, s)

Intermediate 99

9H-fluoren-9-ylmethyl N-({3-chloro-5-[6-(dimethylamino)pyridin-3-yl]-2-[(3-formylpyridin-2-yl)sulfanyl]phenyl}methyl)carbamate

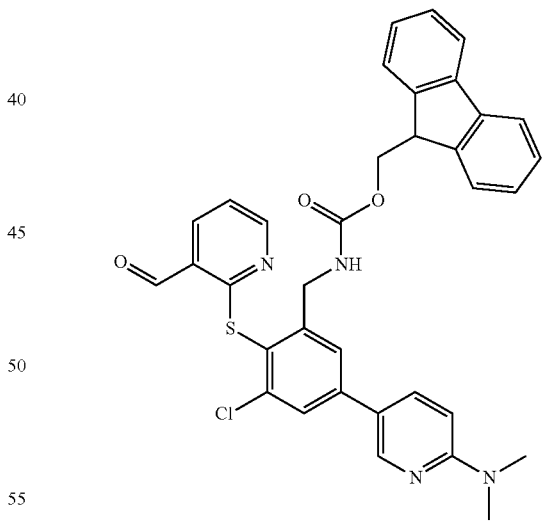

A solution of NA{5-bromo-2-[(3-{[(tert-butyldimethylsilyl)oxy]methyl}pyridin-2-yl)sulfanyl]-3-chlorophenyl}methyl)-2-methylpropane-2-sulfinamide (2.5 g, 4.33 mmol), [6-(dimethylamino)pyridine-3-yl]boronic acid (0.93 g, 5.63 mmol) and sodium carbonate (1.38 g, 13 mmol) in 1,4-dioxane (20 mL) and water (5 mL) was degassed with argon for 10 min and Pd(PPh$_3$)$_4$ (0.25 g, 0.22 mmol) was added. Then the reaction mixture was heated at 120° C. for 2 h. Progress of the reaction was monitored by TLC. Crude reaction mixture was diluted with water and extracted with EtOAc (100 mL×2). Combined organic layer was washed with brine and dried over sodium sulphate and concentrated under reduced pressure. Crude compound was purified by combiflash (80% ethyl acetate in hexane) to afford N-({2-[(3-{[(tert-butyldimethylsilyl)oxy]methyl}pyridin-2-yl)sulfanyl]-3-chloro-5-[6-(dimethylamino)pyridin-3-yl]phenyl}methyl)-2-methylpropane-2-sulfinamide (0.85 g) as an off-white solid. LC-MS: 618.8 [M+H]$^+$ To an ice-cooled solution of N-({2-[(3-{[(tert-butyldimethylsilyl)oxy]methyl}pyridin-2-yl) sulfanyl]-3-chloro-5-[6-(dimethylamino)pyridin-3-yl]phenyl}methyl)-2-methylpropane-2-sulfinamide (0.85 g, 1.4 mmol) in MeOH (20 mL) was added 4M HCl in dioxane (8.0 mL) and the reaction mixture was stirred at 25° C. for 2h. Volatiles were removed under reduced pressure to get crude compound which was washed with diethyl ether (50 mL×2) to get [2-({2-chloro-4-[6-(dimethylamino)pyridin-3-yl]-6-ethylphenyl}sulfanyl)pyridin-3-yl]methanol hydrochloride (1.0 g) as yellow solid. LC-MS: 400.8 [M+H]$^+$ To a stirred suspension of [2-({2-chloro-4-[6-(dimethylamino)pyridin-3-yl]-6-ethylphenyl}sulfanyl)pyridin-3-yl]methanol hydrochloride (1.0 g, crude, 2.5 mmol) in CH$_3$CN (20.0 mL) was added 5% NaHCO$_3$ (20 mL) followed by Fmoc-OSu (0.84 g, 2.5 mmol) in CH$_3$CN (30 mL) and the reaction mixture was stirred at 25° C. for 2h. After completion, the reaction mixture was diluted with water (50 mL) and was extracted with ethyl acetate (3×50 mL). Combined organic layer was washed with brine solution (3×20 mL), dried over anhydrous sodium sulphate and evaporated under reduced pressure to get 9H-fluoren-9-ylmethyl N-({3-chloro-5-[6-(dimethylamino)pyridin-3-yl]-2-{[3-(hydroxymethyl)pyridin-2-yl]sulfanyl}phenyl}methyl)carbamate (1.1 g) as white solid. LC-MS: 623.3 [M+H]$^+$ To an ice-cooled solution of 9H-fluoren-9-ylmethyl N-({3-chloro-5-[6-(dimethylamino)pyridin-3-yl]-2-{[3-(hydroxymethyl)pyridin-2-yl]sulfanyl}phenyl}methyl)carbamate (1.1 g) in DCM (30 mL) was added Dess-Martin periodinane (1.12 g, 2.65 mmol) portion-wise and the reaction mixture was then stirred at 25° C. for 2 h. Then the reaction mixture was poured onto saturated sodium bicarbonate solution (2×50 mL) and organic layer was separated off. Organic layer was washed with sodium thiosulphate solution (2×50 mL), dried over sodium sulphate and concentrated under reduced pressure to give crude compound which was purified by combiflash (2% MeOH in DCM) to afford 9H-fluoren-9-ylmethyl N-({3-chloro-5-[6-(dimethylamino)pyridin-3-yl]-2-[(3-formylpyridin-2-yl)sulfanyl]phenyl}methyl)carbamate (0.35 g) as brown-orange solid with 91% LCMS purity. LC-MS: 621.2 [M+H]$^+$ 1H NMR (400 MHz, DMSO-d6) δ 3.10 (6H, s), 4.22 (1H, d, J=6.1 Hz), 4.27 (2H, d, J=6.6 Hz), 4.33 (2H, d, J=5.9 Hz), 7.29 (2H, t, J=7.5 Hz), 7.33-7.46 (4H, m), 7.62 (1H, s), 7.69 (2H, d, J=7.5 Hz), 7.81 (1H, d, J=1.6 Hz), 7.88 (4H, d, J=8.1 Hz), 8.37 (1H, dd, J=7.6, 1.6 Hz), 8.45 (1H, dd, J=4.6, 1.6 Hz), 8.52 (1H, d, J=2.2 Hz), 10.21 (1H, s)

Intermediate 100

9H-fluoren-9-ylmethyl N-[[4-bromo-3-chloro-2-(2-formylphenyl)sulfanyl-phenyl]methyl]carbamate

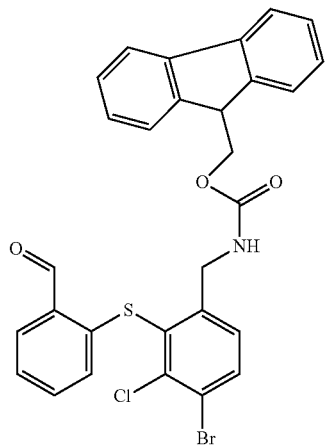 [SMILES: O=Cc1ccccc1Sc1c(CNC(=O)OCC2c3ccccc3-c3ccccc32)ccc(Br)c1Cl]

To a mechanical-stirred solution of diisopropylamine (5.02 g, 7.08 ml, 49.7 mmol, Eq: 1.04) in THF (35 ml) was added dropwise (5 min) at −20° C. n-butyllithium, 1.6 M in hexane (31 ml, 49.7 mmol, Eq: 1.04) and stirred at 0° C. for 20 minutes. The mixture was cooled to −78° C. followed by dropwise addition (20 minutes) of a solution of 1-bromo-2-chloro-3-fluorobenzene (10 g, 47.7 mmol, Eq: 1) in THF (10 ml) and the thick yellow suspension was stirred at −78° C. for 60 min. Then was added dropwise (5 minutes—exotherm) N,N-dimethylformamide (5.23 g, 5.55 ml, 71.6 mmol, Eq: 1.5), the cooling bath was removed and the mixture was allowed to warm to −20° C. to give complete conversion. At −20° C. the clear yellow solution was quenched with sat NH$_4$Cl (100 ml) and extracted with TBME (100 ml). The aqueous layer was extracted again with TBME (50 ml). The organic layers were dried and evaporated at only 50 mbar for short time. The yellow residue was dissolved in heptane/ethyl acetate 10:1 (ca. 30 ml) at 55° C., concentrated to ⅓ and stirred to 22° C. while crystallisation started. After 30 minutes the suspension was cooled to 0° C. for 30 minutes, the solid was filtered off, washed with heptane (2×15 ml) and dried (only short time) to give 4-bromo-3-chloro-2-fluorobenzaldehyde (5.27 g, 47%) as light yellow solid.

The filtrate was evaporated and purified by flash chromatography (silica gel, 70 g, adsorbed on isolute sorbent HM-N, EtOAc in heptane, 0% to 5%) to give additional compound (4.073 g, 36%) as off-white solid.

GC-MS: m/z=235.9 M.+ (monoisotopic mass 235.90)

To a solution of 4-bromo-3-chloro-2-fluorobenzaldehyde (4.073 g, 17.2 mmol, Eq: 1) in DMF (41 ml) was added at 22° C. potassium carbonate (2.37 g, 17.2 mmol, Eq: 1) followed by methyl 2-mercaptobenzoate (2.98 g, 2.43 ml, 17.2 mmol, Eq: 1) (internal temperature rised up to 24° C. cooling with waterbath) and stirred for 1 h to give complete conversion. The yellow emulsion was quenched with water (100 ml—exotherm) and extracted with ethyl acetate (100 ml), but no phase separation. Addition of 5 g sodium chloride to give separation of layers. The aqueous layer was extracted with ethyl acetate (1×50 ml). The organic layers were washed with sat NaCl (1×50 ml), dried and evaporated.

The residue was purified by flash chromatography (silica gel, 330 g, adsorbed on 10 g Isolute HM-N, EtOAc in heptane 0% to 10% to 20% to 40%) to give methyl 2-((3-bromo-2-chloro-6-formylphenyl)thio) benzoate (2.546 g, 39%) as a light yellow solid.

LC-MS: m/z=385.0 (M+H)+(monoisotopic mass 383.92)

To a turbid solution of methyl 2-((3-bromo-2-chloro-6-formylphenyl)thio)benzoate (2.48 g, 6.43 mmol, Eq: 1) and 2-methylpropane-2-sulfinamide (779 mg, 6.43 mmol, Eq: 1) in THF (28 ml) was added at 22° C. Titanium(IV)ethoxide (7.33 g, 6.67 ml, 32.2 mmol, Eq: 5) to give a clear yellow solution followed by heating to reflux and stirred at 70° C. for 30 min to give complete conversion. The light turbid yellow solution was cooled to 22° C. and quenched with sat NaCl (30 ml) to give a thick suspension. The mixture was filtered through dicalite and washed with ethyl acetate (2×30 ml). The filtrate (1-phase-system) was dried and evaporated to give a mixture of (E)-methyl 2-((3-bromo-6-(((tert-butylsulfinyl)imino)methyl)-2-chlorophenyl)thio)benzoate and (E)-ethyl 2-((3-bromo-6-(((tert-butylsulfinyl)imino)methyl)-2-chlorophenyl)thio)benzoate (3.04 g, 6.22 mmol, 97% yield) as yellow solid.

NMR: mixture of methyl- and ethyl-ester, ratio ca. 3:1

LC-MS: m/z=488.0 (M+H)+ for methyl ester (MW 486.97 for monoisotopic mass) and 502.0 (M+H)+ for ethyl ester To a solution of (E)-methyl 2-((3-bromo-6-(((tert-butylsulfinyl)imino)methyl)-2-chlorophenyl)thio)benzoate (3.04 g, 6.22 mmol, Eq: 1, 3:1 mixture of methyl and ethyl esters) in THF (60 ml) was added at 22° C. lithium borohydride (1.35 g, 62.2 mmol, Eq: 10) in one portion under waterbath cooling while color changed immediately to intensive green and internal temperature rised up to 31° C. After decolorisation (5 minutes) the mixture was warmed to 50° C. and stirred at 50° C. for 24 h to give complete conversion. The mixture was cooled to 22° C., quenched dropwise (effervescensing and exothermic—cooling with ice-water bath) with sat NH$_4$Cl (50 ml) and completely extracted with ethyl acetate (1×50 ml). The organic layer was washed with 5% KH2PO4 (1×50 ml, pH 5 to destroy borane-complex) and sat NaCl (1×50 ml), dried and evaporated to give crude product as white solid. The solid was dissolved in 50 ml ethyl acetate under reflux, cooled to 22° C. while 50 ml heptane was added in one portion. The solution was stirred for 30 minutes at 22° C. while crystallisation started. Then cooled to 5° C. and stirred for 30 minutes, the solid was filtered off, washed with EtOAc/Hep 1:1 (1×20 ml) and pentane (1×20 ml) and dried in HV to give N-(4-bromo-3-chloro-2-((2-(hydroxymethyl)phenyl)thio) benzyl)-2-methylpropane-2-sulfinamide (2.296 g, 80%) as white solid.

LC-MS: m/z=484.0 (M+Na)+(monoisotopic mass 460.99)

To a suspension of N-(4-bromo-3-chloro-2-((2-(hydroxymethyl)phenyl)thio)benzyl)-2-methylpropane-2-sulfinamide (1.5 g, 3.24 mmol, Eq: 1) in Methanol (15 ml) was added at 0° C. HCl, 4 M in dioxane (8.1 ml, 32.4 mmol, Eq: 10), allowed to warm to 22° C. while solid dissolved completely and stirred at 22° C. for 60 min to give complete conversion. The solvent was removed under reduced pressure and dried in HV to (2-((6-(aminomethyl)-3-bromo-2-chlorophenyl)thio)phenyl)methanol hydrochloride (1.56 g, 122%) as off-white foam.

NMR: contains tert-butylsulfinic acid, no further purification—used as is in next step LC-MS: m/z=358.0 (M+H)+(monoisotopic mass 356.96)

To a solution of (2-((6-(aminomethyl)-3-bromo-2-chlorophenyl)thio)phenyl)methanol hydrochloride (1.51 g, 3.82 mmol, Eq: 1) in Methanol (90 ml) was added at 22° C. pyridine (1.21 g, 1.24 ml, 15.3 mmol, Eq: 4) followed by (9H-fluoren-9-yl)methyl (2,5-dioxopyrrolidin-1-yl) carbonate (1.35 g, 4.01 mmol, Eq: 1.05) and stirred at 22° C. for 20 h while more solid had precipitated to give conversion complete. The solid was filtered off, washed with methanol/pentane 1:2(1×30 ml), pentane (1×30 ml) and dried in HV to give (9H-fluoren-9-yl)methyl 4-bromo-3-chloro-2-((2-(hydroxymethyl)phenyl)thio) benzylcarbamate (1.174 g, 53%) as white solid.

LC-MS: m/z=602.0 (M+Na)+ (monoisotopic mass 579.03)

To a solution of (9H-fluoren-9-yl)methyl 4-bromo-3-chloro-2-((2-(hydroxymethyl)phenyl)thio)benzylcarbamate (1.115 g, 1.92 mmol, Eq: 1) in THF (38 ml) and DCM (38 ml) was added at 22° C. manganese dioxide (3.34 g, 38.4 mmol, Eq: 20) and stirred at 22° C. for 3 h to give conversion complete. The mixture was filtered (membrane-filter), washed with THF/DCM 1:1 (2×10 ml) and the filtrate was evaporated to give crude product as yellow foam The residue was dissolved nearly completely in 15 ml DCM, but then starting crystallisation in syringe (planned to inject onto column). The solid was filtered off, washed with DCM (2×5 ml) and dried to give 208 mg (=19%, P1) white solid. The filtrate was purified by flash chromatography (silica gel, 40 g, EtOAc in heptane 0% to 100% then MeOH in DCM 10%), the product fractions were combined with P1 and all evaporated and dried in HV to give (9H-fluoren-9-yl)methyl 4-bromo-3-chloro-2-((2-formylphenyl)thio)benzylcarbamate (0.95 g, 86%) as white solid.

LC-MS: m/z=560.1 (M+H−H2O)+ (monoisotopic mass 577.01)

1H NMR (600 MHz, CDCl$_3$) δ 10.26 (s, 1H), 7.86 (br d, J=7.1 Hz, 1H), 7.73-7.78 (m, 3H), 7.51 (br d, J=7.5 Hz, 2H), 7.40 (t, J=7.4 Hz, 3H), 7.28-7.33 (m, 1H), 7.27-7.31 (m, 2H), 7.27-7.36 (m, 2H), 6.55 (br d/=7.7 Hz, 1H), 5.22 (br t, J=5.9 Hz, 1H), 4.45 (br d, J=6.3 Hz, 2H), 4.38 (d, J=6.7 Hz, 2H), 4.15 (t, J=6.5 Hz, 2H)

Intermediate 101

9H-fluoren-9-ylmethy N-({3-chloro-2-[(3-formylpyridin-2-yl)sulfanyl]-5-(4-methanesulfonylphenyl)phenyl}methyl)carbamate

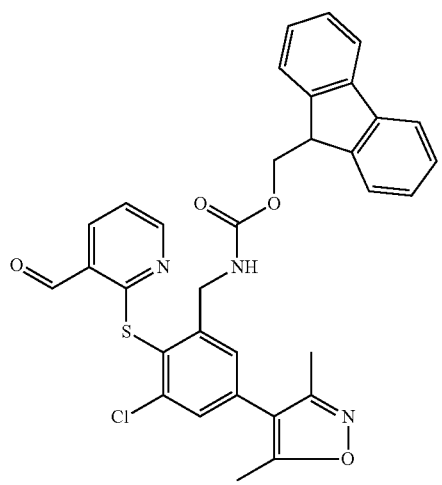 [SMILES: Cc1noc(C)c1-c1cc(Cl)c(Sc2ncccc2C=O)c(CNC(=O)OCC2c3ccccc3-c3ccccc32)c1]

A solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2.5 g, 4.33 mmol), (3,5-dimethyl-1,2-oxazol-4-yl)boronic acid (0.79 g, 5.63 mmol) and sodium carbonate (1.38 g, 13 mmol) in 1,4-dioxane (20 mL) and water (5 mL) was degassed with argon for 10 min and Pd(PPh$_3$)$_4$ (0.25 g, 0.22 mmol) was added. Then the reaction mixture was heated at 120° C. for 16 h. Progress of the reaction was monitored by TLC. Crude reaction mixture was diluted with water, extracted with EtOAc (25 mL×2), washed with brine and dried over sodium sulphate. Organic layer was concentrated under reduced pressure and the crude compound thus obtained was purified by combiflash (70% ethyl acetate in hexane) to afford N-({2-[(3-{[(tert-butyldimethylsilyl)oxy]methyl}pyridin-2-yl)sulfanyl]-3-chloro-5-(3,5-dimethyl-1,2-oxazol-4-yl)phenyl}methyl)-2-methylpropane-2-sulfinamide (2 g) as a brown-orange solid. LC-MS: 594.2 [M+H]$^+$ To an ice-cooled solution of N-({2-[(3-{[(tert-butyldimethylsilyl)oxy]methyl}pyridin-2-yl)sulfanyl]-3-chloro-5-(3,5-dimethyl-1,2-oxazol-4-yl)phenyl}methyl)-2-methylpropane-2-sulfinamide (2.0 g, 3.4 mmol) in MeOH (20 mL) was added 4M HCl in dioxane (15 mL) and the reaction mixture was stirred at 25° C. for 2h. Then the volatiles were removed under reduced pressure to get crude compound which was then washed with diethyl ether (50 mL×2) to get (2-{[2-(aminomethyl)-6-chloro-4-(3,5-dimethyl-1,2-oxazol-4-yl)phenyl]sulfanyl}pyridin-3-yl)methanol hydrochloride (1.0 g, crude) as yellow solid. LC-MS: 376.1 [M+H]$^+$ To a stirred solution of (2-{[2-(aminomethyl)-6-chloro-4-(3,5-dimethyl-1,2-oxazol-4-yl)phenyl]sulfanyl}pyridin-3-yl)methanol hydrochloride (1.0 g, crude) in CH$_3$CN (20 mL) was added 5% NaHCO$_3$ solution (20 mL) followed by Fmoc-OSu (0.9 g, 2.67 mmol) in CH$_3$CN (10.0 mL) dropwise and the reaction mixture was stirred at 25° C. for 2h. Then the reaction mixture was diluted with water (50 mL) and extracted with ethyl acetate (3×50 mL). Combined organic layer was washed with brine solution (3×20 mL), dried over anhydrous sodium sulphate and evaporated under reduced pressure to get 9H-fluoren-9-ylmethyl N-{[3-chloro-5-(3,5-dimethyl-1,2-oxazol-4-yl)-2-{[3-(hydroxymethyl)pyridin-2-yl]sulfanyl}phenyl]methyl}carbamate (1.4 g) as brown solid. LC-MS: 597.8 [M+H]$^+$ To an ice-cooled solution of 9H-fluoren-9-ylmethyl N-{[3-chloro-5-(3,5-dimethyl-1,2-oxazol-4-yl)-2-{[3-(hydroxymethyl)pyridin-2-yl]sulfanyl}phenyl]methyl}carbamate (1.4 g) in DCM (30.0 mL) was added Dess-Martin periodinane (1.49 g, 3.51 mmol) portion-wise and the reaction mixture was stirred at 25° C. for 2 h. Progress of the reaction was monitored by TLC. After completion the reaction mixture was poured in saturated sodium bicarbonate solution (100 mL) and organic layer was separated off. Organic layer was washed with sodium thiosulphate solution (2×50 mL), dried over sodium sulphate and concentrated under reduced pressure and the resulting crude compound was purified by combiflash (1% methanol in DCM) to afford 9H-fluoren-9-ylmethyl N-({3-chloro-2-[(3-formylpyridin-2-yl)sulfanyl]-5-(4-methanesulfonylphenyl)phenyl}methyl)carbamate (0.3 g) as a brown-orange solid with 96% LCMS purity. LC-MS: 596.3 [M+H]$^+$ 1H NMR (400 MHz, DMSO-d6) δ 2.25 (3H, s), 2.41 (3H, s), 4.20 (1H, t, J=6.8 Hz), 4.29 (4H, d, J=6.4 Hz), 7.26 (3H, d, J=8.5 Hz), 7.36-7.40 (3H, m), 7.62 (1H, s), 7.66 (2H, d, J=7.5 Hz), 7.87-7.91 (3H, m), 8.38 (1H, d, J=7.7 Hz), 8.47 (1H, dd, J=4.8, 1.6 Hz), 10.21 (1H, s)

Intermediate 102

9H-fluoren-9-ylmethyl N-({3-chloro-2-[(3-formylpyridin-2-yl)sulfanyl]-5-(4-methanesulfonylphenyl)phenyl}methyl)carbamate

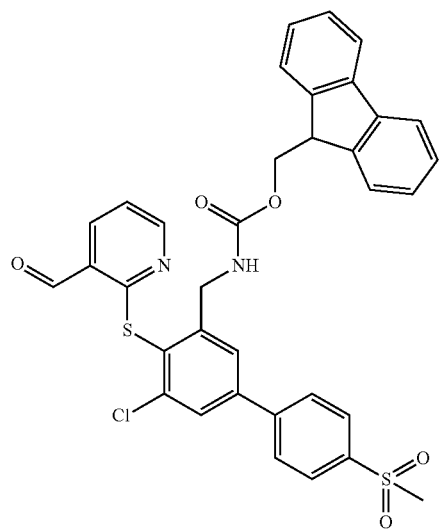 [SMILES: CS(=O)(=O)c1ccc(-c2cc(Cl)c(Sc3ncccc3C=O)c(CNC(=O)OCC3c4ccccc4-c4ccccc43)c2)cc1]

To a stirred solution of N-[(5-bromo-3-chloro-2-{[3-(hydroxymethyl)pyridin-2-yl]sulfanyl}phenyl)methyl]-2-methylpropane-2-sulfinamide (10 g, 21.56 mmol) in DCM (100 mL) were added imidazole (4.4 g, 64.68 mmol) and TBDMSCl (4.87 g, 32.34 mmol) sequentially and the reaction mixture was stirred at 25° C. for 2h. After completion, the reaction mixture was washed with sodium bicarbonate solution and extracted with DCM (100 mL×3). Combined organic layer was concentrated under reduced pressure to get the crude compound which was purified by combiflash (60% ethyl acetate in hexane) to get N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (10 g) as an off-white solid. LC-MS: 579.2 [M+2H]$^+$ A solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2.6 g, 4.51 mmol), (4-methanesulphonyl phenyl)boronic acid (1.17 g, 5.86 mmol) and sodium carbonate (1.43 g, 13.52 mmol) in 1,4-dioxane (20 mL) and water (5.0 mL) was degassed with argon for 10 min and Pd(PPh$_3$)$_4$ (0.26 g, 0.23 mmol) was added. Then the reaction mixture was heated at 120° C. for 4 h. Progress of the reaction was monitored by TLC. Crude mixture was diluted with water, extracted with EtOAc (50 mL×2), washed with brine and dried over sodium sulphate and concentrated under reduced pressure. The crude compound thus obtained was purified by column chromatography (70% ethyl acetate in hexane) to afford N-({2-[(3-{[(tert-butyldimethylsilyl)oxy]methyl}pyridin-2-yl)sulfanyl]-3-chloro-5-(4-methanesulfonylphenyl) phenyl}methyl)-2-methylpropane-2-sulfinamide (2. g, 68%) as yellow solid. LC-MS: 653.4[M+H]+

To an ice cooled solution of N-({2-[(3-{[(tert-butyldimethylsilyl)oxy]methyl}pyridin-2-yl)sulfanyl]-3-chloro-5-(4-methanesulfonylphenyl)phenyl}methyl)-2-methylpropane-2-sulfinamide (2.0 g, 3.1 mmol) in MeOH (20 mL) was added 4M HCl in dioxane (15 mL) and the reaction mixture was at 25° C. for 2h. Then volatiles were removed under reduced pressure to get crude compound which was washed with diethyl ether (50 mL×2) to get (2-{[2-(aminomethyl)-6-chloro-4-(4-methane sulfonylphenyl)phenyl]sulfanyl}pyridin-3-yl)methanol hydrochloride (1.2 g) as yellow solid. LC-MS: 435.0 [M+H]+

To a stirred solution of (2-{[2-(aminomethyl)-6-chloro-4-(4-methanesulfonylphenyl)phenyl]sulfanyl}pyridin-3-yl)methanol hydrochloride (1.2 g, 2.76 mmol) in CH₃CN (20 mL) was added 5% NaHCO₃ solution (20 mL) followed by Fmoc-OSu (0.93 g, 2.77 mmol) in CH₃CN (10.0 mL) drop-wise and the reaction mixture was stirred at 25° C. for 2h. Then the reaction mixture was diluted with water (50 mL) and extracted with ethyl acetate (3×50 mL). Combined organic layer was washed with brine (3×20 mL), dried over anhydrous sodium sulphate and evaporated under reduced pressure to get 9H-fluoren-9-ylmethyl N-[(3-chloro-2-{[3-(hydroxymethyl)pyridin-2-yl]sulfanyl}-5-(4-methanesulfonylphenyl)phenyl)methyl]carbamate (1.2 g) as yellow solid. LC-MS: 656.6 [M+H]+

To an ice-cooled solution of 9H-fluoren-9-ylmethyl N-[(3-chloro-2-{[3-(hydroxymethyl)pyridin-2-yl]sulfanyl}-5-(4-methanesulfonylphenyl)phenyl)methyl]carbamate (0.9 g, crude) in DCM (30 mL) was added Dess-Martin periodinane (0.87 g, 2.05 mmol) portion-wise and the reaction mixture was then stirred at 25° C. for 2 h. Then the reaction mixture was poured onto saturated sodium bicarbonate solution (100 mL) and organic layer was separated off. Organic layer was washed with sodium thiosulphate solution (50×2 mL), dried over sodium sulphate and concentrated under reduced pressure and the resulting crude compound was purified by combiflash (1% methanol in DCM) to afford 9H-fluoren-9-ylmethyl N-({3-chloro-2-[(3-formylpyridin-2-yl)sulfanyl]-5-(4-methanesulfonylphenyl)phenyl}methyl) carbamate (0.3 g, 15% over 3 steps) as brown-orange solid with 96% LCMS purity. LC-MS: 655.3 [M+H]+

1H NMR (400 MHz, DMSO-d6) δ 3.29 (3H, s), 4.21 (1H, d, J=6.7 Hz), 4.27 (2H, d, J=7.0 Hz), 4.37 (2H, d, J=6.1 Hz), 7.24 (2H, t, J=7.4 Hz), 7.37 (2H, d, J=7.4 Hz), 7.38-7.45 (1H, m), 7.67 (2H, d, J=7.4 Hz), 7.73 (1H, s), 7.87 (2H, d, J=7.5 Hz), 7.93 (1H, t, J=5.6 Hz), 7.96-8.00 (2H, m), 8.04 (3H, t, J=9.6 Hz), 8.39 (1H, dd, J=7.6, 1.6 Hz), 8.46 (1H, dd, J=4.7, 1.6 Hz), 10.22 (1H, s)

Intermediate 103

9H-fluoren-9-ylmethyl N-({3-chloro-2-[(3-formylpyridin-2-yl)sulfanyl]-5-(5-methanesulfonylpyridin-3-yl)phenyl}methyl)carbamate

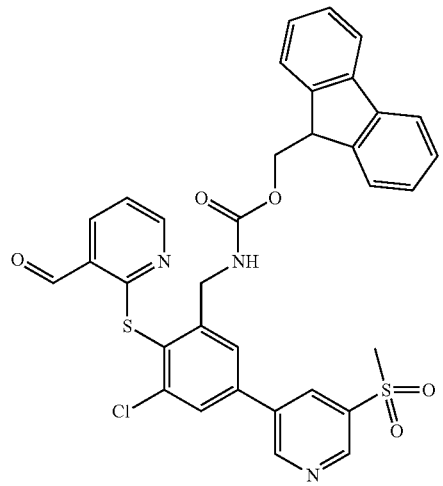 [SMILES: CS(=O)(=O)c1cncc(-c2cc(Cl)c(Sc3ncccc3C=O)c(CNC(=O)OCC3c4ccccc4-c4ccccc43)c2)c1]

A solution of NA{5-bromo-2-[(3-{[(tert-butyldimethylsilyl)oxy]methyl}pyridin-2-yl)sulfanyl]-3-chloro phenyl}methyl)-2-methylpropane-2-sulfinamide (0.6 g, 1.04 mmol), (5-methanesulfonylpyridin-3-yl)boronic acid (0.27 g, 1.35 mmol) and sodium carbonate (0.33 g, 3.12 mmol) in 1,4-dioxane (25 mL) and water (5 mL) in a sealed tube was degassed with argon for 10 min and Pd(PPh₃)₄ (0.06 g, 0.05 mmol) was added. The reaction mixture was heated at 120° C. for 4 h. Progress of the reaction was monitored by TLC. Crude mixture was diluted with water and extracted with EtOAc (50 mL×2). Combined organic layers were washed with brine, dried over sodium sulphate, evaporated under reduced pressure and the crude compound was purified by column chromatography (70% ethyl acetate in hexane) to afford N-({2-[(3-{[(tert-butyldimethylsilyl)oxy]methyl}pyridin-2-yl) sulfanyl]-3-chloro-5-(5-methanesulfonylpyridin-3-yl)phenyl}methyl)-2-methylpropane-2-sulfinamide (0.42 g, 62%) as yellow solid. LC-MS: 653.6 [M+H]+

To an ice-cooled solution of N-({2-[(3-{[(tert-butyldimethylsilyl)oxy]methyl}pyridin-2-yl)sulfanyl]-3-chloro-5-(5-methanesulfonylpyridin-3-yl)phenyl}methyl)-2-methylpropane-2-sulfinamide (1.2 g, 1.83 mmol) in MeOH (20 mL) was added 4M HCl in dioxane (12 mL) and the reaction mixture was stirred at 25° C. for 2h. Volatiles were removed under reduced pressure to give crude compound which was washed with diethyl ether (50 mL×2) and dried to get (2-{[2-(aminomethyl)-6-chloro-4-(5-methanesulfonylpyridin-3-yl)phenyl]sulfanyl}pyridin-3-yl)methanol (1 g, crude) as white solid. LC-MS: 436.1 [M+H]+

To a stirred solution of {2-[2-aminomethyl-6-chloro-4-(5-methanesulfonyl-pyridin-3-yl)-phenyl sulfanyl]-pyridin-3-yl}-methanol hydrochloride (1 g, 2.3 mmol) in CH₃CN (20 mL) was added 5% NaHCO₃ solution (20 mL) followed by Fmoc-OSu (0.78 g, 2.3 mmol) in CH₃CN (10 mL) drop-wise and the reaction mixture was stirred at 25° C. for 2h. Then the reaction mixture was diluted with water (50 mL) and extracted with ethyl acetate (3×50 mL). Combined organic layer was washed with brine solution (3×20 mL), dried over anhydrous sodium sulphate and evaporated under reduced pressure to get 9H-fluoren-9-ylmethyl N-[(3-chloro-2-{[3-(hydroxymethyl)pyridin-2-yl]sulfanyl}-5-(5-methanesulfonylpyridin-3-yl)phenyl)methyl]carbamate (1.1 g, crude) as white solid. LC-MS: 658.4 [M+H]$^+$ To an ice-cooled solution of 9H-fluoren-9-ylmethyl N-[(3-chloro-2-{[3-(hydroxymethyl)pyridin-2-yl]sulfanyl}-5-(5-methanesulfonylpyridin-3-yl)phenyl)methyl]carbamate (1.1 g, crude) in DCM (30 mL) was added Dess-Martin periodinane (1.06 g, 2.51 mmol) portion-wise and the reaction mixture was then stirred at 25° C. for 2 h. Then the reaction mixture was poured onto saturated sodium bicarbonate solution (2×50 mL) and organic layer was separated off. Organic layer was washed with sodium thiosulphate solution (2×50 mL), dried over sodium sulphate and concentrated under reduced pressure and the resulting crude compound was purified by column chromatography (50% ethyl acetate in hexane) to afford 9H-fluoren-9-ylmethyl N-({3-chloro-2-[(3-formylpyridin-2-yl)sulfanyl]-5-(5-methanesulfonylpyridin-3-yl)phenyl}methyl)carbamate (0.55 g) as brown-orange solid with 91% LCMS purity. LC-MS: 656.3 [M+H]$^+$ 1H NMR (400 MHz, DMSO-d6) δ 3.42 (3H, s), 4.20 (1H, d, J=6.7 Hz), 4.27 (2H, d, J=6.9 Hz), 4.38 (2H, d, J=5.6 Hz), 7.25 (2H, t, J=7.4 Hz), 7.37 (3H, t, J=7.5 Hz), 7.65 (2H, d, J=7.5 Hz), 7.82-7.92 (4H, m), 8.13 (1H, s), 8.39 (1H, d, J=7.5 Hz), 8.43 (1H, d, J=4.7 Hz), 8.66 (1H, s), 9.14 (1H, s), 9.30 (1H, s), 10.22 (1H, s)

Intermediate 104

4-[3-Chloro-5-[(9H-fluoren-9-ylmethoxycarbonylamino)-methyl]-4-(3-formyl-pyridin-2-ylsulfanyl)-phenyl]-3,5-dimethyl-pyrazole-1-carboxylic acid 9H-fluoren-9-ylmethyl Ester

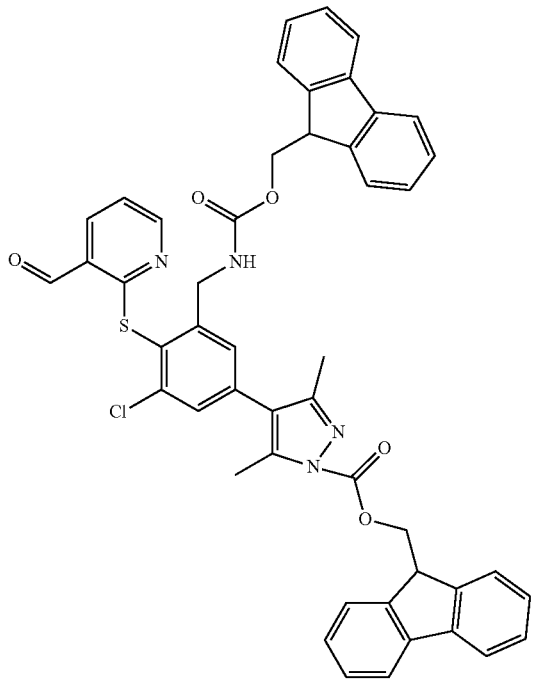 [SMILES: Cc1nn(C(=O)OCC2c3ccccc3-c3ccccc32)c(C)c1-c1cc(Cl)c(Sc2ncccc2C=O)c(CNC(=O)OCC2c3ccccc3-c3ccccc32)c1]

A solution of NA{5-bromo-2-[(3-{[(tert-butyldimethylsilyl)oxy]methyl}pyridin-2-yl)sulfanyl]-3-chloro phenyl}methyl)-2-methylpropane-2-sulfinamide (2.5 g, 4.33 mmol), 3,5-dim ethyl-4-(4,4,5,5-tetramethyl-1,3,2-dioxaborolan-2-yl)-1H-pyrazole (1.25 g, 5.63 mmol) and sodium carbonate (1.38 g, 12.99 mmol) in 1,4-dioxane (20 mL) and water (5.0 mL) was degassed with argon for 10 min and Pd(PPh$_3$)$_4$ (0.25 g, 0.22 mmol) was added. Then the reaction mixture was heated at 120° C. for 16 h. Progress of the reaction was monitored by TLC. Then the crude reaction mixture was diluted with water and extracted with EtOAc (50 mL×2), washed with brine, dried over sodium sulphate and evaporated under reduced pressure. The crude compound thus obtained was purified by column chromatography (90% ethyl acetate in hexane) to afford N-({2-[(3-{[(tert-butyldimethylsilyl)oxy]methyl}pyridin-2-yl) sulfanyl]-3-chloro-5-(3,5-dimethyl-1H-pyrazol-4-yl) phenyl}methyl)-2-methyl propane-2-sulfinamide (0.9 g) as brown solid. LC-MS: 593.1 [M+H]$^+$ To an ice-cooled solution of N-({2-[(3-{[(tert-butyldimethylsilyl)oxy]methyl}pyridin-2-yl)sulfanyl]-3-chloro-5-(3,5-dimethyl-1H-pyrazol-4-yl)phenyl}methyl)-2-methylpropane-2-sulfinamide (0.9 g, 1.517 mmol) in MeOH (20 mL) was added 4M HCl in dioxane (10.0 mL) and the reaction mixture was stirred at 25° C. for 2h. Then volatiles were removed under reduced pressure to give pale orange colored crude solid compound which was then washed with diethyl ether (50 mL×2) to get (2-{[2-(aminomethyl)-6-chloro-4-(3,5-dimethyl-1H-pyrazol-4-yl)phenyl]sulfanyl}pyridin-3-yl) methanol hydrochloride (0.9 g, crude) as yellow solid. LC-MS: 374.8 [M+H]$^+$ To a stirred solution of (2-{[2-(aminomethyl)-6-chloro-4-(3,5-dimethyl-1H-pyrazol-4-yl)phenyl]sulfanyl}pyridin-3-yl)methanol hydrochloride (1.1 g, 2.94 mmol) in CH$_3$CN (20 mL) was added 5% NaHCO$_3$ solution (10 mL) followed by Fmoc-OSu (1.98 g, 5.88 mmol) in CH$_3$CN (10.0 mL) drop-wise and the reaction mixture was stirred at 25° C. for 2h. Then the reaction mixture was diluted with water (50 mL) and extracted with ethyl acetate (3×50 mL). Combined organic layer was washed with brine (3×20 mL), dried over anhydrous sodium sulphate and concentrated under reduced pressure. The crude compound thus obtained was purified by combiflash (2-5% methanol in DCM) to get 9H-fluoren-9-ylmethyl N-{[3-chloro-5-(3,5-dimethyl-1H-pyrazol-4-yl)-2-{[3-(hydroxymethyl)pyridin-2-yl]sulfanyl}phenyl] methyl}carbamate (0.4 g) as a white solid and 9H-fluoren-9-ylmethyl 4-[3-chloro-5-({[(9H-fluoren-9-ylmethoxy) carbonyl]amino}methyl)-4-{[3-(hydroxymethyl)pyridin-2-yl]sulfanyl}phenyl]-3,5-dimethyl-1H-pyrazole-1-carboxylate (0.6 g) as an off-white solid. LC-MS: 819.7 [M+H]$^+$ To an ice-cooled solution of 9H-fluoren-9-ylmethyl 4-[3-chloro-5-({[(9H-fluorene-9-ylmethoxy) carbonyl] amino}methyl)-4-{[3-(hydroxymethyl)pyridine-2-yl] sulfanyl}phenyl]-3,5-di methyl-1H-pyrazol-1-carboxylate (0.5 g, 0.61 mmol) in DCM (20.0 mL) was added Dess-Martin periodinane (0.39 g, 0.92 mmol) portion-wise and the reaction mixture was stirred at 25° C. for 2 h. Then the reaction mixture was poured onto saturated sodium bicarbonate solution (100 mL) and organic layer was separated off. Organic layer was washed with sodium thiosulphate solution (2×50 mL), dried over sodium sulphate and concentrated under reduced pressure and the resulting crude compound was purified by combiflash (1% methanol in DCM) to afford 9H-fluoren-9-ylmethyl 4-[3-chloro-5-({[(9H-fluoren-9-ylmethoxy)carbonyl]amino}methyl)-4-[(3-formyl pyridin-2-yl)sulfanyl]phenyl]-3,5-dimethyl-1H-pyrazole-1-carboxylate (0.27 g, 54%) as brown-orange solid with 91% LCMS purity. LC-MS: 817.4 [M+H]$^+$ 1H NMR (400 MHz, DMSO-d6) δ 2.03 (3H, s), 2.21 (3H, s), 4.29 (5H, d, J=5.9 Hz), 4.48 (1H, t, J=5.6 Hz), 4.84 (2H, d, J=6.0 Hz), 7.15-7.22 (6H, m), 7.28-7.36 (6H, m), 7.41 (4H, t, J=7.5 Hz), 7.50 (1H, s), 7.65 (2H, d, J=7.4 Hz), 7.80 (2H, d, J=7.5 Hz), 7.88 (5H, t, J=6.6 Hz), 8.38 (1H, d, J=7.3 Hz), 8.47 (1H, d, J=3.6 Hz), 10.21 (1H, s)

Intermediate 105

9H-Fluoren-9-ylmethyl N-{[3-chloro-5-(2-fluoropyridin-4-yl)-2-[(3-formylpyridin-2-yl)sulfanyl]phenyl]methyl}carbamate

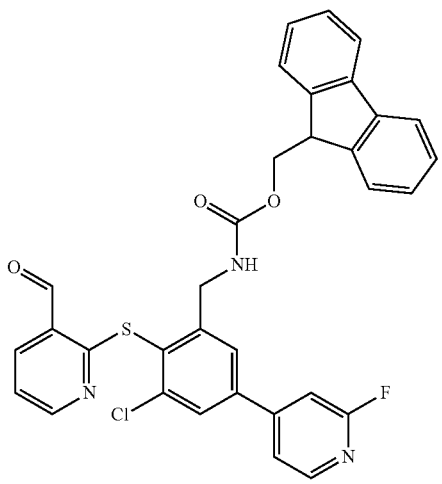 [SMILES: O=Cc1cccnc1Sc1c(Cl)cc(-c2ccnc(F)c2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (10.0 g, 17.3 mmol) in dioxan (50 mL) were added (2-fluoropyridin-4-yl)boronic acid (2.93 g, 20.8 mmol), Na₂CO₃ (5.51 g, 52 mmol), water (25 mL) and degassed for 10 min in argon atmosphere. Then to it was added Pd(PPh₃)₄ (2.0 g, 1.73 mmol) and again degassed for 5 min. The reaction mass was heated 10 to 120° C. for 16 h. Reaction mixture was then cooled to 25° C., filtered through celite pad and washed with EtOAc. The separated organic layer was washed with brine solution, dried over sodium sulfate and concentrated under reduced pressure to get the crude which was purified by column chromatography (SiO₂; 100-200 mesh; 50-90% EtOAc/Hexanes) to get N-({2-[(3-{[(tert-butyldimethylsilyl)oxy]methyl}pyridin-2-yl)sulfanyl]-3-chloro-5-(2-fluoropyridin-4-yl)phenyl}methyl)-2-methylpropane-2-sulfinamide (7.5 g, 72%) as off white solid. LC-MS: 593.9 [M+H]⁺

To a stirred solution of N-({2-[(3-{[(tert-butyldimethylsilyl)oxy]methyl}pyridin-2-yl)sulfanyl]-3-chloro-5-(2-fluoropyridin-4-yl)phenyl}methyl)-2-methylpropane-2-sulfinamide (7.5 g, 12.6 mmol) in MeOH (50 mL), was added 4M HCl in dioxan (25 mL) at 0° C. and reaction mixture was stirred at 25° C. for 2h. Reaction mass was evaporated under reduced pressure to get (2-{[2-(aminomethyl)-6-chloro-4-(2-fluoropyridin-4-yl)phenyl]sulfanyl}pyridin-3-yl)methanol hydrochloride (6.5 g, crude) which was directly used for next step without further purification. LC-MS: 376.0 [M+H]⁺

To a stirred suspension of (2-{[2-(aminomethyl)-6-chloro-4-(2-fluoropyridin-4-yl)phenyl]sulfanyl}pyridin-3-yl)methanol hydrochloride (6.5 g, 17.33 mmol) in 5% NaHCO₃ (50 mL) was added Fmoc-OSU (5.84 g, 17.33 mmol) in dioxan (50 mL) at 25° C. and reaction mass was stirred at the same temperature for 16h. Then reaction mass was diluted with water and extracted with 10% methanol in dichloromethane. The separated organic layer was washed with brine solution, dried over sodium sulfate and evaporated under reduced pressure to 9H-fluoren-9-ylmethyl N-{[3-chloro-5-(2-fluoropyridin-4-yl)-2-{[3-(hydroxymethyl)pyridin-2-yl]sulfanyl}phenyl]methyl}carbamate (8.0 g) as off-white solid; which was used for next step without further purification. LC-MS: 598.1 [M+H]⁺

To a stirred solution of 9H-fluoren-9-ylmethyl N-{[3-chloro-5-(2-fluoropyridin-4-yl)-2-{[3-(hydroxymethyl)pyridin-2-yl]sulfanyl}phenyl]methyl}carbamate in DCM/THF (1:1, 100 mL) was added MnO₂ (23.3 g, 268.0 mmol) and reaction mass was stirred at 25° C. for 2 h. The reaction mass was filtered through celite pad; filtrate was evaporated under reduced pressure. The crude thus obtained was purified by column chromatography (SiO₂; 100-200 mesh; 40-80% EtOAc/Hexanes) to get 9H-fluoren-9-ylmethyl N-{[3-chloro-5-(2-fluoropyridin-4-yl)-2-[(3-formylpyridin-2-yl)sulfanyl]phenyl]methyl}carbamate (5.2 g) as off-white solid with 95.7% purity. LC-MS: 596.1 [M+H]⁺

1H NMR (400 MHz, DMSO-d6): δ 4.20 (1H, t, J=7.1 Hz), 4.28 (2H, d, J=6.9 Hz), 4.38 (2H, d, J=5.5 Hz), 7.26 (2H, t, J=7.4 Hz), 7.36-7.40 (3H, m), 7.62 (1H, s), 7.67 (2H, d, J=7.5 Hz), 7.74 (1H, d, J=5.0 Hz), 7.82 (1H, s), 7.87 (3H, d, J=7.5 Hz), 8.08 (1H, s), 10.21 (1H, s).

Intermediate 106 RO7189105-000

(9H-Fluoren-9-yl)methyl ((5-chloro-2-((2-formylphenyl)thio)pyridin-3-yl)methyl)carbamate

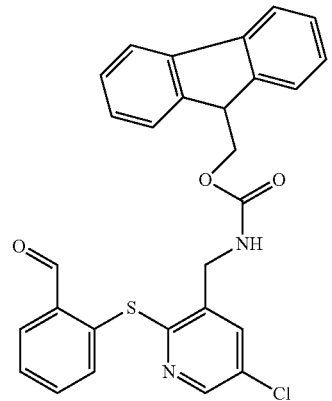 [SMILES: O=Cc1ccccc1Sc1ncc(Cl)cc1CNC(=O)OCC1c2ccccc2-c2ccccc21]

This material was prepared in analogy to Intermediate 68 starting from 2,5-dichloronicotinaldehyde and methyl 2-mercaptobenzoate. The title compound was obtained as light yellow foam (230 mg). MS ESI (m/z): 501.1 [(M+H)⁺]

Intermediate 107

9H-Fluoren-9-ylmethyl N-({3-chloro-5-cyano-2-[(3-formylpyridin-2-yl) sulfanyl]phenyl}methyl)carbamate

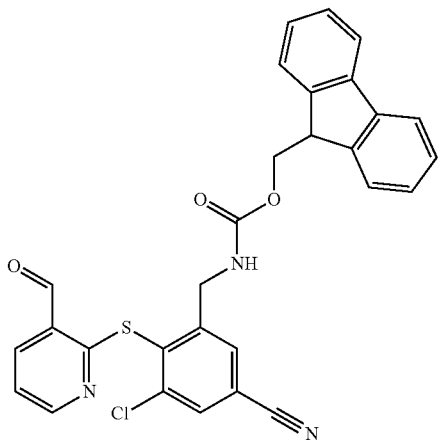 [SMILES: N#Cc1cc(Cl)c(Sc2ncccc2C=O)c(CNC(=O)OCC2c3ccccc3-c3ccccc32)c1]

To the stirred solution of 5-bromo-3-chloro-2-fluorobenzaldehyde (1.5 g, 6.3 mmol) in NMP (11.5 ml) was added CuCN (680 mg, 7.59 mmol) and heated at 170° C. for 30 min under microwave condition. Then reaction mass was diluted with water and extracted with ethyl acetate. The separated organic layer was washed with water, brine solution, dried over sodium sulfate and evaporated under reduced pressure to get the crude. The crude thus obtained was purified by normal silica column using 5-15% ethyl acetate in hexane to get 3-chloro-4-fluoro-5-formylbenzonitrile (562 mg, 48%) as yellow solid.

To a stirred solution of 2-mercapto nicotinic acid (1.4 g, 9.0 mmol) in DMF (15 mL) was added NaH (60%, 0.393 g, 16.39 mmol) and reaction mass was stirred at 25° C. for 30 min. Then 3-chloro-4-fluoro-5-formylbenzonitrile (1.5 g, 8.19 mmol) was added and reaction mixture was stirred at 70° C. for 4h. Then K$_2$CO$_3$ (3.39 g, 24.59 mmol) was added followed by addition of MeI (1.54 mL, 24.6 mmol) and reaction mass was stirred at 25° C. for 16h. Reaction mass was quenched with water and extracted with ethyl acetate. The separated organic layer was washed with brine solution, dried over anhydrous sodium sulfate and evaporated under reduced pressure. The crude thus obtained was purified by normal silica column using 4-20% ethyl acetate in hexane to get methyl 2-[(2-chloro-4-cyano-6-formylphenyl) sulfanyl]pyridine-3-carboxylate (1.0 g, 36%) as a light yellow solid.

To a stirred solution of methyl 2-[(2-chloro-4-cyano-6-formylphenyl)sulfanyl]pyridine-3-carboxylate (1.0 g, 3.01 mmol) in THF (20 mL) were added 2-methylpropane-2-sulfinamide (365 mg, 3.01 mmol), Ti(OEt)$_4$ (3.15 ml, 15.06 mmol) and reaction mass was heated to 70° C. for 45 min. The reaction mass was quenched with saturated sodium chloride solution, solid obtained was filtered through celite pad, washed with ethyl acetate. The separated organic layer was dried over anhydrous sodium sulfate and concentrated under reduced pressure to afford Ethyl 2-[(2-chloro-4-cyano-6-{[(2-methylpropane-2-sulfinyl)imino] methyl}phenyl) sulfanyl]pyridine-3-carboxylate (1,2 g) which was directly used for next step without further purification. LC-MS: 449.8 [M+H]$^+$ To a stirred solution of ethyl 2-[(2-chloro-4-cyano-6-{[(2-methylpropane-2-sulfinyl)imino]methyl}phenyl)sulfanyl] pyridine-3-carboxylate (1.3 g, 2.89 mmol) in THF (15 mL) was added LiBH4 (189.0 mg, 8.68 mmol) at 0° C. and reaction mass was heated to 70° C. for 2h. Reaction mixture was quenched with saturated ammonium chloride solution and extracted with ethyl acetate. The separated organic layer was washed with water, brine solution, dried over anhydrous sodium sulfate and evaporated under reduced pressure to get the crude. The crude thus obtained was purified by normal silica column using 0-60% ethyl acetate in hexane to get N-[(3-chloro-5-cyano-2-{[3-(hydroxymethyl)pyridin-2-yl] sulfanyl}phenyl)methyl]-2-methylpropane-2-sulfinamide as off-white solid (510 mg) as off white solid. LC-MS: 410.1 [M+H]$^+$ To a stirred solution of N-[(3-chloro-5-cyano-2-{[3-(hydroxymethyl)pyridin-2-yl]sulfanyl}phenyl)methyl]-2-methylpropane-2-sulfinamide (510 mg, 1.25 mmol) in MeOH (8 mL), was added 4M HCl in dioxane (4 mL) at 0° C. and reaction mixture was stirred at 25° C. for 20 mins. After completion of reaction, reaction mixture was quenched with saturated sodium bicarbonate solution, extracted with ethyl acetate, washed with brine, dried over anhydrous sodium sulfate and concentrated under vacuum to get 3-(aminomethyl)-5-chloro-4-{[3-(hydroxymethyl)pyridin-2-yl] sulfanyl}benzonitrile HCl salt (350 mg, crude) which was directly used for next step. LC-MS: 306.0 [M+H]$^+$ To a stirred suspension of 3-(amino methyl)-5-chloro-4-{[3-(hydroxymethyl)pyridin-2-yl]sulfanyl}benzonitrile HCl salt (350 mg, 1.15 mmol) in 5% NaHCO$_3$ (10 mL) was added Fmoc-OSU (386.95 mg, 1.148 mmol) in dioxan (10 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-5-cyano-2-{[3-(hydroxymethyl)pyridin-2-yl]sulfanyl}phenyl)methyl]carbamate (450 mg) which was directly used for next step. LC-MS: 528.1 [M+H]$^+$ To a stirred solution of 9H-fluoren-9-ylmethyl N-[(3-chloro-5-cyano-2-{[3-(hydroxymethyl)pyridin-2-yl] sulfanyl}phenyl)methyl]carbamate (450 mg, 0.85 mmol) in DCM:THF (1:1, 14 mL) was added MnO$_2$ (1.48 g, 17.07 mmol) and reaction mass was stirred at 25° C. for 1 h. The reaction mass was filtered through celite pad; filtrate was evaporated under reduced pressure. The crude thus obtained was purified by normal silica column using 20-40% ethyl acetate in hexane to get 9H-fluoren-9-ylmethyl N-({3-chloro-5-cyano-2-[(3-formylpyridin-2-yl)sulfanyl] phenyl}methyl)carbamate (200 mg) as off-white solid with 94% LCMS purity. LC-MS: 525.8 [M+H]$^+$ 1H NMR (400 MHz, DMSO-d6): δ 4.15-4.38 (5H, m), 7.28-7.36 (2H, m), 7.42 (2H, t, J=8.2 Hz), 7.68 (2H, d, J=7.9 Hz), 7.89 (2H, d, J=7.1 Hz), 8.11-8.21 (1H, m), 8.36-8.48 (2H, m), 10.14-10.23 (1H, m).

Intermediate 108

9H-Fluoren-9-ylmethyl N-({3-chloro-2-[(3-form-ylpyridin-2-yl) sulfanyl]-5-{2-oxa-5-azabicyclo[2.2.1]heptan-5-yl}phenyl}methyl)carbamate

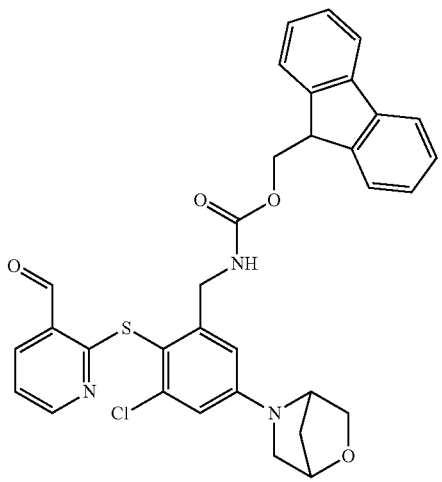 [SMILES: O=Cc1cccnc1Sc1c(Cl)cc(N2CC3CC2CO3)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (500 mg, 0.86 mmol) in toluene (5 mL) were added 2-oxa-5-azabicyclo[2.2.1]heptane hydrochloride (141 mg, 1.04 mmol) and sodium tertiary butoxide (333 mg, 3.46 mmol) and degassed in argon atmosphere for 5 min. Then to it were added 2-ditertiary butyl phosphino biphenyl (23.3 mg, 0.078 mmol) and Pd(dba)$_2$ (39.9 mg, 0.07 mmol) and heated to 110° C. for 16h. The reaction mass was filtered through celite pad and the filtrate was evaporated under reduced pressure. The crude thus obtained was purified by combi-flash column chromatography using 5% methanol in dichloromethane to get N-({2-[(3-{[(tert-butyldimethylsilyl)oxy]methyl}pyridin-2-yl) sulfanyl]-3-chloro-5-{2-oxa-5-azabicyclo[2.2.1]heptan-5-yl}phenyl}methyl)-2-methylpropane-2-sulfinamide (300 mg, 58%) as light yellow solid. LC-MS: 595.8 [M+H]$^+$ To a stirred solution of N-({2-[(3-{[(tert-butyldimethylsilyl)oxy]methyl}pyridin-2-yl)sulfanyl]-3-chloro-5-{2-oxa-5-azabicyclo[2.2.1]heptan-5-yl}phenyl}methyl)-2-methylpropane-2-sulfinamide (900 mg, 1.51 mmol) in MeOH (10 mL), was added 4M HCl in dioxan (5 mL) at 0° C. and reaction mixture was stirred at 25° C. for 2h. The reaction mass was evaporated under reduced pressure to get (2-{[2-(amino methyl)-6-chloro-4-{2-oxa-5-azabicyclo[2.2.1]heptan-5-yl}phenyl]sulfanyl}pyridin-3-yl) methanol hydrochloride (700 mg) which was directly used for next step. LC-MS: 377.6 [M+H]$^+$ To a stirred suspension of (2-{[2-(aminomethyl)-6-chloro-4-{2-oxa-5-azabicyclo[2.2.1]heptan-5-yl}phenyl]sulfanyl}pyridin-3-yl)methanol HCl salt (700 mg, 1.85 mmol) in 5% NaHCO$_3$ (10 mL) was added Fmoc-OSU (626 mg, 1.85 mmol) in dioxan (10 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure to get 9H-Fluoren-9-ylmethyl N-[(3-chloro-2-{[3-(hydroxymethyl)pyridin-2-yl]sulfanyl}-5-{2-oxa-5-azabicyclo[2.2.1]heptan-5-yl}phenyl)methyl]carbamate (800 mg) as off white solid, which was used for next step without further purification. LC-MS: 600.2 [M+H]$^+$ To a stirred solution of 9H-fluoren-9-ylmethyl N-[(3-chloro-2-{[3-(hydroxymethyl)pyridin-2-yl]sulfanyl}-5-{2-oxa-5-azabicyclo[2.2.1]heptan-5-yl}phenyl)methyl]carbamate (800 mg, 1.33 mmol) in DCM:THF (1:1, 20 mL) was added MnO$_2$ (2.32 g, 26.7 mmol) and reaction mass was stirred at 25° C. for 2 h. The reaction mass was filtered through celite pad and the filtrate was evaporated under reduced pressure. The crude thus obtained was purified by normal silica column using 30%-80% ethylacetate in hexane to get 9H-fluoren-9-ylmethyl N-({3-chloro-2-[(3-form-ylpyridin-2-yl)sulfanyl]-5-{2-oxa-5-azabicyclo[2.2.1]heptan-5-yl}phenyl}methyl)carbamate (170 mg) as off white solid with 90.89% purity. LC-MS: 598.0 [M+H]$^+$ 1H NMR (400 MHz, DMSO-d6): δ 3.02 (1H, d, J=9.5 Hz), 3.44 (1H, d, J=10.1 Hz), 3.64 (1H, d, J=7.1 Hz), 3.71 (1H, d, J=8.0 Hz), 4.22 (5H, dd, J=16.7, 6.3 Hz), 4.62 (2H, d, J=22.8 Hz), 6.56 (1H, s), 6.79 (1H, s), 7.27-7.38 (3H, m), 7.42 (2H, t, J=6.9 Hz), 7.69 (2H, d, J=7.7 Hz), 7.70-7.78 (1H, m), 7.89 (2H, d, J=7.7 Hz), 8.30 (1H, d, J=7.1 Hz), 8.43 (1H, d, J=5.0 Hz), 10.20 (1H, s).

Intermediate 109

9H-fluoren-9-ylmethyl N-({5-[3-(benzyloxy)prop-1-yn-1-yl]-3-chloro-2-[(3-formylpyridin-2-yl)sulfanyl]phenyl}methyl)carbamate

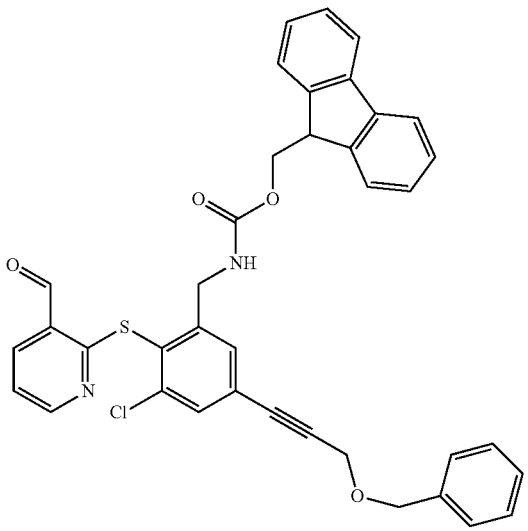 [SMILES: O=Cc1cccnc1Sc1c(Cl)cc(C#CCOCc2ccccc2)cc1CNC(=O)OCC1c2ccccc2-c2ccccc21]

To a stirred and degassed suspension of N-({5-bromo-2-[(3-{[(tert-butyldimethylsilyl)oxy]methyl}pyridin-2-yl) sulfanyl]-3-chlorophenyl}methyl)-2-methylpropane-2-sulfinamide (2 g, 3.46 mmol), [(prop-2-yn-1-yloxy)methyl] benzene (1 mL, 6.9 mmol) in triethylamine (8 mL) were added CuI (13 mg, 0.07 mmol), palladium acetate (8 mg, 0.04 mmol), PPh$_3$(18 mg, 0.07 mmol) and reaction mass was heated to 80° C. for 6h. Reaction mass was evaporated under reduced pressure and the crude material obtained was purified by normal silica column using 0-30% ethyl acetate in hexane to get N-({5-[3-(benzyloxy)prop-1-yn-1-yl]-2-[(3-{[(tert-butyldimethylsilyl)oxy]methyl}pyridin-2-yl)sulfanyl]-3-chlorophenyl}methyl)-2-methylpropane-2-sulfinamide (1 g, 45%) as colourless sticky liquid. LC-MS: 643.2 [M+H]$^+$ To a stirred solution of N-({5-[3-(benzyloxy)prop-1-yn-1-yl]-2-[(3-{[(tert-butyldimethylsilyl)oxy]methyl}pyridin-2-yl) sulfanyl]-3-chlorophenyl}methyl)-2-methylpropane-2-sulfinamide (1 g, 1.5 mmol) in MeOH (8 mL), was added 4M HCl in dioxan (4 mL) at 0° C. and reaction mixture was stirred at 25° C. for 2h. Reaction mass was evaporated under reduced pressure to get (2-{[2-(aminomethyl)-4-[3-(benzyloxy)prop-1-yn-1-yl]-6-chlorophenyl]sulfanyl}pyridin-3-yl)methanol HCl salt (700 mg) which was directly used for next step. LC-MS: 425.1 [M+H]$^+$ To a stirred suspension of (2-{[2-(aminomethyl)-4-[3-(benzyloxy)prop-1-yn-1-yl]-6-chlorophenyl]sulfanyl}pyridin-3-yl)methanol HCl salt (700 mg, 1.5 mmol) in 5% NaHCO$_3$ (20 mL) was added Fmoc-OSU (511 mg, 1.5 mmol) in dioxan (40 mL) at 25° C. and reaction mass was stirred at the same temperature for 2h. Then the reaction mass was diluted with water and extracted with ethyl acetate. The separated organic layer was washed with brine solution, dried over sodium sulfate and evaporated under reduced pressure to get 9H-fluoren-9-ylmethyl N-({5-[3-(benzyloxy)prop-1-yn-1-yl]-3-chloro-2-{[3-(hydroxymethyl)pyridin-2-yl]sulfanyl}phenyl}methyl) carbamate (850 mg) as off white solid which was used for next step without further purification. LC-MS: 647.0 [M+H]$^+$ To a stirred solution of 9H-fluoren-9-ylmethyl N-({5-[3-(benzyloxy)prop-1-yn-1-yl]-3-chloro-2-{[3-(hydroxymethyl)pyridin-2-yl]sulfanyl}phenyl}methyl)carbamate (850 mg, 1.31 mmol) in DCM:THF (1:1, 40 mL) was added MnO$_2$ (2.28 g, 26.3 mmol) and reaction mass was stirred at 25° C. for 2 h. The reaction mass was filtered through celite pad and the filtrate was evaporated under reduced pressure. The crude material obtained was purified by normal silica column using 10%-50% ethylacetate in hexane to get 9H-fluoren-9-ylmethyl N-({5-[3-(benzyloxy)prop-1-yn-1-yl]-3-chloro-2-[(3-formylpyridin-2-yl)sulfanyl] phenyl}methyl)carbamate (500 mg) as off white solid with 91% purity. LC-MS: 645.3 [M+H]$^+$ 1H NMR (400 MHz, DMSO-d6): δ 4.26-4.30 (5H, m), 4.49 (2H, s), 4.62 (2H, s), 7.30-7.42 (11H, m), 7.68 (3H, d, J=7.0 Hz), 7.88 (3H, d, J=7.1 Hz), 8.38 (1H, d, J=7.6 Hz), 8.42 (1H, d, J=4.6 Hz), 10.19 (1H, s).

Intermediate 110

9H-fluoren-9-ylmethyl N-({3-chloro-2-[(3-formylpyridin-2-yl)sulfanyl]-6-(pyridin-4-yl) phenyl}methyl)carbamate

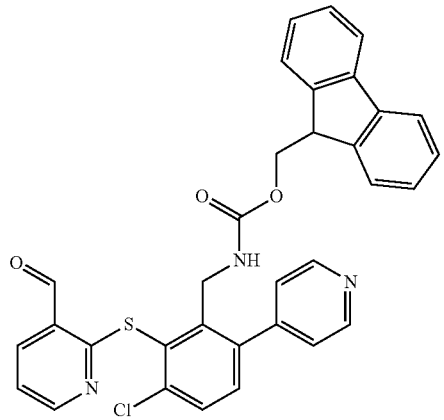 [SMILES: O=Cc1cccnc1Sc1c(Cl)ccc(-c2ccncc2)c1CNC(=O)OCC1c2ccccc2-c2ccccc21]

To a stirred solution of compound N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (4 g, 6.93 mmol) in dioxan (30 mL) were added pyridine-4-boronic acid (1.1 g, 9.01 mmol), Na$_2$CO$_3$ (2.2 g, 20.79 mmol), water (15 mL) and degassed for 10 min in argon atmosphere. Then to it was added Pd(PPh$_3$)$_4$ (0.8 g, 0.69 mmol) and again degassed for 5 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under vacuum to get the crude which was purified by normal silica column using 5-80% ethyl acetate in hexane to get N-({2-[(3-{[(tert-butyldimethylsilyl)oxy]methyl}pyridin-2-yl)sulfanyl]-3-chloro-6-(pyridin-4-yl)phenyl}methyl)-2-methylpropane-2-sulfinamide (2.2 g, 55%) as off white solid. LC-MS: 575.8 [M+H]$^+$ To a stirred solution of N-({2-[(3-{[(tert-butyldimethylsilyl)oxy]methyl}pyridin-2-yl)sulfanyl]-3-chloro-6-(pyridin-4-yl)phenyl}methyl)-2-methylpropane-2-sulfinamide (2.2 g, 3.82 mmol) in MeOH (20 mL), was added 4M HCl in dioxan (10 mL) at 0° C. and reaction mixture was stirred at 25° C. for 2h. Reaction mass was evaporated under reduced pressure to get (2-{[2-(aminomethyl)-6-chloro-3-(pyridin-4-yl)phenyl]sulfanyl}pyridin-3-yl)methanol HCl salt (1.3 g) which was directly used for next step. LC-MS: 358.2 [M+H]$^+$ To a stirred suspension of (2-{[2-(aminomethyl)-6-chloro-3-(pyridin-4-yl)phenyl]sulfanyl}pyridin-3-yl)methanol HCl salt (1.3 g, 3.64 mmol) in 5% NaHCO$_3$ (20 mL) was added Fmoc-OSU (1.22 g, 3.64 mmol) in dioxan (20 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl] sulfanyl}-6-(pyridin-4-yl)phenyl)methyl]carbamate (2 g) which was directly used for next step. LC-MS: 580.2 [M+H]$^+$ To a stirred solution of 9H-fluoren-9-ylmethyl N-[(3-chloro-2-{[3-(hydroxymethyl)pyridin-2-yl]sulfanyl}-6-(pyridin-4-yl)phenyl)methyl]carbamate (2.0 g, 3.45 mmol) in DCM:THF (1:1, 40 mL) was added MnO$_2$ (6.0 g, 69 mmol) and reaction mass was stirred at 25° C. for 2 h. The reaction mass was filtered through celite pad; filtrate was evaporated under reduced pressure. The crude thus obtained was purified by normal silica column using 40-80% ethyl acetate in hexane to get 9H-fluoren-9-ylmethyl N-({3-chloro-2-[(3-formylpyridin-2-yl)sulfanyl]-6-(pyridin-4-yl)phenyl}methyl)carbamate (650 mg) as off white solid with 90% LCMS purity. LC-MS: 577.9 [M+H]$^+$ 1H NMR (400 MHz, DMSO-d6): δ 4.10-4.14 (5H, m), 7.33-7.46 (8H, m), 7.58 (1H, s), 7.65 (2H, d, J=7.3 Hz), 7.73 (1H, d, J=8.3 Hz), 7.89 (2H, d, J=7.4 Hz), 8.35 (1H, d, J=7.7 Hz), 8.48 (1H, d, J=3.1 Hz), 8.59 (2H, d, J=5.5 Hz), 10.21 (1H, s).

Intermediate 111 (RO7189173-000-001)

9H-fluoren-9-ylmethyl N-({3-chloro-2-[(3-formylpyridin-2-yl)sulfanyl]-6-(pyridin-3-yl)phenyl}methyl)carbamate

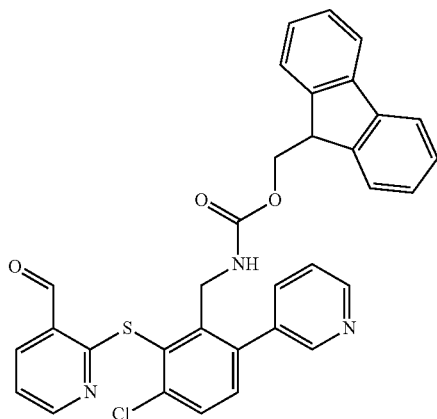 [SMILES: O=Cc1cccnc1Sc1c(Cl)ccc(-c2cccnc2)c1CNC(=O)OCC1c2ccccc2-c2ccccc21]

To a stirred solution of compound N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (4 g, 6.9 mmol) in dioxan (40 mL) were added pyridine-3-boronic acid (1.1 g, 8.9 mmol), Na$_2$CO$_3$ (2.2 g, 20.7 mmol), water (20 mL) and degassed for 10 min in argon atmosphere. Then to it was added Pd(PPh$_3$)$_4$ (400 mg, 0.34 mmol) and again degassed for 5 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under reduced pressure to get N-({2-[(3-{[(tert-butyldimethylsilyl)oxy]methyl}pyridin-2-yl)sulfanyl]-3-chloro-6-(pyridin-3-yl)phenyl}methyl)-2-methylpropane-2-sulfinamide (4 g, crude) which was directly used for next step without further purification. LC-MS: 575.6 [M+H]$^+$ To a stirred solution of N-({2-[(3-{[(tert-butyldimethylsilyl)oxy]methyl}pyridin-2-yl)sulfanyl]-3-chloro-6-(pyridin-3-yl)phenyl}methyl)-2-methylpropane-2-sulfinamide (4 g, 6.9 mmol) in MeOH (40 mL), was added 4M HCl in dioxan (20 mL) at 0° C. and reaction mixture was stirred at 25° C. for 2h. Reaction mass was evaporated under reduced pressure to get (2-{[2-(aminomethyl)-6-chloro-3-(pyridin-3-yl)phenyl]sulfanyl}pyridin-3-yl)methanol HCl salt (2.5 g) which was directly used for next step. LC-MS: 357.8 [M+H]$^+$ To a stirred suspension of (2-{[2-(aminomethyl)-6-chloro-3-(pyridin-3-yl)phenyl]sulfanyl}pyridin-3-yl)methanol HCl salt (2.5 g, 6.3 mmol) in 5% NaHCO$_3$ (40 mL) was added Fmoc-OSU (2.13 g, 6.3 mmol) in dioxan (80 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-6-(pyridin-3-yl)phenyl)methyl]carbamate (3 g) which was directly used for next step. LC-MS: 580.0 [M+H]$^+$ To a stirred solution of 9H-fluoren-9-ylmethyl N-[(3-chloro-2-{[3-(hydroxymethyl)pyridin-2-yl]sulfanyl}-6-(pyridin-3-yl)phenyl)methyl]carbamate (3 g, 5.17 mmol) in DCM:THF (1:1, 60 mL) was added MnO$_2$ (8.99 g, 103.4 mmol) and reaction mass was stirred at 25° C. for 2 h. The reaction mass was filtered through celite pad and the filtrate was evaporated under reduced pressure. The crude thus obtained was purified by normal silica column using 10-50% ethyl acetate in hexane to get 9H-fluoren-9-ylmethyl N-({3-chloro-2-[(3-formylpyridin-2-yl)sulfanyl]-6-(pyridin-3-yl)phenyl}methyl)carbamate (1.2 g) as off white solid with 89% LCMS purity. LC-MS: 577.7 [M+H]$^+$ 1H NMR (400 MHz, DMSO-d6): δ 4.07-4.16 (5H, m), 7.29-7.50 (7H, m), 7.59 (1H, s), 7.65 (2H, d, J=7.5 Hz), 7.72 (1H, d, J=8.3 Hz), 7.88 (3H, t, J=7.8 Hz), 8.34 (1H, d, J=6.3 Hz), 8.48 (1H, d, J=4.6 Hz), 8.61 (1H, d, J=4.1 Hz), 8.65 (1H, s), 10.21 (1H, s).

Intermediate 112

9H-Fluoren-9-ylmethyl N-[[2-(2-formylphenyl)sulfanyl-6-morpholin-4-ylpyridin-3-yl]methyl]carbamate

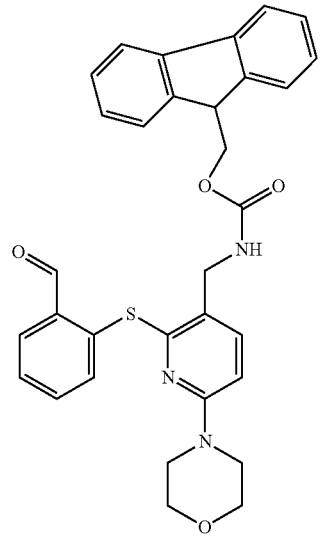 [SMILES: O=Cc1ccccc1Sc1nc(N2CCOCC2)ccc1CNC(=O)OCC1c2ccccc2-c2ccccc21]

To a solution of 2,6-dichloronicotinaldehyde (200 mg, 1.14 mmol, Eq: 1) and Et$_3$N (115 mg, 158 µl, 1.14 mmol, Eq: 1) in DMF (2.6 ml) was added a solution of morpholine (99 mg, 99.4 µl, 1.14 mmol, Eq: 1) in DMF (520 µl). The reaction mixture was stirred at room temperature for 1 h. The reaction mixture was concentrated in vacuo and the obtained 2-chloro-6-morpholinonicotinaldehyde (350 mg yellow solid) was used in the next step without further purification. MS ESI (m/z): 227.1 [(M+H)+]

This material was prepared in analogy to Intermediate 68 starting from 2-chloro-6-morpholinonicotinaldehyde and methyl 2-mercaptobenzoate. The title compound was obtained as light yellow solid (50 mg). MS ESI (m/z): 552.2 [(M+H)⁺]

Intermediate 113

(9H-Fluoren-9-yl)methyl ((4-((2-formylphenyl)thio)-2-morpholinopyridin-3-yl)methyl)carbamate

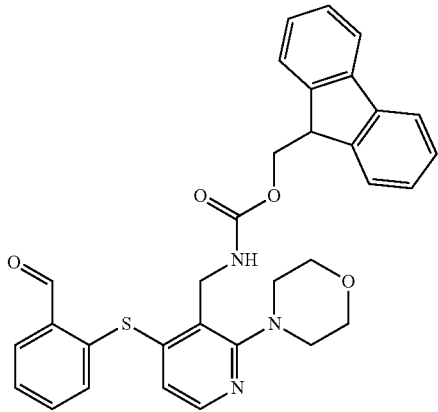 [SMILES: O=Cc1ccccc1Sc1ccnc(N2CCOCC2)c1CNC(=O)OCC1c2ccccc2-c2ccccc21]

To a stirred solution of methyl 2-sulfanylbenzoate (5 g, 29.72 mmol) in DMF (50 ml) was added Cs₂CO₃ (19.369 g, 59.45 mmol) followed by 2,4-dichloropyridine-3-carbaldehyde (5.231 g 29.72 mmol) and heated at 70° C. for 2 h. The reaction mixture was diluted with water and extracted with ethyl acetate. The combined organic layers were washed with water, dried over anhydrous sodium sulfate and concentrated under vacuum. The crude, thus obtained was purified by silica gel column chromatography using ethyl acetate in n-hexane (0-8%) as eluting solvent to afford methyl 2-[(2-chloro-3-formylpyridin-4-yl)sulfanyl]benzoate (6.1 g, 66.69%) as light yellow solid. LC-MS: 307.9 [M+H]⁺.

To a stirred solution of methyl 2-[(2-chloro-3-formylpyridin-4-yl)sulfanyl]benzoate (2.5 g, 8.12 mmol) in toluene (30 ml) were added Cs₂CO₃ (7.93 g, 24.35 mmol), morpholine (0.8 ml, 9.74 mmol) and purged with argon. Then xantphos (0.235 g, 0.41 mmol), Pd₂(dba)₃ (0.372 g, 0.41 mmol) were added to the reaction mixture, again purged with argon and heated at 110° C. for 6 h. The reaction mixture was quenched with water and extracted with ethyl acetate. The combined organic layers were washed with brine, dried over anhydrous sodium sulfate and concentrated under vacuum. The crude, thus obtained was purified by silica gel column chromatography using ethyl acetate in n-hexane (0-40%) as eluting solvent to afford methyl 2-{[3-formyl-2-(morpholin-4-yl)pyridin-4-yl]sulfanyl}benzoate (2.1 g, 72%) as white solid. LC-MS: 359.6 [M+H]⁺.

To a stirred solution of methyl 2-{[3-formyl-2-(morpholin-4-yl)pyridin-4-yl]sulfanyl}benzoate (2.1 g, 5.87 mmol) in THF (40 ml) were added 2-methylpropane-2-sulfinamide (0.711 g, 5.87 mmol) and Ti(OEt)₄ (6.2 ml, 29.33 mmol) and heated at 70° C. for 2 h. The reaction mixture was quenched with brine solution, ethyl acetate was added and filtered. The aqueous layer was extracted with ethyl acetate, dried the combined organic layers over anhydrous sodium sulfate and concentrated under vacuum. The crude, thus obtained was purified by combi flash column chromatography using ethyl acetate in hexane (0-40%) as eluting solvent to afford methyl 2-({3-[(1E)-[(2-methylpropane-2-sulfinyl)imino]methyl]-2-(morpholin-4-yl)pyridin-4-yl}sulfanyl)benzoate (690 mg, 26%) as yellow solid. LC-MS: 462.1 [M+H]⁺.

To a stirred solution of methyl 2-({3-[(1E)-[(2-methylpropane-2-sulfinyl)imino]methyl]-2-(morpholin-4-yl)pyridin-4-yl}sulfanyl)benzoate (900 mg, 1.95 mmol) in THF (15 ml) was added LiAlH₄ (2M in THF, 1.95 ml, 3.91 mmol) at 0° C. and stirred at 25° C. for 30 min. The reaction mixture was quenched with aqueous saturated sodium sulfate solution (15 ml), filtered and concentrated under vacuum to afford N-[(4-{[2-(hydroxymethyl)phenyl]sulfanyl}-2-(morpholin-4-yl)pyridin-3-yl)methyl]-2-methylpropane-2-sulfinamide (720 mg, crude), which was used without further purification. LC-MS: 435.7 [M+H]⁺.

To a stirred solution of N-[(4-{[2-(hydroxymethyl)phenyl]sulfanyl}-2-(morpholin-4-yl)pyridin-3-yl)methyl]-2-methylpropane-2-sulfinamide (crude, 700 mg, 1.62 mmol) in MeOH (6 ml) was added 4N HCl in dioxane (10 ml) at 0° C. and stirred at 25° C. for 30 min. The reaction mixture was concentrated under vacuum to afford (2-{[3-(aminomethyl)-2-(morpholin-4-yl)pyridin-4-yl]sulfanyl}phenyl)methanol hydrochloride (670 mg, crude) as brown solid and was used without further purification. LC-MS: 332.4 [M+H]⁺.

To a stirred suspension of (2-{[3-(aminomethyl)-2-(morpholin-4-yl)pyridin-4-yl]sulfanyl}phenyl) methanol hydrochloride (crude, 650 mg, 1.64 mmol) in 5% aqueous NaHCO₃ (5 ml) was added Fmoc-OSu (609.241 mg, 1.81 mmol) in dioxane (5 ml) and stirred at 25° C. for 30 min. The reaction mixture was filtered and concentrated under vacuum. The crude, thus obtained was purified by silica gel chromatography using ethyl acetate in n-hexane (0-40%) as eluting solvent to afford 9H-fluoren-9-ylmethyl N-[(4-{[2-(hydroxymethyl)phenyl]sulfanyl}-2-(morpholin-4-yl)pyridin-3-yl)methyl]carbamate (700 mg, 65% over 3 steps) as white solid. LC-MS: 553.9 [M+H]⁺.

To a stirred suspension of 9H-fluoren-9-ylmethyl N-[(4-{[2-(hydroxymethyl)phenyl]sulfanyl}-2-(morpholin-4-yl)pyridin-3-yl)methyl]carbamate (650 mg, 1.18 mmol) in DCM (10 ml) was added dess-martin periodinane (747.8 mg, 1.76 mmol) at 0° C. and stirred at 25° C. for 2 h. The reaction mixture was diluted with DCM, washed with aqueous saturated NaHCO₃ solution, followed by brine. The organic layer was separated, dried over anhydrous sodium sulfate and concentrated under vacuum. The crude, thus obtained was purified by silica gel column chromatography using ethyl acetate in n-hexane (0-40%) as eluting solvent to afford 9H-fluoren-9-ylmethyl N-({4-[(2-formylphenyl)sulfanyl]-2-(morpholin-4-yl)pyridin-3-yl}methyl) carbamate (230 mg, 36%) as white solid. LC-MS: 551.9 [M+H]⁺.

1H NMR: (400 MHz, DMSO-d6) δ 3.07 (4H, s), 3.70 (4H, s), 4.18-4.26 (1H, m), 4.32 (2H, d, J=6.6 Hz), 4.40-4.47 (2H, m), 6.41 (1H, d, J=5.3 Hz), 7.28 (2H, t, J=6.7 Hz), 7.38 (2H, t, J=6.9 Hz), 7.48 (1H, d, J=7.7 Hz), 7.65-7.77 (5H, m), 7.87 (2H, d, J=7.2 Hz), 7.99 (1H, d, J=6.4 Hz), 8.04 (1H, d, J=5.2 Hz), 10.29 (1H, s).

Intermediate 114

(9H-Fluoren-9-yl)methyl ((6-bromo-3-((3-formylpyridin-2-yl)thio)pyridin-2-yl)methyl)carbamate

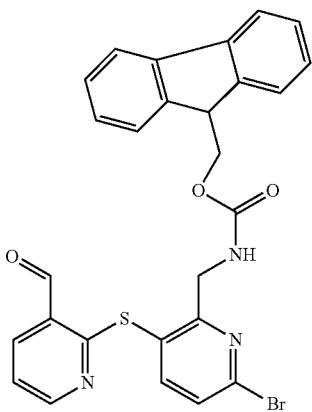 [SMILES: O=Cc1cccnc1Sc1ccc(Br)nc1CNC(=O)OCC1c2ccccc2-c2ccccc21]

This material was prepared in analogy to Intermediate 95 starting from 6-bromo-3-fluoropicolinaldehyde and 2-mercaptonicotinic acid. The title compound was obtained as light red foam (133 mg). MS ESI (m/z): 546.0, 548.0 [(M+H)+]

Intermediate 115

[2-(4-Bromo-2-formyl-phenylsulfanyl)-3-chlorobenzyl]-carbamic Acid 9H-fluoren-9-ylmethyl Ester

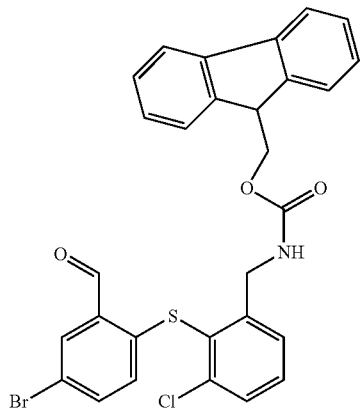 [SMILES: O=Cc1cc(Br)ccc1Sc1c(Cl)cccc1CNC(=O)OCC1c2ccccc2-c2ccccc21]

To a suspension of sodium sulfide, anhydrous (4.14 g, 2.23 ml, 53 mmol, Eq: 2) in DMF, anhydrous (100 ml) was added at 22° C. methyl 3-chloro-2-fluorobenzoate (5.00 g, 26.5 mmol, Eq: 1), warmed to 70° C. while color changed to dark green and stirred at 70° C. for 2 h while color changed to yellow to give complete conversion. The mixture was cooled to 5° C. and quenched by dropping slowly into an ice-cold 10% HCl-solution (200 ml), diluted with sat NaCl (200 ml) and extracted with ethyl acetate (2×300 ml). The organic layers were dried and evaporated to give a yellow oil. The crude product was purified by flash chromatography (silica gel, 80 g, adsorbed on Isolute HM-N, EtOAc in heptane 0% to 10% to 50%) to give methyl 3-chloro-2-mercaptobenzoate (2.95 g, 55%) as a light yellow oil.

To a solution of methyl 3-chloro-2-mercaptobenzoate (2.5 g, 12.3 mmol, Eq: 1) in DMF (50 ml) was added at 22° C. 5-bromo-2-fluorobenzaldehyde (3.76 g, 18.5 mmol, Eq: 1.5) followed by potassium carbonate (1.7 g, 12.3 mmol, Eq: 1), warmed to 70° C. and stirred at 70° C. for 3 h to give conversion complete. The suspension was cooled to 22° C., the precipitated solid was filtered off, washed with ether (1×15 ml). The filtrate was evaporated and the yellow turbid oil was purified by flash chromatography (silica gel, 120 g, adsorbed on Isolute sorbent HM-N, EtOAc in heptane 0% to 30%) to give methyl 2-((4-bromo-2-formylphenyl)thio)-3-chlorobenzoate (2.536 g, 53%) as a light yellow solid.

LC-MS: m/z=385.0 (M+H)+(monoisotopic mass 383.92)

To a solution of methyl 2-((4-bromo-2-formylphenyl)thio)-3-chlorobenzoate (2.41 g, 6.25 mmol, Eq: 1) in toluene (72 ml) was added at 22° C. ethylene glycol (776 mg, 697 µl, 12.5 mmol, Eq: 2) followed by p-toluenesulfonic acid monohydrate (119 mg, 625 µmol, Eq: 0.1), heated to reflux with a Dean-Stark-trap and stirred at 111° C. (oil bath 145° C.) for 10 h, but only 72% conversion by LC-MS. Further addition of 1.4 ml ethylene glycol (=4 eq) followed by an additional 119 mg (=0.1 eq) p-toluenesulfonic acid monohydrate and again stirring at reflux as described for 4 h gave more impurities (LC-MS) and no further conversion. The solvent was removed under reduced pressure, the residue was treated with sat NaHCO3 (100 ml) and extracted with ethyl acetate (2×100 ml). The organic layers were dried and evaporated. The residue was purified by flash chromatography (silica gel, 120 g, adsorbed on Isolute HM-N, Hep/DCM 2:1 to 100% DCM) to give methyl 2-((4-bromo-2-(1,3-dioxolan-2-yl)phenyl)thio)-3-chlorobenzoate (2.257 g, 84%) as a colorless oil.

LC-MS: m/z=429.0 (M+H)+(for monoisotopic mass 427.95)

To a solution of methyl 2-((4-bromo-2-(1,3-dioxolan-2-yl)phenyl)thio)-3-chlorobenzoate (2.2 g, 5.12 mmol, Eq: 1) in tetrahydrofuran (44 ml) was added dropwise at 0° C. lithium aluminum hydride, 2 M in THF (7.68 ml, 15.4 mmol, Eq: 3) and stirred at 0° C. for 3 h to give complete conversion. The mixture was quenched by dropwise addition of 2.5 ml water (ca. 2.5 eq—exotherm, gas evolution) and stirred for 1 h at 0° C. Then allowed to warm to 22° C., treated with Na2SO4 and diluted with ethyl acetate (16 ml) and filtered off. The filtrate was evaporated and dried to give the title compound (1.711 g, 83%) as colorless oil. Used as is in next step.

LC-MS: 69% with m/z=339.1 (M+H−ethylene glycole)+ for product (for monoisotopic mass 399.95) and 20% impurity with m/z=261.0 (M+H−ethylene glycole)+ for des-bromo-byproduct To a solution of (2-((4-bromo-2-(1,3-dioxolan-2-yl)phenyl)thio)-3-chlorophenyl)methanol (1.65 g, 4.11 mmol, Eq: 1) in dichloromethane (17 ml) was added at 0° C. triethylamine (1.25 g, 1.72 ml, 12.3 mmol, Eq: 3) followed dropwise (5 minutes) by methanesulfonyl chloride (706 mg, 480 µl, 6.16 mmol, Eq: 1.5) while internal temperature was kept below 5° C. and stirred at 0° C. for 30 min to give complete conversion. The mixture was quenched with water (50 ml)

and extracted with dichloromethane (2×50 ml). The organic layers were dried and evaporated. The residue was purified by flash chromatography (silica gel, 80 g, adsorbed on Isolute HM-N, EtOAc in heptane 0% to 50%) to give 2-((4-bromo-2-(1,3-dioxolan-2-yl)phenyl)thio)-3-chlorobenzyl methanesulfonate (1.132 g, 57%) as a colorless oil.

LC-MS: m/z=479.0 (M+H)+ (477.93 for monoisotopic mass)

To a solution of 2-((4-bromo-2-(1,3-dioxolan-2-yl)phenyl)thio)-3-chlorobenzyl methanesulfonate (1.05 g, 2.19 mmol, Eq: 1) in Tetrahydrofuran (8 ml) was added at −78° C. ammonia (11.2 g, 14.2 ml, 657 mmol, Eq: 300) via condensation at −78° C. and followed by transfer into dry-ice cold autoclave via funnel, closed and allowed to warm to 22° C. After total 2 h the autoclave was again cooled to ca. −50° C., valve opened and allowed to warm while excess ammonia was absorbed into wash-bottle containing 5 M HCl. The remaining reaction mixture was purged with argon for 20 minutes and the mixture was filtered. The filtrate was evaporated to give (2-((4-bromo-2-(1,3-dioxolan-2-yl)phenyl)thio)-3-chlorophenyl)methanamine (715 mg, 82%) as colorless oil.

LC-MS: m/z=400.0 (M+H)+ (398.97 for monoisotopic mass)

To an emulsion of (2-((4-bromo-2-(1,3-dioxolan-2-yl)phenyl)thio)-3-chlorophenyl)methanamine (660 mg, 1.65 mmol, Eq: 1) in sodium bicarbonate, 5% aq (8.3 g, 7.69 ml, 4.94 mmol, Eq: 3) was added at 22° C. a solution of (9H-fluoren-9-yl)methyl (2,5-dioxopyrrolidin-1-yl) carbonate (556 mg, 1.65 mmol, Eq: 1) in Acetonitrile (6.6 ml) and stirred at 22° C. for 2 h. The organic solvent was removed under reduced pressure, diluted with water (10 ml) and extracted with ethyl acetate (2×20 ml). The organic layers were washed with sat NaCl (1×20 ml), dried and evaporated. The residue was purified by flash chromatography (silica gel, 24 g, adsorbed on Isolute HM-N, EtOAc in heptane 0% to 30%) to give (9H-fluoren-9-yl)methyl 2-((4-bromo-2-(1,3-dioxolan-2-yl)phenyl)thio)-3-chlorobenzylcarbamate (920 mg, 90%) as a white foam.

LC-MS: m/z=622.0 (M+H)+ (621.04 for monoisotopic mass)

To a solution of (9H-fluoren-9-yl)methyl 2-((4-bromo-2-(1,3-dioxolan-2-yl)phenyl)thio)-3-chlorobenzylcarbamate (872 mg, 1.4 mmol, Eq: 1) in Acetone (26 ml) was added at 22° C. hydrochloric acid, 5 M aq (11.2 ml, 56 mmol, Eq: 40) and stirred at 22° C. for 2 h while a solid precipitated to give complete conversion. The mixture was concentrated under reduced pressure to half volume and the solid was filtered off, washed with acetonitrile (1×5 ml), pentane (2×5 ml) and dried in HV to give (9H-fluoren-9-yl)methyl 2-((4-bromo-2-formylphenyl)thio)-3-chlorobenzylcarbamate (785 mg, 97%) as a white solid.

LC-MS: m/z=560.0 (M+H−H2O)+ (MW 577.0 for monoisotopic mass)

1H NMR (400 MHz, CDCl$_3$) δ 10.25 (s, 1H), 7.96 (m, 1H), 7.76 (m, 3H), 7.52 (br s, 3H), 7.41 (m, 6H), 7.28 (m, 3H), 6.45 (br d, J=8.5 Hz, 1H), 5.22 (br t, J=5.9 Hz, 1H), 4.50 (m, 2H), 4.39 (d, J=6.9 Hz, 2H), 4.15 (m, 2H)

Intermediate 116

9H-fluoren-9-ylmethyl N-{[3-chloro-5-(4-cyanophenyl)-2-[(3-formylpyridin-2-yl)sulfanyl]phenyl]methyl}carbamate

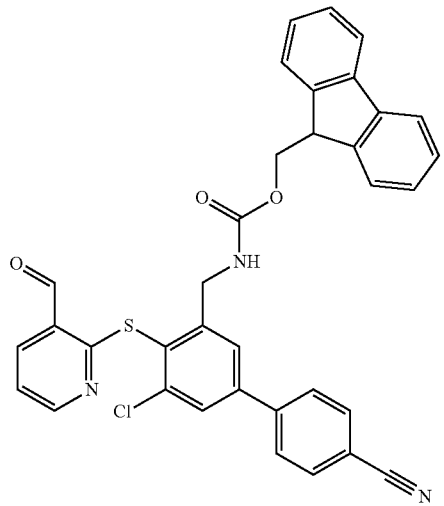 [SMILES: N#Cc1ccc(-c2cc(Cl)c(Sc3ncccc3C=O)c(CNC(=O)OCC3c4ccccc4-c4ccccc43)c2)cc1]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2 g, 3.46 mmol) in dioxan (20 mL) were added (4-cyanophenyl)boronic acid (661 mg, 4.49 mmol), Na$_2$CO$_3$ (1.1 g, 10.38), and degassed for 10 min in argon atmosphere. Then to it was added Pd(PPh$_3$)$_4$ (200 mg, 0.17 mmol) and again degassed for 10 min. The reaction mass was heated to 120° C. for 16 h. Reaction mixture was then cooled to 25° C., filtered through celite pad, washed with EtOAc. The separated organic layer was washed with brine solution, dried over sodium sulfate and concentrated under reduced pressure. The crude thus obtained was purified by silica column chromatography (SiO$_2$; 100-200 mesh; 0%-30% ethyl acetate in hexane) to get N-({2-[(3-{[(tert-butyldimethylsilyl)oxy]methyl}pyridin-2-yl)sulfanyl]-3-chloro-5-(4-cyanophenyl)phenyl}methyl)-2-methylpropane-2-sulfinamide (1.4 g, 67%) as off white solid. LC-MS: 600.2 [M+H]$^+$ To a stirred solution of N-({2-[(3-{[(tert-butyldimethylsilyl)oxy]methyl}pyridin-2-yl)sulfanyl]-3-chloro-5-(4-cyanophenyl)phenyl}methyl)-2-methylpropane-2-sulfinamide (1.4 g, 2.33 mmol) in MeOH (8 mL), was added 4M HCl in dioxan (4 mL) at 0° C. and reaction mixture was stirred at 25° C. for 2h. Reaction mass was evaporated under reduced pressure to get 4-[3-(aminomethyl)-5-chloro-4-{[3-(hydroxymethyl)pyridin-2-yl]sulfanyl}phenyl]benzonitrile hydrochloride (1 g) which was directly used for next step without further purification. LC-MS: 381.7 [M+H]$^+$ To a stirred suspension of 4-[3-(aminomethyl)-5-chloro-4-{[3-(hydroxymethyl)pyridin-2-yl]sulfanyl}phenyl]benzonitrile hydrochloride (1 g, 2.39 mmol) in 5% NaHCO$_3$ (20 mL) was added Fmoc-OSU (0.81 g, 2.39 mmol) in dioxan (40 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-{[3-chloro-5-(4-cyanophenyl)-2-{

[3-(hydroxymethyl)pyridin-2-yl]sulfanyl}phenyl]methyl}carbamate (1.6 g) as off white solid; which was used for next step without further purification. LC-MS: 604.1 [M+H]+

To a stirred solution of 9H-fluoren-9-ylmethyl N-{[3-chloro-5-(4-cyanophenyl)-2-{[3-(hydroxymethyl)pyridin-2-yl]sulfanyl}phenyl]methyl}carbamate (1.6 g, 2.65 mmol) in DCM:THF (1:1, 80 mL) was added MnO₂ (4.6 g, 52.97 mmol) and reaction mass was stirred at 25° C. for 2 h. The reaction mass was filtered through celite pad and the filtrate was evaporated under reduced pressure. The crude material obtained was purified by silica column chromatography (SiO₂; 100-200 mesh; 10%-50% EtOAc/Hexane) to get 9H-fluoren-9-ylmethyl N-{[3-chloro-5-(4-cyanophenyl)-2-[(3-formylpyridin-2-yl)sulfanyl]phenyl]methyl}carbamate (730 mg) as a off white solid with 97% LCMS purity. LC-MS: 602.1 [M+H]+

1H NMR (400 MHz, DMSO-d6): δ 4.20 (1H, d, J=6.8 Hz), 4.27 (2H, d, J=7.1 Hz), 4.37 (2H, d, J=5.5 Hz), 7.25 (2H, t, J=7.5 Hz), 7.39 (3H, q, J=7.8, 6.9 Hz), 7.66 (2H, d, J=7.2 Hz), 7.74 (1H, s), 7.89 (3H, t, J=7.6 Hz), 7.97 (5H, q, J=8.9 Hz), 8.38 (1H, d, J=7.6 Hz), 8.44 (1H, d, J=4.4 Hz), 10.22 (1H, s).

Intermediate 117

9H-fluoren-9-ylmethyl N-({3-chloro-2-[(3-formylpyridin-2-yl)sulfanyl]-6-(2-methylpyridin-4-yl)phenyl}methyl)carbamate

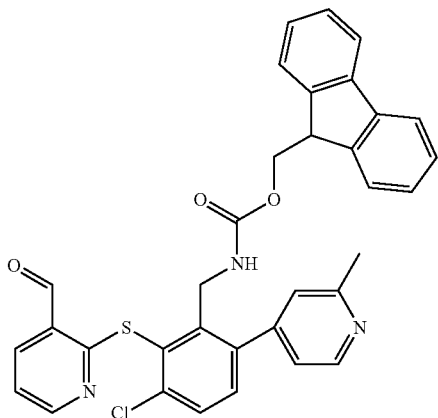 [SMILES: Cc1cc(-c2ccc(Cl)c(Sc3ncccc3C=O)c2CNC(=O)OCC2c3ccccc3-c3ccccc32)ccn1]

To a stirred solution of compound N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (3 g, 5.18 mmol) in dioxan (20 mL) were added (2-methylpyridin-4-yl)boronic acid (924 mg, 6.74 mmol), Na₂CO₃ (1.65 g, 15.56 mmol), water (10 mL) and degassed for 10 min in argon atmosphere. Then to it was added Pd(PPh₃)₄ (300 mg, 0.25 mmol) and again degassed for 10 min. The reaction mass was heated to 120° C. for 16 h. The reaction mass was filtered through celite pad and filtrate was evaporated under reduced pressure to get N-({2-[(3-{[(tert-butyldimethylsilyl)oxy]methyl}pyridin-2-yl)sulfanyl]-3-chloro-6-(2-methylpyridin-4-yl)phenyl}methyl)-2-methylpropane-2-sulfinamide (3 g) as off white solid. LC-MS: 589.7 [M+H]+

To a stirred solution of N-({2-[(3-{[(tert-butyldimethylsilyl)oxy]methyl}pyridin-2-yl)sulfanyl]-3-chloro-6-(2-methylpyridin-4-yl)phenyl}methyl)-2-methylpropane-2-sulfinamide (3 g, 5.08 mmol) in MeOH (12 mL), was added 4M HCl in dioxan (6 mL) at 0° C. and reaction mixture was stirred at 25° C. for 2h. Reaction mass was evaporated under reduced pressure to get (2-{[2-(aminomethyl)-6-chloro-3-(2-methylpyridin-4-yl)phenyl]sulfanyl}pyridin-3-yl)methanol (1.7 g) which was directly used for next step without further purification. LC-MS: 371.9 [M+H]+

To a stirred suspension of (2-{[2-(aminomethyl)-6-chloro-3-(2-methylpyridin-4-yl)phenyl]sulfanyl}pyridin-3-yl)methanol (1.7 g, 4.16 mmol) in 5% NaHCO₃ (20 mL) was added Fmoc-OSU (1.4 g, 4.16 mmol) in dioxan (40 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-6-(2-methylpyridin-4-yl)phenyl)methyl]carbamate (2 g, crude) as off white solid; which was used for next step without further purification. LC-MS: 593.6 [M+H]+

To a stirred solution of 9H-fluoren-9-ylmethyl N-[(3-chloro-2-{[3-(hydroxymethyl)pyridin-2-yl]sulfanyl}-6-(2-methylpyridin-4-yl)phenyl)methyl]carbamate (2.0 g, 3.36 mmol) in DCM:THF (1:1, 60 mL) was added MnO₂ (5.85 g, 67.32 mmol) and reaction mass was stirred at 25° C. for 2 h. The reaction mass was filtered through celite pad; filtrate was evaporated under reduced pressure. The crude thus obtained was purified by silica column chromatography (SiO₂; 100-200 mesh; 10%-50% EtOAc/Hexane) to get 9H-fluoren-9-ylmethyl N-({3-chloro-2-[(3-formylpyridin-2-yl)sulfanyl]-6-(2-methylpyridin-4-yl)phenyl}methyl)carbamate (650 mg, 21%, 4 steps) as off white solid with 94.83% purity. LC-MS: 591.7 [M+H]+

1H NMR (400 MHz, DMSO-d6): δ 2.43 (3H, s), 4.12 (5H, s), 7.25 (1H, d, J=4.8 Hz), 7.28-7.35 (4H, m), 7.33-7.40 (1H, m), 7.39 (1H, d, J=4.3 Hz), 7.43 (2H, d, J=8.1 Hz), 7.60 (1H, s), 7.66 (2H, d, J=7.4 Hz), 7.71 (1H, d, J=8.3 Hz), 7.89 (2H, d, J=7.5 Hz), 8.35 (1H, d, J=7.6 Hz), 8.44 (1H, d, J=5.0 Hz), 8.47 (1H, d, J=3.5 Hz), 10.21 (1H, s).

Intermediate 118 (RO7125868-000-001)

9H-fluoren-9-ylmethyl N-({3-chloro-2-[(3-formylpyridin-2-yl)sulfanyl]-5-(pyrimidin-5-yl)phenyl}methyl)carbamate

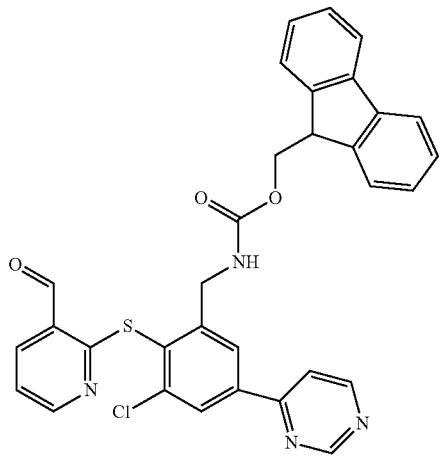 [SMILES: O=Cc1cccnc1Sc1c(Cl)cc(-c2ccncn2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (650 mg, 1.13 mmol) in toluene (7 mL) were added 4-(tributylstannyl)pyrimidine (623 mg, 1.69 mmol) and LiCl (14 mg, 0.034 mmol) and degassed in argon atmosphere for 10 min. Then to it was added Pd(PPh3)4 (130.1 mg, 0.11 mmol) and reaction mass was heated to 110° C. for 16h. Reaction mixture was then filtered through celite pad and evaporated under reduced pressure. The crude thus obtained was purified by normal silica column using 1-8% methanol in DCM to get N-({2-[(3-{[(tert-butyldimethylsilyl)oxy]methyl}pyridin-2-yl)sulfanyl]-3-chloro-5-(pyrimidin-4-yl)phenyl}methyl)-2-methylpropane-2-sulfinamide (260 mg, 40%) as light yellow solid. LC-MS: 576.8 [M+H]+

To a stirred solution of N-({2-[(3-{[(tert-butyldimethylsilyl)oxy]methyl}pyridin-2-yl)sulfanyl]-3-chloro-5-(pyrimidin-4-yl)phenyl}methyl)-2-methylpropane-2-sulfinamide (260 mg, 0.45 mmol) in MeOH (8 mL), was added 4M HCl in dioxan (4 mL) at 0° C. and reaction mixture was stirred at 25° C. for 2h. The reaction mass was evaporated under reduced pressure to get (2-{[2-(aminomethyl)-6-chloro-4-(pyrimidin-4-yl)phenyl]sulfanyl}pyridin-3-yl)methanol HCl salt (200 mg) which was directly used for next step. LC-MS: 358.9 [M+H]+

To a stirred suspension of (2-{[2-(aminomethyl)-6-chloro-4-(pyrimidin-4-yl)phenyl]sulfanyl}pyridin-3-yl)methanol HCl salt (200 mg, 0.56 mmol) in 5% NaHCO3 (5 mL) was added Fmoc-OSU (188 mg, 0.56 mmol) in dioxan (5 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(pyrimidin-4-yl)phenyl)methyl]carbamate (250 mg) as off white solid. LC-MS: 581.0 [M+H]+

To a stirred solution of 9H-fluoren-9-ylmethyl N-[(3-chloro-2-{[3-(hydroxymethyl)pyridin-2-yl]sulfanyl}-5-(pyrimidin-4-yl)phenyl)methyl]carbamate (250 mg, 0.43 mmol) in DCM:THF (1:1, 10 mL) was added MnO2 (749.3 mg, 8.62 mmol) and reaction mass was stirred at 25° C. for 2 h. The reaction mass was filtered through celite pad and the filtrate was evaporated under reduced pressure. The crude material obtained was purified by normal silica column using 30-80% ethyl acetate in hexane to get 9H-fluoren-9-ylmethyl N-({3-chloro-2-[(3-formylpyridin-2-yl)sulfanyl]-5-(pyrazin-2-yl)phenyl}methyl)carbamate (145 mg) as off white solid with 96% LCMA purity. LC-MS: 578.8 [M+H]+

1H NMR (400 MHz, DMSO-d6): δ 4.23 (1H, dd, J=5.0, 1.2 Hz), 4.28 (2H, d, J=6.5 Hz), 4.38 (2H, d, J=5.4 Hz), 7.28 (2H, t, J=6.5 Hz), 7.40 (3H, t, J=6.6 Hz), 7.69 (2H, d, J=7.4 Hz), 7.89 (2H, d, J=7.6 Hz), 7.95-8.03 (1H, m), 8.18 (1H, d, J=5.2 Hz), 8.26 (1H, s), 8.34 (1H, s), 8.39 (1H, d, J=7.8 Hz), 8.42-8.47 (1H, m), 8.95 (1H, d, J=5.2 Hz), 9.25 (1H, s), 10.22 (1H, s).

Intermediate 119

9H-fluoren-9-ylmethyl N-({3-chloro-2-[(3-formylpyridin-2-yl)sulfanyl]-5-(4-sulfamoylphenyl)phenyl}methyl)carbamate

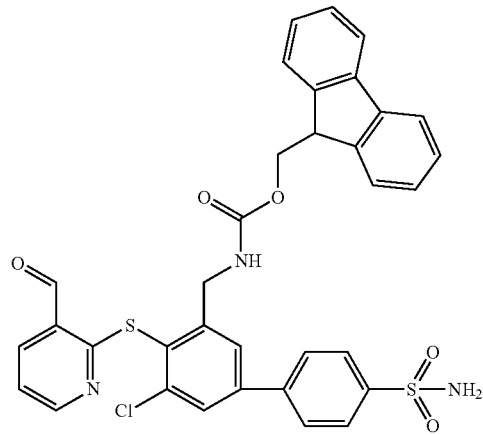 [SMILES: NS(=O)(=O)c1ccc(-c2cc(Cl)c(Sc3ncccc3C=O)c(CNC(=O)OCC3c4ccccc4-c4ccccc43)c2)cc1]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (3 g, 5.19 mmol) in dioxan (30 mL) were added (4-sulfamoylphenyl)boronic acid (1.35 g, 6.7 mmol), Na2CO3 (1.65 g, 15.5 mmol), water (15 mL) and degassed for 10 min in argon atmosphere. Then to it was added Pd(PPh3)4 (300 mg, 0.26 mmol) and again degassed for 5 min. The reaction mass was heated to 120° C. for 16 h. Reaction mixture was then cooled to 25° C., filtered through celite pad and washed with EtOAc. The separated organic layer was washed with brine solution, dried over sodium sulfate and concentrated under reduced pressure to get 4-{4-[(3-{[(tert-butyldimethylsilyl)oxy]methyl}pyridin-2-yl)sulfanyl]-3-chloro-5-{[(2-methylpropane-2-sulfinyl)amino]methyl}phenyl}benzene-1-sulfonamide (3 g) as colourless sticky liquid. LC-MS: 654.0 [M+H]+

To a stirred solution of 4-{4-[(3-{[(tert-butyldimethylsilyl)oxy]methyl}pyridin-2-yl)sulfanyl]-3-chloro-5-{[(2-methylpropane-2-sulfinyl)amino]methyl}phenyl}benzene-1-sulfonamide (3 g, 4.58 mmol) in MeOH (12 mL), was added 4M HCl in dioxan (6 mL) at 0° C. and reaction mixture was stirred at 25° C. for 2h. Reaction mass was evaporated under reduced pressure to get 4-[3-(aminomethyl)-5-chloro-4-{[3-(hydroxymethyl)pyridin-2-yl]sulfanyl}phenyl]benzene-1-sulfonamide hydrochloride (2.2 g) which was directly used for next step. LC-MS: 435.7 [M+H]+

To a stirred suspension of 4-[3-(aminomethyl)-5-chloro-4-{[3-(hydroxymethyl)pyridin-2-yl]sulfanyl}phenyl]benzene-1-sulfonamide hydrochloride (2 g, 4.23 mmol) in 5% NaHCO3 (20 mL) was added Fmoc-OSU (1.43 g, 4.23 mmol) in dioxan (40 mL) at 25° C. and reaction mass was stirred at the same temperature for 2h. Then reaction mass was diluted with water and extracted with 10% methanol in dichloromethane. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(4-sulfamoylphenyl)phenyl)methyl]carbamate (2.5 g) as off white solid. LC-MS: 657.9 [M+H]+

To a stirred solution of 9H-fluoren-9-ylmethyl N-[(3-chloro-2-{[3-(hydroxymethyl)pyridin-2-yl]sulfanyl}-5-(4-sulfamoylphenyl)phenyl)methyl]carbamate (2.5 g, 3.8 mmol) in DCM/THF (1:1, 60 mL) was added MnO$_2$ (6.6 g, 75.9 mmol) and reaction mass was stirred at 25° C. for 2 h. The reaction mass was filtered through celite pad and filtrate was evaporated under reduced pressure. The crude material obtained was purified by silica column (SiO$_2$; 100-200 mesh; 10-50% ethyl acetate in hexane) to give 9H-fluoren-9-ylmethyl N-({3-chloro-2-[(3-formylpyridin-2-yl)sulfanyl]-5-(4-sulfamoylphenyl)phenyl}methyl)carbamate (520 mg) as off white solid with 95% LCMS purity. LC-MS: 654.2 [M+H]$^+$ 1H NMR (400 MHz, DMSO-d6): δ 4.21 (1H, d, J=6.5 Hz), 4.28 (2H, d, J=6.8 Hz), 4.37 (2H, d, J=5.7 Hz), 7.25 (2H, t, J=7.4 Hz), 7.39 (4H, q, J=7.4 Hz), 7.48 (2H, s), 7.67 (2H, d, J=7.5 Hz), 7.72 (1H, s), 7.89 (4H, dd, J=12.8, 7.0 Hz), 7.93-8.02 (1H, m), 8.38 (1H, d, J=6.3 Hz), 8.45 (1H, d, J=3.4 Hz), 10.22 (1H, s).

Intermediate 120

(9H-fluoren-9-yl)methyl 2-((5-bromo-2-formylphenyl)thio)-3-chlorobenzylcarbamate

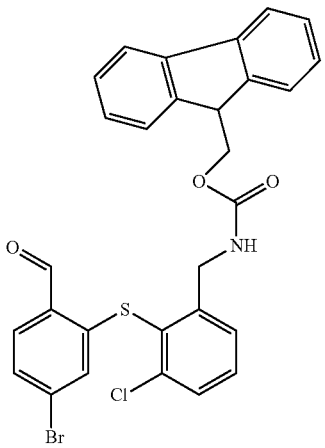 [SMILES: O=Cc1ccc(Br)cc1Sc1c(Cl)cccc1CNC(=O)OCC1c2ccccc2-c2ccccc21]

To a suspension of sodium sulfide, anhydrous (2.46 g, 1.32 ml, 31.5 mmol, Eq: 2) in DMF, anhydrous (73 ml) was added at 22° C. methyl 4-bromo-2-fluorobenzoate (3.67 g, 15.7 mmol, Eq: 1), warmed to 70° C. while color changed to brown and stirred at 70° C. for 2 h to give complete conversion. The mixture was cooled to 5° C. and quenched by dropping slowly into an ice-cold 10% HCl-solution (100 ml), diluted with sat NaCl (100 ml) while internal temperature was kept below 10° C. and extracted with ethyl acetate (2×100 ml). The organic layers were dried and evaporated to give a yellow semi-solid. The crude product was purified by flash chromatography (silica gel, 80 g, adsorbed on Isolute HM-N, EtOAc in heptane 5% to 10% to 20% to 60%) to give methyl 4-bromo-2-mercaptobenzoate (1.29 g, 33%) as a light yellow oil.

LC-MS: m/z=245.0 (M−H)$^-$ (MW 245.94 for monoisotopic mass)

To a solution of methyl 4-bromo-2-mercaptobenzoate (1.29 g, 5.22 mmol, Eq: 1) in DMF (25.8 ml) was added at 22° C. 3-chloro-2-fluorobenzaldehyde (1.24 g, 7.83 mmol, Eq: 1.5) followed by potassium carbonate (721 mg, 5.22 mmol, Eq: 1), warmed to 70° C. and stirred at 70° C. for 30 min to give nearly conversion complete. The suspension was cooled to 22° C., the precipitated solid was filtered off (dicalite) and washed with ether (1×15 ml). The filtrate was evaporated in HV and the yellow oil was purified by flash chromatography (silica gel, 80 g, EtOAc in heptane 0% to 20% to 60%) to give methyl 4-bromo-2-((2-chloro-6-formylphenyl)thio)benzoate (1.73 g, 86%) as a light yellow solid.

LC-MS: m/z=385.0 (M+H)+ (monoisotopic mass 383.92)

To a solution of methyl 4-bromo-2-((2-chloro-6-formylphenyl)thio)benzoate (1.73 g, 4.49 mmol, Eq: 1) and 2-methylpropane-2-sulfinamide (544 mg, 4.49 mmol, Eq: 1) in THF (19 ml) was added at 22° C. Titanium(IV)ethoxide (5.12 g, 4.65 ml, 22.4 mmol, Eq: 5) to give a clear yellow solution followed by heating to reflux and stirred at 70° C. for 1 h to give complete conversion. The light turbid yellow suspension was cooled to 22° C. and quenched with sat NaCl (25 ml) to give a thick suspension. The mixture was filtered through dicalite and washed with ethyl acetate (2×25 ml). The filtrate (2-phase-system) was transferred into a separation funnel, the aqueous layer was separated and the organic layer was dried and evaporated to give a mix of (E)-methyl 4-bromo-2-((2-(((tert-butylsulfinyl)imino)methyl)-6-chlorophenyl)thio)benzoate and (E)-ethyl 4-bromo-2-((2-(((tert-butylsulfinyl)imino)methyl)-6-chlorophenyl)thio)benzoate (2.16 g, 97%) as a light yellow foam.

NMR: mixture of methyl- and ethyl-ester ratio ca. 7:4.

LC-MS: m/z=488.1 and 502.1 (M+H)+(MW for monoisotopic mass: 486.97 and 500.98)

To a solution of (E)-methyl 4-bromo-2-((2-(((tert-butylsulfinyl)imino)methyl)-6-chlorophenyl)thio)benzoate and (E)-ethyl 4-bromo-2-((2-(((tert-butylsulfinyl)imino)methyl)-6-chlorophenyl)thio)benzoate (ratio 7:4, 2.16 g, 4.42 mmol, Eq: 1) in THF (21.6 ml) was added at 22° C. lithium borohydride (963 mg, 44.2 mmol, Eq: 10) while color changed immediately to intensive green and internal temperature rised up to 31° C. The mixture was warmed to 50° C. and stirred at 50° C. for 20 h to give complete conversion. The mixture was cooled to 22° C., quenched dropwise (effervescensing and exothermic—cooling with ice-water bath) with sat NH$_4$Cl (100 ml) and completely extracted with ethyl acetate (1×50 ml) by stirring for 30 minutes until gas evolution has ceased. The organic layer was washed with 5% KH2PO4 (1×50 ml, pH 5) and sat. NaCl (1×50 ml), dried and evaporated to give the crude product as white solid. The solid was suspended in 20 ml ethyl acetate under reflux, The oil bath was removed, 20 ml heptane was added in one portion and cooled to 22° C. while solid precipitated. The suspension was cooled to 5° C. and stirred for 60 minutes, the solid was filtered off, washed with EtOAc/Hep 1:1(1×10 ml) and dried in HV to give N-(2-((5-bromo-2-(hydroxymethyl)phenyl)thio)-3-chlorobenzyl)-2-methylpropane-2-sulfinamide (1.538 g, 75%) as white solid.

LC-MS: m/z=462.1 (M+H)+ for monoisotopic mass 460.99

To a suspension of N-(2-((5-bromo-2-(hydroxymethyl)phenyl)thio)-3-chlorobenzyl)-2-methylpropane-2-sulfinamide (1.478 g, 3.19 mmol, Eq: 1) in Methanol (14.8 ml) was added at 0° C. HCl, 4 M in dioxane (7.98 ml, 31.9 mmol, Eq: 10), allowed to warm to 22° C. while solid dissolved completely and stirred at 22° C. for 30 min to give complete conversion. After total 60 minutes the solvent was removed under reduced pressure and dried in HV to give (2-((2-(aminomethyl)-6-chlorophenyl)thio)-4-bromophenyl) methanol hydrochloride (1.26 g, 100%) as white solid.

LC-MS: m/z=358.0 (M+H)+(free amine MW 356.96 for monoisotopic mass)

To a solution of (2-((2-(aminomethyl)-6-chlorophenyl)thio)-4-bromophenyl)methanol hydrochloride (1.23 g, 3.11 mmol, Eq: 1) in Methanol (73.4 ml) was added at 22° C. pyridine (985 mg, 1.01 ml, 12.5 mmol, Eq: 4) followed by (9H-fluoren-9-yl)methyl (2,5-dioxopyrrolidin-1-yl) carbonate (1.1 g, 3.27 mmol, Eq: 1.05) and stirred at 22° C. for 3 days while more solid had precipitated to give conversion complete. The solid was filtered off, washed with methanol (2×15 ml) and dried in HV to give (9H-fluoren-9-yl)methyl 2-((5-bromo-2-(hydroxymethyl)phenyl)thio)-3-chlorobenzylcarbamate (1.538 g, 85%) as white solid.

LC-MS: m/z=562.2 (M+H−H2O)+ (MW 579.03 for monoisotopic mass)

To a solution of (9H-fluoren-9-yl)methyl 2-((5-bromo-2-(hydroxymethyl)phenyl)thio)-3-chlorobenzylcarbamate (1.485 g, 2.56 mmol, Eq: 1) in THF (50 ml) and DCM (50 ml) was added at 22° C. manganese dioxide (4.44 g, 51.1 mmol, Eq: 20) and stirred at 22° C. for 3 h to give conversion complete. The mixture was filtered (membrane-filter), washed with THF/DCM 1:1 (2×15 ml) and the filtrate was evaporated to give the product as yellow solid. The crude product was suspended in 15 ml MeOH (ultrasonic bath for 30 minutes and then suspended at 22° C. for 30 minutes), the solid was filtered off, washed with MeOH (2×6 ml), dried in HV to give (9H-fluoren-9-yl)methyl 2-((5-bromo-2-formylphenyl)thio)-3-chlorobenzylcarbamate (1.287 g, 87%) as off-white solid.

LC-MS: m/z=578.0 (M+H)+ for monoisotopic mass 577.01

1H NMR (600 MHz, DMSO-d$_6$) δ 10.15 (s, 1H), 7.95 (d, J=8.2 Hz, 1H), 7.86-7.91 (m, 2H), 7.66-7.69 (m, 1H), 7.68 (d, J=7.6 Hz, 1H), 7.57-7.64 (m, 2H), 7.37-7.44 (m, 2H), 7.37-7.40 (m, 1H), 7.33 (t, J=7.5 Hz, 2H), 6.52 (s, 1H), 4.31 (dd, J=9.8, 6.5 Hz, 4H), 4.20 (br d, J=6.5 Hz, 1H)

Intermediate 121

9H-fluoren-9-ylmethyl N-{[3-chloro-6-(2-fluoropyridin-4-yl)-2-[(3-formylpyridin-2-yl) sulfanyl]phenyl]methyl}carbamate

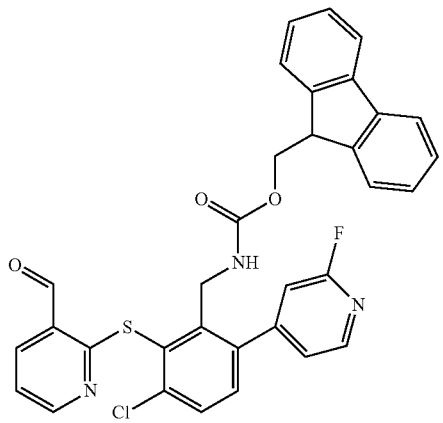 [SMILES: O=Cc1cccnc1Sc1c(Cl)ccc(-c2ccnc(F)c2)c1CNC(=O)OCC1c2ccccc2-c2ccccc21]

To a stirred solution of N-({6-bromo-2-[(3-{[(tert-butyldimethylsilyl)oxy]methyl}pyridin-2-yl)sulfanyl]-3-chlorophenyl}methyl)-2-methylpropane-2-sulfinamide (4.0 g, 6.93 mmol) in dioxan (30 mL) were added (2-fluoropyridin-4-yl)boronic acid (1.17 g, 8.3 mmol), Na$_2$CO$_3$ (2.2 g, 20.8 mmol), water (15 mL) and degassed for 10 min in argon atmosphere. Then to it was added Pd(PPh$_3$)$_4$ (801 mg, 0.69 mmol) and again degassed for 5 min. The reaction mass was heated to 120° C. for 16 h. Reaction mixture was then cooled to 25° C., filtered through celite pad and washed with EtOAc. The separated organic layer was washed with brine solution, dried over sodium sulfate and concentrated under reduced pressure to get the crude which was purified by column chromatography (SiO$_2$; 100-200 mesh; 40-80% EtOAc/Hexane) to get N-({2-[(3-{[(tert-butyldimethylsilyl)oxy]methyl}pyridin-2-yl)sulfanyl]-3-chloro-6-(2-fluoropyridin-4-yl)phenyl}methyl)-2-methylpropane-2-sulfinamide (2 g, 48%) as light yellow sticky solid. LC-MS: 593.8 [M+H]+

To a stirred solution of N-({2-[(3-{[(tert-butyldimethylsilyl)oxy]methyl}pyridin-2-yl)sulfanyl]-3-chloro-6-(2-fluoropyridin-4-yl)phenyl}methyl)-2-methylpropane-2-sulfinamide (2 g, 3.37 mmol) in THF (20 mL), was added 4M HCl in dioxan (10 mL) at 0° C. and reaction mixture was stirred at 25° C. for 2h. Reaction mass was evaporated under reduced pressure to get (2-{[2-(aminomethyl)-6-chloro-3-(2-fluoropyridin-4-yl)phenyl]sulfanyl}pyridin-3-yl)methanol hydrochloride (1.2 g) which was directly used for next step without further purification. LC-MS: 376.0 [M+H]+.

To a stirred suspension of (2-{[2-(aminomethyl)-6-chloro-3-(2-fluoropyridin-4-yl)phenyl]sulfanyl}pyridin-3-yl)methanol hydrochloride (1.2 g, 3.2 mmol) in 5% NaHCO$_3$ (20 mL) was added Fmoc-OSU (1.08 g, 3.2 mmol) in dioxan (20 mL) at 25° C. and reaction mass was stirred at the same temperature for 16h. Then reaction mass was diluted with water and extracted with 10% methanol in dichloromethane. The separated organic layer was washed with brine solution, dried over sodium sulfate and evaporated under reduced pressure to 9H-fluoren-9-ylmethyl N-{[3-chloro-6-(2-fluoropyridin-4-yl)-2-{[3-(hydroxymethyl)pyridin-2-yl]sulfanyl}phenyl]methyl}carbamate (2 g) as off-white solid; which was used for next step without further purification. LC-MS: 597.8 [M+H]+

To a stirred solution of 9H-fluoren-9-ylmethyl N-{[3-chloro-6-(2-fluoropyridin-4-yl)-2-{[3-(hydroxymethyl)pyridin-2-yl]sulfanyl}phenyl]methyl}carbamate in DCM:THF (1:1, 30 mL) was added MnO$_2$ (5.82 g, 67.0 mmol) and reaction mass was stirred at 25° C. for 2 h. The reaction mass was filtered through celite pad and the filtrate was evaporated under reduced pressure. The crude thus obtained was purified by column chromatography (SiO$_2$; 100-200 mesh; 40-80% EtOAc/Hexane) to get 9H-fluoren-9-ylmethyl N-{[3-chloro-6-(2-fluoropyridin-4-yl)-2-[(3-formylpyridin-2-yl)sulfanyl]phenyl]methyl}carbamate (610 mg) as off-white solid with 90% LCMS purity. LC-MS: 596.0 [M+H]+

1H NMR (400 MHz, DMSO-d6): δ 4.10 (3H, s), 4.14-4.19 (2H, m), 7.27-7.51 (8H, m), 7.59 (1H, s), 7.64 (2H, d, J=7.4 Hz), 7.74 (1H, d, J=8.3 Hz), 7.82-7.98 (2H, m), 8.25 (1H, d, J=4.7 Hz), 8.35 (1H, d, J=6.2 Hz), 8.44-8.49 (1H, m), 10.20 (1H, s).

Intermediate 122

9H-fluoren-9-ylmethyl N-[[5-[2-(tert-butoxycarbonylamino)-4-pyridyl]-3-chloro-2-[(3-formyl-2-pyridyl) sulfanyl]phenyl]methyl]carbamate

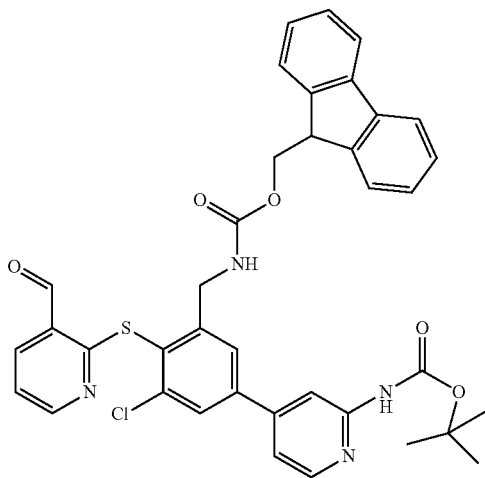 [SMILES: CC(C)(C)OC(=O)Nc1cc(-c2cc(Cl)c(Sc3ncccc3C=O)c(CNC(=O)OCC3c4ccccc4-c4ccccc43)c2)ccn1]

To a stirred solution of N-[[5-bromo-2-[[3-[[tert-butyl(dimethyl)silyl]oxymethyl]-2-pyridyl]sulfanyl]-3-chloro-phenyl]methyl]-2-methyl-propane-2-sulfinamide (2.0 g, 3.46 mmol) in 1,4-dioxane (20 mL) were added tert-butyl N-[4-(4,4,5,5-tetramethyl-1,3,2-dioxaborolan-2-yl)-2-pyridyl]carbamate (1.44 g, 4.5 mmol), Na$_2$CO$_3$ (11 mg, 0.1 mmol), water (10 mL) and reaction mass was purged with argon for 15 min. Then Pd(PPh$_3$)$_4$ (0.2 g, 0.17 mmol) was added and reaction mass was heated to 120° C. in a sealed tube for 16h. Reaction mass was filtered through celite pad and the filtrate was evaporated under reduced pressure to get N-[[5-(2-amino-4-pyridyl)-2-[[3-[[tert-butyl(dimethyl)silyl]oxymethyl]-2-pyridyl]sulfanyl]-3-chloro-phenyl]methyl]-2-methyl-propane-2-sulfinamide (2 g) as brown resin. LC-MS: 590.7 [M+H]$^+$ To a stirred solution of N-[[5-(2-amino-4-pyridyl)-2-[[3-[[tert-butyl(dimethyl)silyl]oxymethyl]-2-pyridyl]sulfanyl]-3-chloro-phenyl]methyl]-2-methyl-propane-2-sulfinamide (2.0 g, 3.38 mmol) in THF (10 mL) was added 4M HCl in dioxan (10 mL, 40 mmol) and reaction mass was stirred at 25° C. for 2h. Reaction mass was evaporated under reduced pressure to get [2-[2-(aminomethyl)-4-(2-amino-4-pyridyl)-6-chloro-phenyl]sulfanyl-3-pyridyl]methanol hydrochloride (1.2 g) as off white solid. LC-MS: 373.0[M+H]$^+$ To a stirred suspension of [2-[2-(aminomethyl)-4-(2-amino-4-pyridyl)-6-chloro-phenyl]sulfanyl-3-pyridyl] methanol hydrochloride (1.2 g, 2.93 mmol) in 5% NaHCO3 (20 mL) was added Fmoc-OSU (988.8 mg, 2.93 mmol) in 1,4-dioxane (30 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure. The crude material obtained was purified by normal silica column using 5-80% ethyl acetate in hexane to get 9H-fluoren-9-ylmethyl N-[[5-(2-amino-4-pyridyl)-3-chloro-2-[[3-(hydroxymethyl)-2-pyridyl]sulfanyl]phenyl]methyl]carbamate (1.4 g) as off white solid. LC-MS: 594.7[M+H]$^+$ To a stirred solution of 9H-fluoren-9-ylmethyl N-[[5-(2-amino-4-pyridyl)-3-chloro-2-[[3-(hydroxymethyl)-2-pyridyl]sulfanyl]phenyl]methyl]carbamate (1.4 g, 2.35 mmol) in tert-butanol (10 mL) was added BOC anhydride (2.7 mL, 11.76 mmol) and the reaction mass was stirred at 25° C. for 16h. The reaction mass was evaporated under reduced pressure and crude thus obtained was purified by normal silica column using 5-40% ethyl acetate in hexane to get 9H-fluoren-9-ylmethyl N-[[5-[2-(tert-butoxycarbonylamino)-4-pyridyl]-3-chloro-2-[[3-(hydroxymethyl)-2-pyridyl]sulfanyl]phenyl]methyl]carbamate (850 mg) as off white solid. LC-MS: 695.2[M+H]$^+$ To a stirred solution of 9H-fluoren-9-ylmethyl N-[[5-[2-(tert-butoxycarbonylamino)-4-pyridyl]-3-chloro-2-[[3-(hydroxymethyl)-2-pyridyl]sulfanyl]phenyl]methyl]carbamate (850 mg, 1.22 mmol) DCM:THF (1:1, 40 mL) was added MnO$_2$ (2.13 g, 24.45 mmol) and the reaction mass was stirred at 25° C. for 2 h. The reaction mass was filtered through celite pad and the filtrate was evaporated under reduced pressure. The crude material obtained was purified by normal silica column using 10-50% ethyl acetate in hexane to get 9H-fluoren-9-ylmethyl N-[[5-[2-(tert-butoxycarbonylamino)-4-pyridyl]-3-chloro-2-[(3-formyl-2-pyridyl)sulfanyl]phenyl]methyl]carbamate (425 mg) as a off white solid. LC-MS: 693.1 [M+H]$^+$ $^1$H-NMR: (400 MHz, DMSO-d6): δ 1.42 (9H; s); 4.27-4.36 (5H, m), 7.22-7.25 (m; 2H); 7.35-7.40 (4H; m); 7.64-7.87 (2H; m); 7.85-7.87 (2H; m); 7.94 (1H; m); 8.09 (1H; s); 8.34-8.39 (2H; m); 8.46 (1H; m); 9.94 (1H; s); 10.21 (1H, s).

Intermediate 123

9H-fluoren-9-ylmethyl N-[[3-chloro-2-[(3-formyl-2-pyridyl)sulfanyl]-6-(4-sulfamoylphenyl)phenyl] methyl]carbamate

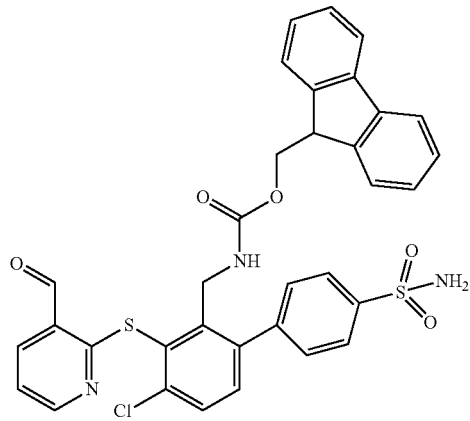 [SMILES: NS(=O)(=O)c1ccc(-c2ccc(Cl)c(Sc3ncccc3C=O)c2CNC(=O)OCC2c3ccccc3-c3ccccc32)cc1]

To a stirred solution of N-[[6-bromo-2-[[3-[[tert-butyl(dimethyl)silyl]oxymethyl]-2-pyridyl]sulfanyl]-3-chloro-phenyl]methyl]-2-methyl-propane-2-sulfinamide (2.0 g, 3.46 mmol) in 1,4-dioxane (20 mL) were added (4-aminosulfonylphenyl)boronic acid (904 mg, 4.5 mmol), sodium carbonate (1.1 g, 10.38 mmol), water (10 mL) and the reaction mass was purged with argon for 15 min. Then Pd(PPh3)4 (2 mg, 0.002 mmol) was added and the each on mass was heated to 120° C. in a sealed tube for 16h. Reaction mass was filtered through celite pad and filtrate was evaporated under reduced pressure to get 4-[3-[[3-[[tert-butyl(dimethyl)silyl]oxymethyl]-2-pyridyl]sulfanyl]-2-

[(tert-butylsulfinylamino)methyl]-4-chloro-phenyl]benzenesulfonamide (2 g) as brown resin. LC-MS: 654.1 [M+H]+

To a stirred solution of 4-[3-[[3-[[tert-butyl(dimethyl)silyl]oxymethyl]-2-pyridyl]sulfanyl]-2-[(tert-butylsulfinylamino)methyl]-4-chloro-phenyl]benzenesulfonamide (2.0 g, 3.06 mmol) in THF (20 mL) was added 4M HCl in dioxan (8.0 mL, 32 mmol) and the reaction mass was stirred at 25° C. for 2h. Reaction mass was evaporated under reduced pressure to get 4-[2-(aminomethyl)-4-chloro-3-[[3-(hydroxymethyl)-2-pyridyl]sulfanyl]phenyl]benzenesulfonamide hydrochloride (1.3 g) as off white solid. LC-MS: 435.8 [M+H]+

To a stirred suspension of 4-[2-(aminomethyl)-4-chloro-3-[[3-(hydroxymethyl)-2-pyridyl]sulfanyl]phenyl]benzenesulfonamide hydrochloride (1.3 g, 2.75 mmol) in 5% NaHCO3 (20.0 mL) was added Fmoc-OSU (0.93 g, 2.75 mmol) in 1,4-dioxane (30 mL) at 25° C. and reaction mass was stirred at the same temperature for 2h. Then reaction mass was diluted with water and extracted with ethyl acetate. The separated organic layer was washed with brine solution, dried over sodium sulfate and evaporated under reduced pressure to get 9H-fluoren-9-ylmethyl N-[[3-chloro-2-[[3-(hydroxymethyl)-2-pyridyl]sulfanyl]-6-(4-sulfamoylphenyl)phenyl]methyl]carbamate (1.5 g) as off white solid. LC-MS: 657.9[M+H]+

To a stirred solution of 9H-fluoren-9-ylmethyl N-[[3-chloro-2-[[3-(hydroxymethyl)-2-pyridyl]sulfanyl]-6-(4-sulfamoylphenyl)phenyl]methyl]carbamate (1.5 g, 2.28 mmol) in DCM:THF (1:1, 30 mL) was added MnO2 (3.96 g, 45.58 mmol) and the reaction mass was stirred at 25° C. for 2 h. The reaction mass was filtered through celite pad and the filtrate was evaporated under reduced pressure. The crude material obtained was purified by normal silica column using 10-50% ethyl acetate in hexane to get 9H-fluoren-9-ylmethyl N-[[3-chloro-2-[(3-formyl-2-pyridyl)sulfanyl]-6-(4-sulfamoylphenyl)phenyl]methyl]carbamate (640 mg) as a off white solid. LC-MS: 656.0 [M+H]+

1H-NMR: (400 MHz, DMSO-d6): δ 4.13-4.11 (5H, m), 7.31-7.45 (7H; m); 7.5-7.72 (5h: m); 7.86-7.90 (4H; m); 8.35 (1H; m); 8.48 (1H; m); 10.21 (1H, s).

Intermediate 124

9H-fluoren-9-ylmethyl N-[[3-chloro-2-[(3-formyl-2-pyridyl)sulfanyl]-6-(4-methylsulfonylphenyl)phenyl]methyl]carbamate

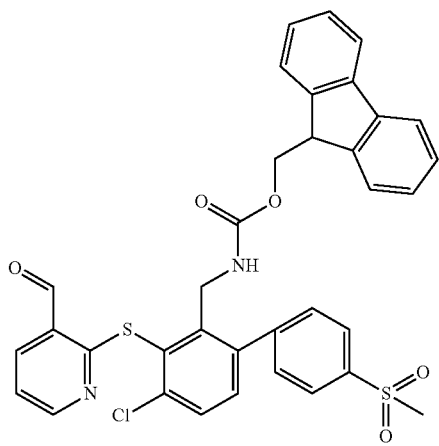 [SMILES: CS(=O)(=O)c1ccc(-c2ccc(Cl)c(Sc3ncccc3C=O)c2CNC(=O)OCC2c3ccccc3-c3ccccc32)cc1]

To a stirred solution of N-[[6-bromo-2-[[3-[[tert-butyl(dimethyl)silyl]oxymethyl]-2-pyridyl]sulfanyl]-3-chloro-phenyl]methyl]-2-methyl-propane-2-sulfinamide (2.0 g, 3.46 mmol) in 1,4-dioxane (20 mL) were added 4-(methylsulfonyl)phenylboronic acid (0.9 g, 4.5 mmol), sodium carbonate (1.1 g, 10.38 mmol), water (10 mL) and the reaction mass was purged with argon for 15 min. Pd(PPh3)4 (0.2 g, 0.17 mmol) was added and reaction mass was heated to 120° C. in a sealed tube for 16h. The reaction mass was filtered through celite pad and the filtrate was evaporated under reduced pressure to get N-[[2-[[3-[[tert-butyl(dimethyl)silyl]oxymethyl]-2-pyridyl]sulfanyl]-3-chloro-6-(4-methylsulfonylphenyl)phenyl]methyl]-2-methyl-propane-2-sulfinamide (2 g) as a brown resin. LC-MS: 653.2 [M+H]+

To a stirred solution of N-[[2-[[3-[[tert-butyl(dimethyl)silyl]oxymethyl]-2-pyridyl]sulfanyl]-3-chloro-6-(4-methylsulfonylphenyl)phenyl]methyl]-2-methyl-propane-2-sulfinamide (2.0 g, 3.06 mmol) in THF (20 mL) was added 4M HCl in dioxan (8.0 mL, 32 mmol) and reaction mass was stirred at 25° C. for 2h. Reaction mass was evaporated under reduced pressure to get [2-[2-(aminomethyl)-6-chloro-3-(4-methylsulfonylphenyl)phenyl]sulfanyl-3-pyridyl]methanol hydrochloride (1.4 g) as off white solid. LC-MS: 434.7 [M+H]+

To a stirred suspension of [2-[2-(aminomethyl)-6-chloro-3-(4-methylsulfonylphenyl)phenyl]sulfanyl-3-pyridyl]methanol hydrochloride (1.4 g, 2.97 mmol) in 5% NaHCO3 (20 mL) was added Fmoc-OSU (1.0 g, 2.97 mmol) in 1,4-dioxane (40 mL) at 25° C. and reaction mass was stirred at the same temperature for 2h. Then reaction mass was diluted with water and extracted with 10% methanol in DCM. The separated organic layer was washed with brine, dried over sodium sulfate and evaporated under reduced pressure to get 9H-fluoren-9-ylmethyl N-[[3-chloro-2-[[3-(hydroxymethyl)-2-pyridyl]sulfanyl]-6-(4-methylsulfonylphenyl)phenyl]methyl]carbamate (1.8 g) as off white solid. LC-MS: 656.8 [M+H]+

To a stirred solution of 9H-fluoren-9-ylmethyl N-[[3-chloro-2-[[3-(hydroxymethyl)-2-pyridyl]sulfanyl]-6-(4-methylsulfonylphenyl)phenyl]methyl]carbamate (1.8 g, 2.74 mmol) in DCM:THF (1:1, 80 mL) was added MnO2 (4.76 g, 54.78 mmol) and reaction mass was stirred at 25° C. for 2 h. Reaction mass was filtered through celite pad and the filtrate was evaporated under reduced pressure. The crude material obtained was purified by normal silica column using 10-50% ethyl acetate in hexane to get 9H-fluoren-9-ylmethyl N-[[3-chloro-2-[(3-formyl-2-pyridyl)sulfanyl]-6-(4-methylsulfonylphenyl)phenyl]methyl]carbamate (920 mg) as a off white solid. LC-MS: 654.9 [M+H]+

1H-NMR: (400 MHz, DMSO-d6): δ 3.18 (3H; s); 4.03-4.11 (5H, m), 7.30-7.38 (3H; m); 7.38-7.45 (3H; m); 7.58 (1H; m); 7.64-7.71 (5h; m); 7.89 (2H; m); 7.95-7.97 (2H; m); 8.35 (1H; br d; J=7.04 Hz); 8.48 (1H; m); 10.20 (1H, s).

Intermediate 125

(9H-Fluoren-9-yl)methyl 2-((5-fluoro-3-formylpyridin-2-yl)thio)benzylcarbamate

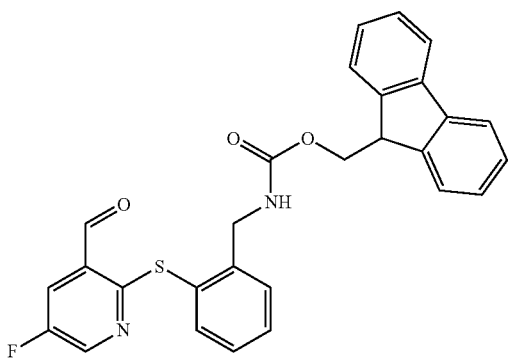 [SMILES: O=Cc1cc(F)cnc1Sc1ccccc1CNC(=O)OCC1c2ccccc2-c2ccccc21]

To a stirred solution of methyl 2-sulfanylbenzoate (2.5 g, 14.86 mmol) in DMF (30 ml) were added Cs$_2$CO$_3$ (7.267 g, 22.29 mmol) followed by 2-chloro-5-fluoropyridine-3-carbaldehyde (2.371 g, 14.86 mmol) and heated at 70° C. for 30 min. The reaction mixture was diluted with water and extracted with ethyl acetate. The combined organic layers were washed with water, dried over anhydrous sodium sulfate and concentrated under vacuum. The crude thus obtained, was purified by silica gel column chromatography using ethyl acetate in n-hexane (0-6%) as an eluting solvent to afford methyl 2-[(5-fluoro-3-formylpyridin-2-yl)sulfanyl]benzoate (2.65 g, 61%) as off white solid. LC-MS: 292.0 [M+H]$^+$.

To a stirred solution of methyl 2-[(5-fluoro-3-formylpyridin-2-yl)sulfanyl]benzoate (2.6 g, 8.93 mmol) in toluene (50 ml) were added ethylene glycol (1.5 ml, 26.78 mmol), p-TSA (0.17 g, 0.89 mmol) and heated at 100° C. for 2 h. The reaction mixture was filtered and concentrated under vacuum. The crude, thus obtained was purified by silica gel chromatography using ethyl acetate in n-hexane (0-10%) as eluting solvent to afford methyl 2-{[3-(1,3-dioxolan-2-yl)-5-fluoro pyridin-2-yl]sulfanyl}benzoate (2.26 g, 75%) as light yellow liquid. LC-MS: 335.7 [M+H]$^+$.

To a stirred solution of methyl 2-{[3-(1,3-dioxolan-2-yl)-5-fluoropyridin-2-yl]sulfanyl}benzoate (1.5 g, 4.47 mmol) in THF (15 ml) was added LiBH$_4$ (0.292 g, 13.42 mmol) at 0° C. and heated at 60° C. for 4 h. The reaction mixture was quenched with saturated aqueous ammonium chloride solution, diluted with water and extracted with ethyl acetate. The combined organic layers were dried over anhydrous sodium sulfate and concentrated under vacuum. The crude, thus obtained was purified by silica gel column chromatography using ethyl acetate in n-hexane (0-10%) as eluting solvent to afford (2-{[3-(1,3-dioxolan-2-yl)-5-fluoropyridin-2-yl]sulfanyl}phenyl)methanol (855 mg, 62%) as off white solid. LC-MS: 308.1 [M+H]$^+$.

To a stirred solution of (2-{[3-(1,3-dioxolan-2-yl)-5-fluoropyridin-2-yl]sulfanyl}phenyl)methanol (250 mg, 0.81 mmol) in THF (5 ml) was added DPPA (0.3 ml, 1.22 mmol) followed by DBU (0.2 ml, 1.22 mmol) and stirred at 25° C. for 15 h. The reaction mixture was diluted with water and extracted with ethyl acetate. The combined organic layers were dried over anhydrous sodium sulfate and concentrated under vacuum. The crude, thus obtained was purified by silica gel column chromatography using ethyl acetate in n-hexane (0-8%) as eluting solvent to afford 2-{[2-(azidomethyl)phenyl]sulfanyl}-3-(1,3-dioxolan-2-yl)-5-fluoropyridine (200 mg, 74%) as light yellow liquid. LC-MS: 332.9 [M+H]$^+$.

To a stirred solution of 2-{[2-(azidomethyl)phenyl]sulfanyl}-3-(1,3-dioxolan-2-yl)-5-fluoropyridine (200 mg, 0.60 mmol) in 2-propanol (5 ml) were added 1,3-propanedithiol (6.5 ml, 0.06 mmol), Et$_3$N (0.2 ml, 1.20 mmol), NaBH$_4$ (34 mg, 0.90 mmol) and stirred at 25° C. for 2 h. The reaction mixture was concentrated under vacuum. The crude, thus obtained was purified by amine silica gel column chromatography using ethyl acetate in n-hexane as eluting solvent to afford (2-{[3-(1,3-dioxolan-2-yl)-5-fluoropyridin-2-yl]sulfanyl}phenyl)methanamine (125 mg, 68%) as colorless liquid. LC-MS: 306.8 [M+H]$^+$.

To a stirred suspension of [2-[[3-(1,3-dioxolan-2-yl)-5-fluoro-2-pyridyl]sulfanyl]phenyl]methanamine (400 mg, 1.31 mmol) in 5% aqueous NaHCO$_3$ (5 ml) was added Fmoc-OSu (440.44 mg, 1.31 mmol) in acetonitrile (8 ml) and stirred at 25° C. for 4 h. The reaction mixture was diluted with water and extracted with ethyl acetate. The combined organic layers were dried over anhydrous sodium sulfate and concentrated under vacuum. The crude, thus obtained was purified by combi flash column chromatography using ethyl acetate in n-hexane (0-10%) as eluting solvent to afford 9H-fluoren-9-ylmethyl N-[[2-[[3-(1,3-dioxolan-2-yl)-5-fluoro-2-pyridyl]sulfanyl]phenyl]methyl]carbamate (330 mg, 47.82% yield) as white solid. LC-MS: 528.8 [M+H]$^+$.

To a solution of 9H-fluoren-9-ylmethyl N-[[2-[[3-(1,3-dioxolan-2-yl)-5-fluoro-2-pyridyl]sulfanyl]phenyl]methyl]carbamate (485 mg, 0.920 mmol) in acetone (15 ml) was added aqeuous HCl (12N, 3 ml, 36 mmol) and the reaction mixture was stirred at 25° C. for 4 h. The reaction mixture was concentrated under vacuum, diluted the residue with water (10 ml), quenched with aqueous saturated sodium bicarbonate solution (10 ml) and extracted with ethyl acetate. The combined organic layers were dried over anhydrous sodium sulfate and concentrated under vacuum. The crude, thus obtained was purified by silica gel column chromatography using ethyl acetate in n-hexane (0-8%) as eluting solvent to afford 9H-fluoren-9-ylmethyl N-({2-[(5-fluoro-3-formyl pyridin-2-yl)sulfanyl]phenyl}methyl)carbamate (146 mg, 33% yield) as white solid. LC-MS: 484.9 [M+H]$^+$.

1H NMR: (400 MHz, DMSO-d) δ 4.20 (3H, d, J=5.6 Hz), 4.31 (2H, d, J=6.8 Hz), 7.31-7.35 (4H, m), 7.41 (2H, d, J=7.4 Hz), 7.49 (2H, dd, J=15.3, 7.3 Hz), 7.69 (2H, d, J=7.3 Hz), 7.76 (1H, t, J=4.5 Hz), 7.89 (2H, d, J=7.2 Hz), 8.31 (1H, dd, J=8.6, 2.7 Hz), 8.54 (1H, d, J=3.2 Hz), 10.19 (1H, s).

Intermediate 126

9H-fluoren-9-ylmethyl N-[[3-chloro-2-[(3-formyl-2-pyridyl)sulfanyl]-5-imidazol-1-yl-phenyl]methyl] carbamate

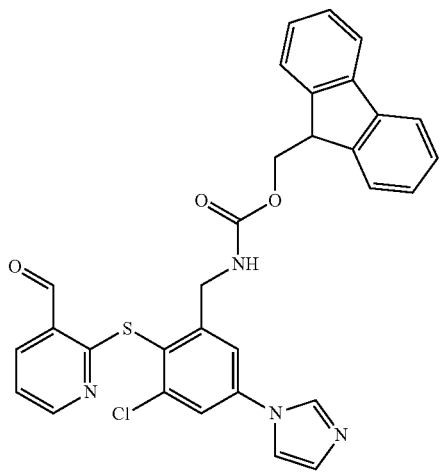 [SMILES: O=Cc1cccnc1Sc1c(Cl)cc(-n2ccnc2)cc1CNC(=O)OCC1c2ccccc2-c2ccccc21]

To a stirred solution of N-[[5-bromo-2-[[3-[[tert-butyl(dimethyl)silyl]oxymethyl]-2-pyridyl]sulfanyl]-3-chlorophenyl]methyl]-2-methyl-propane-2-sulfinamide (500 mg, 0.86 mmol) in 1,4-dioxane (10 mL) was added Imidazole (70.66 mg, 1.04 mmol), K3PO4 (0.37 g, 1.73 mmol) and DMEDA (0.04 mL, 0.35 mmol) and degassed in argon atmosphere for 5 min. Then to it was added CuI (32.94 mg, 0.17 mmol) and heated at 110° C. for 16h. Reaction mixture was then extracted with ethyl acetate and the separated organic layer was washed with brine solution, dried over sodium sulfate and evaporated under reduced pressure to get crude which was purified by column chromatography (1%-10% MeOH in DCM) to afford N-[[2-[[3-[[tert-butyl(dimethyl)silyl]oxymethyl]-2-pyridyl]sulfanyl]-3-chloro-5-imidazol-1-yl-phenyl]methyl]-2-methyl-propane-2-sulfinamide (125 mg) as light yellow solid. LC-MS: 565.0 [M+H]+

To a stirred solution of N-[[2-[[3-[[tert-butyl(dimethyl) silyl]oxymethyl]-2-pyridyl]sulfanyl]-3-chloro-5-imidazol-1-yl-phenyl]methyl]-2-methyl-propane-2-sulfinamide (500 mg, 0.88 mmol) in THF (10 mL) was added 4M HCl in dioxan (4.0 mL, 16 mmol) and the reaction mass was stirred at 25° C. for 2h. The reaction mass was evaporated under reduced pressure to get [2-[2-(aminomethyl)-6-chloro-4-imidazol-1-yl-phenyl]sulfanyl-3-pyridyl]methanol hydrochloride (300 mg) as light brown resin. LC-MS: 346.9 [M+H]+

To a stirred suspension of [2-[2-(aminomethyl)-6-chloro-4-imidazol-1-yl-phenyl]sulfanyl-3-pyridyl]methanol hydrochloride (300 mg, 0.78 mmol) in 5% NaHCO3 (10 mL) was added Fmoc-OSU (264 mg, 0.78 mmol) in 1,4-dioxane (20 mL) at 25° C. and the reaction mass was stirred at the same temperature for 2h. Then reaction mass was diluted with water and extracted with ethyl acetate. The separated organic layer was washed with brine, dried over sodium sulfate and evaporated under reduced pressure to get 9H-fluoren-9-ylmethyl N-[[3-chloro-2-[[3-(hydroxymethyl)-2-pyridyl]sulfanyl]-5-imidazol-1-yl-phenyl]methyl] carbamate.

To a stirred solution of 9H-fluoren-9-ylmethyl N-[[3-chloro-2-[[3-(hydroxymethyl)-2-pyridyl]sulfanyl]-5-imidazol-1-yl-phenyl]methyl]carbamate (400 mg, 0.7 mmol) in DCM:THF (1:1, 40 mL) was added MnO2 (1222 mg, 14.06 mmol) and the reaction mass was stirred at 25° C. for 2 h. The reaction mass was filtered through celite pad and the filtrate was evaporated under reduced pressure. The crude material obtained was purified by normal silica column using 0-3% methanol in DCM to get 9H-fluoren-9-ylmethyl N-[[3-chloro-2-[(3-formyl-2-pyridyl)sulfanyl]-5-imidazol-1-yl-phenyl]methyl]carbamate (127 mg) as off white solid. LC-MS: 566.7 [M+H]+

1H-NMR: (400 MHz, DMSO-d6): δ 4.02-4.08 (1H, m), 4.19-4.28 (2H, m), 4.28-4.48 (2H, m) 7.18 (1H; m); 7.27-7.26 (2H, m), 7.35-7.39 (3H, m), 7.65-7.67 (2H, m), 7.81-7.82 (2H, m), 7.85-7.86 (2H; m); 7.89-7.90 (1H; m); 8.36-8.43 (3H; m); 10.21 (1H, s).

Intermediate 127

9H-fluoren-9-ylmethyl N-[[6-[6-(tert-butoxycarbonylamino)-3-pyridyl]-3-chloro-2-[(3-formyl-2-pyridyl) sulfanyl]phenyl]methyl]carbamate

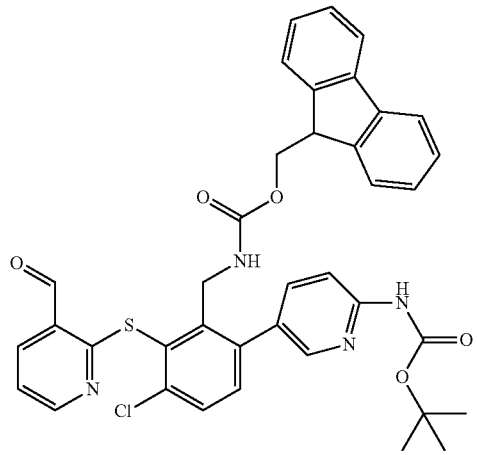 [SMILES: CC(C)(C)OC(=O)Nc1ccc(-c2ccc(Cl)c(Sc3ncccc3C=O)c2CNC(=O)OCC2c3ccccc3-c3ccccc32)cn1]

To a stirred solution of N-[[6-bromo-2-[[3-[[tert-butyl(dimethyl)silyl]oxymethyl]-2-pyridyl]sulfanyl]-3-chlorophenyl]methyl]-2-methyl-propane-2-sulfinamide (2.0 g, 3.46 mmol) in 1,4-dioxane (20 mL) were added 2-Amino-5-(4,4,5,5-tetramethyl-1,3,2-dioxaborolan-2-yl)pyridine (989.8 mg, 4.5 mmol), sodium carbonate (1.1 g, 10.38 mmol), water (10 mL) and reaction mass was purged with argon for 15 min. Then Pd(PPh3)4 (199.97 mg, 0.170 mmol) was added and reaction mass was heated to 120° C. in a sealed tube for 16h. The reaction mass was filtered through celite pad and the filtrate was evaporated under reduced pressure to get N-[[6-(6-amino-3-pyridyl)-2-[[3-[[tert-butyl(dimethyl)silyl]oxymethyl]-2-pyridyl]sulfanyl]-3-chlorophenyl]methyl]-2-methyl-propane-2-sulfinamide (2 g) as light brown resin. LC-MS: 590.7 [M+H]+

To a stirred solution of N-[[6-(6-amino-3-pyridyl)-2-[[3-[[tert-butyl(dimethyl)silyl]oxymethyl]-2-pyridyl]sulfanyl]-3-chloro-phenyl]methyl]-2-methyl-propane-2-sulfinamide (2.0 g, 3.38 mmol) in THF (20 mL) was added 4M HCl in dioxane (10.0 mL, 40 mmol) and the reaction mass was stirred at 25° C. for 2h. The reaction mass was evaporated under reduced pressure to get [2-[2-(aminomethyl)-3-(6-amino-3-pyridyl)-6-chloro-phenyl]sulfanyl-3-pyridyl]methanol hydrochloride (1.3 g) as light yellow solid. LC-MS: 372.8 [M+H]$^+$ To a stirred suspension of [2-[2-(aminomethyl)-3-(6-amino-3-pyridyl)-6-chloro-phenyl]sulfanyl-3-pyridyl]methanol hydrochloride (1.3 g, 3.18 mmol) in 5% NaHCO3 (20 mL) was added Fmoc-OSU (1.07 g, 3.18 mmol) in 1,4-dioxane (40 mL) at 25° C. and reaction mass was stirred at the same temperature for 2h. Then reaction mass was diluted with water and extracted with 10% methanol in DCM. The separated organic layer was washed with brine solution, dried over sodium sulfate and evaporated under reduced pressure. The crude thus obtained was purified by normal silica column using 0-5% methanol in DCM to get 9H-fluoren-9-ylmethyl N-[[6-(6-amino-3-pyridyl)-3-chloro-2-[[3-(hydroxymethyl)-2-pyridyl]sulfanyl]phenyl]methyl]carbamate (1.2 g) as a off white solid. LC-MS: 594.8 [M+H]$^+$ To a stirred solution of 9H-fluoren-9-ylmethyl N-[[6-(6-amino-3-pyridyl)-3-chloro-2-[[3-(hydroxymethyl)-2-pyridyl]sulfanyl]phenyl]methyl]carbamate (1.2 g, 2.02 mmol) in tert-butanol (10 mL) was added BOC anhydride (2.32 mL, 10.08 mmol) and reaction mass was stirred at 25° C. for 16h. The reaction mass was evaporated under reduced pressure and crude thus obtained was purified by normal silica column using 5-40% ethyl acetate in hexane to get 9H-fluoren-9-ylmethyl N-[[6-[6-(tert-butoxycarbonylamino)-3-pyridyl]-3-chloro-2-[[3-(hydroxymethyl)-2-pyridyl]sulfanyl]phenyl]methyl]carbamate (800 mg, 1.15 mmol) as off white solid. LC-MS: 695.0 [M+H]$^+$ To a stirred solution of 9H-fluoren-9-ylmethyl N-[[6-[6-(tert-butoxycarbonylamino)-3-pyridyl]-3-chloro-2-[[3-(hydroxymethyl)-2-pyridyl]sulfanyl]phenyl]methyl]carbamate (800 mg, 1.15 mmol) in DCM:THF (1:1, 40 mL) was added MnO$_2$ (2.0 g, 23.01 mmol) and the reaction mass was stirred at 25° C. for 2 h. The reaction mass was filtered through celite pad and the filtrate was evaporated under reduced pressure. The crude material obtained was purified by normal silica column using 10-50% ethyl acetate in hexane to get 9H-fluoren-9-ylmethyl N-[[6-[6-(tert-butoxycarbonylamino)-3-pyridyl]-3-chloro-2-[(3-formyl-2-pyridyl)sulfanyl]phenyl]methyl]carbamate (420 mg) as a off white solid. LC-MS: 693.1 [M+H]$^+$ $^1$H-NMR: (400 MHz, DMSO-d6): δ 1.46 (9H; s); 4.27-4.36 (5H, m), 7.22-7.25 (7H; m); 7.57-7.70 (4H; m); 7.80-7.89 (4H; m); 8.30-8.35 (2H; m); 8.47 (1H; s); 9.91 (1H; s); 10.21 (1H; s).

Intermediate 128

9H-fluoren-9-ylmethyl N-[[3-chloro-5-(2-cyano-4-pyridyl)-2-[(3-formyl-2-pyridyl)sulfanyl]phenyl]methyl]carbamate

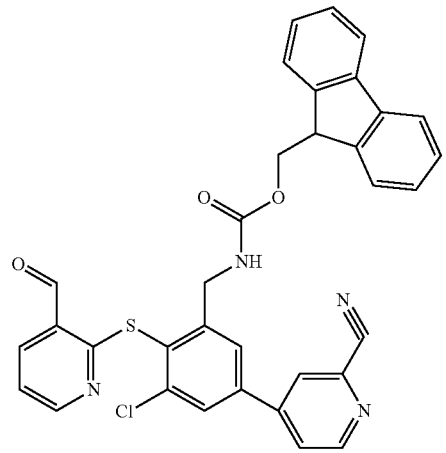 [SMILES: N#Cc1cc(-c2cc(Cl)c(Sc3ncccc3C=O)c(CNC(=O)OCC3c4ccccc4-c4ccccc43)c2)ccn1]

To a stirred solution of compound N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (2 g, 3.46 mmol) in dioxan (20 mL) were added 4-(tetramethyl-1,3,2-dioxaborolan-2-yl)pyridine-2-carbonitrile (1.03 g, 4.5 mmol), Na$_2$CO$_3$ (1.1 g, 10.3 mmol) and degassed for 10 min in argon atmosphere. Then to it was added Pd(PPh$_3$)$_4$ (200 mg, 0.173 mmol) and again degassed for 10 min. The reaction mass was heated to 120° C. for 16 h. The reaction mixture was then cooled to 25° C., filtered through celite pad, washed with EtOAc. The separated organic layer was washed with brine, dried over sodium sulfate and concentrated under reduced pressure. The crude thus obtained was purified by silica column chromatography (SiO$_2$; 100-200 mesh; 10%-60% ethyl acetate in hexane) to get N-[[2-[[3-[[tert-butyl(dimethyl)silyl]oxymethyl]-2-pyridyl]sulfanyl]-3-chloro-5-(2-cyano-4-pyridyl)phenyl]methyl]-2-methyl-propane-2-sulfinamide (850 mg) as yellow solid. LC-MS: 600.9 [M+H]$^+$ To a stirred solution of N-[[2-[[3-[[tert-butyl(dimethyl)silyl]oxymethyl]-2-pyridyl]sulfanyl]-3-chloro-5-(2-cyano-4-pyridyl)phenyl]methyl]-2-methyl-propane-2-sulfinamide (850 mg, 1.41 mmol) in THF (20 mL), was added 4M HCl in dioxan (10 mL) at 0° C. and reaction mixture was stirred at 25° C. for 2h. The reaction mass was evaporated under reduced pressure to get 4-[3-(aminomethyl)-5-chloro-4-[[3-(hydroxymethyl)-2-pyridyl]sulfanyl]phenyl]pyridine-2-carbonitrile hydrochloride (550 mg) which was directly used for next step without further purification. LC-MS: 382.7 [M+H]$^+$ To a stirred suspension of 4-[3-(aminomethyl)-5-chloro-4-[[3-(hydroxymethyl)-2-pyridyl]sulfanyl]phenyl]pyridine-2-carbonitrile hydrochloride (550 mg, 1.31 mmol) in 5% NaHCO$_3$ (20 mL) was added Fmoc-OSU (442 mg, 1.31 mmol) in dioxan (20 mL) at 25° C. and reaction mass was stirred at the same temperature for 2h. Then reaction mass was diluted with water and extracted with 10% methanol in DCM. The separated organic layer was washed with brine, dried over sodium sulfate and evaporated under reduced pressure to get 9H-fluoren-9-ylmethyl N-[[3-chloro-5-(2- cyano-4-pyridyl)-2-[[3-(hydroxymethyl)-2-pyridyl]sulfanyl]phenyl]methyl]carbamate (750 mg) as off white solid, which was used for next step without further purification. LC-MS: 605.0 [M+H]+

To a stirred solution of 9H-fluoren-9-ylmethyl N-[[3-chloro-5-(2-cyano-4-pyridyl)-2-[[3-(hydroxymethyl)-2-pyridyl]sulfanyl]phenyl]methyl]carbamate (750 mg, 1.24 mmol) in DCM:THF (1:1, 60 mL) was added $MnO_2$ (2.15 g, 24.79 mmol) and reaction mass was stirred at 25° C. for 2 h. The reaction mass was filtered through celite pad and the filtrate was evaporated under reduced pressure. The crude thus obtained was purified by silica column chromatography ($SiO_2$; 100-200 mesh; 10%-50% ethyl acetate in hexane) to get 9H-fluoren-9-ylmethyl N-[[3-chloro-5-(2-cyano-4-pyridyl)-2-[(3-formyl-2-pyridyl)sulfanyl]phenyl]methyl] carbamate (430 mg) as a off white solid. LC-MS: 603.1 [M+H]+

$^1$H-NMR: (400 MHz, DMSO-d6): δ 4.02-4.08 (1H, m), 4.19-4.28 (2H, m), 4.28-4.29 (2H, m) 7.27-7.26 (2H, m), 7.35-7.39 (2H, m), 7.65-7.67 (2H, m), 7.86-7.87 (4H, m), 8.11-8.12 (1H; m); 8.14-8.15 (1H; m); 8.38-8.40 (1H; m); 8.40-8.41 (1H; m); 8.51-8.52 (1H; m); 8.78 (1H; br d; J=7.2 Hz) 10.21 (1H, s).

Intermediate 129

9H-fluoren-9-ylmethyl N-[[3-chloro-2-[(3-formyl-2-pyridyl)sulfanyl]-6-(6-hydroxy-3-pyridyl)phenyl]methyl]carbamate

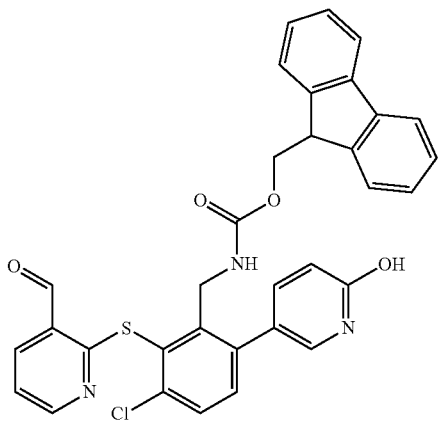 [SMILES: O=Cc1cccnc1Sc1c(Cl)ccc(-c2ccc(O)nc2)c1CNC(=O)OCC1c2ccccc2-c2ccccc21]

To a stirred solution of N-[[6-bromo-2-[[3-[[tert-butyl(dimethyl)silyl]oxymethyl]-2-pyridyl]sulfanyl]-3-chlorophenyl]methyl]-2-methyl-propane-2-sulfinamide (2.0 g, 3.46 mmol) in 1,4-dioxane (20 mL) were added (6-hydroxypyridine-3-yl)boronic acid (0.62 g, 4.5 mmol), sodium carbonate (1.1 g, 10.38 mmol), water (10 mL) and reaction mass was purged with argon for 15 min. Then Pd(PPh3)4 (199.97 mg, 0.17 mmol) was added and reaction mass was heated to 120° C. in a sealed tube for 16h. The reaction mass was filtered through celite pad and filtrate was evaporated under reduced pressure to get N-[[2-[[3-[[tert-butyl(dimethyl)silyl]oxymethyl]-2-pyridyl]sulfanyl]-3-chloro-6-(6-hydroxy-3-pyridyl)phenyl]methyl]-2-methyl-propane-2-sulfinamide (2 g) as light yellow gum. LC-MS: 592.1. [M+H]+

To a stirred solution of N-[[2-[[3-[[tert-butyl(dimethyl)silyl]oxymethyl]-2-pyridyl]sulfanyl]-3-chloro-6-(6-hydroxy-3-pyridyl)phenyl]methyl]-2-methyl-propane-2-sulfinamide (2.0 g, 3.38 mmol) in THF (20 mL) was added 4M HCl in dioxane (12.0 mL, 48 mmol) and reaction mass was stirred at 25° C. for 2h. Reaction mass was evaporated under reduced pressure to get 5-[2-(aminomethyl)-4-chloro-3-[[3-(hydroxymethyl)-2-pyridyl]sulfanyl]phenyl]pyridin-2-ol hydrochloride (1.3 g) as off white solid. LC-MS: 374.0 [M+H]+

To a stirred suspension of 5-[2-(aminomethyl)-4-chloro-3-[[3-(hydroxymethyl)-2-pyridyl]sulfanyl]phenyl]pyridin-2-ol hydrochloride (1.3 g, 3.18 mmol) in 5% NaHCO3 (20 mL) was added Fmoc-OSU (1.07 g, 3.18 mmol) in 1,4-dioxane (40 mL) at 25° C. and reaction mass was stirred at the same temperature for 2h. Then reaction mass was diluted with water and extracted with 10% methanol in DCM. The separated organic layer was washed with brine solution, dried over sodium sulfate and evaporated under reduced pressure to get 9H-fluoren-9-ylmethyl N-[[3-chloro-2-[[3-(hydroxymethyl)-2-pyridyl]sulfanyl]-6-(6-hydroxy-3-pyridyl)phenyl]methyl]carbamate (1.5 g) as a light yellow solid. LC-MS: 596.0 [M+H]+

To a stirred solution of 9H-fluoren-9-ylmethyl N-[[3-chloro-2-[[3-(hydroxymethyl)-2-pyridyl]sulfanyl]-6-(6-hydroxy-3-pyridyl)phenyl]methyl]carbamate (1.5 g, 2.52 mmol) in DCM/THF (1:1, 40 mL) was added MnO2 (4.37 g, 50.33 mmol) and the reaction mass was stirred at 25° C. for 2h. The reaction mass was filtered through celite pad and the filtrate was evaporated under reduced pressure. The crude material obtained was purified by normal silica column using 0-3% methanol in DCM to get 9H-fluoren-9-ylmethyl N-[[3-chloro-2-[(3-formyl-2-pyridyl)sulfanyl]-6-(6-hydroxy-3-pyridyl)phenyl]methyl]carbamate (140 mg) as off white solid. LC-MS: 593.9 [M+H]+

$^1$H-NMR: (400 MHz, DMSO-d6): δ 4.13-4.19 (5H, m), 7.32-7.34 (3H, m), 7.40-7.42 (4H, m), 7.49-7.52 (2H, m), 7.65-7.67 (3H, m), 7.82 (2H, brd, J=6.92 Hz), 8.34 (1H, brd, J=5.2 Hz), 8.45 (1H, s), 10.20 (1H, s), 11.81 (1H, s).

Intermediate 130

9H-fluoren-9-ylmethyl N-[[3-chloro-2-[(3-formyl-2-pyridyl)sulfanyl]-5-(1H-pyrrol-3-yl)phenyl]methyl]carbamate

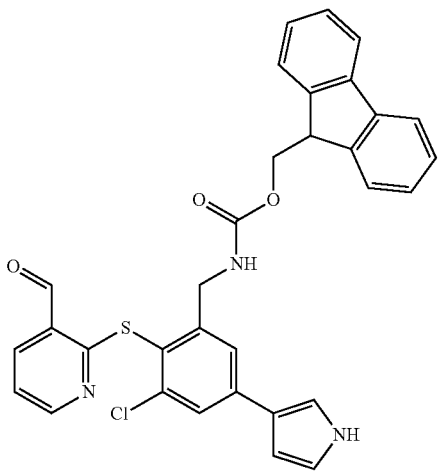 [SMILES: O=Cc1cccnc1Sc1c(Cl)cc(-c2cc[nH]c2)cc1CNC(=O)OCC1c2ccccc2-c2ccccc21]

To a stirred solution of N-[[5-bromo-2-[[3-[[tert-butyl(dimethyl)silyl]oxymethyl]-2-pyridyl]sulfanyl]-3-chlorophenyl]methyl]-2-methyl-propane-2-sulfinamide (2.0 g, 3.46 mmol) in 1,4-dioxane (20 mL) were added tert-butyl 3-(4,4,5,5-tetramethyl-1,3,2-dioxaborolan-2-yl)pyrrole-1-carboxylate (1.32 g, 4.5 mmol), sodium carbonate (1.1 g, 10.38 mmol), water (10 mL) and the reaction mass was purged with argon for 15 min. Then Pd(PPh3)4 (199.89 mg, 0.17 mmol) was added and reaction mass was heated to 120° C. in a sealed tube for 16h. The reaction mass filtered through celite pad and filtrate evaporated under reduced pressure to get N-[[2-[[3-[[tert-butyl(dimethyl)silyl]oxymethyl]-2-pyridyl]sulfanyl]-3-chloro-5-(1H-pyrrol-3-yl)phenyl]methyl]-2-methyl-propane-2-sulfinamide (2 g) as yellow resin LC-MS: 564.3. [M+H]⁺

To a stirred solution of N-[[2-[[3-[[tert-butyl(dimethyl)silyl]oxymethyl]-2-pyridyl]sulfanyl]-3-chloro-5-(1H-pyrrol-3-yl)phenyl]methyl]-2-methyl-propane-2-sulfinamide (2.0 g, 3.54 mmol) in tetrahydrofuran (10 mL) was added 4M HCl in dioxan (6.0 mL, 24 mmol) and the reaction mixture was stirred at 25° C. for 2h. The reaction mass was evaporated under reduced pressure to get [2-[2-(aminomethyl)-6-chloro-4-(1H-pyrrol-3-yl)phenyl]sulfanyl-3-pyridyl]methanol hydrochloride (1.3 g) as off white solid. LC-MS: 345.8 [M+H]⁺

To a stirred suspension of [2-[2-(aminomethyl)-6-chloro-4-(1H-pyrrol-3-yl)phenyl]sulfanyl-3-pyridyl]methanol hydrochloride (1.3 g, 3.4 mmol) in 5% NaHCO3 (20 mL) was added Fmoc-OSU (1.15 g, 3.4 mmol) in 1,4-dioxane (40 mL) at 25° C. and reaction mass was stirred at the same temperature for 2h. Then reaction mass was diluted with water and extracted with ethyl acetate. The separated organic layer was washed with brine, dried over sodium sulfate and evaporated under reduced pressure to 9H-fluoren-9-ylmethyl N-[[3-chloro-2-[[3-(hydroxymethyl)-2-pyridyl]sulfanyl]-5-(1H-pyrrol-3-yl)phenyl]methyl]carbamate (1.5 g) as a off white solid. LC-MS: 568.0 [M+H]⁺

To a stirred solution of 9H-fluoren-9-ylmethyl N-[[3-chloro-2-[[3-(hydroxymethyl)-2-pyridyl]sulfanyl]-5-(1H-pyrrol-3-yl)phenyl]methyl]carbamate (1.5 g, 2.64 mmol) in DCM/THF (1:1, 60 mL) was added MnO₂ (4.59 g, 52.81 mmol) and reaction mass was stirred at 25° C. for 2 h. The reaction mass was filtered through celite pad and the filtrate was evaporated under reduced pressure. The crude material obtained was purified by normal silica column using 10-50% ethyl acetate in hexane to get 9H-fluoren-9-ylmethyl N-[[3-chloro-2-[(3-formyl-2-pyridyl)sulfanyl]-5-(1H-pyrrol-3-yl)phenyl]methyl]carbamate (535 mg) as light yellow solid. LC-MS: 566.1 [M+H]⁺

¹H-NMR: (400 MHz, DMSO-d6): δ 4.19-4.28 (5H, m), 6.48 (1H, brs); 6.85 (1H, brs); 7.28-7.29 (2H; m); 7.32-7.37 (2H; m); 7.47-7.42 (2H; m); 7.53 (1H, brs); 7.69-7.70 (3H; m); 7.81-7.83 (1H; m); 7.88 (2H; d; J=7.44 Hz); 8.34 (1H; d; J=7.0 Hz); 8.34 (1H; brs); 10.21 (1H, s); 11.13 (1H; s).

Intermediate 131

(9H-Fluoren-9-yl)methyl 2-((5-bromo-3-formylpyridin-2-yl)thio)benzylcarbamate

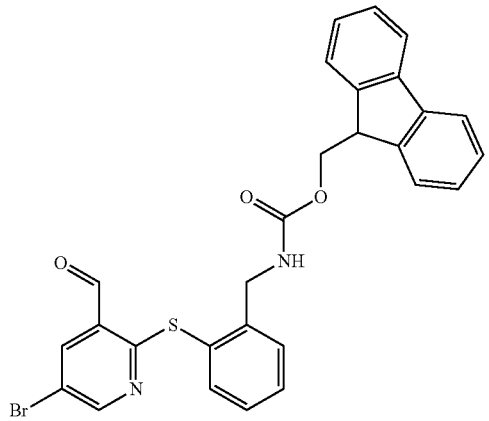 [SMILES: O=Cc1cc(Br)cnc1Sc1ccccc1CNC(=O)OCC1c2ccccc2-c2ccccc21]

This material was prepared in analogy to Intermediate 125 starting from 5-bromo-2-chloro-pyridine-3-carbaldehyde and methyl thiosalicylate, except for the last step which was performed as follows.

To a solution of 9H-fluoren-9-ylmethyl N-[[2-[[5-bromo-3-(1,3-dioxolan-2-yl)-2-pyridyl]sulfanyl]phenyl]methyl]carbamate (800 mg, 1.36 mmol) in acetone (15 ml) and water (3 ml) was added pyridinium p-toluenesulfonate (204.62 mg, 0.810 mmol) and the reaction mixture was heated at 60° C. for 25 h. The reaction mixture was concentrated under vacuum, diluted the residue with water (20 ml), quenched with 5% aqueous saturated sodium bicarbonate solution (10 ml) and extracted with ethyl acetate. The combined organic layers were dried over anhydrous sodium sulfate and concentrated under vacuum. The crude, thus obtained was purified by silica gel column chromatography using ethyl acetate in n-hexane (0-8%) as eluting solvent to afford 9H-fluoren-9-ylmethyl N-[[2-[(5-bromo-3-formyl-2-pyridyl)sulfanyl]phenyl]methyl]carbamate (120 mg, 27% yield) as off white solid. LC-MS: 545.2 [M+H]+.

1H NMR: (400 MHz, DMSO-d6) δ 4.19 (3H, d, J=5.8 Hz), 4.30 (2H, d, J=7.0 Hz), 7.34 (4H, d, J=7.1 Hz), 7.42 (2H, t, J=7.5 Hz), 7.49 (2H, dd, J=12.8, 7.1 Hz), 7.69 (2H, d, J=7.7 Hz), 7.75 (1H, t, J=5.8 Hz), 7.89 (2H, d, J=7.2 Hz), 8.58 (2H, s), 10.13 (1H, s).

Intermediate 132

(9H-Fluoren-9-yl)methyl ((2-(dimethylamino)-4-((3-formylpyridin-2-yl)thio)pyridin-3-yl)methyl)carbamate

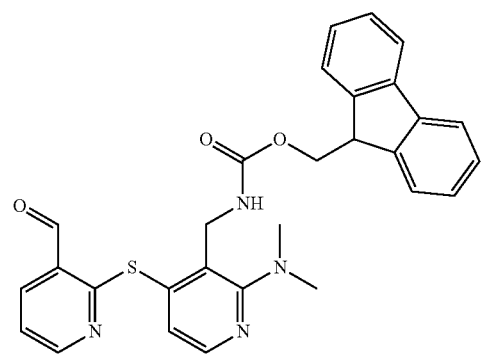 [SMILES: CN(C)c1nccc(Sc2ncccc2C=O)c1CNC(=O)OCC1c2ccccc2-c2ccccc21]

To a stirred solution of 2-mercaptonicotinic acid (10 g, 64.45 mmol) in DMSO (40 ml) was added trifluoroacetic acid (0.49 ml, 6.44 mmol) at 0° C. and the reaction mixture was heated at 60° C. for 24 h. The reaction mixture was then cooled to 0° C., DMF (100 ml) and Potassium carbonate (8.91 g, 64.45 mmol) were then added and stirred for 30 min at 0° C. Then iodomethane (12.04 ml, 193.34 mmol) was slowly added at 0° C. and the reaction mixture was stirred at 25° C. for 16 h. Reaction mixture was then cooled to 0° C., a solution of acetic acid (13 ml) in water (150 ml) was added slowly and the resulting mixture stirred at 25° C. for 6 h. Precipitated white solid was filtered, washed with water (3×70 ml) followed by hexane (3×30 ml), dried under vacuum to afford methyl 2-[(3-methoxycarbonyl-2-pyridyl)disulfanyl]pyridine-3-carboxylate (8.24 g, crude) as white solid which was used without further purification. LC-MS: 336.6 [M+H]+.

To a stirred solution of methyl 2-[(3-methoxycarbonyl-2-pyridyl)disulfanyl]pyridine-3-carboxylate (8.2 g, 24.38 mmol) in 1,4-dioxane (34 ml) were added triphenyl phosphine (8.95 g, 34.13 mmol) and water (18 ml) successively at 25° C. and heated at 65° C. for 16 h. The reaction mixture was concentrated under vacuum. The residue thus obtained was diluted with EtOH (85 ml) and heated at 75° C. for 15 min. Reaction mixture was then cooled to 25° C. slowly followed by to 0° C. by 4 h. Solid was then collected by filtration and dried well under vacuum to afford methyl 2-sulfanylpyridine-3-carboxylate (7.54 g, 69.17% yield over 2 steps) as yellow solid. LC-MS: 170.1 [M+H]+.

To a stirred solution of methyl 2-sulfanylpyridine-3-carboxylate (800 mg, 4.73 mmol) in DMF (8 ml) was added potassium carbonate (1306.91 mg, 9.46 mmol) at 0° C. in portions and stirred for 15 min. Then 2-chloro-4-fluoropyridine-3-carbaldehyde (829.81 mg, 5.2 mmol) in DMF (2 ml) was added slowly at the same temperature and slowly allowed to reach 25° C. and stirred for 2 h. After completion of reaction, reaction mixture was cooled to 0° C., quenched with acetic acid (0.5 ml), followed by water (12 ml) and stirred at 25° C. for 1 h. The yellow solid thus precipitated, was collected by filtration, washed with n-hexane and then dried under vacuum to afford methyl 2-[(2-chloro-3-formyl-4-pyridyl)sulfanyl]pyridine-3-carboxylate (1.05 g, 71.93% yield) as yellow solid. LC-MS: 308.8 [M+H]+.

In a sealed tube, to a stirred solution of methyl 2-[(2-chloro-3-formyl-4-pyridyl)sulfanyl]pyridine-3-carboxylate (1.0 g, 3.24 mmol) in 1,4-dioxane (10 ml) was added dimethyl amine (2M in THF, 16.19 ml, 32.39 mmol) and heated at 120° C. for 12 h. The reaction mixture was concentrated under vacuum. The crude, thus obtained was purified by silica gel chromatography using ethyl acetate in n-hexane (0-30%) as eluting solvent to afford methyl 2-[[2-(dimethylamino)-3-formyl-4-pyridyl]sulfanyl]pyridine-3-carboxylate (930 mg, 90.47%) as yellow solid. LC-MS: 317.8 [M+H]+.

To a stirred solution of methyl 2-[[2-(dimethylamino)-3-formyl-4-pyridyl]sulfanyl]pyridine-3-carboxylate (910 mg, 2.87 mmol) in tetrahydrofuran (20 ml) were added 2-methyl-2-propanesulfinamide (347.53 mg, 2.87 mmol) and titanium(IV) ethoxide (1.8 ml, 8.6 mmol) and heated at 70° C. for 2 h. The reaction mixture was quenched with brine (30 ml), ethyl acetate (50 ml) was added and filtered. The aqueous layer was extracted with ethyl acetate, the combined organic layers dried over anhydrous sodium sulfate and concentrated under vacuum. The crude, thus obtained was purified by silica gel column chromatography using ethyl acetate in hexane (0-20%) as eluting solvent to afford ethyl 2-[[3-[(E)-tert-butylsulfinyliminomethyl]-2-(dimethylamino)-4-pyridyl]sulfanyl]pyridine-3-carboxylate (1.22 g, crude, mixture of ethyl and isopropylester) as brown viscous liquid which was used without further purification. LC-MS: 434.6, 448.6 [M+H]+.

To a stirred solution of ethyl 2-[[3-[(E)-tert-butylsulfinyliminomethyl]-2-(dimethylamino)-4-pyridyl]sulfanyl]pyridine-3-carboxylate (1.2 g, 2.76 mmol) in tetrahydrofuran (15 ml) was slowly added lithium aluminium hydride (2M in THF, 2.7 ml, 5.52 mmol) at 0° C. The reaction mixture was then slowly allowed to reach 25° C. and stirred for 30 min. Then the reaction mixture was quenched with aqueous saturated sodium sulfate solution (25 ml), diluted with ethyl acetate (50 ml) and filtered. The aqueous layer was then extracted with ethyl acetate, the combined organic layers dried over anhydrous sodium sulfate and concentrated under vacuum to afford N-[[2-(dimethylamino)-4-[[3-(hydroxymethyl)-2-pyridyl]sulfanyl]-3-pyridyl]methyl]-2-methyl-propane-2-sulfinamide (1.01 g, crude) as light brown liquid, which was used without further purification. LC-MS: 394.8 [M+H]+.

To a stirred solution of N-[[2-(dimethylamino)-4-[[3-(hydroxymethyl)-2-pyridyl]sulfanyl]-3-pyridyl]methyl]-2-methyl-propane-2-sulfinamide (1 g, 2.53 mmol) in methanol (10 ml) was added hydrogen chloride (4 M in dioxane) (15.0 ml) at 0° C. The reaction mixture was then allowed to reach 25° C. and stirred for 30 min. Then the reaction mixture was concentrated under vacuum to afford [2-[[3-(aminomethyl)-2-(dimethylamino)-4-pyridyl]sulfanyl]-3-pyridyl]methanol hydrochloride (805 mg, crude) as off white solid, which was used without further purification. LC-MS: 291.2 [M+H]+.

To a stirred solution of [2-[[3-(aminomethyl)-2-(dimethylamino)-4-pyridyl]sulfanyl]-3-pyridyl]methanol hydrochloride (800 mg, 2.45 mmol) in aqueous 5% NaHCO₃ (15.0 ml, 2.45 mmol) was added Fmoc-OSu (825.68 mg, 2.45 mmol) in acetonitrile (20 ml) and stirred at 25° C. for 1 h. The reaction mixture was diluted with water (10 ml) and extracted with ethyl acetate. The combined organic layers were dried over anhydrous sodium sulfate and concentrated under vacuum. The crude, thus obtained was purified by trituration with 30% ethyl acetate in n-hexane to afford 9H-fluoren-9-ylmethyl N-[[2-(dimethylamino)-4-[[3-(hydroxymethyl)-2-pyridyl]sulfanyl]-3-pyridyl]methyl]carbamate (680 mg, 46% 4 steps yield) as white solid. LC-MS: 512.8[M+H]+.

To a stirred solution of 9H-fluoren-9-ylmethyl N-[[2-(dimethylamino)-4-[[3-(hydroxymethyl)-2-pyridyl]sulfanyl]-3-pyridyl]methyl]carbamate (500 mg, 0.980 mmol) in dichloromethane (10 ml) and tetrahydrofuran (10 ml) was added manganese(IV) oxide (1695.93 mg, 19.51 mmol) and stirred at 25° C. for 1 h. After completion of reaction, reaction mixture was filtered and concentrated under vacuum. The crude, thus obtained was purified by trituration with 20% ethyl acetate in n-hexane to afford 9H-fluoren-9-ylmethyl N-[[2-(dimethylamino)-4-[(3-formyl-2-pyridyl)sulfanyl]-3-pyridyl]methyl]carbamate (247.7 mg, 49.74% yield) as white solid. LC-MS: 330.1[M+H]+.

1H NMR: (400 MHz, DMSO-d6) δ 2.83 (6H, s), 4.19 (1H, d, J=6.6 Hz), 4.23 (2H, d, J=6.9 Hz), 4.28 (2H, d, J=3.9 Hz), 6.92 (1H, d, J=5.0 Hz), 7.30 (2H, t, J=7.1 Hz), 7.36-7.48 (3H, m), 7.52-7.59 (1H, m), 7.66 (2H, d, J=7.4 Hz), 7.88 (2H, d, J=7.4 Hz), 8.12 (1H, d, J=5.1 Hz), 8.28-8.35 (1H, m), 8.53 (1H, dd, J=4.6, 1.6 Hz), 10.19 (1H, s).

Intermediate 133 (9H-Fluoren-9-yl)methyl ((2-chloro-4-((3-formylpyridin-2-yl)thio)pyridin-3-yl)methyl)carbamate

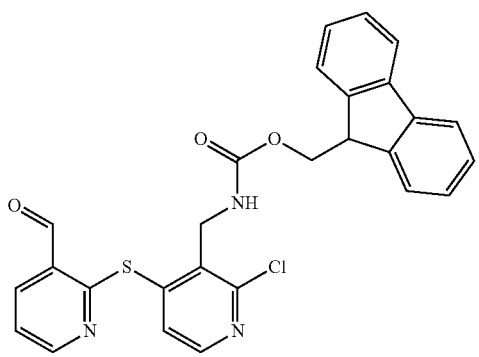 [SMILES: O=Cc1cccnc1Sc1ccnc(Cl)c1CNC(=O)OCC1c2ccccc2-c2ccccc21]

To a stirred solution of 2-mercaptonicotinic acid (10 g, 64.45 mmol) in DMSO (40 ml) was added trifluoroacetic acid (0.49 ml, 6.44 mmol) at 0° C. and the reaction mixture was heated at 60° C. for 24 h. Reaction mixture was then cooled to 0° C., DMF (100 ml) and potassium carbonate (8.91 g, 64.45 mmol) were then added and stirred for 30 min at 0° C. Then iodomethane (12.04 ml, 193.34 mmol) was slowly added at 0° C. and the reaction mixture was stirred at 25° C. for 16 h. The reaction mixture was then cooled to 0° C., a solution of acetic acid (13 ml) in water (150 ml) was slowly added and the resulting mixture stirred at 25° C. for 6 h. Precipitated white solid was filtered, washed with water (3×70 ml) followed by hexane (3×30 ml), dried under vacuum to afford methyl 2-[(3-methoxycarbonyl-2-pyridyl)disulfanyl]pyridine-3-carboxylate (8.24 g, crude) as white solid. LC-MS: 336.6 [M+H]$^+$.

To a stirred solution of methyl 2-[(3-methoxycarbonyl-2-pyridyl)disulfanyl]pyridine-3-carboxylate (8.2 g, 24.38 mmol) in 1,4-dioxane (34 ml) were added triphenyl phosphine (8.95 g, 34.13 mmol) and water (18 ml) successively at 25° C. and heated at 65° C. for 16 h. Then the reaction mixture was concentrated under vacuum. The residue thus obtained was diluted with EtOH (85 ml) and heated at 75° C. for 15 min. The reaction mixture was then cooled to 25° C. slowly followed to 0° C. by 4 h. The solid was then collected by filtration and dried under vacuum to afford methyl 2-sulfanylpyridine-3-carboxylate (7.54 g, 69.17% yield over 2 steps) as yellow solid. LC-MS: 170.1 [M+H]$^+$.

The title compound was then prepared in analogy to Intermediate 63 starting from 2-chloro-4-fluoro-pyridine-3-carbaldehyde and methyl 2-sulfanylpyridine-3-carboxylate. The title compound was obtained as white solid (655 mg). MS ESI (m/z): 502.0 [(M+H)$^+$]

1H NMR: (400 MHz, DMSO-d6) δ 4.18 (1H, d, J=6.2 Hz), 4.24 (2H, d, J=6.8 Hz), 4.37 (2H, d, J=4.2 Hz), 7.31 (2H, t, J=7.3 Hz), 7.40 (2H, t, J=7.4 Hz), 7.45 (1H, dd, J=7.4, 5.0 Hz), 7.50 (1H, d, J=5.0 Hz), 7.67 (3H, d, J=7.3 Hz), 7.88 (2H, d, J=7.4 Hz), 8.35-8.39 (2H, m), 8.52 (1H, d, J=3.3 Hz), 10.18 (1H, s).

Intermediate 134

9H-Fluoren-9-ylmethyl N-({3-chloro-2-[(3-formylpyridin-2-yl) sulfanyl]-5-(pyrrolidin-1-yl)phenyl}methyl)carbamate

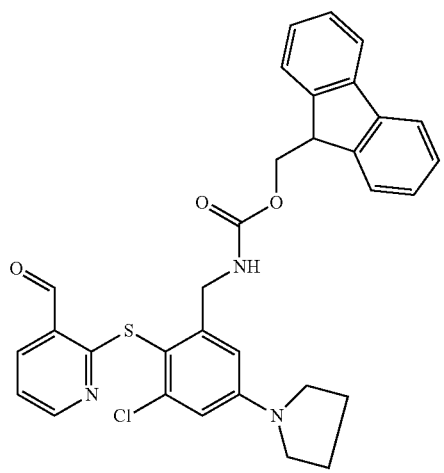 [SMILES: O=Cc1cccnc1Sc1c(Cl)cc(N2CCCC2)cc1CNC(=O)OCC1c2ccccc2-c2ccccc21]

To a stirred solution of N-({5-bromo-2-[(3-{[(tert-butyldimethylsilyl)oxy]methyl}pyridin-2-yl)sulfanyl]-3-chlorophenyl}methyl)-2-methylpropane-2-sulfinamide (500 mg, 0.867 mmol) in toluene (5 mL) were added pyrrolidine (73.955 mg, 1.04 mmol) and sodium tertiary butoxide (224.844 mg, 2.34 mmol) and degassed in argon atmosphere for 5 min. Then to it were added 2-ditertiary butyl phosphino biphenyl (23.272 mg, 0.078 mmol) and Pd(dba)$_2$ (39.861 mg, 0.069 mmol) and heated to 110° C. for 16h. Reaction mass was filtered through celite pad and the filtrate was evaporated under reduced pressure to get N-({2-[(3-{[(tert-Butyldimethylsilyl)oxy]methyl}pyridin-2-yl) sulfanyl]-3-chloro-5-(pyrrolidin-1-yl)phenyl}methyl)-2-methylpropane-2-sulfinamide (500 mg, crude) as off white solid; which was directly used for next step. LC-MS: 584.3 [M+H]$^+$ To a stirred solution of N-({2-[(3-{[(tert-butyldimethylsilyl)oxy]methyl}pyridin-2-yl)sulfanyl]-3-chloro-5-(pyrrolidin-1-yl)phenyl}methyl)-2-methylpropane-2-sulfinamide (600 mg, 1.058 mmol) in MeOH (10 mL), was added 4M HCl in dioxan (5 mL) at 0° C. and reaction mixture was stirred at 25° C. for 2h. Reaction mass was evaporated under reduced pressure to get (2-{[2-(aminomethyl)-6-chloro-4-(pyrrolidin-1-yl)phenyl]sulfanyl}pyridin-3-yl)methanol as HCl salt (350 mg, crude) as off white solid which was directly used for next step. LC-MS: 349.8 [M+H]$^+$ To a stirred suspension of (2-{[2-(aminomethyl)-6-chloro-4-(pyrrolidin-1-yl)phenyl]sulfanyl}pyridin-3-yl)methanol HCl salt (1.0 g, 2.865 mmol) in 5% NaHCO₃ (10 mL) was added Fmoc OSU (966 mg, 2.865 mmol) in dioxan (10 mL) at 25° C. and reaction mass was stirred at the same temperature for 16h. Then reaction mass was diluted with water and extracted with ethyl acetate. The separated organic layer was washed with brine solution, dried over sodium sulfate and evaporated under reduced pressure to get 9H-fluoren-9-ylmethyl N-[(3-chloro-2-{[3-(hydroxymethyl)pyridin-2-yl]sulfanyl}-5-(pyrrolidin-1-yl)phenyl)methyl]carbamate (1.1 g, crude) as off white solid; which was used for next step without further purification. LC-MS: 571.8 [M+H]⁺

To a stirred solution of 9H-fluoren-9-ylmethyl N-[(3-chloro-2-{[3-(hydroxymethyl)pyridin-2-yl]sulfanyl}-5-(pyrrolidin-1-yl)phenyl)methyl]carbamate (1.1 g, 1.926 mmol) in DCM/THF (1:1, 20 mL) was added MnO₂ (2.512 g, 28.897 mmol)) and reaction mass was stirred at 25° C. for 2h. The reaction mass was filtered through celite pad; filtrate was evaporated under reduced pressure. The crude thus obtained was purified by combi-flash column chromatography (40 g; 40-80% EtOAC/Hexanes) to give an impure mixture which was finally purified by reverse phase prep-HPLC to give 9H-fluoren-9-ylmethyl N-({3-chloro-2-[(3-formylpyridin-2-yl)sulfanyl]-5-(pyrrolidin-1-yl)phenyl}methyl)carbamate (150 mg, 10%, 4 steps) as a off white solid. LC-MS: 570.0 [M+H]⁺

¹H-NMR: (400 MHz, DMSO-d6): δ 1.90-1.95 (4H, m), 3.23 (4H, m), 4.20-4.27 (5H, m), 6.51 (1H, s), 6.62 (1H, s) 7.30-7.32 (3H, m), 7.39-7.41 (2H, m), 7.68 (2H, d, J=7.2 Hz), 7.70 (1H, m), 7.90 (2H, d, J=7.12 Hz), 8.31 (1H, m), 8.4 (1H, s), 10.21 (1H, s).

Intermediate 135

3-[(12S,15S,18S)-15-(4-tert-Butoxycarbonylamino-butyl)-18-(3-tert-butoxycarbonylamino-propyl)-6-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-12-ylmethyl]-indole-1-carboxylic Acid Tert-Butyl Ester

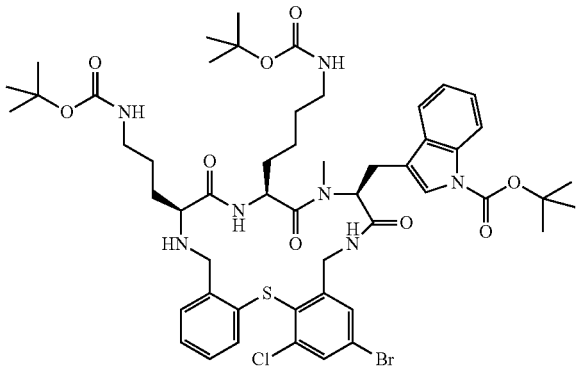 [SMILES: CN1C(=O)[C@H](CCCCNC(=O)OC(C)(C)C)NC(=O)[C@H](CCCNC(=O)OC(C)(C)C)NCc2ccccc2Sc2c(Cl)cc(Br)cc2CNC(=O)[C@@H]1Cc1cn(C(=O)OC(C)(C)C)c2ccccc12]

Intermediate 135 was prepared according to the General Procedure for Peptide Macrocycle Synthesis, but BOC-protecting groups were kept intact (no TFA deprotection) using the following starting materials:
Amino acids:
1. Fmoc-L-Trp(BOC)—OH,
2. Fmoc-L-Lys(BOC)—OH,
3. Fmoc-L-Orn(BOC)—OH.
Tether: Intermediate 89
MS (M+H)⁺: expected 1082.37; observed 1082.5

Intermediate 136

3-[(12S,15S,18S)-15-(4-tert-Butoxycarbonylamino-butyl)-18-(3-tert-butoxycarbonylamino-propyl)-5-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-12-ylmethyl]-indole-1-carboxylic Acid Tert-Butyl Ester

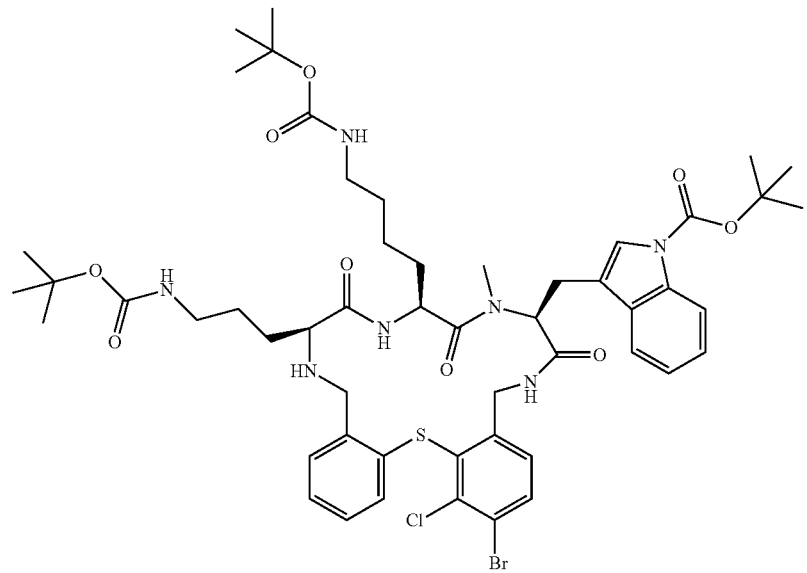 [SMILES: CN1C(=O)[C@H](CCCCNC(=O)OC(C)(C)C)NC(=O)[C@H](CCCNC(=O)OC(C)(C)C)NCc2ccccc2Sc2c(ccc(Br)c2Cl)CNC(=O)[C@@H]1Cc1cn(C(=O)OC(C)(C)C)c2ccccc12]

Intermediate 136 was prepared according to the General Procedure for Peptide Macrocycle Synthesis, but BOC-protecting groups were kept intact (no TFA deprotection) using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 100
MS (M+H)+: expected 1082.37; observed 1082.5

Intermediate 137

3-[(12S,15S,18S)-15-(4-tert-Butoxycarbonylamino-butyl)-18-(3-tert-butoxycarbonylamino-propyl)-23-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-12-ylmethyl]-indole-1-carboxylic Acid Tert-Butyl Ester

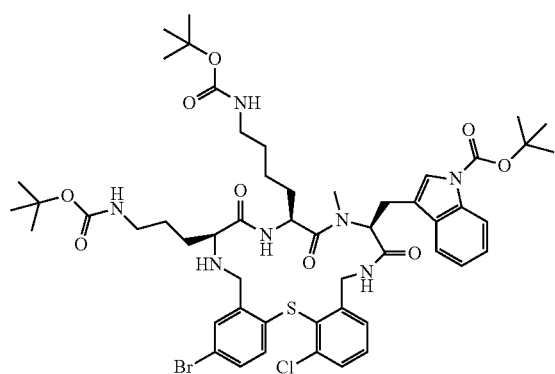 [SMILES: CN1C(=O)[C@H](CCCCNC(=O)OC(C)(C)C)NC(=O)[C@H](CCCNC(=O)OC(C)(C)C)NCc2cc(Br)ccc2Sc2c(Cl)cccc2CNC(=O)[C@@H]1Cc1cn(C(=O)OC(C)(C)C)c2ccccc12]

Intermediate 137 was prepared according to the General Procedure for Peptide Macrocycle Synthesis, but BOC-protecting groups were kept intact (no TFA deprotection) using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 115
MS (M+H)+: expected 1082.37; observed 1082.5

Intermediate 138

3-[(12S,15S,18S)-15-(4-tert-Butoxycarbonylamino-butyl)-18-(3-tert-butoxycarbonylamino-propyl)-24-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-12-ylmethyl]-indole-1-carboxylic Acid Tert-Butyl Ester

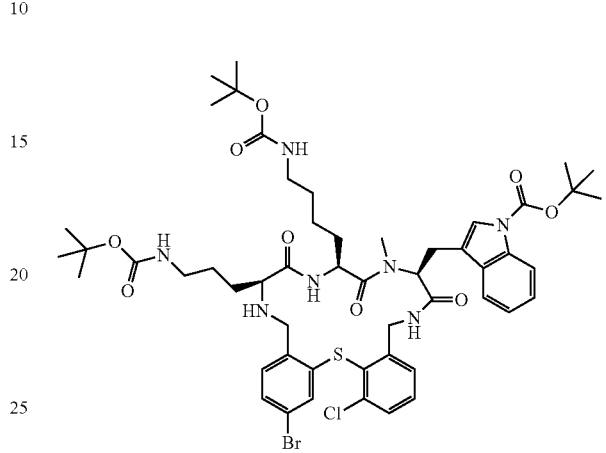

Intermediate 138 was prepared according to the General Procedure for Peptide Macrocycle Synthesis, but BOC-protecting groups were kept intact (no TFA deprotection) using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 120
MS (M+H)+: expected 1082.37; observed 1082.6

Intermediate 138

3-[(12S,15S,18S)-15-(4-tert-Butoxycarbonylamino-butyl)-18-(3-tert-butoxycarbonylamino-propyl)-24-bromo-4-chloro-13-methyl-11,14,17-trioxo-2-thia-10,13,16,19-tetraaza-tricyclo[19.4.0.0*3,8*]pentacosa-1(25),3(8),4,6,21,23-hexaen-12-ylmethyl]-indole-1-carboxylic Acid Tert-Butyl Ester

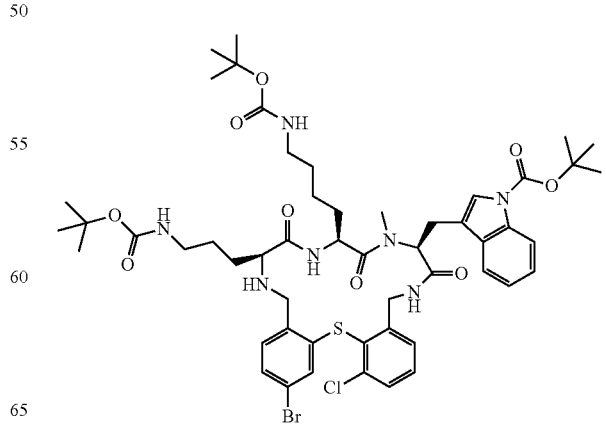

Intermediate 138 was prepared according to the General Procedure for Peptide Macrocycle Synthesis, but BOC-protecting groups were kept intact (no TFA deprotection) using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 120
MS (M+H)$^+$: expected 1082.37; observed 1082.6

Intermediate 139

(7S,10S,13S)-10-(4-aminobutyl)-7-(3-aminopropyl)-20-chloro-6,7,9,10,12,13,15,16-octahydro-12-methyl-13-[(2-methyl-1H-indol-3-yl)methyl]-18-[2-(4-methyl-1-piperazinyl)-4-pyridinyl]pyrido[2,3-b][1,5,8,11,14]benzothiatetraazacycloheptadecine-8,11,14(5H)-trione

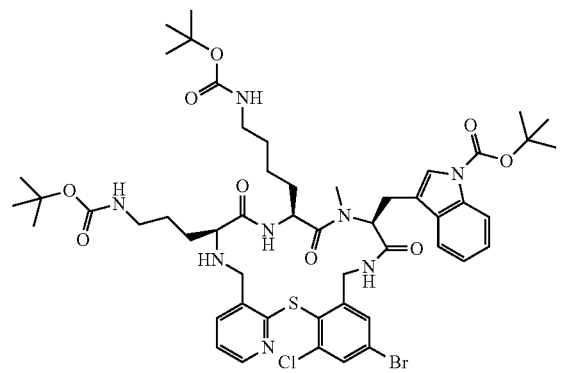 [SMILES: CN1C(=O)[C@H](CCCCNC(=O)OC(C)(C)C)NC(=O)[C@H](CCCNC(=O)OC(C)(C)C)NCc2cccnc2Sc2c(Cl)cc(Br)cc2CNC(=O)[C@@H]1Cc1cn(C(=O)OC(C)(C)C)c2ccccc12]

Intermediate 138 was prepared according to the General Procedure for Peptide Macrocycle Synthesis, but BOC-protecting groups were kept intact (no TFA deprotection) using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 60
MS (M+H)$^+$: expected 1083.3; observed 1084.5

Intermediate 140

1H-indole-1-carboxylic acid, 3-[[(7S,10S,13S)-17-bromo-20-chloro-10-[4-[[(1,1-dimethylethoxy)carbonyl]amino]butyl]-7-[3-[[(1,1-dimethylethoxy)carbonyl]amino]propyl]-5,6,7,8,9,10,11,12,13,14,15,16-dodecahydro-12-methyl-8,11,14-trioxopyrido[2,3-b][1,5,8,11,14]benzothiatetraazacycloheptadecin-13-yl]methyl]-, 1,1-dimethylethyl Ester

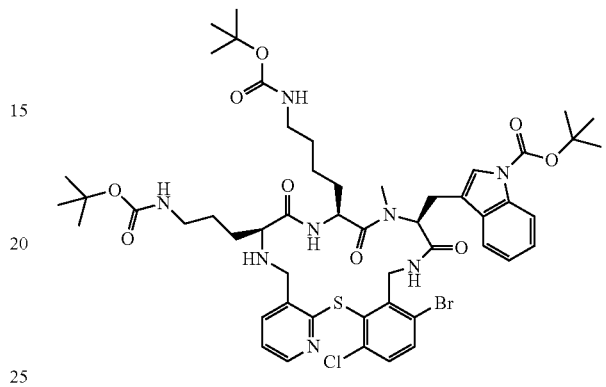

Intermediate 140 was prepared according to the General Procedure for Peptide Macrocycle Synthesis, but BOC-protecting groups were kept intact (no TFA deprotection) using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 59
MS (M+H)$^+$: expected 1083.3; observed 1084.5

Intermediate 141

(2S)-5-[tert-butyl(dimethyl)silyl]oxy-2-(9H-fluoren-9-ylmethoxycarbonylamino)pentanoic Acid

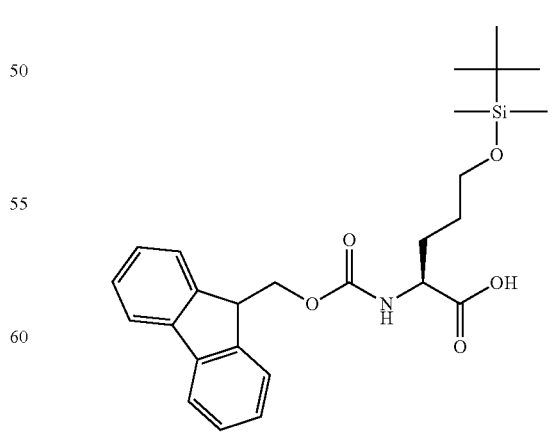

The title compound was prepared according to the following scheme:

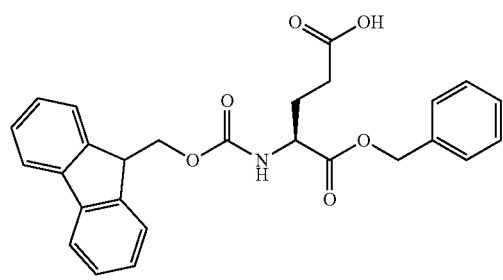

i141a

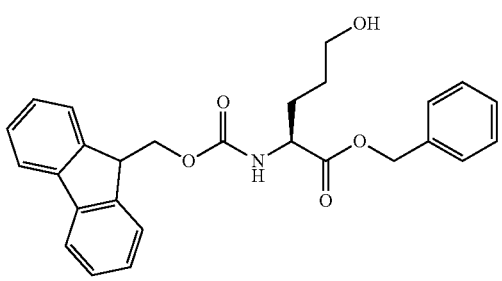

i141b

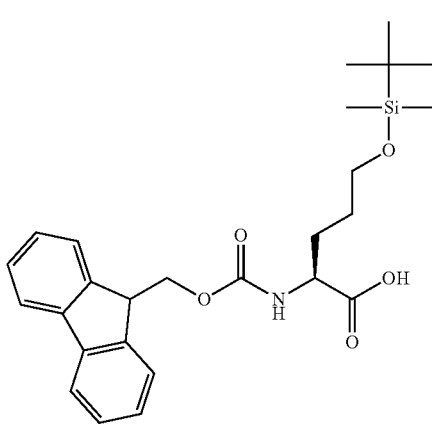

i141

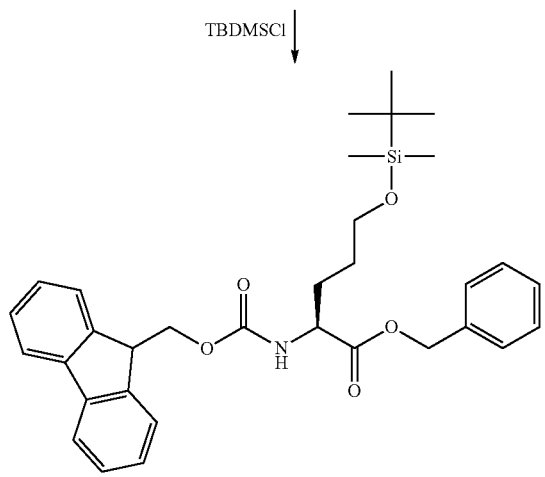

i141c

Step 1: Preparation of benzyl (2S)-2-(9H-fluoren-9-ylmethoxycarbonylamino)-5-hydroxy-pentanoate (Compound i141b)

To a mixture of (4S)-5-benzyloxy-4-(9H-fluoren-9-ylmethoxycarbonylamino)-5-oxo-pentanoic acid (i141a, 1.84 g, 4 mmol) and 4-methylmorpholine (607 mg, 0.66 mL, 6 mmol) in dry THF (20 ml) at −10° C. was added dropwise isobutyl carbonochloridate (660 mg, 4.8 mmol). The resulting reaction mixture was stirred at −10° C. for 2 hours, then poured into a mixture of NaBH$_4$ (460 mg, 12 mmol) and ice (10 g) and stirred for further 30 minutes. The reaction mixture was diluted with ice-cooled water, and extracted with EA twice. The combined organic phase was dried and concentrated. The residue was purified by silica gel column to give compound i141b (1.34 g). MS (M+H$^+$): 446.

Step 2: Preparation of benzyl (2S)-5-[tert-butyl(dimethyl)silyl]oxy-2-(9H-fluoren-9-ylmethoxycarbonylamino)pentanoate (Compound i141c)

To a mixture of benzyl (2S)-2-(9H-fluoren-9-ylmethoxycarbonylamino)-5-hydroxy-pentanoate (compound i141b, 1.34 g, 3 mmol) and imidazole (610 mg, 9 mmol) in DCM (15 ml) was added a solution of tert-butylchlorodimethylsilane (540 mg, 3.6 mmol) in DCM (5 ml). The reaction mixture was stirred at room temperature for 3 hours, and then concentrated. The residue was dissolved in PE/EA=5/1, and washed with water. The organic phase was separated and concentrated. The residue was purified by silica gel column to give compound i141c (1.3 g). MS (M+H$^+$): 560.

Step 3: preparation of (2S)-5-[tert-butyl(dimethyl)silyl]oxy-2-(9H-fluoren-9-ylmethoxycarbonylamino) pentanoic Acid (Intermediate i141)

To a solution of benzyl (2S)-5-[tert-butyl(dimethyl)silyl]oxy-2-(9H-fluoren-9-ylmethoxycarbonylamino)pentanoate (compound i141c, 1.3 g, 2.3 mmol) in EtOH/i-PrOH/H$_2$O=89/5/6 (15 ml) was added Lindlar catalyst (Aldrich, 390 mg). The reaction mixture was heated at 40° C. under a Eh balloon for 5 hours. After cooled to room temperature, the reaction mixture was filtered. The filtrate was treated with aq. HCl solution (1 N) to pH=6 and concentrated. The residue was taken up in EA, washed with brine, dried, and concentrated to give crude compound i141 (1.0 g). MS (M+H$^+$): 470.

General Procedure for Peptide Macrocycle Synthesis

1. Solid Phase Peptide Synthesis

The tripeptide sequence was synthesized manually via state-of-the-art solid phase synthesis protocols (Fmoc-chemistry) as referenced by e.g.: Kates and Albericio, Eds., "Solid Phase Synthesis: A practical guide", Marcel Decker, New York, Basel, 2000.

As a solid support 2-Chlor-tritylchloride resin (1.6 meq/g, 100-200 mesh) was used. This resin was loaded with 0.6 eq of amino acid and 8 eq DIPEA in dry DCM overnight at RT. After extensive washing with DMF and DCM, the Fmoc-group was cleaved off with a mixture of 50% Piperidine in DCM/DMF (1:1) in DMF (freshly prepared) for 30 min at RT. After washing with DMF, DCM and MeOH the resin was dried under vacuum at RT overnight. The resin loading was determined via weight increase.

The second amino acid was coupled with 4 eq Mukaiyama-Reagent as coupling reagent, 6 eq DIPEA in DMF/DCM (1:1) overnight at RT. The resin was extensively washed with DMF and DCM and the coupling rate was controlled by a test-cleavage.

The Fmoc-group from the dipeptide was cleaved with a mixture of 50% Piperidine (25%)/DCM (25%) in DMF for maximally 5 min followed by washings with DMF and DCM. The cleavage rates were again controlled by test-cleavage.

The third amino acid was coupled using an excess of 4 eq using 4 eq HATU as coupling reagent and 6 eq DIPEA. Complete couplings were accomplished at RT for 2-4 hours with the coupling rate again controlled by a test-cleavage.

The Fmoc-group from the tripeptide was cleaved with a mixture of 20% Piperidine in DMF for 2×15-20 min at RT followed by washings with DMF and DCM (test-cleavage).

On-Bead N-Methylation:

In case the N-methylated amino acids were not commercially available they were alkylated on the solid phase as follows:

Resin was swollen in THF (ca. 10 ml/g resin). 12 eq DIPEA were added and the reaction mixture was shaken at RT for 15 min. 3 eq 2-nitrobenzene-1-1sulfonylchloride were added and the resin was shaken at RT overnight. Resin was then drained, washed with DCM and DMF. The coupling rate was controlled via a test-cleavage.

For the second step the Resin was suspended in DMF, 12 eq MTBD (7-methyl-1,5,7-triazabicyclo[4.4.0]dec-5-ene) were added and the reaction mixture was shaken at RT for 10 min. Then 3 eq Methyl-4-nitrobenzenesulfonate was added and the slurry was shaken at RT. After 30 min. The resin was drained and washed with DMF and DCM. The coupling rate was controlled via a test-cleavage.

For removal of the 2-nitrobenzene-1-1 sulfonamide protecting group, the resin was suspended in DMF, 12 eq DBU were added, the slurry shaken for 5 min, then 12 eq mercaptoethanol was added and the reaction mixture was shaken at RT for 1 h. The resin was drained and washed with DMF and DCM. The deprotection rate was controlled via a test-cleavage.

2. Reductive Animation:

Resin with tripeptide was washed with DCM, the corresponding Intermediate dissolved in a mixture of NMP/TMOF/AcOH (49.7/49.7/0.6) and the solution was added to the resin. The mixture was shaken at RT for 30 min up to 3h, then 10 eq NaCNBH$_3$ were added and the reaction mixture was shaken at RT overnight. Finally, the resin was washed with DMF, DCM, MeOH/DCM (1:1) and DMF.

The Fmoc-group on the third amino acid was cleaved with a mixture of 20% Piperidine in DMF for 2×15-20 min at RT followed by washings with DMF and DCM (test-cleavage).

3. Cleavage:

A cleavage-cocktail of 20% HFIP in DCM was added to the resin and the mixture was stirred for 2h at RT. The resin was filtered off and the solution was evaporated to dryness. The residue was dissolved in water/acetonitrile and lyophilized.

4. Cyclisation:

The obtained crude linear compound was cyclized by dissolving the powder in DMF. 1.2 eq HATU and 5 eq DIPEA were added and the reaction mixture stirred at RT. Progress of the reaction was monitored by HPLC. After completion, the solvent was evaporated, the resulting residue taken up in water/acetonitrile (1:1) and lyophilized.

5. Purification:

Peptide macrocycles were purified using reversed phase high-performance liquid chromatography (RP-HPLC) using a Reprospher 100 C18-TDE column (250×20 mm, 5 um particle size) as a stationary phase and water/acetonitrile as eluent (Gradient 40-100% MeCN over 60 min). Fractions were collected and analyzed by LC/MS. Pure product samples were combined and lyophilized. Product identification was obtained via mass spectrometry.

6. Global Deprotection:

Final BOC-deprotection was achieved by 50% TFA (DCM) treatment for 2h at RT. The reaction solution was concentrated down and the residue freeze-dried to yield the deprotected product as TFA salt. All peptides were obtained as white powders with a purity >90%.

General Procedure for Suzuki Coupling of Boronic Acid Derivatives to Peptide Macrocycle Intermediates In a reaction tube to a solution of protected bromide Macrocycle Intermediate (46.1 μmol, Eq: 1) in Dioxane (1.2 ml) was added at 22° C. water (400 μl) followed by sodium carbonate (115 μmol, Eq: 2.5) and the Boronic Acid Derivative (92.3 μmol, Eq: 2). The mixture was degassed by bubbling argon into the reaction mixture for 5 minutes. Then was added tetrakis(triphenylphosphine)palladium (0) (2.31 μmol, Eq: 0.05), the tube was inserted, sealed and the reaction mixture was stirred at 80° C. for 2 h or till complete conversion.

The mixture was evaporated, treated with water (2 ml) and extracted with DCM (2×2 ml). The organic layers were dried, evaporated to dryness, purified by preparative HPLC and lyophilized to give the pure product as a lyophilized solid.

Boc-Deprotection

To a solution of lyophilized solid (15 μmol) in DCM (1.6 ml) was added at 22° C. TFA (0.4 ml) (5.22 mmol=ca. 350 eq) and stirred for 2 h to give complete conversion.

After total 2 h the mixture was evaporated, the residue was dissolved in ACN and H$_2$O (containing 0.1% TFA), allowed to stand for 4 h at 22° C. and dried frozen/lyophilized to give the peptide macrocycle as white lyoph solid.

Example 1

(12S,15S,18S)-15-(4-Amino-butyl)-18-(3-amino-propyl)-12-(1H-indol-3-ylmethyl)-13-methyl-2-thia-10,13,16,19-tetraaza-tricyclo[19.4.0.0*3,8*]penta-cosa-1(21),3,5,7,22,24-hexaene-11,14,17-trione

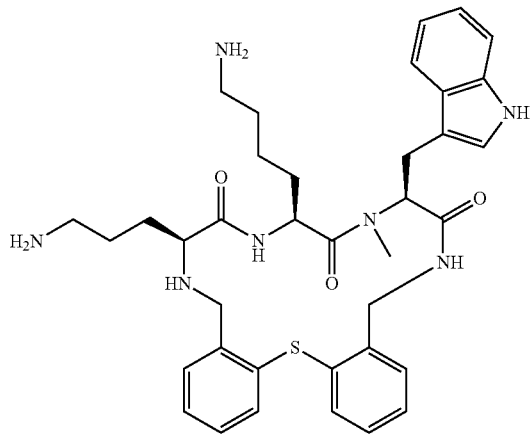 [SMILES: CN1C(=O)[C@H](CCCCN)NC(=O)[C@H](CCCN)NCc2ccccc2Sc2ccccc2CNC(=O)[C@@H]1Cc1c[nH]c2ccccc12]

Example 1 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 4
MS (M+H)$^+$: expected 696.3; observed 670.3

Example 2

(12S,15S,18S)-15,18-Bis-(3-amino-propyl)-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

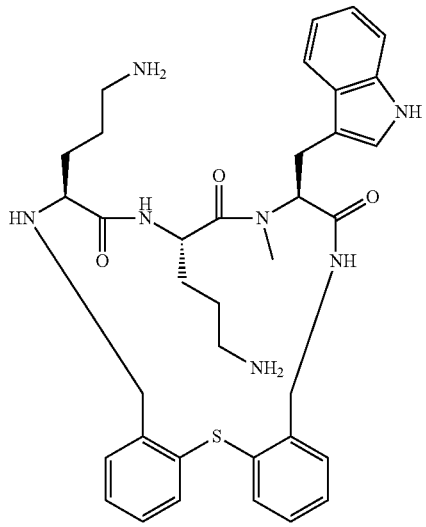 [SMILES: CN1C(=O)[C@H](CCCN)NC(=O)[C@H](CCCN)NCc2ccccc2Sc2ccccc2CNC(=O)[C@@H]1Cc1c[nH]c2ccccc12]

Example 2 was prepared according to the General Procedure for Peptide Macrocycle Synthesis using the following starting materials:
Amino acids:
1. Fmoc-NMe-L-Trp(BOC)—OH,
2. Fmoc-L-Orn(BOC)—OH,
3. Fmoc-L-Orn(BOC)—OH.
Tether: Intermediate 4
MS (M+H)$^+$: expected 655.3; observed 656.3

Example 3

(12S,15S,18S)-15-(4-Amino-butyl)-12-(1H-indol-3-ylmethyl)-13-methyl-18-piperidin-4-yl-2-thia-10,13,16,19-tetraaza-tricyclo[19.4.0.0*3,8*]pentacosa-1(21),3,5,7,22,24-hexaene-11,14,17-trione

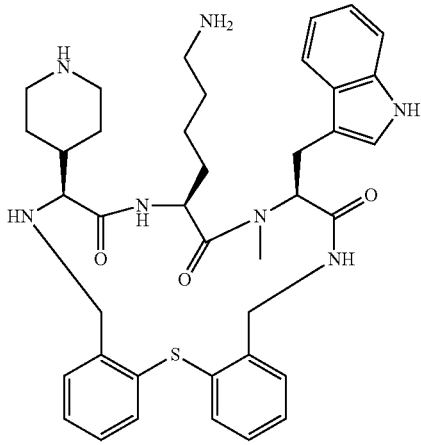 [SMILES: CN1C(=O)[C@H](CCCCN)NC(=O)[C@H](C2CCNCC2)NCc2ccccc2Sc2ccccc2CNC(=O)[C@@H]1Cc1c[nH]c2ccccc12]

Example 3 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. 2-(Fmoc-amino)-2-(1-Boc-4-piperidyl)acetic acid.
Tether: Intermediate 4
MS (M+H)$^+$: expected 695.4; observed 696.4

Example 4

(12S,15S,18S)-15-(4-Amino-butyl)-18-(3-amino-propyl)-6-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

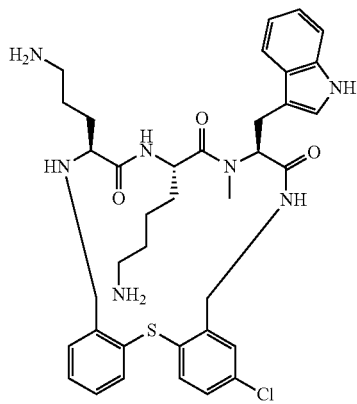 [SMILES: CN1C(=O)[C@H](CCCCN)NC(=O)[C@H](CCCN)NCc2ccccc2Sc2ccc(Cl)cc2CNC(=O)[C@@H]1Cc1c[nH]c2ccccc12]

Example 4 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 3
MS (M+H)$^+$: expected 703.3; observed 704.3

Example 5

N-[(11S,14S,17S)-14-(4-Amino-butyl)-17-(1H-indol-3-ylmethyl)-16-methyl-12,15,18-trioxo-2-thia-10,13,16,19-tetraaza-tricyclo[19.4.0.0*3,8*]pentacosa-1(25),3(8),4,6,21,23-hexaen-11-ylmethyl]-guanidine

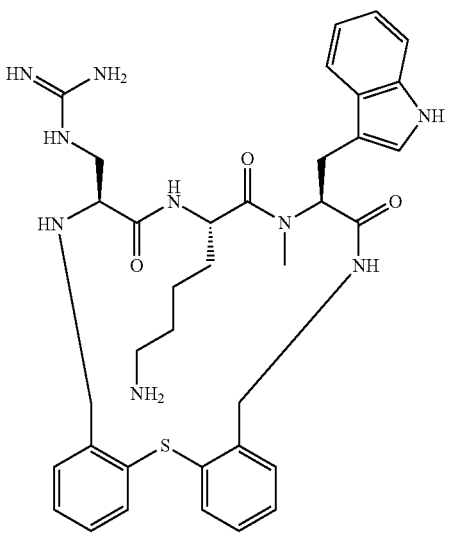 [SMILES: CN1C(=O)[C@H](CCCCN)NC(=O)[C@H](CNC(=N)N)NCc2ccccc2Sc2ccccc2CNC(=O)[C@@H]1Cc1c[nH]c2ccccc12]

Example 5 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Agp(Boc2)-OH.
Tether: Intermediate 4
MS (M+H)$^+$: expected 683.3; observed 684.3

Example 6

(12S,15S,18S)-15-(4-Amino-butyl)-18-(3-amino-propyl)-5-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

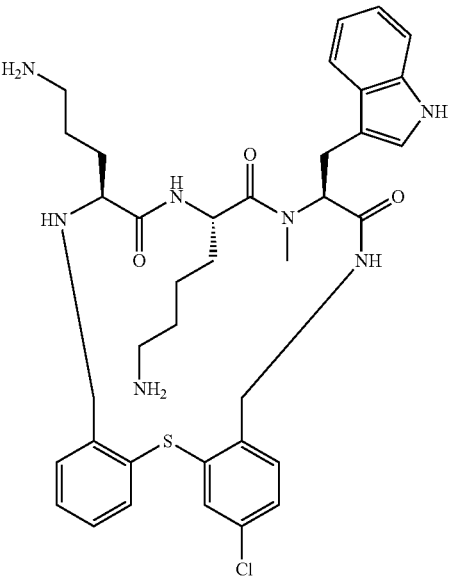 [SMILES: CN1C(=O)[C@H](CCCCN)NC(=O)[C@H](CCCN)NCc2ccccc2Sc2cc(Cl)ccc2CNC(=O)[C@@H]1Cc1c[nH]c2ccccc12]

Example 6 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 2
MS (M+H)$^+$: expected 703.3; observed 704.3

Example 7

(12S,15S,18S)-15-(4-Amino-butyl)-18-(3-amino-propyl)-12-(1H-indol-3-ylmethyl)-6-methoxy-13-methyl-2-thia-10,13,16,19-tetraaza-tricyclo[19.4.0.0*3,8*]pentacosa-1(21),3,5,7,22,24-hexaene-11,14,17-trione

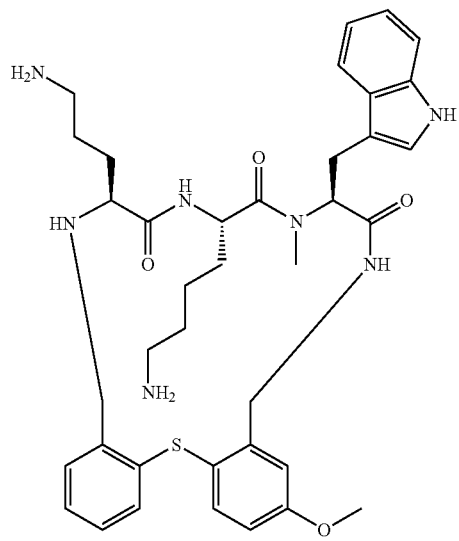 [SMILES: COc1ccc2c(c1)CNC(=O)[C@H](Cc1c[nH]c3ccccc13)N(C)C(=O)[C@H](CCCCN)NC(=O)[C@H](CCCN)NCc1ccccc1S2]

Example 7 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 5
MS (M+H)+: expected 699.4; observed 700.4

Example 8

(12S,15S,18S)-15-(4-Amino-butyl)-18-(3-amino-propyl)-12-(1H-indol-3-ylmethyl)-4,13-dimethyl-2-thia-10,13,16,19-tetraaza-tricyclo[19.4.0.0*3,8*]pentacosa-1(21),3,5,7,22,24-hexaene-11,14,17-trione

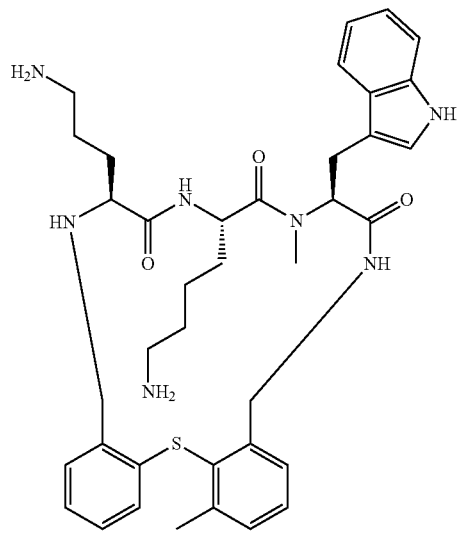 [SMILES: Cc1cccc2c1Sc1ccccc1CN[C@@H](CCCN)C(=O)N[C@@H](CCCCN)C(=O)N(C)[C@@H](Cc1c[nH]c3ccccc13)C(=O)NC2]

Example 8 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 6
MS (M+H)+: expected 683.4; observed 684.4

Example 9

(12S,15S,18S)-15-(4-Amino-butyl)-18-(3-amino-propyl)-12-(1H-indol-3-ylmethyl)-5,13-dimethyl-2-thia-10,13,16,19-tetraaza-tricyclo[19.4.0.0*3,8*]pentacosa-1(21),3,5,7,22,24-hexaene-11,14,17-trione

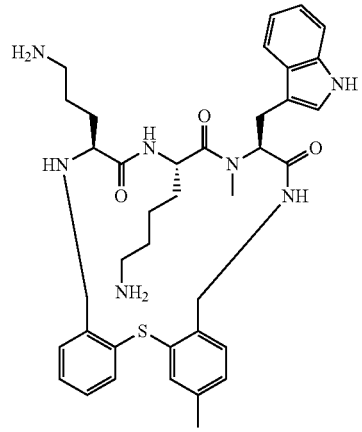 [SMILES: Cc1ccc2c(c1)Sc1ccccc1CN[C@@H](CCCN)C(=O)N[C@@H](CCCCN)C(=O)N(C)[C@@H](Cc1c[nH]c3ccccc13)C(=O)NC2]

Example 9 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 7
MS (M+H)+: expected 683.4; observed 684.4

Example 10

(12S,15S,18S)-15-(4-Amino-butyl)-18-(3-amino-propyl)-12-(1H-indol-3-ylmethyl)-6,13-dimethyl-2-thia-10,13,16,19-tetraaza-tricyclo[19.4.0.0*3,8*]pentacosa-1(21),3,5,7,22,24-hexaene-11,14,17-trione

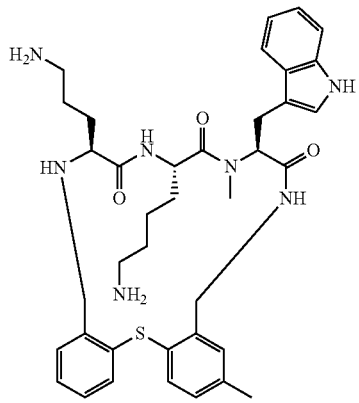 [SMILES: Cc1ccc2c(c1)CNC(=O)[C@H](Cc1c[nH]c3ccccc13)N(C)C(=O)[C@H](CCCCN)NC(=O)[C@H](CCCN)NCc1ccccc1S2]

Example 10 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 8

MS (M+H)$^+$: expected 683.4; observed 684.4

Example 11

(12S,15S,18S)-15-(4-Amino-butyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

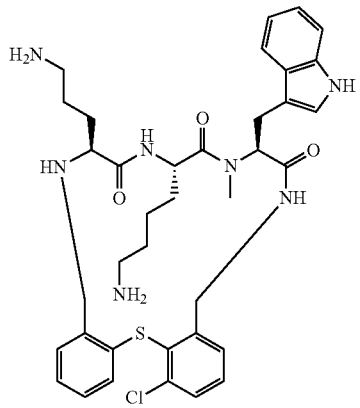 [SMILES: CN1C(=O)[C@H](CCCCN)NC(=O)[C@H](CCCN)NCc2ccccc2Sc2c(Cl)cccc2CNC(=O)[C@@H]1Cc1c[nH]c2ccccc12]

Example 11 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 1

MS (M+H)+: expected 703.3; observed 705.2

Example 12

(12S,15S,18S)-15-(4-Amino-butyl)-18-(3-amino-propyl)-12-(1H-indol-3-ylmethyl)-13-methyl-4-trifluoromethyl-2-thia-10,13,16,19-tetraaza-tricyclo[19.4.0.0*3,8*]pentacosa-1(21),3,5,7,22,24-hexaene-11,14,17-trione

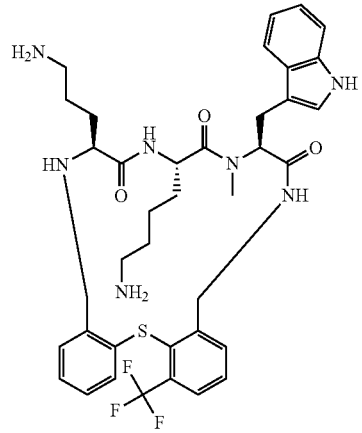 [SMILES: CN1C(=O)[C@H](CCCCN)NC(=O)[C@H](CCCN)NCc2ccccc2Sc2c(cccc2C(F)(F)F)CNC(=O)[C@@H]1Cc1c[nH]c2ccccc12]

Example 12 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 9

MS (M+H)+: expected 737.3; observed 738.1

Example 13

(12S,15S,18S)-15-(4-Amino-butyl)-18-(3-amino-propyl)-12-(1H-indol-3-ylmethyl)-13-methyl-5-trifluoromethyl-2-thia-10,13,16,19-tetraaza-tricyclo[19.4.0.0*3,8*]pentacosa-1(21),3,5,7,22,24-hexaene-11,14,17-trione

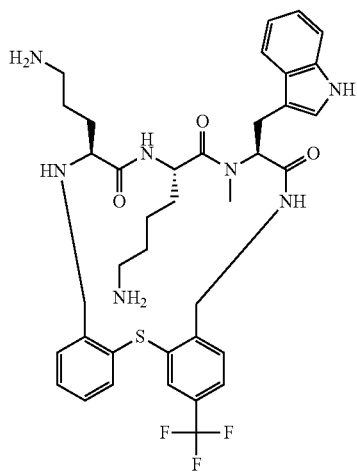 [SMILES: CN1C(=O)[C@H](CCCCN)NC(=O)[C@H](CCCN)NCc2ccccc2Sc2cc(C(F)(F)F)ccc2CNC(=O)[C@@H]1Cc1c[nH]c2ccccc12]

Example 13 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 10
MS (M+H)+: expected 737.3; observed 738.4

Example 14

(12S,15S,18S)-15-(4-Amino-butyl)-18-(3-amino-propyl)-12-(1H-indol-3-ylmethyl)-13-methyl-6-trifluoromethyl-2-thia-10,13,16,19-tetraaza-tricyclo[19.4.0.0*3,8*]pentacosa-1(21),3,5,7,22,24-hexaene-11,14,17-trione

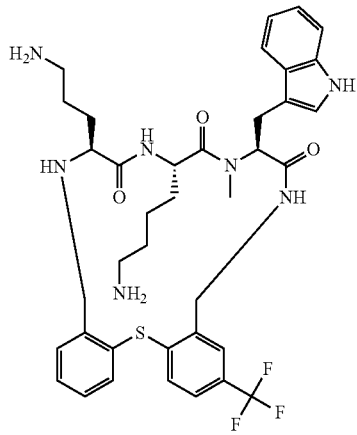 [SMILES: CN1C(=O)[C@H](CCCCN)NC(=O)[C@H](CCCN)NCc2ccccc2Sc2ccc(C(F)(F)F)cc2CNC(=O)[C@@H]1Cc1c[nH]c2ccccc12]

Example 14 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 11
MS (M+H)$^+$: expected 737.3; observed 738.3

Example 15

(12S,15S,18S)-15-(4-Amino-butyl)-18-(3-amino-propyl)-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

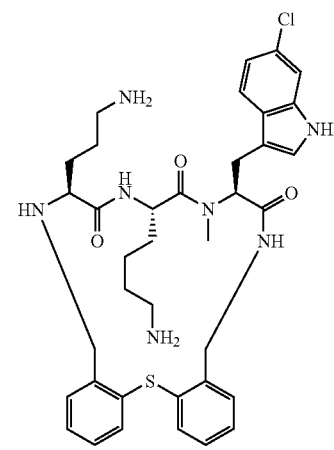 [SMILES: CN1C(=O)[C@H](CCCCN)NC(=O)[C@H](CCCN)NCc2ccccc2Sc2ccccc2CNC(=O)[C@@H]1Cc1c[nH]c2cc(Cl)ccc12]

Example 15 was prepared according to the General Procedure for Peptide Macrocycle Synthesis using the following starting materials:

Amino acids:
1. Fmoc-L-6-Cl-Trp-OH, followed by on-bead N-methylation of the Trp alpha-N,
2. Fmoc-L-Lys(BOC)—OH,
3. Fmoc-L-Orn(BOC)—OH.

Tether: Intermediate 4
MS (M+H)$^+$: expected 703.3; observed 704.3

Example 16

(12S,15S,18S)-15-(4-Amino-butyl)-18-(3-amino-propyl)-12-(6-chloro-1-methyl-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

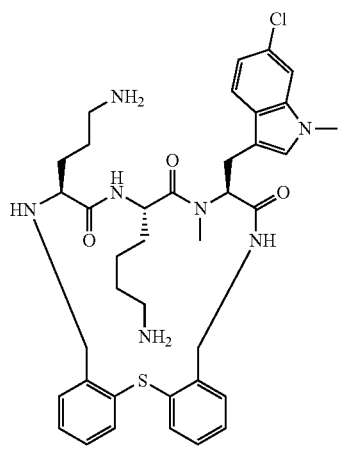 [SMILES: CN1C(=O)[C@H](CCCCN)NC(=O)[C@H](CCCN)NCc2ccccc2Sc2ccccc2CNC(=O)[C@@H]1Cc1cn(C)c2cc(Cl)ccc12]

N-Methylation at Indole nitrogen occurred upon N-alkylation of activated Trp alpha-N. Example 16 was isolated from crude mixture of Example 15 using standard HPLC purification conditions.

MS (M+H)$^+$: expected 717.3; observed 718.3

Example 17

(12S,15S,18S)-15-(4-Amino-butyl)-18-(3-amino-propyl)-6-chloro-13-methyl-12-(1-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

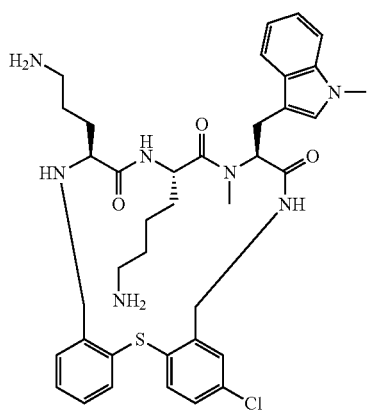 [SMILES: CN1C(=O)[C@H](CCCCN)NC(=O)[C@H](CCCN)NCc2ccccc2Sc2ccc(Cl)cc2CNC(=O)[C@@H]1Cc1cn(C)c2ccccc12]

Example 17 was prepared according to the General Procedure for Peptide Macrocycle Synthesis using the following starting materials:

Amino acids:
1. Fmoc-L-Trp(NMe)-OH, followed by on-bead N-methylation of the Trp alpha-N,
2. Fmoc-L-Lys(BOC)—OH,
3. Fmoc-L-Orn(BOC)—OH.

Tether: Intermediate 3

MS (M+H)$^+$: expected 717.3; observed 718.3

Example 18

(12S,15S,18S)-15-(4-Amino-butyl)-18-(3-amino-propyl)-6-chloro-12-(6-chloro-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

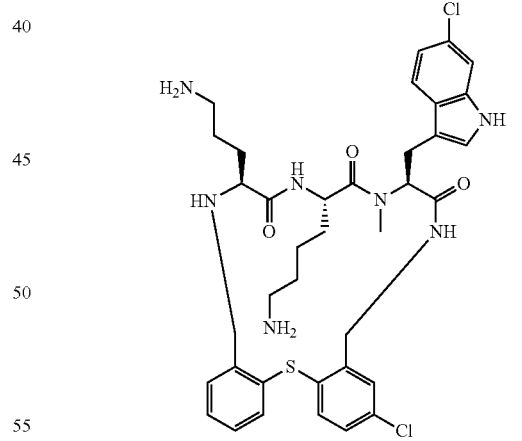

Example 18 was prepared according to the General Procedure for Peptide Macrocycle Synthesis using the following starting materials:

Amino acids:
1. Fmoc-L-6-Cl-Trp-OH, followed by on-bead N-methylation of the Trp alpha-N,
2. Fmoc-L-Lys(BOC)—OH,
3. Fmoc-L-Orn(BOC)—OH.

Tether: Intermediate 3

MS (M+H)+: expected 737.3; observed 738.3

Example 19

(12S,15S,18S)-15-(4-Amino-butyl)-18-(3-amino-propyl)-6-chloro-12-(6-chloro-1-methyl-1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

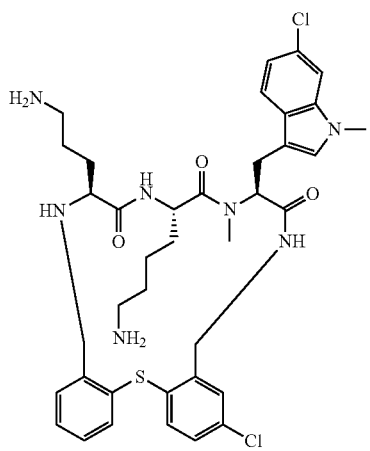 [SMILES: CN1C(=O)[C@H](CCCCN)NC(=O)[C@H](CCCN)NCc2ccccc2Sc2ccc(Cl)cc2CNC(=O)[C@@H]1Cc1cn(C)c2cc(Cl)ccc12]

N-Methylation at Indole nitrogen occurred upon N-alkylation of activated Trp alpha-N. Example 19 was isolated from crude mixture of Example 18 using standard HPLC purification conditions.

MS (M+H)+: expected 751.3; observed 752.3

Example 20

(9S,12S,15S,18S)-15-(4-Amino-butyl)-18-(3-amino-propyl)-6-chloro-12-(1H-indol-3-ylmethyl)-9,13-dimethyl-2-thia-10,13,16,19-tetraaza-tricyclo[19.4.0.0*3,8*]pentacosa-1(25),3,5,7,21,23-hexaene-11,14,17-trione

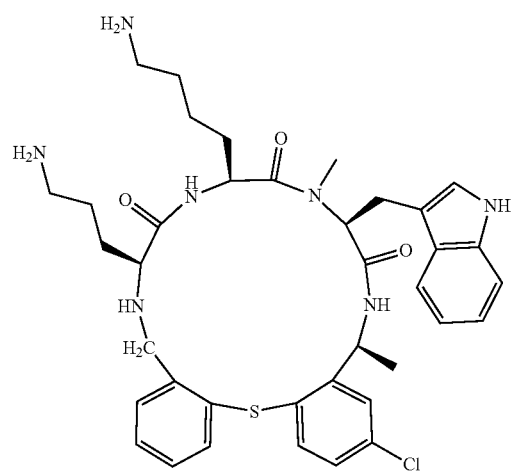 [SMILES: C[C@@H]1NC(=O)[C@H](Cc2c[nH]c3ccccc23)N(C)C(=O)[C@H](CCCCN)NC(=O)[C@H](CCCN)NCc2ccccc2Sc2ccc(Cl)cc21]

Example 20 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 12

MS (M+H)+: expected 717.3; observed 718.3

Example 21

(12S,15S,18S)-15-(4-Amino-butyl)-18-(3-amino-propyl)-6,7-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

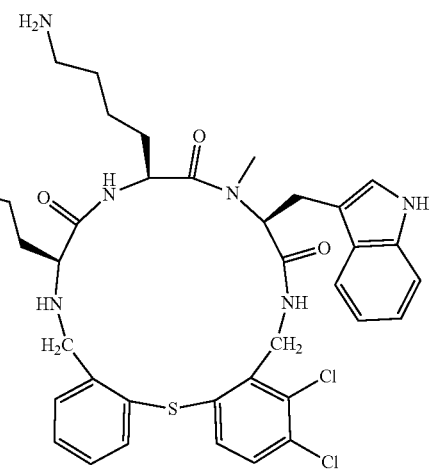

Example 21 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 14

MS (M+H)+: expected 737.3; observed 738.3

Example 22

(12S,15S,18S)-15-(4-Amino-butyl)-18-(3-amino-propyl)-7-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

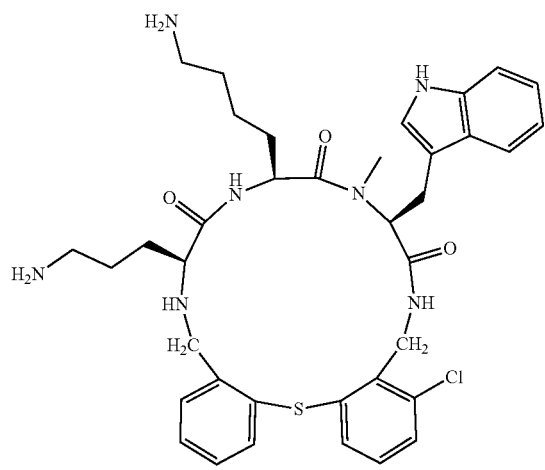 [SMILES: CN1C(=O)[C@H](CCCCN)NC(=O)[C@H](CCCN)NCc2ccccc2Sc2cccc(Cl)c2CNC(=O)[C@@H]1Cc1c[nH]c2ccccc12]

Example 22 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 15

MS (M+H)$^+$: expected 703.3; observed 704.3

Example 23

(12S,15S,18S)-15-(4-Amino-butyl)-18-(3-amino-propyl)-4,7-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

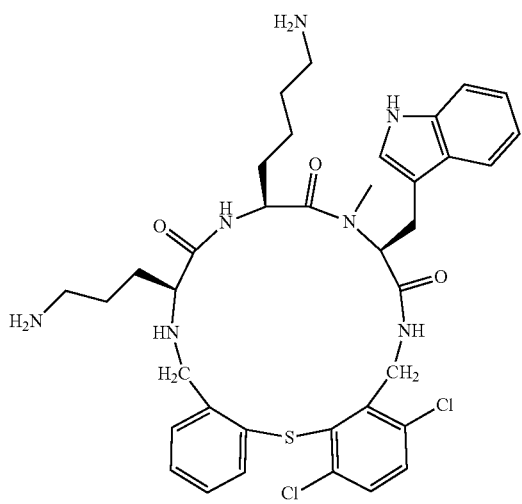 [SMILES: CN1C(=O)[C@H](CCCCN)NC(=O)[C@H](CCCN)NCc2ccccc2Sc2c(Cl)ccc(Cl)c2CNC(=O)[C@@H]1Cc1c[nH]c2ccccc12]

Example 23 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 13

MS (M+H)$^+$: expected 737.3; observed 738.4

Example 24

(12S,15S,18S)-15-(4-Amino-butyl)-18-(3-amino-propyl)-4-chloro-12-(1H-indol-3-ylmethyl)-13-methyl-7-trifluoromethyl-2-thia-10,13,16,19-tetraaza-tricyclo[19.4.0.0*3,8*]pentacosa-1(25),3,5,7,21,23-hexaene-11,14,17-trione Example 24 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 16

MS (M+H)$^+$: expected 771.3; observed 772.2

Example 25

(12S,15S,18S)-15-(4-Amino-butyl)-18-(3-amino-propyl)-4-chloro-12-(1H-indol-3-ylmethyl)-13-methyl-6-trifluoromethyl-2-thia-10,13,16,19-tetraaza-tricyclo[19.4.0.0*3,8*]pentacosa-1(25),3,5,7,21,23-hexaene-11,14,17-trione

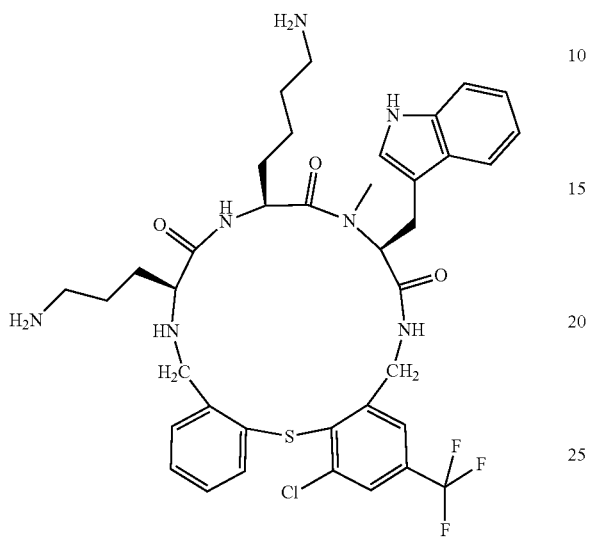

Example 25 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 21
MS (M+H)$^+$: expected 771.2; observed 772.3

Example 26

(12S,15S,18S)-15-(4-Amino-butyl)-18-(3-amino-propyl)-4-chloro-7-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

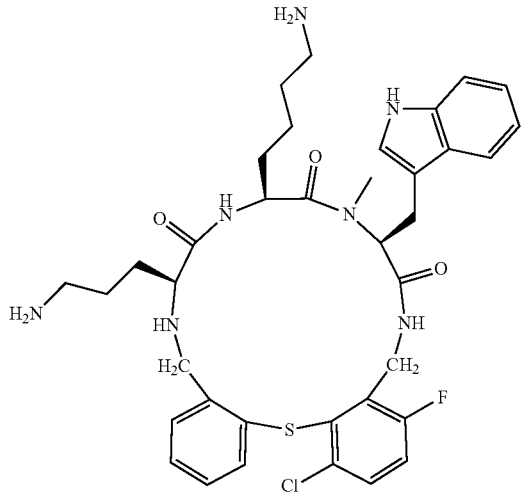 [SMILES: CN1C(=O)[C@H](CCCCN)NC(=O)[C@H](CCCN)NCc2ccccc2Sc2c(Cl)ccc(F)c2CNC(=O)[C@@H]1Cc1c[nH]c2ccccc12]

Example 26 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 22
MS (M+H)$^+$: expected 721.3; observed 722.3

Example 27

(12S,15S,18S)-15-(4-Amino-butyl)-18-(3-amino-propyl)-4,6-dichloro-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

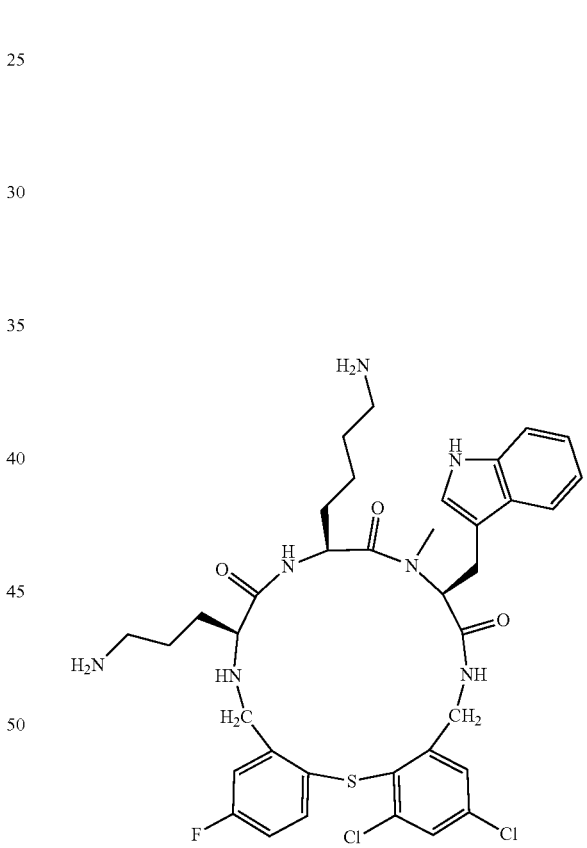

Example 27 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 26
MS (M+H)+: expected 755.3; observed 756.3

Example 28

(11S,14S,17S)-14-(4-Amino-butyl)-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

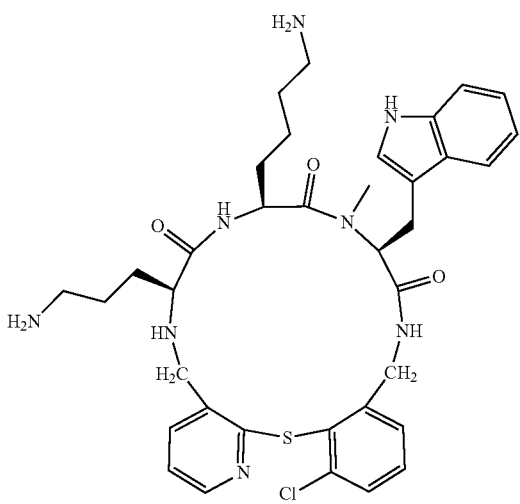 [SMILES: CN1C(=O)[C@H](CCCCN)NC(=O)[C@H](CCCN)NCc2cccnc2Sc2c(Cl)cccc2CNC(=O)[C@@H]1Cc1c[nH]c2ccccc12]

Example 28 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 54
MS (M+H)+: expected 704.3; observed 705.4

Example 29

(12S,15S,18S)-15-(4-Amino-butyl)-18-(3-amino-propyl)-4,7-difluoro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

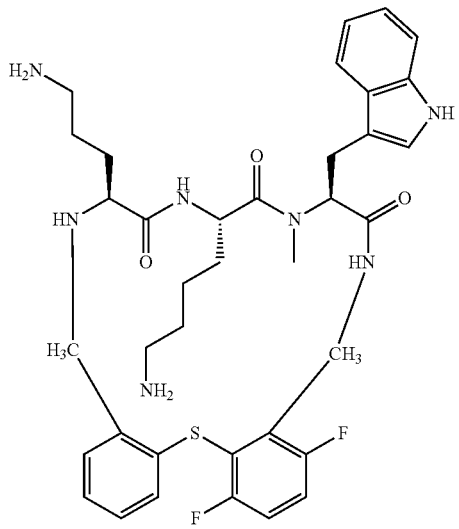 [SMILES: CN1C(=O)[C@H](CCCCN)NC(=O)[C@H](CCCN)NCc2ccccc2Sc2c(F)ccc(F)c2CNC(=O)[C@@H]1Cc1c[nH]c2ccccc12]

Example 29 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 17
MS (M+H)+: expected 705.3; observed 706.3

Example 30

(12S,15S,18S)-15-(4-Amino-butyl)-18-(3-amino-propyl)-4-fluoro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

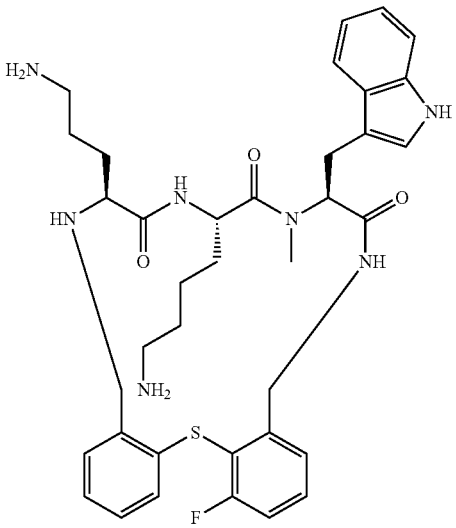 [SMILES: CN1C(=O)[C@H](CCCCN)NC(=O)[C@H](CCCN)NCc2ccccc2Sc2c(F)cccc2CNC(=O)[C@@H]1Cc1c[nH]c2ccccc12]

Example 30 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 19
MS (M+H)+: expected 687.3; observed 688.3

Example 31

(12S,15S,18S)-15-(4-Amino-butyl)-18-(3-amino-propyl)-6-chloro-12-(1H-indol-3-ylmethyl)-13-methyl-4-trifluoromethyl-2-thia-10,13,16,19-tetraaza-tricyclo[19.4.0.0*3,8*]pentacosa-1(25),3,5,7,21,23-hexaene-11,14,17-trione

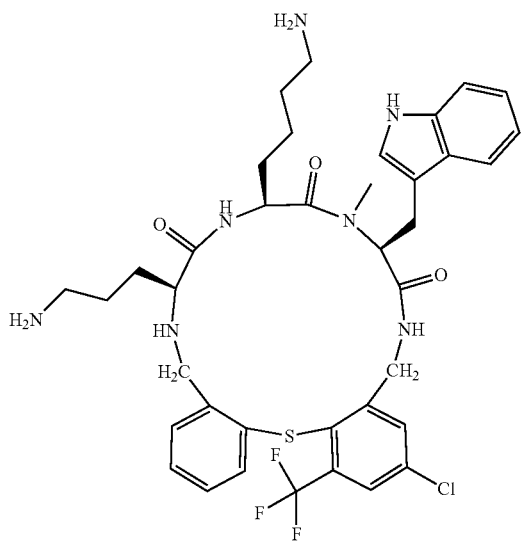 [SMILES: CN1C(=O)[C@H](CCCCN)NC(=O)[C@H](CCCN)NCc2ccccc2Sc2c(cc(Cl)cc2C(F)(F)F)CNC(=O)[C@@H]1Cc1c[nH]c2ccccc12]

Example 31 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 20
MS (M+H)$^+$: expected 771.3; observed 772.3

Example 32

(12S,15S,18S)-15-(4-Amino-butyl)-18-(3-amino-propyl)-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

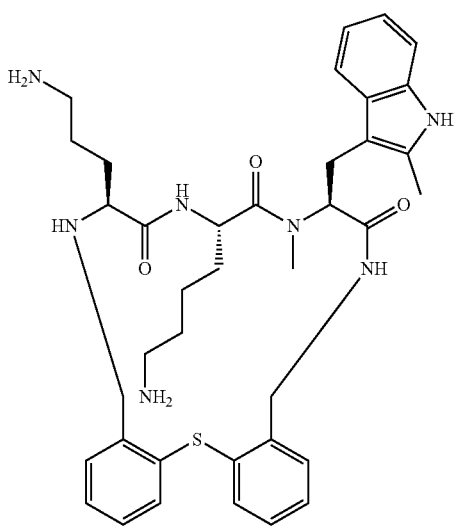 [SMILES: Cc1[nH]c2ccccc2c1C[C@H]1C(=O)NCc2ccccc2Sc2ccccc2CN[C@@H](CCCN)C(=O)N[C@@H](CCCCN)C(=O)N1C]

Example 32 was prepared according to the General Procedure for Peptide Macrocycle Synthesis using the following starting materials:
Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.
Tether: Intermediate 4
MS (M+H)$^+$: expected 683.4; observed 684.4

Example 33

(11S,14S,17S)-14-(4-Amino-butyl)-11-(3-amino-propyl)-23-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

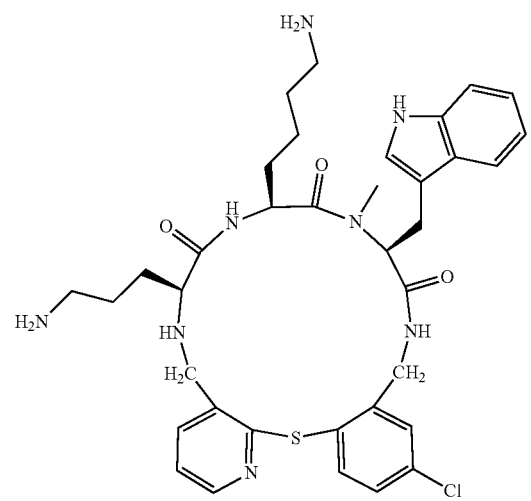 [SMILES: CN1C(=O)[C@H](CCCCN)NC(=O)[C@H](CCCN)NCc2cccnc2Sc2ccc(Cl)cc2CNC(=O)[C@@H]1Cc1c[nH]c2ccccc12]

Example 33 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 24
MS (M+H)$^+$: expected 704.3; observed 705.3

Example 34

(11S,14S,17S)-14-(4-Amino-butyl)-11-(3-amino-propyl)-22-chloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

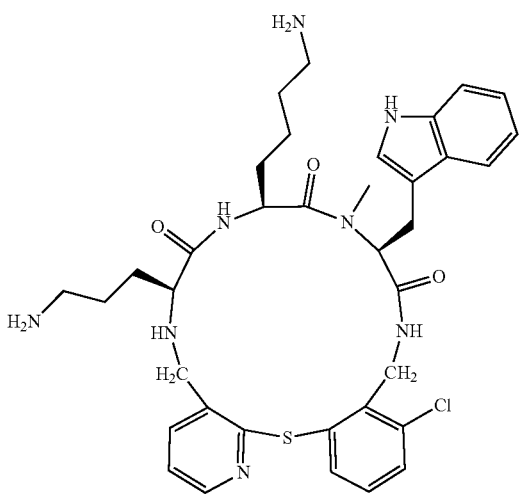 [SMILES: CN1C(=O)[C@H](CCCCN)NC(=O)[C@H](CCCN)NCc2cccnc2Sc2cccc(Cl)c2CNC(=O)[C@@H]1Cc1c[nH]c2ccccc12]

Example 34 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 25

MS (M+H)$^+$: expected 704.3; observed 705.4

Example 35

(12S,15S,18S)-15-(4-Amino-butyl)-18-(3-amino-propyl)-22-fluoro-12-(1H-indol-3-ylmethyl)-13-methyl-2-thia-10,13,16,19-tetraaza-tricyclo[19.4.0.0*3,8*]pentacosa-1(21),3,5,7,22,24-hexaene-11,14,17-trione

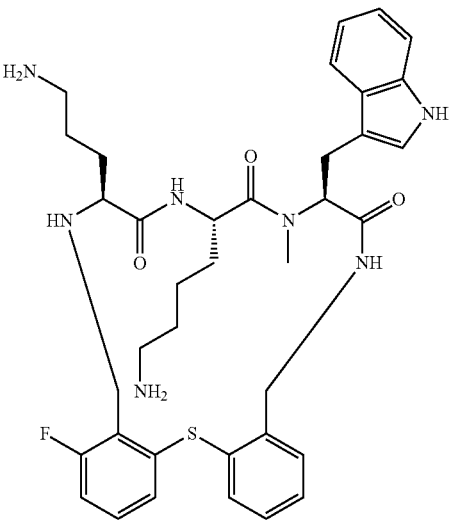 [SMILES: CN1C(=O)[C@H](CCCCN)NC(=O)[C@H](CCCN)NCc2c(F)cccc2Sc2ccccc2CNC(=O)[C@@H]1Cc1c[nH]c2ccccc12]

Example 35 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 53

MS (M+H)+: expected 687.3; observed 688.3

Example 36

(11S,14S,17S)-14-(4-Amino-butyl)-11-(3-amino-propyl)-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione

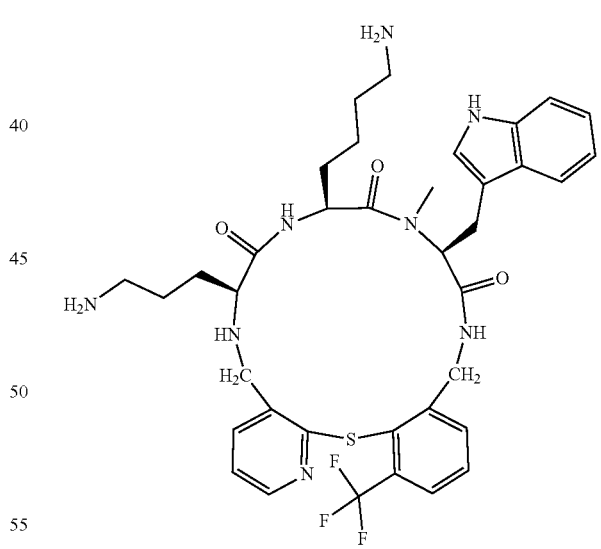

Example 36 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 23

MS (M+H)$^+$: expected 738.3; observed 739.2

Example 37

(11S,14S,17S)-14-(4-Amino-butyl)-11-(3-amino-propyl)-22,23-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

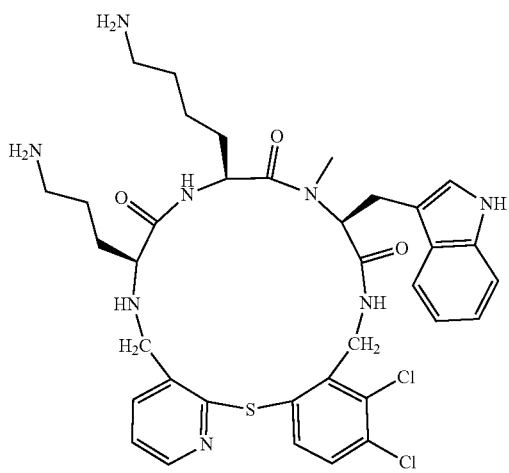

Example 37 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 29
MS (M+H)+: expected 738.3; observed 739.2

Example 38

(11S,14S,17S)-14-(4-Amino-butyl)-11-(3-amino-propyl)-22,25-dichloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

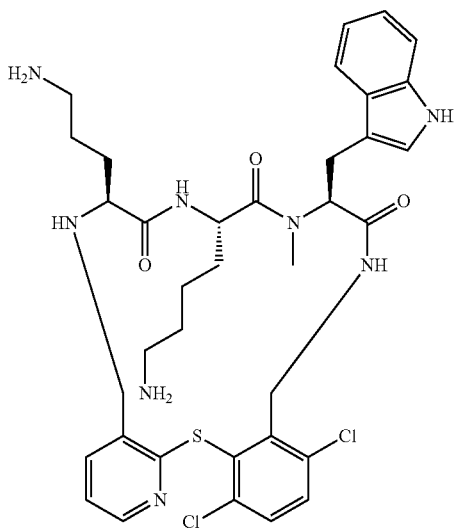 [SMILES: CN1C(=O)[C@H](CCCCN)NC(=O)[C@H](CCCN)NCc2cccnc2Sc2c(Cl)ccc(Cl)c2CNC(=O)[C@@H]1Cc1c[nH]c2ccccc12]

Example 38 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 30
MS (M+H)+: expected 738.3; observed 739.3

Example 39

(11S,14S,17S)-14-(4-Amino-butyl)-11-(3-amino-propyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

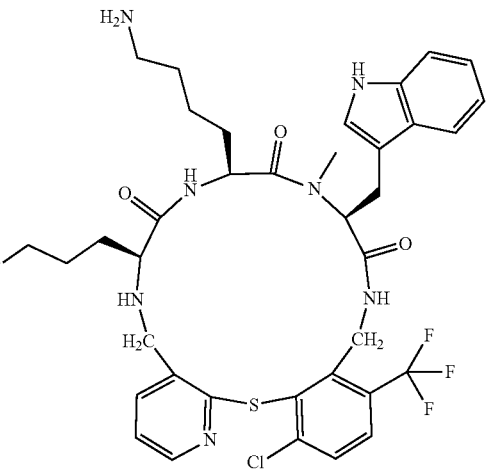

Example 39 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 31
MS (M+H)+: expected 772.3; observed 9773.2

Example 40

(11S,14S,17S)-14-(4-Amino-butyl)-11-(3-amino-propyl)-22,25-difluoro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

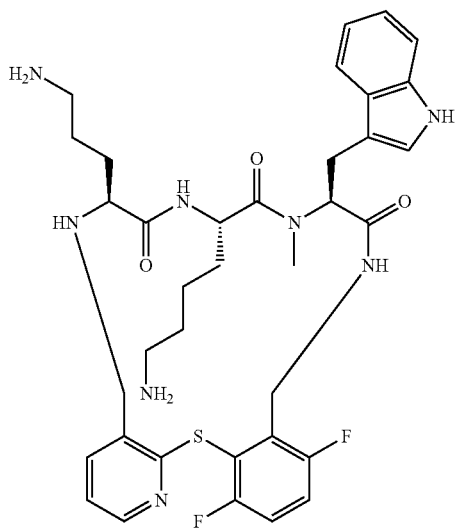 [SMILES: CN1C(=O)[C@H](CCCCN)NC(=O)[C@H](CCCN)NCc2cccnc2Sc2c(F)ccc(F)c2CNC(=O)[C@@H]1Cc1c[nH]c2ccccc12]

Example 40 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 32
MS (M+H)$^+$: expected 706.3; observed 707.3

Example 41

(12S,15S,18S)-15-(4-Amino-butyl)-18-(3-amino-propyl)-4-chloro-12-(1H-indol-3-ylmethyl)-6,13-dimethyl-2-thia-10,13,16,19-tetraaza-tricyclo[19.4.0.0*3,8*]pentacosa-1(25),3,5,7,21,23-hexaene-11,14,17-trione

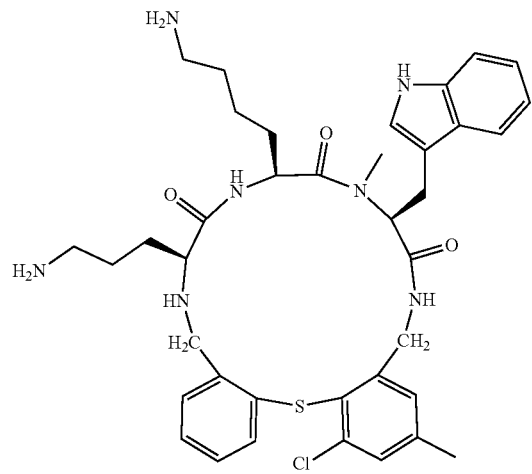 [SMILES: Cc1cc(Cl)c2c(c1)CNC(=O)[C@H](Cc1c[nH]c3ccccc13)N(C)C(=O)[C@H](CCCCN)NC(=O)[C@H](CCCN)NCc1ccccc1S2]

Example 41 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 36
MS (M+H)$^+$: expected 717.3; observed 718.3

Example 42

(12S,15S,18S)-15-(4-Amino-butyl)-18-(3-amino-propyl)-4,6-dichloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione Example 42 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 37
MS (M+H)+: expected 737.3; observed 738.3

Example 43

(12S,15S,18S)-15-(4-Amino-butyl)-18-(3-amino-propyl)-6-chloro-13-ethyl-12-(1H-indol-3-ylmethyl)-2-thia-10,13,16,19-tetraaza-tricyclo[19.4.0.0*3,8*]pentacosa-1(21),3,5,7,22,24-hexaene-11,14,17-trione

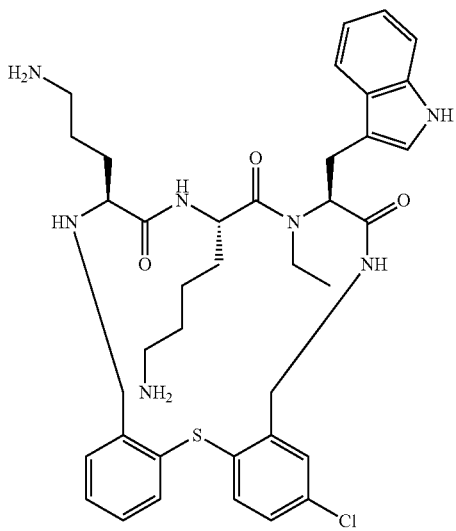 [SMILES: CCN1C(=O)[C@H](CCCCN)NC(=O)[C@H](CCCN)NCc2ccccc2Sc2ccc(Cl)cc2CNC(=O)[C@@H]1Cc1c[nH]c2ccccc12]

Example 43 was prepared according to the General Procedure for Peptide Macrocycle Synthesis using the following starting materials:

Amino acids:
1. Fmoc-NEt-L-Trp(BOC)—OH (Intermediate 55),
2. Fmoc-L-Lys(BOC)—OH,
3. Fmoc-L-Orn(BOC)—OH.

Tether: Intermediate 3

MS (M+H)$^+$: expected 717.3; observed 718.3

Example 44

(12S,15S,18S)-15-(4-Amino-butyl)-18-(3-amino-propyl)-13-ethyl-12-(1H-indol-3-ylmethyl)-6-methoxy-2-thia-10,13,16,19-tetraaza-tricyclo[19.4.0.0*3,8*]pentacosa-1(21),3,5,7,22,24-hexaene-11,14,17-trione

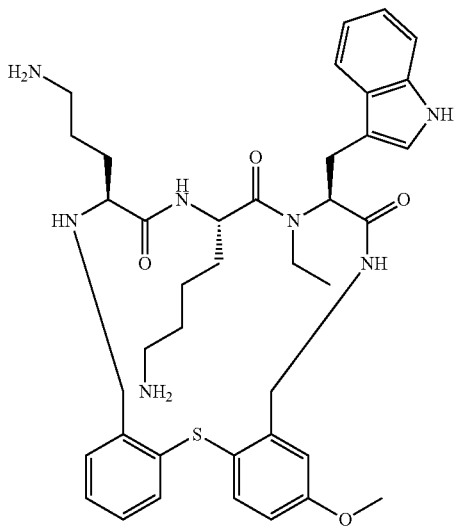 [SMILES: CCN1C(=O)[C@H](CCCCN)NC(=O)[C@H](CCCN)NCc2ccccc2Sc2ccc(OC)cc2CNC(=O)[C@@H]1Cc1c[nH]c2ccccc12]

Example 44 was prepared according to the General Procedure for Peptide Macrocycle Synthesis using the following starting materials:

Amino acids:
1. Fmoc-NEt-L-Trp(BOC)—OH (Intermediate 55),
2. Fmoc-L-Lys(BOC)—OH,
3. Fmoc-L-Orn(BOC)—OH.

Tether: Intermediate 5

MS (M+H)$^+$: expected 729.4; observed 730.4

Example 45

(12S,15S,18S)-15-(4-Amino-butyl)-18-(3-amino-propyl)-4-chloro-13-ethyl-12-(1H-indol-3-ylmethyl)-2-thia-10,13,16,19-tetraaza-tricyclo[19.4.0.0*3,8*]pentacosa-1(21),3,5,7,22,24-hexaene-11,14,17-trione

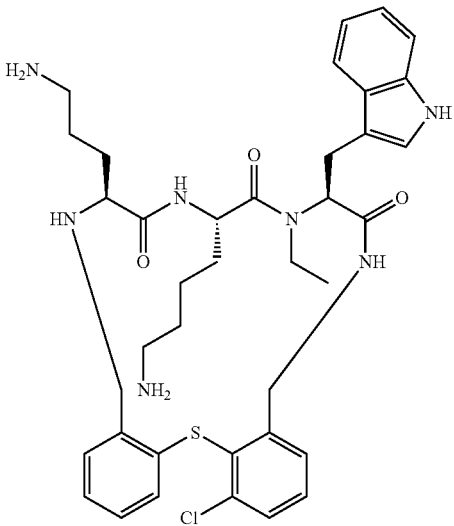 [SMILES: CCN1C(=O)[C@H](CCCCN)NC(=O)[C@H](CCCN)NCc2ccccc2Sc2c(Cl)cccc2CNC(=O)[C@@H]1Cc1c[nH]c2ccccc12]

Example 45 was prepared according to the General Procedure for Peptide Macrocycle Synthesis using the following starting materials:

Amino acids:
1. Fmoc-NEt-L-Trp(BOC)—OH (Intermediate 55),
2. Fmoc-L-Lys(BOC)—OH,
3. Fmoc-L-Orn(BOC)—OH.

Tether: Intermediate 1

MS (M+H)$^+$: expected 717.3; observed 718.3

Example 46

(12S,15S,18S)-15-(4-Amino-butyl)-18-(3-amino-propyl)-13-ethyl-12-(1H-indol-3-ylmethyl)-4-methyl-2-thia-10,13,16,19-tetraaza-tricyclo[19.4.0.0*3,8*]pentacosa-1(21),3,5,7,22,24-hexaene-11,14,17-trione

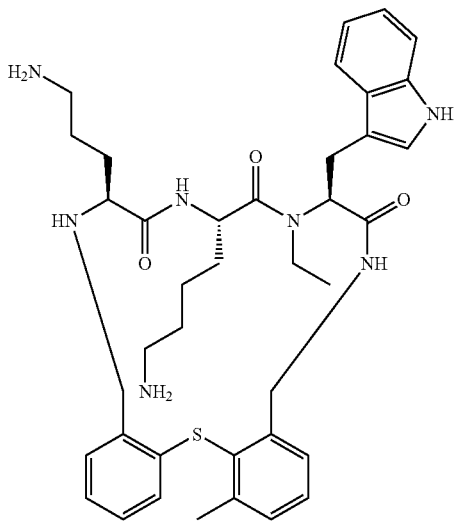 [SMILES: CCN1C(=O)[C@H](CCCCN)NC(=O)[C@H](CCCN)NCc2ccccc2Sc2c(C)cccc2CNC(=O)[C@@H]1Cc1c[nH]c2ccccc12]

Example 46 was prepared according to the General Procedure for Peptide Macrocycle Synthesis using the following starting materials:

Amino acids:
1. Fmoc-NEt-L-Trp(BOC)—OH (Intermediate 55),
2. Fmoc-L-Lys(BOC)—OH,
3. Fmoc-L-Orn(BOC)—OH.

Tether: Intermediate 6

MS (M+H)+: expected 697.4; observed 698.4

Example 47

(12S,15S,18S)-15-(4-Amino-butyl)-18-(3-amino-propyl)-6-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

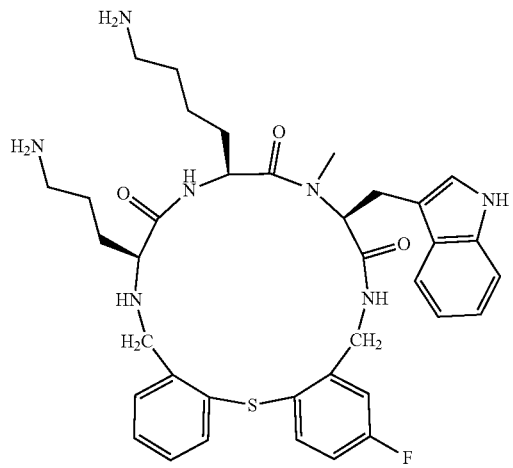 [SMILES: CN1C(=O)[C@H](CCCCN)NC(=O)[C@H](CCCN)NCc2ccccc2Sc2ccc(F)cc2CNC(=O)[C@@H]1Cc1c[nH]c2ccccc12]

Example 47 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 35

MS (M+H)+: expected 687.3; observed 688.3

Example 48

(12S,15S,18S)-15-(4-Amino-butyl)-4-chloro-12-(1H-indol-3-ylmethyl)-13-methyl-18-(4-methyl-amino-butyl)-2-thia-10,13,16,19-tetraaza-tricyclo[19.4.0.0*3,8*]pentacosa-1(21),3,5,7,22,24-hexaene-11,14,17-trione

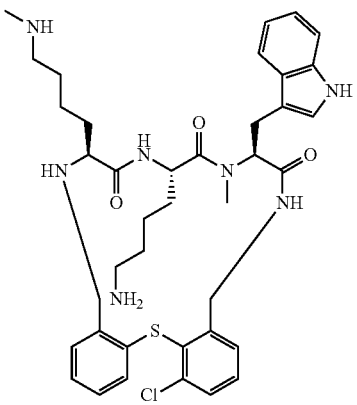 [SMILES: CNCCCC[C@@H]1NCc2ccccc2Sc2c(Cl)cccc2CNC(=O)[C@H](Cc2c[nH]c3ccccc23)N(C)C(=O)[C@H](CCCCN)NC1=O]

Example 48 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-Lys(Me,BOC)—OH.

Tether: Intermediate 1

MS (M+H)+: expected 731.4; observed 732.4

Example 49

(12S,15S,18S)-15-(4-Amino-butyl)-18-(3-amino-propyl)-4-chloro-12-(1H-indol-3-ylmethyl)-6-methoxy-13-methyl-2-thia-10,13,16,19-tetraaza-tricyclo[19.4.0.0*3,8*]pentacosa-1(25),3,5,7,21,23-hexaene-11,14,17-trione

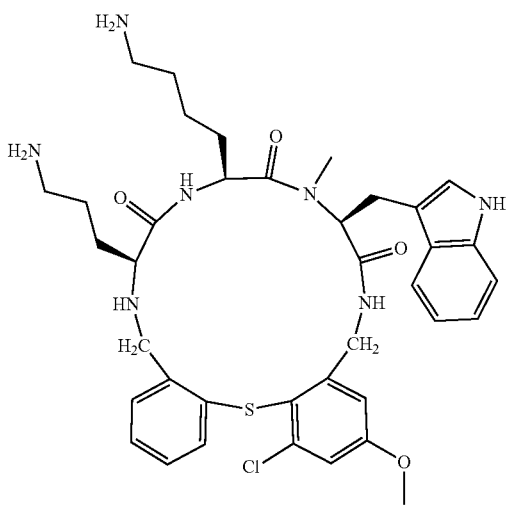 [SMILES: COc1cc(Cl)c2c(c1)CNC(=O)[C@H](Cc1c[nH]c3ccccc13)N(C)C(=O)[C@H](CCCCN)NC(=O)[C@H](CCCN)NCc1ccccc1S2]

Example 49 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 33
MS (M+H)+: expected 733.3; observed 734.3

Example 50

(12S,15S,18S)-15-(4-Amino-butyl)-18-(3-amino-propyl)-12-(1H-indol-3-ylmethyl)-6-methoxy-4,13-dimethyl-2-thia-10,13,16,19-tetraaza-tricyclo[19.4.0.0*3,8*]pentacosa-1(25),3,5,7,21,23-hexaene-11,14,17-trione

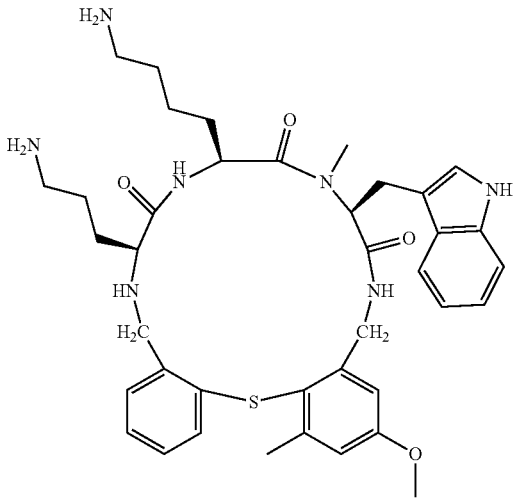 [SMILES: COc1cc(C)c2c(c1)CNC(=O)[C@H](Cc1c[nH]c3ccccc13)N(C)C(=O)[C@H](CCCCN)NC(=O)[C@H](CCCN)NCc1ccccc1S2]

Example 50 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 34
MS (M+H)+: expected 713.4; observed 714.4

Example 51

(11S,14S,17S)-14-(4-Amino-butyl)-11-(3-amino-propyl)-17-(1H-indol-3-ylmethyl)-16,25-dimethyl-2-thia-4,10,13,16,19-pentaaza-tricyclo[19.4.0.0*3,8*]pentacosa-1(25),3,5,7,21,23-hexaene-12,15,18-trione

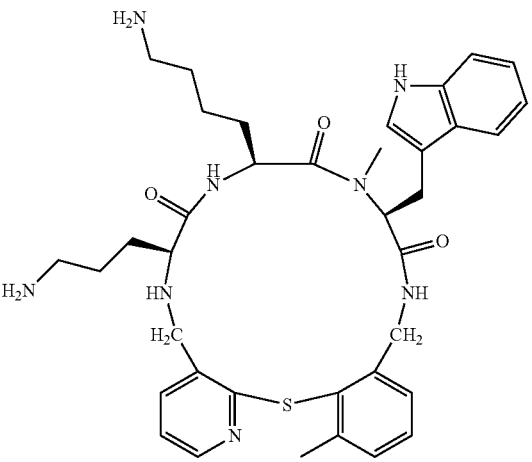 [SMILES: Cc1cccc2c1Sc1ncccc1CN[C@@H](CCCN)C(=O)N[C@@H](CCCCN)C(=O)N(C)[C@@H](Cc1c[nH]c3ccccc13)C(=O)NC2]

Example 51 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 40
MS (M+H)+: expected 684.4; observed 685.3

Example 52

(11S,14S,17S)-14-(4-Amino-butyl)-11-(3-amino-propyl)-23-chloro-22-fluoro-17-(1H-indol-3-ylmethyl)-16-methyl-2-thia-4,10,13,16,19-pentaazatricyclo[19.4.0.0*3,8*]pentacosa-1(25),3(8),4,6,21,23-hexaene-12,15,18-trione

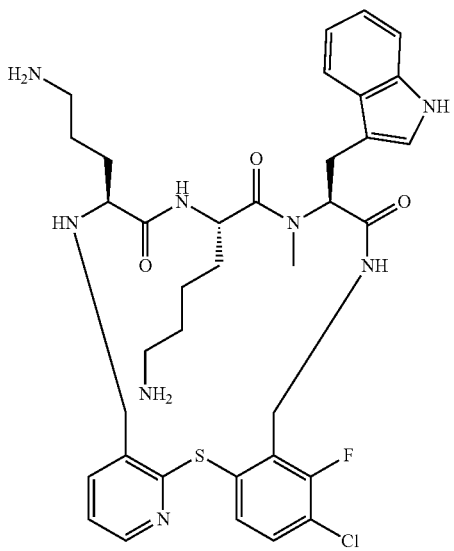 [SMILES: CN1C(=O)[C@H](CCCCN)NC(=O)[C@H](CCCN)NCc2cccnc2Sc2ccc(Cl)c(F)c2CNC(=O)[C@@H]1Cc1c[nH]c2ccccc12]

Example 52 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 28
MS (M+H)$^+$: expected 722.3; observed 723.3

Example 53

(11S,14S,17S)-14-(4-Amino-butyl)-11-(3-amino-propyl)-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

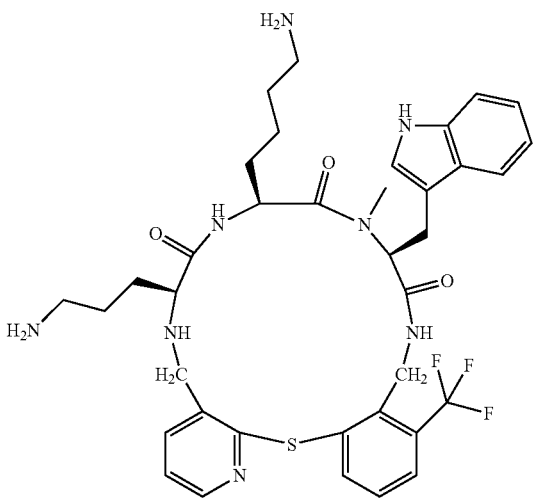 [SMILES: CN1C(=O)[C@H](CCCCN)NC(=O)[C@H](CCCN)NCc2cccnc2Sc2cccc(C(F)(F)F)c2CNC(=O)[C@@H]1Cc1c[nH]c2ccccc12]

Example 53 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 23
MS (M+H)$^+$: expected 738.3; observed 739.3

Example 54

(11S,14S,17S)-14-(4-Amino-butyl)-11-(3-amino-propyl)-25-chloro-22-fluoro-17-(1H-indol-3-ylmethyl)-16-methyl-2-thia-4,10,13,16,19-pentaazatricyclo[19.4.0.0*3,8*]pentacosa-1(25),3(8),4,6,21,23-hexaene-12,15,18-trione

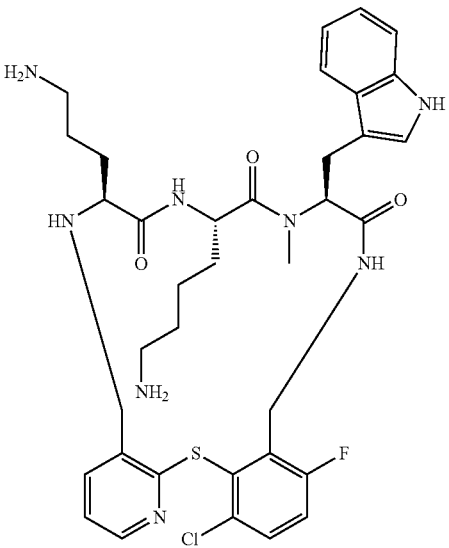 [SMILES: CN1C(=O)[C@H](CCCCN)NC(=O)[C@H](CCCN)NCc2cccnc2Sc2c(Cl)ccc(F)c2CNC(=O)[C@@H]1Cc1c[nH]c2ccccc12]

Example 54 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 27
MS (M+H)$^+$: expected 722.3; observed 723.3

Example 55

(12S,15S,18S)-15-(4-Amino-butyl)-18-(3-amino-propyl)-6-chloro-12-(1H-indol-3-ylmethyl)-4,13-dimethyl-2-thia-10,13,16,19-tetraaza-tricyclo[19.4.0.0*3,8*]pentacosa-1(25),3,5,7,21,23-hexaene-11,14,17-trione

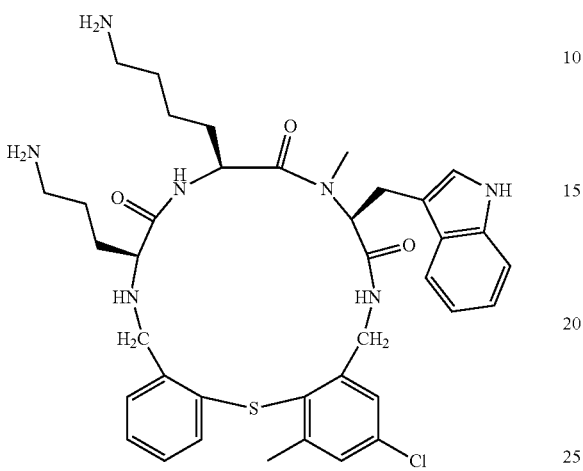

Example 55 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 38

MS (M+H)⁺: expected 717.3; observed 718.3

Example 56

(12S,15S,18S)-15-(4-Amino-butyl)-18-(3-amino-propyl)-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

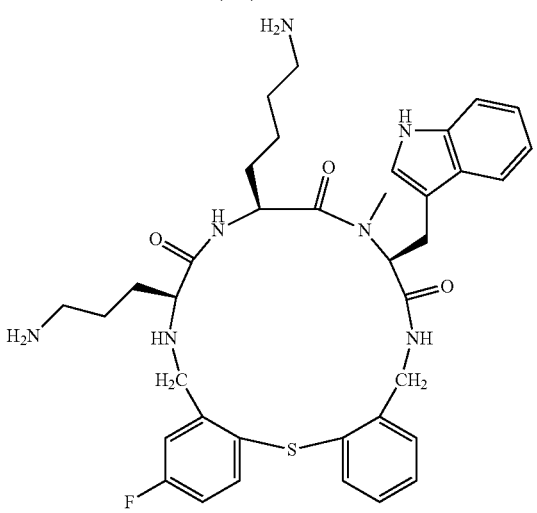

Example 56 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 39

MS (M+H)+: expected 687.3; observed 688.3

Example 57

(12S,15S,18S)-15-(4-Amino-butyl)-18-(3-amino-propyl)-6-chloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

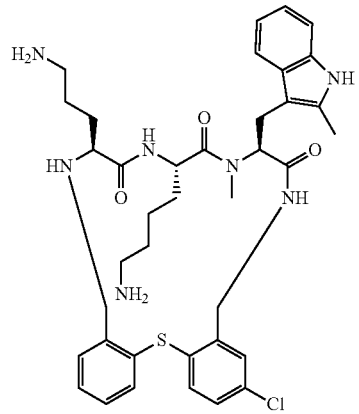 [SMILES: Cc1[nH]c2ccccc2c1C[C@H]1C(=O)NCc2cc(Cl)ccc2Sc2ccccc2CN[C@@H](CCCN)C(=O)N[C@@H](CCCCN)C(=O)N1C]

Example 57 was prepared according to the General Procedure for Peptide Macrocycle Synthesis using the following starting materials:

Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.

Tether: Intermediate 3

MS (M+H)+: expected 717.3; observed 718.3

Example 58

(12S,15S,18S)-15-(4-Amino-butyl)-18-(3-amino-propyl)-4,13-dimethyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

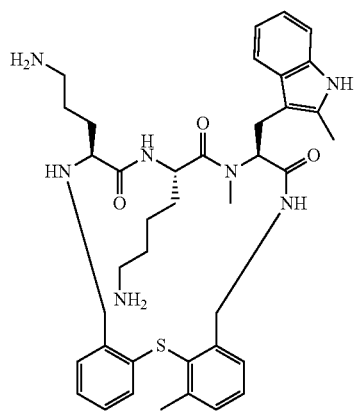 [SMILES: Cc1cccc2c1Sc1ccccc1CN[C@@H](CCCN)C(=O)N[C@@H](CCCCN)C(=O)N(C)[C@@H](Cc1c(C)[nH]c3ccccc13)C(=O)NC2]

Example 58 was prepared according to the General Procedure for Peptide Macrocycle Synthesis using the following starting materials:

Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.

Tether: Intermediate 6
MS (M+H)+: expected 697.7; observed 698.4

Example 59

(12S,15S,18S)-15-(4-Amino-butyl)-18-(3-amino-propyl)-4,6-dichloro-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

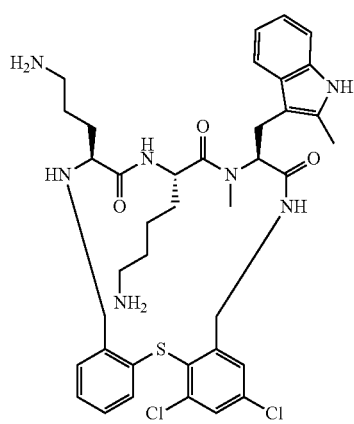 [SMILES: Cc1[nH]c2ccccc2c1C[C@H]1C(=O)NCc2cc(Cl)cc(Cl)c2Sc2ccccc2CN[C@@H](CCCN)C(=O)N[C@@H](CCCCN)C(=O)N1C]

Example 59 was prepared according to the General Procedure for Peptide Macrocycle Synthesis using the following starting materials:

Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.

Tether: Intermediate 37
MS (M+H)+: expected 751.3; observed 752.3

Example 60

(9S,12S,15S,18S)-15-(4-Amino-butyl)-18-(3-amino-propyl)-4-chloro-12-(1H-indol-3-ylmethyl)-9,13-dimethyl-2-thia-10,13,16,19-tetraaza-tricyclo[19.4.0.0*3,8*]pentacosa-1(25),3,5,7,21,23-hexaene-11,14,17-trione

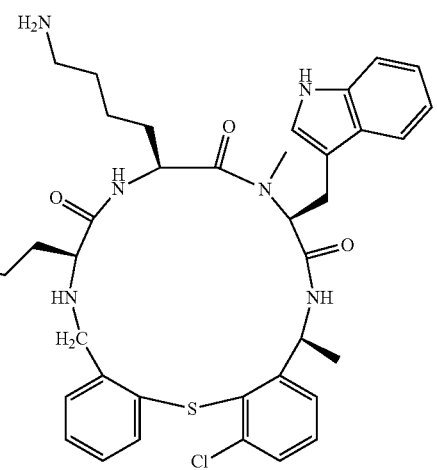

Example 60 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 41
MS (M+H)+: expected 717.3; observed 718.3

Example 61

(11S,14S,17S)-14-(4-Amino-butyl)-11-(3-amino-propyl)-17-(1H-indol-3-ylmethyl)-23-methoxy-16-methyl-2-thia-4,10,13,16,19-pentaaza-tricyclo[19.4.0.0*3,8*]pentacosa-1(25),3,5,7,21,23-hexaene-12,15,18-trione

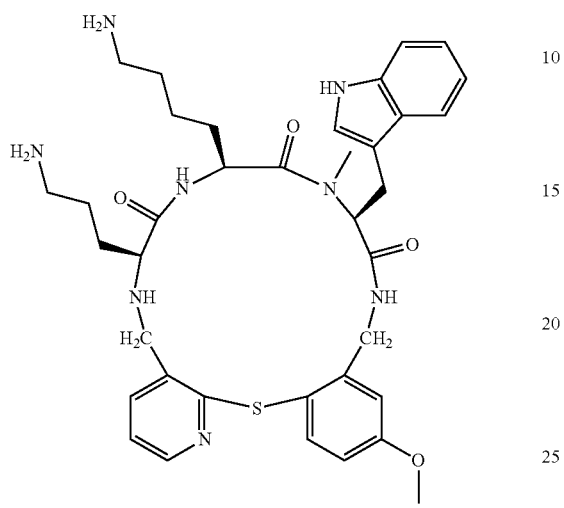

Example 61 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 43
MS (M+H)⁺: expected 700.3; observed 701.6

Example 62

(11S,14S,17S)-14-(4-Amino-butyl)-11-(3-amino-propyl)-25-chloro-17-(1H-indol-3-ylmethyl)-16-methyl-23-trifluoromethyl-2-thia-4,10,13,16,19-pentaaza-tricyclo[19.4.0.0*3,8*]pentacosa-1(25),3,5,7,21,23-hexaene-12,15,18-trione

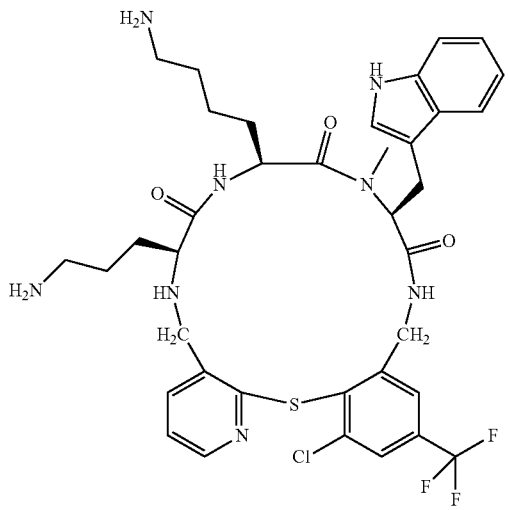 [SMILES: CN1C(=O)[C@H](CCCCN)NC(=O)[C@H](CCCN)NCc2cccnc2Sc2c(Cl)cc(C(F)(F)F)cc2CNC(=O)[C@@H]1Cc1c[nH]c2ccccc12]

Example 62 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 45
MS (M+H)⁺: expected 772.3; observed 773.3

Example 63

(12S,15S,18S)-15-(4-Amino-butyl)-18-(3-amino-propyl)-12-(1H-indol-3-ylmethyl)-13-methyl-2-thia-5,10,13,16,19-pentaaza-tricyclo[19.4.0.0*3,8*]pentacosa-1(25),3,5,7,21,23-hexaene-11,14,17-trione

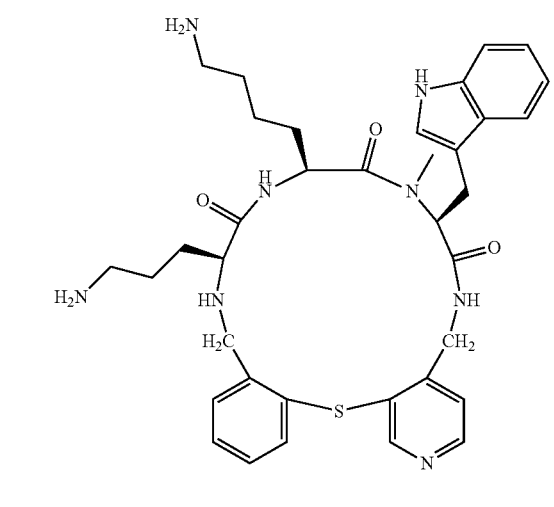 [SMILES: CN1C(=O)[C@H](CCCCN)NC(=O)[C@H](CCCN)NCc2ccccc2Sc2cnccc2CNC(=O)[C@@H]1Cc1c[nH]c2ccccc12]

Example 63 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 46
MS (M+H)⁺: expected 670.3; observed 671.3

Example 64

(12S,15S,18S)-15-(4-Amino-butyl)-18-(3-amino-propyl)-4-chloro-23-fluoro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

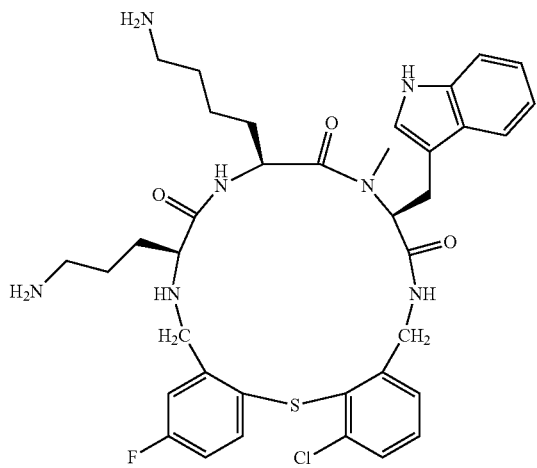 [SMILES: CN1C(=O)[C@H](CCCCN)NC(=O)[C@H](CCCN)NCc2cc(F)ccc2Sc2c(Cl)cccc2CNC(=O)[C@@H]1Cc1c[nH]c2ccccc12]

Example 64 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 42
MS (M+H)+: expected 721.3; observed 772.3

Example 65

(12S,15S,18S)-15-(4-Amino-butyl)-18-(3-amino-propyl)-23-fluoro-12-(1H-indol-3-ylmethyl)-4,13-dimethyl-2-thia-10,13,16,19-tetraaza-tricyclo[19.4.0.0*3,8*]pentacosa-1(25),3,5,7,21,23-hexaene-11,14,17-trione

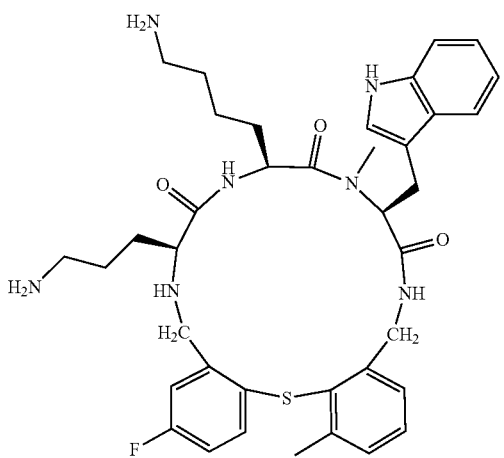 [SMILES: Cc1cccc2c1Sc1ccc(F)cc1CN[C@@H](CCCN)C(=O)N[C@@H](CCCCN)C(=O)N(C)[C@@H](Cc1c[nH]c3ccccc13)C(=O)NC2]

Example 65 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 44
MS (M+H)+: expected 701.3; observed 702.6

Example 66

(12S,15S,18S)-15-(4-Amino-butyl)-18-(3-amino-propyl)-6-ethyl-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

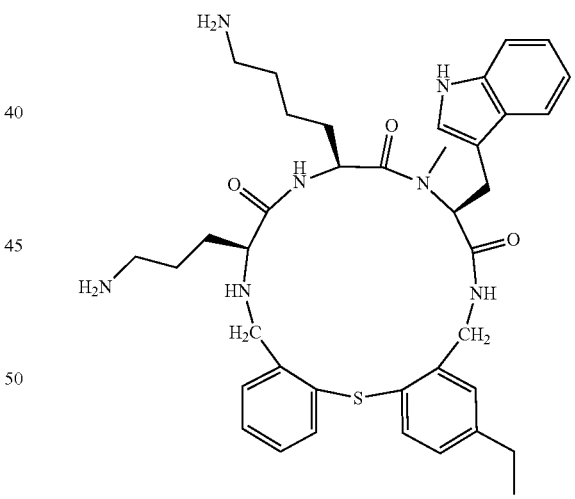

Example 66 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 49
MS (M+H)+: expected 997.4; observed 998.4

Example 67

(11S,14S,17S)-14-(4-Amino-butyl)-11-(3-amino-propyl)-23,25-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

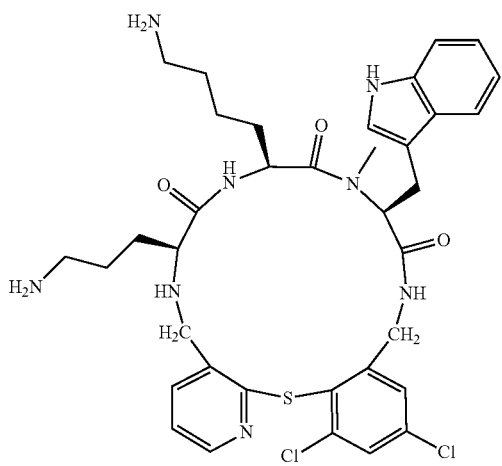 [SMILES: CN1C(=O)[C@H](CCCCN)NC(=O)[C@H](CCCN)NCc2cccnc2Sc2c(Cl)cc(Cl)cc2CNC(=O)[C@@H]1Cc1c[nH]c2ccccc12]

Example 67 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 47

MS (M+H)+: expected 738.3; observed 739.3

Example 68

(11S,14S,17S)-14-(4-Amino-butyl)-11-(3-amino-propyl)-22-chloro-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione

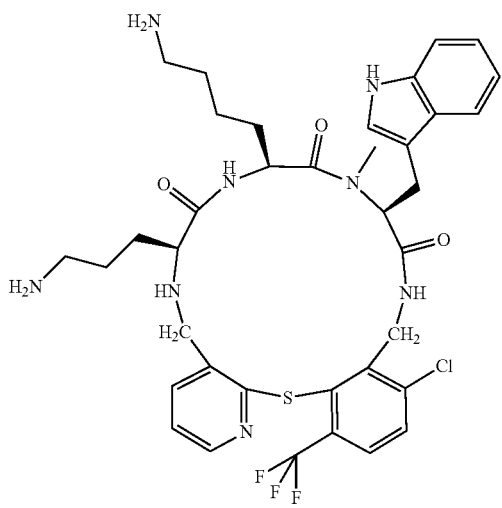 [SMILES: CN1C(=O)[C@H](CCCCN)NC(=O)[C@H](CCCN)NCc2cccnc2Sc2c(C(F)(F)F)ccc(Cl)c2CNC(=O)[C@@H]1Cc1c[nH]c2ccccc12]

Example 68 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 48

MS (M+H)+: expected 772.3; observed 773.3

Example 69

(12S,15S,18S)-15-(4-Amino-butyl)-18-(3-amino-propyl)-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione

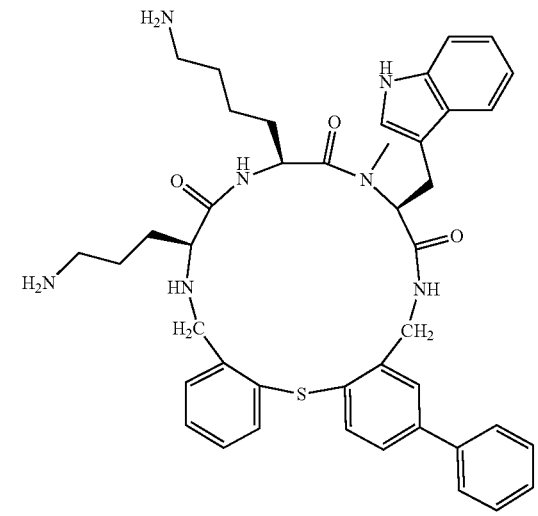 [SMILES: CN1C(=O)[C@H](CCCCN)NC(=O)[C@H](CCCN)NCc2ccccc2Sc2ccc(-c3ccccc3)cc2CNC(=O)[C@@H]1Cc1c[nH]c2ccccc12]

Example 69 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 50

MS (M+H)+: expected 745.4; observed 746.4

Example 70

(12S,15S,18S)-15-(4-Amino-butyl)-18-(3-amino-propyl)-6-tert-butyl-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

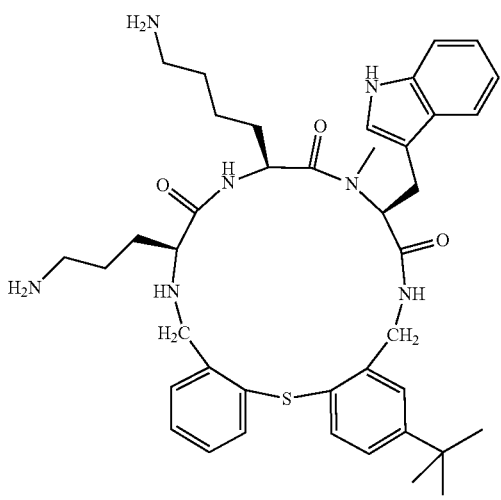 [SMILES: CN1C(=O)[C@H](CCCCN)NC(=O)[C@H](CCCN)NCc2ccccc2Sc2ccc(C(C)(C)C)cc2CNC(=O)[C@@H]1Cc1c[nH]c2ccccc12]

Example 70 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 51
MS (M+H)⁺: expected 725.4; observed 726.4

Example 71

(12S,15S,18S)-15-(4-Amino-butyl)-18-(3-amino-propyl)-6-methoxy-13-methyl-12-(2-methyl-1H-indol-3-ylmethyl)-2-thia-10,13,16,19-tetraaza-tricyclo[19.4.0.0*3,8*]pentacosa-1(21),3,5,7,22,24-hexaene-11,14,17-trione

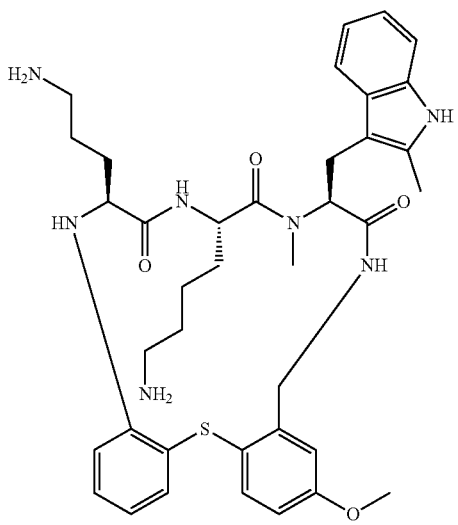 [SMILES: COc1ccc2c(c1)CNC(=O)[C@H](Cc1c(C)[nH]c3ccccc13)N(C)C(=O)[C@H](CCCCN)NC(=O)[C@H](CCCN)Nc1ccccc1S2]

Example 71 was prepared according to the General Procedure for Peptide Macrocycle Synthesis using the following starting materials:
Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.
Tether: Intermediate 5
MS (M+H)⁺: expected 713.9; observed 714.4

Example 72

(12S,15S,18S)-15-(4-Amino-butyl)-18-(3-amino-propyl)-12-(1H-indol-3-ylmethyl)-6-isopropyl-13-methyl-2-thia-10,13,16,19-tetraaza-tricyclo[19.4.0.0*3,8*]pentacosa-1(25),3,5,7,21,23-hexaene-11,14,17-trione

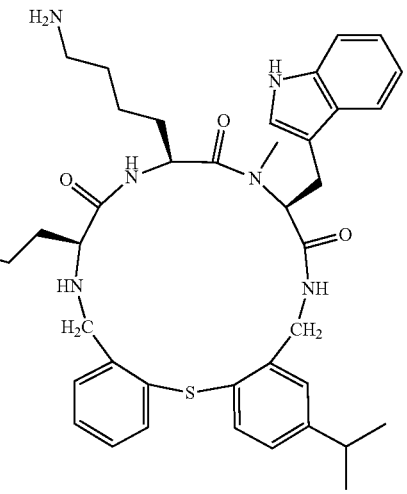

Example 72 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 52
MS (M+H)+: expected 711.4; observed 712.4

Example 73

(11S,14S,17S)-14-(4-Amino-butyl)-11-(3-amino-propyl)-25-chloro-22-fluoro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

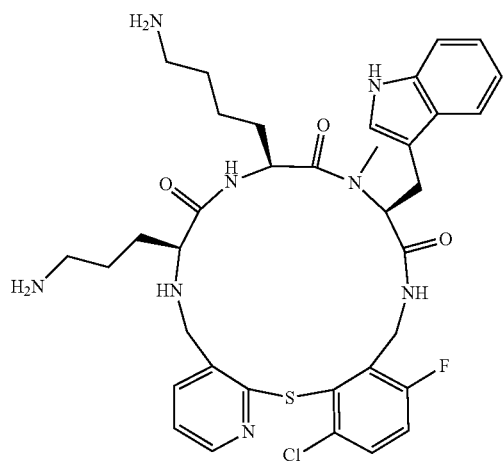 [SMILES: CN1C(=O)[C@H](CCCCN)NC(=O)[C@H](CCCN)NCc2cccnc2Sc2c(Cl)ccc(F)c2CNC(=O)[C@@H]1Cc1c[nH]c2ccccc12]

Example 73 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 27
MS (M+H)$^+$: expected 722.3; observed 723.3

Example 74

(11S,14S,17S)-14-(4-Amino-butyl)-11-(3-amino-propyl)-25-chloro-16-methyl-17-(2-methyl-1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione

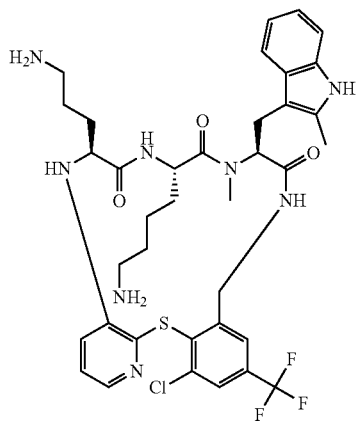 [SMILES: Cc1[nH]c2ccccc2c1C[C@H]1C(=O)NCc2cc(C(F)(F)F)cc(Cl)c2Sc2ncccc2N[C@@H](CCCN)C(=O)N[C@@H](CCCCN)C(=O)N1C]

Example 74 was prepared according to the General Procedure for Peptide Macrocycle Synthesis using the following starting materials:
Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.
Tether: Intermediate 45
MS (M+H)$^+$: expected 786.6; observed 787.3

Example 75

(11S,14S,17S)-14-(4-Amino-butyl)-11-(3-amino-propyl)-25-chloro-16-methyl-17-(2-methyl-1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione

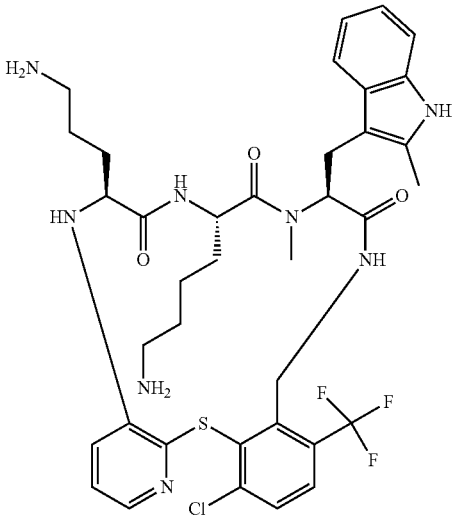 [SMILES: Cc1[nH]c2ccccc2c1C[C@H]1C(=O)NCc2c(C(F)(F)F)ccc(Cl)c2Sc2ncccc2N[C@@H](CCCN)C(=O)N[C@@H](CCCCN)C(=O)N1C]

Example 75 was prepared according to the General Procedure for Peptide Macrocycle Synthesis using the following starting materials:
Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.
Tether: Intermediate 31
MS (M+H)+: expected 786.3; observed 787.3

Example 76

(11S,14S,17S)-14-(4-Amino-butyl)-11-(3-amino-propyl)-23,25-dichloro-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

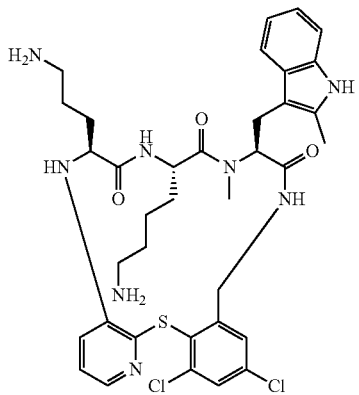 [SMILES: Cc1[nH]c2ccccc2c1C[C@H]1C(=O)NCc2cc(Cl)cc(Cl)c2Sc2ncccc2N[C@@H](CCCN)C(=O)N[C@@H](CCCCN)C(=O)N1C]

Example 76 was prepared according to the General Procedure for Peptide Macrocycle Synthesis using the following starting materials:
Amino acids:
1. Fmoc-2-Methyl-L-Trp-OH, followed by on-bead N-methylation of the Trp alpha-N,
2. Fmoc-L-Lys(BOC)—OH,
3. Fmoc-L-Orn(BOC)—OH.
Tether: Intermediate 47
MS (M+H)+: expected 752.3; observed 753.3

Example 77

(11S,14S,17S)-14-(4-Amino-butyl)-11-(3-amino-propyl)-25-chloro-16-ethyl-17-(1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione

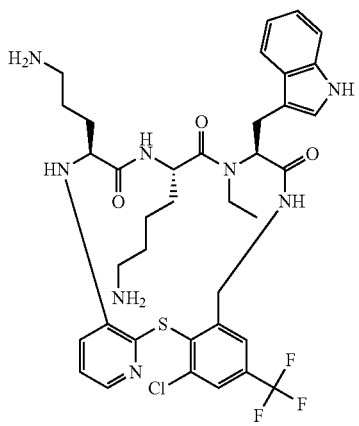 [SMILES: CCN1C(=O)[C@H](CCCCN)NC(=O)[C@H](CCCN)Nc2cccnc2Sc2c(Cl)cc(C(F)(F)F)cc2CNC(=O)[C@@H]1Cc1c[nH]c2ccccc12]

Example 77 was prepared according to the General Procedure for Peptide Macrocycle Synthesis using the following starting materials:
Amino acids:
1. Fmoc-NEt-L-Trp(BOC)—OH (Intermediate 55),
2. Fmoc-L-Lys(BOC)—OH,
3. Fmoc-L-Orn(BOC)—OH.
Tether: Intermediate 45
MS (M+H)+: expected 786.3; observed 787.4

Example 78

(11S,14S,17S)-14-(4-Amino-butyl)-11-(3-amino-propyl)-22,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

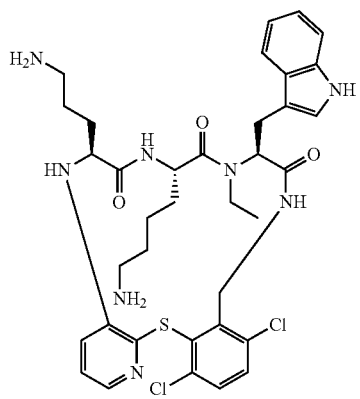 [SMILES: CCN1C(=O)[C@H](CCCCN)NC(=O)[C@H](CCCN)Nc2cccnc2Sc2c(Cl)ccc(Cl)c2CNC(=O)[C@@H]1Cc1c[nH]c2ccccc12]

Example 78 was prepared according to the General Procedure for Peptide Macrocycle Synthesis using the following starting materials:
Amino acids:
1. Fmoc-NEt-L-Trp(BOC)—OH (Intermediate 55),
2. Fmoc-L-Lys(BOC)—OH,
3. Fmoc-L-Orn(BOC)—OH.
Tether: Intermediate 30
MS (M+H)+: expected 752.3; observed 753.3

Example 79

(11S,14S,17S)-14-(4-Amino-butyl)-11-(3-amino-propyl)-25-chloro-16-ethyl-17-(1H-indol-3-ylmethyl)-22-trifluoromethyl-2-thia-4,10,13,16,19-pentaaza-tricyclo[19.4.0.0*3,8*]pentacosa-1(25),3(8),4,6,21,23-hexaene-12,15,18-trione

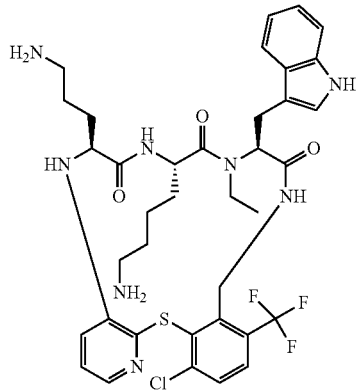 [SMILES: CCN1C(=O)[C@H](CCCCN)NC(=O)[C@H](CCCN)Nc2cccnc2Sc2c(Cl)ccc(C(F)(F)F)c2CNC(=O)[C@@H]1Cc1c[nH]c2ccccc12]

Example 79 was prepared according to the General Procedure for Peptide Macrocycle Synthesis using the following starting materials:

Amino acids:
1. Fmoc-NEt-L-Trp(BOC)—OH (Intermediate 55),
2. Fmoc-L-Lys(BOC)—OH,
3. Fmoc-L-Orn(BOC)—OH.

Tether: Intermediate 31

MS (M+H)$^+$: expected 786.3; observed 787.3

Example 80

(11S,14S,17S)-14-(4-Amino-butyl)-11-(3-amino-propyl)-23,25-dichloro-16-ethyl-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

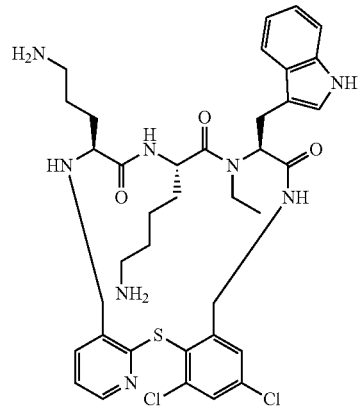 [SMILES: CCN1C(=O)[C@H](CCCCN)NC(=O)[C@H](CCCN)NCc2cccnc2Sc2c(Cl)cc(Cl)cc2CNC(=O)[C@@H]1Cc1c[nH]c2ccccc12]

Example 80 was prepared according to the General Procedure for Peptide Macrocycle Synthesis using the following starting materials:

Amino acids:
1. Fmoc-NEt-L-Trp(BOC)—OH (Intermediate 55),
2. Fmoc-L-Lys(BOC)—OH,
3. Fmoc-L-Orn(BOC)—OH.

Tether: Intermediate 47

MS (M+H)$^+$: expected 752.3; observed 753.3

Example 81

(11S,14S,17S)-14-(4-Amino-butyl)-11-(3-amino-propyl)-23,25-dichloro-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione Example 81 was prepared according to the General Procedure for Peptide Macrocycle Synthesis using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 47

MS (M+H)$^+$: expected 724.2; observed 725.2

Example 82

(11S,14S,17S)-14-(4-Amino-butyl)-11-(3-amino-propyl)-22,25-dichloro-17-(1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

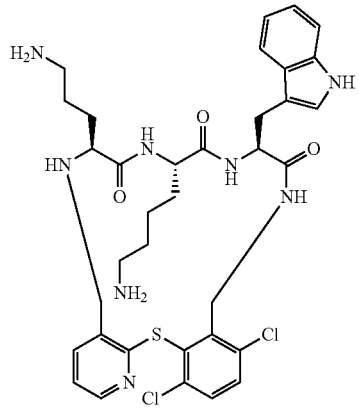 [SMILES: NCCCC[C@@H]1NC(=O)[C@H](CCCN)NCc2cccnc2Sc2c(Cl)ccc(Cl)c2CNC(=O)[C@H](Cc2c[nH]c3ccccc23)NC1=O]

Example 82 was prepared according to the General Procedure for Peptide Macrocycle Synthesis using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 30
MS (M+H)+: expected 724.2; observed 725.2

Example 83

(11S,14S,17S)-14-(4-Amino-butyl)-11-(3-amino-propyl)-25-chloro-16-ethyl-17-(1H-indol-3-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione

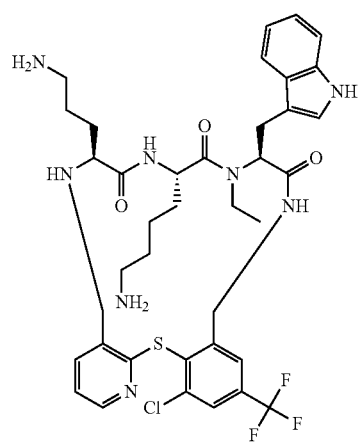 [SMILES: CCN1C(=O)[C@H](CCCCN)NC(=O)[C@H](CCCN)NCc2cccnc2Sc2c(Cl)cc(C(F)(F)F)cc2CNC(=O)[C@@H]1Cc1c[nH]c2ccccc12]

Example 83 was prepared according to the General Procedure for Peptide Macrocycle Synthesis using the following starting materials:

Amino acids:
1. Fmoc-NEt-L-Trp(BOC)—OH (intermediate 55),
2. Fmoc-L-Lys(BOC)—OH,
3. Fmoc-L-Orn(BOC)—OH.

Tether: Intermediate 45
MS (M+H+): expected 796.3; observed 787.3

Example 84

(11S,14S,17S)-14-(4-Amino-butyl)-11-(3-amino-propyl)-23-bromo-16-ethyl-17-(1H-indol-3-ylmethyl)-25-methyl-2-thia-4,10,13,16,19-pentaaza-tricyclo[19.4.0.0*3,8*]pentacosa-1(25),3(8),4,6,21,23-hexaene-12,15,18-trione

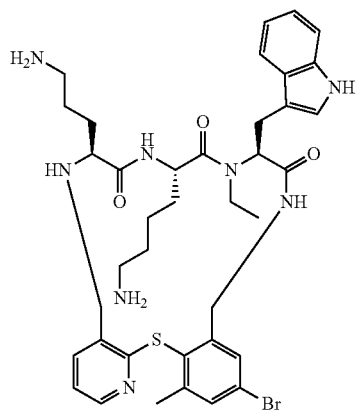 [SMILES: CCN1C(=O)[C@H](CCCCN)NC(=O)[C@H](CCCN)NCc2cccnc2Sc2c(C)cc(Br)cc2CNC(=O)[C@@H]1Cc1c[nH]c2ccccc12]

Example 84 was prepared according to the General Procedure for Peptide Macrocycle Synthesis using the following starting materials:

Amino acids:
1. Fmoc-NEt-L-Trp(BOC)—OH (intermediate 55),
2. Fmoc-L-Lys(BOC)—OH,
3. Fmoc-L-Orn(BOC)—OH.

Tether: Intermediate 56
MS (M+H+): expected 776.8; observed 777.3

Example 85

(11S,14S,17S)-14-(4-Amino-butyl)-25-chloro-17-(1H-indol-3-ylmethyl)-16-methyl-11-(3-methyl-3H-imidazol-4-ylmethyl)-23-trifluoromethyl-2-thia-4,10,13,16,19-pentaaza-tricyclo[19.4.0.0*3,8*]pentacosa-1(25),3(8),4,6,21,23-hexaene-12,15,18-trione

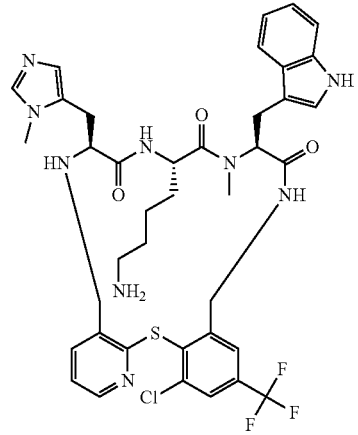 [SMILES: CN1C(=O)[C@H](CCCCN)NC(=O)[C@H](Cc2cncn2C)NCc2cccnc2Sc2c(Cl)cc(C(F)(F)F)cc2CNC(=O)[C@@H]1Cc1c[nH]c2ccccc12]

Example 85

Example 85 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. (S)-2-(9H-Fluoren-9-ylmethoxycarbonylamino)-3-(3-methyl-3H-imidazol-4-yl)-propionic acid.

Tether: Intermediate 45
MS (M+H$^+$): expected 809.3; observed 810.3

Example 86

(11S,14S,17S)-14-(4-Amino-butyl)-25-chloro-17-(1H-indol-3-ylmethyl)-16-methyl-11-pyridin-3-ylmethyl-23-trifluoromethyl-2-thia-4,10,13,16,19-pentaaza-tricyclo[19.4.0.0*3,8*]pentacosa-1(25),3(8),4,6,21,23-hexaene-12,15,18-trione

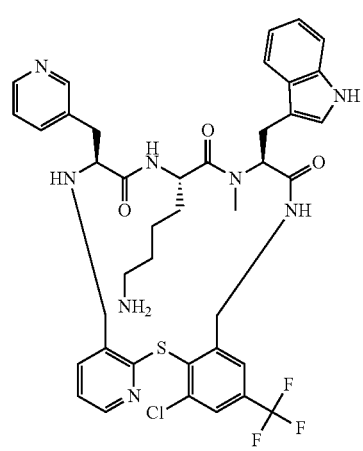 [SMILES: CN1C(=O)[C@H](CCCCN)NC(=O)[C@H](Cc2cccnc2)NCc2cccnc2Sc2c(Cl)cc(C(F)(F)F)cc2CNC(=O)[C@@H]1Cc1c[nH]c2ccccc12]

Example 86 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. (S)-2-(9H-Fluoren-9-ylmethoxycarbonylamino)-3-pyridin-3-yl-propionic acid.

Tether: Intermediate 45
MS (M+H$^+$): expected 806.3; observed 807.3

Example 87

(11S,14S,17S)-14-(4-Amino-butyl)-11-(3-aminopropyl)-17-(1H-indol-3-ylmethyl)-16-methyl-23-phenyl-25-trifluoromethyl-2-thia-4,10,13,16,19-pentaaza-tricyclo[19.4.0.0*3,8*]pentacosa-1(25),3,5,7,21,23-hexaene-12,15,18-trione

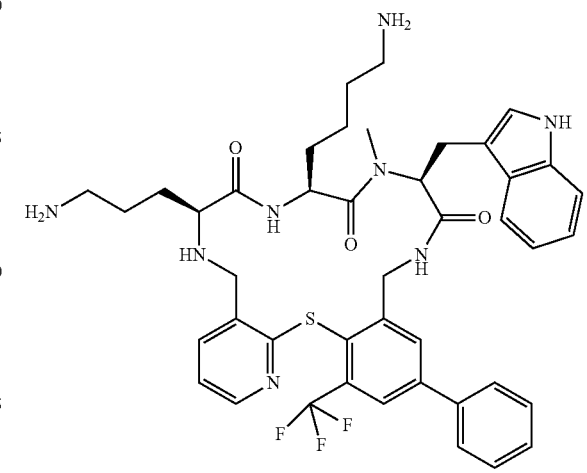

Example 87 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 57
MS (M+H$^+$): expected 806.3; observed 807.3

Example 88

(11S,14S,17S)-14-(4-Amino-butyl)-11-(3-aminopropyl)-23-bromo-17-(1H-indol-3-ylmethyl)-16-methyl-25-trifluoromethyl-2-thia-4,10,13,16,19-pentaaza-tricyclo[19.4.0.0*3,8*]pentacosa-1(25),3,5,7,21,23-hexaene-12,15,18-trione

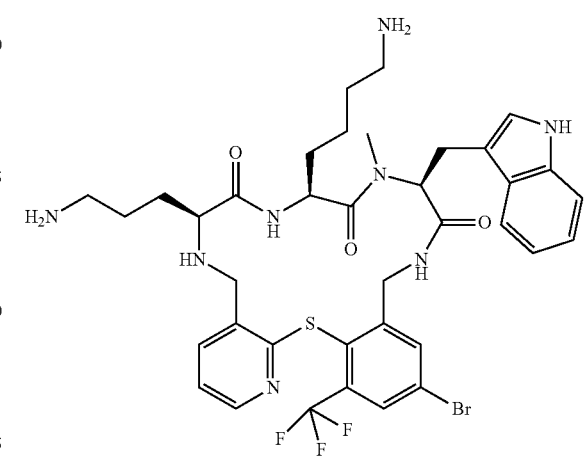

Example 88 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 58

MS (M+H$^+$): expected 816.8; observed 817.5

Example 89

(11S,14S,17S)-14-(4-Amino-butyl)-11-(3-amino-propyl)-23-bromo-25-chloro-17-(1H-indol-3-ylm-ethyl)-16-methyl-2-thia-4,10,13,16,19-pentaaza-tricyclo[19.4.0.0*3,8*]pentacosa-1(25),3,5,7,21,23-hexaene-12,15,18-trione

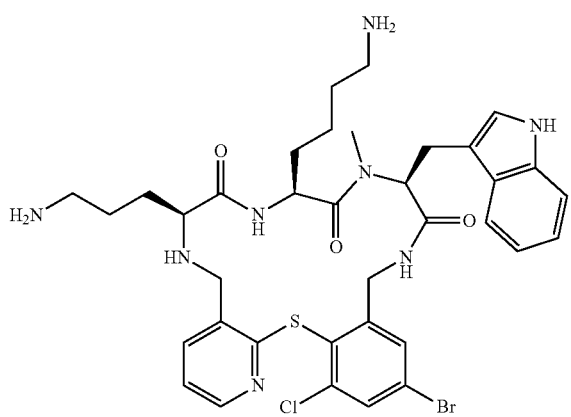 [SMILES: CN1C(=O)[C@H](CCCCN)NC(=O)[C@H](CCCN)NCc2cccnc2Sc2c(Cl)cc(Br)cc2CNC(=O)[C@@H]1Cc1c[nH]c2ccccc12]

Example 89 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 59

MS (M+H$^+$): expected 783.2; observed 784.2

Example 90

(11S,14S,17S)-14-(4-Amino-butyl)-11-(3-amino-propyl)-22-bromo-25-chloro-17-(1H-indol-3-ylm-ethyl)-16-methyl-2-thia-4,10,13,16,19-pentaaza-tricyclo[19.4.0.0*3,8*]pentacosa-1(25),3,5,7,21,23-hexaene-12,15,18-trione

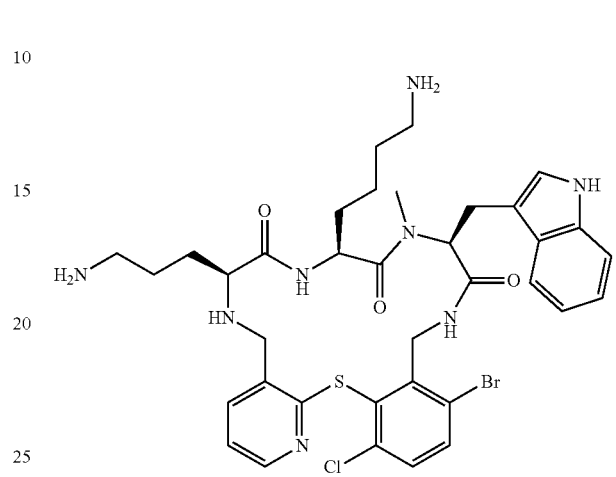

Example 90 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 60

MS (M+H$^+$): expected 783.2; observed 784.2

Example 91

(11S,14S,17S)-14-(4-Amino-butyl)-11-(3-amino-propyl)-17-(1H-indol-3-ylmethyl)-16-methyl-23,25-bis-trifluoromethyl-2-thia-4,10,13,16,19-pentaaza-tricyclo[19.4.0.0*3,8*]pentacosa-1(25),3,5,7,21,23-hexaene-12,15,18-trione

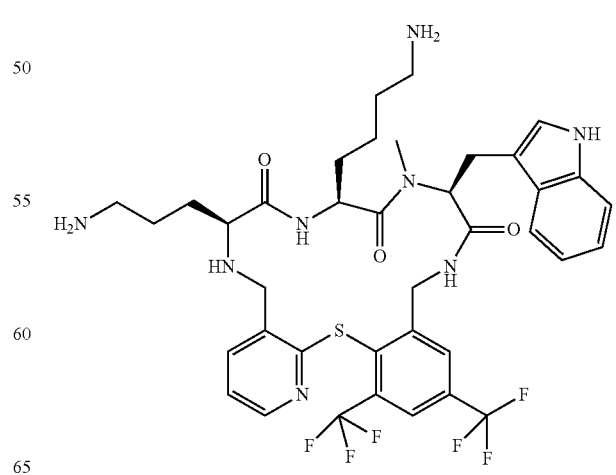

Example 91 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 61

MS (M+H⁺): expected 805.9; observed 807.3

Example 92

(11S,14S,17S)-14-(4-Amino-butyl)-11-(3-amino-propyl)-25-chloro-17-(1H-indol-3-ylmethyl)-16-methyl-23-morpholin-4-yl-2-thia-4,10,13,16,19-pentaaza-tricyclo[19.4.0.0*3,8*]pentacosa-1(25),3,5,7,21,23-hexaene-12,15,18-trione

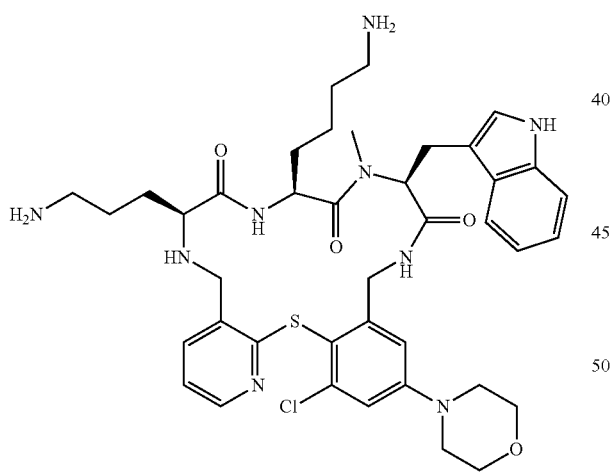

Example 92 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 62

MS (M+H⁺): expected 789.4; observed 790.3

Example 93

(14S,17S)-14-(4-Amino-butyl)-23,25-dichloro-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

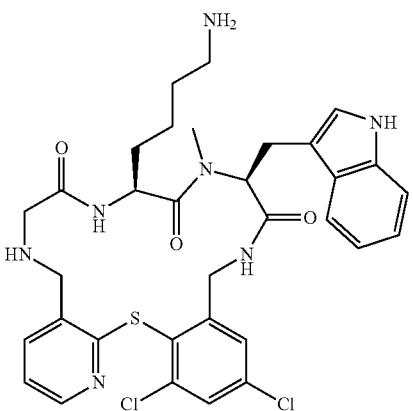 [SMILES: CN1C(=O)[C@H](CCCCN)NC(=O)CNCc2cccnc2Sc2c(Cl)cc(Cl)cc2CNC(=O)[C@@H]1Cc1c[nH]c2ccccc12]

Example 93 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Gly-OH.

Tether: Intermediate 47

MS (M+H⁺): expected 682.7; observed 683.2

Example 94

(11S,14S,17S)-14-(4-Amino-butyl)-23,25-dichloro-17-(1H-indol-3-ylmethyl)-11,16-dimethyl-2-thia-4,10,13,16,19-pentaaza-tricyclo[19.4.0.0*3,8*]pentacosa-1(25),3,5,7,21,23-hexaene-12,15,18-trione

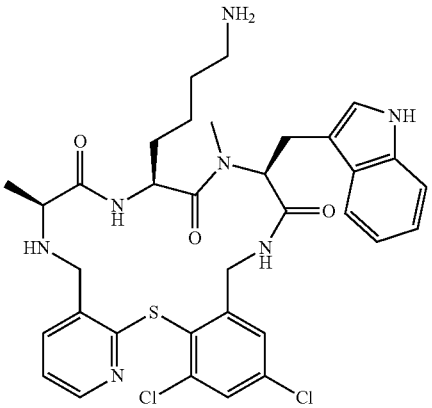 [SMILES: C[C@@H]1NCc2cccnc2Sc2c(Cl)cc(Cl)cc2CNC(=O)[C@H](Cc2c[nH]c3ccccc23)N(C)C(=O)[C@H](CCCCN)NC1=O]

Example 94 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Ala-OH.

Tether: Intermediate 47

MS (M+H⁺): expected 695.7; observed 696.2

Example 95

(11S,14S,17S)-14-(4-Amino-butyl)-23,25-dichloro-17-(1H-indol-3-ylmethyl)-11-isopropyl-16-methyl-2-thia-4,10,13,16,19-pentaaza-tricyclo[19.4.0.0*3,8*]pentacosa-1(25),3,5,7,21,23-hexaene-12,15,18-trione

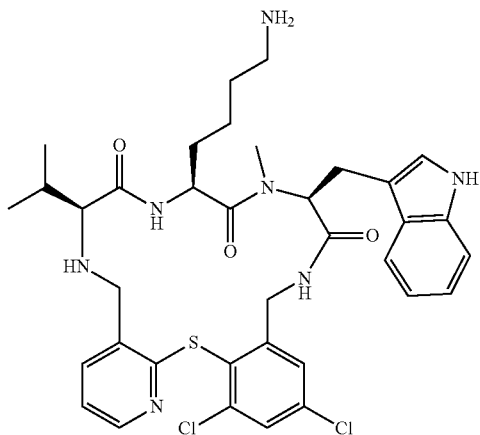 [SMILES: CC(C)[C@@H]1NCc2cccnc2Sc2c(Cl)cc(Cl)cc2CNC(=O)[C@H](Cc2c[nH]c3ccccc23)N(C)C(=O)[C@H](CCCCN)NC1=O]

Example 95 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Leu-OH.

Tether: Intermediate 47

MS (M+H⁺): expected 723.7; observed 724.3

Example 96

(11S,14S,17S)-14-(4-Amino-butyl)-23,25-dichloro-11-hydroxymethyl-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

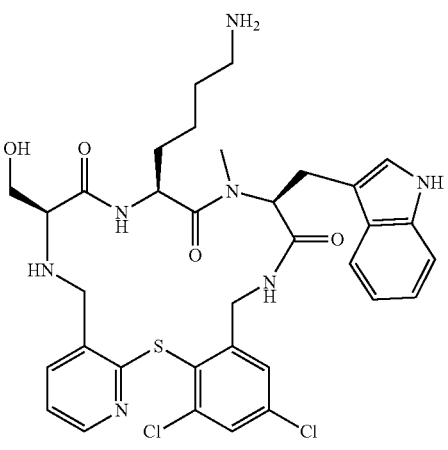 [SMILES: CN1C(=O)[C@H](CCCCN)NC(=O)[C@H](CO)NCc2cccnc2Sc2c(Cl)cc(Cl)cc2CNC(=O)[C@@H]1Cc1c[nH]c2ccccc12]

Example 96 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Ser(tBu)—OH.

Tether: Intermediate 47

MS (M+H⁺): expected 711.7; observed 712.2

Example 97

(11S,14S,17S)-14-(4-Amino-butyl)-11-(3-amino-propyl)-25-chloro-17-(1H-indol-3-ylmethyl)-16-methyl-23-trifluoromethyl-2-thia-4,7,10,13,16,19-hexaaza-tricyclo[19.4.0.0*3,8*]pentacosa-1(21),3,5,7,22,24-hexaene-12,15,18-trione

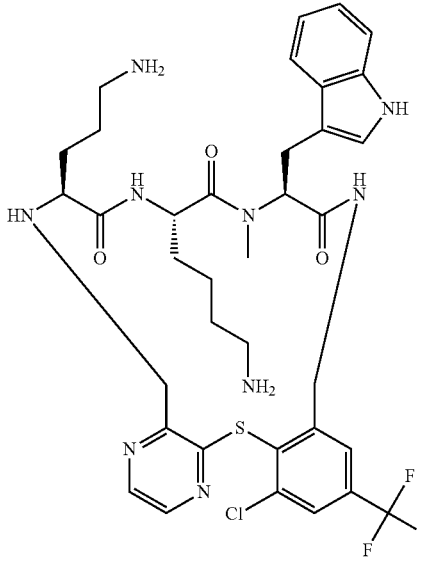

Example 97 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 63

MS (M+H⁺): expected 773.3; observed 774.3

Example 98

(11S,14S,17S)-14-(4-Amino-butyl)-11-(3-amino-propyl)-25-chloro-17-(1H-indol-3-ylmethyl)-16-methyl-22-trifluoromethyl-2-thia-4,7,10,13,16,19-hexaaza-tricyclo[19.4.0.0*3,8*]pentacosa-1(21),3,5,7,22,24-hexaene-12,15,18-trione

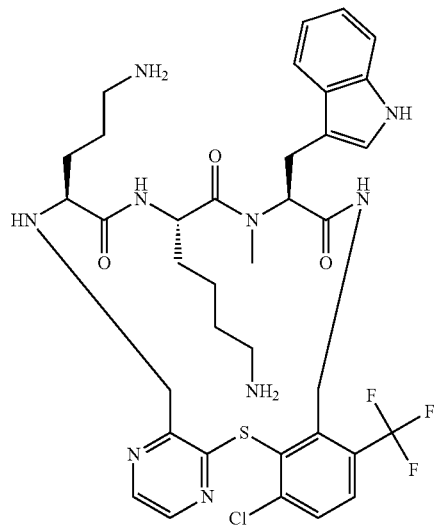 [SMILES: CN1C(=O)[C@H](CCCCN)NC(=O)[C@H](CCCN)NCc2nccnc2Sc2c(Cl)ccc(C(F)(F)F)c2CNC(=O)[C@@H]1Cc1c[nH]c2ccccc12]

Example 98 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 64

MS (M+H⁺): expected 773.3; observed 774.3

Example 99

(11S,14S,17S)-14-(4-Amino-butyl)-11-(3-amino-propyl)-25-chloro-17-(1H-indol-3-ylmethyl)-16-methyl-23-pyridin-3-yl-2-thia-4,10,13,16,19-pentaaza-tricyclo[19.4.0.0*3,8*]pentacosa-1(25),3,5,7,21,23-hexaene-12,15,18-trione

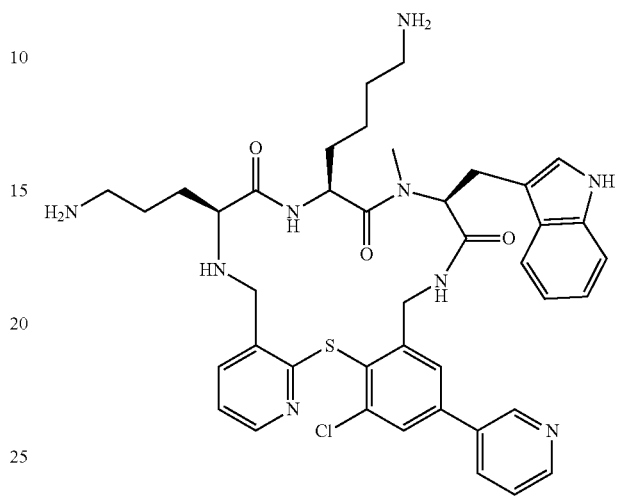

Example 99 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 65

MS (M+H⁺): expected 781.4; observed 782.4

Example 100

(11S,14S,17S)-14-(4-Amino-butyl)-11-(3-amino-propyl)-25-chloro-17-(1H-indol-3-ylmethyl)-16-methyl-23-pyridin-4-yl-2-thia-4,10,13,16,19-pentaaza-tricyclo[19.4.0.0*3,8*]pentacosa-1(25),3,5,7,21,23-hexaene-12,15,18-trione

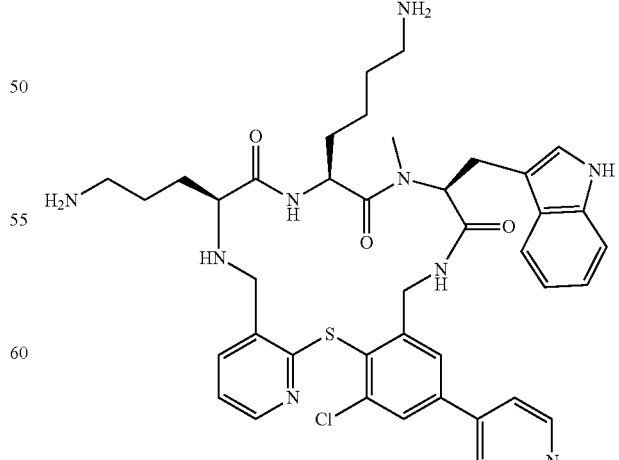

Example 100

Example 100 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 66

MS (M+H⁺): expected 781.4; observed 782.4

Example 101

(11S,14S,17S)-14-(4-Amino-butyl)-23,25-dichloro-17-(1H-indol-3-ylmethyl)-11-isobutyl-16-methyl-2-thia-4,10,13,16,19-pentaaza-tricyclo[19.4.0.0*3,8*]pentacosa-1(25),3,5,7,21,23-hexaene-12,15,18-trione

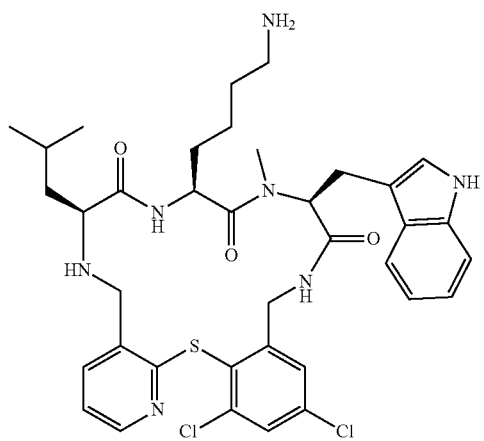 [SMILES: CC(C)C[C@@H]1NCc2cccnc2Sc2c(Cl)cc(Cl)cc2CNC(=O)[C@H](Cc2c[nH]c3ccccc23)N(C)C(=O)[C@H](CCCCN)NC1=O]

Example 101 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Leu-OH.

Tether: Intermediate 47

MS (M+H⁺): expected 737.8; observed 738.3

Example 102

(11S,14S,17S)-14-(4-Amino-butyl)-11-(3-aminopropyl)-25-chloro-17-(1H-indol-3-ylmethyl)-23-(2-methoxy-pyridin-4-yl)-16-methyl-2-thia-4,10,13,16,19-pentaaza-tricyclo[19.4.0.0*3,8*]pentacosa-1(25),3,5,7,21,23-hexaene-12,15,18-trione

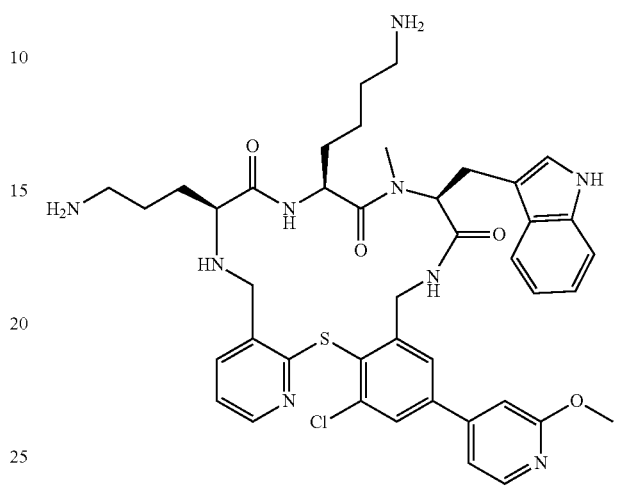

Example 102 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 67

MS (M+H⁺): expected 811.4; observed 812.4

Example 103

3-[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3,5,7,21,23-hexaen-11-yl]-propionamide

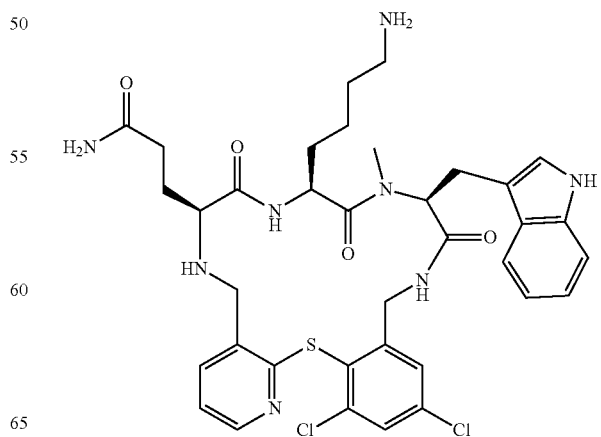

Example 103 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Gln(Trt)-OH.
Tether: Intermediate 47
MS (M+H$^+$): expected 752.7; observed 753.3

Example 104

(11S,14S,17S)-14-(4-Amino-butyl)-11-(3-amino-propyl)-22,25-dichloro-17-(1H-indol-3-ylmethyl)-16-methyl-2-thia-7,10,13,16,19-pentaaza-tricyclo[19.4.0.0*3,8*]pentacosa-1(21),3,5,7,22,24-hexaene-12,15,18-trione

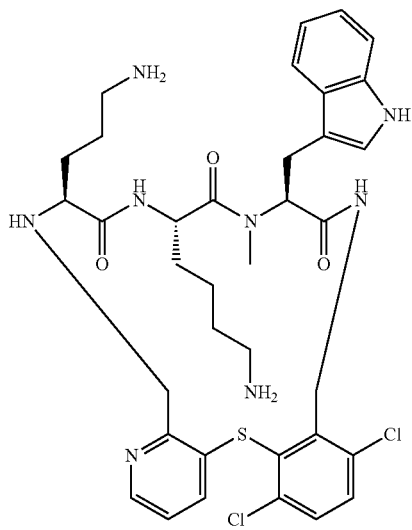 [SMILES: CN1C(=O)[C@H](CCCCN)NC(=O)[C@H](CCCN)NCc2ncccc2Sc2c(Cl)ccc(Cl)c2CNC(=O)[C@@H]1Cc1c[nH]c2ccccc12]

Example 104 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 68
MS (M+H$^+$): expected 738.4; observed 739.3 [(M+H)$^+$]

Example 105

(11S,14S,17S)-14-(4-Amino-butyl)-11-(3-amino-propyl)-25-chloro-17-(1H-indol-3-ylmethyl)-16-methyl-23-(2-methyl-pyridin-4-yl)-2-thia-4,10,13,16,19-pentaaza-tricyclo[19.4.0.0*3,8*]pentacosa-1(25),3,5,7,21,23-hexaene-12,15,18-trione

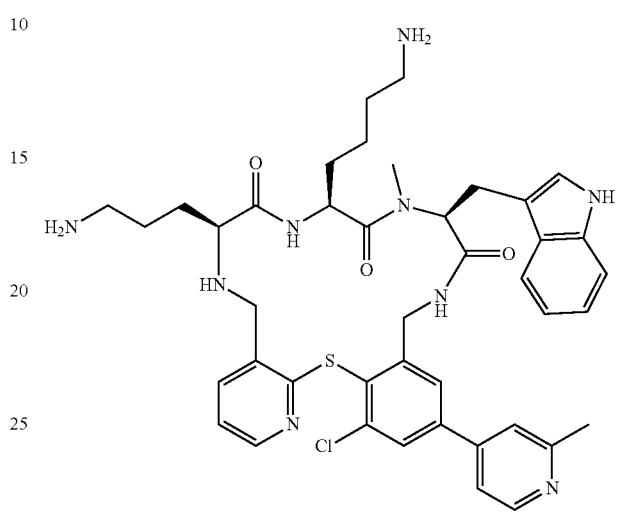

Example 105 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 65
MS (M+H$^+$): expected 795.4; observed 796.4

Example 106

(11S,14S,17S)-14-(4-Amino-butyl)-23,25-dichloro-11-((S)-1-hydroxy-ethyl)-17-(1H-indol-3-ylmethyl)-16-methyl-2-thia-4,10,13,16,19-pentaaza-tricyclo[19.4.0.0*3,8*]pentacosa-1(25),3,5,7,21,23-hexaene-12,15,18-trione

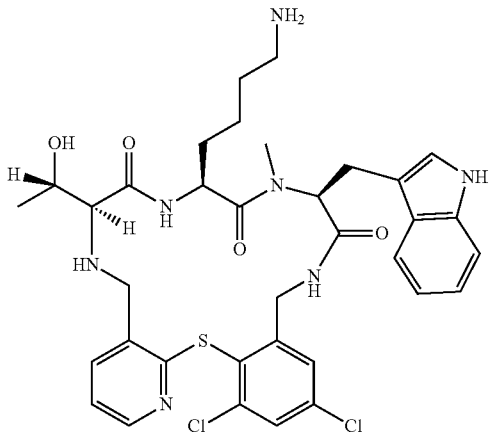 [SMILES: C[C@H](O)[C@@H]1NCc2cccnc2Sc2c(Cl)cc(Cl)cc2CNC(=O)[C@H](Cc2c[nH]c3ccccc23)N(C)C(=O)[C@H](CCCCN)NC1=O]

Example 106 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Thr(tBu)—OH.

Tether: Intermediate 47

MS (M+H⁺): expected 725.7; observed 726.3

Example 107

(14S,17S)-14-(4-Amino-butyl)-23,25-dichloro-17-(1H-indol-3-ylmethyl)-11,11,16-trimethyl-2-thia-4,10,13,16,19-pentaaza-tricyclo[19.4.0.0*3,8*]pentacosa-1(25),3,5,7,21,23-hexaene-12,15,18-trione

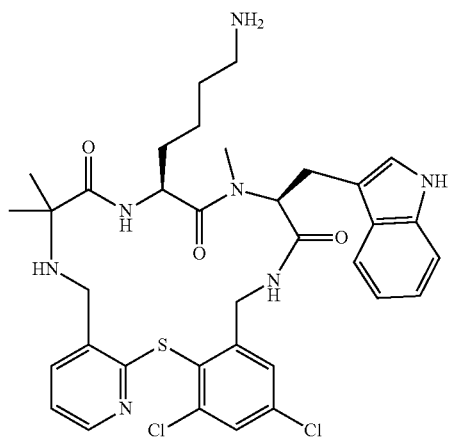 [SMILES: CN1C(=O)[C@H](CCCCN)NC(=O)C(C)(C)NCc2cccnc2Sc2c(Cl)cc(Cl)cc2CNC(=O)[C@@H]1Cc1c[nH]c2ccccc12]

Example 107 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-Aib-OH.

Tether: Intermediate 47

MS (M+H⁺): expected 709.7; observed 710.3

Example 108

(11S,14S,17S)-14-(4-Amino-butyl)-23,25-dichloro-17-(1H-indol-3-ylmethyl)-16-methyl-11-naphthalen-2-ylmethyl-2-thia-4,10,13,16,19-pentaaza-tricyclo[19.4.0.0*3,8*]pentacosa-1(25),3,5,7,21,23-hexaene-12,15,18-trione

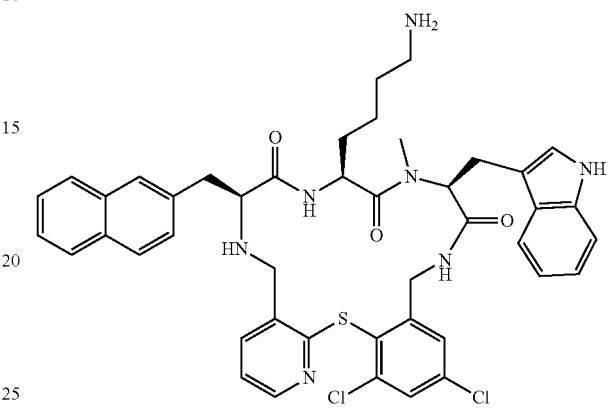

Example 108 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-2-Nal-OH.

Tether: Intermediate 47

MS (M+H⁺): expected 821.8; observed 822.3

Example 109

(11S,14S,17S)-14-(4-Amino-butyl)-11-(3-aminopropyl)-23-(6-amino-pyridin-3-yl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

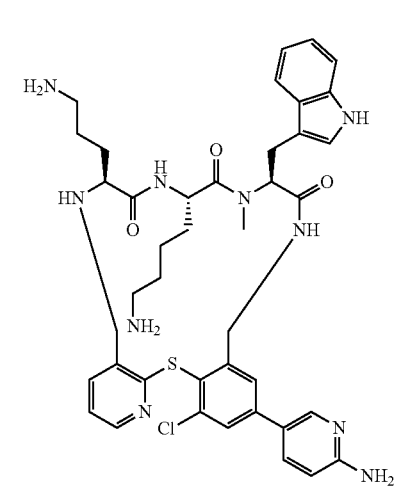 [SMILES: CN1C(=O)[C@H](CCCCN)NC(=O)[C@H](CCCN)NCc2cccnc2Sc2c(Cl)cc(-c3ccc(N)nc3)cc2CNC(=O)[C@@H]1Cc1c[nH]c2ccccc12]

Example 109 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 70
MS (M+H⁺): expected 796.4; observed 797.3

Example 110

(11S,14S,17S)-14-(4-Amino-butyl)-11-(3-amino-propyl)-22,25-dichloro-17-(1H-indol-3-ylmethyl)-16-methyl-2-thia-4,7,10,13,16,19-hexaaza-tricyclo[19.4.0.0*3,8*]pentacosa-1(25),3,5,7,21,23-hexaene-12,15,18-trione

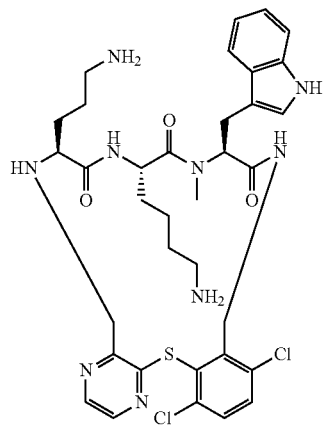 [SMILES: CN1C(=O)[C@H](CCCCN)NC(=O)[C@H](CCCN)NCc2nccnc2Sc2c(Cl)ccc(Cl)c2CNC(=O)[C@@H]1Cc1c[nH]c2ccccc12]

Example 110 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 71
MS (M+H⁺): expected 739.3; observed 740.3 [(M+H)⁺]

Example 111

(11S,14S,17S)-14-(4-Amino-butyl)-11-(3-amino-propyl)-25-chloro-17-(1H-indol-3-ylmethyl)-16-methyl-22-trifluoromethyl-2-thia-7,10,13,16,19-pentaaza-tricyclo[19.4.0.0*3,8*]pentacosa-1(25),3(8),4,6,21,23-hexaene-12,15,18-trione

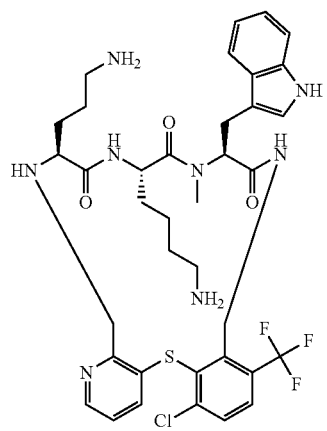 [SMILES: CN1C(=O)[C@H](CCCCN)NC(=O)[C@H](CCCN)NCc2ncccc2Sc2c(Cl)ccc(C(F)(F)F)c2CNC(=O)[C@@H]1Cc1c[nH]c2ccccc12]

Example 111 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 72
MS (M+H⁺): expected 772.3; observed 773.3 [(M+H)⁺]

Example 112

(11S,14S,17S)-14-(4-Amino-butyl)-11-(3-amino-propyl)-25-chloro-17-(1H-indol-3-ylmethyl)-16-methyl-23-trifluoromethyl-2-thia-7,10,13,16,19-pentaaza-tricyclo[19.4.0.0*3,8*]pentacosa-1(25),3,5,7,21,23-hexaene-12,15,18-trione

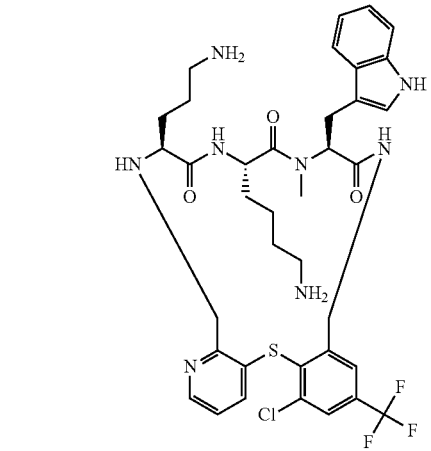 [SMILES: CN1C(=O)[C@H](CCCCN)NC(=O)[C@H](CCCN)NCc2ncccc2Sc2c(Cl)cc(C(F)(F)F)cc2CNC(=O)[C@@H]1Cc1c[nH]c2ccccc12]

Example 112 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 73
MS (M+H$^+$): expected 772.3; observed 773.3 [(M+H)$^+$]

Example 113

(12S,15S,18S)-15-(4-Amino-butyl)-18-(3-amino-propyl)-4-chloro-12-(1H-indol-3-ylmethyl)-13-methyl-2-thia-5,10,13,16,19-pentaaza-tricyclo[19.4.0.0*3,8*]pentacosa-1(25),3,5,7,21,23-hexaene-11,14,17-trione

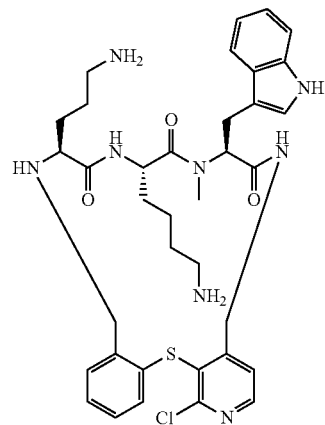 [SMILES: CN1C(=O)[C@H](CCCCN)NC(=O)[C@H](CCCN)NCc2ccccc2Sc2c(ccnc2Cl)CNC(=O)[C@@H]1Cc1c[nH]c2ccccc12]

Example 113 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 74
MS (M+H$^+$): expected 704.3; observed 705.3 [(M+H)$^+$]

Example 114

(11S,14S,17S)-14-(4-Amino-butyl)-23,25-dichloro-17-(1H-indol-3-ylmethyl)-16-methyl-11-naphthalen-1-ylmethyl-2-thia-4,10,13,16,19-pentaaza-tricyclo[19.4.0.0*3,8*]pentacosa-1(25),3,5,7,21,23-hexaene-12,15,18-trione

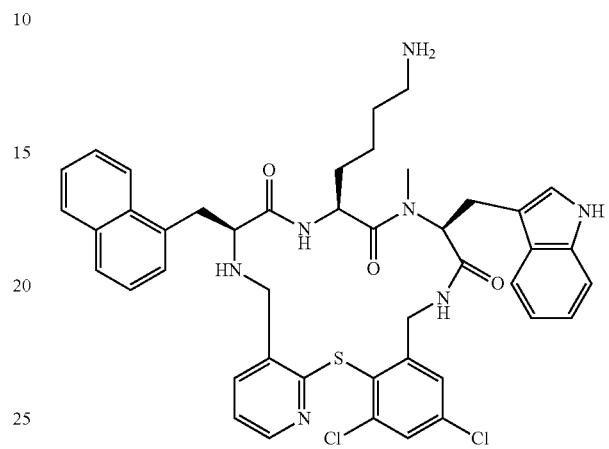

Example 114 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-1-Nal-OH.

Tether: Intermediate 47
MS (M+H$^+$): expected 821.8; observed 822.3

Example 115

(11S,14S,17S)-14-(4-Amino-butyl)-11-(3-amino-propyl)-25-chloro-17-(1H-indol-3-ylmethyl)-16-methyl-23-[2-(4-methyl-piperazin-1-yl)-pyridin-4-yl]-2-thia-4,10,13,16,19-pentaaza-tricyclo[19.4.0.0*3,8*]pentacosa-1(25),3,5,7,21,23-hexaene-12,15,18-trione

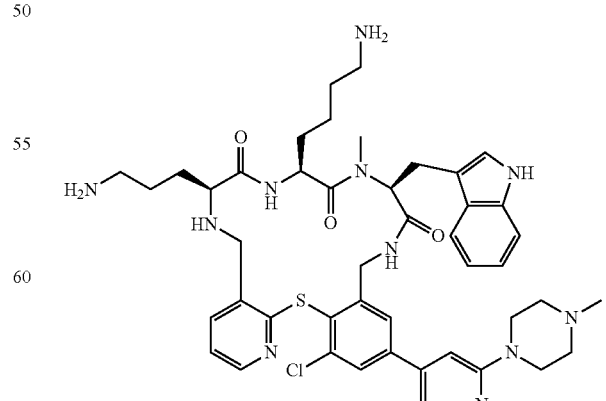

Example 115 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 75

MS (M+H$^+$): expected 821.8; observed 822.3

Example 116

{(7S,10S,13S)-10-(4-aminobutyl)-7-(3-aminopropyl)-20-chloro-13-[(1H-indol-3-yl)methyl]-12-methyl-8,11,14-trioxo-5,6,7,8,9,10,11,12,13,14,15,16-dodecahydropyrido[2,3-b][1,5,8,11,14]benzothiatetraazacycloheptadecin-18-yl}boronic Acid

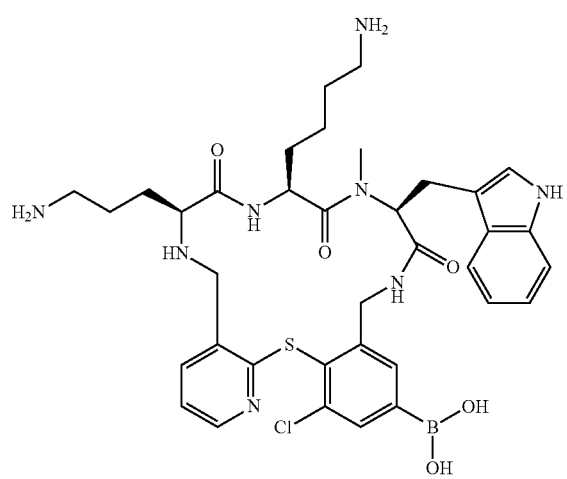 [SMILES: CN1C(=O)[C@H](CCCCN)NC(=O)[C@H](CCCN)NCc2cccnc2Sc2c(Cl)cc(B(O)O)cc2CNC(=O)[C@@H]1Cc1c[nH]c2ccccc12]

Example 116 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Orn(BOC)—OH.

Tether: Intermediate 76

MS (M+H$^+$): expected 748.1; observed 749.4

Example 117

(12S,15S,18S)-15-(3-Amino-propyl)-18-biphenyl-4-ylmethyl-12-(1H-indol-3-ylmethyl)-19-methyl-2-thia-10,13,16,19-tetraaza-tricyclo[19.4.0.0*3,8*]pentacosa-1(25),3,5,7,21,23-hexaene-11,14,17-trione

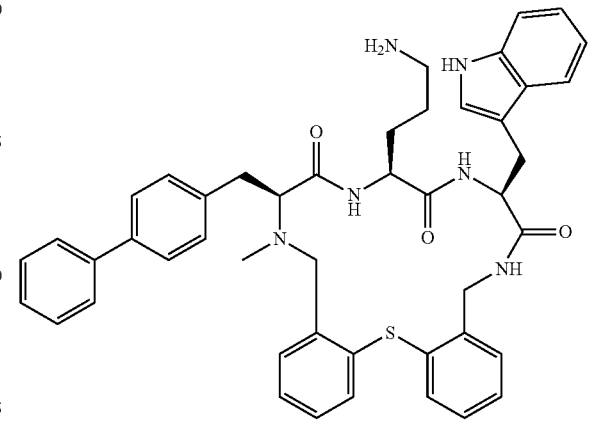

Example 117 was prepared according to the General Procedure for Peptide Macrocycle Synthesis using the following starting materials:

Amino acids:
1. Fmoc-L-Trp(BOC)—OH,
2. Fmoc-L-Orn(BOC)—OH,
3. Fmoc-L-NMe-Bip(BOC)—OH.

Tether: Intermediate 4

MS (M+H)$^+$: expected 765.35; observed 765.42

Example 118

(11S,14S,17S)-14-(4-Amino-butyl)-11-(2-aminoethoxymethyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

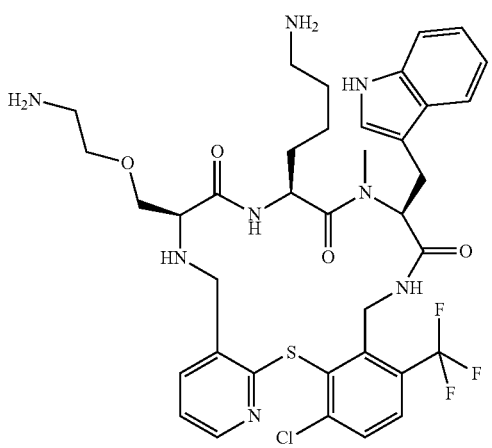 [SMILES: CN1C(=O)[C@H](CCCCN)NC(=O)[C@H](COCCN)NCc2cccnc2Sc2c(Cl)ccc(C(F)(F)F)c2CNC(=O)[C@@H]1Cc1c[nH]c2ccccc12]

Example 118 was prepared according to the General Procedure for Peptide Macrocycle Synthesis using the following starting materials:

Amino acids:
1. Fmoc-L-NMe-Trp(BOC)—OH,
2. Fmoc-L-Lys(BOC)—OH,
3. (S)-3-(2-tert-Butoxycarbonylamino-ethoxy)-2-(9H-fluoren-9-ylmethoxycarbonylamino)-propionic acid Tether: Intermediate 31
MS (M+H)$^+$: expected 789.29; observed 789.34

Example 119

(11S,14S,17S)-11,14-Bis-(2-amino-ethoxymethyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

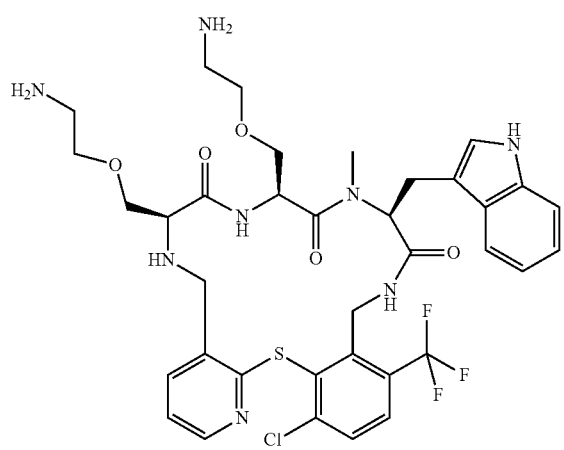 [SMILES: CN1C(=O)[C@H](COCCN)NC(=O)[C@H](COCCN)NCc2cccnc2Sc2c(Cl)ccc(C(F)(F)F)c2CNC(=O)[C@@H]1Cc1c[nH]c2ccccc12]

Example 119 was prepared according to the General Procedure for Peptide Macrocycle Synthesis using the following starting materials:

Amino acids:
1. Fmoc-L-NMe-Trp(BOC)—OH,
2. (S)-3-(2-tert-Butoxycarbonylamino-ethoxy)-2-(9H-fluoren-9-ylmethoxycarbonylamino)-propionic acid
3. (S)-3-(2-tert-Butoxycarbonylamino-ethoxy)-2-(9H-fluoren-9-ylmethoxycarbonylamino)-propionic acid Tether: Intermediate 31
MS (M+H)$^+$: expected 791.26; observed 791.27

Example 120

(11S,14S,17S)-14-(2-Amino-ethoxymethyl)-11-(3-amino-propyl)-25-chloro-17-(1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

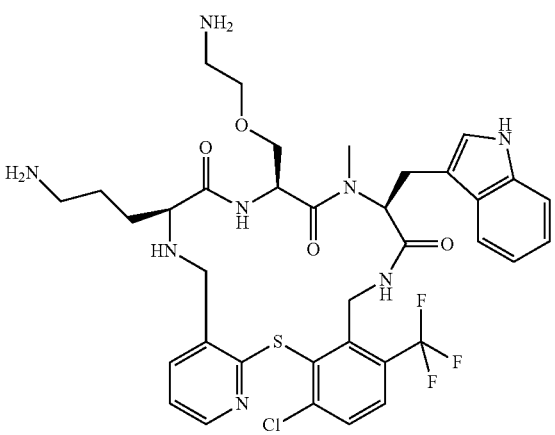 [SMILES: CN1C(=O)[C@H](COCCN)NC(=O)[C@H](CCCN)NCc2cccnc2Sc2c(Cl)ccc(C(F)(F)F)c2CNC(=O)[C@@H]1Cc1c[nH]c2ccccc12]

Example 120 was prepared according to the General Procedure for Peptide Macrocycle Synthesis using the following starting materials:

Amino Acids:
Fmoc-L-NMe-Trp(BOC)—OH,
(S)-3-(2-tert-Butoxycarbonylamino-ethoxy)-2-(9H-fluoren-9-ylmethoxycarbonylamino)-propionic acid
Fmoc-L-Orn(BOC)—OH.

Tether: Intermediate 31
MS (M+H)$^+$: expected 775.27; observed 775.22

Example 121

3-[(11S,14S,17S)-14-(4-Amino-butyl)-22,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3,5,7,21,23-hexaen-11-yl]-propionamide

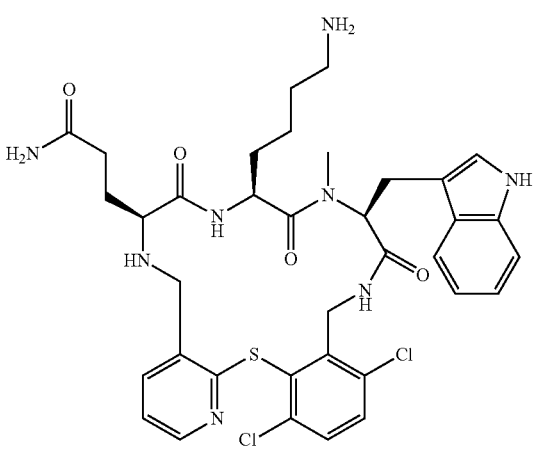 [SMILES: CN1C(=O)[C@H](CCCCN)NC(=O)[C@H](CCC(N)=O)NCc2cccnc2Sc2c(Cl)ccc(Cl)c2CNC(=O)[C@@H]1Cc1c[nH]c2ccccc12]

Example 121 was prepared according to the General Procedure for Peptide Macrocycle Synthesis using the following starting materials:

Amino acids:
1. Fmoc-NMe-L-Trp(BOC)—OH,
2. Fmoc-L-Lys(BOC)—OH,
3. Fmoc-L-Gln(Trt)-OH.

Tether: Intermediate 30

MS (M+H⁺): expected 752.7; observed 753.3

Example 122

(11S,14S,17S)-14-(4-Amino-butyl)-11-(3-amino-propyl)-25-chloro-17-(1H-indol-3-ylmethyl)-16-methyl-22-trifluoromethyl-2-thia-5,10,13,16,19-pentaaza-tricyclo[19.4.0.0*3,8*]pentacosa-1(25),3,5,7,21,23-hexaene-12,15,18-trione

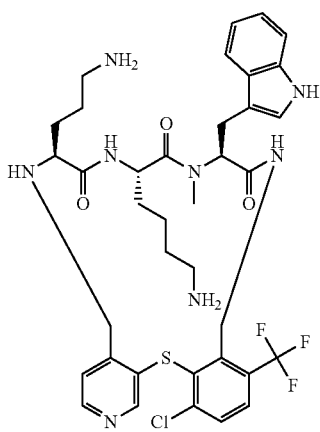 [SMILES: CN1C(=O)[C@H](CCCCN)NC(=O)[C@H](CCCN)NCc2ccncc2Sc2c(Cl)ccc(C(F)(F)F)c2CNC(=O)[C@@H]1Cc1c[nH]c2ccccc12]

Example 122 was prepared according to the General Procedure for Peptide Macrocycle Synthesis using the following starting materials:

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 77. Macrocyclization: 2.4 eq HATU, 10 eq DIPEA, in DMF at rt 4 h. Deprotection: DCM/TFA 2:1. The title compound was obtained as light yellow powder (6 mg). MS ESI (m/z): 773.3 [(M+H)⁺]

Example 123

(11S,14S,17S)-14-(4-Amino-butyl)-11-(3-amino-propyl)-25-chloro-17-(1H-indol-3-ylmethyl)-16-methyl-23-trifluoromethyl-2-thia-5,10,13,16,19-pentaaza-tricyclo[19.4.0.0*3,8*]pentacosa-1(25),3,5,7,21,23-hexaene-12,15,18-trione

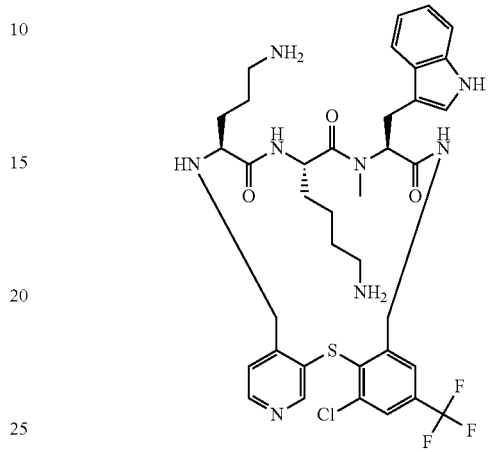

Example 123 was prepared according to the General Procedure for Peptide Macrocycle Synthesis using the following starting materials:

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 78. Macrocyclization: 2.4 eq HATU, 10 eq DIPEA, in DMF at rt 2 h. Deprotection: DCM/TFA 2:1. The title compound was obtained as red solid (12 mg). MS ESI (m/z): 773.3 [(M+H)⁺]

Example 124

(11R,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[19.4.0.0*3,8*]pentacosa-1(25),3,5,7,21,23-hexaene-12,15,18-trione

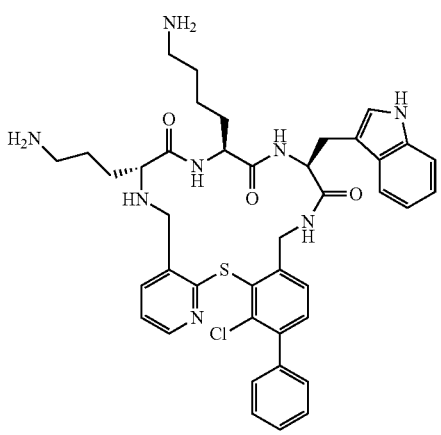 [SMILES: NCCCC[C@@H]1NC(=O)[C@@H](CCCN)NCc2cccnc2Sc2c(ccc(-c3ccccc3)c2Cl)CNC(=O)[C@H](Cc2c[nH]c3ccccc23)NC1=O]

Example 124

Example 124 was prepared according to the General Procedure for Peptide Macrocycle Synthesis using the following starting materials:

Amino acids:
1. Fmoc-L-Trp(BOC)—OH,
2. Fmoc-L-Lys(BOC)—OH,
3. Fmoc-D-Orn(BOC)—OH.

Tether: Intermediate 79
MS (M+H)$^+$: expected 767.32; observed 767.33

Example 125

(11S,14S,17S)-14-(4-Amino-butyl)-11-(3-amino-propyl)-25-chloro-17-(1H-indol-3-ylmethyl)-24-phenyl-2-thia-4,10,13,16,19-pentaaza-tricyclo[19.4.0.0*3,8*]pentacosa-1(25),3,5,7,21,23-hexaene-12,15,18-trione

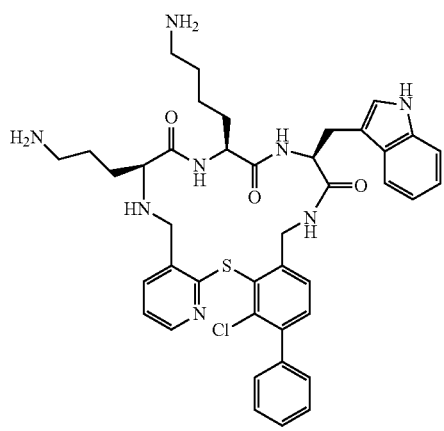 [SMILES: NCCCC[C@@H]1NC(=O)[C@H](CCCN)NCc2cccnc2Sc2c(ccc(-c3ccccc3)c2Cl)CNC(=O)[C@H](Cc2c[nH]c3ccccc23)NC1=O]

Example 125 was prepared according to the General Procedure for Peptide Macrocycle Synthesis using the following starting materials:

Amino acids:
1. Fmoc-L-Trp(BOC)—OH,
2. Fmoc-L-Lys(BOC)—OH,
3. Fmoc-L-Orn(BOC)—OH.

Tether: Intermediate 79
MS (M+H)$^+$: expected 767.32; observed 767.32

Example 126

(11R,14S,17S)-14-(4-Amino-butyl)-11-(3-amino-propyl)-25-chloro-17-(1H-indol-3-ylmethyl)-16-methyl-24-phenyl-2-thia-4,10,13,16,19-pentaaza-tricyclo[19.4.0.0*3,8*]pentacosa-1(25),3,5,7,21,23-hexaene-12,15,18-trione

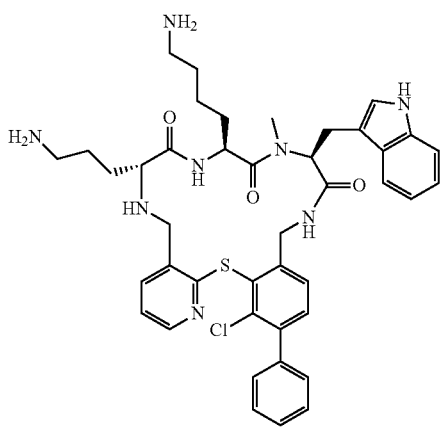 [SMILES: CN1C(=O)[C@H](CCCCN)NC(=O)[C@@H](CCCN)NCc2cccnc2Sc2c(ccc(-c3ccccc3)c2Cl)CNC(=O)[C@@H]1Cc1c[nH]c2ccccc12]

Example 126 was prepared according to the General Procedure for Peptide Macrocycle Synthesis using the following starting materials:

Amino acids:
1. Fmoc-L-NMe-Trp(BOC)—OH,
2. Fmoc-L-Lys(BOC)—OH,
3. Fmoc-D-Orn(BOC)—OH.

Tether: Intermediate 79
MS (M+H)$^+$: expected 781.33; observed 781.34

Example 127

2-[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-acetamide

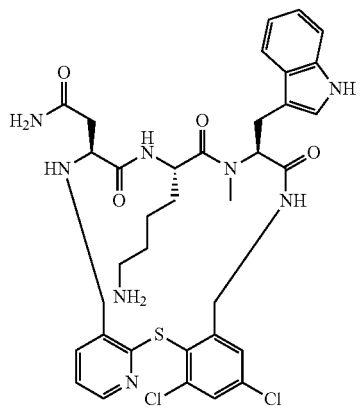 [SMILES: CN1C(=O)[C@H](CCCCN)NC(=O)[C@H](CC(N)=O)NCc2cccnc2Sc2c(Cl)cc(Cl)cc2CNC(=O)[C@@H]1Cc1c[nH]c2ccccc12]

Example 127 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Asn(Trt)-OH.
Tether: Intermediate 47
MS (M+H$^+$): expected 738.7; observed 739.2

Example 128

(12S,15S,18S)-15-(4-Amino-butyl)-18-(3-aminopropyl)-12-(1H-indol-3-ylmethyl)-13-methyl-6-phenyl-4-trifluoromethyl-2-thia-10,13,16,19-tetraazatricyclo[19.4.0.0*3,8*]pentacosa-1(25),3,5,7,21,23-hexaene-11,14,17-trione

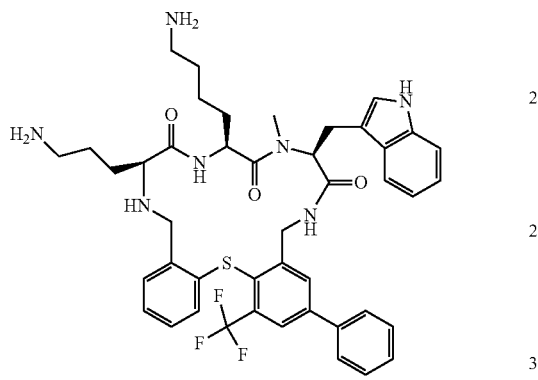

Example 128 was prepared according to the General Procedure for Peptide Macrocycle Synthesis using the following starting materials:
Amino acids:
1. Fmoc-L-NMe-Trp(BOC)—OH,
2. Fmoc-L-Lys(BOC)—OH,
3. Fmoc-L-Orn(BOC)—OH.
Tether: Intermediate 80
MS (M+H)$^+$: expected 814.36; observed 814.37

Example 129

(11S,14S,17S)-14-(4-Amino-butyl)-11-(3-aminopropyl)-25-chloro-17-(1H-indol-3-ylmethyl)-16-methyl-22-phenyl-2-thia-4,10,13,16,19-pentaazatricyclo[19.4.0.0*3,8*]pentacosa-1(25),3(8),4,6,21,23-hexaene-12,15,18-trione

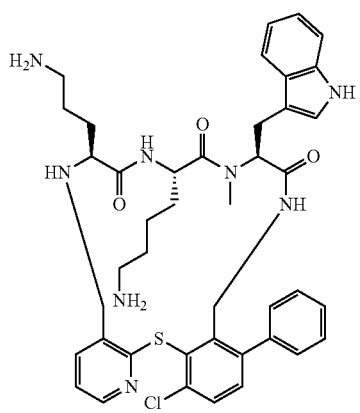 [SMILES: CN1C(=O)[C@H](CCCCN)NC(=O)[C@H](CCCN)NCc2cccnc2Sc2c(Cl)ccc(-c3ccccc3)c2CNC(=O)[C@@H]1Cc1c[nH]c2ccccc12]

Example 129 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 81
MS (M+H$^+$): expected 780.4; observed 781.3

Example 130

(11S,14S,17S)-14-(4-Amino-butyl)-11-(3-aminopropyl)-25-chloro-17-(1H-indol-3-ylmethyl)-16-methyl-23-pyrrolidin-1-yl-2-thia-4,10,13,16,19-pentaaza-tricyclo[19.4.0.0*3,8*]pentacosa-1(25),3(8),4,6,21,23-hexaene-12,15,18-trione

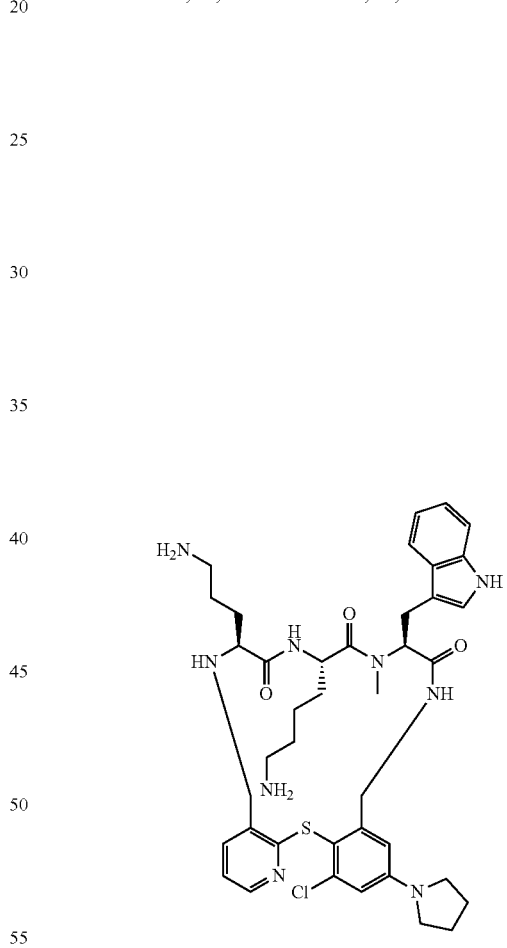

Example 130 was prepared according to the General Procedure for Peptide Macrocycle Synthesis using the following starting materials:
Amino acids:
1. Fmoc-NMe-L-Trp(BOC)—OH,
2. Fmoc-L-Lys(BOC)—OH,
3. Fmoc-L-Orn(BOC)—OH.
Tether: Intermediate 134
MS (M+H$^+$): expected 773.4; observed 774.4

Example 131

(11S,14S,17S)-14-(4-Amino-butyl)-11-(3-amino-propyl)-25-chloro-17-(5-fluoro-1H-indol-3-ylm-ethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

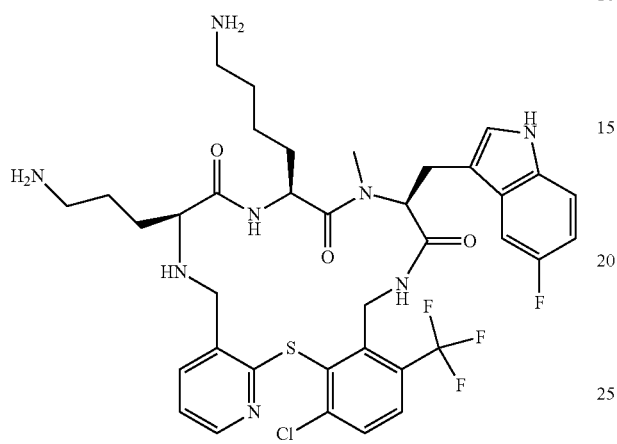

Example 131 was prepared according to the General Procedure for Peptide Macrocycle Synthesis using the following starting materials:

Amino acids:
1. Fmoc-L-NMe-5-F-Trp-OH,
2. Fmoc-L-Lys(BOC)—OH,
3. Fmoc-L-Orn(BOC)—OH.
Tether: Intermediate 31
MS (M+H)$^+$: expected 791.28; observed 791.44

Example 132

(11S,14S,17S)-14-(4-Amino-butyl)-11-(3-amino-propyl)-25-chloro-16-methyl-17-quinolin-2-ylm-ethyl-22-trifluoromethyl-2-thia-4,10,13,16,19-pentaaza-tricyclo[19.4.0.0*3,8*]pentacosa-1(25),3,5,7,21,23-hexaene-12,15,18-trione

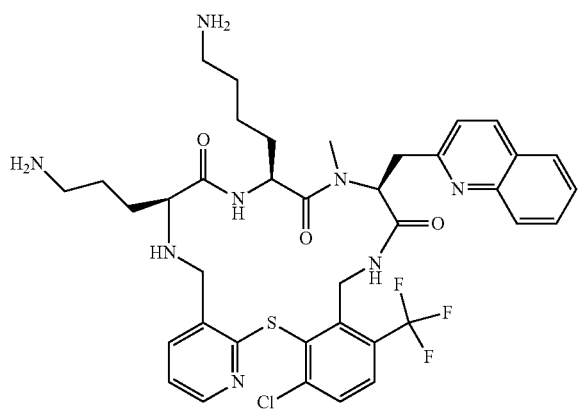 [SMILES: CN1C(=O)[C@H](CCCCN)NC(=O)[C@H](CCCN)NCc2cccnc2Sc2c(Cl)ccc(C(F)(F)F)c2CNC(=O)[C@@H]1Cc1ccc2ccccc2n1]

Example 132 was prepared according to the General Procedure for Peptide Macrocycle Synthesis using the following starting materials:

Amino acids:
1. Fmoc-L-NMe-β-(2-quinolyl)-Ala-OH,
2. Fmoc-L-Lys(BOC)—OH,
3. Fmoc-L-Orn(BOC)—OH.
Tether: Intermediate 31
MS (M+H)$^+$: expected 785.29; observed 785.43

Example 133

(12S,15S,18S)-15,18-Bis-(3-amino-propyl)-4,6-di-chloro-12-(1H-indol-3-ylmethyl)-13-methyl-2-thia-10,13,16,19-tetraaza-tricyclo[19.4.0.0*3,8*]penta-cosa-1(25),3,5,7,21,23-hexaene-11,14,17-trione

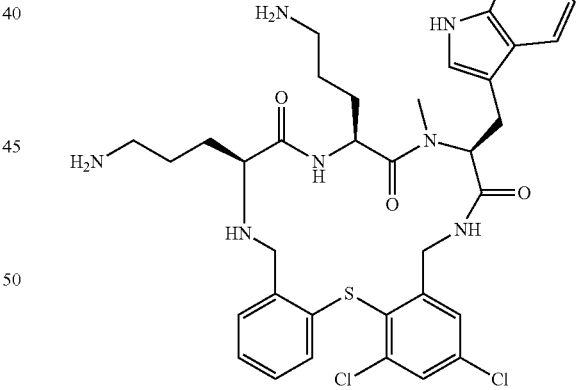

Example 133 was prepared according to the General Procedure for Peptide Macrocycle Synthesis using the following starting materials:

Amino acids:
1. Fmoc-NMe-L-Trp(BOC)—OH,
2. Fmoc-L-Orn(BOC)—OH.
3. Fmoc-L-Orn(BOC)—OH.
Tether: Intermediate 47
MS (M+H)$^+$: expected 724.25; observed 724.20

Example 134

3-[(11S,14S,17S)-14-(4-Amino-butyl)-25-chloro-17-(1H-indol-3-ylmethyl)-23-(2-methoxy-pyridin-4-yl)-16-methyl-12,15,18-trioxo-2-thia-4,10,13,16,19-pentaaza-tricyclo[19.4.0.0*3,8*]pentacosa-1(25),3(8),4,6,21,23 exaen-11-yl]-propionamide

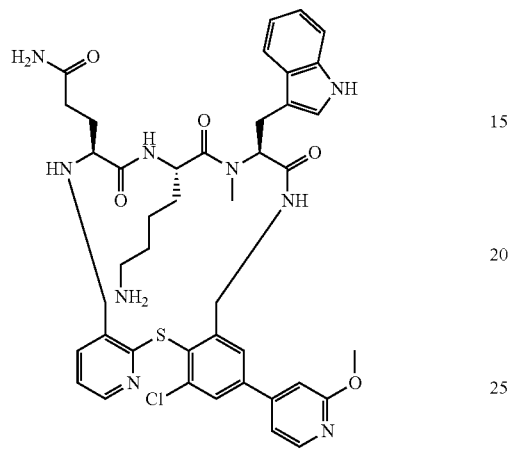

Example 134 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.

Tether: Intermediate 67

MS (M+H$^+$): expected 825.4; observed 826.3

Example 135

(11S,14S,17S)-14-(4-Amino-butyl)-11-(3-amino-propyl)-25-chloro-17-(5-chloro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

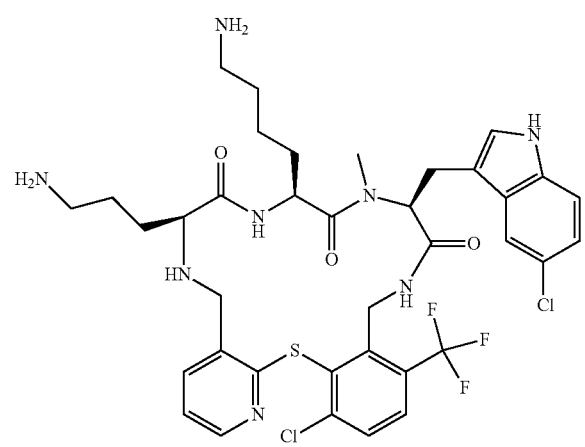 [SMILES: CN1C(=O)[C@H](CCCCN)NC(=O)[C@H](CCCN)NCc2cccnc2Sc2c(Cl)ccc(C(F)(F)F)c2CNC(=O)[C@@H]1Cc1c[nH]c2ccc(Cl)cc12]

Example 135 was prepared according to the General Procedure for Peptide Macrocycle Synthesis using the following starting materials:

Amino acids:
1. Fmoc-L-NMe-5-Cl-Trp-OH,
2. Fmoc-L-Lys(BOC)—OH,
3. Fmoc-L-Orn(BOC)—OH.

Tether: Intermediate 31

MS (M+H)$^+$: expected 807.25; observed 807.39

Example 136

(11S,14S,17S)-14-(4-Amino-butyl)-11-(3-amino-propyl)-25-chloro-17-(2,3-dihydro-1H-indol-3-ylmethyl)-16-methyl-22-trifluoromethyl-2-thia-4,10,13,16,19-pentaaza-tricyclo[19.4.0.0*3,8*]pentacosa-1(25),3,5,7,21,23-hexaene-12,15,18-trione

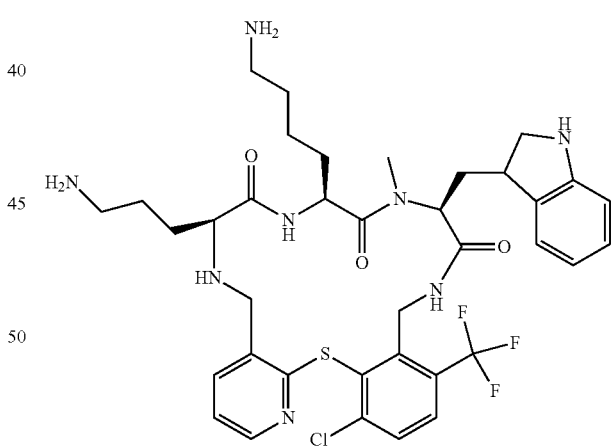

Example 136 was prepared according to the General Procedure for Peptide Macrocycle Synthesis using the following starting materials:

Amino acids:
1. Fmoc-L-NMe-DHT(BOC)—OH (wherein DHT is dihydrotryptophan),
2. Fmoc-L-Lys(BOC)—OH,
3. Fmoc-L-Orn(BOC)—OH.

Tether: Intermediate 31

MS (M+H)$^+$: expected 775.30; observed 775.42

Example 137

3-[(11S,14S,17S)-14-(4-Amino-butyl)-25-chloro-17-(1H-indol-3-ylmethyl)-16-methyl-23-morpholin-4-yl-12,15,18-trioxo-2-thia-4,10,13,16,19-pentaaza-tricyclo[19.4.0.0*3,8*]pentacosa-1(25),3(8),4,6,21,23-hexaen-11-yl]-propionamide

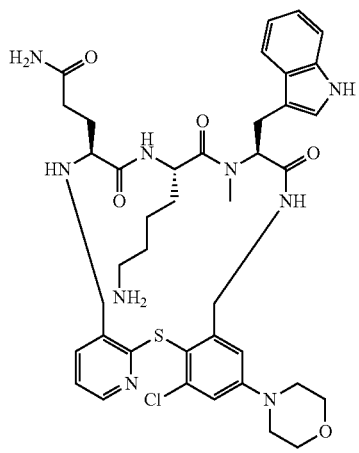 [SMILES: CN1C(=O)[C@H](CCCCN)NC(=O)[C@H](CCC(N)=O)NCc2cccnc2Sc2c(Cl)cc(N3CCOCC3)cc2CNC(=O)[C@@H]1Cc1c[nH]c2ccccc12]

Example 137 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.
Tether: Intermediate 62
MS (M+H$^+$): expected 803.4; observed 804.3

Example 138

(11S,14S,17S)-14-(4-Amino-butyl)-11-(3-amino-propyl)-25-chloro-23-(3,6-dihydro-2H-pyran-4-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

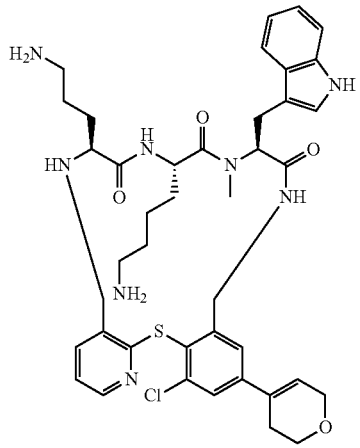 [SMILES: CN1C(=O)[C@H](CCCCN)NC(=O)[C@H](CCCN)NCc2cccnc2Sc2c(Cl)cc(C3=CCOCC3)cc2CNC(=O)[C@@H]1Cc1c[nH]c2ccccc12]

Example 138 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 83
MS (M+H$^+$): expected 786.4; observed 787.4

Example 139

{3-[(11S,14S,17S)-14-(4-Amino-butyl)-22,25-di-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-propyarbamic acid benzyl Ester

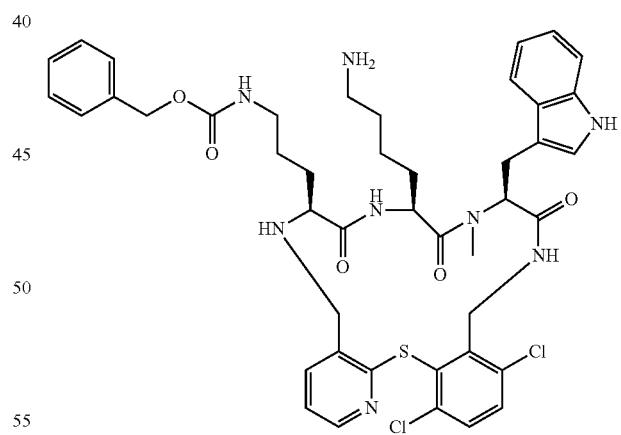

Example 139 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(CBZ)—OH.
Tether: Intermediate 30
MS (M+H$^+$): expected 872.9; observed 873.3

Example 140

(12S,15S,18S)-15-(4-Amino-butyl)-18-(3-amino-propyl)-4-chloro-12-(1H-indol-3-ylmethyl)-13-methyl-6-phenyl-2-thia-10,13,16,19-tetraaza-tricyclo[19.4.0.0*3,8*]pentacosa-1(25),3,5,7,21,23-hexaene-11,14,17-trione

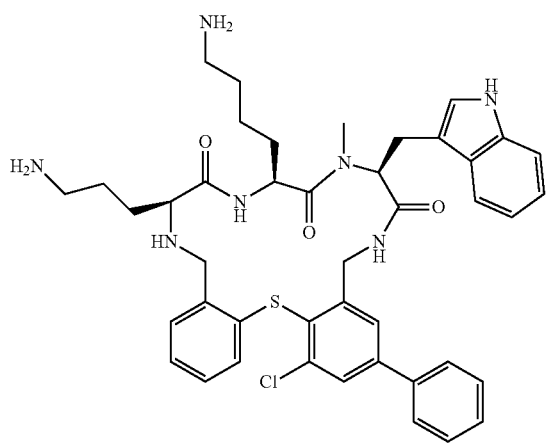 [SMILES: CN1C(=O)[C@H](CCCCN)NC(=O)[C@H](CCCN)NCc2ccccc2Sc2c(Cl)cc(-c3ccccc3)cc2CNC(=O)[C@@H]1Cc1c[nH]c2ccccc12]

Example 140 was prepared according to the General Procedure for Suzuki Coupling of boronic acid derivatives to Peptide Macrocycle Intermediates using the following starting materials:
Macrocycle Intermediate: Intermediate 135
Boronic Acid Derivative: Phenylboronic acid
MS (M+H)$^+$: expected 780.34; observed 780.5

Example 141

(12S,15S,18S)-15-(4-Amino-butyl)-18-(3-amino-propyl)-4-chloro-6-(2-chloro-phenyl)-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

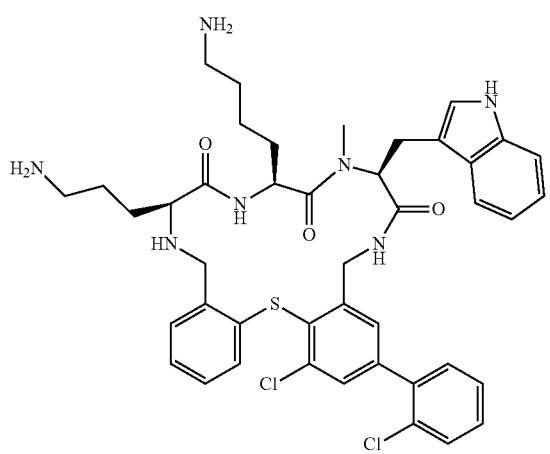 [SMILES: CN1C(=O)[C@H](CCCCN)NC(=O)[C@H](CCCN)NCc2ccccc2Sc2c(Cl)cc(-c3ccccc3Cl)cc2CNC(=O)[C@@H]1Cc1c[nH]c2ccccc12]

Example 141 was prepared according to the General Procedure for Suzuki Coupling of boronic acid derivatives to Peptide Macrocycle Intermediates using the following starting materials:
Macrocycle Intermediate: Intermediate 135
Boronic Acid Derivative: (2-chlorophenyl)boronic acid
MS (M+H)$^+$: expected 814.30; observed 814.5

Example 142

(12S,15S,18S)-15-(4-Amino-butyl)-18-(3-amino-propyl)-4-chloro-12-(1H-indol-3-ylmethyl)-13-methyl-6-pyridin-3-yl-2-thia-10,13,16,19-tetraaza-tricyclo[19.4.0.0*3,8*]pentacosa-1(25),3,5,7,21,23-hexaene-11,14,17-trione

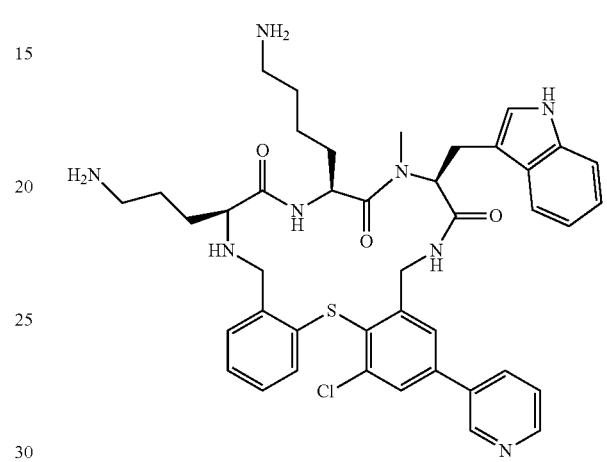

Example 142 was prepared according to the General Procedure for Suzuki Coupling of boronic acid derivatives to Peptide Macrocycle Intermediates using the following starting materials:
Macrocycle Intermediate: Intermediate 135
Boronic Acid Derivative: Pyridin-3-yl boronic acid
MS (M+H)$^+$: expected 781.33; observed 781.6

Example 143

(12S,15S,18S)-15-(4-Amino-butyl)-18-(3-amino-propyl)-4-chloro-12-(1H-indol-3-ylmethyl)-13-methyl-6-pyridin-4-yl-2-thia-10,13,16,19-tetraaza-tricyclo[19.4.0.0*3,8*]pentacosa-1(25),3,5,7,21,23-hexaene-11,14,17-trione

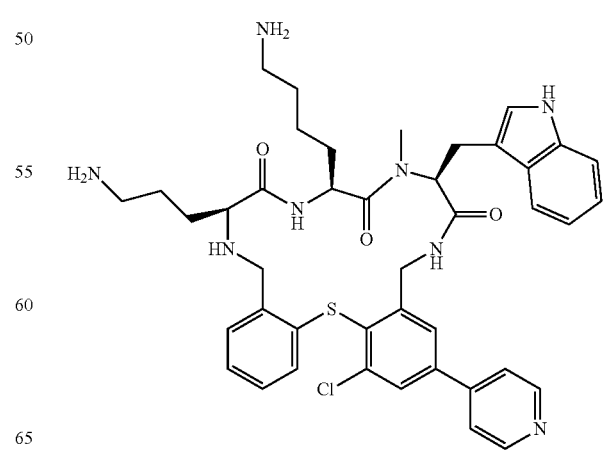

Example 143 was prepared according to the General Procedure for Suzuki Coupling of boronic acid derivatives to Peptide Macrocycle Intermediates using the following starting materials:

Macrocycle Intermediate: Intermediate 135
Boronic Acid Derivative: Pyridin-4-yl boronic acid
MS (M+H)+: expected 781.33; observed 781.5

Example 144

(12S,15S,18S)-15-(4-Amino-butyl)-18-(3-amino-propyl)-4-chloro-12-(1H-indol-3-ylmethyl)-13-methyl-6-(1-methyl-1H-pyrazol-3-yl)-2-thia-10,13,16,19-tetraaza-tricyclo[19.4.0.0*3,8*]pentacosa-1(25),3,5,7,21,23-hexaene-11,14,17-trione

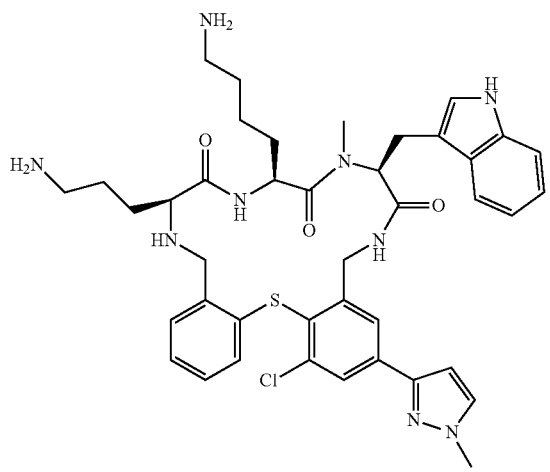 [SMILES: CN1C(=O)[C@H](CCCCN)NC(=O)[C@H](CCCN)NCc2ccccc2Sc2c(Cl)cc(-c3ccn(C)n3)cc2CNC(=O)[C@@H]1Cc1c[nH]c2ccccc12]

Example 144 was prepared according to the General Procedure for Suzuki Coupling of boronic acid derivatives to Peptide Macrocycle Intermediates using the following starting materials:

Macrocycle Intermediate: Intermediate 135
Boronic Acid Derivative: 1-Methyl-3-(4,4,5,5-tetramethyl-1,3,2-dioxaborolan-2-yl)-1H-pyrazole
MS (M+H)+: expected 783.34; observed 784.4

Example 145

3-[(11S,14S,17S)-14-(4-Amino-butyl)-25-chloro-17-(1H-indol-3-ylmethyl)-16-methyl-23-(2-methyl-pyridin-4-yl)-12,15,18-trioxo-2-thia-4,10,13,16,19-pentaaza-tricyclo[19.4.0.0*3,8*]pentacosa-1(25),3(8),4,6,21,23-hexaen-11-yl]-propionamide

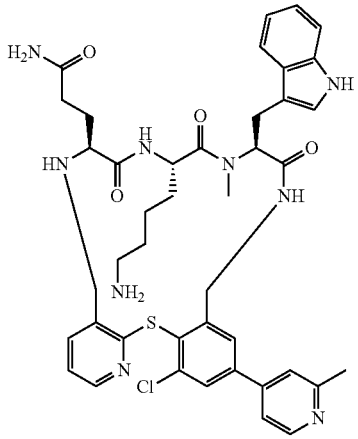 [SMILES: Cc1cc(-c2cc(Cl)c3c(c2)CNC(=O)[C@H](Cc2c[nH]c4ccccc24)N(C)C(=O)[C@H](CCCCN)NC(=O)[C@H](CCC(N)=O)NCc2cccnc2S3)ccn1]

Example 145 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.
Tether: Intermediate 69
MS (M+H+): expected 809.4; observed 810.3

Example 146

(11S,14S,17S)-14-(4-Amino-butyl)-11-(3-amino-propyl)-25-chloro-17-(1H-indol-3-ylmethyl)-16-methyl-23-pyrazin-2-yl-2-thia-4,10,13,16,19-pentaaza-tricyclo[19.4.0.0*3,8*]pentacosa-1(25),3(8),4,6,21,23-hexaene-12,15,18-trione

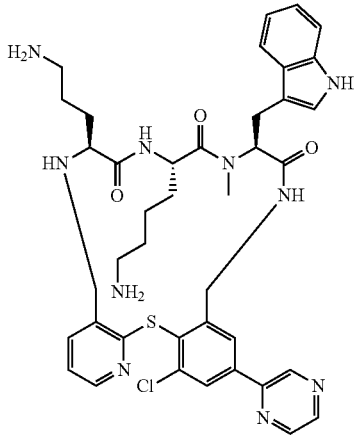 [SMILES: CN1C(=O)[C@H](CCCCN)NC(=O)[C@H](CCCN)NCc2cccnc2Sc2c(Cl)cc(-c3cnccn3)cc2CNC(=O)[C@@H]1Cc1c[nH]c2ccccc12]

Example 146 was prepared according to the General Procedure for Peptide Macrocycle Synthesis using the following:

1. Fmoc-NMe-L-Trp(BOC)—OH,
2. Fmoc-L-Lys(BOC)—OH,
3. Fmoc-L-Orn(BOC)—OH.
Tether: Intermediate 84
MS (M+H$^+$): expected 782.4; observed 783.3

Example 147

(11S,14S,17S)-14-(4-Amino-butyl)-11-(3-amino-propyl)-25-chloro-17-(1H-indol-3-ylmethyl)-16-methyl-22-morpholin-4-yl-2-thia-4,10,13,16,19-pentaaza-tricyclo[19.4.0.0*3,8*]pentacosa-1(25),3(8),4,6,21,23-hexaene-12,15,18-trione

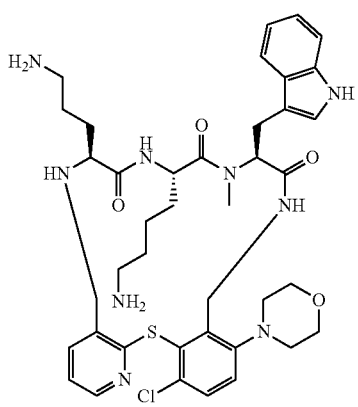 [SMILES: CN1C(=O)[C@H](CCCCN)NC(=O)[C@H](CCCN)NCc2cccnc2Sc2c(Cl)ccc(N3CCOCC3)c2CNC(=O)[C@@H]1Cc1c[nH]c2ccccc12]

Example 147 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 85
MS (M+H$^+$): expected 789.4; observed 790.4

Example 148

(11S,14S,17S)-14-(4-Amino-butyl)-11-(3-amino-propyl)-25-chloro-17-(1H-indol-3-ylmethyl)-16-methyl-23-pyridazin-4-yl-2-thia-4,10,13,16,19-pentaaza-tricyclo[19.4.0.0*3,8*]pentacosa-1(25),3(8),4,6,21,23-hexaene-12,15,18-trione

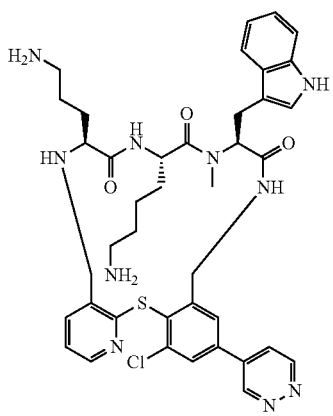 [SMILES: CN1C(=O)[C@H](CCCCN)NC(=O)[C@H](CCCN)NCc2cccnc2Sc2c(Cl)cc(-c3ccnnc3)cc2CNC(=O)[C@@H]1Cc1c[nH]c2ccccc12]

Example 148 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 86
MS (M+H$^+$): expected 782.4; observed 783.3

Example 149

11-(3-amino-propyl)-25-chloro-17-(1H-indol-3-ylmethyl)-16-methyl-23-phenyl-2-thia-4,10,13,16,19-pentaaza-tricyclo[19.4.0.0*3,8*]pentacosa-1(25),3(8),4,6,21,23-hexaene-12,15,18-trione

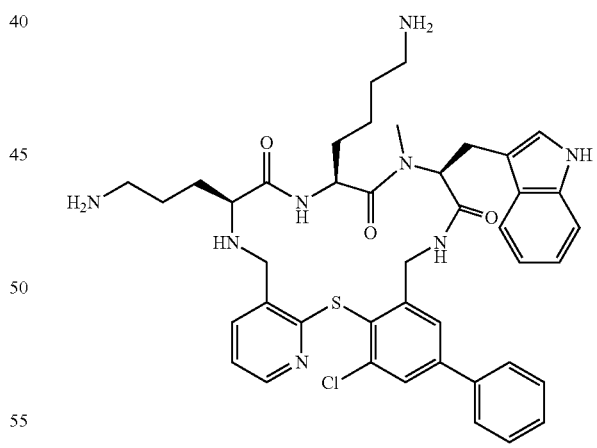

Example 149 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 87
MS (M+H$^+$): expected 780.4; observed 781.5

Example 150

(11S,14S,17S)-14-(4-Amino-butyl)-11-(3-amino-propyl)-25-chloro-17-(1H-indol-3-ylmethyl)-16-methyl-23-pyridin-2-yl-2-thia-4,10,13,16,19-pentaaza-tricyclo[19.4.0.0*3,8*]pentacosa-1(25),3(8),4,6,21,23-hexaene-12,15-18-trione

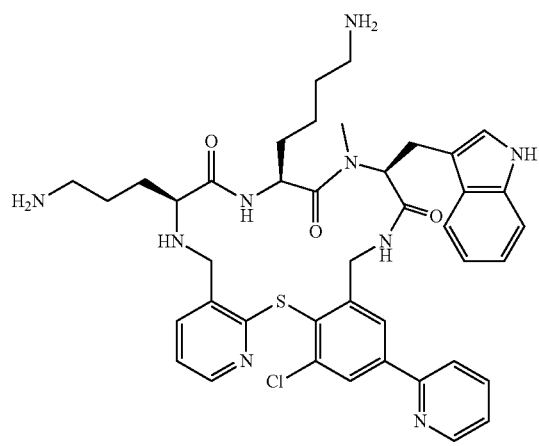 [SMILES: CN1C(=O)[C@H](CCCCN)NC(=O)[C@H](CCCN)NCc2cccnc2Sc2c(Cl)cc(-c3ccccn3)cc2CNC(=O)[C@@H]1Cc1c[nH]c2ccccc12]

Example 150 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 88
MS (M+H$^+$): expected 781.4; observed 782.6

Example 151

(12S,15S,18S)-15-(4-Amino-butyl)-18-(3-amino-propyl)-6-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

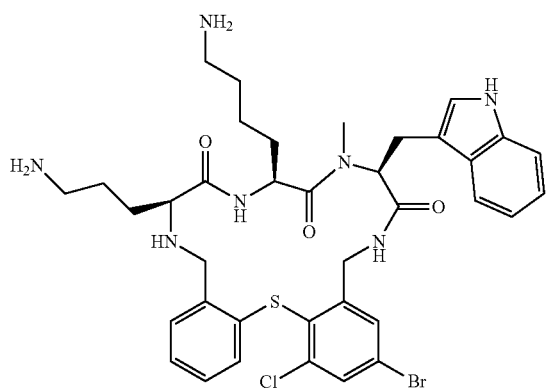 [SMILES: CN1C(=O)[C@H](CCCCN)NC(=O)[C@H](CCCN)NCc2ccccc2Sc2c(Cl)cc(Br)cc2CNC(=O)[C@@H]1Cc1c[nH]c2ccccc12]

Example 151 was prepared by BOC-deprotection of intermediate 135.
MS (M+H)$^+$: expected 782.22; observed 782.3

Example 152

(8S,11S,14S)-8-((1H-Indol-3-yl)methyl)-11-(4-aminobutyl)-14-(3-aminopropyl)-1,4-dichloro-9-methyl-5,6,8,9,11,12,15,16-octahydrobenzo[b]pyrido[4,3-p][1,5,8,11,14]thiatetraazacycloheptadecine-7,10,13(14H)-trione

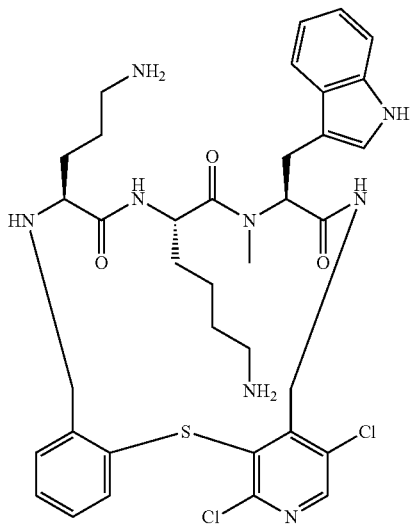 [SMILES: CN1C(=O)[C@H](CCCCN)NC(=O)[C@H](CCCN)NCc2ccccc2Sc2c(Cl)ncc(Cl)c2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 90. Macrocyclization: 1.4 eq HATU, 10 eq DIPEA, in DCM at rt over night. Deprotection: DCM/TFA 1:1 at 40° C. The title compound was obtained as blue powder (13 mg). MS ESI (m/z): 739.3 [(M+H)$^+$]

Example 153

(8S,11S,14S)-8-((1H-Indol-3-yl)methyl)-11-(4-aminobutyl)-14-(3-aminopropyl)-3-chloro-9-methyl-5,6,8,9,11,12,15,16-octahydrobenzo[b]pyrido[4,3-p][1,5,8,11,14]thiatetraazacycloheptadecine-7,10,13(14H)-trione

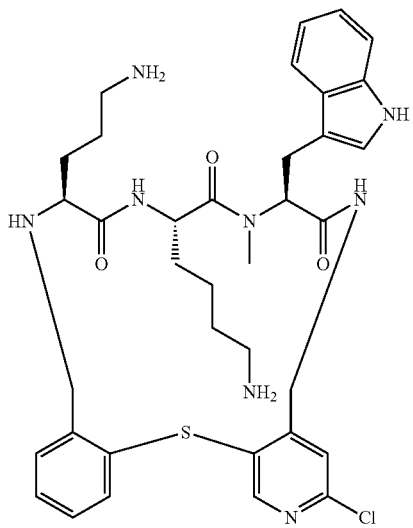 [SMILES: CN1C(=O)[C@H](CCCCN)NC(=O)[C@H](CCCN)NCc2ccccc2Sc2cnc(Cl)cc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 91 using NMP/MeOH/AcOH 1:1:0.012 as solvent mixture. Macrocyclization: 2.4 eq HATU, 10 eq DIPEA, in DCM at rt over night. Deprotection: DCM/TFA 1:1 at 30° C. The title compound was obtained as off white powder (6 mg). MS ESI (m/z): 705.3 [(M+H)$^+$]

Example 154

(12S,15S,18S)-15-(4-Amino-butyl)-18-(3-amino-propyl)-4-chloro-12-(1H-indol-3-ylmethyl)-13-methyl-6-(1-methyl-1H-imidazol-4-yl)-2-thia-10,13,16,19-tetraaza-tricyclo[19.4.0.0*3,8*]pentacosa-1(25),3,5,7,21,23-hexaene-11,14,17-trione

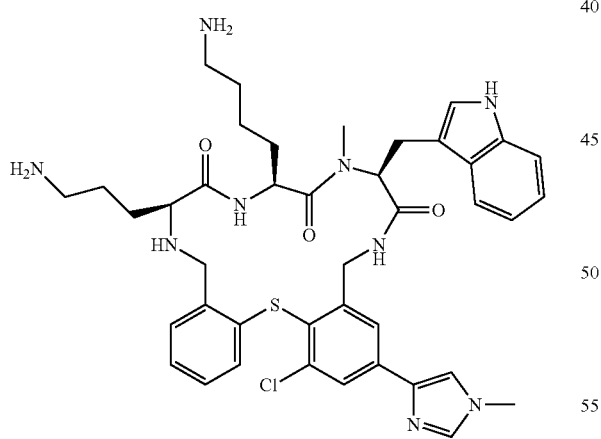

Example 154 was prepared according to the General Procedure for Suzuki Coupling of boronic acid derivatives to Peptide Macrocycle Intermediates using the following starting materials:

Macrocycle Intermediate: Intermediate 135

Boronic Acid Derivative: 1-methyl-4-(4,4,5,5-tetramethyl-1,3,2-dioxaborolan-2-yl)-1H-imidazole MS (M+H)$^+$: expected 784.34; observed 784.4

Example 155

3-[(11S,14S,17S)-14-(4-Amino-butyl)-17-(1H-indol-3-ylmethyl)-16-methyl-12,15,18-trioxo-23-phenyl-25-trifluoromethyl-2-thia-10,13,16,19-tetraaza-tricyclo[19.4.0.0*3,8*]pentacosa-1(25),3,5,7,21,23-hexaen-11-yl]-propionamide

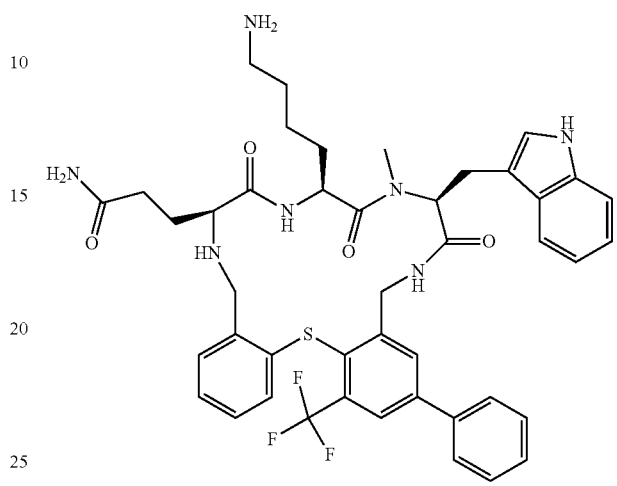

Example 155 was prepared according to the General Procedure for Peptide Macrocycle Synthesis using the following starting materials:

Amino acids:
1. Fmoc-L-NMe-Trp(BOC)—OH,
2. Fmoc-L-Lys(BOC)—OH,
3. Fmoc-L-Gln(TRT)-OH.

Tether: Intermediate 80

MS (M+H)$^+$: expected 828.34; observed 828.6

Example 156

(7S,10S,13S)-13-((1H-Indol-3-yl)methyl)-10-(4-aminobutyl)-7-(3-aminopropyl)-20-chloro-12-methyl-18-(trifluoromethyl)-6,7,9,10,12,13,15,16-octahydrobenzo[b]pyrido[3,4-p][1,5,8,11,14]thiatetraazacycloheptadecine-8,11,14(5H)-trione

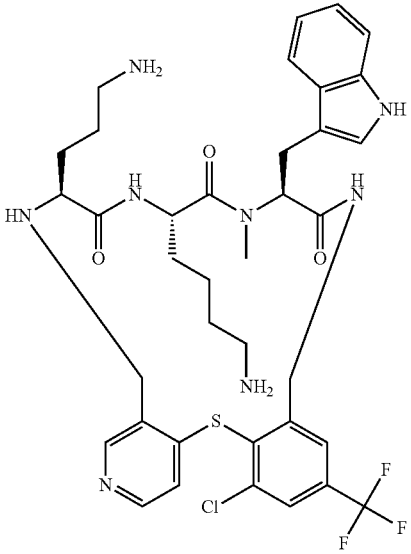 [SMILES: CN1C(=O)[C@H](CCCCN)NC(=O)[C@H](CCCN)NCc2cnccc2Sc2c(Cl)cc(C(F)(F)F)cc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 92 using NMP/MEOH/AcOH 1:1:0.01 as solvent mixture. Macrocyclization: 2.4 eq HATU, 10 eq DIPEA, in DCM at rt 1 h. Deprotection: DCM/TFA 1:1 at 30° C. The title compound was obtained as white solid (3 mg). MS ESI (m/z): 773.3 [(M+H)$^+$]

Example 157

(7S,10S,13S)-13-((1H-Indol-3-yl)methyl)-10-(4-aminobutyl)-7-(3-aminopropyl)-20-chloro-12-methyl-6,7,9,10,12,13,15,16-octahydrodipyrido[2,3-b:3',4'-p][1,5,8,11,14]thiatetraazacycloheptadecine-8,11,14(5H)-trione

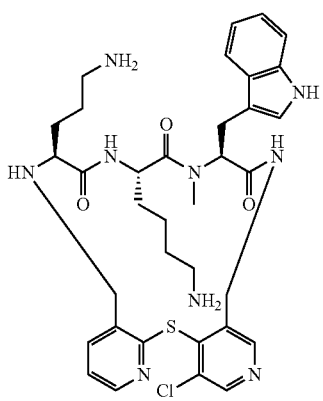 [SMILES: CN1C(=O)[C@H](CCCCN)NC(=O)[C@H](CCCN)NCc2cccnc2Sc2c(Cl)cncc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 93 using DMF/MeOH/AcOH 1:1:0.02 as solvent mixture. Macrocyclization: 1.2 eq HATU, 4 eq DIPEA, in DCM at rt 1 h. Deprotection: DCM/TFA 1:1, then concentrating in vacuo, addition of water and stirring over night. The title compound was obtained as orange solid (31 mg). MS ESI (m/z): 706.4 [(M+H)$^+$]

Example 158

(8S,11S,14S)-8-((1H-Indol-3-yl)methyl)-11-(4-aminobutyl)-14-(3-aminopropyl)-1-chloro-9-methyl-5,6,8,9,11,12,15,16-octahydrobenzo[b]pyrido[3,4-p][1,5,8,11,14]thiatetraazacycloheptadecine-7,10,13(14H)-trione

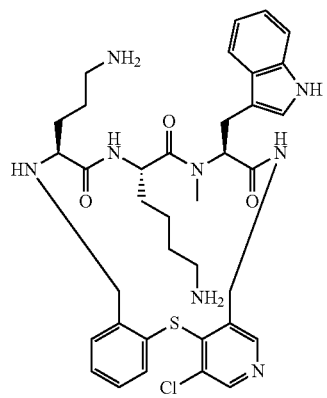 [SMILES: CN1C(=O)[C@H](CCCCN)NC(=O)[C@H](CCCN)NCc2ccccc2Sc2c(Cl)cncc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1 eq Intermediate 94 using NMP/MeOH/AcOH 1:1:0.01 as solvent mixture. Macrocyclization: 2.4 eq HATU, 10 eq DIPEA, in DCM at rt 1 h. Deprotection: DCM/TFA 1:1 at 30° C. The title compound was obtained as yellow solid (9 mg). MS ESI (m/z): 705.3 [(M+H)$^+$]

Example 159

(7S,10S,13S)-13-((1H-Indol-3-yl)methyl)-10-(4-aminobutyl)-7-(3-aminopropyl)-18-chloro-12-methyl-6,7,9,10,12,13,15,16-octahydrodipyrido[2,3-b:4',3'-p][1,5,8,11,14]thiatetraazacycloheptadecine-8,11,14(5H)-trione

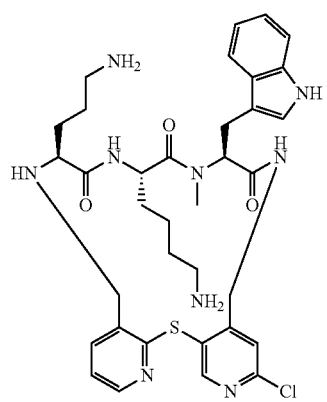 [SMILES: CN1C(=O)[C@H](CCCCN)NC(=O)[C@H](CCCN)NCc2cccnc2Sc2cnc(Cl)cc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 95 using NMP/MeOH/AcOH 1:1:0.01 as solvent mixture. Macrocyclization: 2.4 eq HATU, 10 eq DIPEA, in DCM at rt 1 h. Deprotection: DCM/TFA 1:1 at 30° C. The title compound was obtained as light yellow solid (4 mg). MS ESI (m/z): 706.5 [(M+H)$^+$]

Example 160

3-[(11S,14S,17S)-14-(3-Amino-propyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-propionamide

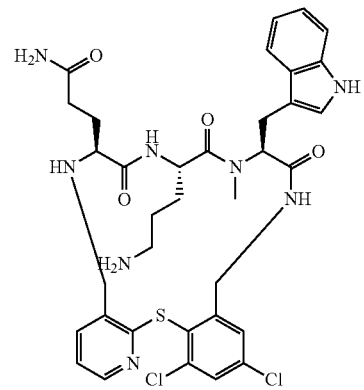 [SMILES: CN1C(=O)[C@H](CCCN)NC(=O)[C@H](CCC(N)=O)NCc2cccnc2Sc2c(Cl)cc(Cl)cc2CNC(=O)[C@@H]1Cc1c[nH]c2ccccc12]

Example 160 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.
Tether: Intermediate 47
MS (M+H$^+$): expected 738.7; observed 739.7

Example 161

3-[(11S,14S,17S)-11-(3-Amino-propyl)-17-(1H-indol-3-ylmethyl)-16-methyl-12,15,18-trioxo-23-phenyl-25-trifluoromethyl-2-thia-10,13,16,19-tetraaza-tricyclo[19.4.0.0*3,8*]pentacosa-1(25),3,5,7,21,23-hexaen-14-yl]-propionamide

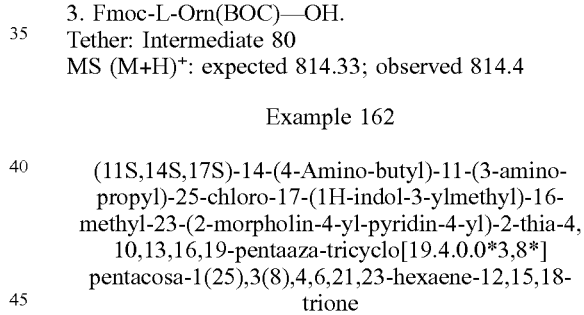

Example 161 was prepared according to the General Procedure for Peptide Macrocycle Synthesis using the following starting materials:
Amino acids:
1. Fmoc-L-NMe-Trp(BOC)—OH,
2. Fmoc-L-Gln(TRT)-OH,
3. Fmoc-L-Orn(BOC)—OH.
Tether: Intermediate 80
MS (M+H)$^+$: expected 814.33; observed 814.4

Example 162

(11S,14S,17S)-14-(4-Amino-butyl)-11-(3-amino-propyl)-25-chloro-17-(1H-indol-3-ylmethyl)-16-methyl-23-(2-morpholin-4-yl-pyridin-4-yl)-2-thia-4,10,13,16,19-pentaaza-tricyclo[19.4.0.0*3,8*]pentacosa-1(25),3(8),4,6,21,23-hexaene-12,15,18-trione

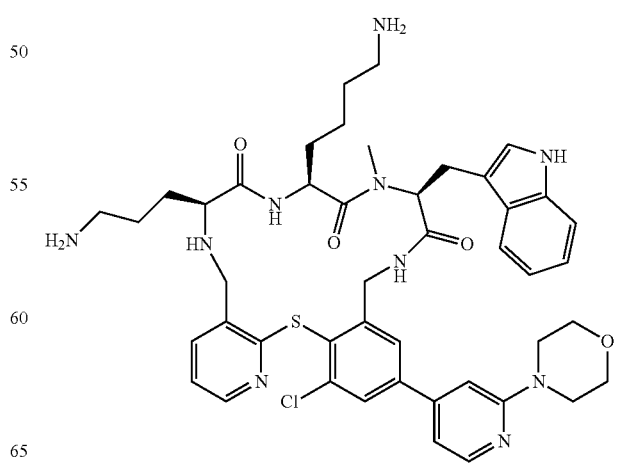

Example 162 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.

Tether: Intermediate 96
MS (M+H⁺): expected 867.6; observed 868.5

Example 163 (RO7188308-001-001)

3-[(11S,14S,17S)-14-(4-Amino-butyl)-25-chloro-17-(1H-indol-3-ylmethyl)-16-methyl-12,15,18-trioxo-23-pyridin-2-yl-2-thia-4,10,13,16,19-pentaaza-tricyclo[19.4.0.0*3,8*]pentacosa-1(25),3(8),4,6,21,23-hexaen-11-yl]-propionamide

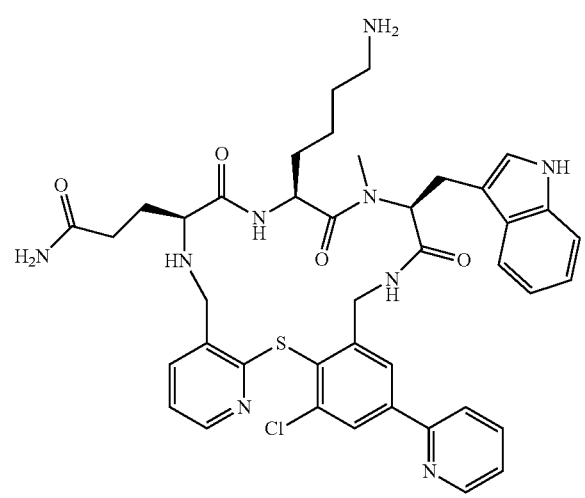 [SMILES: CN1C(=O)[C@H](CCCCN)NC(=O)[C@H](CCC(N)=O)NCc2cccnc2Sc2c(Cl)cc(-c3ccccn3)cc2CNC(=O)[C@@H]1Cc1c[nH]c2ccccc12]

Example 163 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.

Tether: Intermediate 88
MS (M+H⁺): expected 795.4; observed 796.6

Example 164

(11S,14S,17S)-14-(4-Amino-butyl)-11-(3-aminopropyl)-25-chloro-23-(2-chloro-pyridin-4-yl)-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione

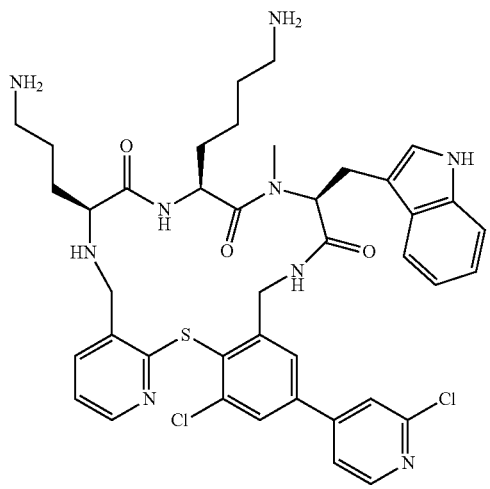 [SMILES: CN1C(=O)[C@H](CCCCN)NC(=O)[C@H](CCCN)NCc2cccnc2Sc2c(Cl)cc(-c3ccnc(Cl)c3)cc2CNC(=O)[C@@H]1Cc1c[nH]c2ccccc12]

Example 164 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.

Tether: Intermediate 97
MS (M+H⁺): expected 815.8; observed 816.6

Example 165

(11S,14S,17S)-14-(4-Amino-butyl)-11-(3-aminopropyl)-25-chloro-23-(6-hydroxy-pyridin-3-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

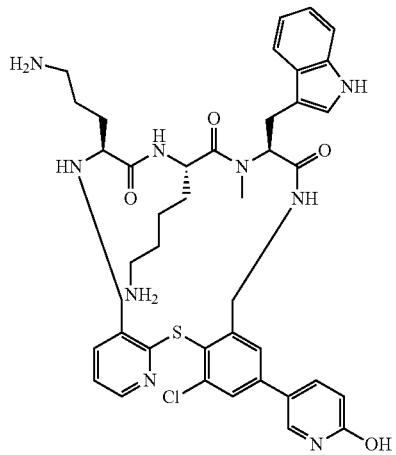 [SMILES: CN1C(=O)[C@H](CCCCN)NC(=O)[C@H](CCCN)NCc2cccnc2Sc2c(Cl)cc(-c3ccc(O)nc3)cc2CNC(=O)[C@@H]1Cc1c[nH]c2ccccc12]

Example 165 was prepared according to the General Procedure for Peptide Macrocycle Synthesis using the following starting materials:

1. Fmoc-NMe-L-Trp(BOC)—OH,
2. Fmoc-L-Lys(BOC)—OH,
3. Fmoc-L-Orn(BOC)—OH.

Tether: Intermediate 98

MS (M+H⁺): expected 797.4; observed 798.3

Example 166

(11S,14S,17S)-14-(4-Amino-butyl)-11-(3-amino-propyl)-25-chloro-23-(6-dimethylamino-pyridin-3-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

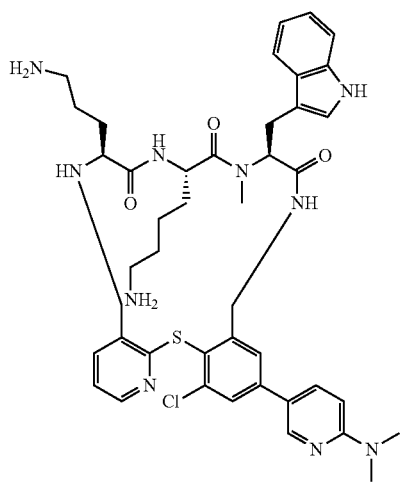 [SMILES: CN(C)c1ccc(-c2cc(Cl)c3c(c2)CNC(=O)[C@H](Cc2c[nH]c4ccccc24)N(C)C(=O)[C@H](CCCCN)NC(=O)[C@H](CCCN)NCc2cccnc2S3)cn1]

Example 166 was prepared according to the General Procedure for Peptide Macrocycle Synthesis using the following starting materials:

1. Fmoc-NMe-L-Trp(BOC)—OH,
2. Fmoc-L-Lys(BOC)—OH,
3. Fmoc-L-Orn(BOC)—OH.

Tether: Intermediate 99

MS (M+H⁺): expected 824.5; observed 825.5

Example 167

(7S,10S,13S)-13-((1H-Indol-3-yl)methyl)-10-(4-aminobutyl)-7-(3-aminopropyl)-12-methyl-18-(2-methylpyridin-4-yl)-6,7,9,10,12,13,15,16-octahydrodipyrido[2,3-b:4',3'-p][1,5,8,11,14]thiatetraazacycloheptadecine-8,11,14(5H)-trione

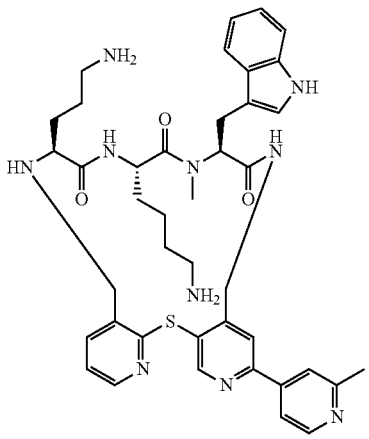 [SMILES: Cc1cc(-c2cc3c(cn2)Sc2ncccc2CN[C@@H](CCCN)C(=O)N[C@@H](CCCCN)C(=O)N(C)[C@@H](Cc2c[nH]c4ccccc24)C(=O)NC3)ccn1]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 95 using NMP/MeOH/AcOH 1:1:0.01 as solvent mixture. Macrocyclization: 2.4 eq HATU, 10 eq DIPEA, in DCM at rt 1 h. Suzuki in analogy to Example 189 using (2-methylpyridin-4-yl)boronic acid. Deprotection: DCM/TFA 1:1, concentration in vacuo, then stirring in acetonitrile water. The title compound was obtained as brown solid (12 mg). MS ESI (m/z): 763.5 [(M+H)⁺]

Example 168

(12S,15S,18S)-15-(4-Amino-butyl)-18-(3-amino-propyl)-5-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

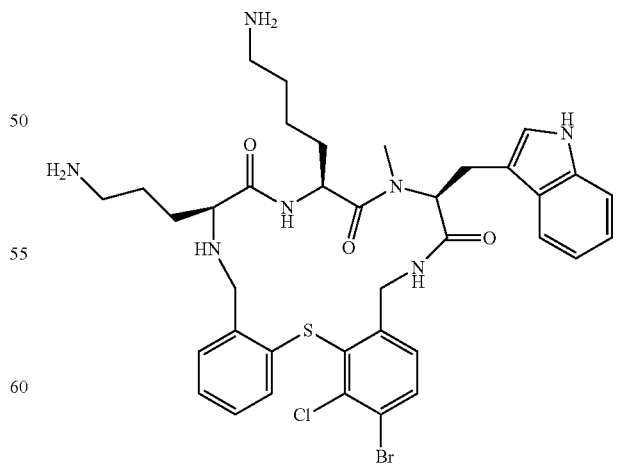

Example 168 was prepared by BOC-deprotection of intermediate 136.

MS (M+H)⁺: expected 782.22; observed 782.5

Example 169

3-[(11S,14S,17S)-14-(4-Amino-butyl)-25-chloro-23-(3,5-dimethyl-isoxazol-4-yl)-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-propionamide

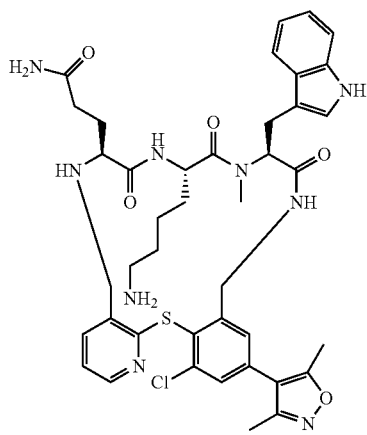 [SMILES: Cc1noc(C)c1-c1cc(Cl)c2c(c1)CNC(=O)[C@H](Cc1c[nH]c3ccccc13)N(C)C(=O)[C@H](CCCCN)NC(=O)[C@H](CCC(N)=O)NCc1cccnc1S2]

Example 169 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.
Tether: Intermediate 101
MS (M+H$^+$): expected 813.4; observed 814.3

Example 170

(11S,14S,17S)-14-(4-Amino-butyl)-11-(3-amino-propyl)-25-chloro-16-methyl-17-(2-methyl-1H-indol-3-ylmethyl)-23-(2-methyl-pyridin-4-yl)-2-thia-4,10,13,16,19-pentaaza-tricyclo[19.4.0.0*3,8*]pentacosa-1(25),3(8),4,6,21,23-hexaene-12,15,18-trione

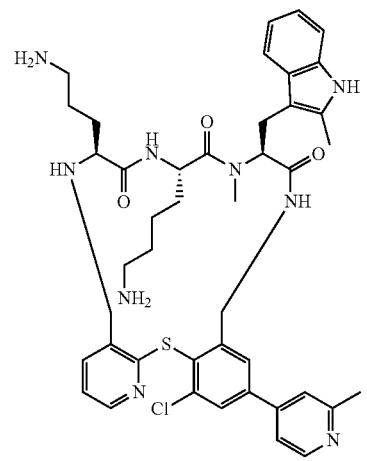 [SMILES: Cc1cc(-c2cc(Cl)c3c(c2)CNC(=O)[C@H](Cc2c(C)[nH]c4ccccc24)N(C)C(=O)[C@H](CCCCN)NC(=O)[C@H](CCCN)NCc2cccnc2S3)ccn1]

Example 170 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid
2. Fmoc-L-Lys(BOC)—OH,
3. Fmoc-L-Orn(BOC)—OH.
Tether: Intermediate 69
MS (M+H$^+$): expected 809.5; observed 810.4

Example 171

(11S,14S,17S)-14-(4-Amino-butyl)-11-(3-amino-propyl)-25-chloro-23-(2-methoxy-pyridin-4-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

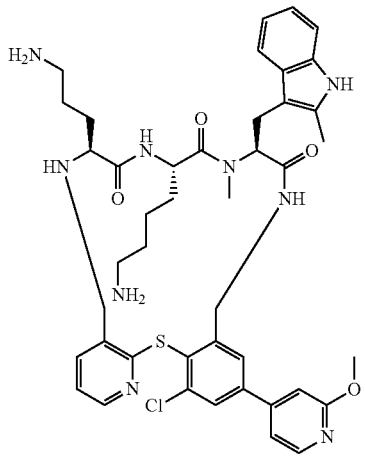 [SMILES: COc1cc(-c2cc(Cl)c3c(c2)CNC(=O)[C@H](Cc2c(C)[nH]c4ccccc24)N(C)C(=O)[C@H](CCCCN)NC(=O)[C@H](CCCN)NCc2cccnc2S3)ccn1]

Example 171 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.
Tether: Intermediate 67
MS (M+H$^+$): expected 825.4; observed 826.4

Example 172

(11S,14S,17S)-14-(4-Amino-butyl)-11-(3-amino-propyl)-25-chloro-17-(1H-indol-3-ylmethyl)-23-(4-methanesulfonyl-phenyl)-16-methyl-2-thia-4,10,13,16,19-pentaaza-tricyclo[19.4.0.0*3,8*]pentacosa-1(25),3(8),4,6,21,23-hexaene-12,15,18-trione

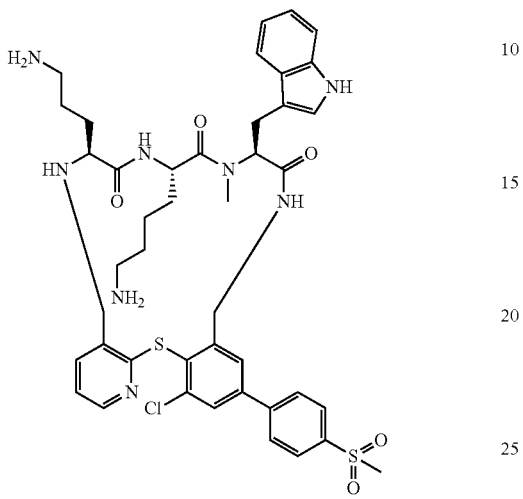

Example 172 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 102
MS (M+H$^+$): expected 858.5; observed 859.3

Example 173

(11S,14S,17S)-14-(4-Amino-butyl)-11-(3-amino-propyl)-25-chloro-17-(1H-indol-3-ylmethyl)-23-(5-methanesulfonyl-pyridin-3-yl)-16-methyl-2-thia-4,10,13,16,19-pentaaza-tricyclo[19.4.0.0*3,8*]pentacosa-1(25),3(8),4,6,21,23-hexaene-12,15,18-trione

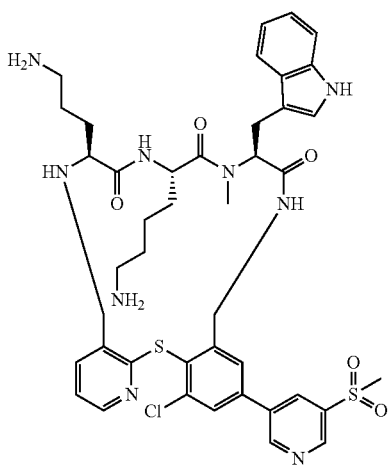 [SMILES: CN1C(=O)[C@H](CCCCN)NC(=O)[C@H](CCCN)NCc2cccnc2Sc2c(Cl)cc(-c3cncc(S(C)(=O)=O)c3)cc2CNC(=O)[C@@H]1Cc1c[nH]c2ccccc12]

Example 173 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 103
MS (M+H$^+$): expected 859.5; observed 860.3

Example 174

(11S,14S,17S)-14-(4-Amino-butyl)-11-(3-amino-propyl)-23-(3-amino-pyrrolidin-1-yl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

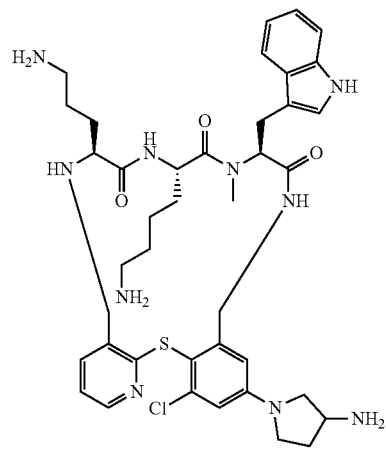 [SMILES: CN1C(=O)[C@H](CCCCN)NC(=O)[C@H](CCCN)NCc2cccnc2Sc2c(Cl)cc(N3CCC(N)C3)cc2CNC(=O)[C@@H]1Cc1c[nH]c2ccccc12]

Example 174 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 82
MS (M+H$^+$): expected 788.4; observed 789.4

Example 175

(11S,14S,17S)-14-(4-Amino-butyl)-11-(3-amino-propyl)-25-chloro-23-(3,5-dimethyl-1H-pyrazol-4-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

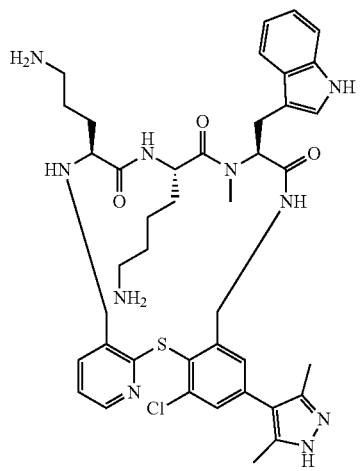 [SMILES: Cc1n[nH]c(C)c1-c1cc(Cl)c2c(c1)CNC(=O)[C@H](Cc1c[nH]c3ccccc13)N(C)C(=O)[C@H](CCCCN)NC(=O)[C@H](CCCN)NCc1cccnc1S2]

Example 175 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 104
MS (M+H$^+$): expected 798.4; observed 799.4

Example 176

(12S,15S,18S)-15-(4-Amino-butyl)-18-(3-amino-propyl)-4-chloro-12-(1H-indol-3-ylmethyl)-13-methyl-5-phenyl-2-thia-10,13,16,19-tetraaza-tricyclo[19.4.0.0*3,8*]pentacosa-1(25),3,5,7,21,23-hexaene-11,14,17-trione

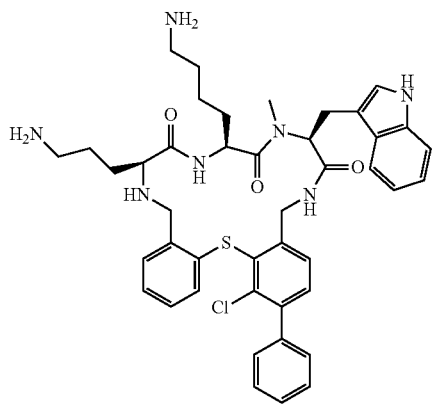 [SMILES: CN1C(=O)[C@H](CCCCN)NC(=O)[C@H](CCCN)NCc2ccccc2Sc2c(ccc(-c3ccccc3)c2Cl)CNC(=O)[C@@H]1Cc1c[nH]c2ccccc12]

Example 176 was prepared according to the General Procedure for Suzuki Coupling of boronic acid derivatives to Peptide Macrocycle Intermediates using the following starting materials:

Macrocycle Intermediate: Intermediate 136
Boronic Acid Derivative: Phenylboronic acid
MS (M+H)$^+$: expected 780.34; observed 780.5

Example 177

(11S,14S,17S)-14-(4-Amino-butyl)-11-(3-amino-propyl)-25-chloro-23-(2-fluoro-pyridin-4-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

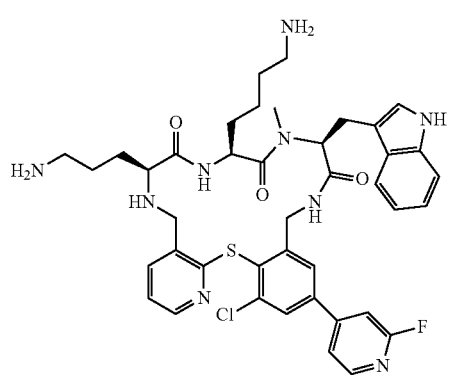 [SMILES: CN1C(=O)[C@H](CCCCN)NC(=O)[C@H](CCCN)NCc2cccnc2Sc2c(Cl)cc(-c3ccnc(F)c3)cc2CNC(=O)[C@@H]1Cc1c[nH]c2ccccc12]

Example 177 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 105
MS (M+H$^+$): expected 799.4; observed 800.6

Example 178

(7S,10S,13S)-13-((1H-Indol-3-yl)methyl)-10-(4-aminobutyl)-7-(3-aminopropyl)-12-methyl-18-(6-methylpyridin-3-yl)-6,7,9,10,12,13,15,16-octahydrodipyrido[2,3-b:4',3'-p][1,5,8,11,14]thiatetraazacycloheptadecine-8,11,14(5H)-trione

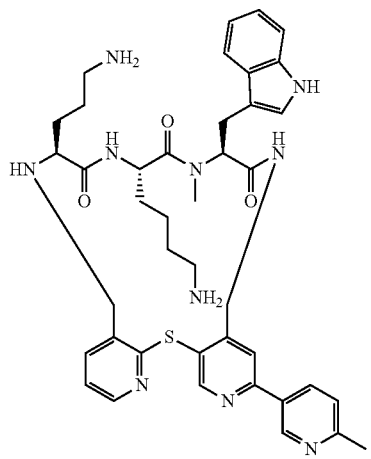 [SMILES: Cc1ccc(-c2cc3c(cn2)Sc2ncccc2CN[C@@H](CCCN)C(=O)N[C@@H](CCCCN)C(=O)N(C)[C@@H](Cc2c[nH]c4ccccc24)C(=O)NC3)cn1]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 95 using NMP/MeOH/AcOH 1:1:0.012 as solvent mixture. Macrocyclization: 1.2 eq HATU, 4 eq DIPEA, in DCM at rt 1 h. Suzuki in analogy to Example 189 using (6-methylpyridin-3-yl)boronic acid. Deprotection: DCM/TFA 1:1, concentrated in vacuo, then stirring in acetonitrile/water. The title compound was obtained as orange solid (9 mg). MS ESI (m/z): 763.6 [(M+H)$^+$]

Example 179

(8S,11S,14S)-8-((1H-Indol-3-yl)methyl)-11-(4-aminobutyl)-14-(3-aminopropyl)-3-chloro-9-methyl-5,6,8,9,11,12,15,16-octahydrobenzo[b]pyrido[3,2-p][1,5,8,11,14]thiatetraazacycloheptadecine-7,10,13(14H)-trione

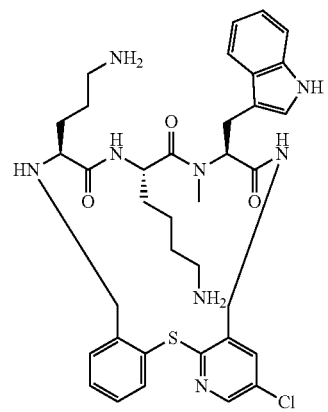 [SMILES: CN1C(=O)[C@H](CCCCN)NC(=O)[C@H](CCCN)NCc2ccccc2Sc2ncc(Cl)cc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 106 in NMP/MeOH/AcOH 1:1:0.012 as solvent mixture. Macrocyclization: 1.2 eq HATU, 4 eq DIPEA, in DCM at rt 1 h. Deprotection: DCM/TFA 1:1, then concentrating in vacuo and stirring with acetonitrile/water 1:1. The title compound was obtained as light yellow foam (46 mg). MS ESI (m/z): 705.5 [(M+H)$^+$]

Example 180

[(11S,14S,17S)-14-(4-Amino-butyl)-23,25-dichloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-ylmethyl]-urea

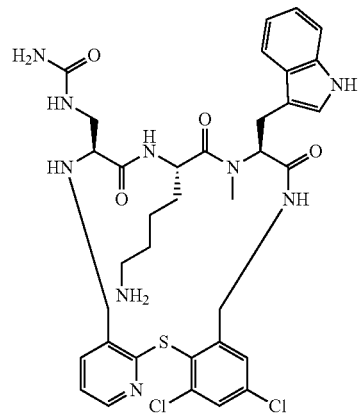 [SMILES: CN1C(=O)[C@H](CCCCN)NC(=O)[C@H](CNC(N)=O)NCc2cccnc2Sc2c(Cl)cc(Cl)cc2CNC(=O)[C@@H]1Cc1c[nH]c2ccccc12]

Example 180 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. (S)-2-(9H-Fluoren-9-ylmethoxycarbonylamino)-3-ureido-propionic acid.
Tether: Intermediate 47
MS (M+H$^+$): expected 753.7; observed 754.2

Example 181

(11S,14S,17S)-14-(4-Amino-butyl)-11-(3-aminopropyl)-25-chloro-16-methyl-17-(2-methyl-1H-indol-3-ylmethyl)-23-pyridin-4-yl-2-thia-4,10,13,16,19-pentaaza-tricyclo[19.4.0.0*3,8*]pentacosa-1(25),3(8),4,6,21,23-hexaene-12,15,18-trione

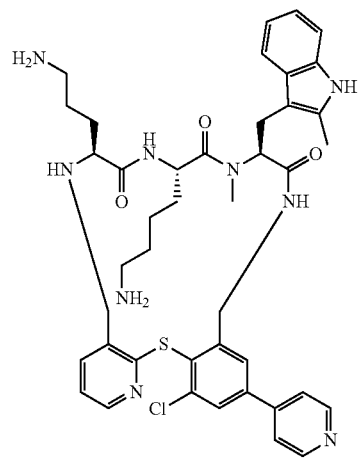

Example 181 was prepared according to the General Procedure for Peptide Macrocycle Synthesis using the following starting materials:
1. (S)-2-(9H-Fluoren-9-yl-methoxycarbonylamino)-3-(2-methyl-1H-indol-3-yl)-propionic acid,
2. Fmoc-L-Lys(BOC)—OH,
3. Fmoc-L-Orn(BOC)—OH.
Tether: Intermediate 66
MS (M+H$^+$): expected 795.4; observed 796.4

Example 182

(11S,14S,17S)-14-(4-Amino-butyl)-11-(3-amino-propyl)-25-chloro-23-(2-chloro-pyridin-4-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

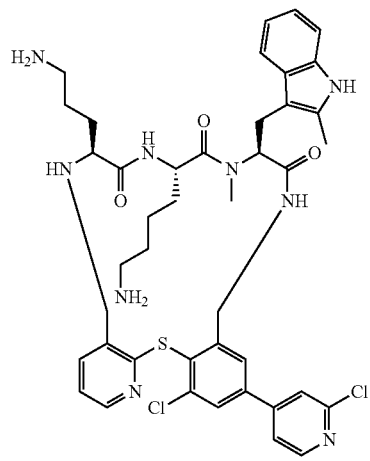 [SMILES: Cc1[nH]c2ccccc2c1C[C@H]1C(=O)NCc2cc(-c3ccnc(Cl)c3)cc(Cl)c2Sc2ncccc2CN[C@@H](CCCN)C(=O)N[C@@H](CCCCN)C(=O)N1C]

Example 182 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.
Tether: Intermediate 97
MS (M+H$^+$): expected 829.9; observed 830.3

Example 183

(11S,14S,17S)-14-(4-Amino-butyl)-11-(3-amino-propyl)-25-chloro-23-(2-fluoro-pyridin-4-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

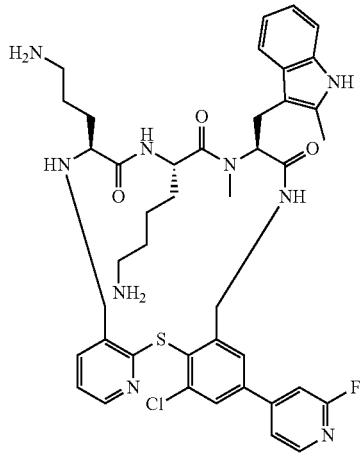

Example 183 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.
Tether: Intermediate 105
MS (M+H$^+$): expected 813.4; observed 814.4

Example 184

3-[(11S,14S,17S)-14-(4-Amino-butyl)-25-chloro-17-(1H-indol-3-ylmethyl)-16-methyl-12,15,18-trioxo-23-phenyl-2-thia-4,10,13,16,19-pentaaza-tricyclo[19.4.0.0*3,8*]pentacosa-1(25),3(8),4,6,21,23-hexaen-11-yl]-propionamide

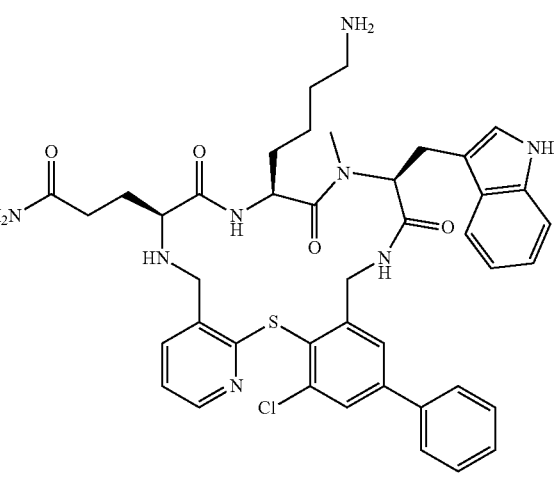

Example 184 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.
Tether: Intermediate 87
MS (M+H$^+$): expected 794.4; observed 795.6

Example 185

(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaene-23-carbonitrile

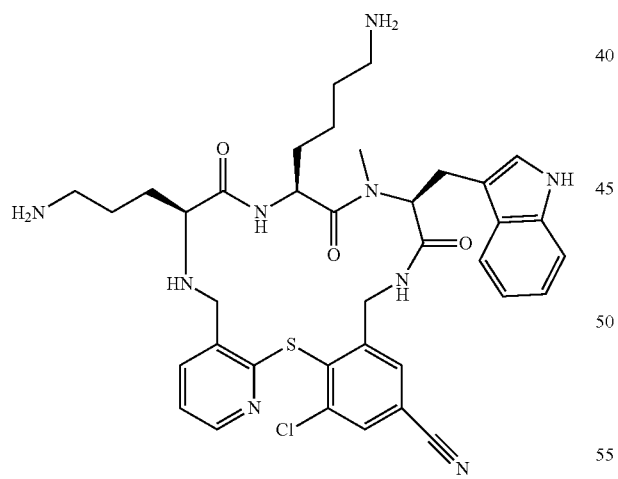

Example 185 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 107
MS (M+H$^+$): expected 729.3; observed 730.4

Example 186

(11S,14S,17S)-14-(4-Amino-butyl)-11-(3-amino-propyl)-25-chloro-23-(3,5-dimethyl-isoxazol-4-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

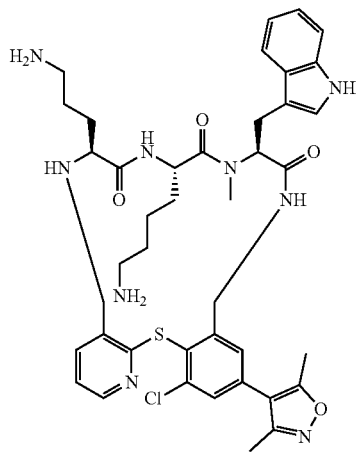 [SMILES: Cc1noc(C)c1-c1cc(Cl)c2c(c1)CNC(=O)[C@H](Cc1c[nH]c3ccccc13)N(C)C(=O)[C@H](CCCCN)NC(=O)[C@H](CCCN)NCc1cccnc1S2]

Example 186 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 101
MS (M+H$^+$): expected 799.4; observed 800.3

Example 187

(11S,14S,17S)-14-(4-Amino-butyl)-11-(3-amino-propyl)-25-chloro-17-(1H-indol-3-ylmethyl)-16-methyl-23-(2-oxa-5-aza-bicyclo[2.2.1]hept-5-yl)-2-thia-4,10,13,16,19-pentaaza-tricyclo[19.4.0.0*3,8*]pentacosa-1(25),3(8),4,6,21,23-hexaene-12,15,18-trione

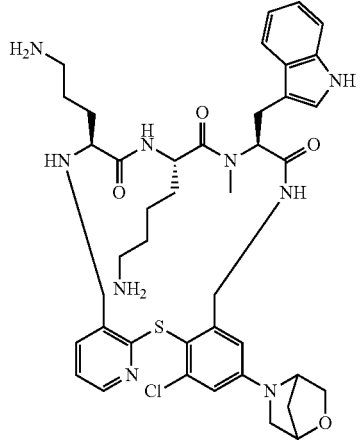 [SMILES: CN1C(=O)[C@H](CCCCN)NC(=O)[C@H](CCCN)NCc2cccnc2Sc2c(Cl)cc(N3CC4CC3CO4)cc2CNC(=O)[C@@H]1Cc1c[nH]c2ccccc12]

Example 187 was prepared according to the General Procedure for Peptide Macrocycle Synthesis using the following starting materials:

1. Fmoc-NMe-L-Trp(BOC)—OH,
2. Fmoc-L-Lys(BOC)—OH,
3. Fmoc-L-Orn(BOC)—OH.

Tether: Intermediate 108

MS (M+H$^+$): expected 801.4; observed 802.4

Example 188

(11S,14S,17S)-14-(4-Amino-butyl)-11-(3-aminopropyl)-23-(3-benzyloxy-prop-1-ynyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

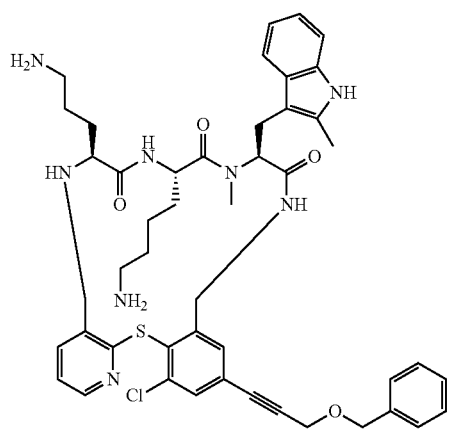 [SMILES: Cc1[nH]c2ccccc2c1C[C@H]1C(=O)NCc2cc(C#CCOCc3ccccc3)cc(Cl)c2Sc2ncccc2CN[C@@H](CCCN)C(=O)N[C@@H](CCCCN)C(=O)N1C]

Example 188 was prepared according to the General Procedure for Peptide Macrocycle Synthesis using the following starting materials:

1. Fmoc-NMe-L-Trp(BOC)—OH,
2. Fmoc-L-Lys(BOC)—OH,
3. Fmoc-L-Orn(BOC)—OH.

Tether: Intermediate 109

MS (M+H$^+$): expected 848.5; observed 849.4

Example 189

(8S,11S,14S)-8-((1H-Indol-3-yl)methyl)-11-(4-aminobutyl)-14-(3-aminopropyl)-4-chloro-9-methyl-1-phenyl-5,6,8,9,11,12,15,16-octahydrobenzo[b]pyrido[4,3-p][1,5,8,11,14]thiatetraazacycloheptadecine-7,10,13(14H)-trione

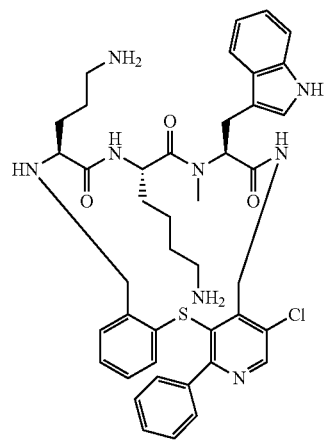 [SMILES: CN1C(=O)[C@H](CCCCN)NC(=O)[C@H](CCCN)NCc2ccccc2Sc2c(-c3ccccc3)ncc(Cl)c2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 90 using NMP/MeOH/AcOH 1:1:0.02 as solvent mixture. Macrocyclization: 1.2 eq HATU, 4 eq DIPEA, in DMF at rt 2 h.

In a pressure tube to a solution of tert-butyl 3-(((8S,11S,14S)-11-(4-((tert-butoxycarbonyl)amino)butyl)-14-(3-((tert-butoxycarbonyl)amino)propyl)-1,4-dichloro-9-methyl-7,10,13-trioxo-5,6,7,8,9,10,11,12,13,14,15,16-dodecahydrobenzo[b]pyrido[4,3-p][1,5,8,11,14]thiatetraazacycloheptadecin-8-yl)methyl)-1H-indole-1-carboxylate (0.025 g, 24 µmol, Eq: 1) and phenylboronic acid pinacol ester (6.38 mg, 31.2 µmol, Eq: 1.3) in dioxane (192 µl) was added 2M aqueous sodium carbonate (48.1 µl). The mixture was sparged with argon for 2 minutes while sonicating the vessel in an ultra sonic bath. Then Pd(Ph$_3$P)$_4$ (5.56 mg, 4.81 µmol, Eq: 0.2) was added, sparging continued for 1 minute, the vessel sealed and the reaction mixture heated to 80° C. for 1.5 hours, then to 100° C. over night. The reaction mixture was diluted with ethyl acetate, 1M aqueous Na$_2$CO$_3$ solution and brine. The mixture was extracted ethyl acetate and the organic layers were washed with brine. The combined organic layers were dried with sodium sulfate, filtered and concentrated in vacuo. The obtained material was directly used without further purification in the deprotection step.

Deprotection: DCM/TFA 2:1, then concentrating in vacuo at room temperature and stirring in acetonitrile/water 1:1. The obtained solution was directly purified by preparative reversed phase HPLC (Column: Phenomenex Gemini-NX 5u 110A, l: 100 mm, dia: 30 mm) using water containing 0.1% TFA/acetonitrile as eluent. The title compound was obtained as light brown powder (17 mg). MS ESI (m/z): 781.4 [(M+H)$^+$]

Example 190

(11S,14S,17S)-14-(4-Amino-butyl)-11-(3-amino-propyl)-25-chloro-17-(1H-indol-3-ylmethyl)-16-methyl-22-pyridin-4-yl-2-thia-4,10,13,16,19-pentaaza-tricyclo[19.4.0.0*3,8*]pentacosa-1(21),3,5,7,22,24-hexaene-12,15,18-trione

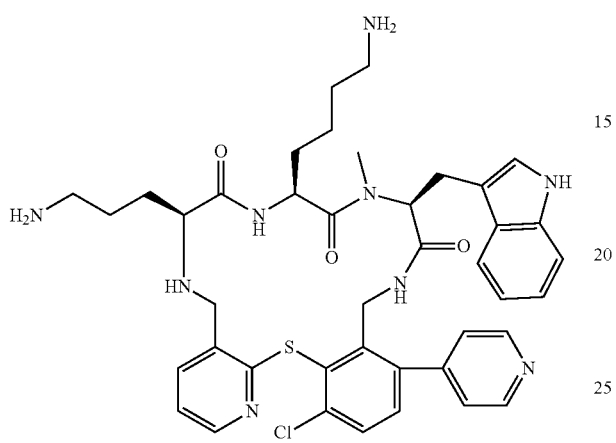

Example 190 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.

Tether: Intermediate 110
MS (M+H⁺): expected 781.4; observed 782.5

Example 191

(11S,14S,17S)-14-(4-Amino-butyl)-11-(3-amino-propyl)-25-chloro-17-(1H-indol-3-ylmethyl)-16-methyl-22-pyridin-3-yl-2-thia-4,10,13,16,19-pentaaza-tricyclo[19.4.0.0*3,8*]pentacosa-1(25),3(8),4,6,21,23-hexaene-12,15,18-trione

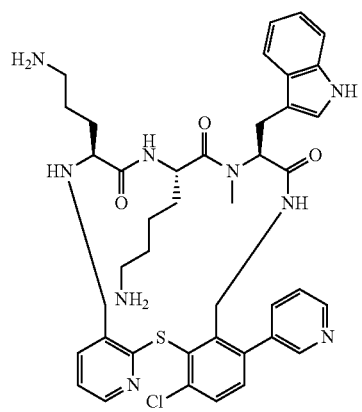

Example 191 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.

Tether: Intermediate 111
MS (M+H⁺): expected 781.4; observed 781.3

Example 192

(8S,11S,14S)-8-((1H-Indol-3-yl)methyl)-11-(4-aminobutyl)-14-(3-aminopropyl)-9-methyl-2-morpholino-5,6,8,9,11,12,15,16-octahydrobenzo[b]pyrido[3,2-p][1,5,8,11,14]thiatetraazacycloheptadecine-7,10,13(14H)-trione

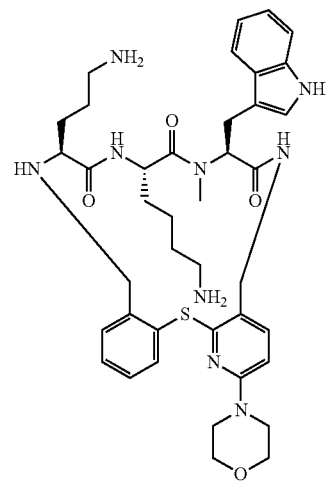 [SMILES: CN1C(=O)[C@H](CCCCN)NC(=O)[C@H](CCCN)NCc2ccccc2Sc2nc(N3CCOCC3)ccc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 0.9 eq Intermediate 112 in NMP/MeOH/AcOH 1:1:0.012 as solvent mixture. Macrocyclization: 1.2 eq HATU, 4 eq DIPEA, in DCM at rt 1 h. Deprotection: DCM/TFA 1:1. The title compound was obtained as white powder (16 mg). MS ESI (m/z): 756.6 [(M+H)⁺]

Example 193

(8S,11S,14S)-8-((1H-Indol-3-yl)methyl)-11-(4-aminobutyl)-14-(3-aminopropyl)-9-methyl-4-morpholino-5,6,8,9,11,12,15,16-octahydrobenzo[b]pyrido[3,4-p][1,5,8,11,14]thiatetraazacycloheptadecine-7,10,13(14H)-trione

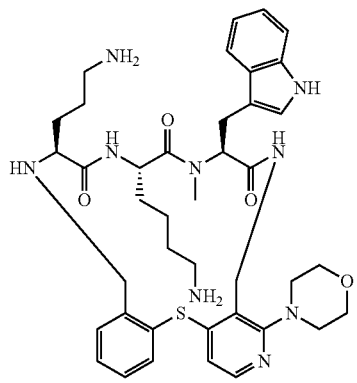 [SMILES: CN1C(=O)[C@H](CCCCN)NC(=O)[C@H](CCCN)NCc2ccccc2Sc2ccnc(N3CCOCC3)c2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.3 eq Intermediate 113 using NMP/MeOH/AcOH 1:1:0.02 as solvent mixture. Macrocyclization: 1.2 eq HATU, 5 eq DIPEA, in DMF at rt 3 h. Deprotection: DCM/TFA 2:1, concentration in vacuo, then stirring in water. The title compound was obtained as brown foam (87 mg). MS ESI (m/z): 756.5 [(M+H)⁺]

Example 194

(8S,11S,14S)-8-((1H-Indol-3-yl)methyl)-11-(4-aminobutyl)-14-(3-aminopropyl)-4-chloro-9-methyl-1-(pyridin-3-yl)-5,6,8,9,11,12,15,16-octahydrobenzo[b]pyrido[4,3-p][1,5,8,11,14]thiatetraazacycloheptadecine-7,10,13(14H)-trione

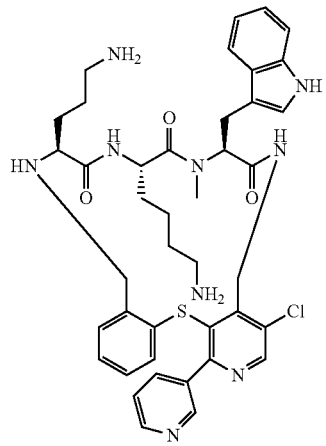 [SMILES: CN1C(=O)[C@H](CCCCN)NC(=O)[C@H](CCCN)NCc2ccccc2Sc2c(-c3cccnc3)ncc(Cl)c2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.3 eq Intermediate 90 using NMP/MeOH/AcOH 1:1:0.02 as solvent mixture. Macrocyclization: 1.2 eq HATU, 4 eq DIPEA, in DMF at rt 2 h. Suzuki in analogy to Example 189 using 3-pyridineboronic acid pinacol ester. Deprotection: DCM/TFA 2:1, concentrating under vacuo, stirring with water. The title compound was obtained as white foam (29 mg). MS ESI (m/z): 782.6 [(M+H)⁺]

Example 195

(8S,11S,14S)-8-((1H-Indol-3-yl)methyl)-11-(4-aminobutyl)-14-(3-aminopropyl)-4-chloro-9-methyl-1-(pyridin-4-yl)-5,6,8,9,11,12,15,16-octahydrobenzo[b]pyrido[4,3-p][1,5,8,11,14]thiatetraazacycloheptadecine-7,10,13(14H)-trione

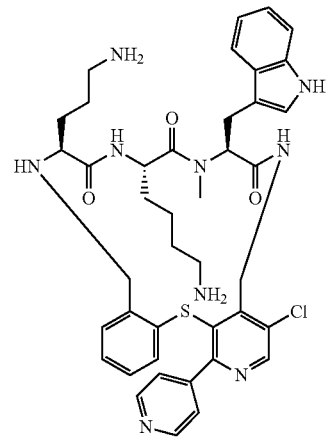 [SMILES: CN1C(=O)[C@H](CCCCN)NC(=O)[C@H](CCCN)NCc2ccccc2Sc2c(-c3ccncc3)ncc(Cl)c2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.3 eq Intermediate 90 using NMP/MeOH/AcOH 1:1:0.02 as solvent mixture. Macrocyclization: 1.2 eq HATU, 4 eq DIPEA, in DMF at rt 2 h. Suzuki in analogy to Example 189 using 4-(4,4,5,5-tetramethyl-1,3,2-dioxaborolan-2-yl)pyridine. Deprotection: DCM/TFA 2:1, concentrating in vacuo, stirring in water. The title compound was obtained as white foam (23 mg). MS ESI (m/z): 782.5 [(M+H)⁺]

Example 196

(8S,11S,14S)-8-((1H-Indol-3-yl)methyl)-11-(4-aminobutyl)-14-(3-aminopropyl)-4-chloro-1-(2-methoxypyridin-4-yl)-9-methyl-5,6,8,9,11,12,15,16-octahydrobenzo[b]pyrido[4,3-p][1,5,8,11,14]thiatetraazacycloheptadecine-7,10,13(14H)-trione

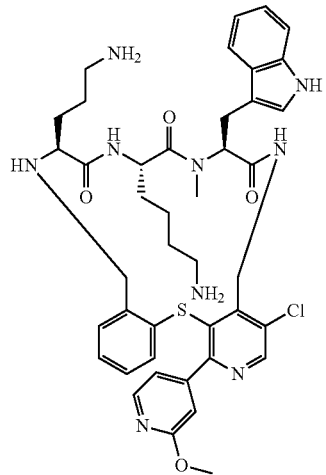 [SMILES: COc1cc(-c2ncc(Cl)c3c2Sc2ccccc2CN[C@@H](CCCN)C(=O)N[C@@H](CCCCN)C(=O)N(C)[C@@H](Cc2c[nH]c4ccccc24)C(=O)NC3)ccn1]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.3 eq Intermediate 90 using NMP/MeOH/AcOH 1:1:0.02 as solvent mixture. Macrocyclization: 1.2 eq HATU, 4 eq DIPEA, in DMF at rt 2 h. Suzuki in analogy to Example 189 using 2-methoxy-4-(4,4,5,5-tetramethyl-1,3,2-dioxaborolan-2-yl)pyridine. Deprotection: DCM/TFA 2:1, concentrating in vacuo, stirring in water. The title compound was obtained as white foam (33 mg). MS ESI (m/z): 812.3 [(M+H)$^+$]

Example 197

(7S,10S,13S)-13-((1H-Indol-3-yl)methyl)-10-(4-aminobutyl)-7-(3-aminopropyl)-18-bromo-12-methyl-6,7,9,10,12,13,15,16-octahydrodipyrido[2,3-b:2',3'-p][1,5,8,11,14]thiatetraazacycloheptadecine-8,11,14(5H)-trione

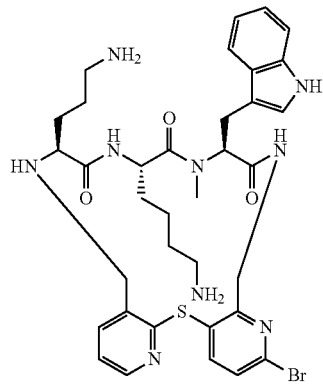 [SMILES: CN1C(=O)[C@H](CCCCN)NC(=O)[C@H](CCCN)NCc2cccnc2Sc2ccc(Br)nc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 114 using NMP/MeOH/AcOH 1:1:0.012 as solvent mixture. Macrocyclization: 1.2 eq HATU, 4 eq DIPEA, in DCM at rt 1 h. Deprotection: DCM/TFA 2:1, concentrating in vacuo, stirring in water. The title compound was obtained as white powder (11 mg). MS ESI (m/z): 752.3 [(M+H)$^+$]

Example 198

(8S,11S,14S)-8-((1H-Indol-3-yl)methyl)-11-(4-aminobutyl)-14-(3-aminopropyl)-4-chloro-9-methyl-1-(2-(trifluoromethyl)pyridin-4-yl)-5,6,8,9,11,12,15,16-octahydrobenzo[b]pyrido[4,3-p][1,5,8,11,14]thiatetraazacycloheptadecine-7,10,13(14H)-trione

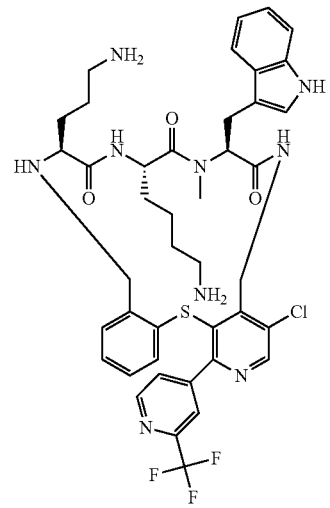 [SMILES: CN1C(=O)[C@H](CCCCN)NC(=O)[C@H](CCCN)NCc2ccccc2Sc2c(-c3ccnc(C(F)(F)F)c3)ncc(Cl)c2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.3 eq Intermediate 90 using NMP/MeOH/AcOH 1:1:0.02 as solvent mixture. Macrocyclization: 1.2 eq HATU, 4 eq DIPEA, in DMF at rt 2 h. Suzuki in analogy to Example 189 using 4-(4,4,5,5-tetramethyl-1,3,2-dioxaborolan-2-yl)-2-(trifluoromethyl)pyridine. Deprotection: DCM/TFA 2:1, concentration in vacuo, stirring in water. The title compound was obtained as white foam (25 mg). MS ESI (m/z): 850.6 [(M+H)$^+$]

Example 199

(11S,14S,17S)-14-(4-Amino-butyl)-11-(3-aminopropyl)-25-chloro-23-(5-methanesulfonyl-pyridin-3-yl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

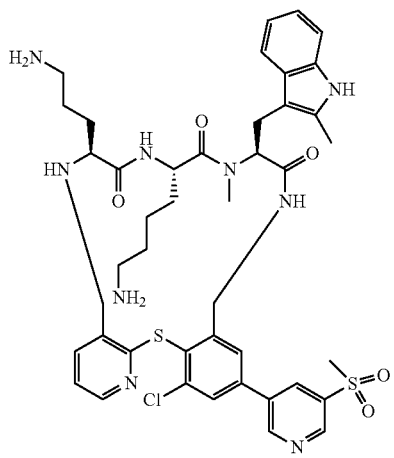 [SMILES: Cc1[nH]c2ccccc2c1C[C@H]1C(=O)NCc2cc(-c3cncc(S(C)(=O)=O)c3)cc(Cl)c2Sc2ncccc2CN[C@@H](CCCN)C(=O)N[C@@H](CCCCN)C(=O)N1C]

Example 199 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.

Tether: Intermediate 103
MS (M+H$^+$): expected 873.5; observed 874.5

Example 200

(11S,14S,17S)-14-(4-Amino-butyl)-11-(3-aminopropyl)-25-chloro-16-methyl-17-(2-methyl-1H-indol-3-ylmethyl)-22-pyridin-3-yl-2-thia-4,10,13,16,19-pentaaza-tricyclo[19.4.0.0*3,8*]pentacosa-1(25),3(8),4,6,21,23-hexaene-12,15,18-trione

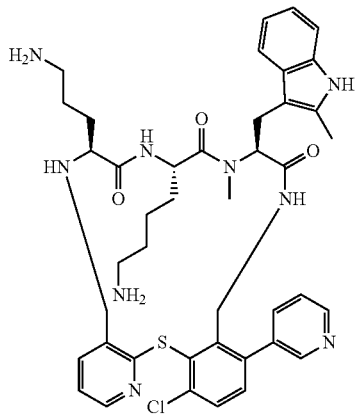 [SMILES: Cc1[nH]c2ccccc2c1C[C@H]1C(=O)NCc2c(-c3cccnc3)ccc(Cl)c2Sc2ncccc2CN[C@@H](CCCN)C(=O)N[C@@H](CCCCN)C(=O)N1C]

Example 200 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)OH.

Tether: Intermediate 111
MS (M+H$^+$): expected 795.4; observed 796.4

Example 201

(8S,11S,14S)-8-((1H-Indol-3-yl)methyl)-11-(4-aminobutyl)-14-(3-aminopropyl)-4-chloro-9-methyl-1-morpholino-5,6,8,9,11,12,15,16-octahydrobenzo[b]pyrido[4,3-p][1,5,8,11,14]thiatetraazacycloheptadecine-7,10,13(14H)-trione

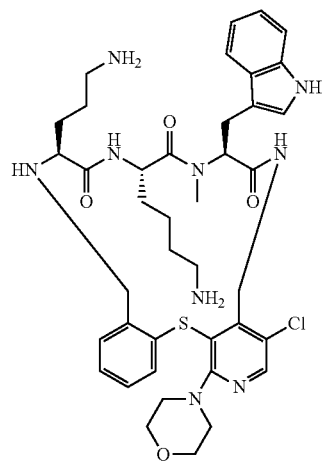 [SMILES: CN1C(=O)[C@H](CCCCN)NC(=O)[C@H](CCCN)NCc2ccccc2Sc2c(N3CCOCC3)ncc(Cl)c2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.3 eq Intermediate 90 using NMP/MeOH/AcOH 1:1:0.02 as solvent mixture. Macrocyclization: 1.2 eq HATU, 4 eq DIPEA, in DMF at rt 2 h.

In a pressure tube morpholine (8.38 mg, 8.38 µl, 96.1 µmol, Eq: 10) was added to tert-butyl 3-(((8S,11S,14S)-11-(4-((tert-butoxycarbonyl)amino)butyl)-14-(3-((tert-butoxycarbonyl)amino)propyl)-1,4-dichloro-9-methyl-7,10,13-trioxo-5,6,7,8,9,10,11,12,13,14,15,16-dodecahydrobenzo[b]pyrido[4,3-p][1,5,8,11,14]thiatetraazacycloheptadecin-8-yl)methyl)-1H-indole-1-carboxylate (0.01 g, 9.61 µmol, Eq: 1) and cesium fluoride (2.92 mg, 19.2 µmol, Eq: 2), the tube flushed with argon, sealed and heated to 100° C. over night. The reaction was dissolved in acetonitrile, treated with water and the mixture lyophilized. The obtained material was used without further purification Deprotection: DCM/TFA 2:1, concentrating in vacuo, stirring in water. The title compound was obtained as light brown foam (10 mg). MS ESI (m/z): 790.4 [(M+H)$^+$]

Example 202

(11S,14S,17S)-14-(4-Amino-butyl)-11-(3-amino-propyl)-25-chloro-16-methyl-17-(2-methyl-1H-indol-3-ylmethyl)-22-pyridin-4-yl-2-thia-4,10,13,16,19-pentaaza-tricyclo[19.4.0.0*3,8*]pentacosa-1(25),3(8),4,6,21,23-hexaene-12,15,18-trione

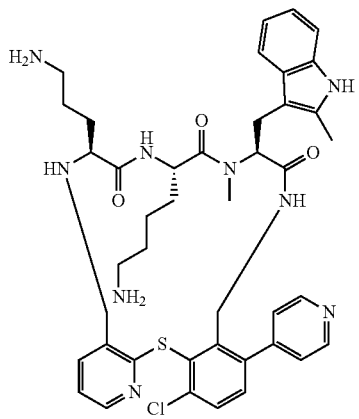 [SMILES: Cc1[nH]c2ccccc2c1C[C@H]1C(=O)NCc2c(-c3ccncc3)ccc(Cl)c2Sc2ncccc2CN[C@@H](CCCN)C(=O)N[C@@H](CCCCN)C(=O)N1C]

Example 202 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.
Tether: Intermediate 110
MS (M+H$^+$): expected 795.4; observed 796.4

Example 203

(7S,10S,13S)-10-(4-aminobutyl)-7-(3-aminopropyl)-20-chloro-6,7,9,10,12,13,15,16-octahydro-12-methyl-13-[(2-methyl-1H-indol-3-yl)methyl]-18-[2-(4-methyl-1-piperazinyl)-4-pyridinyl]pyrido[2,3-b][1,5,8,11,14]benzothiatetraazacycloheptadecine-8,11,14(5H)-trione

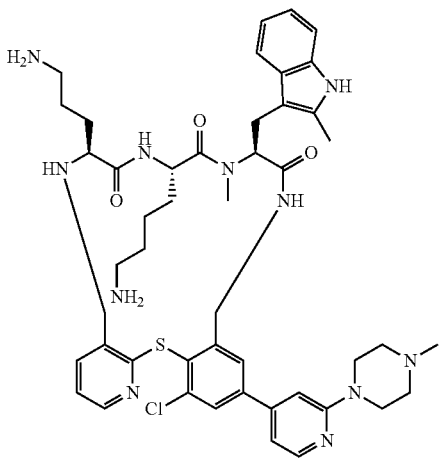 [SMILES: Cc1[nH]c2ccccc2c1C[C@H]1C(=O)NCc2cc(-c3ccnc(N4CCN(C)CC4)c3)cc(Cl)c2Sc2ncccc2CN[C@@H](CCCN)C(=O)N[C@@H](CCCCN)C(=O)N1C]

Example 203 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.
Tether: Intermediate 75
MS (M+H$^+$): expected 894.5; observed 894.4

Example 204 (RO7192360-001-001)

(7S,10S,13S)-13-((1H-Indol-3-yl)methyl)-10-(4-aminobutyl)-7-(3-aminopropyl)-12-methyl-18-morpholino-6,7,9,10,12,13,15,16-octahydrodipyrido[2,3-b:4',3'-p][1,5,8,11,14]thiatetraazacycloheptadecine-8,11,14(5H)-trione

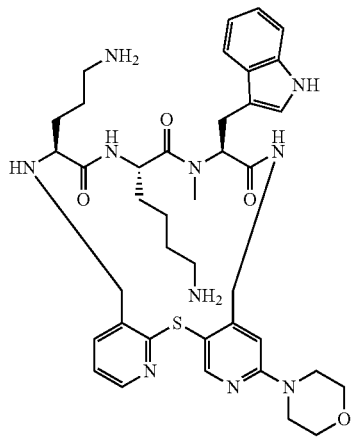 [SMILES: CN1C(=O)[C@H](CCCCN)NC(=O)[C@H](CCCN)NCc2cccnc2Sc2cnc(N3CCOCC3)cc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 95 in NMP/MeOH/AcOH 1:1:0.012 as solvent mixture. Macrocyclization: 1.2 eq HATU, 4 eq DIPEA, in DCM at rt 1 h.

A suspension of tert-butyl 3-(((7S,10S,13S)-10-(4-((tert-butoxycarbonyl)amino)butyl)-7-(3-((tert-butoxycarbonyl)amino)propyl)-18-chloro-12-methyl-8,11,14-trioxo-5,6,7,8,9,10,11,12,13,14,15,16-dodecahydropyrido[2,3-b:4',3'-p][1,5,8,11,14]thiatetraazacycloheptadecin-13-yl)methyl)-1H-indole-1-carboxylate (25 mg, 24.8 μmol, Eq: 1) in morpholine (82.8 μl) in a pressure tube was heated to 100° C. and stirred for 2 h. The reaction mixture was diluted with acetonitrile/water and lyophilized. tert-Butyl 3-(((7S,10S,13S)-10-(4-((tert-butoxycarbonyl)amino)butyl)-7-(3-((tert-butoxycarbonyl)amino)propyl)-12-methyl-18-morpholino-8,11,14-trioxo-5,6,7,8,9,10,11,12,13,14,15,16-dodecahydropyrido[2,3-b:4',3'-p][1,5,8,11,14]thiatetraazacycloheptadecin-13-yl)methyl)-1H-indole-1-carboxylate was obtained as white powder and used without purification.

Deprotection: DCM/TFA 1:1, concentration in vacuo, then stirring with water. The title compound was obtained as white powder (3 mg). MS ESI (m/z): 757.6 [(M+H)$^+$]

Example 205

(7S,10S,13S)-13-((1H-Indol-3-yl)methyl)-10-(4-aminobutyl)-7-(3-aminopropyl)-18-(2-methoxypyridin-4-yl)-12-methyl-6,7,9,10,12,13,15,16-octahydrodipyrido[2,3-b:4',3'-p][1,5,8,11,14]thiatetraazacycloheptadecine-8,11,14(5H)-trione

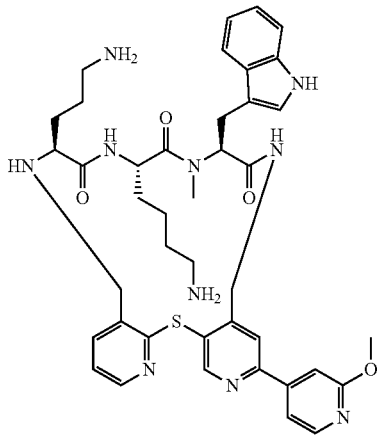 [SMILES: COc1cc(-c2cc3c(cn2)Sc2ncccc2CN[C@@H](CCCN)C(=O)N[C@@H](CCCCN)C(=O)N(C)[C@@H](Cc2c[nH]c4ccccc24)C(=O)NC3)ccn1]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 95 in NMP/MeOH/AcOH 1:1:0.012 as solvent mixture. Macrocyclization: 1.2 eq HATU, 4 eq DIPEA, in DCM at rt 1 h. Suzuki in analogy to Example 189 using 2-methoxy-4-(4,4,5,5-tetramethyl-1,3,2-dioxaborolan-2-yl)pyridine. Deprotection: DCM/TFA 1:1, concentration in vacuo, stirring with water. The title compound was obtained as white powder (3 mg). MS ESI (m/z): 779.5 [(M+H)$^+$]

Example 206

(12S,15S,18S)-15-(4-Amino-butyl)-18-(3-aminopropyl)-23-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

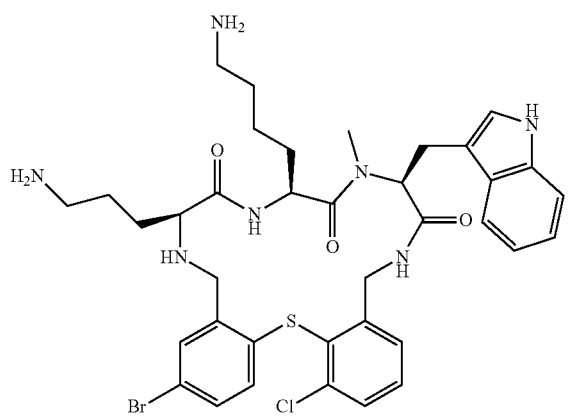 [SMILES: CN1C(=O)[C@H](CCCCN)NC(=O)[C@H](CCCN)NCc2cc(Br)ccc2Sc2c(Cl)cccc2CNC(=O)[C@@H]1Cc1c[nH]c2ccccc12]

Example 206 was prepared by BOC-deprotection of intermediate 137.

MS (M+H)$^+$: expected 782.22; observed 782.2

Example 207

(12S,15S,18S)-15-(4-Amino-butyl)-18-(3-aminopropyl)-4-chloro-12-(1H-indol-3-ylmethyl)-13-methyl-23-phenyl-2-thia-10,13,16,19-tetraaza-tricyclo[19.4.0.0*3,8*]pentacosa-1(25),3,5,7,21,23-hexaene-11,14,17-trione

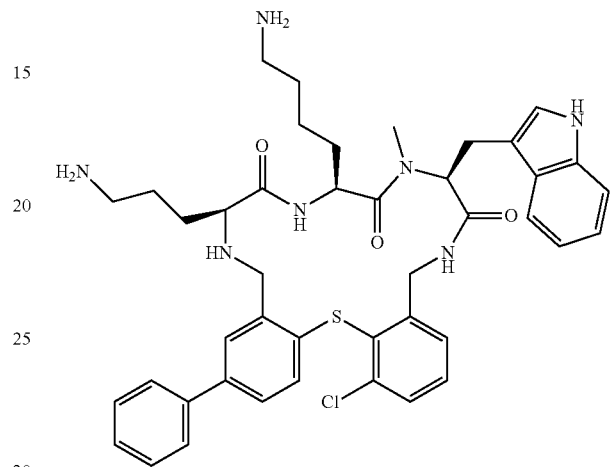

Example 207 was prepared according to the General Procedure for Suzuki Coupling of boronic acid derivatives to Peptide Macrocycle Intermediates using the following starting materials:

Macrocycle Intermediate: Intermediate 137
Boronic Acid Derivative: Phenylboronic acid
MS (M+H)$^+$: expected 780.34; observed 780.5

Example 208

(12S,15S,18S)-15-(4-Amino-butyl)-18-(3-aminopropyl)-4-chloro-12-(1H-indol-3-ylmethyl)-13-methyl-23-pyridin-3-yl-2-thia-10,13,16,19-tetraazatricyclo[19.4.0.0*3,8*]pentacosa-1(25),3,5,7,21,23-hexaene-11,14,17-trione

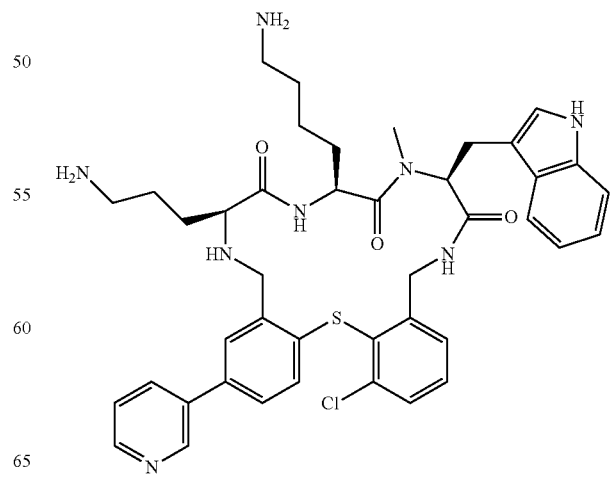

Example 208 was prepared according to the General Procedure for Suzuki Coupling of boronic acid derivatives to Peptide Macrocycle Intermediates using the following starting materials:

Macrocycle Intermediate: Intermediate 137
Boronic Acid Derivative: Pyridin-3-yl boronic acid
MS (M+H)⁺: expected 781.33; observed 781.3

Example 209

(11S,14S,17S)-14-(4-Amino-butyl)-11-(3-amino-propyl)-25-chloro-23-(2,6-difluoro-pyridin-4-yl)-17-(1H-indol-3-ylmethyl)-16-methyl-2-thia-4,10,13,16,19-pentaaza-tricyclo[19.4.0.0*3,8*]pentacosa-1(21),3(8),4,6,22,24-hexaene-12,15,18-trione

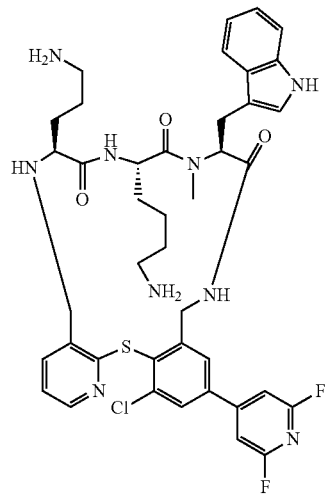 [SMILES: CN1C(=O)[C@H](CCCCN)NC(=O)[C@H](CCCN)NCc2cccnc2Sc2c(Cl)cc(-c3cc(F)nc(F)c3)cc2CNC(=O)[C@@H]1Cc1c[nH]c2ccccc12]

Example 209 was prepared according to the General Procedure for Suzuki Coupling of boronic acid derivatives to Peptide Macrocycle Intermediates using the following starting materials:

Macrocycle Intermediate: Intermediate 139
Boronic Acid Derivative: (2,6-difluoropyridin-4-yl)boronic acid
MS (M+H⁺): expected 817.3; observed 818.3

Example 210

3-[(11S,14S,17S)-14-(4-Amino-butyl)-23,25-di-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-11-yl]-N-methyl-propionamide

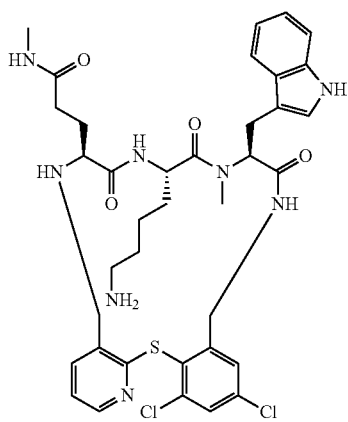 [SMILES: CNC(=O)CC[C@@H]1NCc2cccnc2Sc2c(Cl)cc(Cl)cc2CNC(=O)[C@H](Cc2c[nH]c3ccccc23)N(C)C(=O)[C@H](CCCCN)NC1=O]

Example 210 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. (S)-2-(9H-Fluoren-9-ylmethoxycarbonylamino)-4-methylcarbamoyl-butyric acid
Tether: Intermediate 47
MS (M+H⁺): expected 766.8; observed 767.3

Example 211

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-23-yl]-benzonitrile

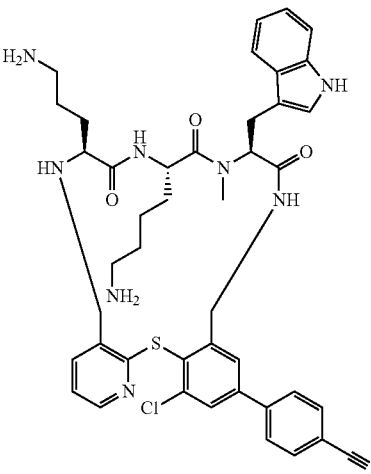

Example 211 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 116
MS (M+H⁺): expected 805.4; observed 806.3

Example 212

(11S,14S,17S)-14-(4-Amino-butyl)-11-(3-amino-propyl)-25-chloro-17-(1H-indol-3-ylmethyl)-16-methyl-22-(2-methyl-pyridin-4-yl)-2-thia-4,10,13,16,19-pentaaza-tricyclo[19.4.0.0*3,8*]pentacosa-1(25),3(8),4,6,21,23-hexaene-12,15,18-trione

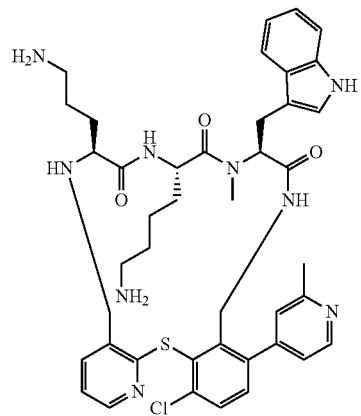 [SMILES: Cc1cc(-c2ccc(Cl)c3c2CNC(=O)[C@H](Cc2c[nH]c4ccccc24)N(C)C(=O)[C@H](CCCCN)NC(=O)[C@H](CCCN)NCc2cccnc2S3)ccn1]

Example 212 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 117
MS (M+H⁺): expected 795.4; observed 796.4

Example 213

(11S,14S,17S)-14-(4-Amino-butyl)-11-(3-amino-propyl)-25-chloro-17-(1H-indol-3-ylmethyl)-16-methyl-23-pyrimidin-4-yl-2-thia-4,10,13,16,19-pentaaza-tricyclo[19.4.0.0*3,8*]pentacosa-1(21),3,5,7,22,24-hexaene-12,15,18-trione

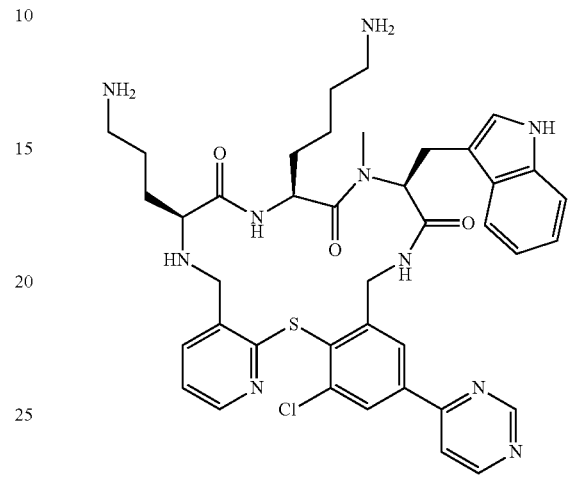

Example 213 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 118
MS (M+H⁺): expected 782.4; observed 783.4

Example 214

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-23-yl]-benzenesulfonamide

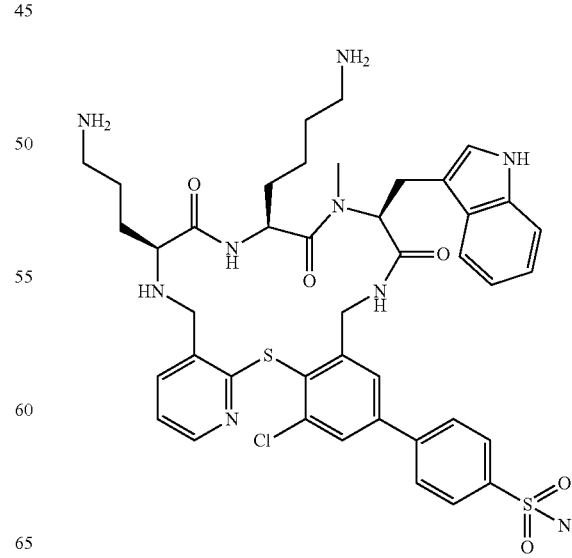

Example 214 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 119
MS (M+H$^+$): expected 859.5; observed 860.7

Example 215

(7S,10S,13S)-13-((1H-Indol-3-yl)methyl)-10-(4-aminobutyl)-7-(3-aminopropyl)-12-methyl-18-(2-methylpyridin-4-yl)-6,7,9,10,12,13,15,16-octahydrodipyrido[2,3-b:2',3'-p][1,5,8,11,14]thiatetraazacycloheptadecine-8,11,14(5H)-trione

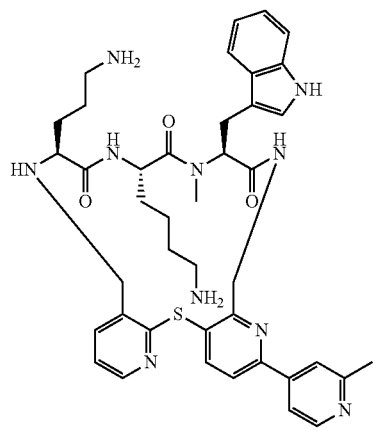 [SMILES: Cc1cc(-c2ccc3c(n2)CNC(=O)[C@H](Cc2c[nH]c4ccccc24)N(C)C(=O)[C@H](CCCCN)NC(=O)[C@H](CCCN)NCc2cccnc2S3)ccn1]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 114 using NMP/MeOH/AcOH 1:1:0.02 as solvent mixture. Macrocyclization: 1.2 eq HATU, 4 eq DIPEA, in DCM at rt 1 h. Suzuki in analogy to Example 189 using 2-methyl-4-(4,4,5,5-tetramethyl-1,3,2-dioxaborolan-2-yl)pyridine. Deprotection: DCM/TFA 1:1, concentration in vacuo, stirring in water. The title compound was obtained as yellow solid (50 mg). MS ESI (m/z): 763.4 [(M+H)$^+$]

Example 216

(12S,15S,18S)-15-(4-Amino-butyl)-23-(4-aminomethyl-phenyl)-18-(3-amino-propyl)-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

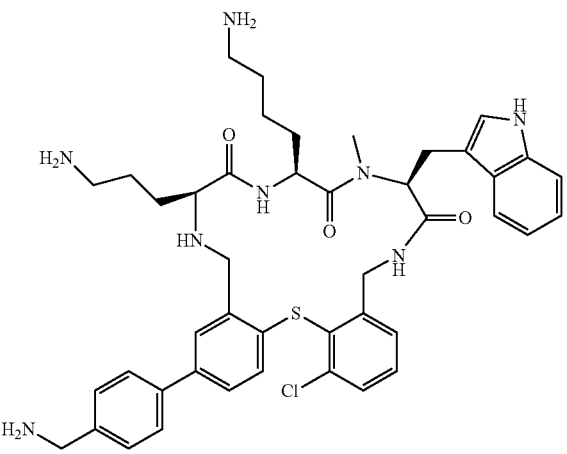 [SMILES: CN1C(=O)[C@H](CCCCN)NC(=O)[C@H](CCCN)NCc2cc(-c3ccc(CN)cc3)ccc2Sc2c(Cl)cccc2CNC(=O)[C@@H]1Cc1c[nH]c2ccccc12]

Example 216 was prepared according to the General Procedure for Suzuki Coupling of boronic acid derivatives to Peptide Macrocycle Intermediates using the following starting materials:
Macrocycle Intermediate: Intermediate 137
Boronic Acid Derivative: (4-(((tert-butoxycarbonyl)amino)methyl)phenyl)boronic acid
MS (M+H)$^+$: expected 809.36; observed 809.7

Example 217

(7S,10S,13S)-13-((1H-Indol-3-yl)methyl)-10-(4-aminobutyl)-7-(3-aminopropyl)-18-(2-methoxypyridin-4-yl)-12-methyl-6,7,9,10,12,13,15,16-octahydrodipyrido[2,3-b:2',3'-p][1,5,8,11,14]thiatetraazacycloheptadecine-8,11,14(5H)-trione

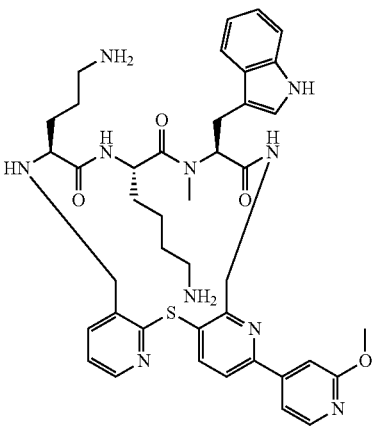 [SMILES: COc1cc(-c2ccc3c(n2)CNC(=O)[C@H](Cc2c[nH]c4ccccc24)N(C)C(=O)[C@H](CCCCN)NC(=O)[C@H](CCCN)NCc2cccnc2S3)ccn1]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 114 using NMP/MeOH/AcOH 1:1:0.02 as solvent mixture. Macrocyclization: 1.2 eq HATU, 4 eq DIPEA, in DCM at rt 1 h. Suzuki in analogy to Example 189 using 2-methoxy-4-(4,4,5,5-tetramethyl-1,3,2-dioxaborolan-2-yl)pyridine. Deprotection: DCM/TFA 1:1, concentrating in vacuo, stirring in water. The title compound was obtained as yellow powder (40 mg). MS ESI (m/z): 779.6 [(M+H)+]

Example 218

(7S,10S,13S)-13-((1H-Indol-3-yl)methyl)-10-(4-aminobutyl)-7-(3-aminopropyl)-12-methyl-18-morpholino-6,7,9,10,12,13,15,16-octahydrodipyrido[2,3-b:2',3'-p][1,5,8,11,14]thiatetraazacycloheptadecine-8,11,14(5H)-trione

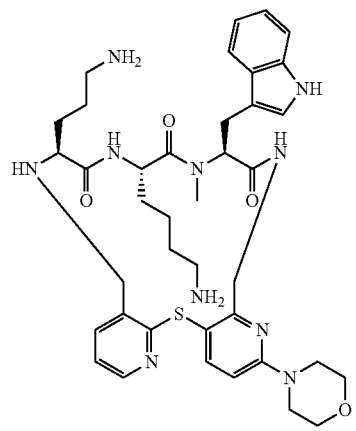 [SMILES: CN1C(=O)[C@H](CCCCN)NC(=O)[C@H](CCCN)NCc2cccnc2Sc2ccc(N3CCOCC3)nc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 114 using NMP/MeOH/AcOH 1:1:0.02 as solvent mixture. Macrocyclization: 1.2 eq HATU, 4 eq DIPEA, in DCM at rt 1 h.

A suspension of tert-butyl 3-(((7S,10S,13S)-18-bromo-10-(4-((tert-butoxycarbonyl)amino)butyl)-7-(3-((tert-butoxycarbonyl)amino)propyl)-12-methyl-8,11,14-tri oxo-5,6,7,8,9,10,11,12,13,14,15,16-dodecahydrodipyrido[2,3-b:2',3'-p][1,5,8,11,14]thiatetraazacycloheptadecin-13-yl)methyl)-1H-indole-1-carboxylate (30 mg, 28.5 µmol, Eq: 1) in morpholine (143 µl) in a sealed tube was heated to 70° C. overnight. The reaction mixture was concentrated in vacuo and used without further purification.

Deprotection: DCM/TFA 1:1, concentrating in vacuo, stirring in water. The title compound was obtained as orange powder (14 mg). MS ESI (m/z): 757.5 [(M+H)+]

Example 219

(12S,15S,18S)-15-(4-Amino-butyl)-18-(3-amino-propyl)-24-bromo-4-chloro-12-(1H-indol-3-ylmethyl)-13-methyl-2-thia-10,13,16,19-tetraaza-tricyclo[19.4.0.0*3,8*]pentacosa-1(25),3,5,7,21,23-hexaene-11,14,17-trione

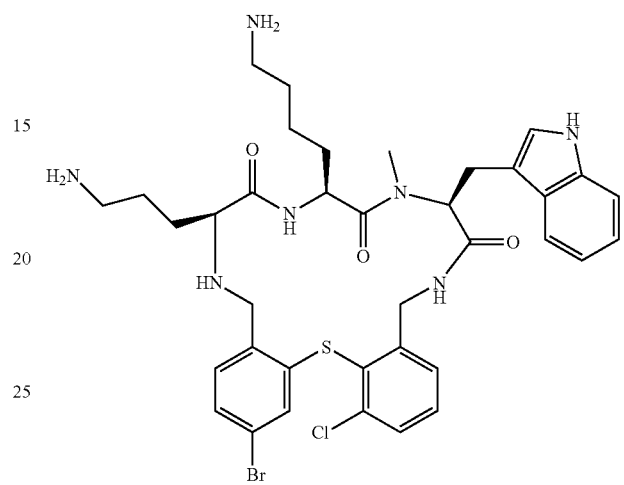

Example 219 was prepared by BOC-deprotection of intermediate 138.
MS (M+H)+: expected 782.22; observed 782.3

Example 220

(12S,15S,18S)-15-(4-Amino-butyl)-18-(3-amino-propyl)-4-chloro-12-(1H-indol-3-ylmethyl)-13-methyl-24-phenyl-2-thia-10,13,16,19-tetraaza-tricyclo[19.4.0.0*3,8*]pentacosa-1(25),3,5,7,21,23-hexaene-11,14,17-trione

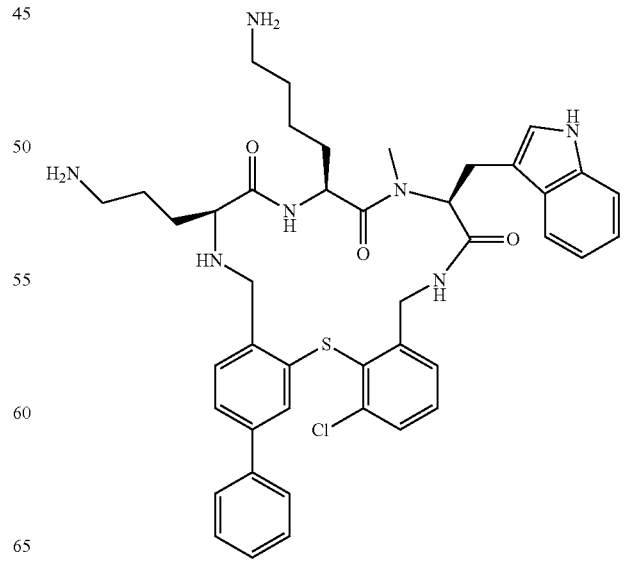

Example 220 was prepared according to the General Procedure for Suzuki Coupling of boronic acid derivatives to Peptide Macrocycle Intermediates using the following starting materials:
Macrocycle Intermediate: Intermediate 138
Boronic Acid Derivative: Phenylboronic acid
MS (M+H)+: expected 780.34; observed 780.5

Example 221

3-[(11S,14S,17S)-14-(4-Amino-butyl)-25-chloro-17-(1H-indol-3-ylmethyl)-16-methyl-12,15,18-trioxo-22-pyridin-3-yl-2-thia-4,10,13,16,19-pentaaza-tricyclo[19.4.0.0*3,8*]pentacosa-1(25),3(8),4,6,21,23-hexaen-11-yl]-propionamide

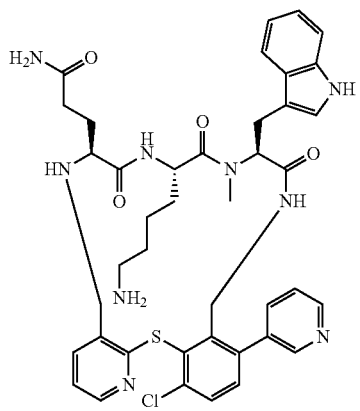 [SMILES: CN1C(=O)[C@H](CCCCN)NC(=O)[C@H](CCC(N)=O)NCc2cccnc2Sc2c(Cl)ccc(-c3cccnc3)c2CNC(=O)[C@@H]1Cc1c[nH]c2ccccc12]

Example 221 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Gln(Trt)-OH.
Tether: Intermediate 111
MS (M+H+): expected 795.4; observed 796.4

Example 222

(11S,14S,17S)-14-(4-Amino-butyl)-11-(3-amino-propyl)-25-chloro-22-(2-fluoro-pyridin-4-yl)-17-(1H-indol-3-ylmethyl)-16-methyl-2-thia-4,10,13,16,19-pentaaza-tricyclo[19.4.0.0*3,8*]pentacosa-1(25),3(8),4,6,21,23hexaene-12,15,18-trione

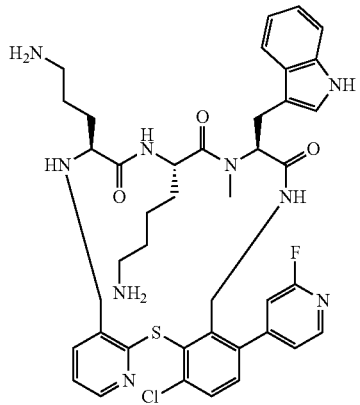 [SMILES: CN1C(=O)[C@H](CCCCN)NC(=O)[C@H](CCCN)NCc2cccnc2Sc2c(Cl)ccc(-c3ccnc(F)c3)c2CNC(=O)[C@@H]1Cc1c[nH]c2ccccc12]

Example 222 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 121
MS (M+H+): expected 799.4; observed 800.3

Example 223

(11S,14S,17S)-14-(4-Amino-butyl)-11-(3-amino-propyl)-23-(2-amino-pyridin-4-yl)-25-chloro-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione

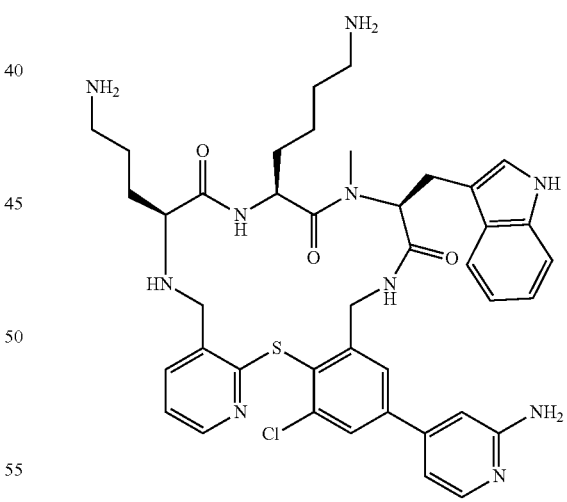

Example 223 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 122
MS (M+H+): expected 796.4; observed 797.7

Example 224

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-22-yl]-benzenesulfonamide

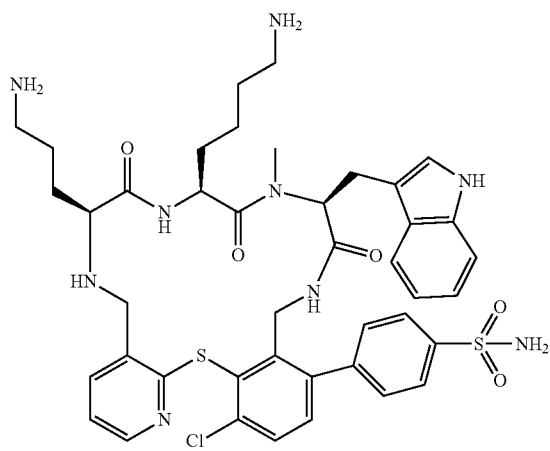 [SMILES: CN1C(=O)[C@H](CCCCN)NC(=O)[C@H](CCCN)NCc2cccnc2Sc2c(Cl)ccc(-c3ccc(S(N)(=O)=O)cc3)c2CNC(=O)[C@@H]1Cc1c[nH]c2ccccc12]

Example 224 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 123
MS (M+H$^+$): expected 859.5; observed 860.7

Example 225

(11S,14S,17S)-14-(4-Amino-butyl)-11-(3-amino-propyl)-25-chloro-17-(1H-indol-3-ylmethyl)-22-(4-methanesulfonyl-phenyl)-16-methyl-2-thia-4,10,13,16,19-pentaaza-tricyclo[19.4.0.0*3,8*]pentacosa-1(21),3,5,7,22,24-hexaene-12,15,18-trione

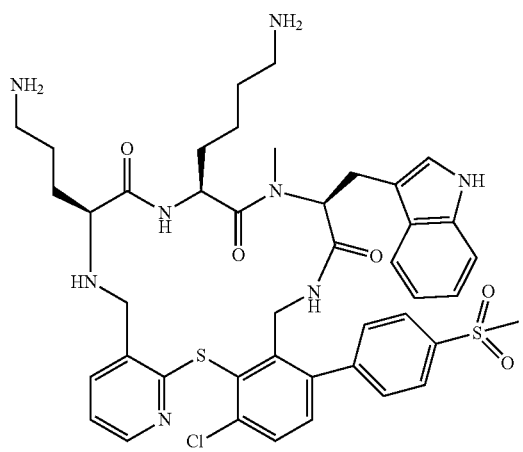 [SMILES: CN1C(=O)[C@H](CCCCN)NC(=O)[C@H](CCCN)NCc2cccnc2Sc2c(Cl)ccc(-c3ccc(S(C)(=O)=O)cc3)c2CNC(=O)[C@@H]1Cc1c[nH]c2ccccc12]

Example 225 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 124
MS (M+H$^+$): expected 858.5; observed 859.7

Example 226

(7S,10S,13S)-13-((1H-Indol-3-yl)methyl)-10-(4-aminobutyl)-7-(3-aminopropyl)-3-fluoro-12-methyl-6,7,9,10,12,13,15,16-octahydrobenzo[b]pyrido[3,2-p][1,5,8,11,14]thiatetraazacycloheptadecine-8,11,14 (5H)-trione

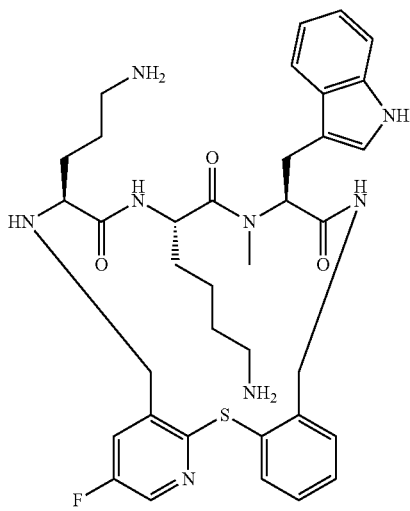 [SMILES: CN1C(=O)[C@H](CCCCN)NC(=O)[C@H](CCCN)NCc2cc(F)cnc2Sc2ccccc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 125 using NMP/MeOH/AcOH 1:1:0.02 as solvent mixture. Macrocyclization: 1.4 eq HATU, 4 eq DIPEA, in DMF at rt 2 h. Deprotection: DCM/TFA 2:1, concentrating in vacuo, stirring in water. The title compound was obtained as white powder (39 mg). MS ESI (m/z): 698.6 [(M+H)$^+$]

Example 227

(11S,14S,17S)-14-(4-Amino-butyl)-11-(3-amino-propyl)-25-chloro-23-imidazol-1-yl-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione

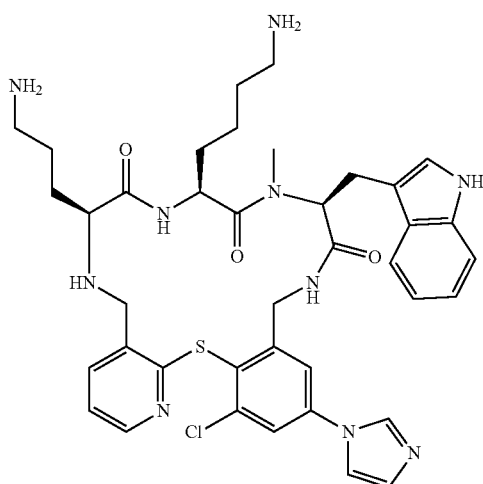 [SMILES: CN1C(=O)[C@H](CCCCN)NC(=O)[C@H](CCCN)NCc2cccnc2Sc2c(Cl)cc(-n3ccnc3)cc2CNC(=O)[C@@H]1Cc1c[nH]c2ccccc12]

Example 227 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 126
MS (M+H$^+$): expected 770.4; observed 771.2

Example 228

(11S,14S,17S)-14-(4-Amino-butyl)-11-(3-amino-propyl)-22-(6-amino-pyridin-3-yl)-25-chloro-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione

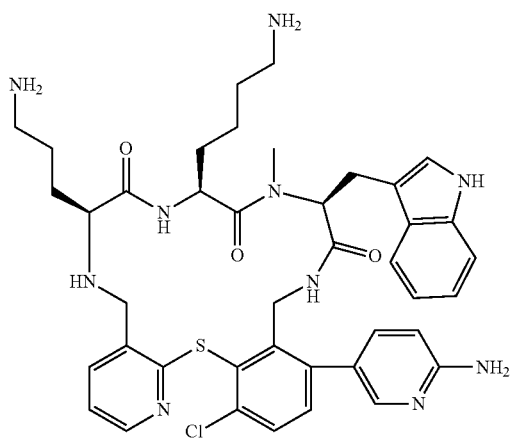 [SMILES: CN1C(=O)[C@H](CCCCN)NC(=O)[C@H](CCCN)NCc2cccnc2Sc2c(Cl)ccc(-c3ccc(N)nc3)c2CNC(=O)[C@@H]1Cc1c[nH]c2ccccc12]

Example 228 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 127
MS (M+H$^+$): expected 796.4; observed 797.3

Example 229

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-23-yl]-pyridine-2-carbonitrile

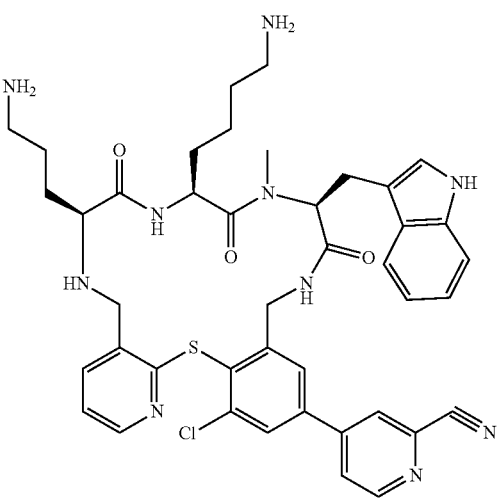 [SMILES: CN1C(=O)[C@H](CCCCN)NC(=O)[C@H](CCCN)NCc2cccnc2Sc2c(Cl)cc(-c3ccnc(C#N)c3)cc2CNC(=O)[C@@H]1Cc1c[nH]c2ccccc12]

Example 229 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 128
MS (M+H$^+$): expected 806.4; observed 807.4

Example 230

(11S,14S,17S)-14-(4-Amino-butyl)-11-(3-amino-propyl)-25-chloro-22-(6-hydroxy-pyridin-3-yl)-17-(1H-indol-3-ylmethyl)-16-methyl-2-thia-4,10,13,16,19-pentaaza-tricyclo[19.4.0.0*3,8*]pentacosa-1(21),3,5,7,22,24-hexaene-12,15,18-trione

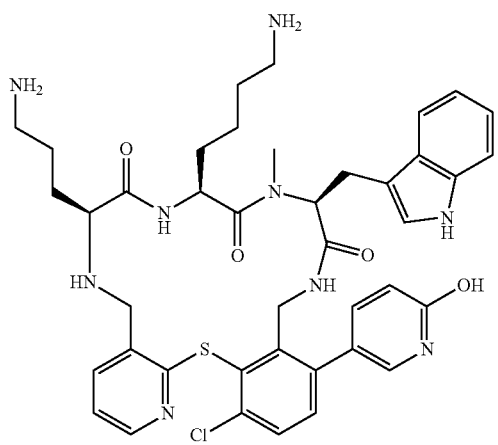 [SMILES: CN1C(=O)[C@H](CCCCN)NC(=O)[C@H](CCCN)NCc2cccnc2Sc2c(Cl)ccc(-c3ccc(O)nc3)c2CNC(=O)[C@@H]1Cc1c[nH]c2ccccc12]

Example 230 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 129
MS (M+H⁺): expected 797.4; observed 798.2

Example 231

3-[(11S,14S,17S)-14-(4-Amino-butyl)-25-chloro-22-(2-fluoro-pyridin-4-yl)-17-(1H-indol-3-ylmethyl)-16-methyl-12,15,18-trioxo-2-thia-4,10,13,16,19-pentaaza-tricyclo[19.4.0.0*3,8*]pentacosa-1(21),3,5,7,22,24-hexaen-11-yl]-propionamide

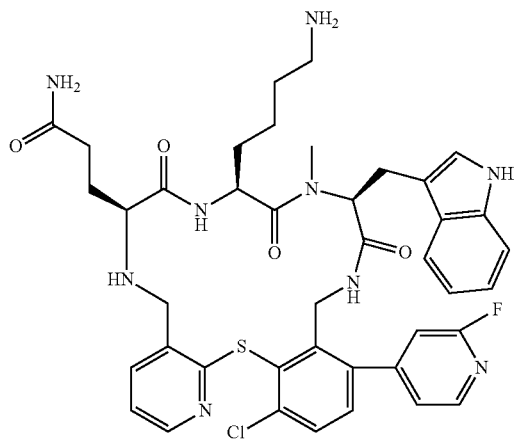 [SMILES: CN1C(=O)[C@H](CCCCN)NC(=O)[C@H](CCC(N)=O)NCc2cccnc2Sc2c(Cl)ccc(-c3ccnc(F)c3)c2CNC(=O)[C@@H]1Cc1c[nH]c2ccccc12]

Example 231 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(Trt)-OH.
Tether: Intermediate 121
MS (M+H⁺): expected 813.4; observed 814.3

Example 232

(11S,14S,17S)-14-(4-Amino-butyl)-11-(3-amino-propyl)-25-chloro-17-(1H-indol-3-ylmethyl)-16-methyl-23-(1H-pyrrol-3-yl)-2-thia-4,10,13,16,19-pentaaza-tricyclo[19.4.0.0*3,8*]pentacosa-1(25),3(8),4,6,21,23-hexaene-12,15,18-trione

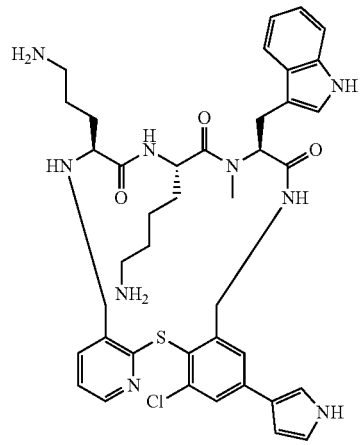 [SMILES: CN1C(=O)[C@H](CCCCN)NC(=O)[C@H](CCCN)NCc2cccnc2Sc2c(Cl)cc(-c3cc[nH]c3)cc2CNC(=O)[C@@H]1Cc1c[nH]c2ccccc12]

Example 232 was prepared according to the General Procedure for Peptide Macrocycle Synthesis using the following starting materials:
1. Fmoc-NMe-L-Trp(BOC)—OH,
2. Fmoc-L-Lys(BOC)—OH,
3. Fmoc-L-Orn(BOC)—OH.
Tether: Intermediate 130
MS (M+H⁺): expected 769.4; observed 770.3

Example 233

(11S,14S,17S)-14-(4-Amino-butyl)-11-(3-amino-propyl)-25-chloro-16-methyl-17-(2-methyl-1H-indol-3-ylmethyl)-12,15,18-trioxo-2-thia-4,10,13,16,19-pentaaza-tricyclo[19.4.0.0*3,8*]pentacosa-1(25),3(8),4,6,21,23-hexaene-23-carbonitrile

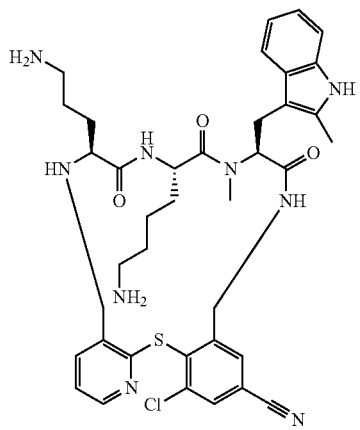 [SMILES: Cc1[nH]c2ccccc2c1C[C@H]1C(=O)NCc2cc(C#N)cc(Cl)c2Sc2ncccc2CN[C@@H](CCCN)C(=O)N[C@@H](CCCCN)C(=O)N1C]

Example 233 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.

Tether: Intermediate 107
MS (M+H$^+$): expected 743.3; observed 744.3

Example 234

(11S,14S,17S)-14-(4-Amino-butyl)-11-(3-amino-propyl)-25-chloro-23-(4-methanesulfonyl-phenyl)-16-methyl-17-(2-methyl-1H-indol-3-ylmethyl)-2-thia-4,10,13,16,19-pentaaza-tricyclo[19.4.0.0*3,8*]pentacosa-1(25),3(8),4,6,21,23-hexaene-12,15,18-trione

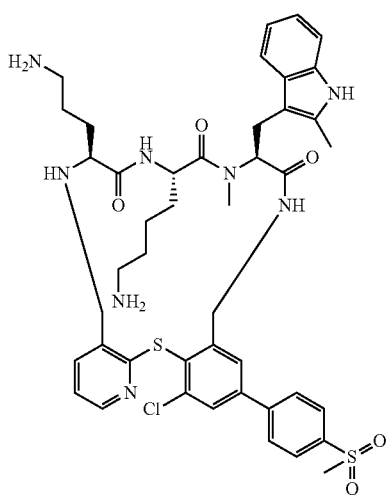 [SMILES: Cc1[nH]c2ccccc2c1C[C@H]1C(=O)NCc2cc(-c3ccc(S(C)(=O)=O)cc3)cc(Cl)c2Sc2ncccc2CN[C@@H](CCCN)C(=O)N[C@@H](CCCCN)C(=O)N1C]

Example 234 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.

Tether: Intermediate 102
MS (M+H$^+$): expected 872.5; observed 873.3

Example 235 (RO7198462-001-001)

4-[(11S,14S,17S)-14-(4-Amino-butyl)-11-(3-amino-propyl)-25-chloro-16-methyl-17-(2-methyl-1H-indol-3-ylmethyl)-12,15,18-trioxo-2-thia-4,10,13,16,19-pentaaza-tricyclo[19.4.0.0*3,8*]pentacosa-1(25),3(8),4,6,21,23-hexaen-23-yl]-benzenesulfonamide

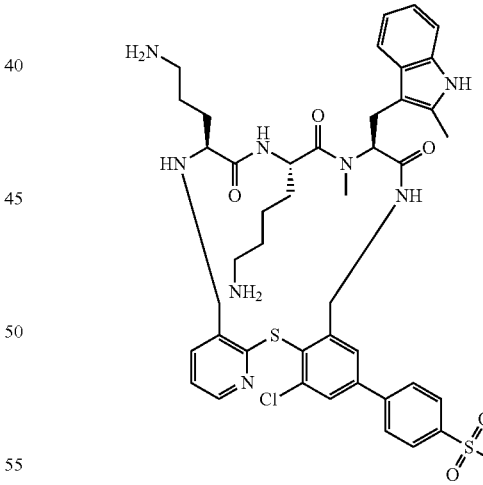

Example 235 was prepared according to the General Procedure for Peptide Macrocycle Synthesis using the following starting materials:
1. (S)-2-(9H-Fluoren-9-ylmethoxycarbonylamino)-3-(2-methyl-1H-indol-3-yl)-propionic acid,
2. Fmoc-L-Lys(BOC)—OH,
3. Fmoc-L-Orn(BOC)—OH.

Tether: Intermediate 119
MS (M+H$^+$): expected 873.5; observed 874.3

Example 236

(7S,10S,13S)-13-((1H-Indol-3-yl)methyl)-10-(4-aminobutyl)-7-(3-aminopropyl)-3-bromo-12-methyl-6,7,9,10,12,13,15,16-octahydrobenzo[b]pyrido[3,2-p][1,5,8,11,14]thiatetraazacycloheptadecine-8,11,14(5H)-trione

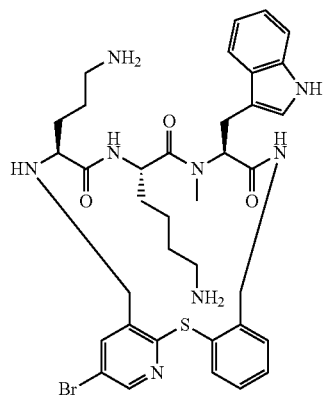 [SMILES: CN1C(=O)[C@H](CCCCN)NC(=O)[C@H](CCCN)NCc2cc(Br)cnc2Sc2ccccc2CNC(=O)[C@@H]1Cc1c[nH]c2ccccc12]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 131 using NMP/MeOH/AcOH 1:1:0.02 as solvent mixture. Macrocyclization: 1.2 eq HATU, 4 eq DIPEA, in DMF at rt 3 h. Deprotection: DCM/TFA 2:1, concentrating in vacuo, stirring in water.

The title compound was obtained as white powder (12 mg). MS ESI (m/z): 749.6 [(M+H)$^+$]

Example 237

(7S,10S,13S)-13-((1H-Indol-3-yl)methyl)-10-(4-aminobutyl)-7-(3-aminopropyl)-17-(dimethylamino)-12-methyl-6,7,9,10,12,13,15,16-octahydrodipyrido[2,3-b:3',4'-p][1,5,8,11,14]thiatetraazacycloheptadecine-8,11,14(5H)-trione

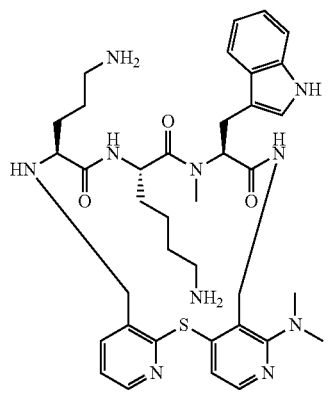 [SMILES: CN(C)c1nccc2c1CNC(=O)[C@H](Cc1c[nH]c3ccccc13)N(C)C(=O)[C@H](CCCCN)NC(=O)[C@H](CCCN)NCc1cccnc1S2]

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 132 using NMP/MeOH/AcOH 1:1:0.02 as solvent mixture. Macrocyclization: 1.2 eq HATU, 4 eq DIPEA, in DMF at rt 2 h. Deprotection: DCM/TFA 2:1, concentrating in vacuo, then stirring in water. The title compound was obtained as light yellow solid (59 mg). MS ESI (m/z): 715.6 [(M+H)$^+$]

Example 238

(7S,10S,13S)-13-((1H-Indol-3-yl)methyl)-10-(4-aminobutyl)-7-(3-aminopropyl)-12-methyl-17-(pyridin-3-yl)-6,7,9,10,12,13,15,16-octahydrodipyrido[2,3-b:3',4'-p][1,5,8,11,14]thiatetraazacycloheptadecine-8,11,14(5H)-trione

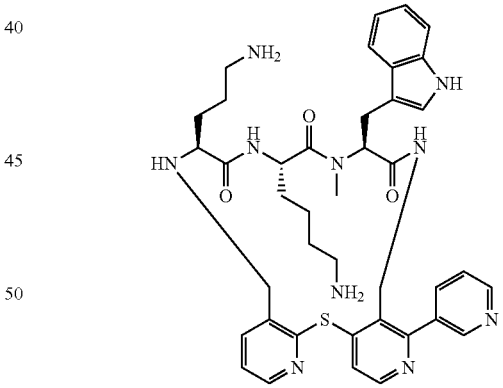

The material was prepared in analogy to the General Procedure for Peptide Macrocycle Synthesis using the following reagents/conditions: Amino Acids: Fmoc-NMe-L-Trp(Boc)-OH, Fmoc-L-Lys(Boc)-OH, Fmoc-L-Orn(Boc)-OH. Reductive Amination: 1.2 eq Intermediate 133 using NMP/MeOH/AcOH 1:1:0.02 as solvent mixture. Macrocyclization: 1.2 eq HATU, 4 eq DIPEA, in DMF at rt 2 h. Suzuki in analogy to Example 189 using 3-(4,4,5,5-tetramethyl-1,3,2-dioxaborolan-2-yl)pyridine. Deprotection: DCM/TFA 2:1. The title compound was obtained as yellow amorphous solid (6 mg). MS ESI (m/z): 749.4 [(M+H)$^+$]

Example 239

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-benzoic Acid

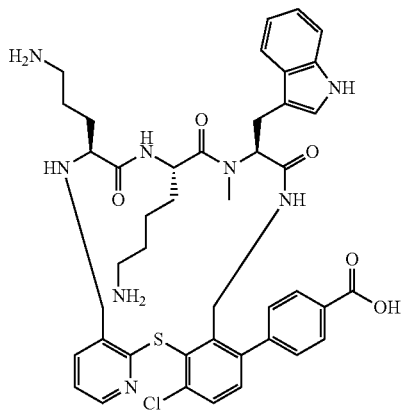 [SMILES: CN1C(=O)[C@H](CCCCN)NC(=O)[C@H](CCCN)NCc2cccnc2Sc2c(Cl)ccc(-c3ccc(C(=O)O)cc3)c2CNC(=O)[C@@H]1Cc1c[nH]c2ccccc12]

Example 239 was prepared according to the General Procedure for Suzuki Coupling of boronic acid derivatives to Peptide Macrocycle Intermediates using the following starting materials:
Macrocycle Intermediate: Intermediate 140
Boronic Acid Derivative: 4-(tert-Butoxycarbonyl)phenyl-boronic acid
MS (M+H$^+$): expected 824.3; observed 825.3

Example 240

(11S,14S,17S)-14-(4-Amino-butyl)-11-(3-amino-propyl)-25-chloro-22-[4-(2,3-dihydroxy-propoxy)-phenyl]-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

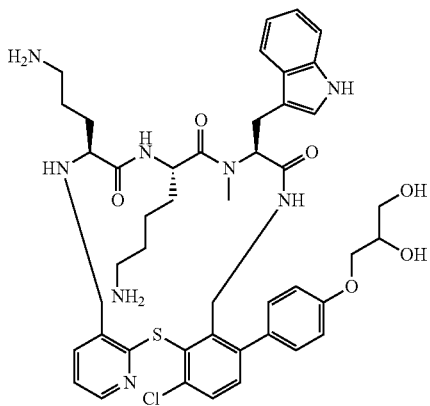 [SMILES: CN1C(=O)[C@H](CCCCN)NC(=O)[C@H](CCCN)NCc2cccnc2Sc2c(Cl)ccc(-c3ccc(OCC(O)CO)cc3)c2CNC(=O)[C@@H]1Cc1c[nH]c2ccccc12]

Example 240 was prepared according to the General Procedure for Suzuki Coupling of boronic acid derivatives to Peptide Macrocycle Intermediates using the following starting materials:
Macrocycle Intermediate: Intermediate 140
Boronic Acid Derivative: 2-(4-((2,2-dimethyl-1,3-dioxolan-4-yl)methoxy)phenyl)-4,4,5,5-tetramethyl-1,3,2-dioxaborolane
MS (M+H$^+$): expected 870.4; observed 871.4

Example 241

{4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-phenoxy}-acetic Acid

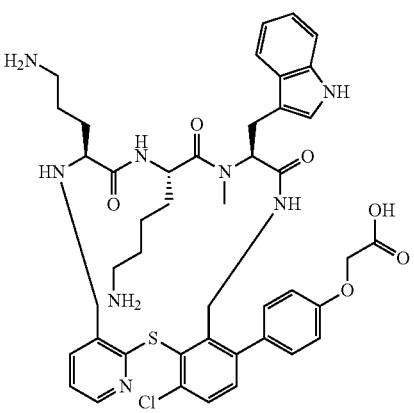 [SMILES: CN1C(=O)[C@H](CCCCN)NC(=O)[C@H](CCCN)NCc2cccnc2Sc2c(Cl)ccc(-c3ccc(OCC(=O)O)cc3)c2CNC(=O)[C@@H]1Cc1c[nH]c2ccccc12]

Example 241 was prepared according to the General Procedure for Suzuki Coupling of boronic acid derivatives to Peptide Macrocycle Intermediates using the following starting materials:
Macrocycle Intermediate: Intermediate 140
Boronic Acid Derivative: tert-butyl 2-(4-(4,4,5,5-tetramethyl-1,3,2-dioxaborolan-2-yl)phenoxy)acetate
MS (M+H$^+$): expected 8554.3; observed 855.3

Example 242

(11S,14S,17S)-14-(4-Amino-butyl)-11-(3-amino-propyl)-25-chloro-17-(1H-indol-3-ylmethyl)-16-methyl-22-[4-(piperidin-4-yloxy)-phenyl]-2-thia-4,10,13,16,19-pentaaza-tricyclo[19.4.0.0*3,8*]pentacosa-1(25),3(8),4,6,21,23-hexaene-12,15,18-trione

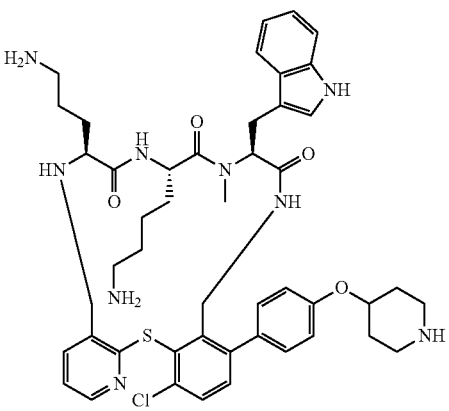 [SMILES: CN1C(=O)[C@H](CCCCN)NC(=O)[C@H](CCCN)NCc2cccnc2Sc2c(Cl)ccc(-c3ccc(OC4CCNCC4)cc3)c2CNC(=O)[C@@H]1Cc1c[nH]c2ccccc12]

Example 242 was prepared according to the General Procedure for Suzuki Coupling of boronic acid derivatives to Peptide Macrocycle Intermediates using the following starting materials:
Macrocycle Intermediate: Intermediate 140
Boronic Acid Derivative: tert-butyl 4-(4-(4,4,5,5-tetramethyl-1,3,2-dioxaborolan-2-yl)phenoxy)piperidine-1-carboxylate
MS (M+H$^+$): expected 879.4; observed 880.4

Example 243

(11S,14S,17S)-14-(4-Amino-butyl)-22-(4-aminomethyl-phenyl)-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

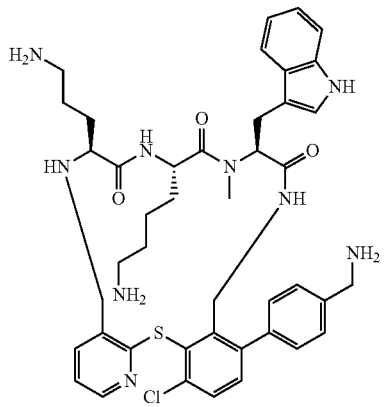 [SMILES: CN1C(=O)[C@H](CCCCN)NC(=O)[C@H](CCCN)NCc2cccnc2Sc2c(Cl)ccc(-c3ccc(CN)cc3)c2CNC(=O)[C@@H]1Cc1c[nH]c2ccccc12]

Example 243 was prepared according to the General Procedure for Suzuki Coupling of boronic acid derivatives to Peptide Macrocycle Intermediates using the following starting materials:
Macrocycle Intermediate: Intermediate 140
Boronic Acid Derivative: (4-(((tert-butoxycarbonyl)amino)methyl)phenyl)boronic acid
MS (M+H$^+$): expected 809.4; observed 810.4

Example 244

(11S,14S,17S)-14-(4-Amino-butyl)-22-[3-(2-aminoethyl)-phenyl]-11-(3-amino-propyl)-25-chloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

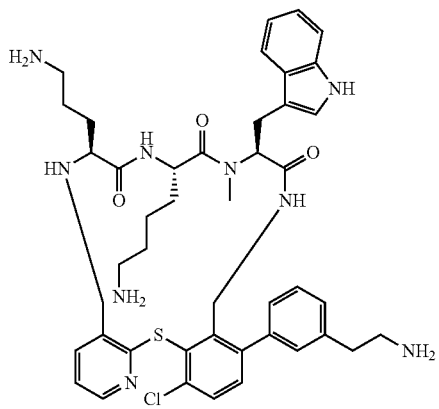 [SMILES: CN1C(=O)[C@H](CCCCN)NC(=O)[C@H](CCCN)NCc2cccnc2Sc2c(Cl)ccc(-c3cccc(CCN)c3)c2CNC(=O)[C@@H]1Cc1c[nH]c2ccccc12]

Example 244 was prepared according to the General Procedure for Suzuki Coupling of boronic acid derivatives to Peptide Macrocycle Intermediates using the following starting materials:
Macrocycle Intermediate: Intermediate 140
Boronic Acid Derivative: (3-(2-((tert-butoxycarbonyl)amino)ethyl)phenyl)boronic acid
MS (M+H$^+$): expected 823.4; observed 824.3

Example 245

(11S,14S,17S)-14-(4-Amino-butyl)-11-(3-amino-propyl)-25-chloro-17-(1H-indol-3-ylmethyl)-16-methyl-22-(4-piperazin-1-yl-phenyl)-2-thia-4,10,13,16,19-pentaaza-tricyclo[19.4.0.0*3,8*]pentacosa-1(25),3(8),4,6,21,2-hexaene-12,15,18-trione

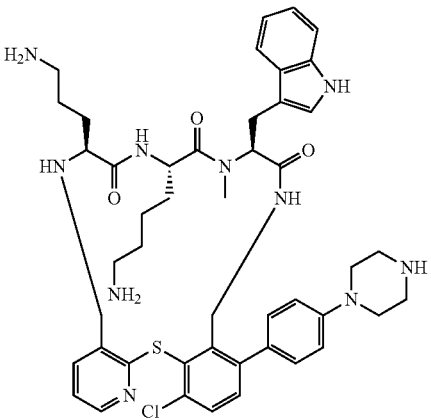 [SMILES: CN1C(=O)[C@H](CCCCN)NC(=O)[C@H](CCCN)NCc2cccnc2Sc2c(Cl)ccc(-c3ccc(N4CCNCC4)cc3)c2CNC(=O)[C@@H]1Cc1c[nH]c2ccccc12]

Example 245 was prepared according to the General Procedure for Suzuki Coupling of boronic acid derivatives to Peptide Macrocycle Intermediates using the following starting materials:
Macrocycle Intermediate: Intermediate 140
Boronic Acid Derivative: [4-(4-tert-butoxycarbonylpiperazin-1-yl)phenyl]boronic acid
MS (M+H$^+$): expected 864.4; observed 865.4

Example 246

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-hydroxy-ethyl)-benzenesulfonamide

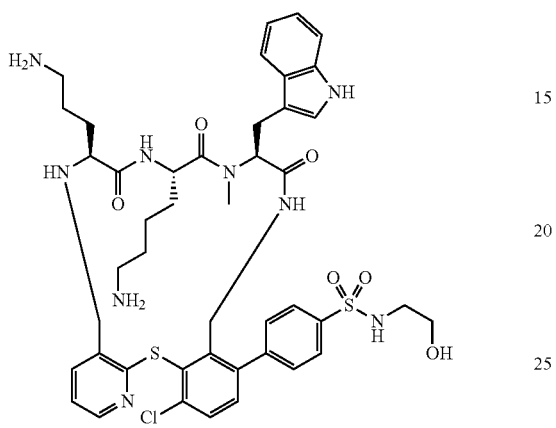

Example 246 was prepared according to the General Procedure for Suzuki Coupling of boronic acid derivatives to Peptide Macrocycle Intermediates using the following starting materials:

Macrocycle Intermediate: Intermediate 140
Boronic Acid Derivative: [4-(2-hydroxyethylsulfamoyl)phenyl]boronic acid
MS (M+H$^+$): expected 903.3; observed 904.3

Example 247

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-hydroxy-ethyl)-benzamide

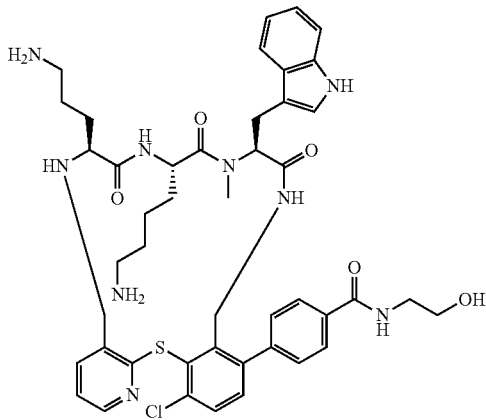 [SMILES: CN1C(=O)[C@H](CCCCN)NC(=O)[C@H](CCCN)NCc2cccnc2Sc2c(Cl)ccc(-c3ccc(C(=O)NCCO)cc3)c2CNC(=O)[C@@H]1Cc1c[nH]c2ccccc12]

Example 247 was prepared according to the General Procedure for Suzuki Coupling of boronic acid derivatives to Peptide Macrocycle Intermediates using the following starting materials:

Macrocycle Intermediate: Intermediate 140
Boronic Acid Derivative: [4-(2-hydroxyethylcarbamoyl)phenyl]boronic acid
MS (M+H$^+$): expected 867.4; observed 868.4

Example 248

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-dimethylamino-ethyl)-benzamide

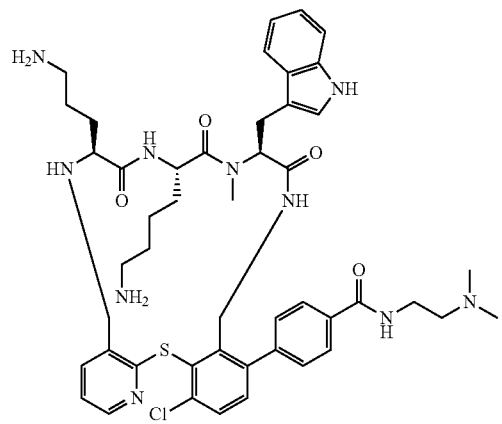 [SMILES: CN(C)CCNC(=O)c1ccc(-c2ccc(Cl)c3c2CNC(=O)[C@H](Cc2c[nH]c4ccccc24)N(C)C(=O)[C@H](CCCCN)NC(=O)[C@H](CCCN)NCc2cccnc2S3)cc1]

Example 248 was prepared according to the General Procedure for Suzuki Coupling of boronic acid derivatives to Peptide Macrocycle Intermediates using the following starting materials:

Macrocycle Intermediate: Intermediate 140
Boronic Acid Derivative: [4-[2-(dimethylamino)ethylcarbamoyl]phenyl]boronic acid; hydrochloride
MS (M+H$^+$): expected 894.4; observed 895.3

Example 249

4-[(11S,14S,17S)-14-(4-Amino-butyl)-11-(3-amino-propyl)-25-chloro-17-(1H-indol-3-ylmethyl)-16-methyl-12,15,18-trioxo-2-thia-4,10,13,16,19-pentaaza-tricyclo[19.4.0.0*3,8*]pentacosa-1(25),3(8),4,6,21,23-hexaen-22-yl]-N-(2-morpholin-4-yl-ethyl)-benzamide

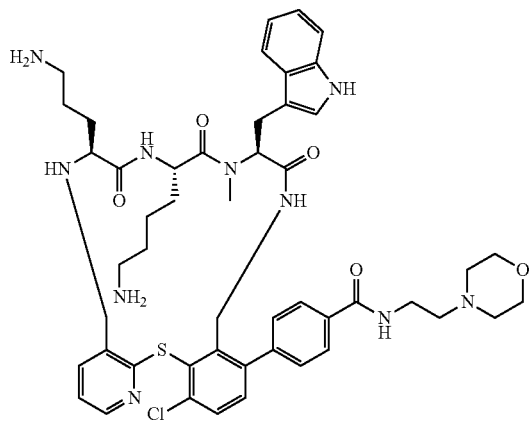 [SMILES: CN1C(=O)[C@H](CCCCN)NC(=O)[C@H](CCCN)NCc2cccnc2Sc2c(Cl)ccc(-c3ccc(C(=O)NCCN4CCOCC4)cc3)c2CNC(=O)[C@@H]1Cc1c[nH]c2ccccc12]

Example 249 was prepared according to the General Procedure for Suzuki Coupling of boronic acid derivatives to Peptide Macrocycle Intermediates using the following starting materials:

Macrocycle Intermediate: Intermediate 140
Boronic Acid Derivative: [4-(2-morpholinoethylcarbamoyl)phenyl]boronic acid
MS (M+H$^+$): expected 936.4; observed 937.4

Example 250

(11S,14S,17S)-14-(4-Amino-butyl)-11-(3-amino-propyl)-25-chloro-17-(1H-indol-3-ylmethyl)-16-methyl-22-(4-piperidin-4-yl-phenyl)-2-thia-4,10,13,16,19-pentaaza-tricyclo[19.4.0.0*3,8*]pentacosa-1(25),3(8),4,6,21,23-hexaene-12,15,18-trione

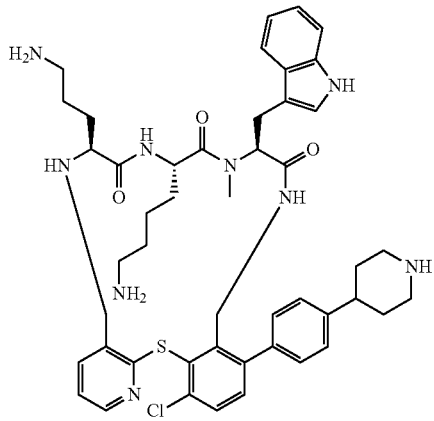 [SMILES: CN1C(=O)[C@H](CCCCN)NC(=O)[C@H](CCCN)NCc2cccnc2Sc2c(Cl)ccc(-c3ccc(C4CCNCC4)cc3)c2CNC(=O)[C@@H]1Cc1c[nH]c2ccccc12]

Example 250 was prepared according to the General Procedure for Suzuki Coupling of boronic acid derivatives to Peptide Macrocycle Intermediates using the following starting materials:

Macrocycle Intermediate: Intermediate 140
Boronic Acid Derivative: [4-(1-tert-butoxycarbonyl-4-piperidyl)phenyl]boronic acid
MS (M+H$^+$): expected 863.4; observed 864.4

Example 251

(11S,14S,17S)-11-(3-Amino-propyl)-23,25-dichloro-17-(1H-indol-3-ylmethyl)-16-methyl-14-(4-methyl-amino-butyl)-2-thia-4,10,13,16,19-pentaaza-tricyclo[19.4.0.0*3,8*]pentacosa-1(25),3(8),4,6,21,23-hexaene-12,15,18-trione

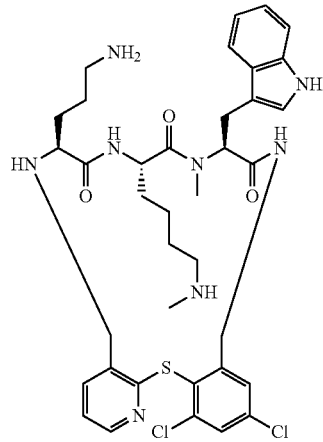 [SMILES: CNCCCC[C@@H]1NC(=O)[C@H](CCCN)NCc2cccnc2Sc2c(Cl)cc(Cl)cc2CNC(=O)[C@H](Cc2c[nH]c3ccccc23)N(C)C1=O]

Example 251 was prepared according to the General Procedure for Peptide Macrocycle Synthesis using the following starting materials:

1. Fmoc-NMe-L-Trp(BOC)—OH,
2. (S)-6-(tert-Butoxycarbonyl-methyl-amino)-2-(9H-fluoren-9-ylmethoxycarbonylamino)-hexanoic acid
3. Fmoc-L-Orn(BOC)—OH.

Tether: Intermediate 47
MS (M+H$^+$): expected 753.7; observed 753.6

Example 252

(11S,14S,17S)-14-(4-Amino-butyl)-23,25-dichloro-11-(3-hydroxy-propyl)-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

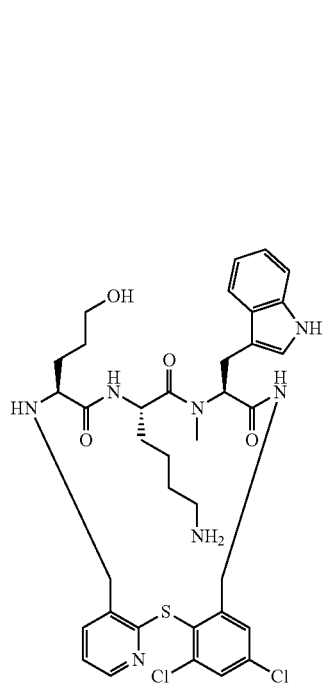 [SMILES: CN1C(=O)[C@H](CCCCN)NC(=O)[C@H](CCCO)NCc2cccnc2Sc2c(Cl)cc(Cl)cc2CNC(=O)[C@@H]1Cc1c[nH]c2ccccc12]

Example 252 was prepared according to the General Procedure for Peptide Macrocycle Synthesis using the following starting materials:

1. Fmoc-NMe-L-Trp(BOC)—OH,
2. Fmoc-L-Lys(BOC)—OH,
3. Intermediate 141)

Tether: Intermediate 47

TBS Deprotection

The globally-protected macrocyle (110 mg, 0.1 mmol, prepared according to general procedures) was mixed with tetrabutylammonium fluoride solution in THF (1.0 M, 1 mL) and stirred at room temperature for 3 hours. The reaction mixture was concentrated and the residue was purified by silica gel column followed by pre-HPLC (Waters SunFire C18, 5 µm, OBD™ 30×100 mm; mobile phase: A, acetonitrile and B, 0.1% TFA in water) to give the desired macrocyle alcohol (20 mg).

Final BOC-Deprotection

To a solution of macrocyle alcohol obtained above (20 mg, 21 µmol) in dichloromethane (500 µl) was added TFA (250 µl). The mixture was stirred at room temperature for 2 hours, and then concentrated in vacuo at room temperature. The residue was taken up in ~2 ml of water and stirred at room temperature overnight. MeCN/H2O (v/v=1/1, 1.5 ml) was added and the mixture was lyophilized to give the final product (16 mg).

MS (M+H$^+$): expected 739.2; observed 740.3

Example 253

(11S,14S,17S)-11-(3-Amino-propyl)-14-butyl-23,25-dichloro-17-(1H-indol-3-ylmethyl)-16-methyl-2-thia-4,10,13,16,19-pentaaza-tricyclo[19.4.0.0*3,8*]pentacosa-1(25),3(8),4,6,21,23-hexaene-12,15,18-trione

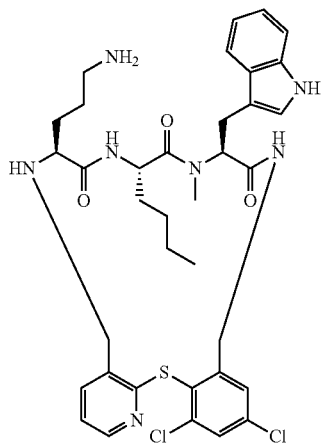 [SMILES: CCCC[C@@H]1NC(=O)[C@H](CCCN)NCc2cccnc2Sc2c(Cl)cc(Cl)cc2CNC(=O)[C@H](Cc2c[nH]c3ccccc23)N(C)C1=O]

Example 253 was prepared according to the General Procedure for Peptide Macrocycle Synthesis using the following starting materials:

1. Fmoc-NMe-L-Trp(BOC)—OH,
2. Fmoc-L-Nle-OH (Fmoc-L-norleucine),
3. Fmoc-L-Orn(BOC)—OH.

Tether: Intermediate 47

MS (M+H$^+$): expected 723.2; observed 724.3

Example 254

Antimicrobial Susceptibility Testing: Minimum Inhibitory Concentration (MIC) Determination The in vitro antimicrobial activity of the compounds was determined through microbroth minimum inhibitory concentration (MIC) methodology performed according to the Clinical and Laboratory Standard Institute guidelines (CLSI-M07-A9 Jan. 2012. Methods for Dilution Antimicrobial Susceptibility Tests for Bacteria That Grow Aerobically; Approved Standard—Ninth Edition, Clinical and Laboratory Standards Institue, Wayne/PA, US and the CLSI-M100-S24 Jan. 2014. Performance Standards for Antimicrobial Susceptibility Testing; Approved Standard—Fourth Informational Supplement, Clinical and Laboratory Standards Institue, Wayne/PA, UK).

The compound stock solution was freshly prepared at 10× the required top concentration for the MIC determination, i.e. at 1280 mg/L, by reconstitution of the dry compound in 50:50 water:DMSO.

Polystyrene non-treated 96 wells microtiter plates were used for preparing panel containing compound serial two-fold diluted at two times the final testing concentration (e.g. range from 64 to 0.06 µg/ml) in cation adjusted Mueller Hinton broth medium (CAMHB).

Inoculum was prepared by the "direct colony suspension method". Colonies of A. baumannii ATCC19606 or clinical isolates were suspended in saline solution and adjusted to 0.5 McFarland, diluted 100 times in CAMHB broth and 50

µl added to each well (final concentration of cells ~5×10$^{(5)}$ CFU/ml and Final volume/well of 100 µl). Microtiter plates were sealed and incubated at 35±2° C.

MICs values were read after 20 hours of incubation and recorded as the lowest concentration of the antimicrobial that inhibits more or equal to 80% of growth of the organism as detected by the unaided eye and using a microtiter plate optical density reader (OD 600 nm).

Tables 2, 3, 4 and 5 provide the minimum inhibitory concentration (MIC) in microgram per milliliter of the compounds of present invention obtained against the *A. baumannii* strain ATCC 19606 (Tables 2, 3, 4 and 5).

Particular compounds of the present invention exhibit a MIC (ATCC19606)≤64 µg/ml.

More particular compounds of the present invention exhibit a MIC (ATCC 19606)≤16 µg/ml.

Most particular compounds of the present invention exhibit a MIC (ATCC19606)≤2 µg/ml.

Example 255

Antimicrobial Susceptibility Testing: 50% Growth Inhibitory Concentration (IC50) Determination The in vitro antimicrobial activity of the compounds was alternatively determined according to the following procedure:

The assay used a 10-points Iso-Sensitest broth medium to measure quantitatively the in vitro activity of the compounds against *A. baumannii* ATCC 17978.

Stock compounds in DMSO were serially twofold diluted (e.g. range from 50 to 0.097 µM final concentration) in 384 wells microtiter plates and inoculated with 49 µl the bacterial suspension in Iso-Sensitest medium to have a final cell concentration of ~5×10$^{(5)}$ CFU/ml in a final volume/well of 50 ul/well. Microtiter plates were incubated at 35±2° C.

Bacterial cell growth was determined with the measurement of optical density at k=600 nm each 20 minutes over a time course of 16h.

Growth inhibition was calculated during the logarithmic growth of the bacterial cells with determination of the concentration inhibiting 50% (IC50) and 90% (IC90) of the growth.

Tables 3, 4 and 5 provide the 50% growth inhibitory concentrations (IC50) in micromoles per liter of the compounds of present invention obtained against the *A. baumannii* strain ATCC17978.

Particular compounds of the present invention exhibit an IC50 (ATCC17978)≤10 µmol/l.

More particular compounds of the present invention exhibit an IC50 (ATCC 17978)≤1 µmol/l.

Most particular compounds of the present invention exhibit an IC50 (ATCC17978)≤0.5 µmol/l.

TABLE 2

Minimum inhibitory concentration (MIC) in microgram per milliliter of the compounds of present invention obtained against *A. baumannii* strain ATCC19606.

| Example | ATCC19606 MIC [µg/ml] |
| --- | --- |
| 1 | 4 |
| 2 | 4 |
| 3 | 16 |
| 4 | 1 |
| 5 | 32 |

TABLE 2-continued

Minimum inhibitory concentration (MIC) in microgram per milliliter of the compounds of present invention obtained against *A. baumannii* strain ATCC19606.

| Example | ATCC19606 MIC [µg/ml] |
| --- | --- |
| 6 | 2 |
| 7 | 0.5 |
| 8 | 0.5 |
| 9 | 16 |
| 10 | 2 |
| 11 | 0.5 |
| 12 | 0.5 |
| 13 | 2 |
| 14 | 1 |
| 15 | 32 |
| 16 | 32 |
| 17 | 32 |
| 18 | 16 |
| 19 | 16 |
| 20 | 2 |
| 21 | 1 |
| 22 | 32 |
| 23 | 0.5 |
| 24 | 1 |
| 25 | 1 |
| 26 | 1 |
| 27 | 2 |
| 28 | 2 |
| 29 | 2 |
| 30 | 2 |
| 31 | 1 |
| 32 | 2 |
| 33 | 1 |
| 34 | 16 |
| 35 | 8 |
| 36 | 1 |
| 37 | 2 |
| 38 | 0.5 |
| 39 | 0.5 |
| 40 | 0.5 |
| 41 | 0.5 |
| 42 | 1 |
| 43 | 1 |
| 44 | 0.5 |
| 45 | 0.5 |
| 46 | 1 |
| 47 | 4 |
| 48 | 2 |
| 49 | 0.5 |
| 50 | 0.25 |
| 51 | 4 |
| 52 | 0.5 |
| 53 | 1 |
| 54 | 1 |
| 55 | 0.5 |
| 56 | 16 |
| 57 | 0.5 |
| 58 | 0.5 |
| 59 | 0.5 |
| 60 | 2 |
| 61 | 4 |
| 62 | 0.12 |
| 63 | 32 |
| 64 | 32 |
| 65 | 32 |
| 66 | 0.5 |
| 67 | 0.12 |
| 68 | 0.5 |
| 69 | 4 |
| 70 | 2 |
| 71 | 0.5 |
| 72 | 64 |
| 73 | 1 |
| 74 | 0.25 |
| 75 | 0.12 |
| 76 | 0.12 |
| 77 | 0.5 |
| 78 | 0.25 |

TABLE 2-continued

Minimum inhibitory concentration (MIC) in microgram per milliliter of the compounds of present invention obtained against *A. baumannii* strain ATCC19606.

| Example | ATCC19606 MIC [µg/ml] |
|---|---|
| 79 | 0.25 |
| 80 | 0.12 |
| 81 | 1 |
| 82 | 4 |

TABLE 3

Minimum inhibitory concentration (MIC) in microgram per milliliter of the compounds of present invention obtained against *A. baumannii* strain ATCC19606 and 50% growth inhibition concentrations (IC50) in micromoles per liter of the compounds of present invention obtained against *A. baumannii* strain ATCC17978.

| Example | ATCC19606 MIC [µg/ml] | IC50 ATCC17978 [µmol/l] |
|---|---|---|
| 83 | 0.5 | |
| 84 | 0.12 | |
| 85 | 0.5 | |
| 86 | 16 | |
| 87 | 8 | |
| 88 | 0.25 | |
| 89 | 0.12 | |
| 90 | 0.25 | |
| 91 | 0.5 | |
| 92 | 0.5 | |
| 93 | 16 | |
| 94 | 1 | |
| 95 | 8 | |
| 96 | 4 | |
| 97 | 0.12 | |
| 98 | 0.12 | |
| 99 | 4 | |
| 100 | 2 | |
| 101 | 32 | |
| 102 | 0.5 | |
| 103 | 0.25 | |
| 104 | 2 | |
| 105 | 1 | |
| 106 | 2 | |
| 107 | 8 | |
| 108 | 16 | |
| 109 | 2 | |
| 110 | 0.5 | |
| 111 | 1 | |
| 112 | 0.5 | |
| 113 | 2 | |
| 114 | 32 | |
| 115 | 2 | |
| 116 | 8 | |
| 117 | | 8.1 |
| 118 | 0.5 | |
| 119 | 4 | |
| 120 | 0.5 | |
| 121 | 2 | |
| 122 | 1 | |
| 123 | 1 | |
| 124 | | 34.9 |
| 125 | | 23.3 |
| 126 | | 30.3 |
| 127 | 16 | |
| 128 | 2 | |
| 129 | 0.25 | |
| 130 | 1 | |
| 131 | 0.25 | |
| 132 | | 17 |
| 133 | | 0.1 |
| 134 | 2 | |
| 135 | | 0.2 |
| 136 | | 0.6 |
| 137 | 32 | |
| 138 | 0.5 | |
| 139 | 2 | |
| 140 | | 0.6 |
| 141 | | 1.3 |
| 142 | | <0.4 |
| 143 | | <0.4 |
| 144 | 1 | |
| 145 | 4 | |
| 146 | 1 | |
| 147 | 0.12 | |
| 148 | 8 | |
| 149 | 1 | |
| 150 | 1 | |

TABLE 4

Minimum inhibitory concentration (MIC) in microgram per milliliter of the compounds of present invention obtained against *A. baumannii* strain ATCC19606 and 50% growth inhibition concentrations (IC50) in micromoles per liter of the compounds of present invention obtained against *A. baumannii* strain ATCC17978.

| Example | ATCC19606 MIC [µg/ml] | IC50 ATCC17978 [µmol/l] |
|---|---|---|
| 151 | | 0.2 |
| 152 | | <0.39 |
| 153 | | <0.39 |
| 154 | 2 | |
| 155 | | 2.7 |
| 156 | 1 | |
| 157 | 16 | |
| 158 | | <0.39 |
| 159 | | <0.39 |
| 160 | 4 | |
| 161 | | 6.8 |
| 162 | 0.5 | |
| 163 | 4 | |
| 164 | 0.25 | |
| 165 | 4 | |
| 166 | 0.5 | |
| 167 | 32 | |
| 168 | | <0.4 |
| 169 | 4 | |
| 170 | 0.5 | |
| 171 | 0.5 | |
| 172 | 0.5 | |
| 173 | 2 | |
| 174 | 16 | |
| 175 | 2 | |
| 176 | | 5.1 |
| 177 | 1 | |
| 178 | 32 | |
| 179 | 32 | |
| 180 | 1 | |
| 181 | 0.25 | |
| 182 | 0.5 | |
| 183 | 0.25 | |
| 184 | 2 | |
| 185 | 0.5 | |
| 186 | 0.5 | |
| 187 | 2 | |
| 188 | 2 | |
| 189 | 4 | |
| 190 | 0.12 | |
| 191 | 0.12 | |

TABLE 4-continued

Minimum inhibitory concentration (MIC) in microgram per milliliter of the compounds of present invention obtained against *A. baumannii* strain ATCC19606 and 50% growth inhibition concentrations (IC50) in micromoles per liter of the compounds of present invention obtained against *A. baumannii* strain ATCC17978.

| Example | ATCC19606 MIC [µg/ml] | IC50 ATCC17978 [µmol/l] |
|---|---|---|
| 192 | 64 | |
| 193 | 64 | |
| 194 | | 3.3 |
| 195 | | 3 |
| 196 | | 0.1 |
| 197 | | 0.2 |
| 198 | | 0.3 |
| 199 | 1 | |
| 200 | 0.12 | |
| 201 | | 0.4 |
| 202 | 0.12 | |
| 203 | 1 | |
| 204 | 64 | |
| 205 | 16 | |
| 206 | | 1.4 |
| 207 | | 9 |
| 208 | | 12.5 |
| 209 | 0.25 | |
| 210 | 16 | |
| 211 | 16 | |
| 212 | 32 | |
| 213 | 2 | |
| 214 | 0.25 | |
| 215 | | 2 |
| 216 | | 0.7 |
| 217 | | 1 |
| 218 | | 2 |

TABLE 5

Minimum inhibitory concentration (MIC) in microgram per milliliter of the compounds of present invention obtained against *A. baumannii* strain ATCC19606 and 50% growth inhibition concentrations (IC50) in micromoles per liter of the compounds of present invention obtained against *A. baumannii* strain ATCC17978.

| Example | ATCC19606 MIC [µg/ml] | IC50 ATCC17978 [µmol/l] |
|---|---|---|
| 219 | | 0.6 |
| 220 | | 5.8 |
| 221 | 0.25 | |
| 222 | 0.12 | |
| 223 | 1 | |
| 224 | 0.12 | |
| 225 | 0.12 | |
| 227 | 4 | |
| 228 | 0.12 | |
| 229 | 1 | |
| 230 | 0.12 | |
| 231 | 1 | |
| 232 | 1 | |
| 233 | 0.25 | |
| 234 | 2 | |
| 235 | 0.5 | |
| 236 | | 3.2 |
| 237 | | 0.8 |
| 238 | | 5.6 |
| 239 | | <1 |
| 240 | | <0.1 |
| 241 | | <0.2 |
| 242 | | <0.2 |
| 243 | | <0.1 |
| 244 | | <0.4 |
| 245 | | <0.1 |
| 246 | | <0.1 |
| 247 | | <0.1 |
| 248 | | <0.1 |
| 249 | | <0.1 |
| 250 | | <0.1 |
| 251 | | <0.1 |
| 252 | | 0.5 |
| 253 | | 4.2 |
| 226 | | 0.9 |

The invention claimed is:

1. A process for the manufacture of a compound according to formula I:

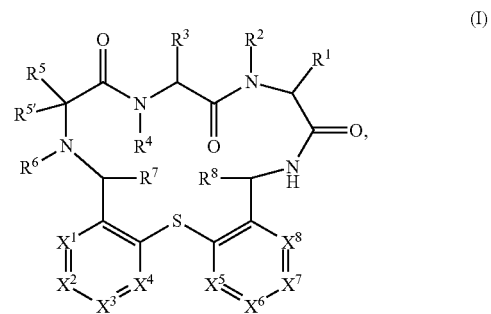

or a pharmaceutically acceptable salt thereof, wherein:
$X^1$ is C-$L^1$-$R^{11}$ or N;
$X^2$ is C-$L^2$-$R^{12}$ or N;
$X^3$ is C-$L^3$-$R^{13}$ or N;
$X^4$ is C-$L^4$-$R^{14}$ or N, with the proviso that not more than three of $X^1$, $X^2$, $X^3$ and $X^4$ are N;
$X^5$ is C-$L^5$-$R^{15}$ or N;
$X^6$ is C-$L^6$-$R^{16}$ or N;
$X^7$ is C-$L^7$ $R^{17}$ or N;
$X^8$ is C-$L^8$-$R^{18}$ or N, with the proviso that not more than three of $X^5$, $X^6$, $X^7$ and $X^8$ are N;
$R^1$ is —$(CH_2)_m$-heteroaryl or —$(CH_2)_m$-heterocycloalkyl, wherein heteroaryl is optionally substituted with one or more halo, cyano, $C_{1-7}$-alkyl, $C_{1-7}$-haloalkyl, $C_{3-7}$-cycloalkyl or $C_{1-7}$-alkoxy;
$R^2$, $R^4$ and $R^6$ are each individually selected from the group consisting of hydrogen, $C_{1-7}$-alkyl, $C_{1-7}$-haloalkyl, and $C_{3-7}$-cycloalkyl;
$R^3$ is —$C_{1-7}$-alkyl, —$(CH_2)_n$—$NR^{20}R^{21}$, —$(CH_2)_n$—C(O)$NR^{20}R^{21}$ or —$(CH_2)_n$—O—$(CH_2)_q$—$NR^{20}R^{21}$;
$R^5$ is hydrogen, $C_{1-7}$-alkyl, hydroxy-$C_{1-7}$-alkyl, —$(CH_2)_o$—$NR^{22}R^{23}$, —$(CH_2)_o$—C(O)—$NR^{22}R^{23}$, —$(CH_2)_o$—O—$(CH_2)_q$—$NR^{20}R^{21}$, —$(CH_2)_o$—NH—C(NH)—$NR^{22}R^{23}$, —$(CH_2)_o$—NH—C(O)—$NR^{22}R^{23}$, —$(CH_2)_o$—NH—C(O)—$OR^{26}$, —$(CH_2)_o$—$C_{3-7}$-cycloalkyl, —$(CH_2)_o$-heterocycloalkyl, —$(CH_2)_o$-heteroaryl, or —$(CH_2)_o$-aryl, wherein cycloalkyl, heterocycloalkyl, heteroaryl and aryl are optionally substituted by halo, cyano, $C_{1-7}$-alkyl, $C_{1-7}$-haloalkyl, $C_{1-7}$-alkoxy or aryl;

$R^{5'}$ is hydrogen;

$R^7$ and $R^8$ are each individually selected from the group consisting of hydrogen, $C_{1-7}$-alkyl, $C_{1-7}$-haloalkyl, $C_{3-7}$-cycloalkyl and $C_{1-7}$-alkoxy;

$R^{11}$, $R^{12}$, $R^{13}$, $R^{14}$, $R^{15}$ and $R^{16}$ are each individually selected from the group consisting of hydrogen, halogen, cyano, $C_{1-7}$-alkyl, $C_{1-7}$-haloalkyl, $-NR^{24}R^{25}$, $C_{1-7}$-alkyl-$NR^{24}R^{25}$, hydroxy, $C_{1-7}$-alkoxy, halo$C_{1-7}$-alkoxy, $-B(OH)_2$, benzyloxy-propynyl ($-C\equiv C-CH_2-O$-benzyl), $C_{3-7}$-cycloalkyl, heterocycloalkyl, aryl and heteroaryl, wherein heteroaryl is optionally substituted with one $C_{1-7}$-haloalkyl or $C_{1-7}$-alkoxy;

$R^{17}$ is hydrogen, halogen, cyano, $C_{1-7}$-alkyl, $C_{1-7}$-haloalkyl, $-NR^{24}R^{25}$, $C_{1-7}$-alkyl-$NR^{24}R^{25}$, hydroxy, $C_{1-7}$-alkoxy, halo$C_{1-7}$-alkoxy, $B(OH)_2$, benzyloxy-prop-1-ynyl, $C_{3-7}$-cycloalkyl, heterocycloalkyl, aryl or heteroaryl, wherein heterocycloalkyl is optionally substituted with one $-NR^{24}R^{25}$, wherein aryl and heteroaryl are optionally substituted with one, two or three substituents selected from the list group consisting of halogen, cyano, $C_{1-7}$-alkyl, $C_{1-7}$-haloalkyl, $C_{1-7}$-hydroxyalkyl, hydroxy, $C_{1-7}$-alkoxy, $-NR^{24}R^{25}$, $-SO_2-C_{1-7}$-alkyl, $-SO_2-NR^{24}R^{25}$, heterocycloalkyl and heterocycloalkyl substituted with $C_{1-7}$-alkyl;

$R^{18}$ is hydrogen, halogen, cyano, $C_{1-7}$-alkyl, $C_{1-7}$-haloalkyl, hydroxy, $C_{1-7}$-hydroxyalkyl, $C_{1-7}$-alkoxy, $C_{1-7}$-haloalkoxy, $-NR^{24}R^{25}$, $C_{1-7}$-alkyl-$NR^{24}R^{25}$, $C_{3-7}$-cycloalkyl, heterocycloalkyl, aryl or heteroaryl, wherein aryl and heteroaryl are optionally substituted with one, two or three substituents selected from the group consisting of halogen, cyano, $C_{1-7}$-alkyl $C_{1-7}$-haloalkyl, hydroxy, $C_{1-7}$-alkoxy, $-NR^{24}R^{25}$, $C_{1-7}$-alkyl-$NR^{24}R^{25}$, $-CO-NH-(CH_2)_r-NR^{24}R^{25}$, $-CO-NH-(CH_2)_r-OH$, $-CO-NH-(CH_2)_r$-heterocycloalkyl, $-CO-OH$, $-O-C_{1-7}$-hydroxyalkyl, $-O-(CH_2)_r-CO-OH$, $-SO_2-C_{1-7}$-alkyl, $-SO_2-NR^{24}R^{25}$, heterocycloalkyl, $-O$-heterocycloalkyl and heterocycloalkyl substituted with $C_{1-7}$-alkyl;

$R^{20}$ and $R^{22}$ are each individually selected from the group consisting of hydrogen, $C_{1-7}$-alkyl, $C_{1-7}$-haloalkyl, $C_{3-7}$-cycloalkyl and $-C(=NH)-NH_2$;

$R^{21}$ and $R^{23}$ are each individually selected from the group consisting of hydrogen and $C_{1-7}$-alkyl;

$R^{24}$ and $R^{25}$ are each individually selected from the group consisting of hydrogen, $C_{1-7}$-alkyl, $C_{1-7}$-haloalkyl, $C_{1-7}$-hydroxyalkyl and $C_{3-7}$-cycloalkyl;

$R^{26}$ is hydrogen, $C_{1-7}$-alkyl or benzyl;

$L^1$, $L^2$, $L^3$, $L^4$, $L^5$, $L^6$, $L^7$ and $L^8$ are each individually selected from the group consisting of a single bond, $-C(O)-$, $-SO_2-$, $-(CH_2)_p-$, $-CH=CH-$ and $-C\equiv C-$;

m is 1, 2, 3, or 4;
n is 1, 2, 3, or 4;
o is 0, 1, 2, 3, or 4;
p is 1, 2, 3, or 4;
q is 1, 2, 3, or 4; and
r is 1, 2, 3, or 4;

the process comprising the steps of:

a) reacting a compound of formula (III) with a compound of formula (IV) using sodium cyanoborohydride (NaCNBH₃) to provide a compound of formula (II);

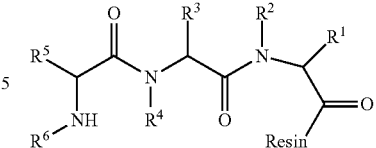

(IV)

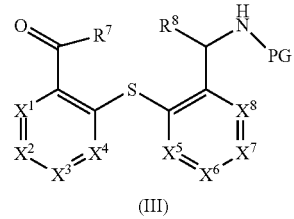

(III)

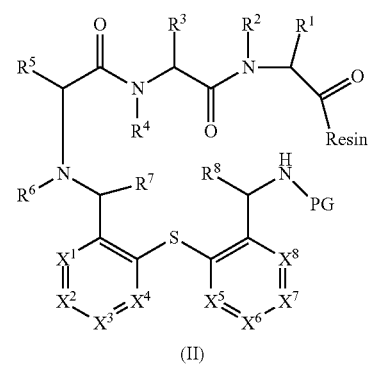

(II)

b) cleaving off the protecting group (PG) and the resin from the compound of formula (II); and

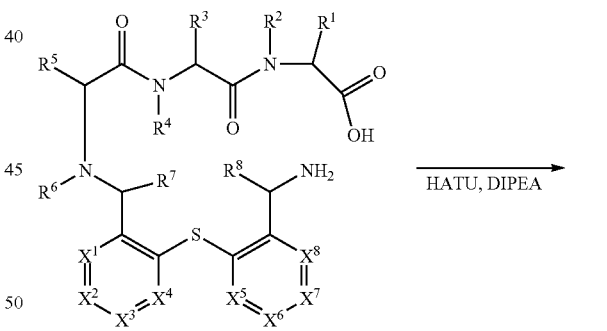

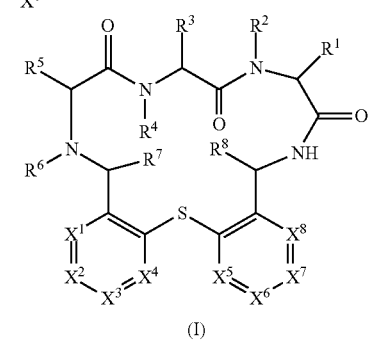

(I)

c) followed by cyclisation of the cleaved compound of formula (II) using HATU and Hünig's base.

2. The process of claim 1, wherein the compound of formula (IV) is washed with DCM prior to adding the compound of formula (IV) to the compound of formula (III).

3. The process of claim 1, wherein the step a) further comprises using a mixture of N-methyl-2-pyrrolidone (NMP), trimethyl orthoformate (TMOF) and acetic acid (AcOH).

4. The process of claim 1, wherein the step c) further comprises using DMF.

5. The process of claim 1, wherein the step b) further comprises using TFA and DCM.

\* \* \* \* \*